United States Patent
Blaskovich et al.

(10) Patent No.: US 9,340,517 B2
(45) Date of Patent: *May 17, 2016

(54) METHODS OF MODULATING THE ACTIVITY OF THE MC5 RECEPTOR AND TREATMENT OF CONDITIONS RELATED TO THIS RECEPTOR

(71) Applicant: Mimetica PTY LTD, Milton (AU)

(72) Inventors: Mark Arnold Thomas Blaskovich, Bardon (AU); Peter Joseph Cassidy, Ashgrove (AU)

(73) Assignee: Mimetica PTY LTD, Milton Queensland (AU)

( * ) Notice: Subject to any disclaimer, the term of this patent is extended or adjusted under 35 U.S.C. 154(b) by 103 days.

This patent is subject to a terminal disclaimer.

(21) Appl. No.: 13/737,653

(22) Filed: Jan. 9, 2013

(65) Prior Publication Data

US 2013/0225563 A1    Aug. 29, 2013

Related U.S. Application Data

(63) Continuation of application No. 12/391,748, filed on Feb. 24, 2009, now Pat. No. 8,377,925.

(60) Provisional application No. 61/032,912, filed on Feb. 29, 2008, provisional application No. 61/032,894, filed on Feb. 29, 2008, provisional application No. 61/032,898, filed on Feb. 29, 2008.

(51) Int. Cl.

| | | |
|---|---|---|
| *A61K 31/55* | (2006.01) | |
| *A61K 31/16* | (2006.01) | |
| *A61K 31/04* | (2006.01) | |
| *A01N 43/62* | (2006.01) | |
| *C07D 243/08* | (2006.01) | |
| *A61K 31/551* | (2006.01) | |
| *C07D 401/06* | (2006.01) | |

(52) U.S. Cl.
CPC ............ *C07D 243/08* (2013.01); *A61K 31/551* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 5,622,860 | A | 4/1997 | Yamada et al. |
| 6,448,032 | B1 | 9/2002 | Wikberg et al. |
| 6,645,738 | B1 | 11/2003 | Fong et al. |
| 2003/0110518 | A1 | 6/2003 | Houseknecht et al. |
| 2003/0162819 | A1 | 8/2003 | Eisinger et al. |
| 2003/0176425 | A1 | 9/2003 | Eisinger et al. |
| 2006/0030604 | A1 | 2/2006 | Elsinger et al. |
| 2006/0128772 | A1 | 6/2006 | Eisinger et al. |

FOREIGN PATENT DOCUMENTS

| | | |
|---|---|---|
| AU | 742747 B2 | 10/1999 |
| WO | WO 96/22304 | 7/1996 |
| WO | WO 97/15577 | 5/1997 |
| WO | WO 98/49186 | 11/1998 |
| WO | WO 99/48913 | 9/1999 |
| WO | WO 03/040117 | 5/2003 |
| WO | WO 03/040118 | 5/2003 |
| WO | WO 2005/061467 | 7/2005 |
| WO | WO 2008/017852 | 2/2008 |

OTHER PUBLICATIONS

Miyuki Anzai, Reiko Yanada, Nobutaka Fujii, Hiroaki Ohno, Toshiro Ibuka, and Yoshiji Takemoto; Asymmetric synthesis of $\beta^{2,3}$-amino acids by Inl-Pd(0)-promoted metalation and addition of chiral 2-vinylaziridines; tetrahedron 58 (2002); p. 5231-5239.

Horacio F. Olivo, Michael S. Hemenway, Amy C. Hartwig, and Raymond Chan; New Preparation of Activated 2-Vinylaziridines from 1,4-Aminoalcohols; Synlett; Mar. 1998; p. 247-248.

B. Moon Kim, Sung Jin Bae, Soon Mog So, Hyun Tae Yoo, Sun Ki Chang, Jung Hwan Lee, and JaeSung Kang; Synthesis of a Chiral Aziridine Derivative as a Versatile Intermediate for HIV Protease Inhibitors; Organic Letters 2001; vol. 3, No. 15; p. 2349-2351.

André Nouvet, Marc Binard, Frédéric Lamaty, and René Lazaro; Convenient introduction of 2-(trimethylsilyl)ethylsulfonyl (SES) amino protection on different amino acids and its use in peptidomimetic chemistry; Letters in Peptide Science, 6; 1999; p. 239-242.

Peter Wipf and Paul C. Fritch; $S_N2'$-Reactions of Peptide Aziridines. A Cuprate-Based Approach to (E)-Alkene Isosteres; J. Org. Chem.; 1994; 59; p. 4875-4886.

Aparecida M. Kawamoto and Martin Wills; Enantioselective synthesis of β-hydroxy amines and aziridines using asymmetric transfer hydrogenation of α-amino ketones; J. Chem. Soc., Perkin Trans. 1; 2001; p. 1916-1928.

P. Barrett, A. MacDonald, R. Helliwell, G. Davidson, and P. Morgan; Cloning and expression of a new member of the melanocyte-stimulating hormone receptor family; Journal of Molecular Endocrinology; (1994); 12; p. 203-213 (Abstract).

(Continued)

*Primary Examiner* — Jeffrey S Lundgren
*Assistant Examiner* — Stephanie Springer
(74) *Attorney, Agent, or Firm* — Brinks Gilson & Lione

(57) ABSTRACT

The present invention provides compounds of Formula (I) that are useful for modulating the biological activity of the melanocortin-5 receptor (MC5R). Compounds of this invention can be used to treat diseases and/or conditions in which downregulation of MC5R is beneficial. Such diseases and/or conditions include, but are not limited to, acne, seborrhea, seborrheic dermatitis, cancer, and inflammatory diseases.

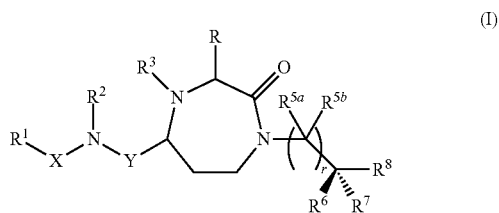

19 Claims, No Drawings

(56) References Cited

OTHER PUBLICATIONS

AK Gupta and R. Bluhm; Seborrheic dermatitis; JEADV; (2004); 18; p. 13-26.
Jarl ES Wikberg; Melanocortin receptors: new opportunities in drug discovery; Exp. Opin. Ther. Pat. (2001); 11; 61; Ashley Publications Ltd. ISSN; 2001; p. 1354-3776.
Jranz-Josef Leinweber; Possible Physiological Roles of Carboxylic Ester Hydrolases; Drug Metabolism Reviews; 1987; 18:4; p. 379-439.
Plewig G. and Jansen T.; Chapter 22 Seborrheic dermatitis; In: Dermatology in General Medicine, Freedberg IM, EisenAZ, Wolff K, Austen KF, Goldsmith LA, Katz SI, Fitzpatrick TB (Eds) 5$^{th}$ ed. McGraw Hill, New York; 1999; p. 1482-1489.
Shari B. Clarke, Amanda M. Nelson, Rosalyn E. George, and Diane M. Thiboutot; Pharmacologic Modulation of Sebaceous Gland Activity: Mechanisms and Clinical Applications; Dermatol Clin; 25; (2007); p. 137-146.
Caurnel Morgan, Ruth E. Thomas, Weidong Ma, Milos V. Novotny, and Roger D. Cone; Melanocortin-5 Receptor Deficiency Reduces a Pheromonal Signal for Aggression in Male Mice; Chem. Senses; 29; 2002; p. 111-115.
Wenbiao Chen, Michele A. Kelly, Ximena Optiz-Araya, Ruth E. Thomas, Malcolm J. Low, and Roger D. Cone; Exocrine Gland Dysfunction in MC5-R-Deficient Mice: Evidence for Coordinated Regulation of Exocrine Gland Function by Melanocortin Peptides; Cell; vol. 91; Dec. 12, 1997; p. 789-798.
Caurnel Morgan and Roger Cone; Melanocortin-5 Receptor Deficiency in Mice Blocks a Novel Pathway Influencing Pheromone-Induced Aggression; Behavior Genetics; vol. 36; No. 2; Mar. 2006; p. 291-300.
Derek H. R. Barton; The Invention of Chemical Reactions; Aldrichimica Acta; vol. 23; No. 1; 1990.
Athanassios Giannis and Thomas Kolter; Peptidomimetics for Receptor Ligands—Discovery, Development, and Medical Prespectives; Angew. Chem. Int. Engl.; 1993; 32; p. 1244-1267.
Herbert Meier and Klaus-Peter Zeller; The Wolff Rearrangement of α-Diazo Carbonyl Compounds; Angew. Chem. Internat. Edit.; vol. 14; No. 1; 1975.
Jörg S. Früchtel and Günther Jung; Organic Chemistry on Solid Supports; Angew. Chem. Int. Ed. Engl.; 1996; 35; p. 17-42.
Kim, K.S.; Marklund, S.; Rothschild, M.F.; The porcine melanocortin-5-receptor (MC5R) gene: polymorphisms, linkage and physical mapping; Animal Genetics; 2000; 31; p. 230-231.
Li Zhang, Mike Anthonavage, Qiuling Huang, Wen-Hwai Li, and Magdalena Eisinger; Proopiomelanocortin Peptides and Sebogenesis; Ann. N.Y. Acad. Sci.; 994; 2003; p. 154-161.
M. Rajan Mariappan, Oluwole Fadare, Dhanpat Jain; Sebaceous Differentiation in Salivary Glands; Arch Pathol Lab Med; vol. 128; Feb. 2004.
Vijay Chhajlani, Ruta Muceniece, and Jarl E. S. Wikberg; Molecular Cloning of a Novel Human Melanocortin Receptor; Biochemical and Biophysical Research Comunications; vol. 195, No. 2; 1993; p. 866-873.
Nathalie Griffon, Virginie Mignon, Patricia Facchinetti, Jorge Diaz, Jean-Charles Schwartz, and Pierre Sokoloff; Molecular Cloning and Characterization of the Rat Fifth Melanocortin Receptor; Biochemical and Biophysical Research Communications; Vo. 200, No. 2; 1994; p. 1007-1014.
Ira Gantz, Yoshimasa Shimoto, Yoshitaka Konda, Hiroto Miwa, Chris J. Dickinson, and Tadataka Yamada; Molecular Cloning, Expression, and Characterization of a Fifth Melanocortin Receptor; Biochemical and Biophysical Research Communications; Vo. 200, No. 3; 1994; p. 1214-1220.
Olivier Labbé, Frank Desarnaud, Dominique Eggerickx, Gilbert Vassart, and Marc Parmentier; Molecular Cloning of a Mouse Melanocortin 5 Receptor Gene Widely Expressed in Peripheral Tissues; Biochemistry; 1994; 33; p. 4543-4549.
John L. Krstenansky, Robert L. Baranowski, and Bruce L. Currie; A New Approach to Conformationally Restricted Peptide Analogs: Rigid β-Bends. 1. Enkephalin as an Example; Biochemical and Biohphysical Research Communications; vol. 109, No. 4; 1982; p. 1368-1374.
Joseph J. Buggy; Binding of α-melanocyte-stimulating hormone to its G-protein-coupled receptor on B-lymphocytes activates the Jak/STAT pathway; Biochem, J.; 1998; 331; p. 211-216.
Tatjana Haitina, Janis Klovins, Jan Andersson, Robert Fredriksson, Malin C. Lagerström, Dan Larhammar, Earl T. Larson, and Helgi B. Schiöth; Cloning, tissue distribution, pharmacology and three-dimensional modeling of melanocortin receptors 4 and 5 in rainbow trout suggest close evolutionary relationship of these subtypes; Biochem. J.; 2004; 380; p. 475-486.
Peter N. Lewis, Frank A. Momany, and Harold A. Scheraga; Chain Reversals in Proteins; Biochemica et Biophysica Acta.; 303; 1973; p. 211-229.
Albert M. Kligman; The Uses of Sebum; British Journal of Dermatology; vol. 75; Issue 8-9; 1963; p. 307-319.
Cotterill, Cunliffe, Williamson; Severity of Acne and Sebum Excretion Rate; British Journal of Dermatology; vol. 85; 1971; p. 93-94.
A.J. Thody, S.K. Goolamali, J.L. Burton, N.A. Plummer, S. Shuster; Plasma β-MSH Levels in Acne Vulgaris; Brithish Journal of Dermatology; vol. 92; Issue 1; 1975; p. 43-47.
King, Jones, Daltrey, Cunliffe; A double-blind study of the effects of 13-cis-reetinoic acid on acne, sebum secretion rate and microbial population; British Journal of Dermatology; vol. 107; Issue 5; 1982; p. 583-590.
Jones, King, Miller, Cunliffe; A dose response study of 13-cis-retinoic acid in acne vularis; British Journal of Dermatology; vol. 108; 1983; p. 333-343.
Goodfellow, Alaghband-Zadeh, Carter, Cream, Holland, Scully, Wise; Oral spironolactone improves acne vulgaris and reduces sebum excretion; British Journal of Dermatology; vol. 111; 1984; p. 209-214.
Burke, BM and Cunliffe, WJ; Oral spironolactone therapy for female patients with acne; British Journal of Dermatology; vol. 112; 1984; p. 124-126.
E. Mallon, J.N. Newton, A. Klassen, S.L. Stewart-Brown, T.J. Ryan, and A.Y. Finlay; The quality of life in acne: a comparison with general medical conditions using generic questionnaires; British Journal of Dermatology; 140; 1999; p. 672-676.
V. Goulden, C.H. Mcgeown, and W.J. Cunliffe; The familial risk of adult acne: a comparison between first-degree relatives of affected and unaffected individuals; British Journal of Dermatology; 141; 1999; p. 297-300.
S-W. Youn, E-S. Park, D-H. Lee, C-H. Huh, and K-C. Park; Does facial sebum excretion really affect the development of acne?; British Journal of Dermatology; 153; 2005; p. 919-924.
K. Mourelatos, E.A. Eady, W.J. Cunliffe, S.M. Clark, and J.H. Cove; Temporal changes in sebum excretion and propionibacterial colonization in preadolescent children with and without acne; British Journal of Dermatology; 156; 2007; p. 22-31.
E. Makrantonaki and C.C. Zouboulis; Testosterone metabolism to 5α-dihydrotestosterone and synthesis of sebaceous lipids is regulated by the peroxisome proliferator-activated receptor ligand linoleic acid in human sebocytes; British Journal of Dermatology; 156; 2007; p. 428-432.
Maria K. Ling, Eri Hotta, Zuzana Kilianova, Tatjana Haitina, Aneta Ringholm, Lisa Johansson, Nicole Gallo-Payet, Sakae Takeuchi & Helgi B. Schiöth; The melanocortin receptor subtypes in chicken have high preference to ACTH-derived peptides; British Journal of Pharmacology; 143; 2004; p. 626-637.
Janusz Jurczak and Adam Golebiowski; Optically active N-protected .alpha.-amino aldehydes in organic synthesis; Chem. Rev.; 1989; 89 (1); p. 149-164.
Yoshiniori Yamamoto and Naoki Asao; Selective reactions using allylic metals; Chem. Rev.; 1993; 93 (6); p. 2207-2293.
Lorin A. Thompson and Jonathan A. Ellman; Synthesis and Applications of Small Molecule Libraries; Chem. Rev.; 1996; 96 (1); p. 555-600.
F. Javier Sardina and Henry Rapoport; Enantiospecific Synthesis of Heterocycles from α-Amino Acids; Chem. Rev.; 1996; 96 (6); p. 1825-1872.

(56) References Cited

OTHER PUBLICATIONS

Patrice Ribière, Valérie Declerck, Jean Martinez, and Frédéric Lamaty; 2-(Trimethylsilyl)ethanesulfonyl (or SES) Group in Amine Protection and Activation; Chem. Ref.; 106 2006; p. 2249-2269.
Heather K. Caldwell and John J. Lepri; Disruption of the Fifth Melanocortin Receptor Alters the Urinary Excretion of Aggression-modifying Pheromones in Male House Mice; Chem. Senses; 27; 2002; p. 91-94.
G.E. Piérard, C. Piérard-Franchimont, T. Lê; Seborrhoea in Acne-Prone and Acne-Free Patients; Dermatologica; 175; 1987; p. 5-9.
Tim Graefe, Uwe Wollina, Hans-Joachim Schulz, Walter Burgdorf; Muir-Torre Syndrome-Treatment with Isotretinoin and Interferon Alpha-2a Can Prevent Tumour Development; Dermatology; 200; 2000; p. 331-333.
Simpson, N.B., and Cunliffe, W.J.; Chapter 43. Disorders of the Sebaceous Glans; In: Rooks' Textbook of Dermatologseicy, Burns, D.A.; Breathnach, S.M.; Cox, N.; Griffiths, C.E. (Eds) 7$^{th}$ Ed Blackwell Science, Malden mass, 2004; p. 43. 1-43.75.
Janis Klovins, Tatjana Haitina, Aneta Ringholm, Maja Löwgren, Davids Fridmanis, Maija Slaidina, Susanne Stier, and Helgi B. Schiöth; Cloning of two melanocortin (MC) receptors in spiny dogfish MC3 receptor in cartilaginous fish shows high affinity to ACTH-derived peptides while it has lower preference to γ-MSH; Eur. J. Biochem.; 271; 2004; p. 4320-4331.
Zouboulis ChC, Böhm M.; Neuroendocrine regulation of sebocytes—a pathogenetic link between stress and acne; Exp. Dermatol; 13 (Suppl. 4); 2004; p. 31-35.
I Follador, L Campelo; Impact of Acne on Quality of Life; Expert Review of Dermatology; vol. 1; Issue 1; 2006; p. 181-184.
C Williams and A.M. Layton; Treatment of Acne: An Update; Expert Review of Dermatology; vol. 1; Issue 3; 2006; p. 429-438.
Martin J. Humphries, Paul M. Doyle and C. John Harris; Integrin antagonists as modulators of adhesion; Exp. Opin. Ther. Patents; 4(3); 1994; p. 227-235.
Caurnel Morgan, Ruth E. Thomas, and Roger D. Cone; Melanocortin-5 receptor deficiency promotes defensive behavior in male mice; Hormones and Behavior; 45; 2004; p. 58-63.
Aw Taylor and K Namba; In Vitro induction of CD25$^+$ CD4$^+$ regulatory T cells by the neuropeptide alpha-melnocyte stimulating hormone (α-MSH); Immunology and Cell Biology; 79; 2001; p. 358-367.
G. Valle, M. Crisma, C. Toniolo, K.-L. Yu, R.L. Johnson; Crystal-state structural analysis of two γ-lactam-restricted analogs of Pro-Leu-Gly-NH$_2$; International Journal of Peptide and Protein Research; vol. 33; Issue 3; 1989; Online 2009; p. 181-190.
Huang RR, Singh G, Van Der Ploeg LH, Fong TM; Species-Dependent Pharmacological Properties of the Melanocortin-5 Receptor; J. Receptor Sig. Trans. Res.; vol. 20; Issue 1; 2000; p. 47-59.
Goldstein, Socha-Szott, Thomsen, Pochi, Shalita, Strauss; Comparative Effect of Isotretinoin and Etritnate on Acne and Sebaceous Gland Secretion; J. Am. Acad. Dermatol.; vol. 6; Issue 4; 1982; p. 760-765.
Harris HH, Downing DT, Stewart ME, Strauss JS; Sustainable rates of sebum secretion in acne patients and matched normal control subjects; J. Am. Acad. Dermatol.; vol. 8; Issue 2; 1983; p. 200-203.
F. William Danby; Why we have sebaceous glands; J Am Acad Dermatol; 52; 2005; p. 1071-2.
Ming H. Jih, Paul M. Friedman, Leonard H. Goldbert, Michele Robles, Adrienne S. Glaich, and Arash Kimyai-Asadi; The 1450-nm diode laser for facial inflammatory acne vulgaris: Dose-response and 12-month follow-up study; the American Academy of Dermatology, Inc.; J. Acad. Dermatol.; vol. 55; No. 1; p. 80-87; 2006.
Robyn N. Smith, Neil J. Mann, Anna Braue, Henna Mäkeläinen, and George A. Varigos; The effect of a high-protein, low glycemic-load diet verses a conventional, high glycemic-load diet on biochemical parameters associated with acne vulgaris: A randomized, investigator-masked, controlled trial; The American Academy of Dermatology, Inc.; J. Acad. Dermatol.; vol. 57; No. 2; p. 247-256; 2007.
Thody, J.J., Shuster, S; Control of sebaceous gland function in the rat by alpha-melanocyte-stimulating hormone; J. Endcr.; vol. 64; Issue 3; 1975; p. 503-510.
Thody AJ, Cooper MJ, Meddis, D, Bowden PE, Shuster S; Proceedings: The sebaceous gland response to alpha-melanocyte stimulating hormone and testosterone; J. Endcr.; vol. 67; 1975; p. 18P-19P.
Pochi, Strauss; Sebum production, casual sebum levels, titratable acidity of sebum, and urinary fractional 17-ketosteroid excretion in males with acne; The Journal of Investigative Dermatology; vol. 43; 1964; p. 383-388.
Diane Thiboutot, Aruntha Sivarajah, Kathryn Gilliland, Zhaoyuan Cong, and Gary Clawson; The Melanocortin 5 Receptor is Expressed in Human Sebaceous Glands and Rat Preputial Cells; The Journal of Investigative Dermatology; 2000; 115; p. 614.
Naohito Hatta, Craig Dixon, Amanda J. Ray, Sion R. Phillips, William J. Cunliffe, Mike Dale, Carol Todd, Simon Meggit, Mark A. Birch-Machin, and Jonathan L. Rees; Expression, Candidate Gene, and Population Studies of the Melanocortin 5 Receptor; The Journal of Investigative Dermatology; 2001; 116; p. 564.
V. Bataille, H. Snieder, A.J. MacGregor, P. Sasieni, and T.D. Spector; The Influence of Genetics and Environmental Factors in the Pathogenesis of Acne: A Twin Study of Acne in Women; The Journal of Investigative Dermatology; 2002; 119; p. 1317.
Roland Kruse, Arno Rütten, Nadine Schweiger, Eva Jakob, Micaela Mathiak, Peter Propping, Elisabeth Mangold, Michele Bisceglia, and Thomas Ruzicka; Frequency of Microsatellite Instability in Unselected Sebaceous Gland Neoplasias and Hyperplasisas; The Journal of Investigative Dermatology; 2003; 120; p. 858.
Markus Böhm, Thomas A. Luger, Desmond J. Tobin, and José Carlos García-Borrón; Melanocortin Receptor Ligands: New Horizons for Skin Biology and Clinical Dermatology; Journal of Investigative Dermatology; vol. 126; 2006; p. 1966-1975.
Amanda M. Nelson, Kathryn L. Gilliland, Zhaoyuan Cong, and Diane M. Thiboutot; 13-cis Retinoic Acid Induces Apoptosis and Cell Cycle Arrest in Human SEB-1 Sebocytes; Journal of Investigative Dermatology; vol. 126; 2006; p. 2178-2189.
Jeong, S.K., et al.; Intracellular calcium mobilization is medicated by the melanocortin receptors in SZ95 sebocytes; J. Investigative Dermatol; 2007; 127; p. S72; Abstract 431; Society for Investigative Dermatology; May 2007; Los Angeles, CA.
Phan, J., et al.; P. acnes induced inflammation via TLR2 and upregulates antimicrobial activity in sebocytes; J. Investigative Dermatol; 2007; 127; p. s126; Abstract 754; Society for Investigative Dermatol; May 2007; Los Angeles, CA.
Smith, K.R., et al.; Iron status affects human sebocyte survival; J. Investigative Dermatol; 2007a; 127; o, S68; Abstract 408; Society for Investigative Dermatoloy; May 2007; Los Angeles, CA.s.
James F. Callahan, John W. Bean, Joelle L. Burgess, Drake S. Eggleston, Shing Mei Hwang, Kenneth D. Kopple, Paul F. Koster, Andrew Nichols, Catherine E. Peishoff; Design and synthesis of a C7 mimetic for the predicted .gamma.-turn conformation found in several constrained RGD antagonists; J. Med. Chem.; 35 (21); 1992; p. 3970-3972.
Kenneth A. Newlander, James F. Callahan, Michael L. Moore, Thaddeus A. Tomaszek Jr., and William F. Huffman; A novel constrained reduced-amide inhibitor of HIV-1 protease derived from the sequential incorporation of .gamma.-turn mimetics into a model substrate; 36 (16); 1993; p. 2321-2331.
Gary L. Olson, David R. Bolin, Mary Pat Bonner, Michael Bos, Charles M. Cook, David C. Fry, Bradford J. Graves, Marcos Hatada, David E. Hill; Concepts and progress in the development of peptide mimetics; J. Med. Chem.; 36 (21); 1993; p. 3039-3049.
Mark A. Gallop, Ronald W. Barrett, William J. Dower, Stephen P.A. Fodor, and Eric M. Gordon; Applications of Combinatorial Technologies to Drug Discovery. 1. Background and Peptide Combinatorial Libraries; J. Med. Chem.; 37 (9); 1994; p. 1233-1251.
Eric M. Gordon, Ronald W. Barrett, William J. Dower, Stephen P.A. Fodor, and Mark A. Gallop; Applications of Combinatorial Technologies to Drug Discovery. 2. Combinatorial Organic Synthesis, Library Screening Strategies, and Future Directions; J. Med. Chem.; 37 (10); 1994; p. 1385-1401.
E.J. Milner-White, et al.; One Type of Gamma-turn, Rather Than the Other Gives Rise to Chain-reversal in Proteins; J. Mol. Biol.; 204; 1988; p. 777-782.

(56) References Cited

OTHER PUBLICATIONS

Ibon Alkorta, Maria Luisa Suarez, Rosario Herranz, Rosario González-Muñiz and M. Teresa García-López; Similarity Study on Peptide γ-turn Conformation Mimetics; J. Mol. Model.; 2; 1996; p. 16-25.

Jonathan B. Ball and Paul F. Alewood; Conformational Constraints: Nnpeptide β-Turn Mimics; Journal of Molecular Recognition; vol. 3; No. 2; 1990.

Aneta Ringholm, Robert Fredriksson, Natalia Poliakova, Yi-Lan Yan, John H. Postlethwait, Dan Larhammar, and Helgi B. Schiöth; One melanocortin 4 and two melanocortin 5 receptors from zebrafish show remarkable conservation in structure and pharmacology; International Society for Neurochemistry; Journal of Neurochemistry; 82; 2002; p. 6-18.

José Miguel Cerdá-Reverter, Maria Kristina Ling, Helgi Birgir Schióth, and Richard Ector Peter; Molecular cloning, characterization and brain mapping of the melanocortin 5 receptor in the goldfish; International Society for Neurochemistry; J. Neurochem.; 10.1046/j.; 2003; p. 1471-4159.

Philip L. Robinson, Carey N. Barry, S. Woody Bass, Susan E. Jarvis, and Slayton A. Evans Jr.; Regioselective cyclodehydration of chiral diols with diethoxytriphenylphosphrane, tripheynlpospinetetrachloromethane-potassium carbonate, and triphenylphosphine-diethyl azodicarboxylate reagents. A comparative study; J. Org. Chem.; 48(26); 1983; p. 5396-5398.

Herbert C. Brown and Prabhaker K. Jadhav; B-Allyldiisocaranylborane: a new, remarkable enantioselective allylborating agent for prochiral aldehydes. Synthesis of homoallylic alcohols approaching 100% enantiomeric purities; J. Org. Chem.; 49 (21); 1984; p. 4089-4091.

Thomas L. Cupps, Raymond H. Boutin, and Henry Rapoport; .alpha.-Amino acids as chiral educts for asymmetric products. The synthesis of .alpha.'-amino-.alpha.,.beta.-ynones; J. Org. Chem.; 50 (21); 1985; p. 3972-3979.

Jeffery W. Kelly, Nita L. Anderson, and Slayton A. Evans Jr.; Cyclodehydration of N- and C-substituted .beta.-amino alcohols to the corresponding aziridines with diethoxytriphenylphosphorane; J. Org. Chem.; 51 (1); 1986; p. 95-97.

John A. Soderquist and M. Ramin Najafi; Selective oxidation of organoboranes with anhydrous trimethylamine N-oxide; J. Org. Chem.; 51 (8); 1986; p. 1330-1336.

Raymond H. Boutin and Henry Rapoport; .alpha.-Amino acid derivatives as chiral educts for asymmetric products. Synthesis of sphingosine from .alpha.'-amino-.alpha.,.beta.-ynones; J. Org. Chem.; 51 (26); 1986; p. 5320-5327.

Ari M. P. Koskinen and Henry Rapoport; Synthesis of 4-substituted pralines as conformationally constrained amino acid analogs; J. Org. Chem.; 54 (8); 1989; p. 1859-1866.

Jean Pierre Wolf and Henry Rapoport; Conformationally constrained peptides. Chirospecific synthesis of 4-alkyl-substituted .gamma.-lactam-bridged dipeptides from L-aspartic acid; J. Org. Chem.; 54 (13); 1989; p. 3164-3173.

Spencer Knapp, Jeffrey J. Hale, Margarita Bastos, Audrey Molina, and Kuang Yu Chen; Synthesis of hypusine and other polyamines using dibenzyltriazones for amino protection; J. Org. Chem.; 57 (23); 1992; p. 6239-6256.

Uday S. Racheria, Yi Liao and Herbert C. Brown; Chiral synthesis via organoboranes. 36. Exceptionally enantioselective allylborations of representative heterocyclic aldehydes at -100 .degree.C under salt-free conditions; J. Org. Chem.; 57 (24); 1992; p. 6614-6617.

Holger Wenschuh, Michael Beyermann, Eberhard Krause, Michael Brudel, Ruediger Winter, Michael Schuemann, Louis A. Carpino, and Michael Bienert; Fmoc Amino Acid Flourides: Convenient Reagents for the Solid-Phase Assembly of Peptides Incorporating Sterically Hindered Residues; J. Org. Chem.; 59 (12); 1994; p. 3275-3280.

Tiziana Basile, Allaye Bocoum, Diego Savoia, and Achille Umani-Ronchi; Enantioselective Synthesis of Homoallylic Amines by Addition of Allylmetal Reagents to Imines Derived from (S)-Valine Esters; J. Org. Chem.; 59 (25); 1994; p. 7766-7773.

Ahmed F. Abdel-Magid, Kenneth G. Carson, Bruce D. Harris, Cynthia A. Maryanoff, and Rekha D. Shah; Reductive Amination of Aldehydes and Ketones with Sodium Triacetoxyborohydride. Studies on Direct and Indirect Reductive Amination Procedures; J. Org. Chem.; 61 (11); 1996; p. 3849-3862.

Alan M W Porter; Why do we have apocrine and sebaceous glands?; J R Soc Med; 94; 2001; p. 236-237.

Richard F. Borch, Mark D. Bernstein, and H. Dupont Durst; Cyanohydridoborate anion as a selective reducing agent; J. Am. Chem. Soc.; 93 (12); 1971; p. 2897-2904.

I.D. Kuntz; Protein folding; J. Am. Chem. Soc.; 94 (11); 1972; p. 4009-4012.

Herbert C. Brown and Prabhakar K. Jadhav; Asymmetric carbon—carbon bond formation via .beta.-allyldiisopinocampheylborane. Simple synthesis of secondary homoallylic alcohols with excellent enantiomeric purities; J. Am. Chem. Soc.; 105 (7); 1983; p. 2092-2093.

Herbert C. Brown and Krishna S. Bhat; Enantiomeric Z- and E-crotyldiisopinocampheylboranes. Synthesis in high optical purity of all four possible stereoisomers of .beta.-methylhomoallyl alcohols; J. Am Chem. Soc.; 108 (2); 1986; p. 293-294.

Herbert C. Brown, Ramnarayan S. Randad, Krishna S. Bhat, Marek Zaidlewicz, and Uday S. Racheria; Chiral synthesis via organoboranes. 24. B-allylbis(2-isocaranyl)borane as a superior reagent for the asymmetric allylboration of aldehydes; J. Am. Chem. Soc.; 112 (6); 1990; p. 2389-2392.

Louis A. Carpino, Dean Sadat-Aalaee, Hann Guang Chao, and Robert H. DeSelms; [(9-Fluorenylmethyl)oxy]carbonyl (FMOC) amino acid fluorides. Convienient new peptide coupling reagents applicable to the FMOC/tert-butyl strategy for solution and solid-phase syntheses; J. Am. Chem. Soc.; 112 (26); 1990; p. 9651-9652.

Ralph Hirschmann, K.C. nicolaou, Sherrie Pientranico, Joseph Salvino, Ellen M. Leahy, Paul A. Sprengeler, George Furst, Catherine D. Strader, Amos B. Smith III; Nonpeptidal peptidomimetics with .beta.-D-glucose scaffolding. A partial somatostatin agonist bearing a close structural relationship to a potent, selective substance P antagonist; J. Am. Chem. Soc.; 114 (23); 1992; p. 9217-9218.

Ralph Hirschmann, .C. Nicolaou, Sharrie Pietranico, Ellen M. Leahy, Joseph Salvino, Byron Arison, Maria A. Cichy, P. Grant Spoors, William C. Shakespeare; De novo design and synthesis of somatostatin non-peptide peptidomimetics utilizing .beta.-D-glucose as a novel scaffolding; J. Am. Chem. Soc.; 115 (26); 1993; p. 12550-12568.

Alex A. Virgilio and Jonathan A. Ellman; Simultaneous Solid-Phase Synthesis of .beta.-Turn Mimetics Incorporating Side-Chain Functionality; J. Am. Chem. Soc.; 116 (25); 1994; p. 11580-11581.

David K. Chalmers and Garland R. Marshall; Pro-D-NMe-Amino Acid and D-Pro-NMe-Amino Acid: Simple, Efficient Reverse-Turn Constraints; J. Am. Chem. Soc.; 117 (22); 1995; p. 5927-5937.

Michael C. Hillier, James P. Davidson, and Stephen F. Martin; Cyclopropane-Derived Peptidomimetics. Design, Synthesis, and Evaluation of Novel Ras Farnesyltransferase Inhibitors; J. Org. Chem.; 66; 2001; p. 1657-1671.

Sabina Quader, Sue E. Boyd, Ian D. Jenkins, and Todd A. Houston; Multisite Modification of Neomycin B: Combined Mitsunobu and Click Chemistry Approach; J. Org. Chem.; 72; 2007; p. 1962-1979.

Sam Shuster; Biological Purpose of Acne; The Lancet; 1976; p. 1328-1329.

Horst Kessler, et al.; Design of superactive and selective integrin receptor antagonists containing the RGD sequence; Letters in Peptide Science; 2; 1995; p. 155-160.

Maher Qabar, et al.; Pharmaceutical applications of peptidomimetics; Letters in Peptide Science; 3; 1996; p. 25-30.

A.J. Thody, et al.; Biological Sciences Possible Role of MSH in the Mammal; Nature; vol. 245; 1973; p. 207-209.

Linda Yaswen, et al.; Obesity in the mouse model of pro-opiomelanocortin deficiency response to peripheral melanocortin; Nature Medicine; vol. 5; No. 9; 1999; p. 1066-1070.

Zahra Fathi, et al.; Cloning, Expression, and Tissue Distribution of a Fifth Melanocortin Receptor Subtype; Neurochemical Research; vol. 20; No. 1; 1995; p. 107-113.

(56) References Cited

OTHER PUBLICATIONS

Fumio Ide, et al.; Benign lymphoepithelial lesion of the parotid gland with sebaceous differentiation; Oral Pathol Oral Radiol Endod; 97; 1999; p. 721-4.
Li Zhang, et al.; Melanocortin-5 receptor: A marker of human sebocyte differentiation; Peptides; 27; 2006; p. 413-420.
William F. Huffman, et al.; Reverse turn mimics; Peptide Mimetics; 1988; p. 105-108.
Shaoxing Chen, et al.; Design and synthesis of a CD4 β-turn mimetic that inhibits human immunodeficiency virus envelope glycoprotein gp120 binding and infection of human lymphocytes; Proc. Natl. Acad. Sci.; vol. 89; 1992; p. 5872-5876.
C.M. Wilmot, et al.; β-Turns and their distortions: a proposed new nomenclature; Protein Engineering; vol. 3; No. 6; 1990; p. 479-493.
Xin Ma, et al.; Synthesis of a Heterocyclic γ-Turn Peptidomimetic Sequence; Propt Pept Lett; 1995; p. 347-350.
G.N. Andersen; Quantitative Measurement of the Levels of Melanocortin Receptor Subtype 1, 2, 3 and 5 and Pro-Opio-Melanocortin Peptide Gene Expression in Subsets of Human Peripheral Blood Leucocytes; Scandinavian Journal of Immunology; 2005; 61; p. 279-284.
Loren Cordian; Implications for the Role of Diet in Acne; Semin Cutan Med Surg; 24; 2005; p. 84-91.
Ann L. Marqueling, et al.; Depression and Suicidal Behavior in Acne Patients Treated with Isotretinoin: A Systematic Review; Semin Cutan Med Surg; 24; 2005; p. 92-102.
Julie C. Harper; Hormonal Therapy for Acne Using Oral Contraceptive Pills; Semin Cutan Med Surg; 24; 2005; p. 103-106.
Sachin S. Bhardwaj, et al.; Lasers and Light Therapy for Acne Vulgaris; Semin Cutan Med Surg; 24; 2005; p. 107-112.
Michael Kahn; Peptide Secondary Structure Mimetics: Recent Advances and Future Challenges; Synlett; 1993; 821-826.
Peter Wipf, et al.; An Investigation of the Mitsunobu Reaction in the Preparation of Peptide Oxazolines, Thiazolines, and Aziridines; Tetrahedron Letters; vol. 33, No. 42; 1992; p. 6267-6270.
V. VanRheenen, et al.; An improved catalytic $OsO^4$ oxidation of olefins to -1,2-glycols using tertiary amine oxides as the oxidant; Tetrahedron Letters; vol. 17; Issue 23; 1976; p. 1973-1976.
John T. Carlock, et al.; A mild quamtitative method for the synthesis of a variety of heterocyclic systems; Tetrahedron Letters; vol. 19; Issue 52; 1978; p. 5153-5156.
Rahul Ray, et al.; Osmium tetroxide catalyzed hydroxylation of hindered; Tetrahedron Letters vol. 21; Issue 5; 1980; p. 449-450.
Steven Nahm, et al.; N-methoxy-n-methylamides as effective acylating agents; Tetrahedron Letters; vol. 22; Issue 39; 1981; p. 3815-3818.
James R. Henry, et al.; Mitsunobu reactions of n-alkyl and n-acyl sulfonamides—an efficient route to protected amines; Tetrahedron Letters; vol. 30; Issue 42; 1989; p. 5709-5712.
Ronald C. Bernotas, et al.; The use of triphenylphosphine/diethyl azodicarboxylate (dead) for the cyclization of 1,4- and 1,5-amino alcohols; Tetrahedron Letters; vol. 32; Issue 2; 1991; p. 161-164.
Allaye Bocoum, et al.; Disasteroselective allylation of chiral imines. Novel application of allylcopper reagents to the enantioselective synthesis of homoallyl amines; Tetrahedron Letters; vol. 32; Issue 10; 1991; p. 1367-1370.
Nathalie Galéotti, et al.; Formation of Oxazolines and Thiazolies in Peptides by the Mitsunobu Reaction; Tetrahedron Letters; vol. 33; No. 20; 1992; p. 2807-2810.
A.Ehrilich, et al.; Synthesis of cyclic peptides via efficient new coupling reagents; Tetrahedron Letters; vol. 34; Issue 30; 1993; p. 4781-4784.
Louis A. Carpino, et al.; Racemization studies during solid-phase peptide synthesis using azabenzotriazole-based coupling reagents; Tetrahedron Letters; vol. 35; Issue 15; 1994; p. 2279-2282.
Marco Frigerio, et al.; A mild oxidizing reagents for alcohols and 1,2-diols: o-iodoxybenzoic acid (IBX) in DMSO; Tetrahedron Letters; vol. 35; Issue 43; 1994; p. 8019-8022.
Tetsto Tsunoda, et al.; Mitsunobu-type Alkylation of p-Toluenesulfonamide. A Convenient New Route to Primary and Secondary Amines; Tetrahedron Letters; vol. 37; No. 14; 1996; p. 2457-2458.
Ralph Hirschmann, et al.; The First Synthesis of a Tricyclic Homodetic Peptide Employing Coordinated Orthogonal Protection; Tetrahedron Letters; vol. 37; No. 32; 1996; p. 5637-5640.
Alex A. Virgilio, et al.; Expedient Solid-Phase Synthesis of Putative β-Turn Mimetics Incorporating the i+1, i+2, and i+3 Sidechains; Tetrahedron Letters; vol. 37; No. 39; 1996; p. 6961-6964.
André Nouvet, et al.; Synthesis of New Perhydro-(1,4)-diazepin-2-ones as Constrained Peptidomimetics; Tetrahedron Letters; 39; 1998; p. 2099-2102.
Herbert C. Brown, et al.; Forty years of hydride reductions; Tetrahedron; vol. 35; Issue 5; 1979; p. 567-607.
Herbert C. Brown, et al.; Organoboranes for synthesis. 4 : Oxidation of organoboranes with pyridinium chlorochromate. A direct synthesis of aldehydes from terminal alkenes via hydroboration; Tetrahedron; vol. 42; Issue 20; 1986; p. 5515-5522.
Jonathan B. Ball, et al.; β-Turn Topography; Tetrahedron; vol. 49; No. 17; 1993; p. 3467-3478.
Benjamin Gardner, et al.; Conformationally Constrained Nonpeptide β-turn Mimetics of Enkephalin; Tetrahedron; vol. 49; No. 17; 1993; p. 3433-3448.
André Nouvet, et al.; Synthesis of perhydrodiazepinones as new putative peptidomimetics; Tetrahedron; 55; 1999; p. 4685-4698.
Hiroshi Nakanishi, et al.; Design of Peptidomimetics; Practice of Medicinal Chemistry; 27; 1996; p. 571-590.
W. Szeja; Phase Transfer-Catalyzed Preparation of Oxiranes; Synthesis; 1985; p. 983-985.
Jürg R. Pfister; A One-Pot Synthesis of Aziridines from 2-Aminoethanols[1]; Synthesis; 1984; p. 969-970.
Jean-Alain Fehrentz, et al.; An Efficient Synthesis of Optically Active α-(tButoxycarbonylamino)-aldehydes Butoxycarbonylamino)-aldehydes from α-Amino Acids; Synthesis; 1983; p. 676-678.
Herbert C. Brown, et al.; Highly Selective Conversion or Terminal Olefins into Aldehydes; Synthesis; 1980; p. 151-153.
T. Arrhenius, et al.; The Chemical Synthesis of Structured Peptides using Covalent Hydrogen-Bond Mimics; Protein Structure, Folding, and Design; 2; 1987; p. 453-465.
David L. Hughes; The Mitsunobu Reaction; Organic Reactions; vol. 42; 1992; p. 335-656.
Robert O. Hutchins, et al.; Cyanoborohydride. Utility and Applications in Organic Synthesis. A Review; Org. Prep. Proc. Int.; 1979; 11; p. 203-241.
Gary W. Kramer, et al.; XIX. The Preparation and Some Unusual Chemistry of B-Allyl Derivatives of 9-Borabicyclo[3.3.1]Nonane; Journal of Organometallic Chemistry; 132; 1977; p. 9-27.
Gary W. Kramer, et al.; XVII. Reaction of Oranometallics with Dialkylborane Derivatives: The Synthesis of Mixed Organoboranes not Available Via Hydroboration; Journal of Organometallic Chemistry; 73; 1974; p. 1-16.
G. Valle, et al.; Crystal-state structural analysis of two γ-lactam-restricted analogs of Pro-Leu-Gly-$NH_2$; Int. J. Peptide Protein res.; 33; 1989; p. 181-190.
George D. Rose, et al.; Turns in Peptides and Proteins; Advances in Protein Chemistry; vol. 37; 1985; p. 1-97.
Gordon W. Gribble, et al.; Sodium Borohydride in Carboxylic Acid Media. A Review of the Synthetic Utility of Acyloxyborohydrides; Organic Preparations and Procecures Int.; 17; (4-5); 1985; p. 317-384.
Jane S. Richardson; The Anatomy and Taxonomy of Protein Structure; Advances in Protein Chemistry; vol. 34; 1985; 167-330.
W.F. Huffman, et al.; Mimics of Secondary Structural Elements of Peptides and Proteins; Synthetic Peptides; 1989; p. 257-266.
G. Hölzemann; Peptide Conformation Mimetics (Part 1); Kontake (Darmstadt); 1991; 1.
G. Hölzemann; Peptide Conformation Mimetics (Part 2); Kontake (Darmstadt); 1991; 2.
Ursula Egner, et al.; Turn Mimetics for Peptide Design; Pesticide Science; 1997; p. 95.

(56) References Cited

OTHER PUBLICATIONS

Stephen Hanessian, et al.; Design and Synthesis of Conformationally Constrained Amino Acids as Versatile Scaffolds and Peptide Mimetics; Tetrahedron Report No. 426; vol. 53; No. 38; 1997; p. 12789-12854.

Guibourdenche, et al.; Aminoacides, Peptides et Chimie Heterocyclique; Bull. Soc. Chim. Belg.; 1994; vol. 103; p. 1-8.

Silverman; The Organic Chemistry of Drug Design and Drug Action, $2^{nd}$ ed.; 2004; p. 25-34.

Patani, et al. Bioisosterism: A Rational Approach in Drug Design; Chem. Rev.; 1996; vol. 96; p. 3147-3176.

Kawai, et al.; Structure-activity relationship study of novel NR2B-selective antagonists with arylamides to avoid reactive metabolites formation; Bioorg. Med. Chem. Lett.; 2007; vol. 17; p. 5537-5542.

Chen, et al.; Phenylguanidines as Selective Nonpeptide Melanocortin-5 Receptor Antagonists; J. Med. Chem.; 2004; vol. 47; p. 4083-4088.

Japanese Office Action Summary; Mailing Date Feb. 17, 2009.

PCT Search Report; PCT/AU2009/000231; Mar. 11, 2009.

PCT Search Report; PCT/AU2009/00230; Mar. 11, 2009.

METHODS OF MODULATING THE ACTIVITY OF THE MC5 RECEPTOR AND TREATMENT OF CONDITIONS RELATED TO THIS RECEPTOR

CROSS REFERENCE TO RELATED APPLICATIONS

This application is a continuation application of U.S. patent application Ser. No. 12/391,748, now allowed, which claims the benefit of U.S. Provisional Application No. 61/032,912, filed on Feb. 29, 2008, U.S. Provisional Application No. 61/032,894, filed on Feb. 29, 2008, and U.S. Provisional Application No. 61/032,898, filed on Feb. 29, 2008, all of which are incorporated by reference in their entirety.

FIELD OF THE INVENTION

The present invention relates to methods of modulating the activity of the melanocortin-5 receptor. In particular the present invention relates to the use of a family of 1,4-diazepan-2-ones and derivatives thereof to modulate the activity of the melanocortin-5 receptor. The invention also relates to methods and uses of the compounds in the treatment of conditions in which antagonism of the melanocortin-5 receptor is beneficial.

BACKGROUND OF THE INVENTION

The melanocortin-5 receptor (MC5R) is a G-protein coupled receptor (GPCR) belonging to the family of melanocortin receptors. There are five melanocortin receptors that have been isolated and cloned to date: MC1R, MC2R, MC3R, MC4R and MC5R. The melanocortin receptors participate in a variety of physiologic functions, providing a number of opportunities for therapeutic intervention in physiologic processes through alteration (i.e., a statistically significant increase or decrease) or modulation (e.g., up-regulation or down-regulation) of melanocortin receptor signalling activity.

Reviews of the melanocortin receptors, and their potential as targets for therapy have been published (Wikberg 2001; Bohm 2006). The melanocortin receptor family members are regulated by natural peptide agonists such as ACTH and the melanocyte-stimulating hormones ($\alpha$-, $\beta$-, $\gamma$-MSH) derived from pro-opiomelanocortin (POMC) and by peptide antagonists such as Agouti signal protein (ASP) and Agouti-related peptide (AGRP). The MC1R is widely expressed and is associated with pigmentation in melanocytes and with inflammation responses in many cells involved in the immune system. The MC2R differs from the other melanocortin receptors in that it binds only ACTH but not MSH ligands. It is highly expressed in the adenal gland and controls corticosteroid synthesis. The MC3R is found in the brain, but also elsewhere in the body, and appears to play a role in the regulation of energy homeostasis, and possibly sexual dysfunction. The MC4R is found almost exclusively in the brain, with some reports of its presence elsewhere. It has been strongly associated with feeding control, and also implicated with sexual desire. The MC5R is widely expressed in peripheral tissues, particularly in the exocrine glands, with some receptor also expressed in the brain. Given the breadth of activity associated with the melanocortin receptors it is desirable when seeking to target one of these receptors to do so selectively in order to avoid side effects associated with antagonism or agonism of another receptor in this family.

The MC5R has been cloned and expressed from multiple species, including humans in 1993 (though called MC2 in this paper) (Chhajlani 1993), rat in 1994 (Griffon 1994) mice in 1994 (Gantz 1994; Labbé1994) and in 1995 (Fathi 1995), canine (Houseknecht 2003), rhesus monkey (Huang 2000), sheep (Barrett 1994), zebrafish (Ringholm 2002), goldfish (Cerdá-Reverter 2003), spiny dogfish (Klovins 2004), rainbow trout (Haitina 2004), and chicken (Ling 2004), with the MC5R gene also identified in pig (Kim 2000). Patents covering the MC5R sequence in humans (Wikberg 2002), mice (Yamada 1997), rhesus monkey (Fong 2003) and dogs (Houseknecht 2003) have been published.

The MC5R has been implicated in regulating sebum secretion by a number of studies, as summarized in 2006 (Zhang 2006). Mice lacking MC5R have reduced sebum production, as evidenced by a marked inability to shed water from their fur, and a reduced quantity of sebum isolated from their hair. Significantly, these mice were otherwise generally healthy, with no readily visible abnormalities (appearance, behaviour, growth, muscle mass, adipose mass, reproduction, basal and stress-induced corticosterone, glucose and insulin levels) (Chen 1997). Further studies have identified reductions in pheromones, causing alterations in aggressive behaviours between mice (Caldwell 2002; Morgan 2004a; Morgan 2004b; Morgan 2006). Mice in which the POMC-derived peptide native ligands of MC5R have been knocked out show a similar phenotype (Yaswen 1999). Rats injected with $\alpha$-MSH had 30-37% increased rates of sebum production, while removal of the neurointermediate lobe (the source of MSH) caused a 35% decrease in sebum secretion, which was restored upon administration of $\alpha$-MSH (Thody 1973). A synergistic effect between $\alpha$-MSH and testosterone was observed in rats, with testosterone increasing sebaceous gland and cell volumes (presumably via increased proliferation), $\alpha$-MSH increasing dermal lipogenesis, and the combination increasing sebum secretion (Thody 1975a; Thody 1975b).

At a cellular level human sebocytes have been shown to express MC5R, via detection of MC5R transcripts in microdissected sebaceous glands (Thiboutot 2000), detection of MC5R in human facial sebaceous glands by immunostaining (Hatta 2001), detection of MC5R mRNA and MC5R in human sebaceous glands, cultured human sebocytes and rat preputial cells (Thiboutot 2000) and detection of MC5R as punctate particles within sebaceous glands by staining with polyclonal antibodies, seen in differentiated but not undifferentiated sebocytes (Zhang 2006). MC5R mRNA was also detected in sebaceous glands from the skin of wild-type mice, but not in skin sections of the MC5R-knockout mice (Chen 1997). Treatment of human sebocytes with cholera toxin (ChT), bovine pituitary extract (BPE), $\alpha$-MSH or NDP-MSH increases lipid droplet formation, squalene synthesis, and MC5R expression (Zhang 2003; Zhang 2006), While both MC1R and MC5R have been detected in sebaceous cells, treatment of primary human sebocyte cell culture with NDP-MSH or BPE caused a substantial increase in human MC5R expression compared to serum-free conditions, correlating with sebocyte differentiation. Immortalized sebaceous cell lines (SZ-95, TSS-1 and SEB-1) also show MC5R expression (Jeong 2007; Smith 2007a; Phan 2007). These studies suggest that MC5R antagonists could be useful in reducing sebum secretion in mammals and hence in treating conditions associated with excess sebum secretion.

A family of 1,2,4-thiadiazole derivatives with MC5R antagonist activity (138-320 nM) were found to reduce sebum formation both in human sebocyte cell cultures and when applied topically to human skin grafted onto immunodeficient mice (Eisinger 2003a-d; 2006a,b).

Excessive sebum secretion, or seborrhoea, is a common affliction. Sebaceous glands occur over most of the body, with dense concentrations of large glands on the face, scalp and upper trunk (Simpson and Cunliffe p43.1). Sebaceous secretion is dependent in part on androgenic hormones, possibly partly mediated by 5α-reductase processing of testosterone to 5α-DHT (dihydrotestosterone). Sebum consists of a species-specific mixture of lipids. In humans this consists of approximately 58% glycerides, 26% wax esters, 12% squalene, and 4% cholesterol/cholesterol esters (Simpson and Cunliffe p43.5). The presence of squalene is almost exclusively characteristic of human sebum. The function of sebum is not well defined, but it is believed to have fungistatic properties, and play a role in moisture loss from, and water repellence of, the epidermis (Simpson and Cunliffe p 43.6; Danby 2005; Porter 2001; Shuster 1976; Kligman 1963).

Excessive sebum secretion has been associated with the development of acne vulgaris. Acne vulgaris is a common disease affecting an estimated 80% of the world's population at some stage in their lives. A person is more likely to develop acne than any other disease, although the severity varies greatly (Simpson and Cunliffe p 43.16). Acne peaks in prevalence and severity in adolescents aged 14-19 years old, with approximately 35-40% affected, but in a significant number of patients (7-24%) it persists beyond 25 years of age (Simpson and Cunliffe p 43.15). Of patients treated for acne, one study found 80% still had symptoms at 30-40 years of age (Simpson and Cunliffe p 43.16). While acne is not a life-threatening disease it can have a severe impact on a patient's quality of life (Follador 2006), with one study of severe acne patients showing similar impact as much more serious chronic medical conditions such as asthma, epilepsy, diabetes, back pain or arthritis (Mallon 1999).

Four major factors are believed to be involved in the pathogenesis of acne: (i) increased sebum production (seborrhoea), (ii) hypercornification/blockage of the pilosebaceous duct (comedogenesis), (iii) infection of the duct with *P. acnes*, and (iv) inflammation of the pilosebaceous duct (Simpson and Cunliffe p 43.15; Williams 2006). A number of studies have demonstrated a clear link between increased production of sebum, and the presence and severity of acne (Simpson and Cunliffe p 43.17; Youn 2005; Pierard 1987; Harris 1983; Cotterill 1981; Thody 1975c; Pochi 1964). A 2007 study found a correlation between sebum excretion and development of acne in preadolescent children (Mourelatos 2007). Sebum is the main nutrient of *P. acnes*, thus reduction of sebum will reduce the subsequent bacterial infection and inflammation response.

Androgenic sex hormones appear to play a role in the development of acne, with strong correlations with sebum production (Makrantonaki 2007). Two oral contraceptive pills are approved by the FDA for the treatment of acne vulgaris (Harper 2005), and these compounds appear to act by reducing androgen mediated sebum formation. Diet (Cordain 2005; Smith 2007b), stress (Zouboulis 2004) and genetic factors (Goulden 1999; Bataille 2006) also may play a role in acne, again potentially via increased sebum production.

Current treatments for acne vulgaris focus predominantly on treating the infection and inflammation stages of the disease, with a large number of different formulations of topical antibiotics (e.g. benzoyl peroxide, tetracycline, erythromycin, clindamycin) and retinoids (e.g. retinoic acid, isotretinoin, adapalene, tazarotene) in use, either alone or in combination; some of these also possess anti-inflammatory action (Simpson and Cunliffe p 43.36-43.38). Many of these treatments are of limited efficacy, particularly for severe cases of acne. A growing problem is the development of antibiotic-resistant strains of *P. acnes* (Simpson and Cunliffe p 43.37, 43.46; Williams 2006). Both topical retinoids and benzoyl peroxide cause skin irritation, and retinoids can cause photosensitivity (Williams 2006). Oral therapies include isotretinoin, antibiotics, hormones, and steroids. In females, antiandrogens have been shown to reduce sebum production (by approximately 40-80%, though with no placebo control group) and improve acne (Simpson and Cunliffe p 43.44; Burke 1984; Goodfellow 1984). Laser and UV-based therapies are gaining acceptance, and are believed to act through heating of the sebaceous gland followed by reduction in sebum formation; with reductions in both sebum formation and acne lesions measured (Jih 2006; Bhardwaj 2005). Of the many therapies available for acne, only oral isotretinoin and hormonal therapies act by regulating the sebaceous gland to reduce sebum secretion (Clarke 2007).

The most effective acne treatment, oral isotretinoin (13-cis-retinoic acid, Roaccutane, Accutane) was introduced in 1983 and still remains the most clinically effective anti-acne therapy. It is the only known treatment with strong sebusuppressive activity, reducing sebum excretion by up to 90% after 8-12 weeks of therapy (60-70% by 2 weeks) (Simpson and Cunliffe p 43.47; Jones 1983; Goldstein 1982; King 1982). Topical retinoids, in contrast, have no effect on sebum production. Oral isotretinoin is also anti-inflammatory, reduces comedogenesis, and reduces *P. acnes* infection. The mechanism of action is still unclear, and metabolites of isotretinoin appear to play a significant role. Isotretinoin induces apoptosis and cell cycle arrest in human immortalized SEB-1 sebocyte cell culture (Nelson 2006). Unfortunately, oral isotretinoin has serious side effects; most significantly it is a teratogen and requires a registration program for use in the USA. The FDA has issued a warning against online purchases of isotretinoin. Blood testing for fasting lipids and liver function is also recommended during treatment (Williams 2006). Isotretinoin has been implicated (though not substantively) with adverse psychological effects, including suicide and depression (Marqueling 2005).

Other forms of acne, such as acne conglobata or acne fulminans, may also respond to a sebum-reducing agent. Seborrhoea, or excessive skin oil production, is often associated with severe acne. Seborrheic dermatitis (SD) is a skin disease associated with sebum-rich areas of the scalp, face and trunk with scaly, flaky, itchy red skin affecting 3-5% of the population; dandruff represents a mild form of this dermatitis affecting 15-20% of the population. Seborrhoea and SD appear more common in patients with Parkinson's disease or mood disorders (facial paralysis, supraorbital injury, poliomyelitis, syringomyelia, quadriplegia, unilateral injury to the ganglion Gasser and those with HIV/AIDS) (Plewig 1999). Studies have shown that seborrheic dermatitis is also associated with chronic alcoholic pancreatitis, hepatitis C virus and various cancers. It is also common in patients with genetic disorders, such as Down's syndrome, Hailey-Hailey disease and cardio-facio cutaneous syndrome (Gupta 2004). MC5R antagonists may be useful for treating these indications.

Although rare, a variety of tumours involving sebaceous glands or sebaceous cells have been described (e.g. Ide 1999; Mariappan 2004; Kruse 2003). Muir-Torre syndrome consists of sebaceous gland adenomas associated with an internal adenocarcinoma (usually colon, breast, ovary or prostate). Preventing sebaceous cell differentiation may provide an effective treatment for arresting tumour growth. Oral isotretinoin has been used for this purpose (Graefe 2000). Sebaceous hyperplasia is a benign hyperplasia of the sebaceous glands, generating yellowish small papules on the skin surface, usually the face. The disease is associated with excessive undifferentiated sebocyte proliferation, but not excessive sebum formation. Ectopic sebaceous glands (Fordyce spots) are similar yellow papules found in the mouth or on the penile shaft. Both respond to oral isotreinoin. A compound that reduced sebocyte proliferation could be an effective treatment.

α-MSH shows immunosuppressive effects in humans, suppressing a variety of inflammation responses, and the MC5R has been implicated in these immunomodulating activities. MC5R mRNA was found to be expressed at high levels in human CD4+ T helper (Th) cells and in moderate levels in other human peripheral blood leukocytes (Andersen 2005). In mice, MC5R was detected in the lymphoid organs (Labbé, 1994), and MC5R was found on the surface of mouse pro-B-lymphocyte cells where it appears to mediate α-MSH activation of the JAK2 signalling pathway, enhancing cellular proliferation (Buggy 1998). Induction of CD25+ CD4+ regulatory T-cells by α-MSH also appears to be through MC5R (Taylor 2001).

For the reasons described above it would be desirable to provide MC5R antagonists that could be used in a number of therapeutic areas. Therapeutic regulation of biological signal transduction includes modulation of MC5R-mediated cellular events including, inter alia, inhibition or potentiation of interactions among MC5R-binding and activating or deactivating molecules, or of other agents that regulate MC5R activities. An increased ability to so regulate MC5R may facilitate the development of methods for modulating sebum secretion or other biological processes, and for treating conditions associated with such pathways such as acne as described above.

Accordingly there is still the need to develop improved methods of modulating the activity of MC5R which would facilitate the treatment of MC5R related conditions.

SUMMARY OF THE INVENTION

The present invention provides a method of down-regulating the activity of MC5R or a fragment, analogue or functional equivalent thereof comprising exposing the MC5R or a fragment or analogue or functional equivalent thereof to a compound of the formula (I):

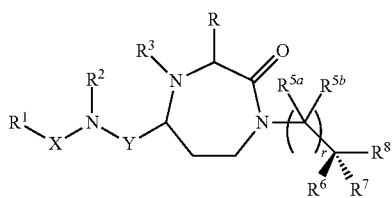

Formula (I)

wherein

Y is a group of formula —$(CR^9R^{10})_n$—;

X is selected from the group consisting of —C(=O)—, —OC(=O)—, —NHC(=O)—, —$(CR^{11}R^{12})_s$, and —S(=O)$_2$—;

R is an amino acid side chain group;

$R^1$ is selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl;

$R^2$ and $R^3$ are each independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl;

each $R^{5a}$ and $R^{5b}$ are independently selected from the group consisting of H, halogen, $C_1$-$C_{12}$alkyl, $C_1$-$C_{12}$hydroxyalkyl and $C_1$-$C_{12}$haloalkyl, or one or more of $R^{5a}$ and $R^{5b}$ when taken together with one or more of $R^6$, $R^7$ and $R^8$ and the atoms to which they are attached form a moiety selected from the group consisting of an optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl;

$R^6$, $R^7$ and $R^8$ are each independently selected from the group consisting of H, halogen, hydroxy, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$ heteroalkyl, optionally substituted $C_1$-$C_{10}$ heteroalkenyl, optionally substituted $C_3$-$C_{12}$cycloalkyl, optionally substituted $C_2$-$C_{12}$ heterocycloalkyl, optionally substituted $C_6$-$C_{18}$aryl, optionally substituted $C_1$-$C_{18}$heteroaryl, optionally substituted amino, optionally substituted carboxy, $C_1$-$C_{12}$alkyloxy, and optionally substituted thio, or (a) when taken together with the carbon atom to which they are attached two or more of $R^6$, $R^7$ and $R^8$ form a moiety selected from the group consisting of optionally substituted $C_2$-$C_{12}$alkenyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl, or (b) one or more of $R^6$, $R^7$ and $R^8$ when taken together with one or more of $R^{5a}$ and $R^{5b}$ and the atoms to which they are attached form a moiety selected from the group consisting of an optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl;

each $R^9$ and $R^{10}$ is independently selected from the group consisting of H, optionally substituted $C_1$-$C_{12}$alkyl, optionally substituted $C_6$-$C_{18}$aryl, and optionally substituted $C_1$-$C_{18}$heteroaryl;

each $R^{11}$ and $R^{12}$ is independently selected from the group consisting of H, and optionally substituted $C_1$-$C_{12}$alkyl;

n is an integer selected from the group consisting of 1, 2, 3 and 4;

r is an integer selected from the group consisting of 1, 2, 3, and 4;

s is an integer selected from the group consisting of 1, 2, 3, and 4;

or a pharmaceutically acceptable salt or prodrug thereof.

In one embodiment the MC5R or fragment or analogue or functional equivalent thereof is in a cell and the method comprises exposing the cell to a compound of formula (I). In one embodiment the invention provides a method of down-regulating the activity of MC5R or fragment or analogue or functional equivalent thereof in a mammal comprising administering a MC5R-modulating amount of a compound of the invention to the mammal.

In yet a further aspect the invention provides the use of a compound of the formula (I) in down-regulating the activity of MC5R or a fragment, analogue or functional equivalent thereof.

In yet a further aspect the invention provides the use of a compound of formula (I) in the preparation of a medicament for down-regulating the activity of MC5R or fragment or analogue or functional equivalent thereof in a mammal.

In yet an even further aspect the invention provides a method of treating, preventing, or controlling a condition associated with the activity of MC5R or a fragment, analogue or functional equivalent thereof in a mammal the method comprising administering a therapeutically effective amount of a compound of formula (I). The compound may be administered in any way known in the art although in one aspect the compound is administered topically. In another aspect the compound is administered orally. In another aspect the compound is administered parenterally. In one embodiment of the method the condition is selected from the group consisting of acne, seborrhoea, and seborrheic dermatitis. In one embodiment the condition is acne vulgaris. In one embodiment the compound of formula (I) is administered in combination with a second active agent. In one embodiment the second active agent is selected from the group consisting of antibiotics, retinoids, anti-androgens, and steroids.

In yet an even further aspect the invention provides the use of a compound of formula (I) in the preparation of a medicament for treating, preventing, or controlling a condition associated with the activity of MC5R or a fragment, analogue or functional equivalent thereof in a mammal. In one aspect the medicament is adapted to be administered topically. In another aspect the medicament is adapted to be administered orally. In another aspect the compound is administered parenterally. In one embodiment of the method the condition is selected from the group consisting of acne, seborrhoea, and seborrheic dermatitis. In a specific embodiment of the invention the condition is acne vulgaris.

In yet an even further aspect the invention provides a method of reducing sebum secretion by a mammal the method comprising administering a therapeutically effective amount of a compound of formula (I) to the mammal. The compound of the invention may be administered in any way known in the art although in one aspect the compound is administered topically. In another aspect the compound is administered orally. In another aspect the compound is administered parenterally.

In yet an even further aspect the invention provides the use of a compound of formula (I) in the preparation of a medicament for reducing sebum secretion in a mammal. In one embodiment the medicament is adapted to be administered topically. In another embodiment the medicament is adapted to be administered orally. In another embodiment the compound is administered parenterally.

DETAILED DESCRIPTION OF THE INVENTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, $=O$, $=S$, $-CN$, $-NO_2$, $-CF_3$, $-OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, $-C(=O)OH$, $-C(=O)R^a$, $-C(=O)OR^a$, $C(=O)NR^aR^b$, $C(=NOH)R^a$, $C(=NR^a)NR^bR^c$, $NR^aR^b$, $NR^aC(=O)R^b$, $NR^aC(=O)OR^b$, $NR^aC(=O)NR^bR^c$, $NR^aC(=NR^b)NR^cR^d$, $NR^aSO_2R^b$, $-SR^a$, $SO_2NR^aR^b$, $-OR^a$, $OC(=O)NR^aR^b$, $OC(=O)R^a$ and acyl, wherein $R^a$, $R^b$, $R^c$ and $R^d$ are each independently selected from the group consisting of H, $C_1$-$C_{12}$ alkyl, $C_1$-$C_{12}$ haloalkyl, $C_2$-$C_{12}$ alkenyl, $C_2$-$C_{12}$ alkynyl, $C_1$-$C_{10}$ heteroalkyl, $C_3$-$C_{12}$ cycloalkyl, $C_3$-$C_{12}$ cycloalkenyl, $C_1$-$C_{12}$ heterocycloalkyl, $C_1$-$C_{12}$ heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In one embodiment each optional substituent is independently selected from the group consisting of: halogen, $=O$, $=S$, $-CN$, $-NO_2$, $-CF_3$, $-OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, $-COOH$, $-SH$, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

The term "amino acid side chain group" represents a natural or unnatural side chain group present in a protein. The term includes side chain moieties present in naturally occurring proteins including the naturally occurring amino acid side chain moieties identified in table 1 below.

TABLE 1

Amino Acid Side Chain Moieties

| Amino Acid Side Chain Moiety | Amino Acid |
|---|---|
| H | Glycine |
| $CH_3$ | Alanine |
| $CH(CH_3)_2$ | Valine |
| $CH_2CH(CH_3)_2$ | Leucine |
| $CH(CH_3)CH_2CH_3$ | Isoleucine |
| $(CH_2)_4NH_3^+$ | Lysine |
| $(CH_2)_3NHC(NH_2)NH_{2+}$ | Arginine |
| $CH_2$-(imidazol-4-yl) | Histidine |
| $CH_2COO^-$ | Aspartic Acid |
| $CH_2CH_2COO^-$ | Glutamic acid |
| $CH_2CONH_2$ | Asparagine |
| $CH_2CH_2CONH_2$ | Glutamine |
| $CH_2Ph$ | Phenylalanine |
| $CH_2C_6H_4OH$ | Tyrosine |
| $CH_2$(Indolin-3-yl) | Tryptophan |
| $CH_2SH$ | Cysteine |

TABLE 1-continued

Amino Acid Side Chain Moieties

| Amino Acid Side Chain Moiety | Amino Acid |
|---|---|
| CH$_2$CH$_2$SCH$_3$ | Methionine |
| CH$_2$OH | Serine |
| CH(OH)CH$_3$ | Threonine |

In addition to naturally occurring amino acid side chain groups as identified above the term also includes derivatives or analogs thereof. As used herein the term derivative or analogue of an amino acid side chain group includes modifications and variations to naturally occurring side chain groups. With reference to the table above most of the naturally occurring amino acid side chain groups may be classified as alkyl, aryl, arylalkyl or heteroalkyl moieties. As such derivatives of amino acid side chain groups include straight or branched, cyclic or non-cyclic alkyl, aryl, heteroaryl, heteroarylalkyl, arylalkyl or heteroalkyl moieties.

Amino acid side chain groups as discussed above also include optionally substituted derivatives of alkyl, aryl, arylalkyl, heteroaryl, heteroarylalkyl, or heteroalkyl moieties. The optional substituents may be selected from the group defined above. For example, the optional substituents may be selected from but are not limited to OH, Cl, Br, F, COOH, COOR$^Z$, CONH$_2$, NH$_2$, NHR$^Z$, NR$^Z$R$^Z$, SH, SR$^Z$, SO$_2$R$^Z$, SO$_2$H and SOR$^Z$ wherein R$^Z$ is an alkyl, aryl or arylalkyl moiety.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

Several terms are prefaced by the a modifier indicating the number of carbon atoms present in the moiety. For example, the modifier "C$_1$-C$_6$" in front of the term "alkyl" indicates that the alkyl moiety has from 1 to 6 carbon atoms. Further, the modifier "C$_1$-C$_{18}$" in front of the term "heteroaryl" indicates that the heteroaromatic ring may have from 1 to 18 carbon atoms as part of the total number of atoms in the ring system.

"Acyl" means an R—C(═O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group it is bonded to the remainder of the molecule through the carbonyl carbon.

"Acylamino" means an R—C(═O)—NH— group in which the R group may be an alkyl, cycloalkyl, heterocycloalkyl, aryl or heteroaryl group as defined herein. The group may be a terminal group or a bridging group. If the group is a terminal group it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are C$_1$-C$_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a C$_1$-C$_{14}$ alkyl, more preferably a C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a Alkyl-NH— group, in which alkyl is as defined herein. "Dialkylamino" means a (alkyl)$_2$N— group, in which each alkyl may be the same or different and are each as defined herein for alkyl. The alkyl group is preferably a C$_1$-C$_6$ alkyl group. The group may be a terminal group or a bridging group. If the group is a terminal group it is bonded to the remainder of the molecule through the nitrogen atom.

"Alkylaminocarbonyl" refers to a group of the formula (Alkyl)$_x$(H)$_y$NC(═O)— in which x is 1 or 2, and the sum of x+y=2. The group may be a terminal group or a bridging group. If the group is a terminal group it is bonded to the remainder of the molecule through the carbonyl carbon.

"Alkyloxy" refers to an alkyl-O— group in which alkyl is as defined herein. Preferably the alkyloxy is a C$_1$-C$_6$alkyloxy. Examples include, but are not limited to, methoxy and ethoxy. The group may be a terminal group or a bridging group.

"Alkyloxyalkyl" refers to an alkyloxy-alkyl-group in which the alkyloxy and alkyl moieties are as defined herein. The group may be a terminal group or a bridging group. If the group is a terminal group it is bonded to the remainder of the molecule through the alkyl group.

"Alkyloxyary" refers to an alkyloxy-aryl-group in which the alkyloxy and aryl moieties are as defined herein. The group may be a terminal group or a bridging group. If the group is a terminal group it is bonded to the remainder of the molecule through the aryl group.

"Alkyloxycarbonyl" refers to an alkyl-O—C(═O)— group in which alkyl is as defined herein. The alkyl group is preferably a C$_1$-C$_6$ alkyl group. Examples include, but are not limited to, methoxycarbonyl and ethoxycarbonyl. The group may be a terminal group or a bridging group. If the group is a terminal group it is bonded to the remainder of the molecule through the carbonyl carbon.

"Alkyloxycycloalkyl" refers to an alkyloxy-cycloalkyl-group in which the alkyloxy and cycloalkyl moieties are as defined herein. The group may be a terminal group or a bridging group. If the group is a terminal group it is bonded to the remainder of the molecule through the cycloalkyl group.

"Alkyloxyheteroary" refers to an alkyloxy-heteroaryl-group in which the alkyloxy and heteroaryl moieties are as defined herein. The group may be a terminal group or a bridging group. If the group is a terminal group it is bonded to the remainder of the molecule through the heteroaryl group.

"Alkyloxyheterocycloalkyl" refers to an alkyloxy-heterocycloalkyl-group in which the alkyloxy and heterocycloalkyl moieties are as defined herein. The group may be a terminal group or a bridging group. If the group is a terminal group it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$ alkyl group. Examples include, but not limited to methylsulfonyl and ethylsulfonyl. The group may be a terminal group or a bridging group. If the group is a terminal group it is bonded to the remainder of the molecule through the sulfur atom.

"Alkynyl" as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$ alkynyloxy groups. The group may be a terminal group or a bridging group. If the group is a terminal group it is bonded to the remainder of the molecule through the oxygen atom.

"Aminoalkyl" means an NH$_2$-alkyl-group in which the alkyl group is as defined herein. The group may be a terminal group or a bridging group. If the group is a terminal group it is bonded to the remainder of the molecule through the alkyl group.

"Aminosulfonyl" means an NH$_2$—S(=O)$_2$— group. The group may be a terminal group or a bridging group. If the group is a terminal group it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Arylalkenyl" means an aryl-alkenyl-group in which the aryl and alkenyl are as defined herein. Exemplary arylalkenyl groups include phenylallyl. The group may be a terminal group or a bridging group. If the group is a terminal group it is bonded to the remainder of the molecule through the alkenyl group.

"Arylalkyl" means an aryl-alkyl-group in which the aryl and alkyl moieties are as defined herein. Preferred arylalkyl groups contain a $C_{1-5}$ alkyl moiety. Exemplary arylalkyl groups include benzyl, phenethyl, 1-naphthalenemethyl and 2-naphthalenemethyl. The group may be a terminal group or a bridging group. If the group is a terminal group it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. di-arylamino means a group of formula (aryl)$_2$N— where each aryl may be the same or different and are each as defined herein for aryl. The group may be a terminal group or a bridging group. If the group is a terminal group it is bonded to the remainder of the molecule through the nitrogen atom.

"Arylheteroalkyl" means an aryl-heteroalkyl-group in which the aryl and heteroalkyl moieties are as defined herein. The group may be a terminal group or a bridging group. If the group is a terminal group it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group it is bonded to the remainder of the molecule through the sulfur atom.

A "bond" is a linkage between atoms in a compound or molecule. The bond may be a single bond, a double bond, or a triple bond.

"Cyclic group" refers to saturated, partially unsaturated or fully unsaturated monocyclic, bicyclic or polycyclic ring system. Examples of cyclic groups include cycloalkyl, cycloalkenyl and aryl.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkylalkyl" means a cycloalkyl-alkyl-group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group it is bonded to the remainder of the molecule through the alkyl group.

"Cycloalkylalkenyl" means a cycloalkyl-alkenyl-group in which the cycloalkyl and alkenyl moieties are as defined herein. The group may be a terminal group or a bridging group. If the group is a terminal group it is bonded to the remainder of the molecule through the alkenyl group.

"Cycloalkylheteroalkyl" means a cycloalkyl-heteroalkyl-group in which the cycloalkyl and heteroalkyl moieties are as defined herein. The group may be a terminal group or a bridging group. If the group is a terminal group it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group it is bonded to the remainder of the molecule through the oxygen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl-group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{12}$heteroaryloxy. The group may be a terminal group or a bridging group. If the group is a terminal group it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl as defined herein but containing at least one double bond. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

"Heterocycloalkylalkyl" refers to a heterocycloalkyl-alkyl-group in which the heterocycloalkyl and alkyl moieties are as defined herein. Exemplary heterocycloalkylalkyl groups include (2-tetrahydrofuryl)methyl, (2-tetrahydrothiofuranyl) methyl. The group may be a terminal group or a bridging group. If the group is a terminal group it is bonded to the remainder of the molecule through the alkyl group.

"Heterocycloalkylalkenyl" refers to a heterocycloalkyl-alkenyl-group in which the heterocycloalkyl and alkenyl moieties are as defined herein. The group may be a terminal group or a bridging group. If the group is a terminal group it is bonded to the remainder of the molecule through the alkenyl group.

"Heterocycloalkylheteroalkyl" means a heterocycloalkyl-heteroalkyl-group in which the heterocycloalkyl and heteroalkyl moieties are as defined herein. The group may be a terminal group or a bridging group. If the group is a terminal group it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group it is bonded to the remainder of the molecule through the oxygen atom.

"Heterocycloalkenyloxy" refers to a heterocycloalkenyl-O— group in which heterocycloalkenyl is as defined herein. Preferably the heterocycloalkenyloxy is a $C_1$-$C_6$ heterocycloalkenyloxy. The group may be a terminal group or a bridging group. If the group is a terminal group it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group it is bonded to the remainder of the molecule through the sulfur atom.

"Sulfonylamino" means an R—S(=O)$_2$—NH— group. The group may be a terminal group or a bridging group. If the group is a terminal group it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

The present invention includes all pharmaceutically acceptable isotopically-labeled compounds of formula (I) wherein one or more atoms have the same atomic number as, but an atomic mass or mass number different from, the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}C$, fluorine, such $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$ can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987). Similarly, an acyl prodrug of a compound of formula (I) containing an amino group may be convertible by hydrolysis in vivo to the parent molecule (Many examples of prodrugs for these and other functional groups, including amines, are described in Prodrugs: Challenges and Rewards (Parts 1 and 2); Ed V. Stella, R. Borchardt, M. Hageman, R. Oliyai, H. Maag and J Tilley; Springer, 2007).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "functional equivalent" is intended to include variants of the specific receptor described herein. It will be understood that receptors may have isoforms, such that while the primary, secondary, tertiary or quaternary structure of a given receptor isoform is different to the prototypical receptor; the molecule maintains biological activity as a receptor. Isoforms may arise from normal allelic variation within a population and include mutations such as amino acid substitution, deletion, addition, truncation, or duplication. Also included within the term "functional equivalent" are variants generated at the level of transcription.

In the methods and uses of the invention it is observed that certain of the compounds of the Formula (I), are more active than others and therefore it is desirable to use these compounds in the methods and uses of the present invention.

In the methods and uses of the invention the preferred stereochemistry at the 3 and 5 positions of the ring of the compounds of formula (I) is the 3S, 5S diastereomer. Accordingly, in one embodiment of the methods and uses of the invention the compound of formula (I) used is a compound of formula (Ia):

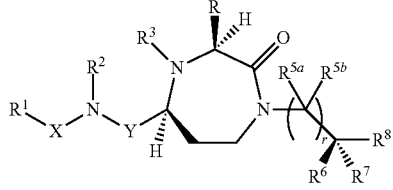

Formula (Ia)

wherein R, $R^1$, $R^2$, $R^3$, $R^{5a}$, $R^{5b}$, $R^6$, $R^7$, $R^8$, X, Y and r are as defined in formula I, or a pharmaceutically acceptable salt or prodrug thereof.

In the methods and uses of the invention a particularly useful subset of compounds of formula (I) are compounds of formula (Ib) as shown below.

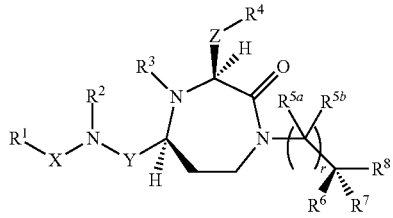

Formula (Ib)

wherein $R^1$, $R^2$, $R^3$, $R^{5a}$, $R^{5b}$, $R^6$, $R^7$, $R^8$, X, Y and r are as defined above, Z is a group of formula $-(CR^{13}R^{14})_q-$;

$R^4$ is selected from the group consisting of H, $C_1-C_{12}$alkyl, optionally substituted $C_2-C_{12}$alkenyl, optionally substituted $C_2-C_{12}$alkynyl, optionally substituted $C_3-C_{12}$cycloalkyl, optionally substituted $C_6-C_{18}$aryl, optionally substituted $C_1-C_{18}$heteroaryl, $NR^{4a}R^{4b}$b, $C(=O)R^{15}$, $C(=O)NR^{16}R^{17}$, $-C(=NR^{16})NR^{17}R^{18}$, $SR^{20}$, $SC(=O)$, $SO_2R^{20}$, $OR^{20}$, $ONR^{16}R^{17}$, $OCR^{17}R^{18}R^{20}$, $OC(=O)R^{20}$, $OC(=O)OR^{20}$, $OC(=O)NR^{16}R^{17}$, and $ONR^{16}C(=NR^{17})NR^{18}R^{19}$;

$R^{4a}$ is selected from the group consisting of H, optionally substituted $C_1-C_{12}$alkyl, optionally substituted $C_2-C_{12}$alkenyl, optionally substituted $C_2-C_{12}$alkynyl, optionally substituted $C_1-C_{12}$heteroalkyl, optionally substituted $C_3-C_{12}$cycloalkyl, optionally substituted $C_2-C_{12}$heterocycloalkyl, optionally substituted $C_6-C_{18}$aryl, optionally substituted $C_1-C_{18}$heteroaryl, $C(=O)R^{15a}$, $C(=O)NR^{15a}R^{16a}$, $C(=O)OR^{15a}$, $SO_2R^{15a}$, $C(=O)H$, $-C(=NR^{15a})-NR^{16a}R^{17a}$, and $OR^{15a}$, $R^{4b}$ is selected from the group consisting of H, optionally substituted $C_1-C_{12}$alkyl, optionally substituted $C_2-C_{12}$alkenyl, optionally substituted $C_2-C_{12}$alkynyl, optionally substituted $C_1-C_{12}$heteroalkyl, optionally substituted $C_3-C_{12}$cycloalkyl, optionally substituted $C_2-C_{12}$heterocycloalkyl, optionally substituted $C_6-C_{18}$aryl, optionally substituted $C_1-C_{18}$heteroaryl, $C(=O)R^{15a}$, $C(=O)NR^{15a}R^{16a}$, $C(=O)OR^{15a}$, or $R^{4a}$ and $R^{4b}$ when taken together with the nitrogen atom to which they are attached form an optionally substituted heterocyclic moiety, or one of $R^{4a}$ and $R^{4b}$ when taken together with any $R^{13}$ or $R^{14}$ and the atoms to which they are attached forms an optionally substituted heterocyclic moiety;

$R^{13}$ and $R^{14}$ are each independently selected from the group consisting of H, halogen, OH, $C_1-C_{12}$alkyl, $C_6-C_{18}$aryl, $C_1-C_{12}$hydroxyalkyl, $C_1-C_{12}$haloalkyl, $C_1-C_{12}$alkyloxy and $C_1-C_{12}$haloalkyloxy, or when taken together with the carbon to which they are attached $R^{13}$ and $R^{14}$ form an optionally substituted $C_3-C_{12}$cycloalkyl, or an optionally substituted $C_1-C_{12}$heterocycloalkyl group, or one of $R^{13}$ and $R^{14}$ when taken together with one of $R^{4a}$, and $R^{4b}$ and the atoms to which they are attached form an optionally substituted heterocyclic moiety, or one of $R^{13}$ and $R^{14}$ when taken together with one of $R^{15}$, $R^{16}$, $R^{17}$, $R^{18}$, $R^{19}$ or $R^{20}$ and the atoms to which they are attached form an optionally substituted cyclic moiety;

each $R^{15}$, $R^{15a}$, $R^{16}$, $R^{16a}$, $R^{17}$, $R^{17a}$, $R^{18}$, $R^{19}$ and $R^{20}$ is independently selected from the group consisting of H, optionally substituted $C_1-C_{12}$alkyl, optionally substituted $C_1-C_{12}$heteroalkyl, optionally substituted $C_3-C_{12}$cycloalkyl, optionally substituted $C_2-C_{12}$ heterocycloalkyl, optionally substituted $C_6-C_{18}$aryl, and optionally substituted $C_1-C_{18}$heteroaryl, or any two of $R^{15}$, $R^{15a}$, $R^{16}$, $R^{16a}$, $R^{17}$, $R^{17a}$, $R^{18}$, $R^{19}$ and $R^{20}$ when taken together with the atoms to which they are attached form an optionally substituted cyclic group, or one of $R^{15}$, $R^{16}$, $R^{17}$, $R^{18}$, $R^{19}$ and $R^{20}$ when taken together with one of $R^{13}$ and $R^{14}$ and the atoms to which they are attached form an optionally substituted cyclic moiety;

q is an integer selected from the group consisting of 0, 1, 2, 3, 4, and 5;

or a pharmaceutically acceptable salt or prodrug thereof.

In the methods and uses of the invention a particularly useful subset of compounds of formula (I) are compounds where Y is a group of the formula $-(CR^9R^{10})_n-$. In one embodiment of the suitable compounds n is 1 and Y is $-CR^9R^{10}-$. In another embodiment of the suitable compounds n is 2 and Y is $-CR^9R^{10}CR^9R^{10}-$.

In one embodiment of the compounds suitable for use in the invention each $R^9$ and $R^{10}$ is independently selected from H and $CH_3$. In one specific embodiment $R^9$ and $R^{10}$ are both H. Accordingly in one embodiment of the compounds suitable for use in the invention Y is $-CH_2-$. In another embodiment of compounds suitable for use in the invention Y is $-CH_2CH_2-$. In yet an even further embodiment of compounds suitable for use in the invention Y is $-C(CH_3)_2-$.

In one embodiment of the compounds suitable for use in the invention $R^2$ is H or $C_1$-$C_6$ alkyl. In a specific embodiment $R^2$ is H.

In one embodiment of the compounds suitable for use in the invention $R^3$ is H or $C_1$-$C_6$ alkyl. In a specific embodiment $R^3$ is H.

In one embodiment of the compounds suitable for use in the invention X is selected from the group consisting of —C(=O)— and —(CR$^{11}$R$^{12}$)$_s$—. In one specific embodiment X is —C(=O)—. In one embodiment of the compounds suitable for use in the invention X is —(CR$^{11}$R$^{12}$)$_s$—, s is 1. In another embodiment of compounds suitable for use in the invention X is —(CR$^{11}$R$^{12}$)$_s$—, is 2. In one form of each of these embodiments $R^{11}$ and $R^{12}$ are each independently selected from the group consisting of H and $C_1$-$C_6$ alkyl. In a specific embodiment both $R^{11}$ and $R^{12}$ are H, and s is 1 such that X is —CH$_2$—.

In one embodiment of the compounds suitable for use in the present invention $R^2$=H, $R^3$=H, X=C(=O) and Y=CH$_2$. This provides compounds of formula (Ic).

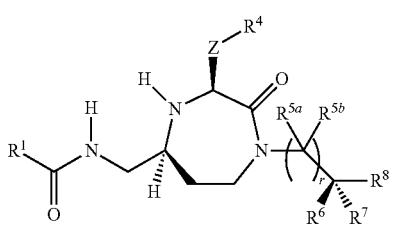

Formula (Ic)

wherein $R^1$, $R^4$, $R^{5a}$, $R^{5b}$, $R^6$, $R^7$, $R^8$ and r are as defined above.

In one embodiment of the compounds suitable for use in the invention and in particular the compounds of formula (Ib) and (Ic) $R^4$ is selected from the group consisting of H, $C_1$-$C_{12}$alkyl, optionally substituted $C_2$-$C_{12}$alkenyl, optionally substituted $C_2$-$C_{12}$alkynyl, $C_3$-$C_{12}$cycloalkyl, optionally substituted $C_6$-$C_{18}$aryl, optionally substituted C-linked $C_1$-$C_{18}$heteroaryl, C(=O)R$^{15}$, C(=O)NR$^{16}$R$^{17}$, —C(=NR$^{16}$)NR$^{17}$R$^{18}$, SR$^{20}$, SC(=O)R$^{20}$, SO$_2$R$^{20}$, OR$^{20}$, ONR$^{16}$R$^{17}$, OCR$^{17}$R$^{18}$R$^{20}$, OC(=O)R$^{20}$, OC(=O)OR$^{20}$, OC(=O)NR$^{16}$R$^{17}$, and ONR$^{16}$C(=NR$^{17}$)NR$^{18}$R$^{19}$.

In one specific embodiment $R^4$ is optionally substituted $C_1$-$C_{18}$heteroaryl. In another embodiment $R^4$ is optionally substituted $C_3$-$C_{12}$cycloalkyl. In another embodiment $R^4$ is $C_1$-$C_{12}$alkyl In another specific embodiment $R^4$ is C(=O)NR$^{16}$R$^{17}$.

In another specific embodiment $R^4$ is C(=O)NR$^{16}$R$^{17}$ and $R^{16}$ and $R^{17}$, when taken together with the nitrogen atom to which they are attached, form an optionally substituted $C_2$-$C_{12}$heterocycloalkyl group. In specific embodiments $R^{15}$ and $R^{16}$ when taken together with the nitrogen atom to which they are attached form an optionally substituted heterocycloalkyl group selected from the group consisting of piperidin-1-yl, pyrrolidin-1-yl, azetidin-1-yl, morpholin-4-yl, piperazin-1-yl, 4-methyl-piperazin-1-yl and 1-azepanyl.

In one embodiment of the compounds suitable for use in the invention $R^{16}$ is selected from the group consisting of H, CH$_3$, CH$_2$CH$_3$, CH$_2$CH$_2$CH$_3$, CH(CH$_3$)$_2$, CH$_2$CH$_2$CH$_2$CH$_3$, CH(CH$_3$)CH$_2$CH$_3$, CH$_2$CH(CH$_3$)$_2$, C(CH$_3$)$_3$, cyclopropyl, cyclobutyl, cyclopentyl, cyclohexyl, benzyl, and phenyl, or a halogenated derivative thereof.

In one embodiment of the compounds suitable for use in the invention $R^{17}$ is selected from the group consisting of H, CH$_3$, CH$_2$CH$_3$, CH$_2$CH$_2$CH$_3$, CH(CH$_3$)$_2$, CH$_2$CH$_2$CH$_2$CH$_3$, CH(CH$_3$)CH$_2$CH$_3$, CH$_2$CH(CH$_3$)$_2$, C(CH$_3$)$_3$, cyclopropyl, cyclobutyl, cyclopentyl, cyclohexyl, benzyl, and phenyl, or a halogenated derivative thereof.

In one embodiment of the methods and uses of the invention the compound of formula (I) used is one in which $R^4$=NR$^{4a}$R$^{4b}$. Accordingly a useful subset of compounds for use in the methods and uses of the present invention are compounds of formula (Id):

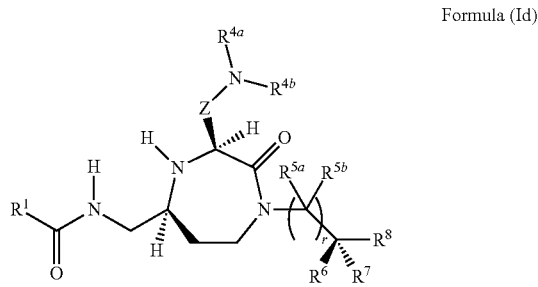

Formula (Id)

wherein $R^1$, $R^{4a}$, $R^{4b}$, $R^{5a}$, $R^{5b}$, $R^6$, $R^7$, $R^8$, Z and r are as defined for formula (I).

In one embodiment of the compounds suitable for use in the invention, r is selected from the group consisting of 1, 2, 3, and 4. In one specific embodiment r is 1.

In another specific embodiment r is 2. In yet a further specific embodiment r is 3. In an even further specific embodiment r is 4.

In one embodiment of the compounds suitable for use in the invention, $R^{5a}$ and $R^{5b}$ are independently selected from H and $C_1$-$C_6$ alkyl. In one embodiment $R^{5a}$ and $R^{5b}$ are each independently selected from H and CH$_3$. In one specific embodiment $R^{5a}$ and $R^{5b}$ are both H. In yet another embodiment at least one of $R^{5a}$ and $R^{5b}$ when taken together with at least one of $R^6$, $R^7$ and $R^8$ and the atoms to which they are attached form an optionally substituted cycloalkyl group. In one specific embodiment at least one of $R^{5a}$ and $R^{5b}$ when taken together with at least one of $R^6$, $R^7$ and $R^8$ and the atoms to which they are attached forms a cyclohexyl group.

In one embodiment of the compounds of the invention, Y is CH$_2$, $R^2$ is H, $R^3$ is H, $R^{5a}$ and $R^{5b}$ are H' and X is —C(=O)—, and r is 1. This provides compounds of formula (II).

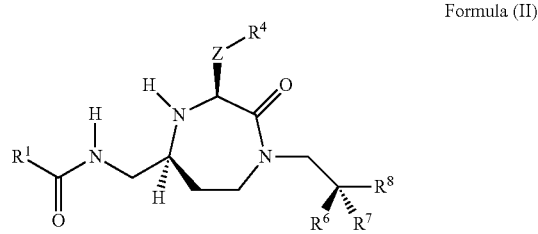

Formula (II)

wherein $R^1$, $R^4$, $R^6$, $R^7$, $R^8$ and Z are as defined for formula (I).

In one embodiment of the compounds of the invention, Y is CH$_2$, $R^2$ is H, $R^3$ is H, $R^{5a}$ and $R^{5b}$ are H, X is —C(=O)—, $R^4$ is NR$^{4a}$R$^{4b}$, and r is 1. This provides compounds of formula (IIa).

Formula (IIa)

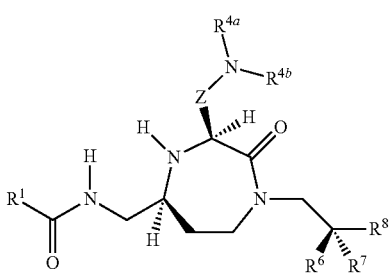

wherein $R^1$, $R^{4a}$, $R^{4b}$, $R^6$, $R^7$, $R^8$, and Z are as defined for formula (I).

In the compounds of the invention Z is a group of formula —$(CR^{13}R^{14})_q$—. In one embodiment of the compounds suitable for use in the invention, and in particular the compounds of formula (I), formula (Ia), formula (Ib), formula (Ic), formula (Id), formula (II) and Formula (IIa) $R^{13}$ and $R^{14}$ are independently selected from H and $C_1$-$C_6$ alkyl. In one embodiment $R^{13}$ and $R^{14}$ are each independently selected from H and $CH_3$. In one specific embodiment $R^{13}$ and $R^{14}$ are both H. In yet another embodiment at least one of $R^{13}$ and $R^{14}$ when taken together with at least one of $R^{4a}$ and $R^{4b}$ and the atoms to which they are attached form an optionally substituted heterocycloalkyl group. In one embodiment Z is —$(CH_2)_q$—

In one embodiment of the compounds suitable for use in the invention q is an integer selected from the group consisting of 0, 1, 2, 3, 4, and 5. In one specific embodiment q is 1. In another specific embodiment q is 2, in yet an even further specific embodiment q is 3, and in yet an even further specific embodiment q is 4.

Compounds in which $R^7$, $R^{13}$ and $R^{14}$ are H and q is from 1 to 4 lead to compounds (IIIa), (IIIb), (IIIc) and (IIId) respectively.

Formula (IIIa)

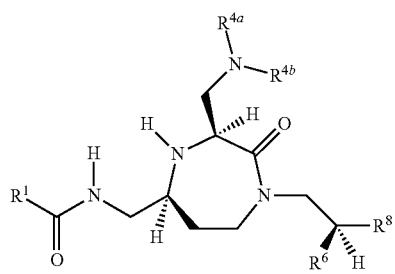

wherein $R^1$, $R^{4a}$, $R^{4b}$, $R^6$, and $R^8$ are as defined for formula (I).

Formula (IIIb)

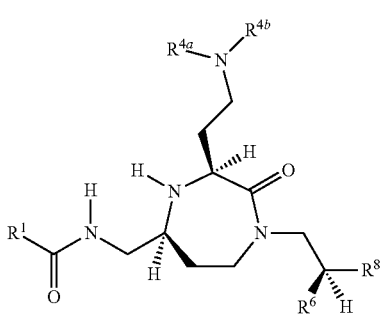

wherein $R^1$, $R^{4a}$, $R^{4b}$, $R^6$, and $R^8$ are as defined for formula (I).

Formula (IIIc)

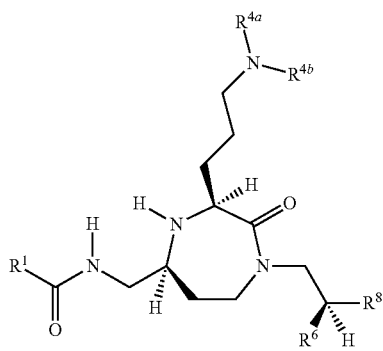

wherein $R^1$, $R^{4a}$, $R^{4b}$, $R^6$, and $R^8$ are as defined for formula (I).

Formula (IIId)

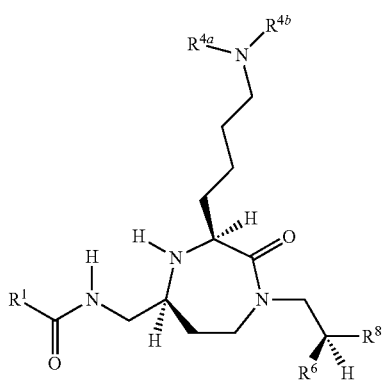

wherein $R^1$, $R^{4a}$, $R^{4b}$, $R^6$, and $R^8$ are as defined for formula (I).

In one form of the compounds suitable for use in the invention $R^{4a}$ is selected from the group consisting of H, —C(=N)NH_2, —C(=N)N(CH_3)_2, —C(=N)NCH(CH_3)_2, —C(=O)CH_3, —C(=O)cyclohexyl, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof. In one form of the compounds suitable for use in the invention $R^{4b}$ is selected from the group consisting of H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof.

In another form of the compounds suitable for use in the invention $R^{4a}$ and $R^{4b}$ when taken together with the nitrogen atom to which they are attached form an optionally substituted $C_2$-$C_{12}$ heterocycloalkyl group, an optionally substituted $C_2$-$C_{12}$ heterocycloalkenyl group or an optionally substituted $C_1$-$C_{18}$ heteroaryl group.

In a particular embodiment of the compounds suitable for use in the invention $R^{4a}$ and $R^{4b}$ when taken together with the nitrogen atom to which they are attached form an optionally substituted heterocycloalkyl group selected from the group consisting of piperidin-1-yl, pyrrolidin-1-yl, azetidin-1-yl, piperazin-1-yl, morpholin-4-yl and 1-azepanyl.

In one embodiment of the methods and uses of the invention, the compound of formula (I) is one in which one of $R^{4a}$ and $R^{4b}$ when taken together with the nitrogen atom to which it is attached and one of $R^{13}$ and $R^{14}$ and the carbon atom to which it is attached form an optionally substituted $C_2$-$C_{12}$heterocycloalkyl group. In a particular embodiment one of $R^{4a}$ and $R^{4b}$ when taken together with the nitrogen atom to which it is attached and one of $R^{13}$ and $R^{14}$ and the carbon atom to which it is attached form an optionally substituted heterocycloalkyl group selected from the group consisting of piperidinyl, pyrrolidinyl, azetidinyl, morpholinyl, piperazinyl, and azepanyl.

Specific examples of $NR^{4a}R^{4b}$ in the compounds which are useful in the methods and uses of the invention include:

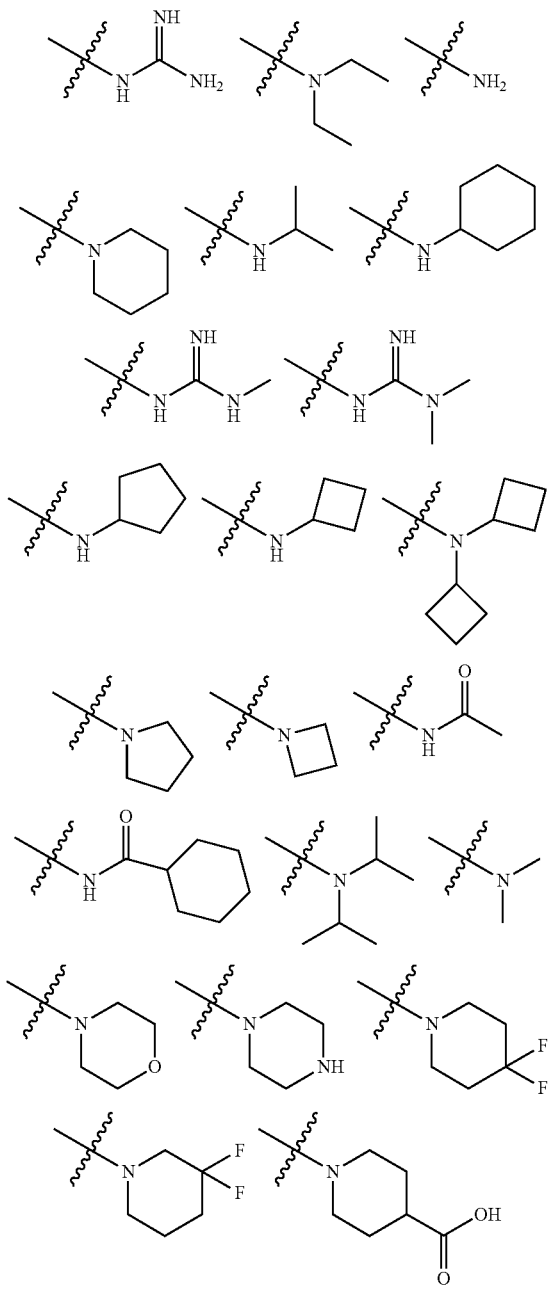

-continued

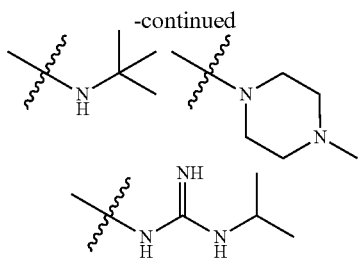

In one embodiment of the compounds suitable for use in the invention, $R^7$ is H.

In one embodiment of the compounds suitable for use in the invention, $R^6$ and $R^8$ are each independently selected from the group consisting of H, optionally substituted $C_1$-$C_{12}$ alkyl, optionally substituted $C_2$-$C_{12}$ alkenyl, optionally substituted $C_6$-$C_{18}$ aryl and optionally substituted $C_1$-$C_{18}$heteroaryl.

In one specific embodiment of the compounds suitable for use in the invention $R^6$ is selected from the group consisting of H, methyl, trifluoromethyl, ethyl, 2,2,2-trifluoroethyl, isopropyl, isopropenyl, propyl, 2-ethyl-propyl, 3,3-dimethyl-propyl, butyl, 2-methylbutyl, isobutyl, 3,3-dimethyl-butyl, 2-ethyl-butyl, pentyl, 2-methyl-pentyl, optionally substituted phenyl and optionally substituted $C_1$-$C_5$ heteroaryl In one specific embodiment of the compounds suitable for use in the invention $R^6$ is optionally substituted phenyl or optionally substituted $C_1$-$C_{18}$heteroaryl.

In one specific embodiment of the compounds suitable for use in the invention $R^8$ is selected from the group consisting of H, methyl, trifluoromethyl, ethyl, 2,2,2-trifluoroethyl, isopropyl, isopropenyl, propyl, 2-ethyl-propyl, 3,3-dimethyl-propyl, butyl, 2-methyl-butyl, isobutyl, 3,3-dimethyl-butyl, 2-ethyl-butyl, pentyl, 2-methyl-pentyl, pent-4-enyl, hexyl, heptyl, octyl, optionally substituted phenyl and optionally substituted $C_1$-$C_5$ heteroaryl.

In one specific embodiment of the compounds suitable for use in the invention $R^8$ is methyl, ethyl, phenyl or optionally substituted $C_1$-$C_5$ heteroaryl.

In one specific embodiment of the compounds suitable for use in the invention $R^6$, $R^7$ and $R^8$ when taken together with the carbon to which they are attached form a moiety selected from the group consisting of optionally substituted $C_2$-$C_{12}$alkenyl, optionally substituted $C_3$-$C_{12}$cycloalkyl, optionally substituted $C_2$-$C_{12}$heterocycloalkyl, optionally substituted $C_6$-$C_{18}$aryl, and optionally substituted $C_1$-$C_{18}$heteroaryl.

In one specific embodiment of the compounds suitable for use in the invention $R^6$, $R^7$ and $R^8$ when taken together with the carbon to which they are attached form an optionally substituted $C_6$-$C_{18}$aryl group.

In one specific embodiment of the compounds of the invention and specifically of the compounds of formula (I), (II) (IIa) (IIIa), (IIIb), (IIIc), and (IIId), $R^6$, $R^7$ and $R^8$ when taken together with the carbon atom to which they are attached form a disubstituted phenyl group. In one embodiment the disubstituted phenyl group is a 2,4-disubstituted phen-1-yl group or a 3,5-disubstituted phen-1-yl group. A wide variety of substituents may be present on the disubstituted phenyl group as defined above. Examples of particularly suitable substituents include, but are not limited to, F, Br, Cl, methyl, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, cyano, phenoxy, hydroxy, methoxy, ethoxy, methylenedioxy, pyrrol-1-yl, and 3,5-dimethyl-pyrazol-1-yl. In one specific embodiment the disubstituted phenyl group is a 3,5-dichlorophen-1-yl group.

In one specific embodiment of the compounds suitable for use in the invention $R^1$ is selected from the group consisting of optionally substituted $C_2$-$C_{12}$alkenyl, optionally substituted $C_6$-$C_{18}$aryl and optionally substituted $C_1$-$C_{18}$heteroaryl.

In one specific embodiment of the compounds suitable for use in the invention $R^1$ is optionally substituted $C_6$-$C_{18}$aryl. The $C_6$-$C_{18}$aryl may be a monocyclic, bicyclic or polycyclic moiety. In certain embodiments the $C_6$-$C_{18}$aryl is a monocyclic moiety. In certain embodiments the $C_6$-$C_{18}$aryl is a bicyclic moiety.

In one specific embodiment $R^1$ is an optionally substituted $C_6$-$C_{18}$aryl selected from the group consisting of optionally substituted phenyl, biphenyl, and optionally substituted naphthyl. The moieties may be unsubstituted or may be substituted with one or more optional substituents. A wide variety of optional substituents may be used as defined above. Examples of particularly suitable optional substituents include, but are not limited to, F, Br, Cl, methyl, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, cyano, phenoxy, hydroxy, methoxy, ethoxy, pyrrol-1-yl, and 3,5-dimethyl-pyrazol-1-yl.

The substituents may be located at any substitutable position around the aryl ring available for substitution as would be clear to a skilled addressee. Examples of suitable optionally substituted phenyl compounds include, but are not limited to, 2-methoxy-phenyl, 3-methoxy-phenyl, 4-methoxy-phenyl, 2-trifluoromethyl-phenyl, 3-trifluoromethyl-phenyl, 4-trifluoromethyl-phenyl, 2-chloro-phenyl, 3-chloro-phenyl, 4-chloro-phenyl, 4-bromo-phenyl, 2-fluoro-phenyl, 3-fluoro-phenyl, 4-fluoro-phenyl, 4-hydroxy-phenyl, 4-phenyl-phenyl, 4-methyl-phenyl, 2,4-dichloro-phenyl, 3,4-dichloro-phenyl, 2,5-dichloro-phenyl, 2,6-difluoro-phenyl, 2-chloro-6-fluoro-phenyl, 3-fluoro-4-chloro-phenyl, 3-methyl-4-chloro-phenyl, 3-chloro-4-fluoro-phenyl, 3-chloro-4-methyl-phenyl, 2-hydroxy-phenyl, 3-hydroxy-phenyl, 4-hydroxy-phenyl, 4-ethoxy-phenyl, 3-phenoxy-phenyl, 4-phenoxy-phenyl, 2-methyl-phenyl, 3-methyl-phenyl, 4-methyl-phenyl, 4-isopropyl-phenyl, 4-cyano-phenyl 3,4-dimethyl-phenyl, 2,4-dimethyl-phenyl, 4-t-butyl-phenyl, 2,4-dimethoxy-phenyl, and 3,4-methylenedioxy-phenyl.

When $R^1$ is optionally substituted biphenyl the point of attachment of $R^1$ to the remainder of the molecule may be at the 2-, 3- or 4-position relative to the point of attachment of the second phenyl ring. As such the biphenyl may be an optionally substituted biphen-2-yl, or an optionally substituted biphen-3-yl, or an optionally substituted biphen-4-yl. In general the optionally substituted biphenyl is an optionally substituted biphen-4-yl. The optionally substituted biphenyl may be substituted in any suitable position.

When $R^1$ is optionally substituted naphthyl the point of attachment of $R^1$ to the remainder of the molecule may be at the 1 or 2 position. As such the naphthyl may be an optionally substituted naphth-1-yl, or an optionally substituted naphth-2-yl. In general the optionally substituted naphthyl is an optionally substituted naphth-2-yl. The optionally substituted naphthyl may be substituted in any suitable position. Examples of suitable optionally substituted naphth-2-yls include, but are not limited to, 6-fluoro-naphth-2-yl, 6-bromo-naphth-2-yl, 6-chloro-naphth-2-yl, 1-methoxy-naphth-2-yl, 3-methoxy-naphth-2-yl, 6-methoxy-naphth-2-yl, 1-hydroxy-naphth-2-yl, and 6-amino-naphth-2-yl.

In one specific embodiment of the compounds suitable for use in the invention $R^1$ is optionally substituted $C_1$-$C_{18}$heteroaryl. The $C_1$-$C_{18}$heteroaryl may be a monocyclic, bicyclic or polycyclic moiety. In certain embodiments the $C_1$-$C_{18}$heteroaryl is a monocyclic moiety. In certain embodiments the $C_1$-$C_{18}$heteroaryl is a bicyclic moiety. Examples of suitable heteroaryl moieties include, but are not limited to, indol-2-yl, indol-3-yl quinolin-2-yl quinolin-3-yl, isoquinolin-3-yl, quinoxaline-2-yl, benzo[b]furan-2-yl, benzo[b]thiophen-2-yl, benzo[b]thiophen-5-yl, thiazole-4-yl, benzimidazole-5-yl, benzotriazol-5-yl, furan-2-yl, benzo[d]thiazole-6-yl, pyrazole-1-yl, pyrazole-4-yl and thiophen-2-yl. These may also be optionally substituted as discussed above.

In one specific embodiment of the compounds suitable for use in the invention $R^1$ is an optionally substituted $C_2$-$C_{12}$alkenyl. The optionally substituted alkenyl may contain one or more double bonds with each of the double bonds being independently in the E or Z configuration. In one embodiment of the invention the alkenyl contains a single double bond which is in the E configuration.

In one specific form of this embodiment $R^1$ is an optionally substituted $C_2$-$C_{12}$alkenyl of the formula:

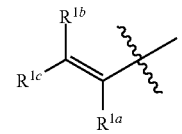

$R^{1a}$ is selected from the group consisting of H, halogen and optionally substituted $C_1$-$C_{12}$ alkyl;

$R^{1b}$ and $R^{1c}$ are each independently selected from the group consisting of H, halogen, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{12}$heteroalkyl, optionally substituted $C_3$-$C_{12}$cycloalkyl, optionally substituted $C_2$-$C_{12}$ heterocycloalkyl, optionally substituted $C_6$-$C_{18}$aryl, and optionally substituted $C_1$-$C_{18}$heteroaryl.

In one form of this embodiment $R^{1a}$ is H. In one form of this embodiment $R^{1b}$ is H. This provides compounds where $R^1$ is of the formula:

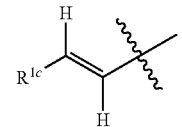

In one embodiment of the compounds of the invention $R^{1c}$ is optionally substituted $C_6$-$C_{18}$aryl. The $C_6$-$C_{18}$aryl may be monocyclic, bicyclic or polycyclic moiety. In certain embodiments the $C_6$-$C_{18}$aryl is a monocyclic moiety. In certain embodiments the $C_6$-$C_{18}$aryl is a bicyclic moiety.

In one specific embodiment $R^{1c}$ is an optionally substituted $C_6$-$C_{18}$aryl selected from the group consisting of optionally substituted phenyl and optionally substituted naphthyl. The moieties may be unsubstituted or may be substituted with one or more optional substituents. A wide variety of optional substituents may be used as defined above. Examples of particularly suitable optional substituents include, but are not limited to, F, Br, Cl, methyl, trifluoromethyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, NH₂, cyano, phenoxy, hydroxy, methoxy, ethoxy, methylenedioxy, pyrrol-1-yl, and 3,5-dimethyl-pyrazol-1-yl.

The substituents may be located at any substitutable position around the aryl ring available for substitution as would be clear to a skilled addressee. Examples of suitable optionally substituted phenyl compounds include, but are not limited to, 2-methoxy-phenyl, 3-methoxy-phenyl, 4-methoxy-phenyl, 2-trifluoromethyl-phenyl, 3-trifluoromethyl-phenyl, 4-trifluoromethyl-phenyl, 2-chloro-phenyl, 3-chloro-phenyl, 4-chloro-phenyl, 4-bromo-phenyl, 2-fluoro-phenyl, 3-fluoro-phenyl, 4-fluoro-phenyl, 4-hydroxy-phenyl, 4-phenyl-phenyl, 4-methyl-phenyl, 2,4-dichloro-phenyl, 3,4-dichloro-phenyl, 2,5-dichloro-phenyl, 2,6-difluoro-phenyl, 2-chloro-6-fluoro-phenyl, 3-fluoro-4-chloro-phenyl, 3-methyl-4-chloro-phenyl, 3-chloro-4-fluoro-phenyl, 3-chloro-4-methyl-phenyl, 2-hydroxy-phenyl, 3-hydroxy-phenyl, 4-hydroxy-phenyl, 4-ethoxy-phenyl, 3-phenoxy-phenyl, 4-phenoxy-phenyl, 2-methyl-phenyl, 3-methyl-phenyl, 4-methyl-phenyl, 4-isopropyl-phenyl, 4-cyano-phenyl 3,4-dimethyl-phenyl, 2,4-dimethyl-phenyl, 4-t-butyl-phenyl, 2,4-dimethoxy-phenyl, and 3,4-methylenedioxy-phenyl.

Specific compounds suitable for use in the methods and uses of the invention include the following:

(14)

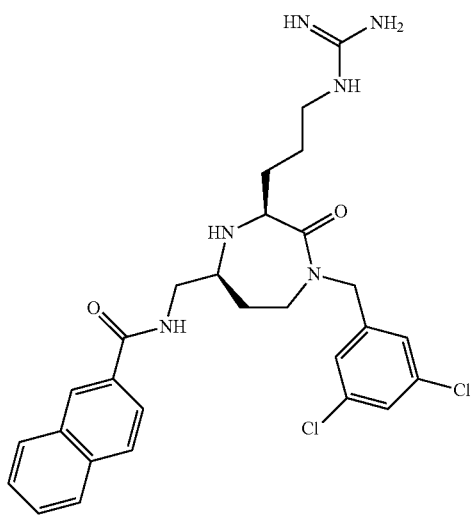

(25)

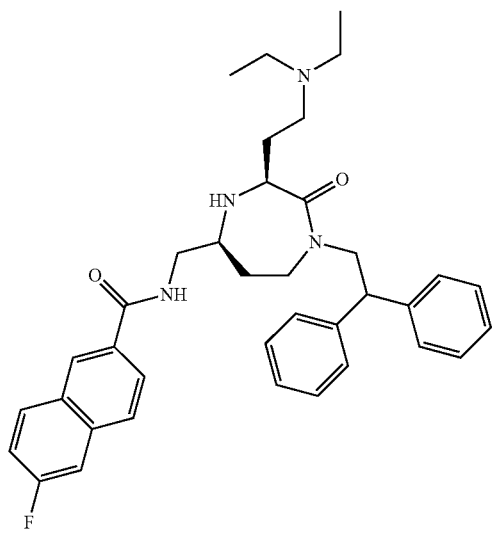

(31)

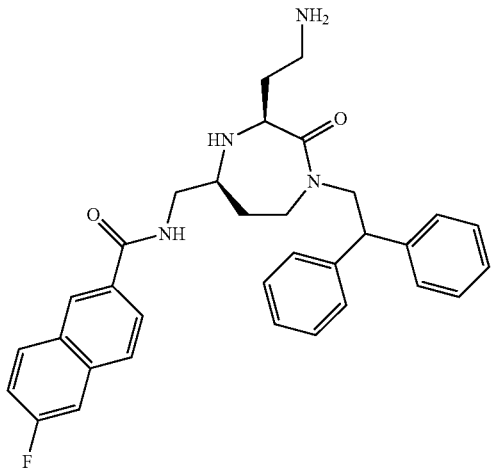

(33)

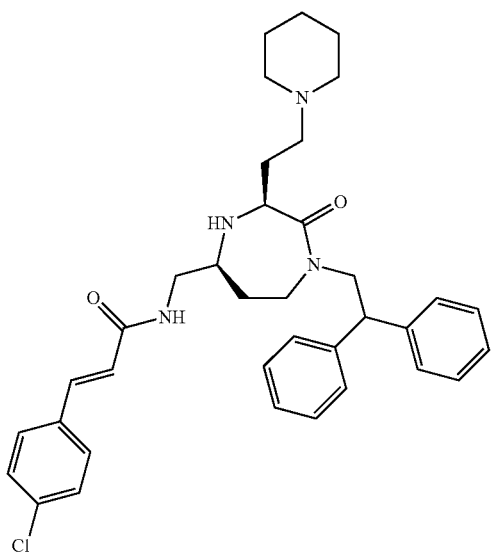

(37)

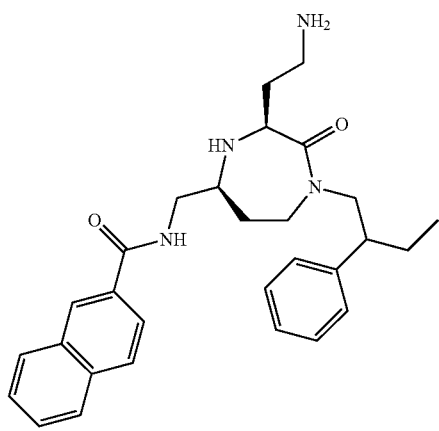

-continued
(38)
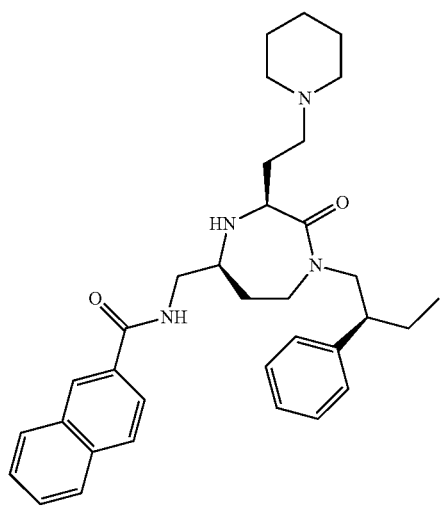
(39)
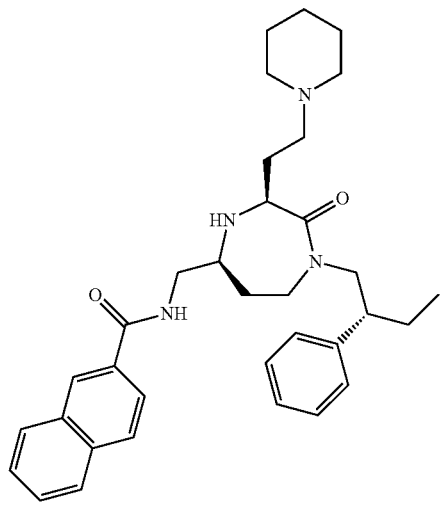
(49)
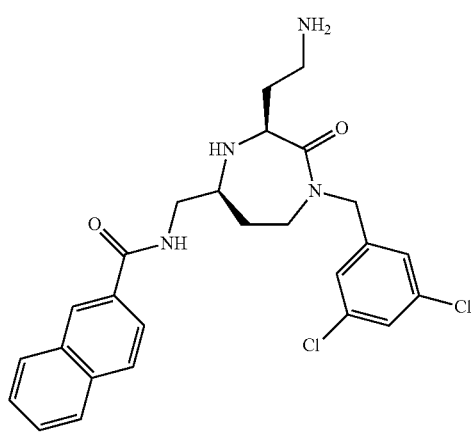
-continued
(50)
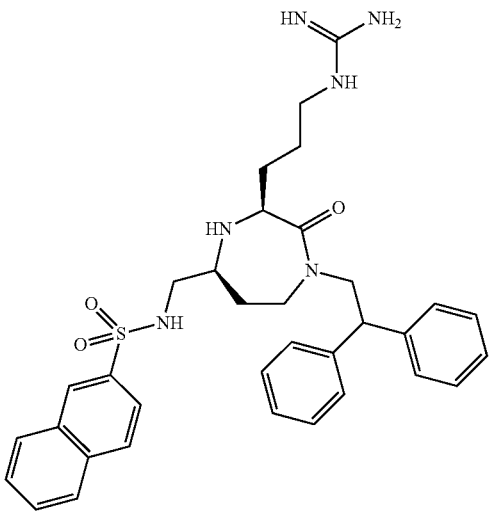
(54)
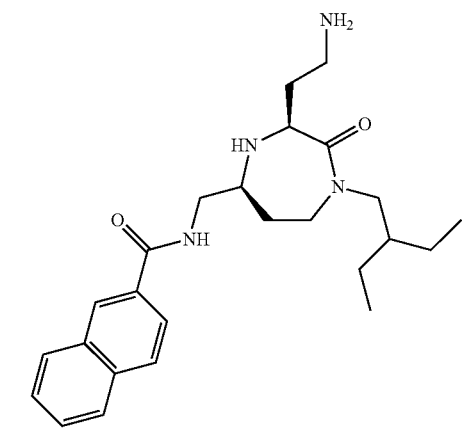
(60)
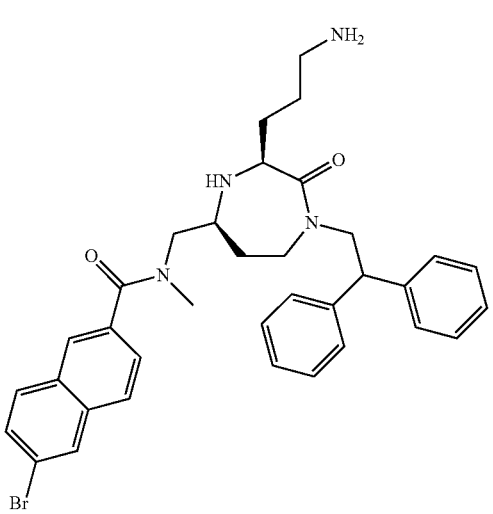

(62) 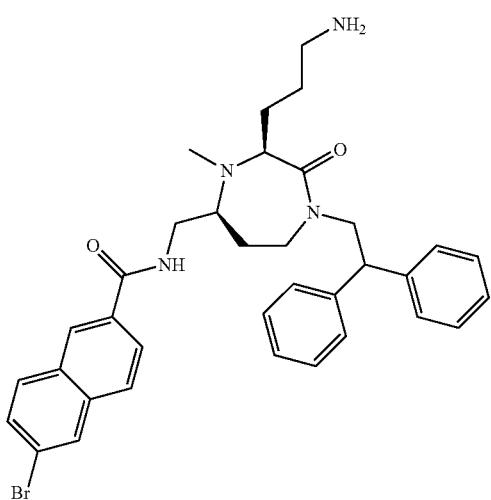
(65) 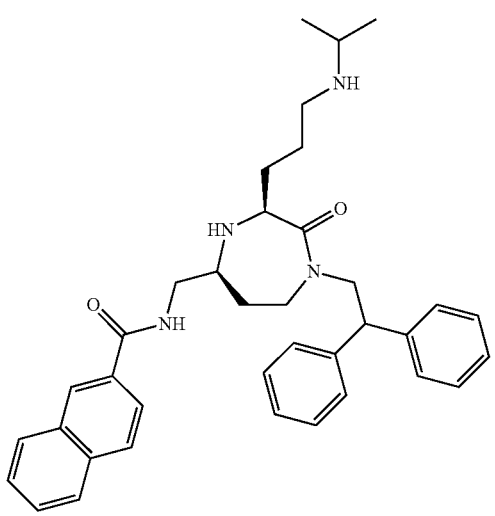
(63) 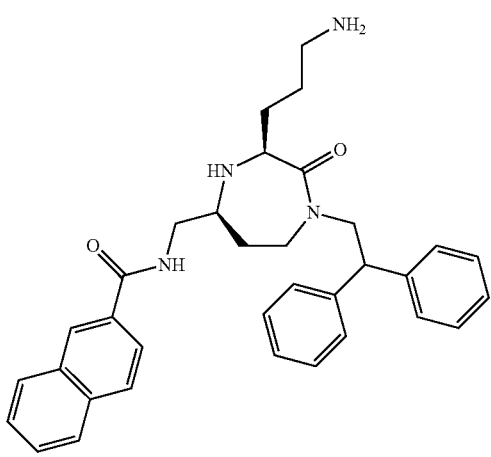
(67) 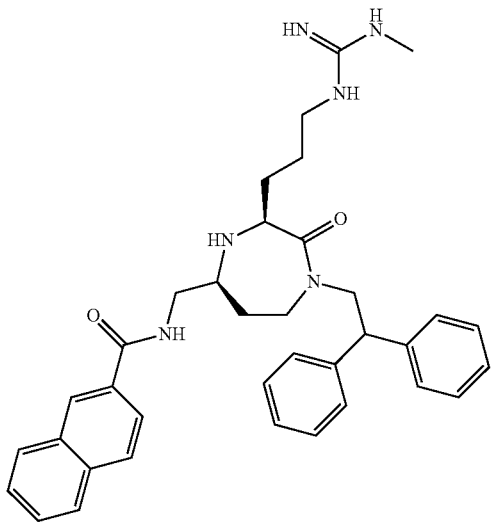
(64) 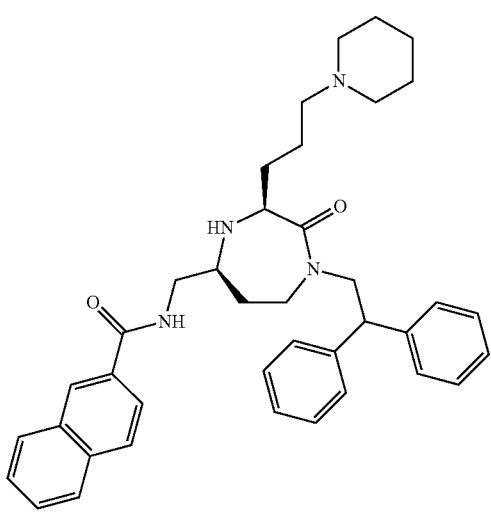
(71) 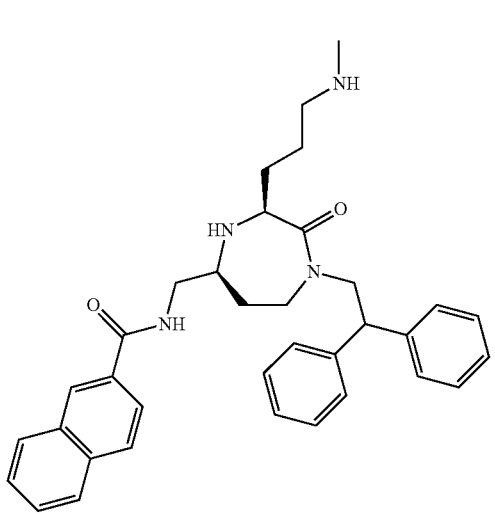

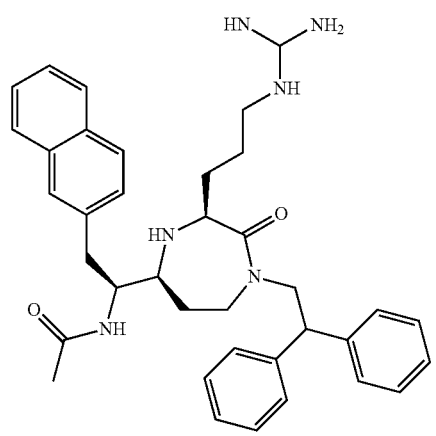
(79)
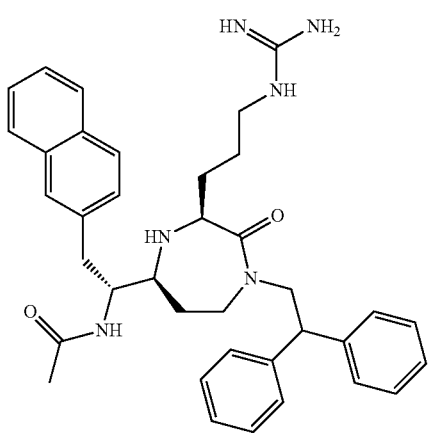
(85)
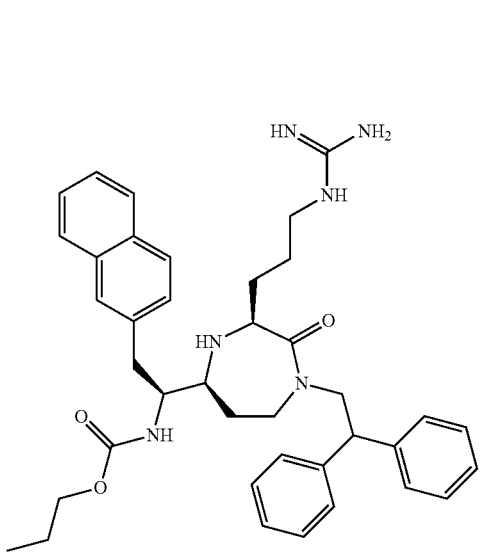
(81)
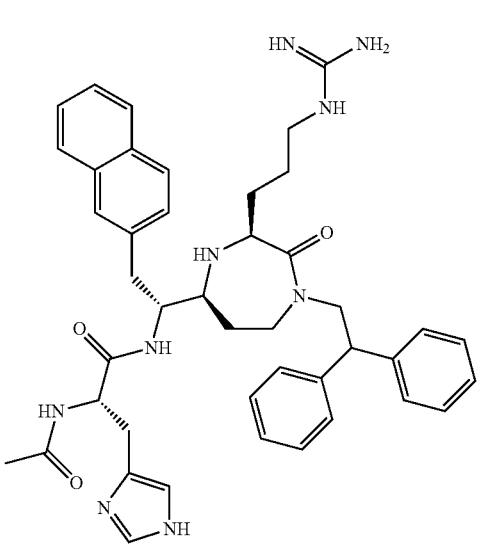
(86)
(83)
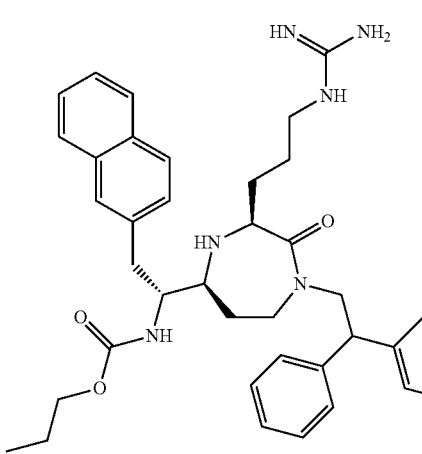
(87)

(102)
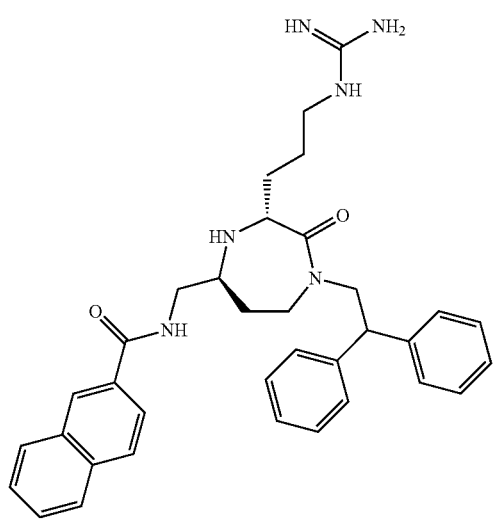
(103)
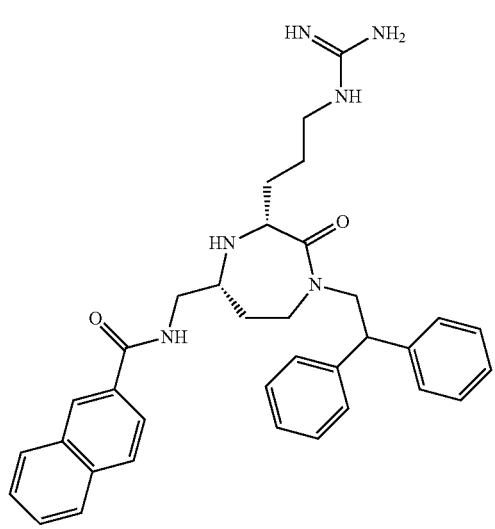
(104)
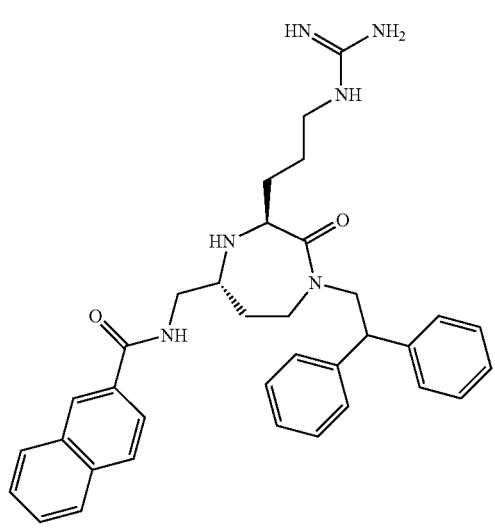
(105)
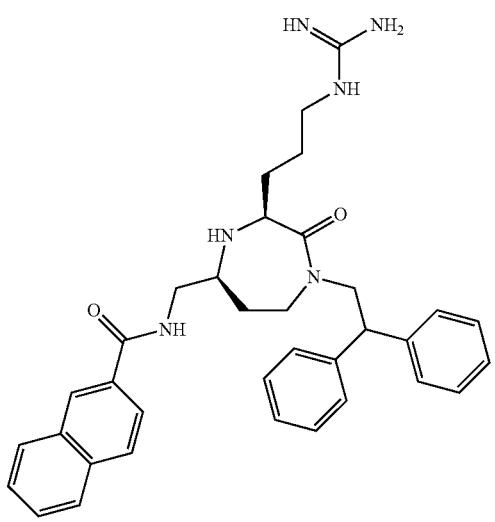
(106)
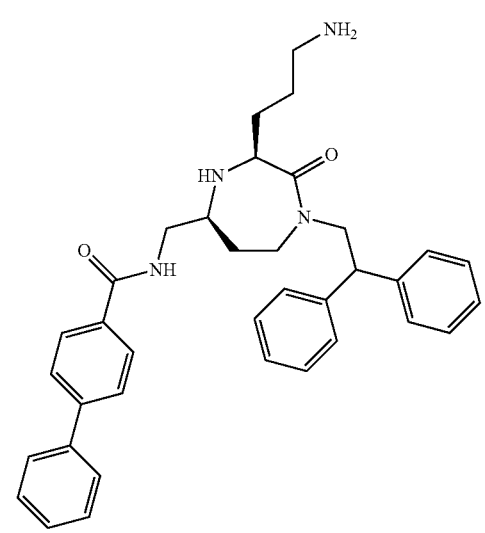
(107)
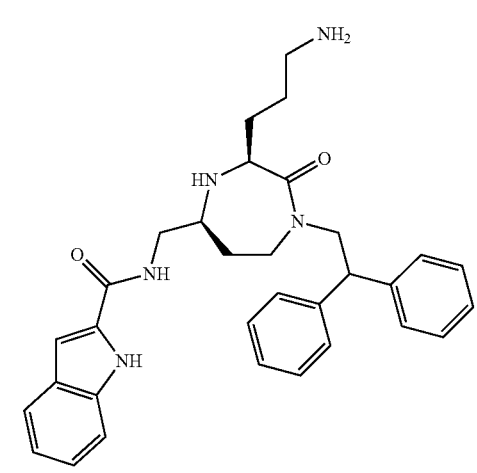

(108)
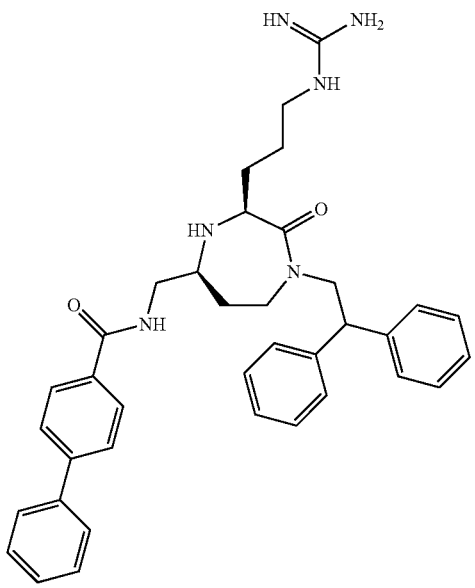
(109)
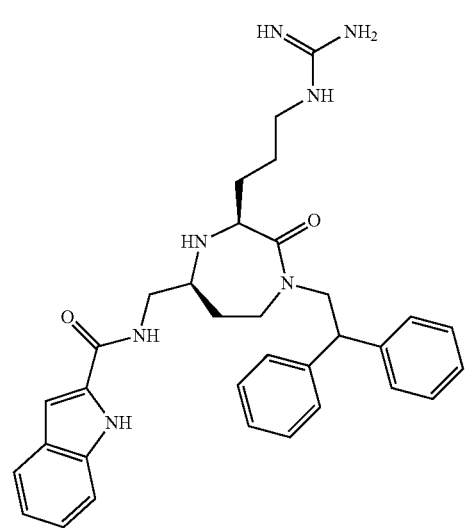
(110)
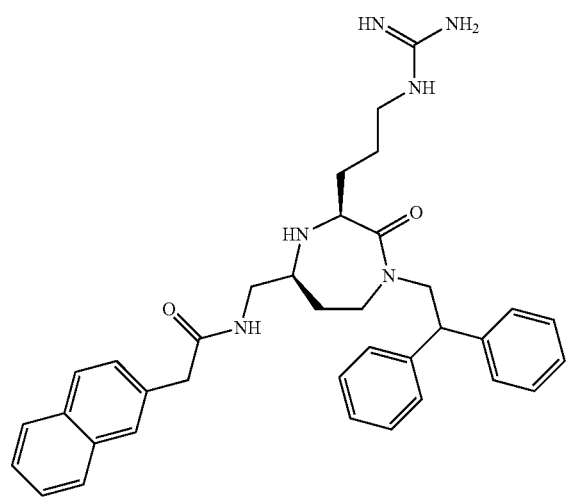
(111)
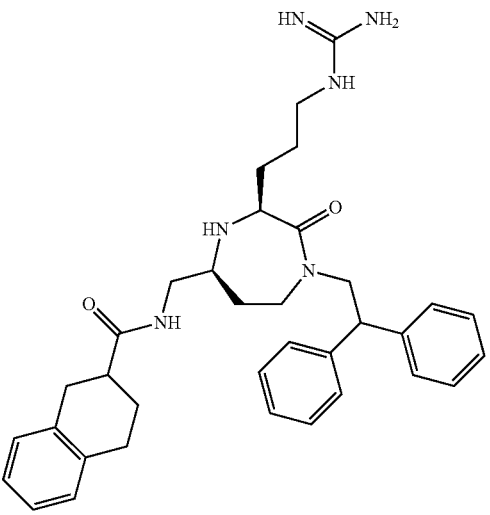
(112)
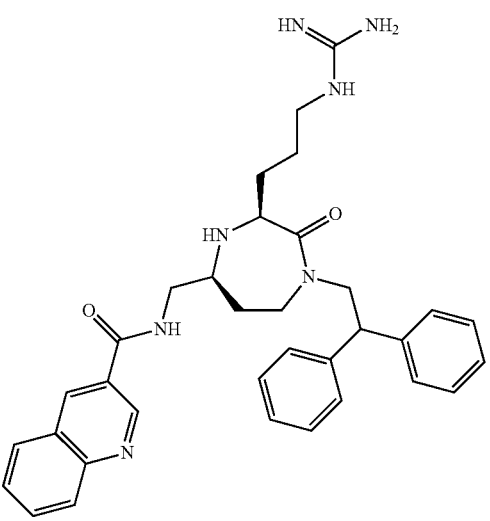
(113)
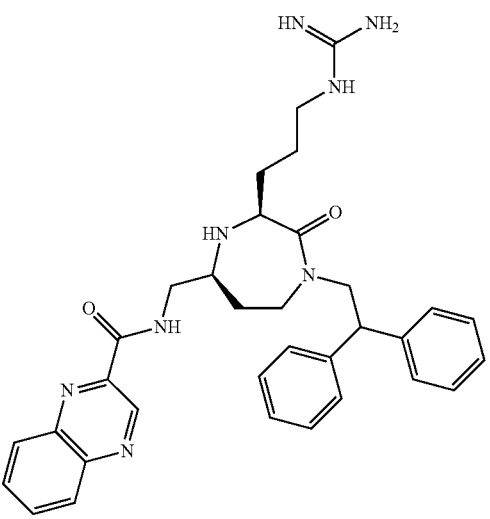

-continued
(114)
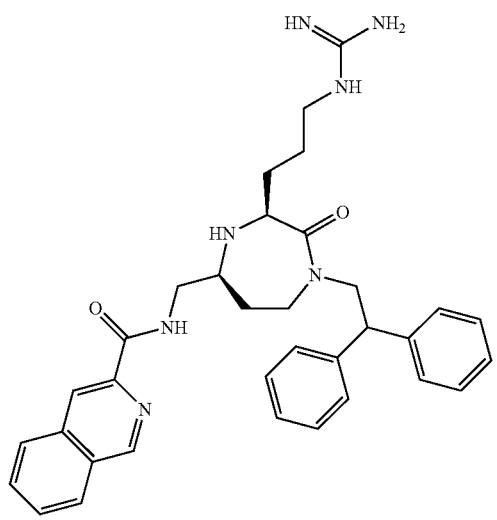
(117)
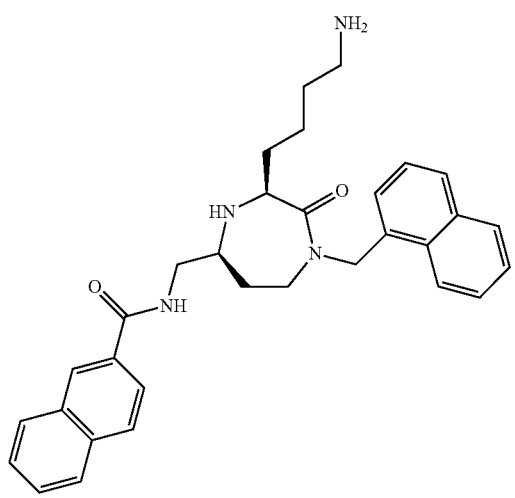
(115)
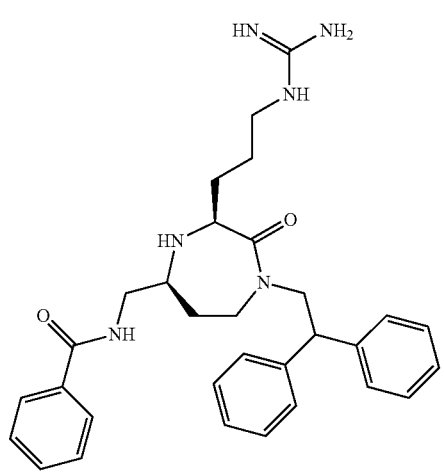
(118)
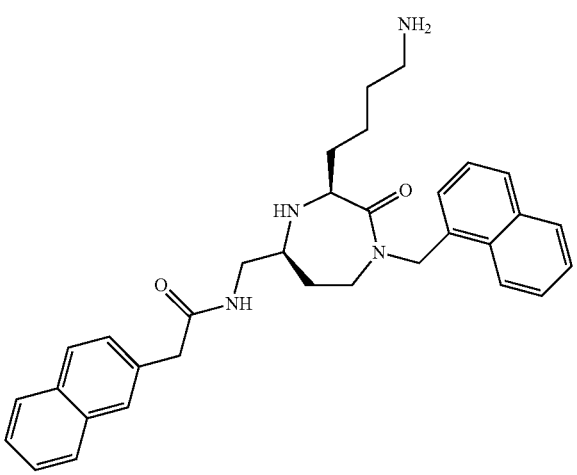
(116)
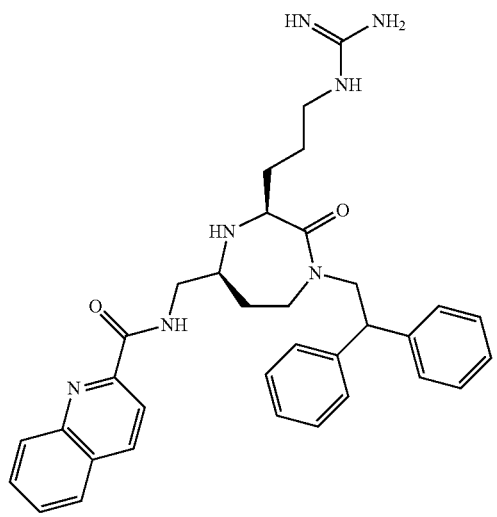
(119)
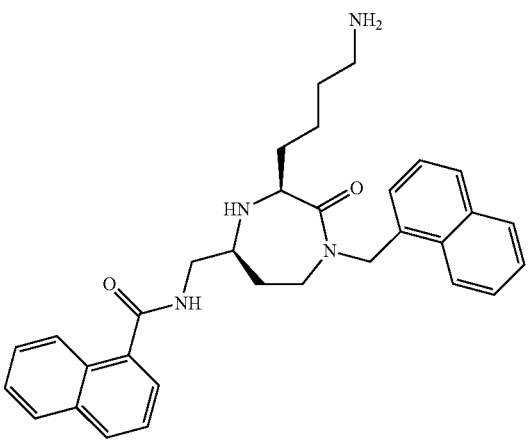

(120)
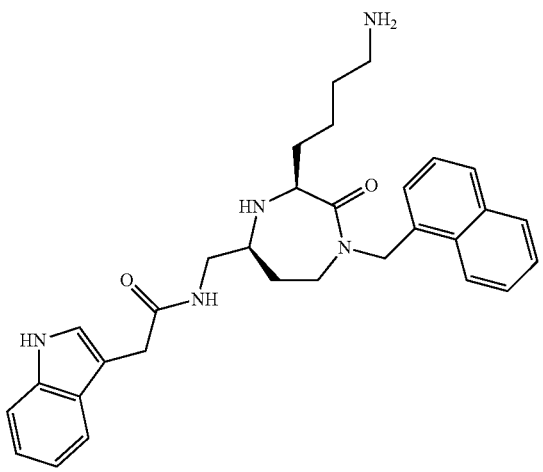
(121)
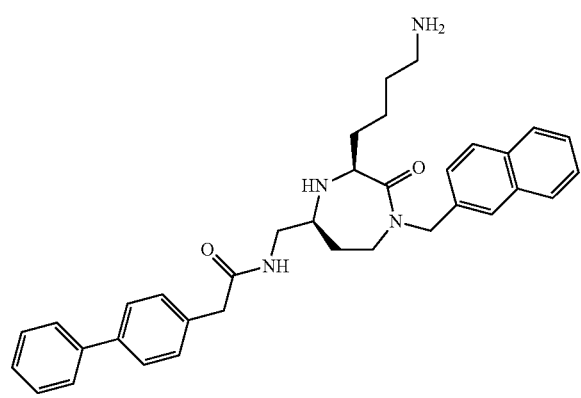
(122)
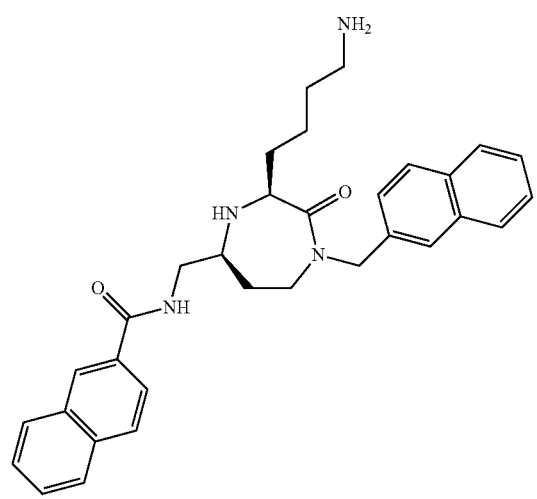
(123)
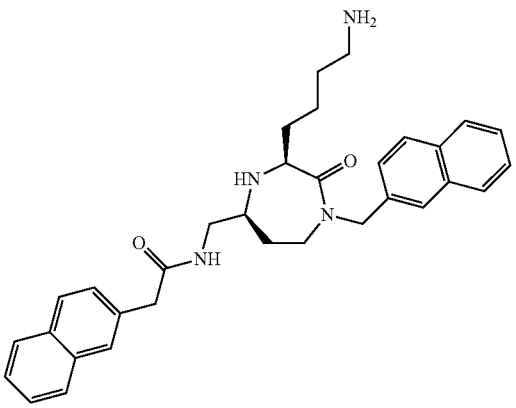
(124)
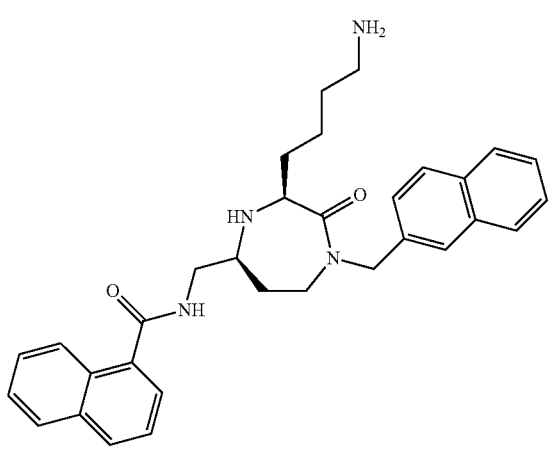
(125)
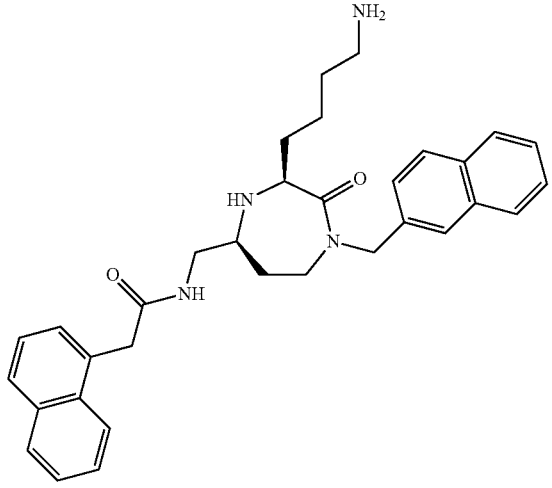

(126) 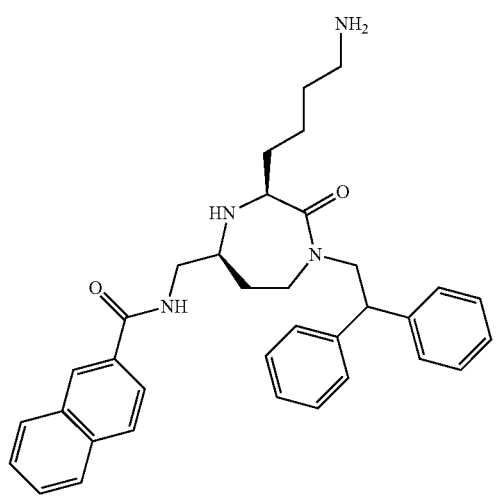
(129) 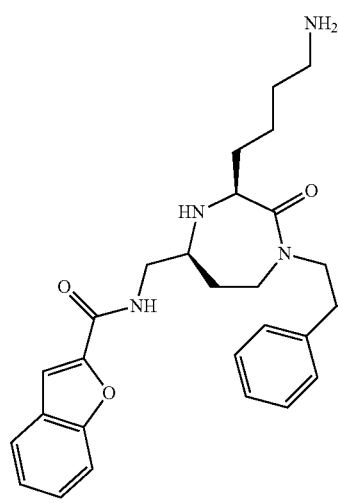
(127) 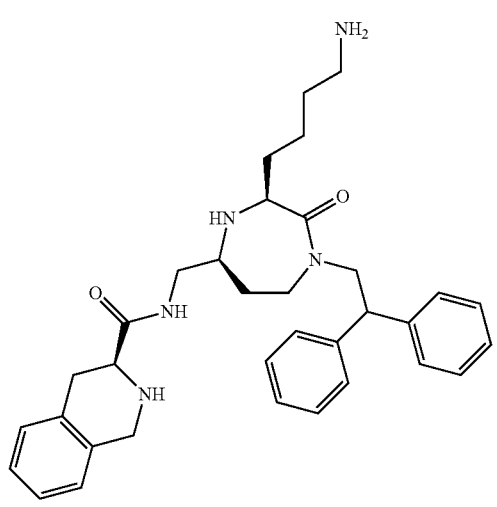
(130) 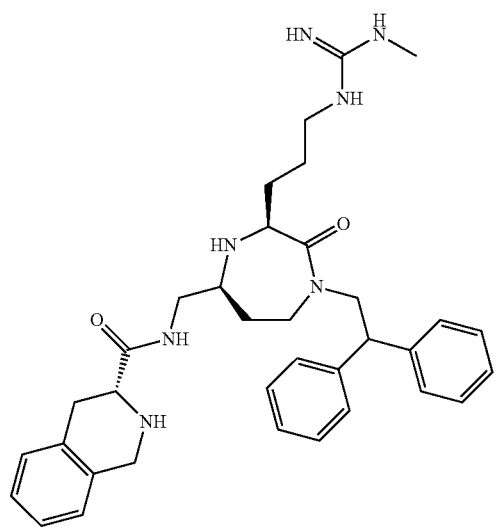
(128) 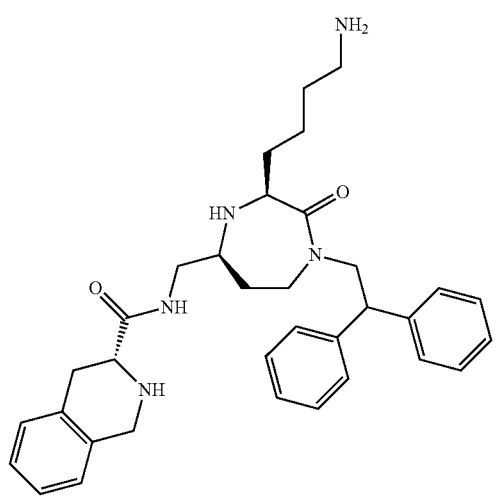
(131) 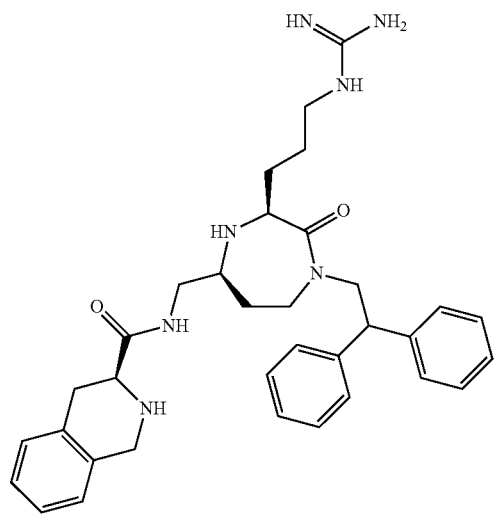

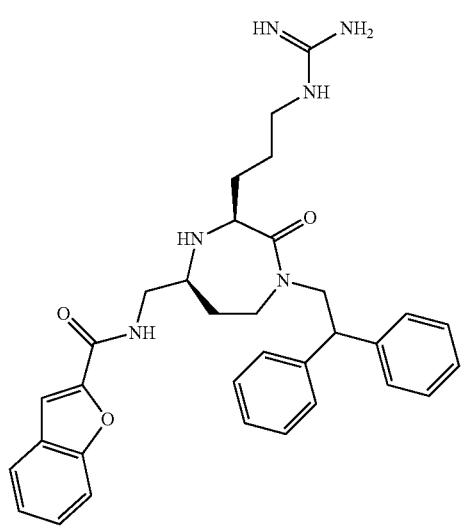
(132)
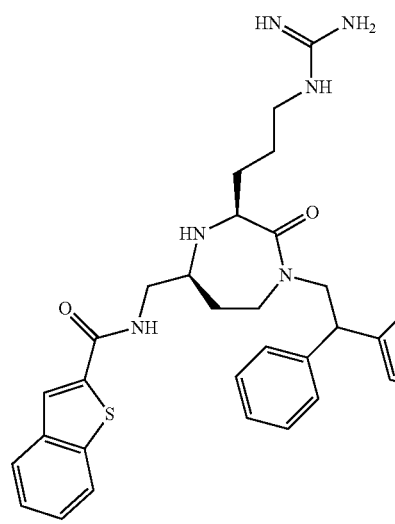
(135)
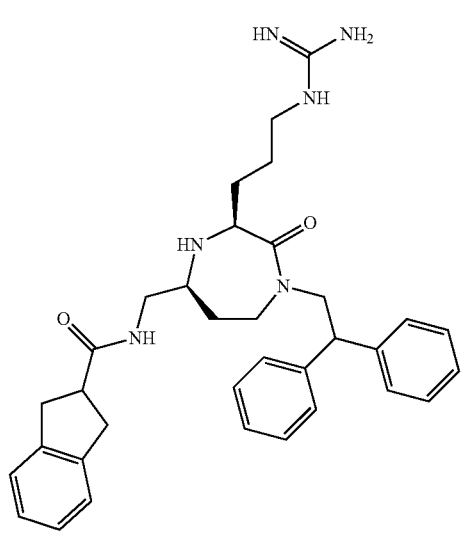
(133)
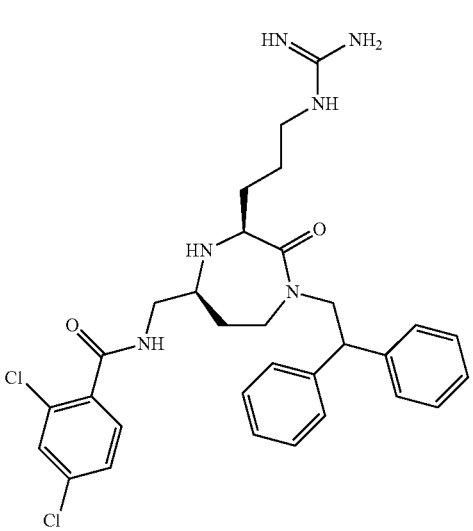
(136)
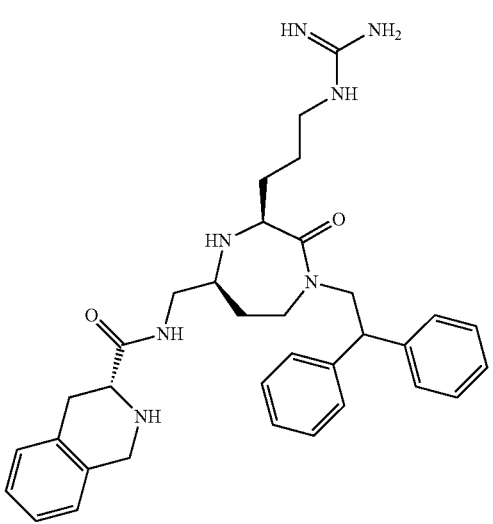
(134)
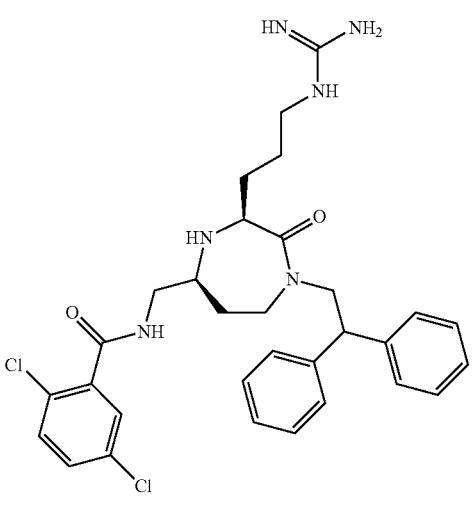
(137)

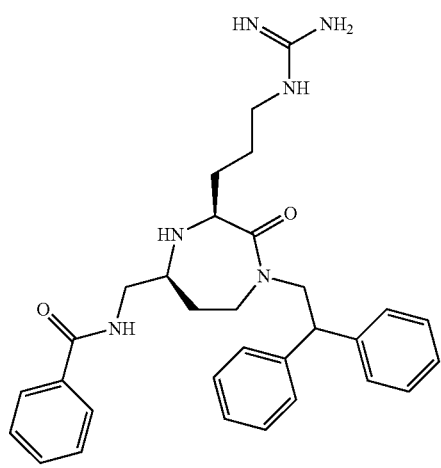
(138)
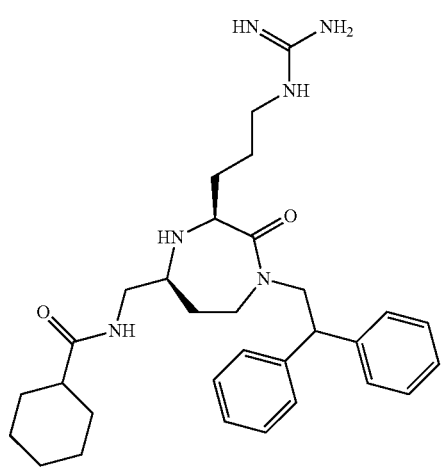
(139)
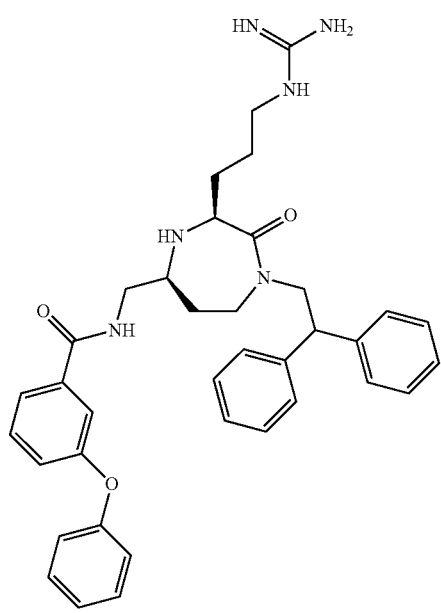
(140)
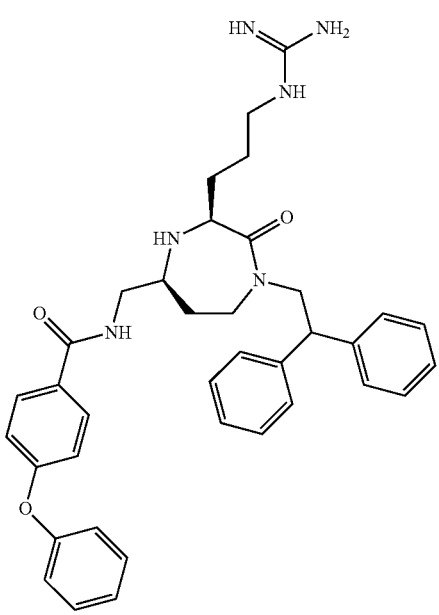
(141)
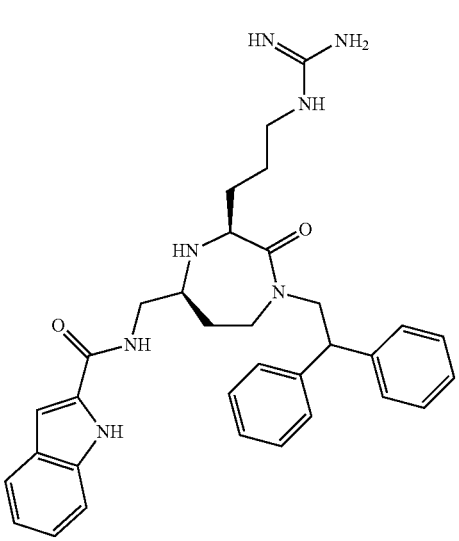
(142)
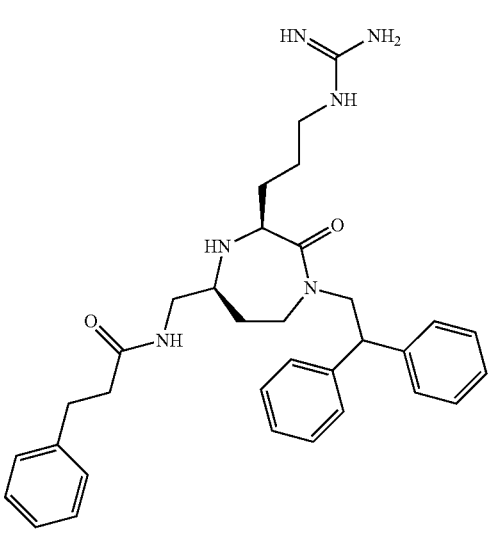
(143)

49
-continued
(144)
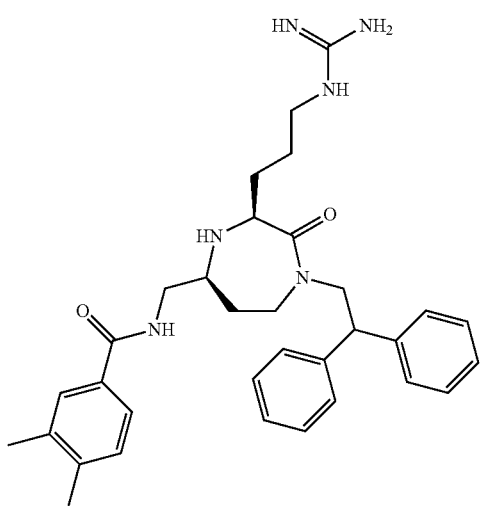
(145)
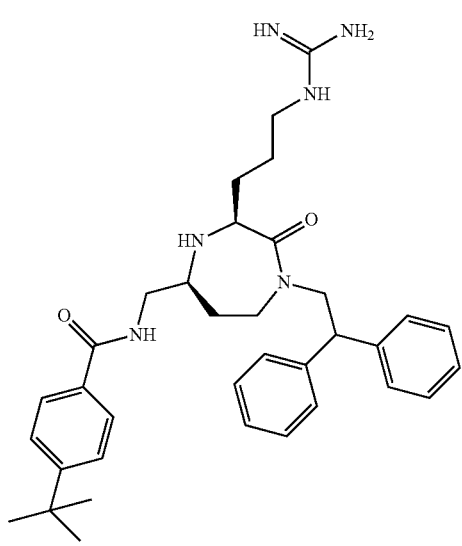
(146)
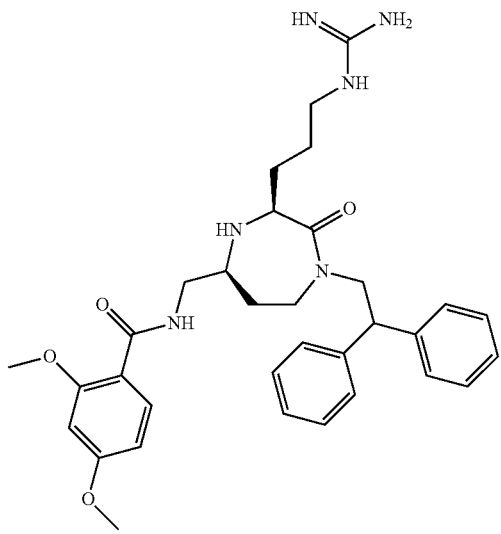
50
-continued
(147)
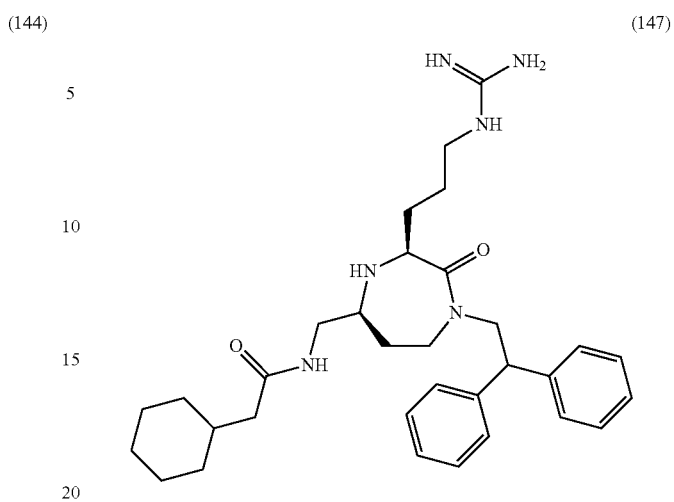
(148)
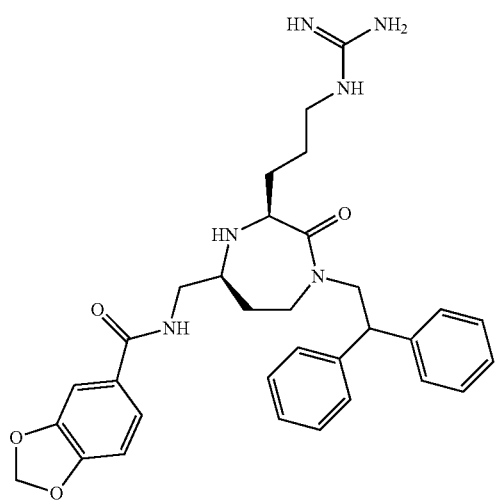
(149)
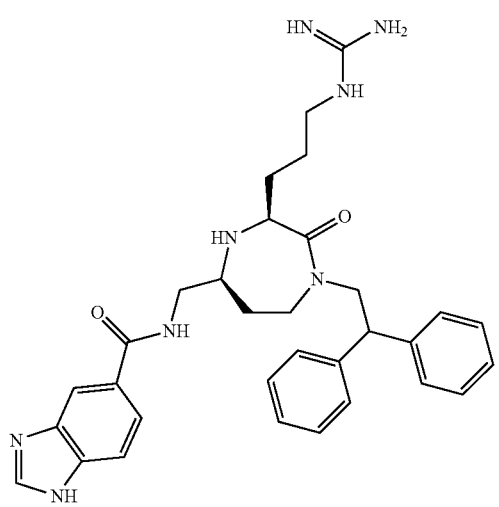

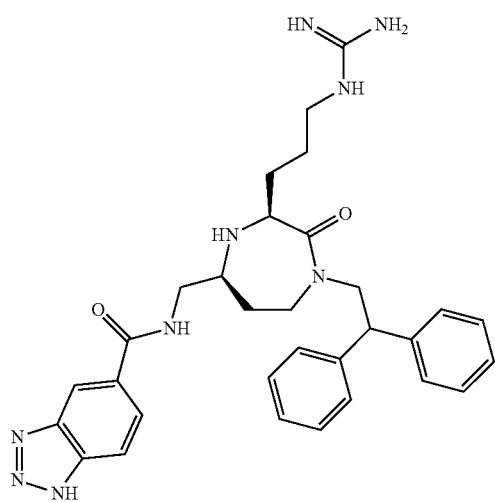
(150)
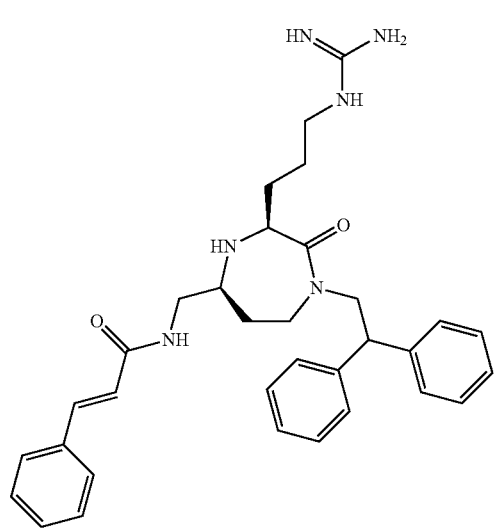
(153)
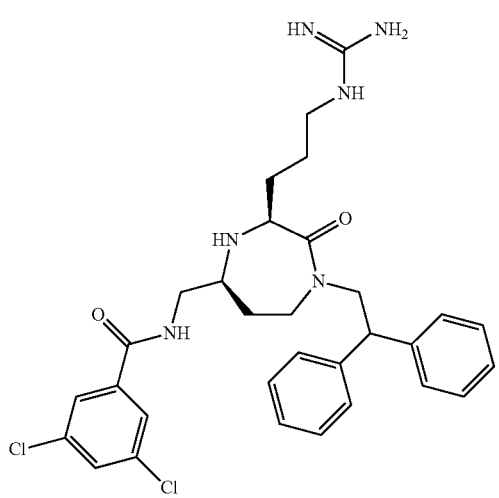
(154)
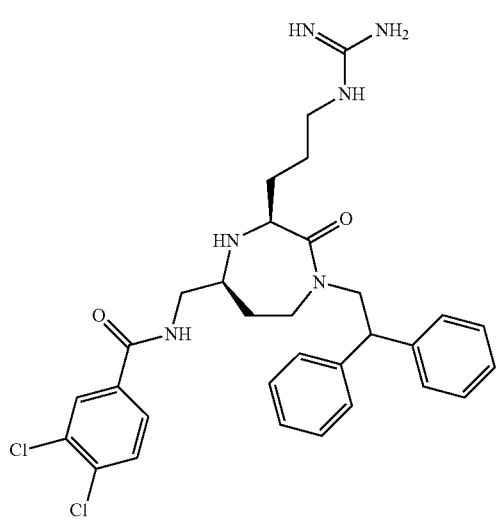
(151)
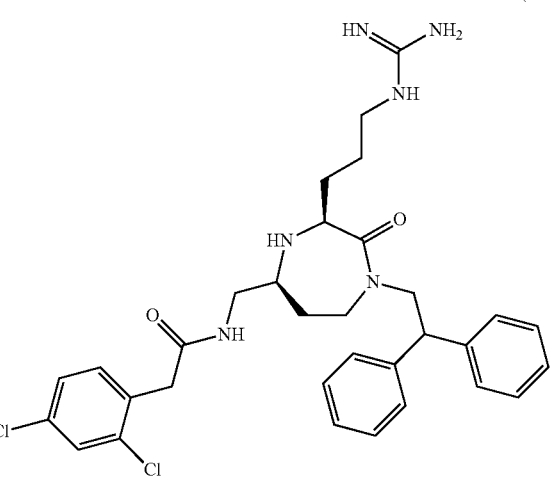
(155)
(152)

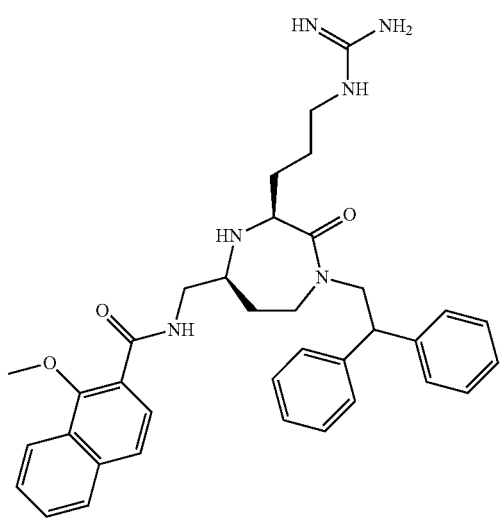
(156)
(157)
(158)
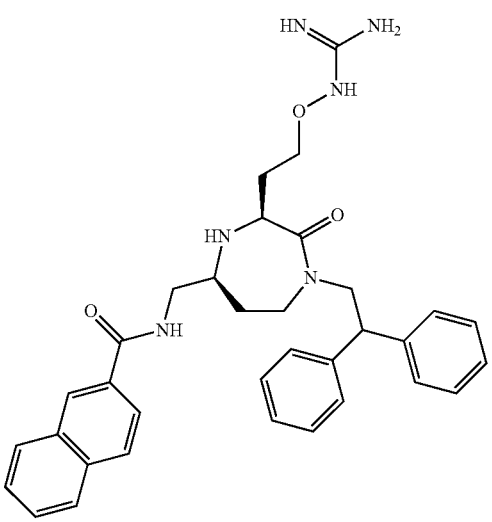
(159)
(160)
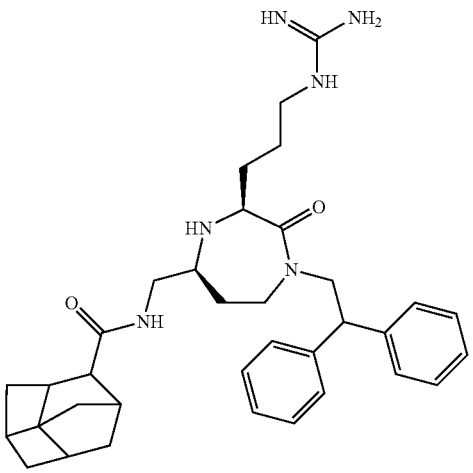
(161)

55
(162)
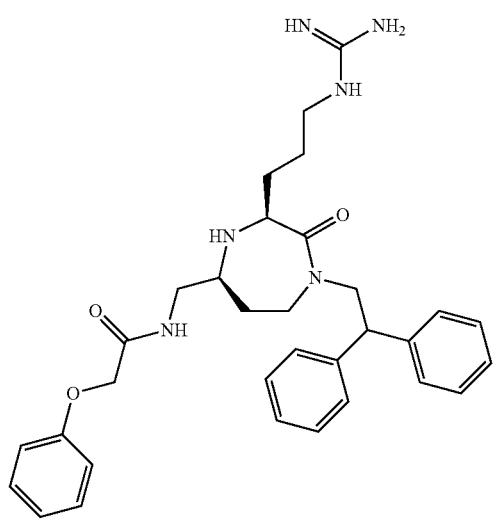
56
(165)
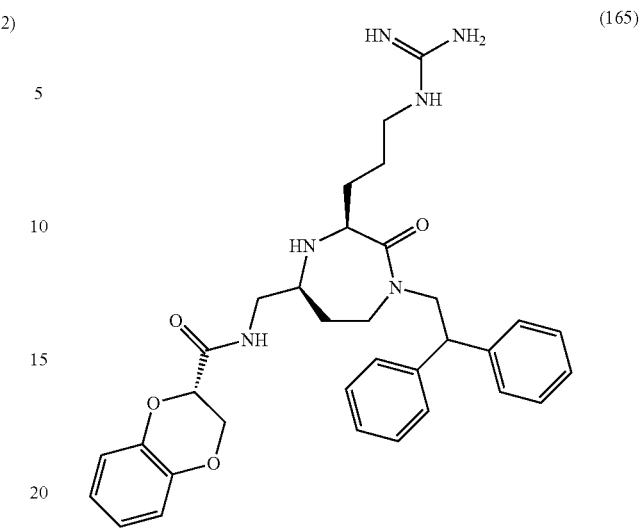
(163)
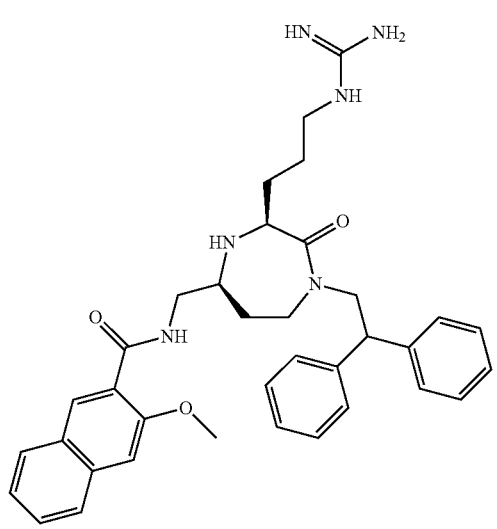
(166)
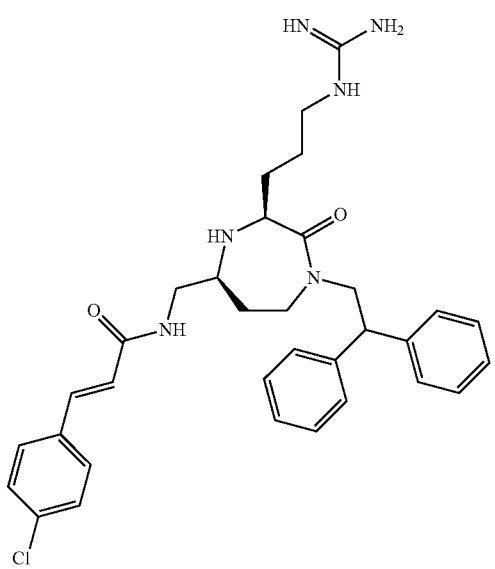
(164)
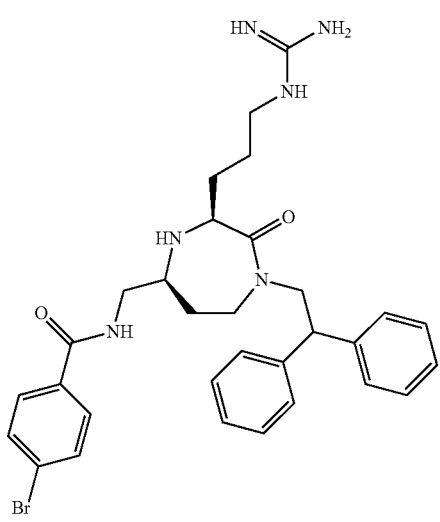
(167)
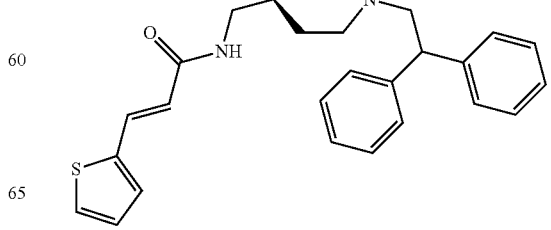

(168)
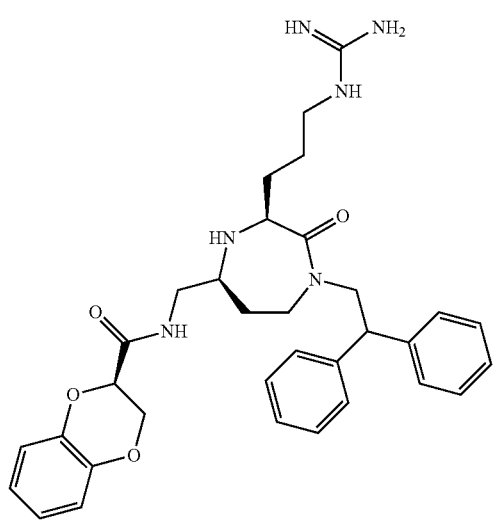
(169)
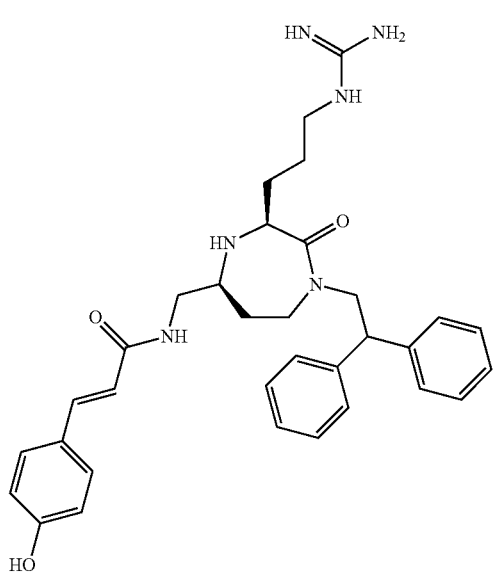
(170)
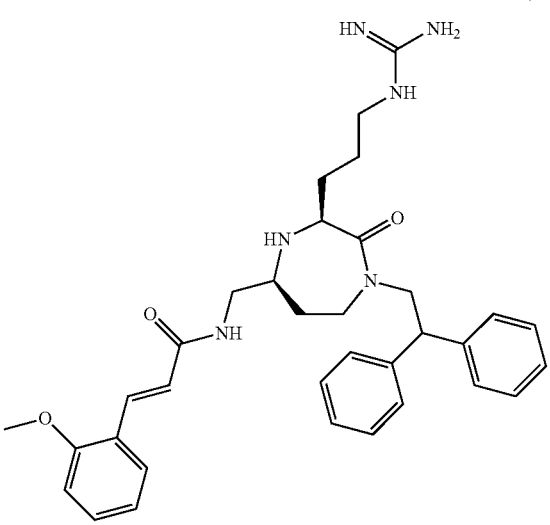
(171)
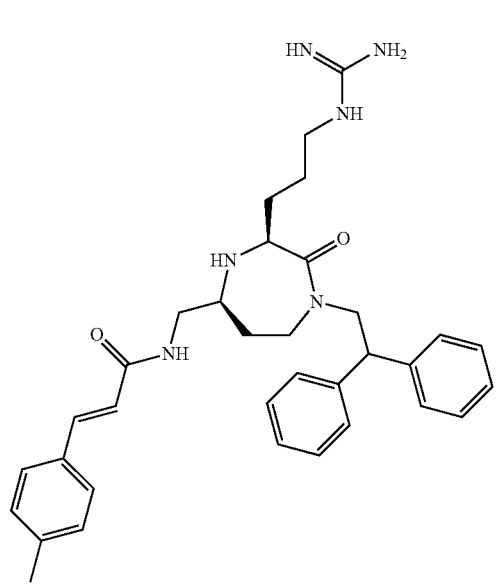
(172)
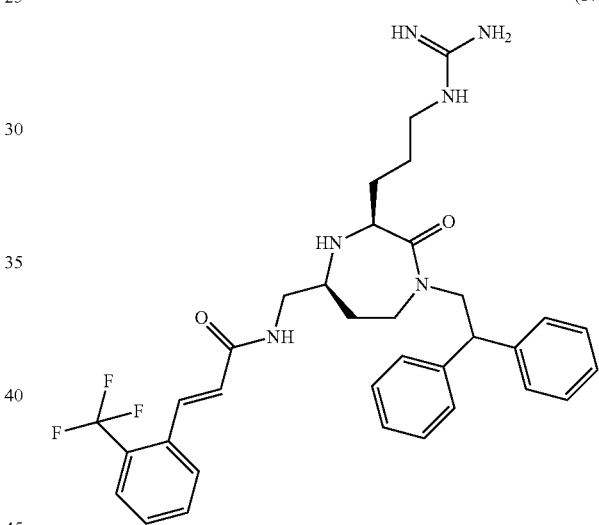
(173)
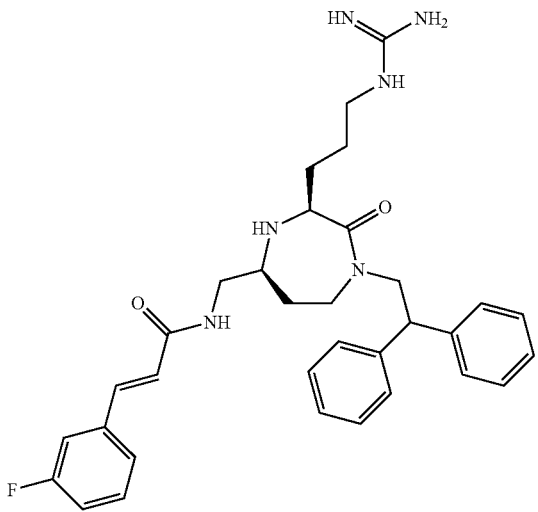

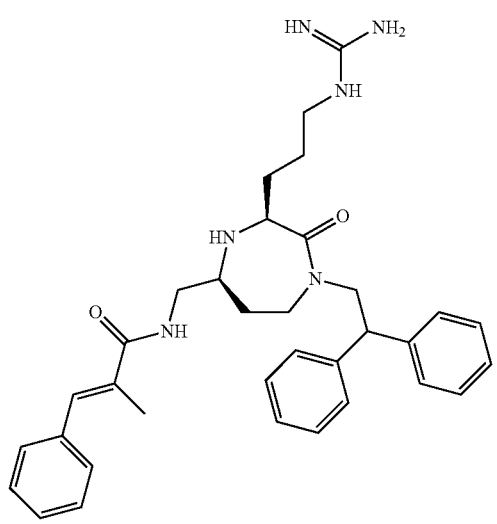
(174)
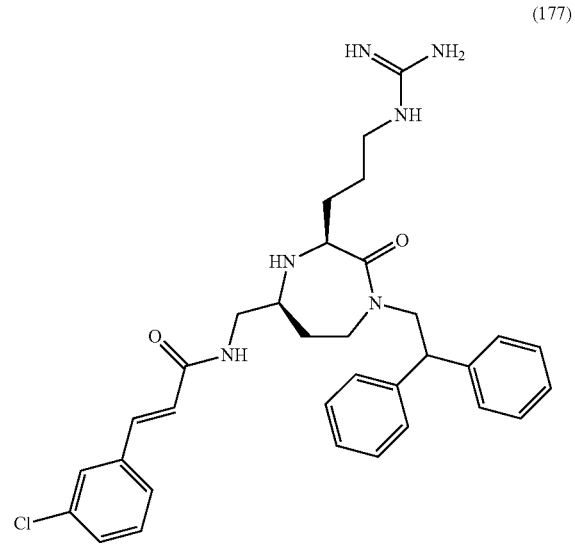
(177)
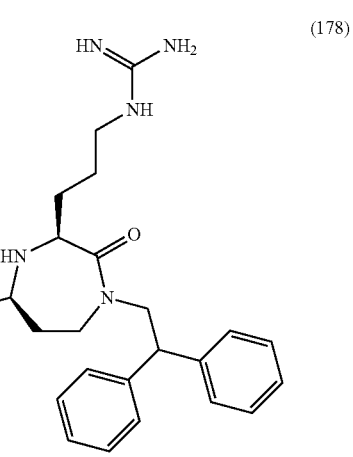
(175)
(178)
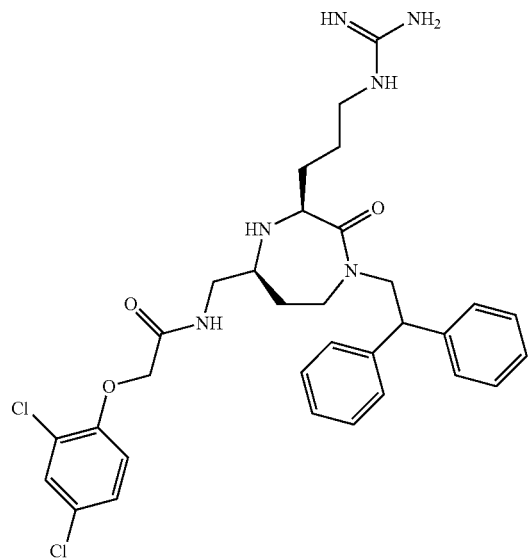
(176)
(179)

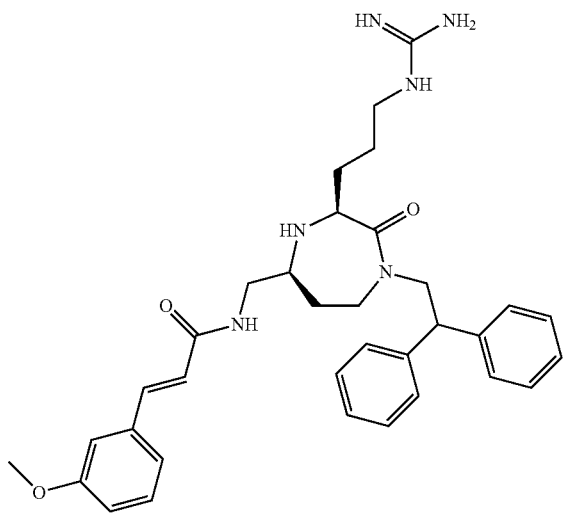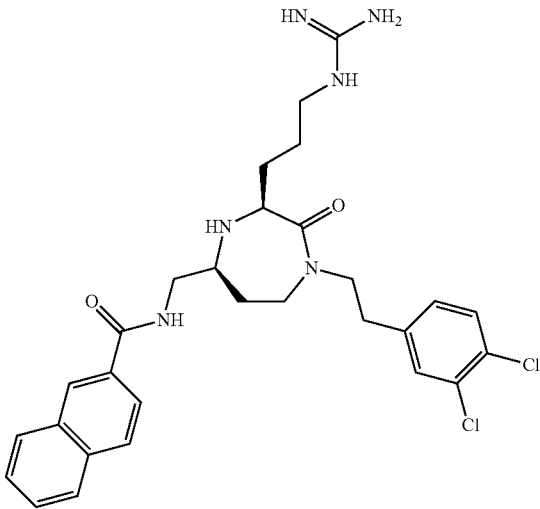

(186)
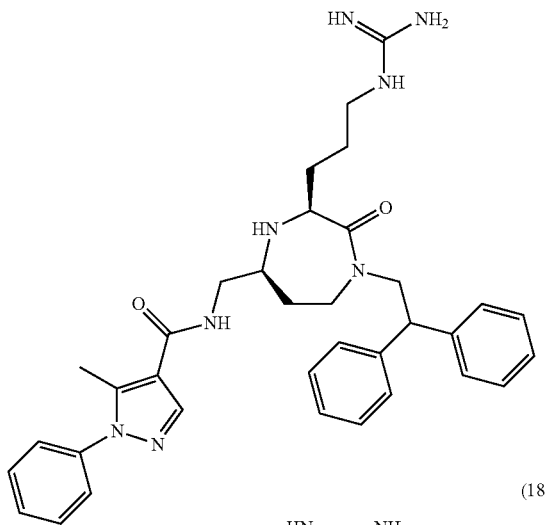
(189)
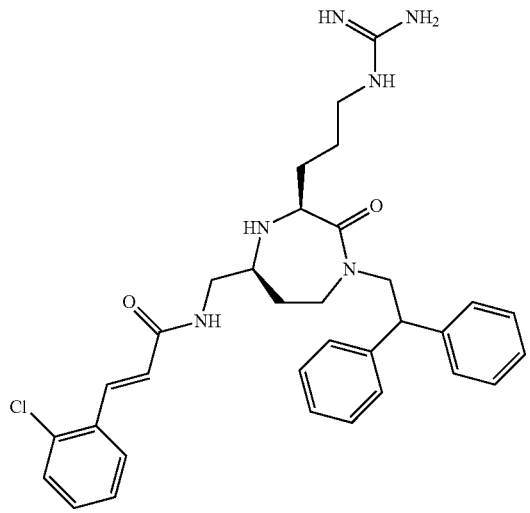
(187)
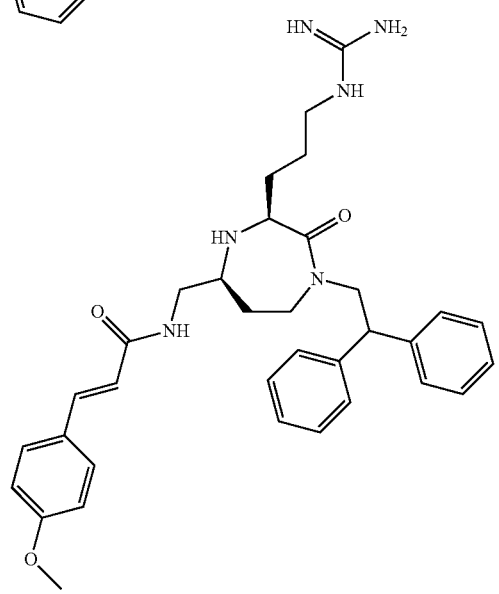
(190)
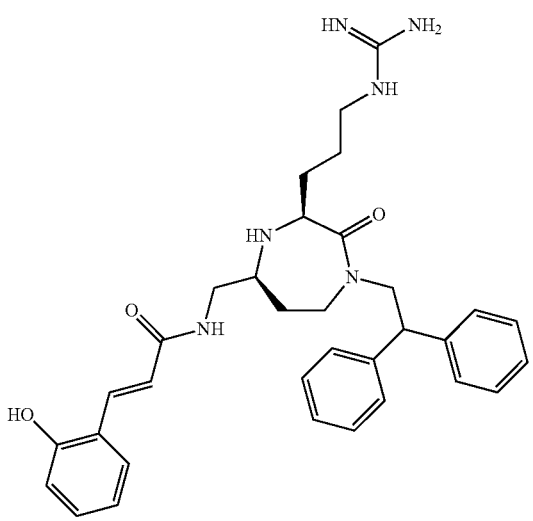
(188)
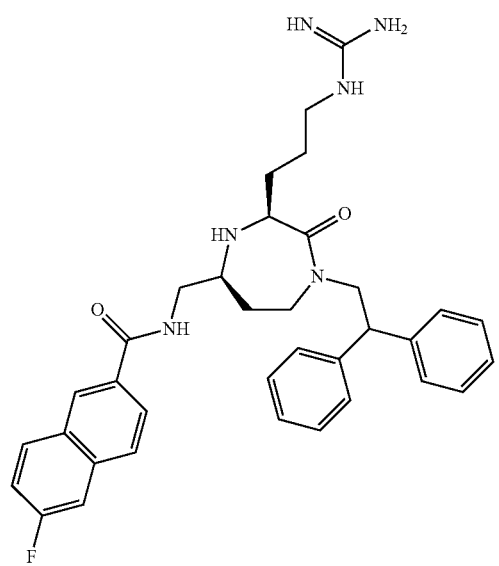
(191)
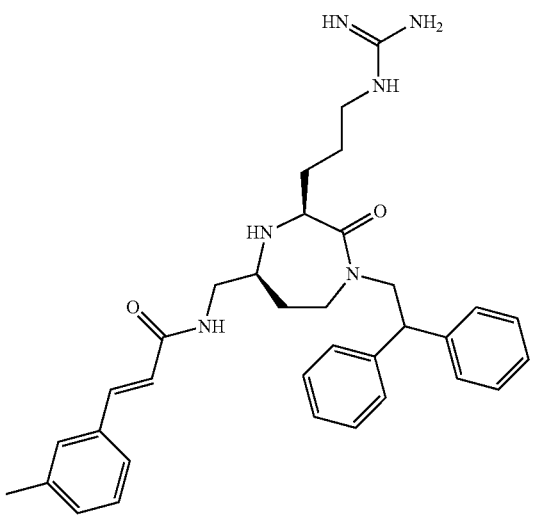

-continued
(192) 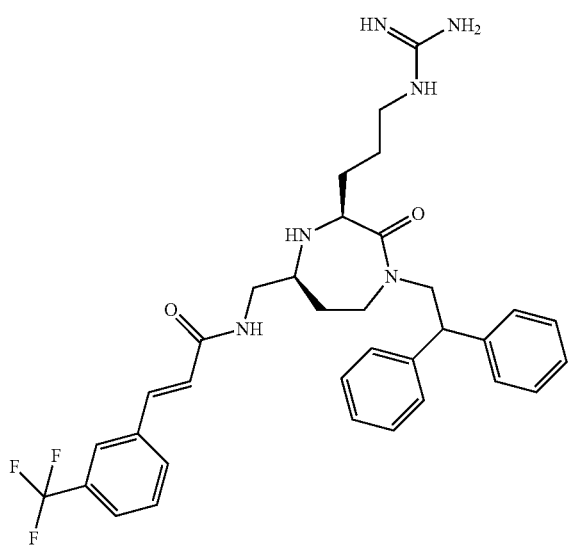
(193) 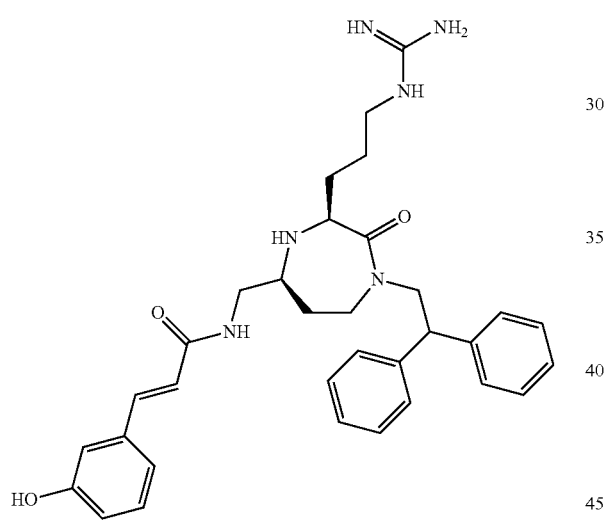
(194) 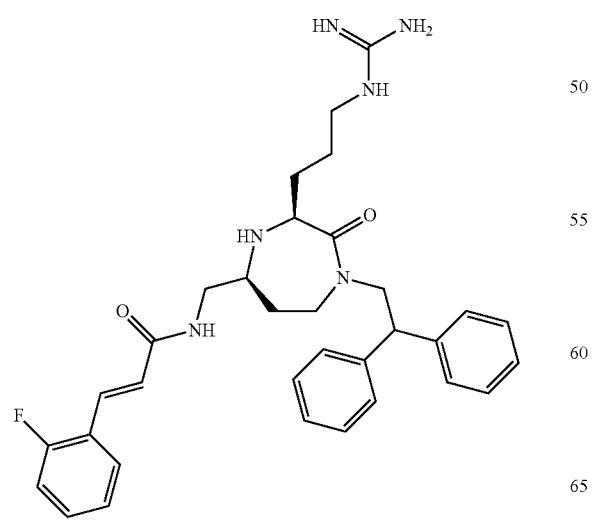
(195) 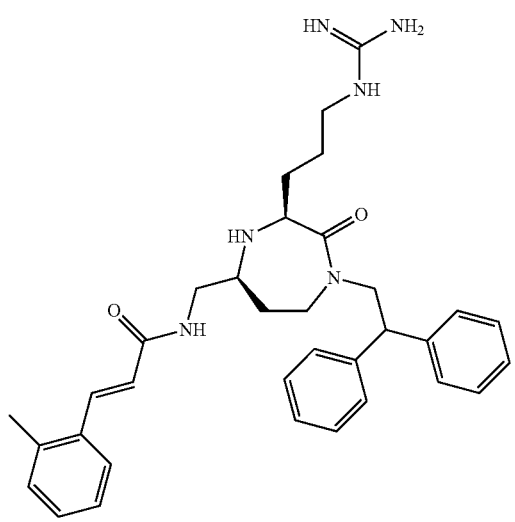
(196) 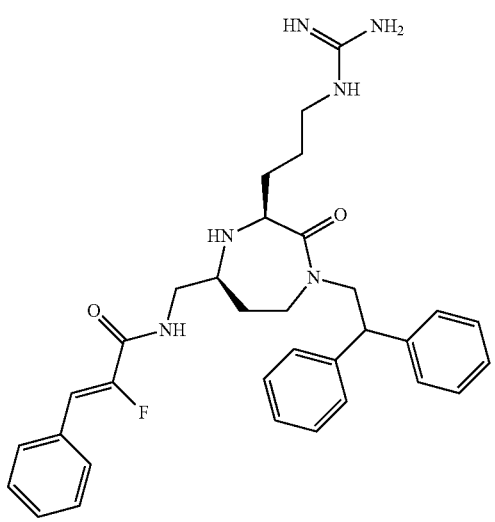
(197) 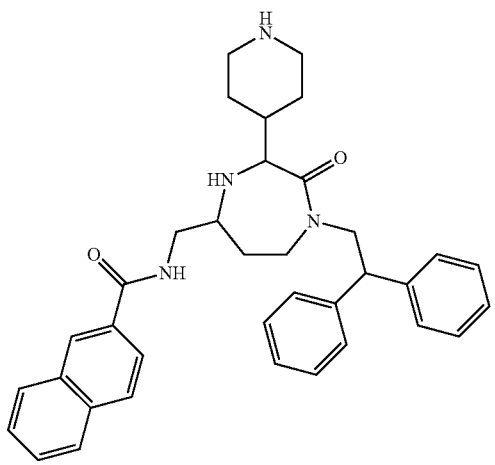

67
-continued
(198)
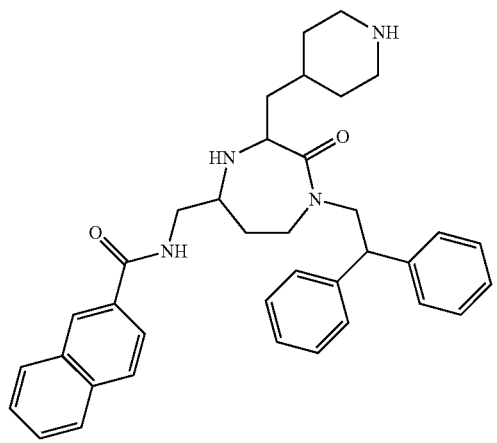
(199)
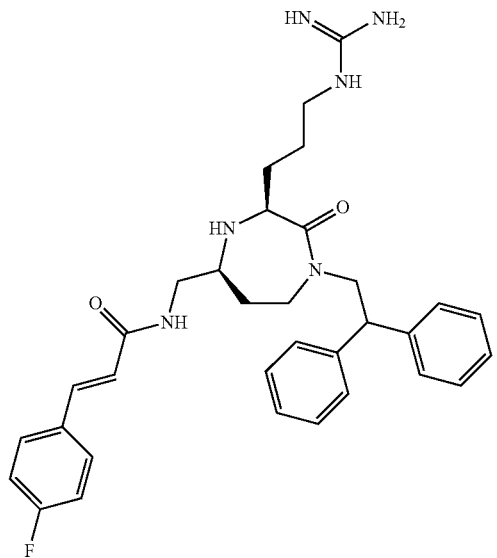
(200)
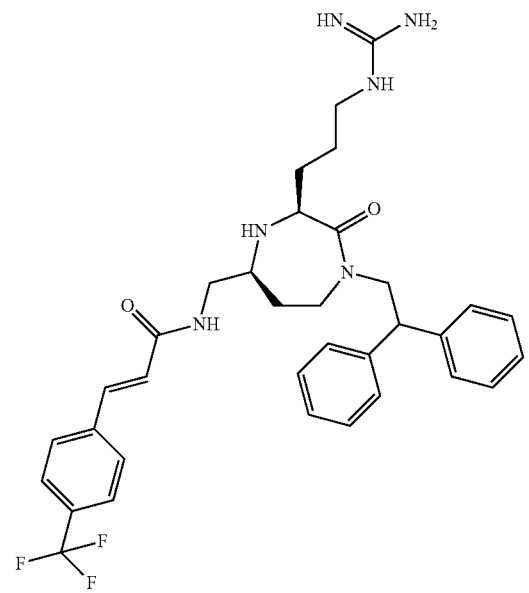
68
-continued
(201)
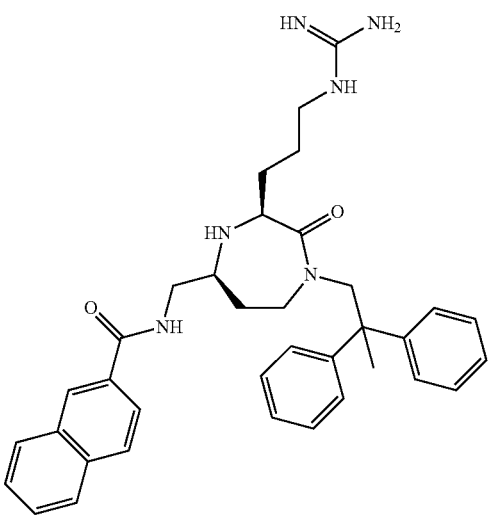
(202)
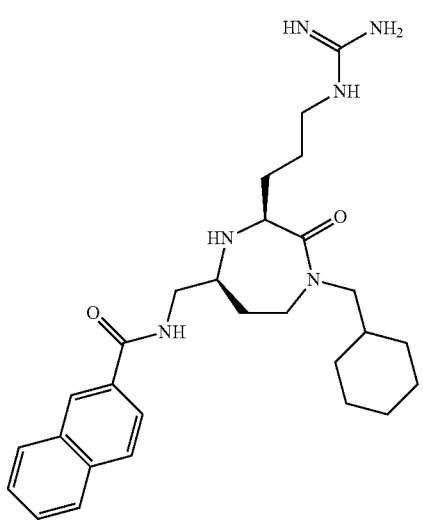
(203)
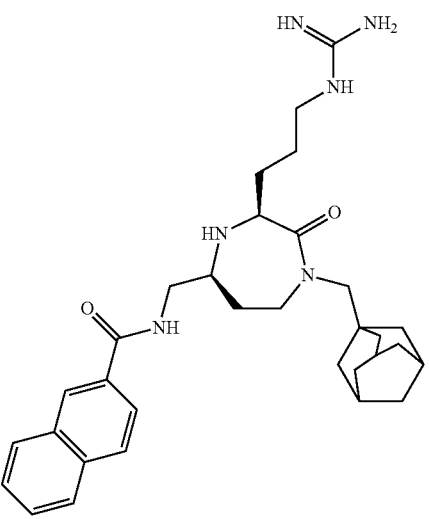

69
-continued
(204)
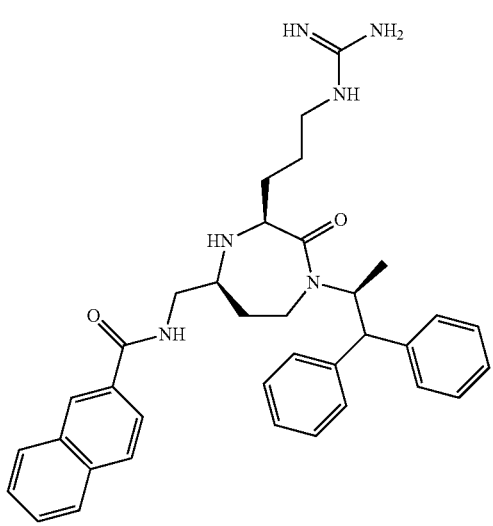
(205)
(206)
70
-continued
(207)
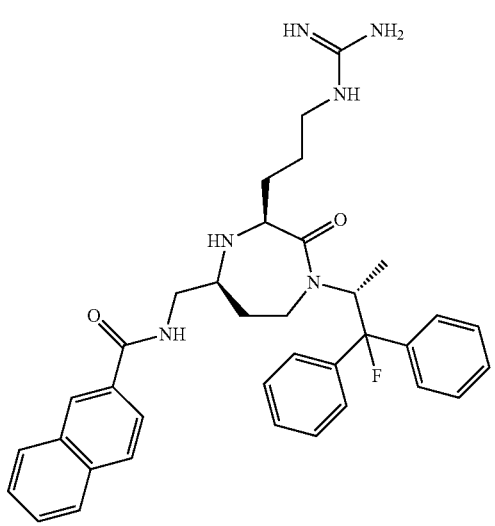
(208)
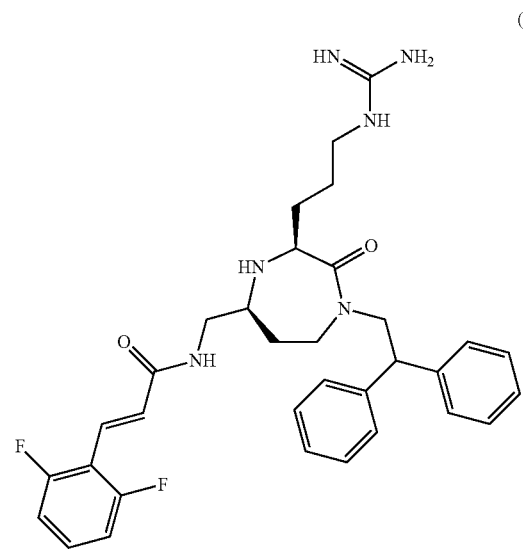
(209)
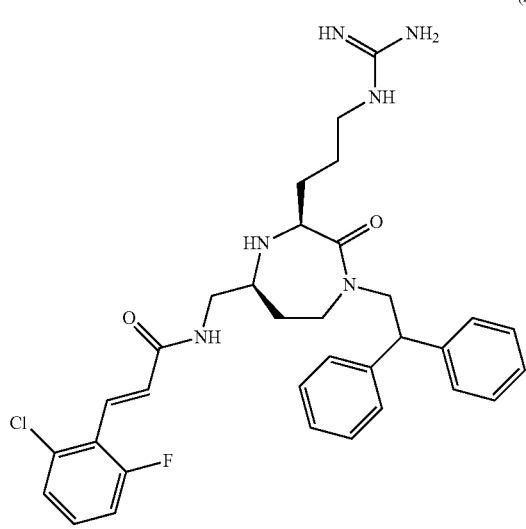

71
-continued
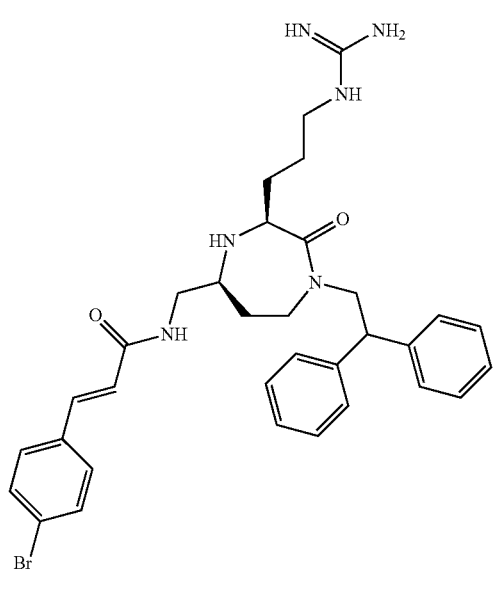
(210)
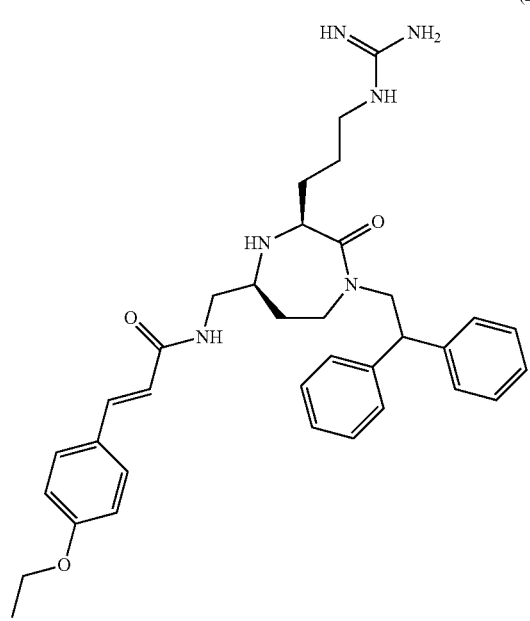
(211)
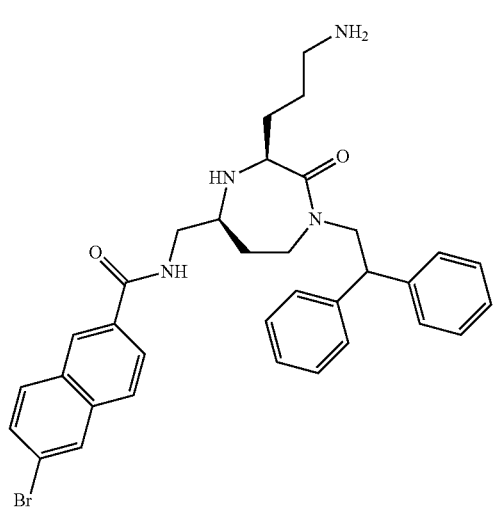
(212)
72
-continued
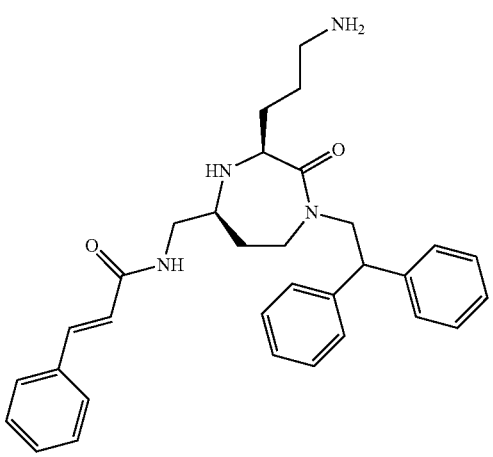
(213)
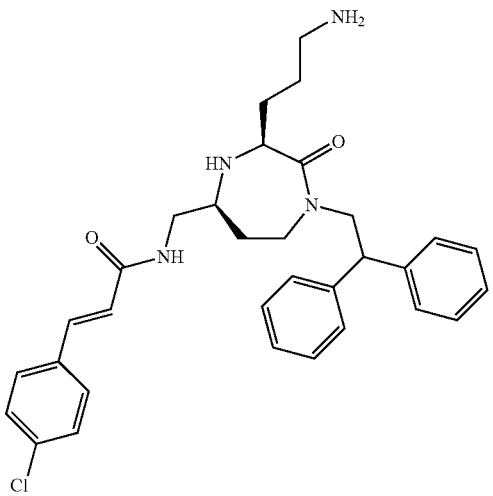
(214)
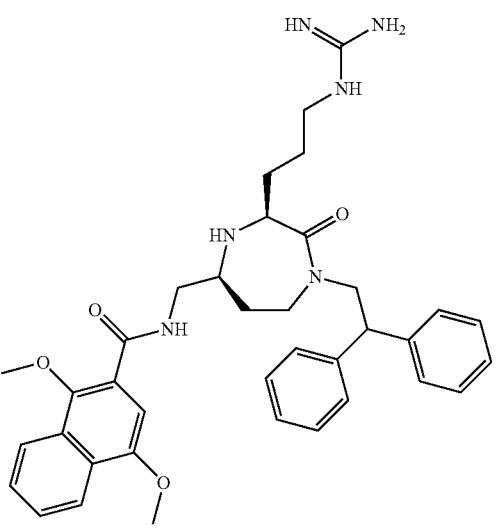
(215)

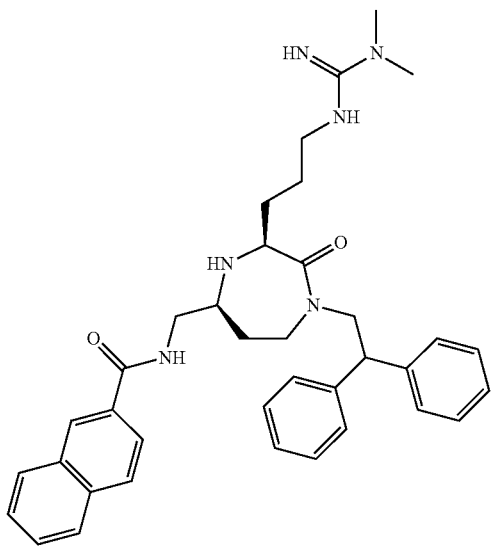
(216)
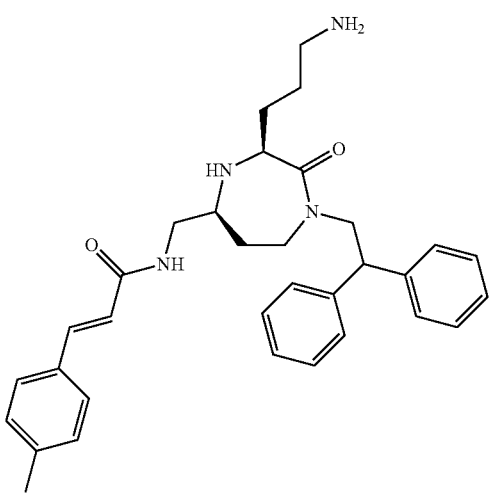
219
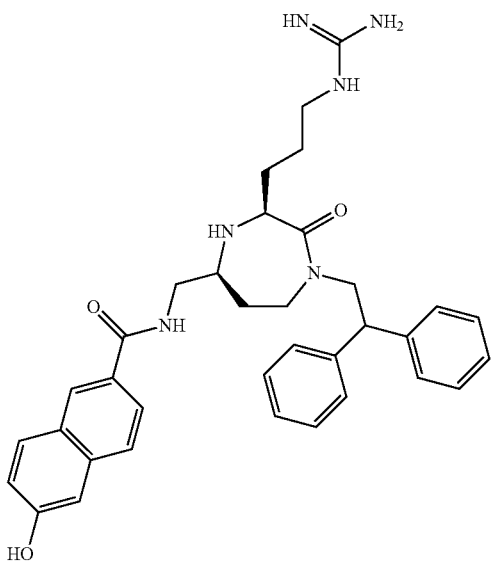
(217)
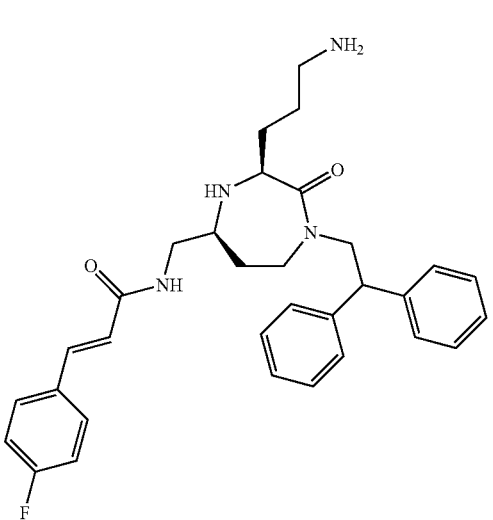
(220)
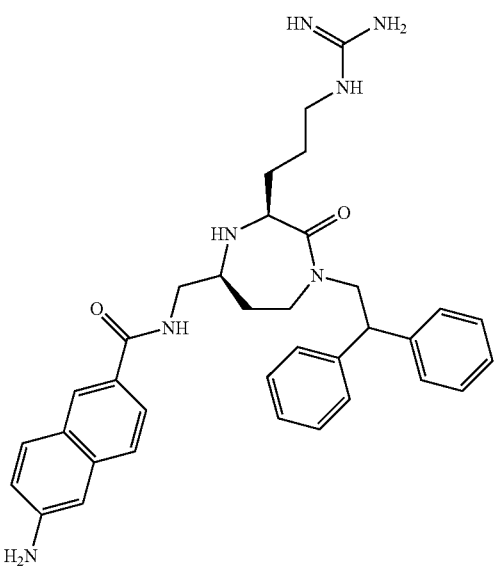
(218)
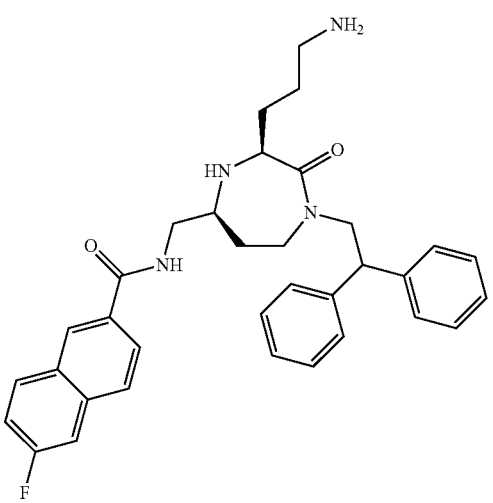
(221)

75
-continued
(222)
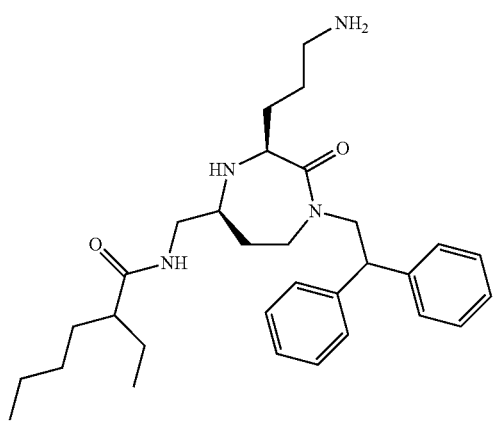
(223)
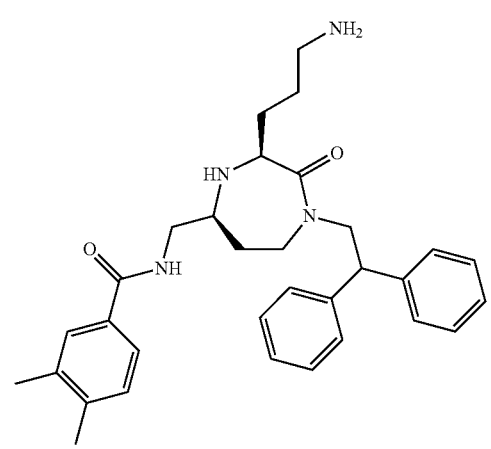
(224)
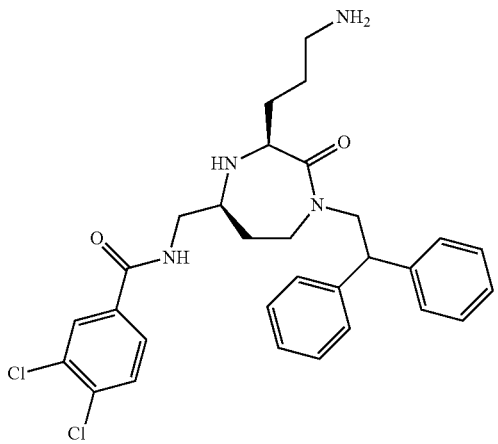
76
-continued
(225)
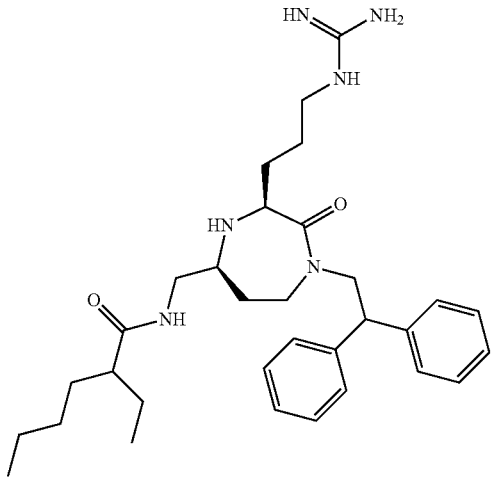
(226)
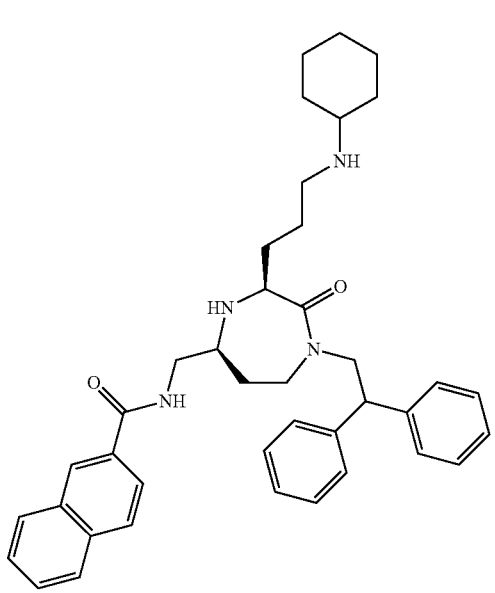
(227)
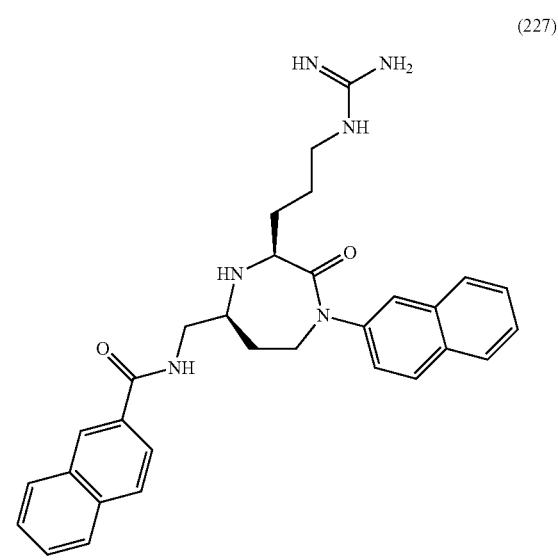

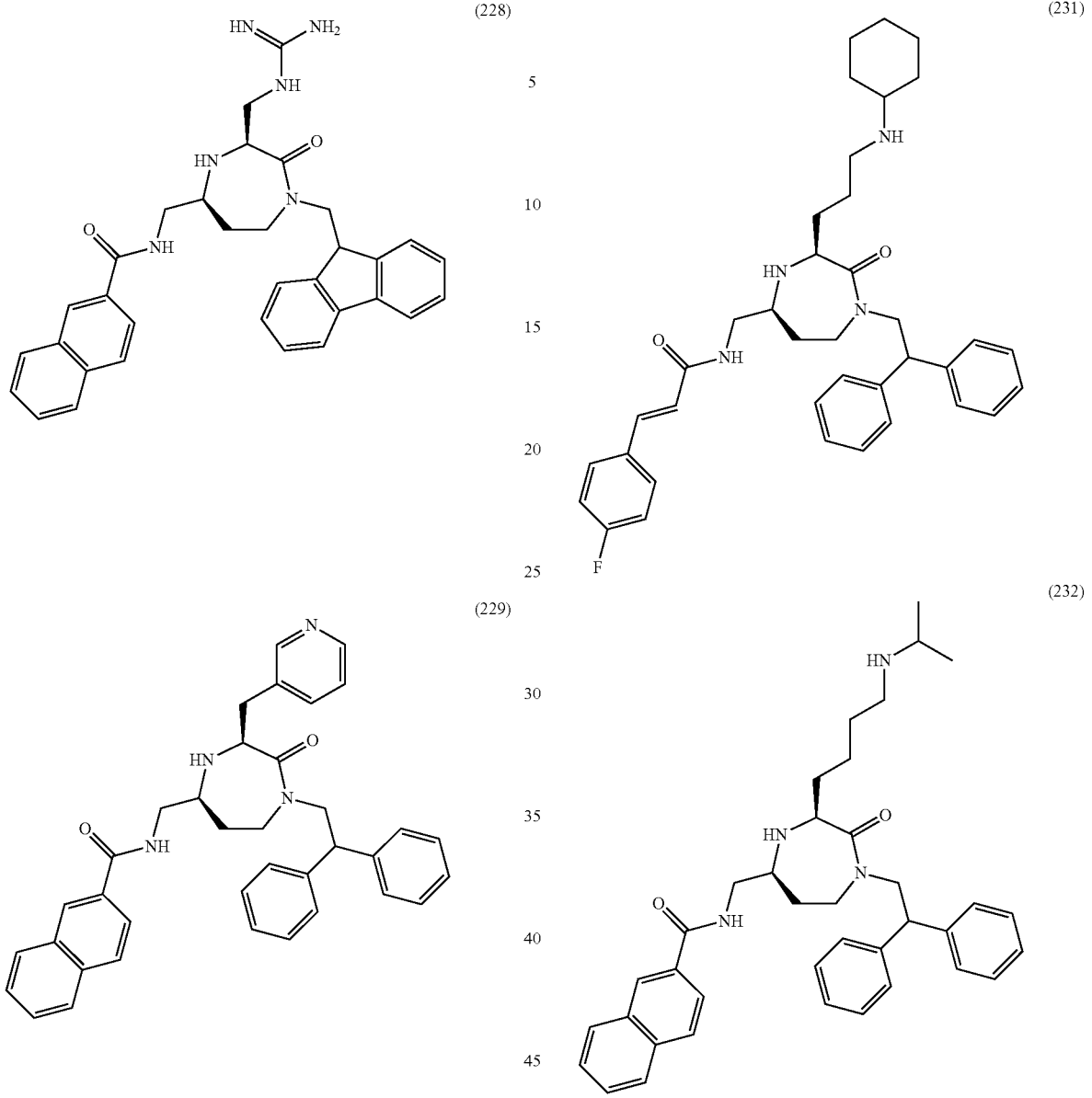

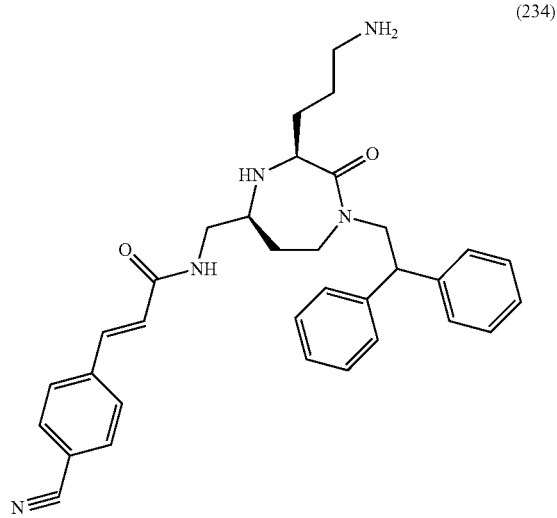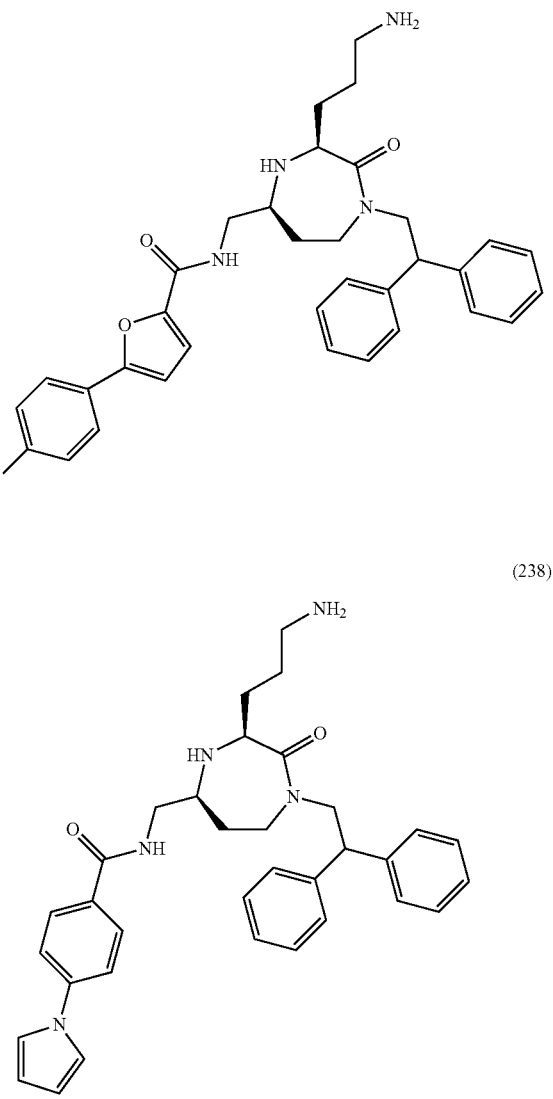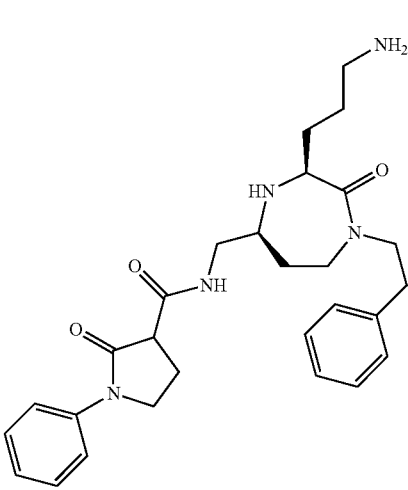

-continued
(240)
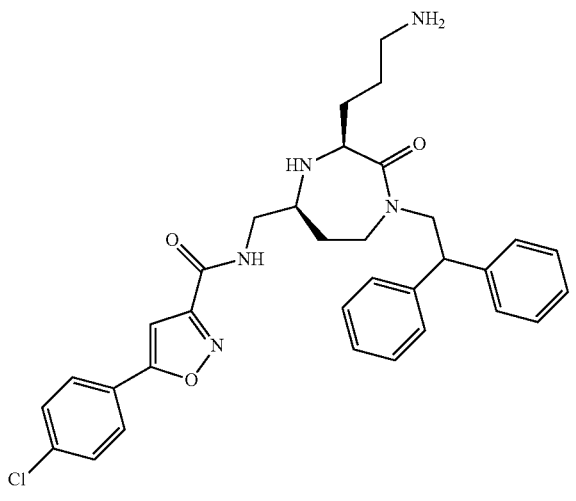
(243)
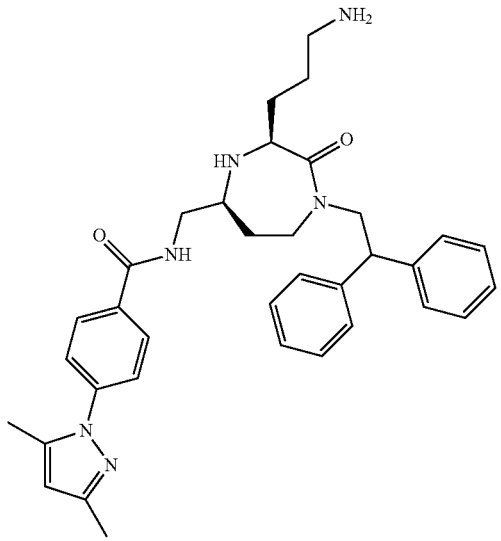
(241)
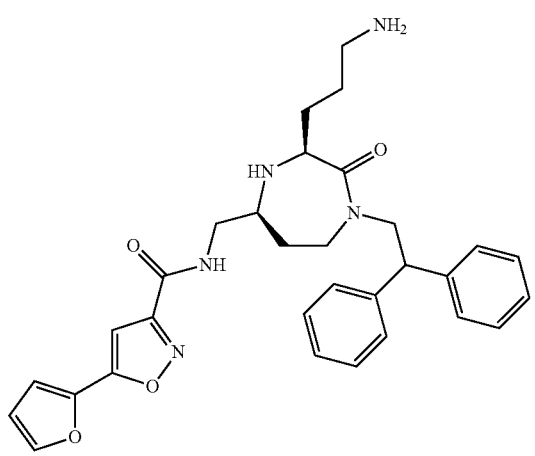
(244)
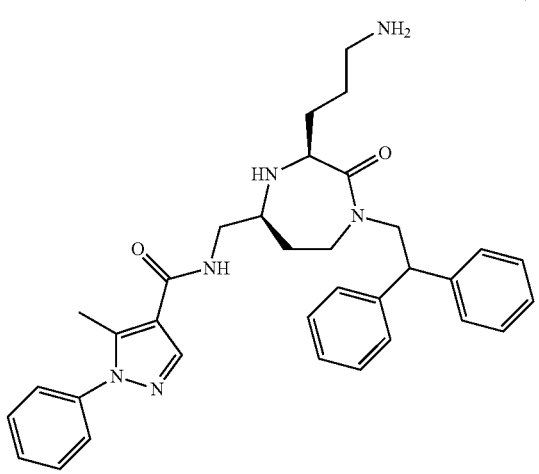
(242)
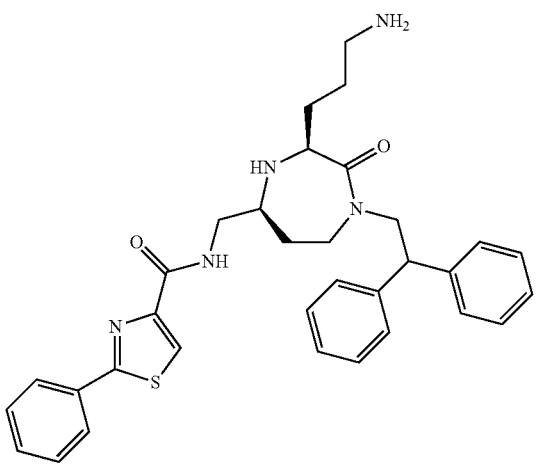
(245)
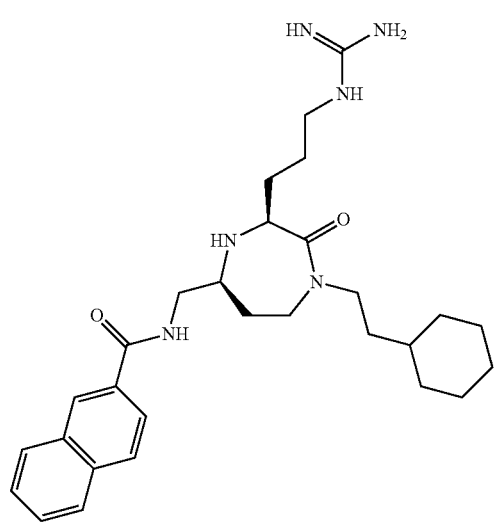

83
-continued
(246)
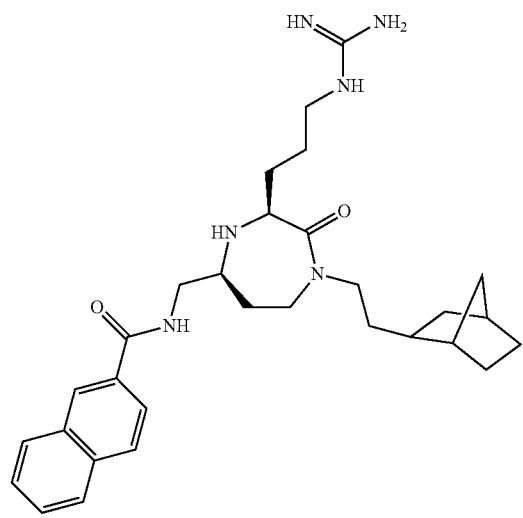
(247)
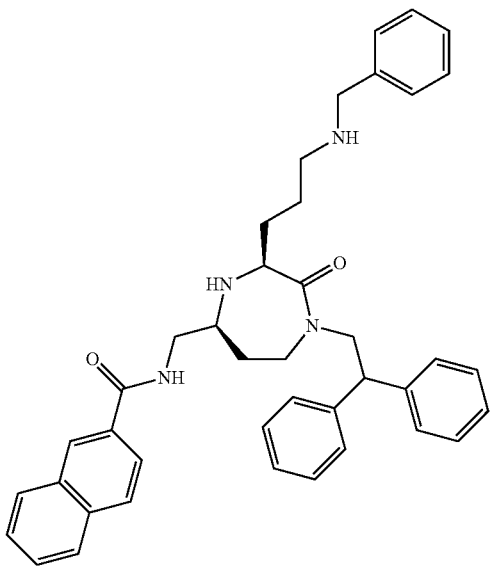
(248)
84
-continued
(249)
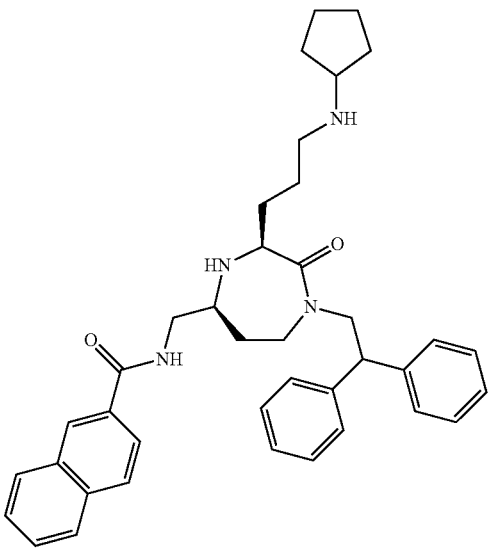
(250)
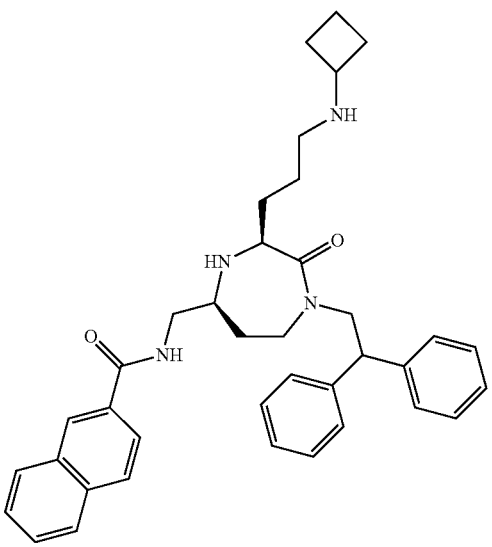
(251)
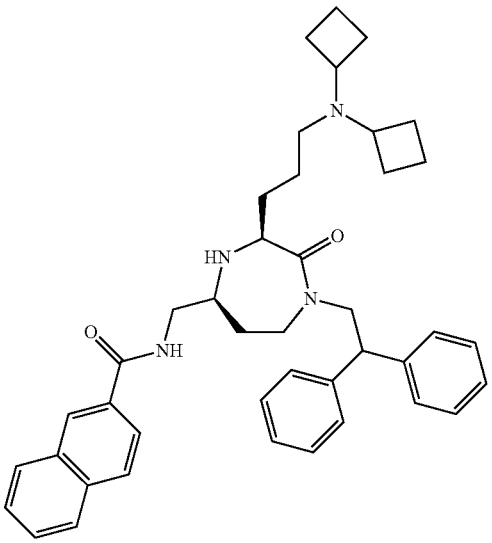

85
-continued
(252)
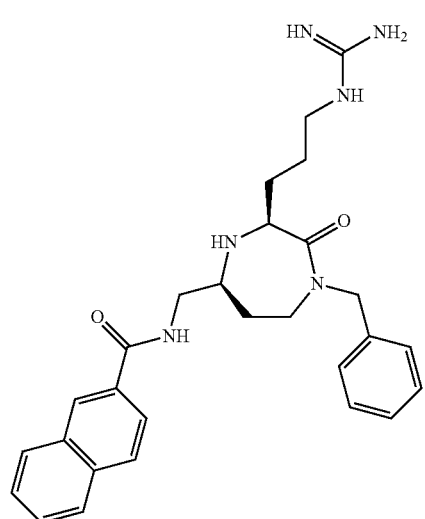
(253)
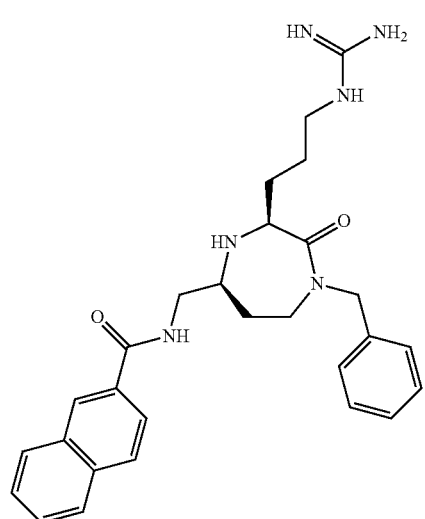
(254)
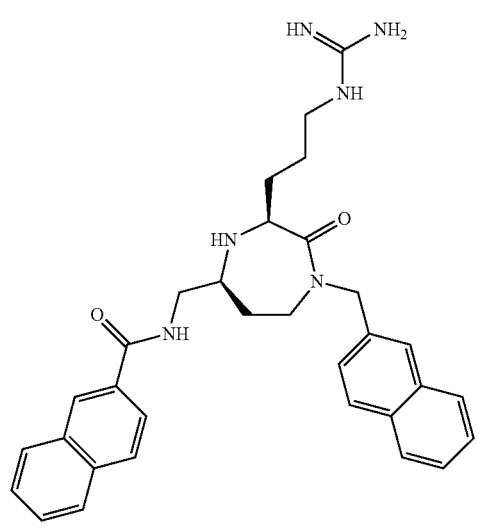
86
-continued
(255)
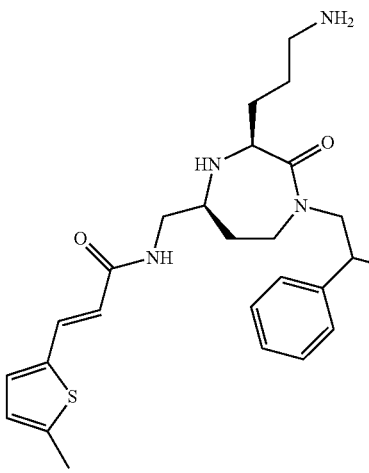
(256)
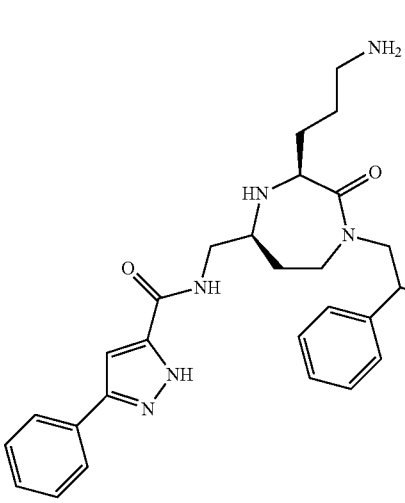
(257)
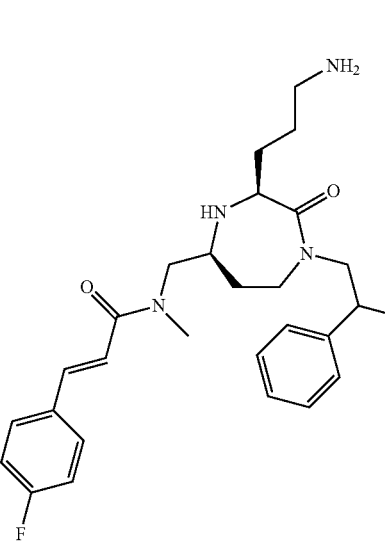

(258) 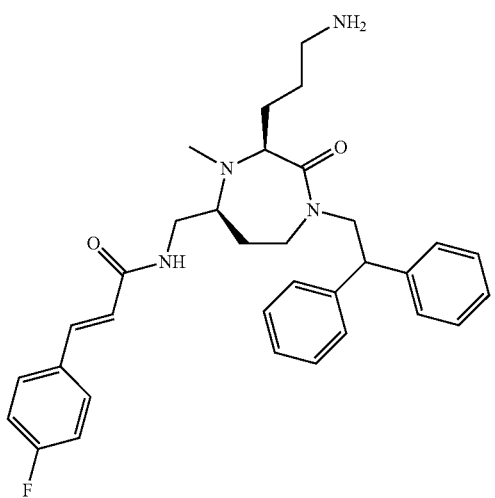
(259) 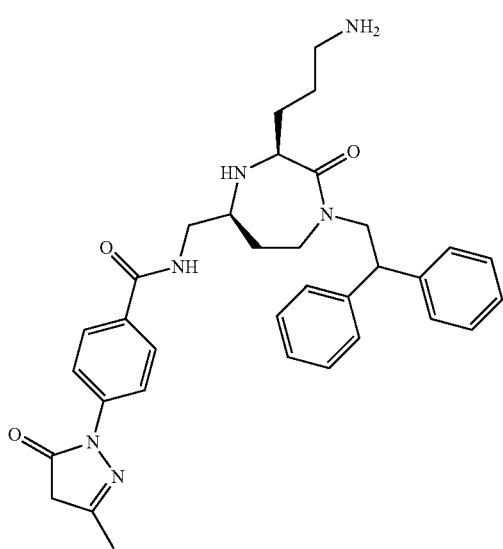
(260) 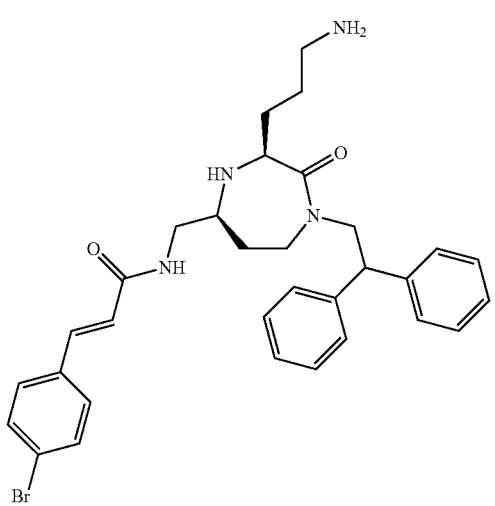
(261) 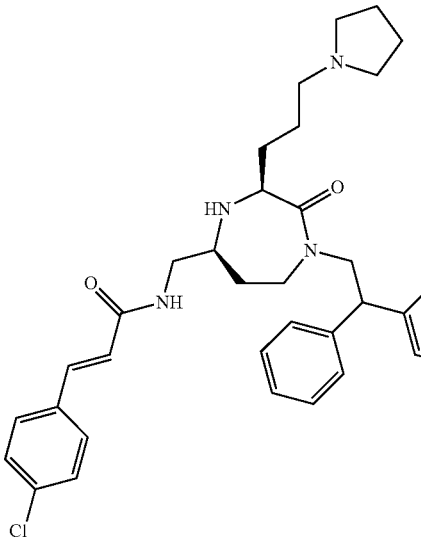
(262) 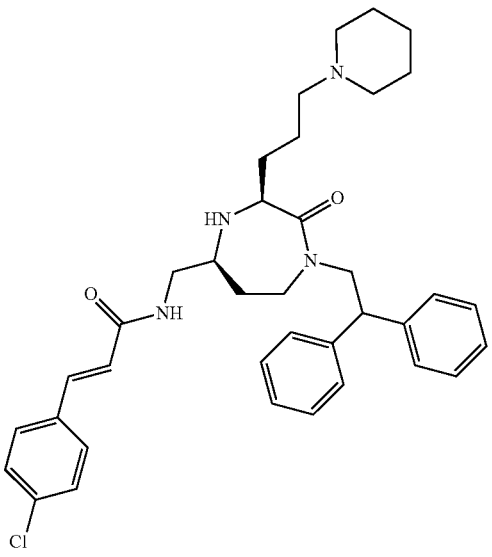
(263) 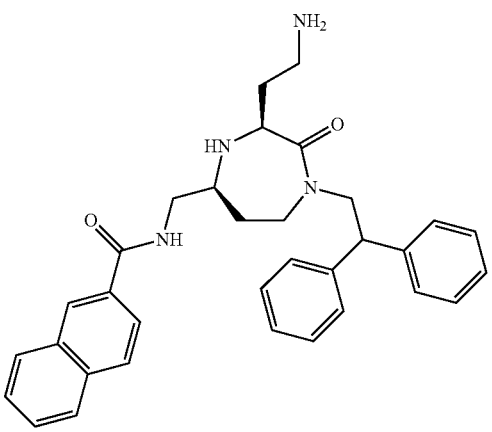

89
-continued
(264)
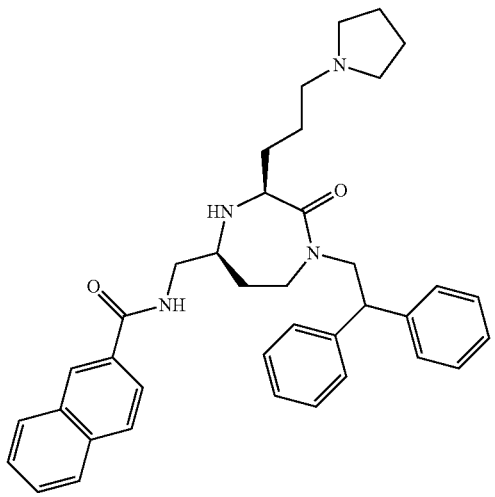
(265)
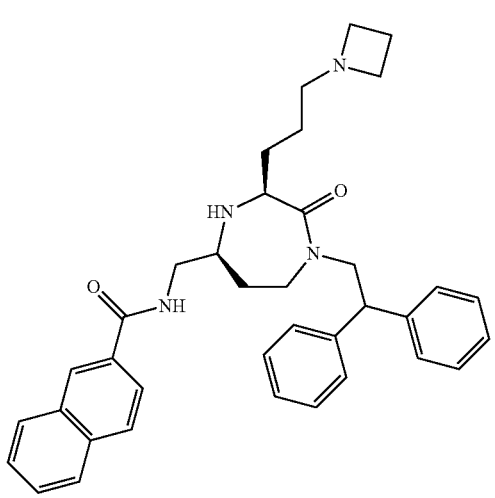
(266)
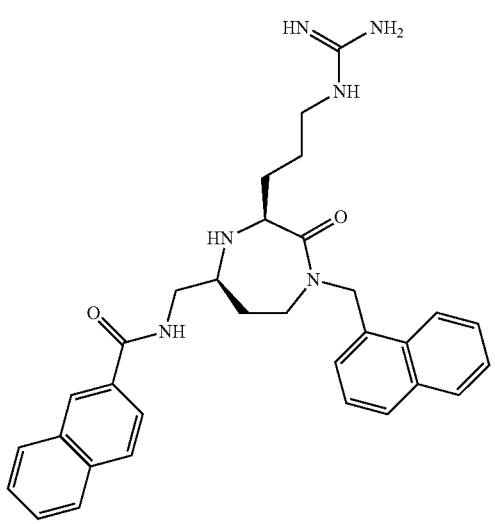
90
-continued
(267)
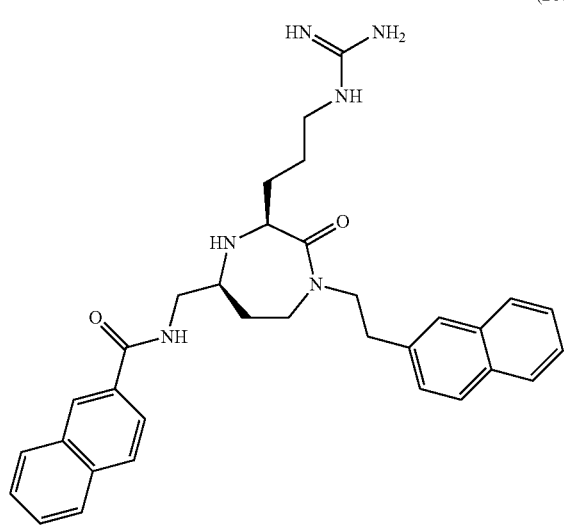
(268)
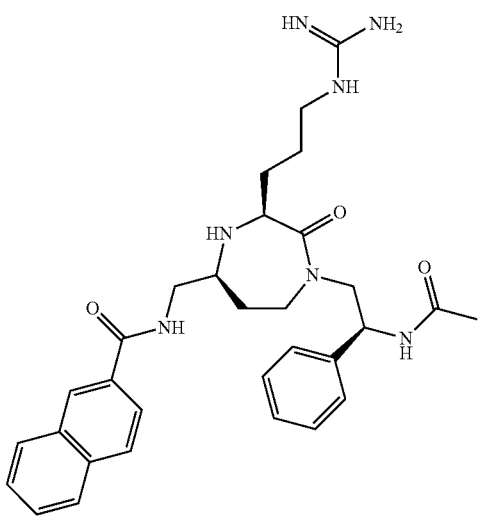
(269)
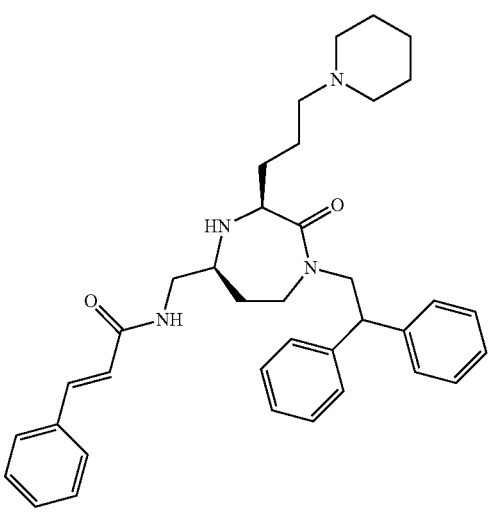

(270)
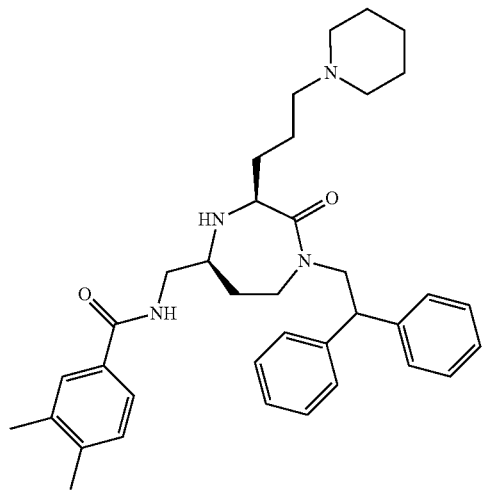
(271)
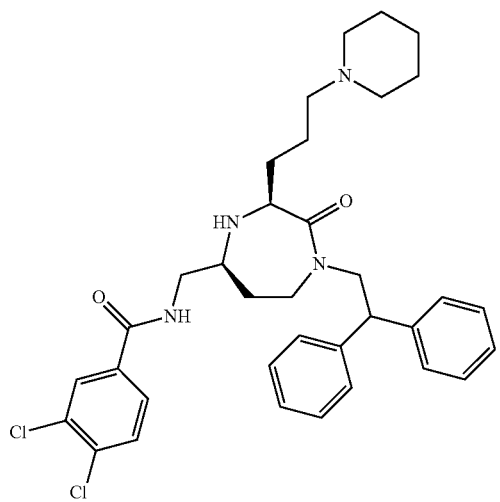
(272)
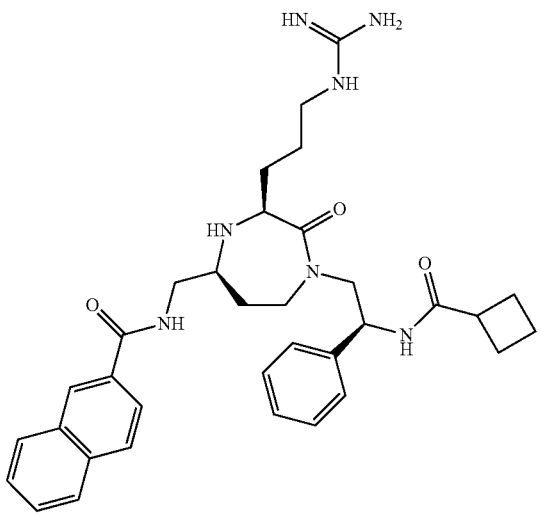
(273)
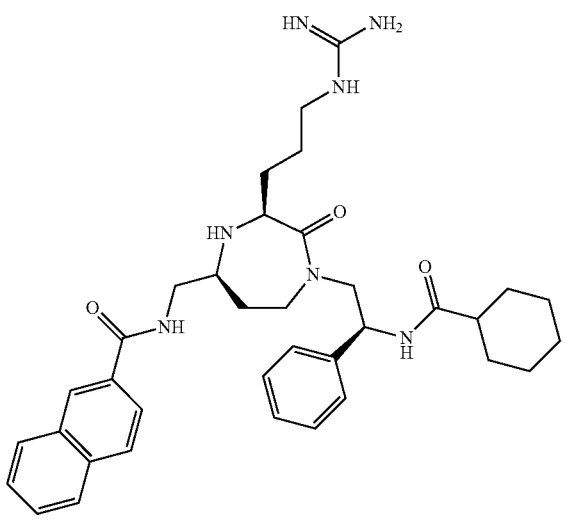
(274)
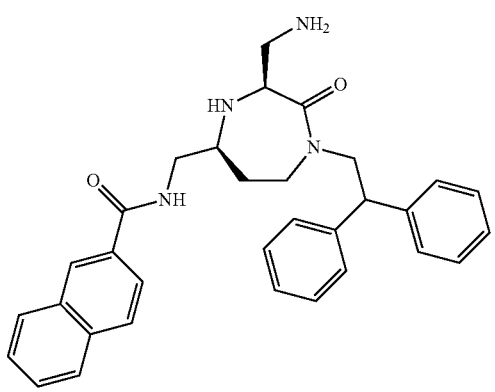
(275)
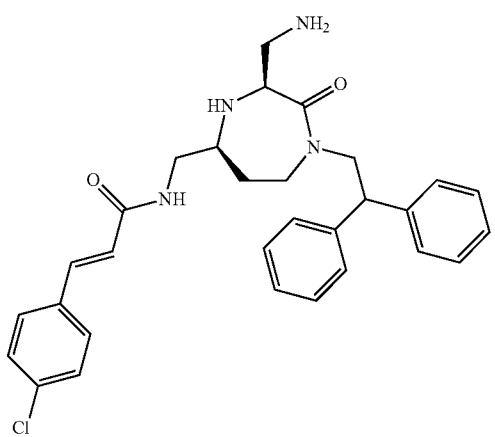

93
-continued
(276)
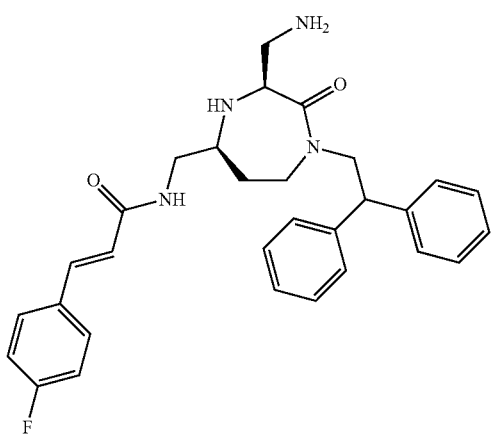
(277)
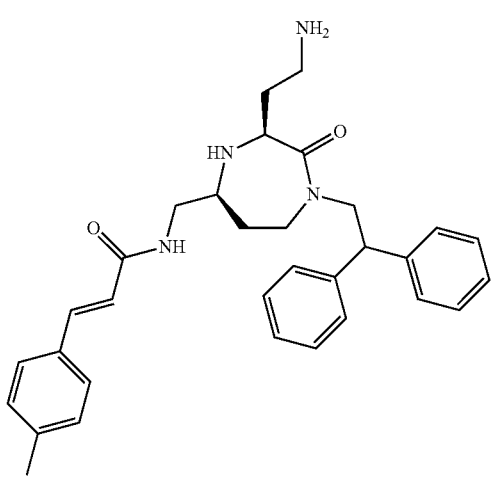
(278)
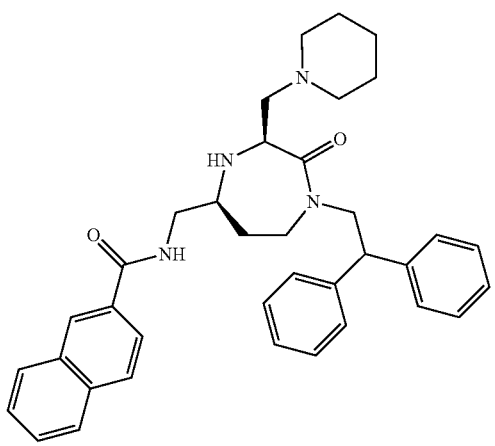
94
-continued
(279)
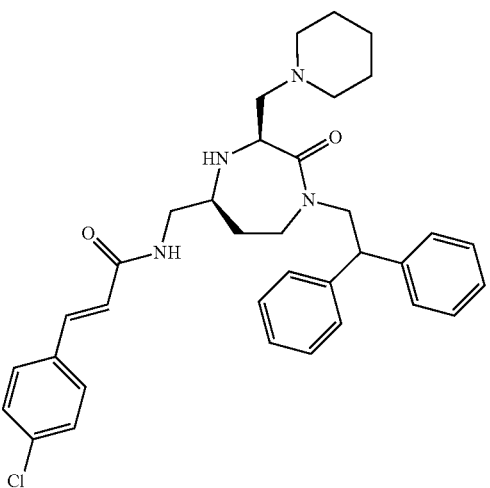
(280)
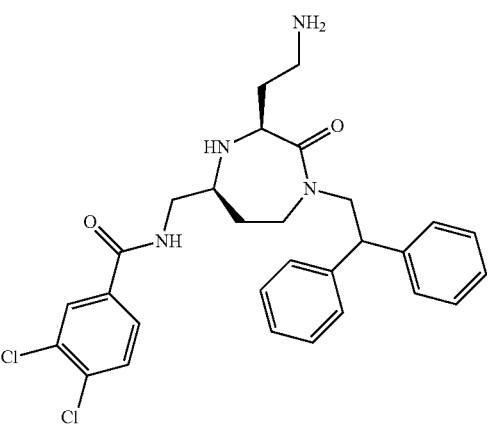
(281)
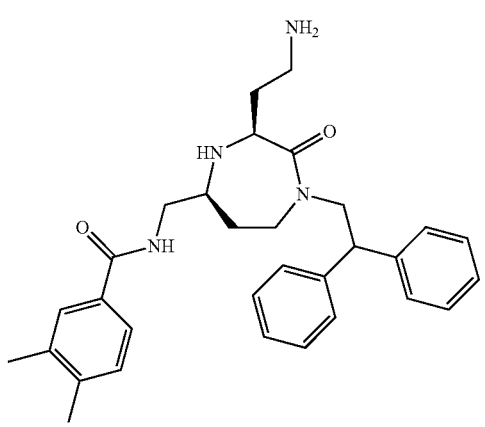

(282)
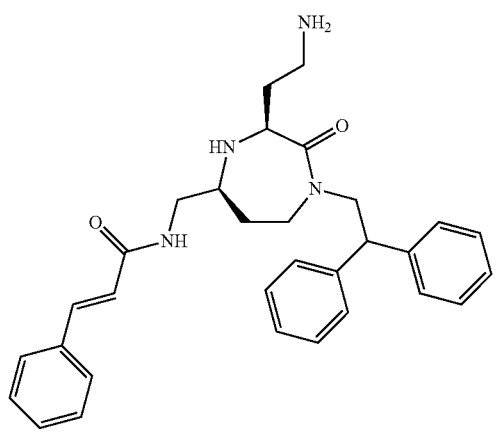
(283)
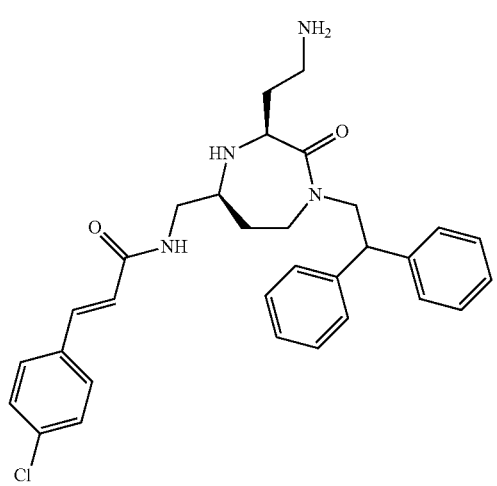
(284)
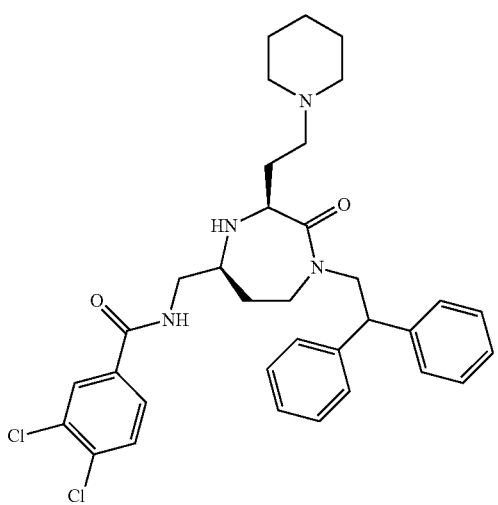
(285)
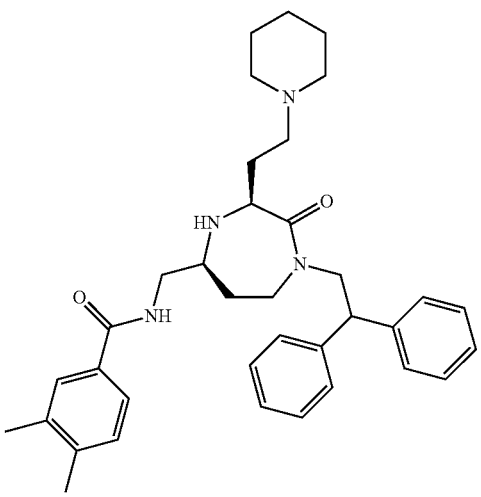
(286)
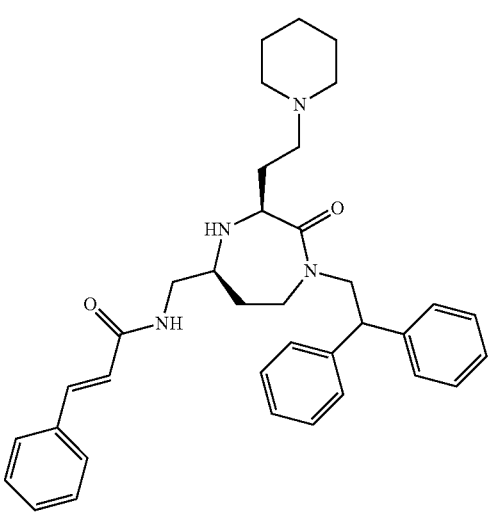
(287)
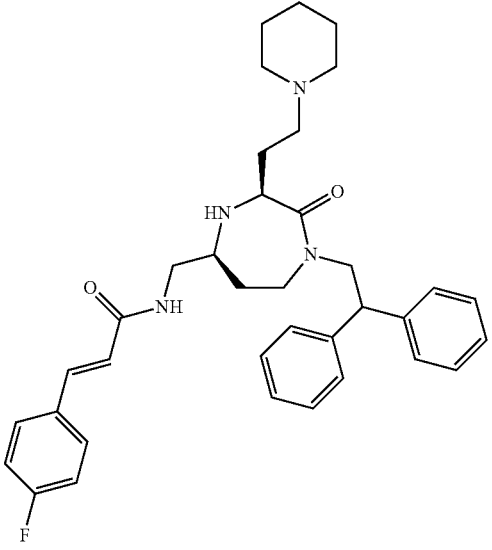

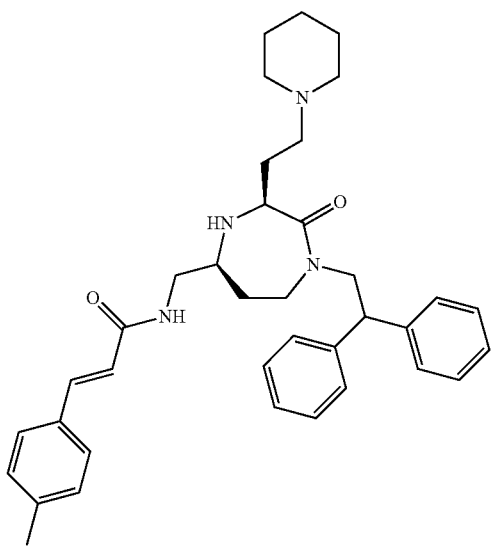
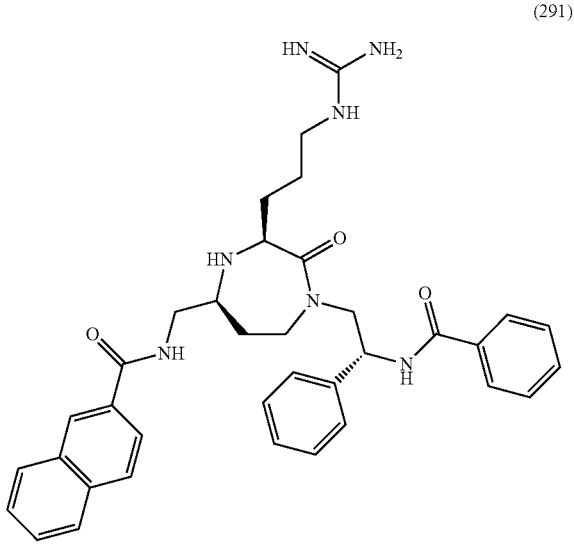

99
(294)
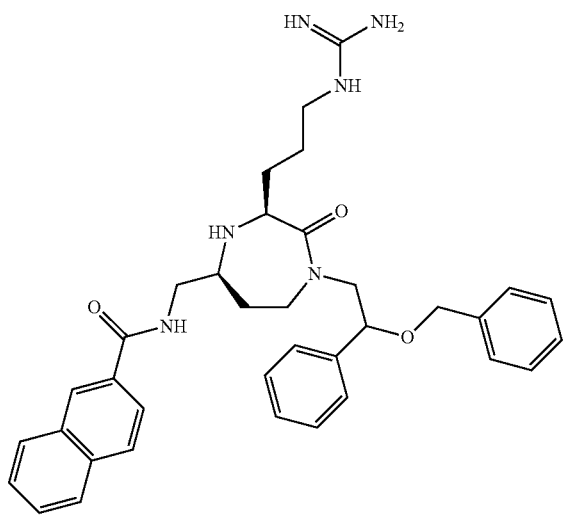
(295)
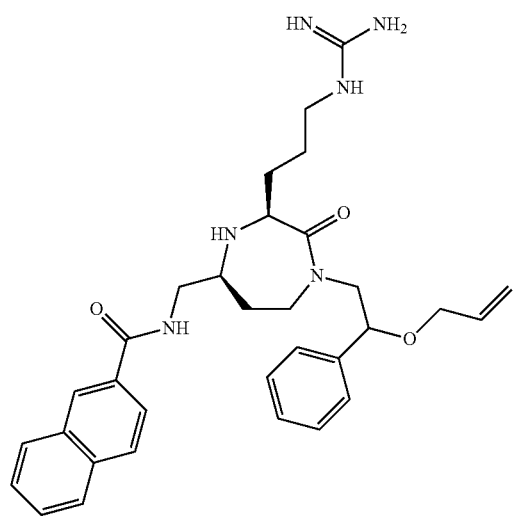
(296)
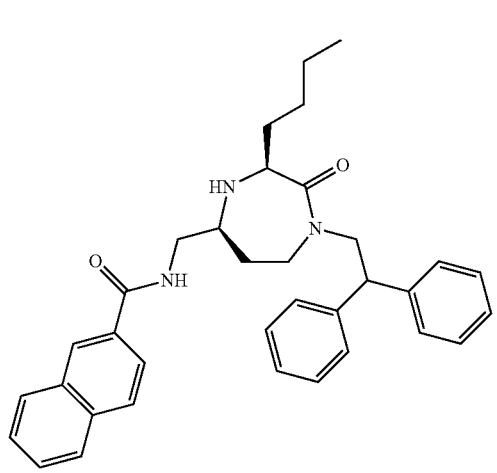
100
(297)
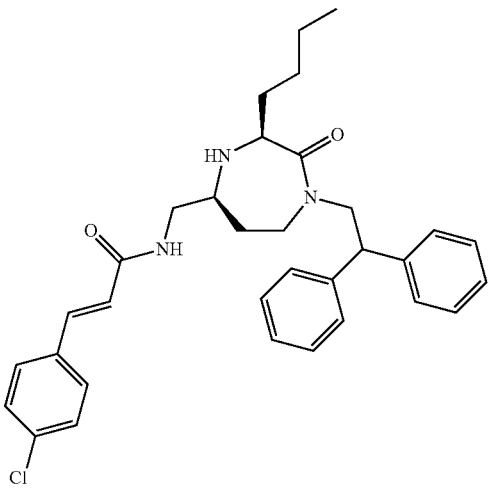
(298)
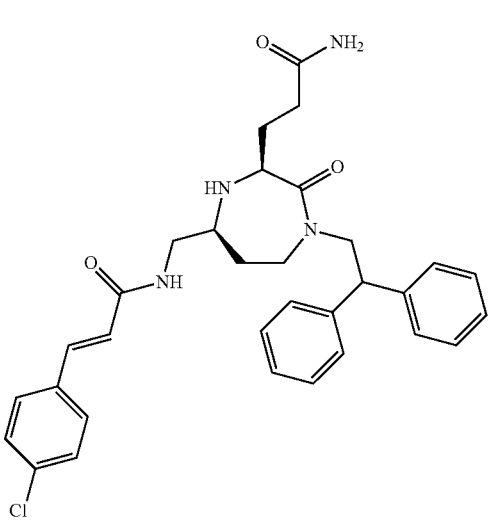
(299)
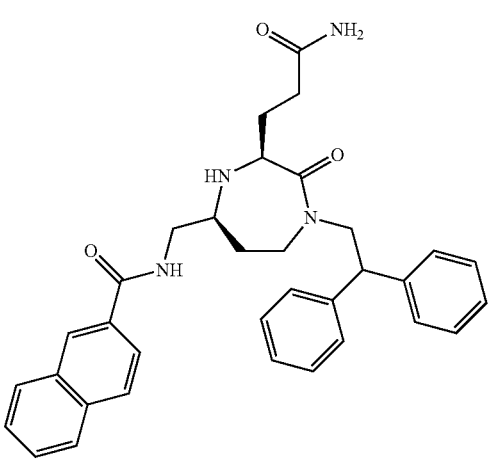

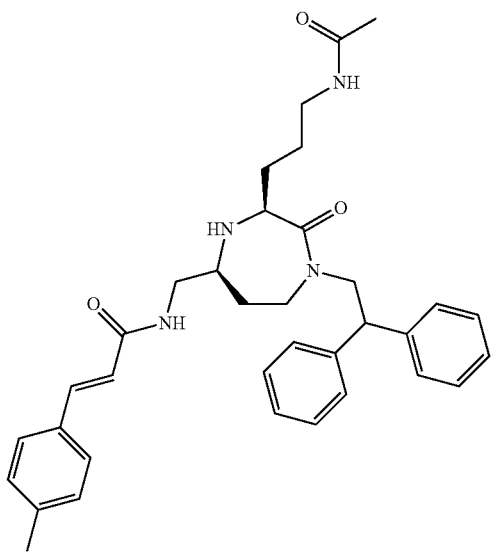
(300)
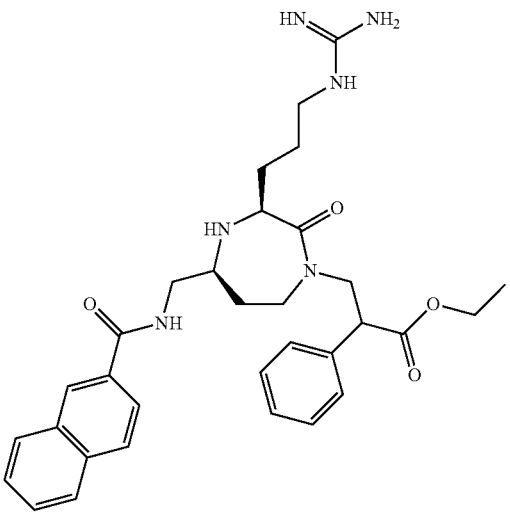
(303)
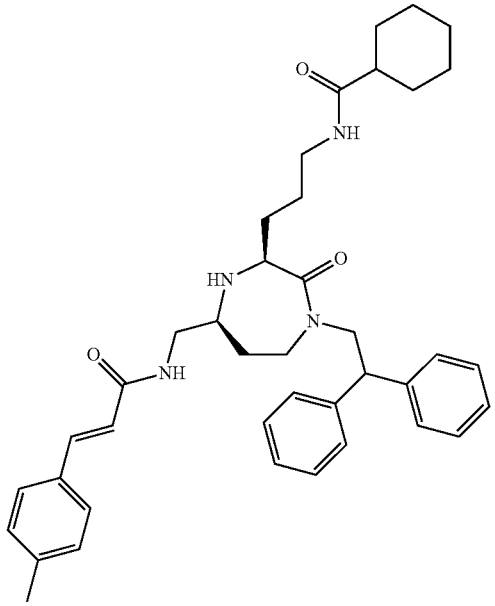
(301)
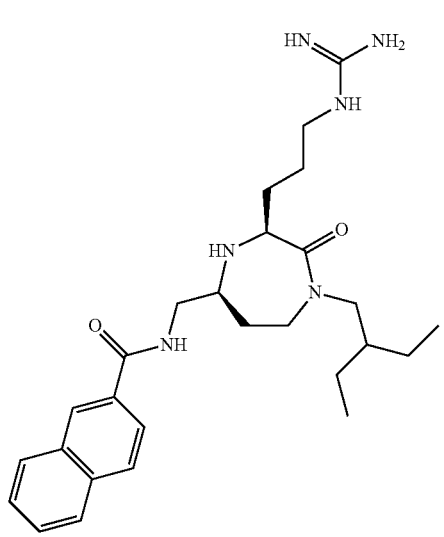
(304)
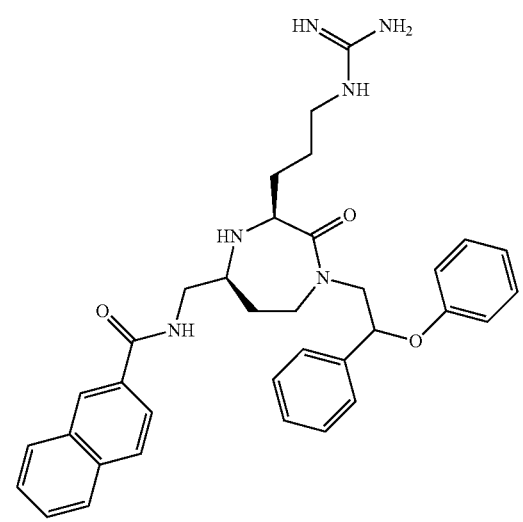
(302)
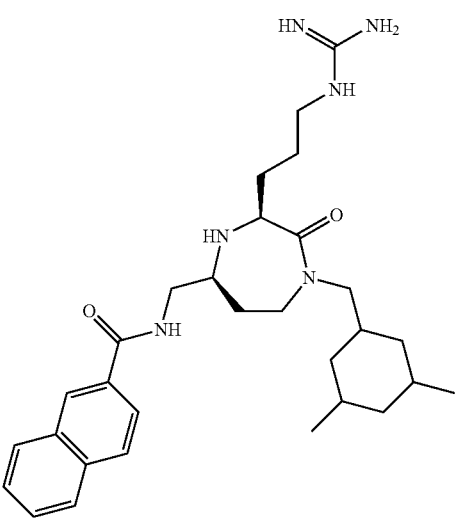
(305)

(306)
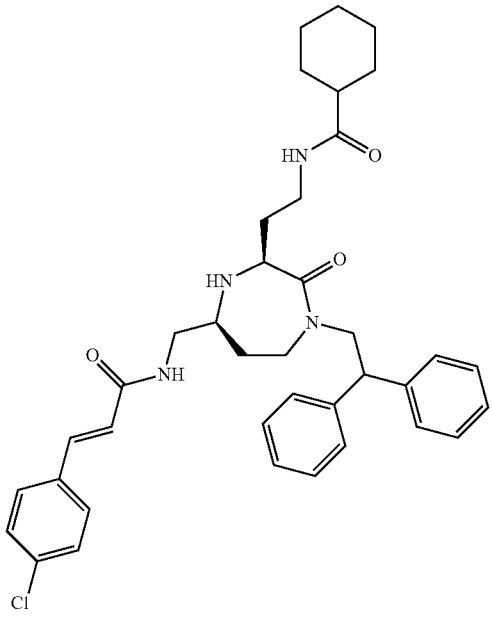
(307)
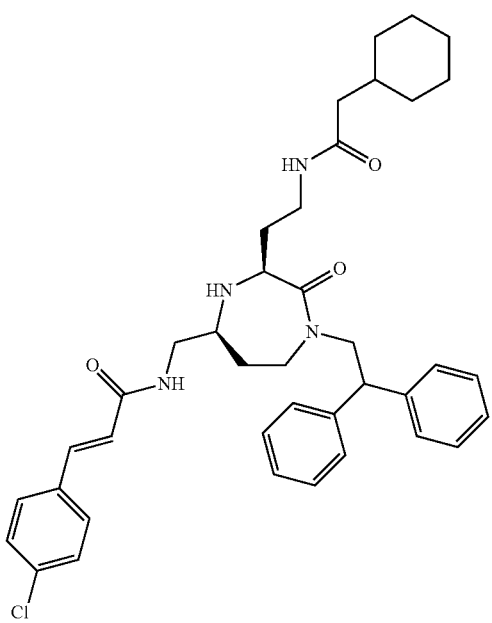
(308)
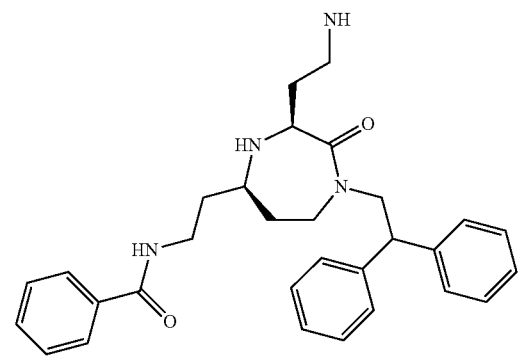
(309)
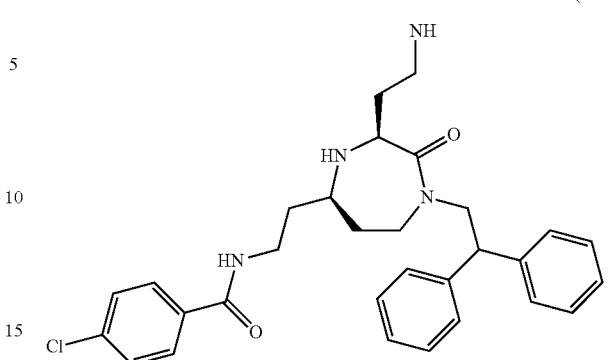
(310)
(311)
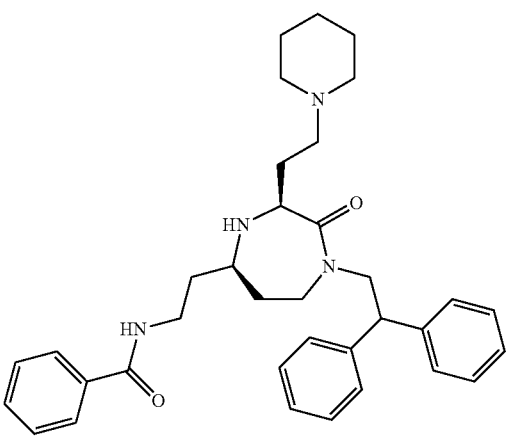

105
-continued
(312)
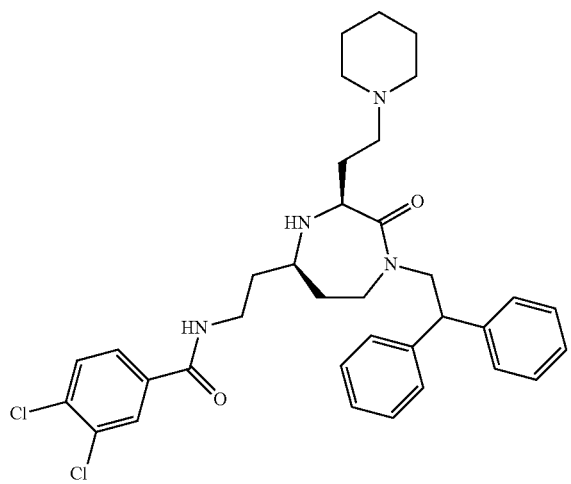
(313)
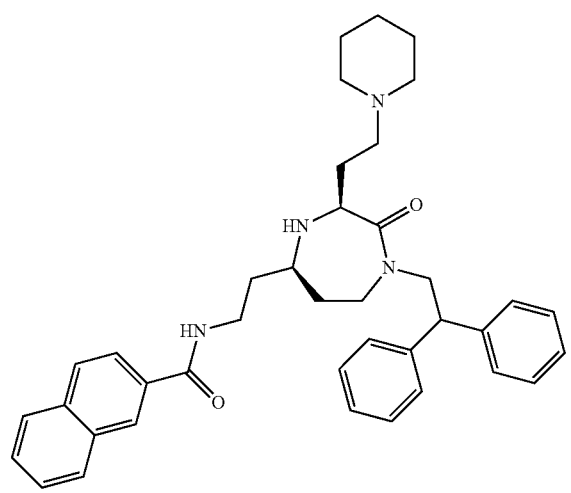
(314)
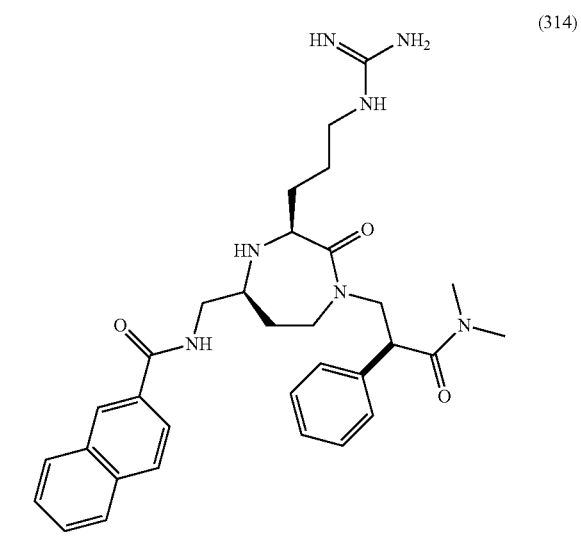
106
-continued
(315)
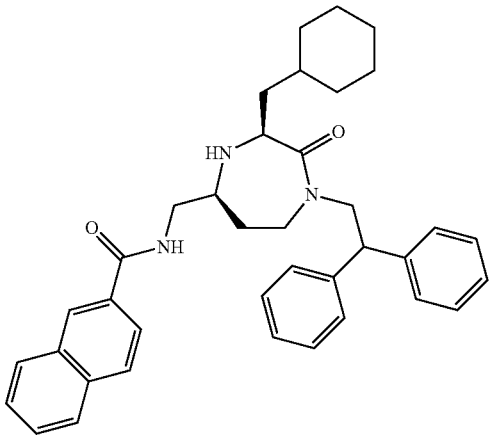
(316)
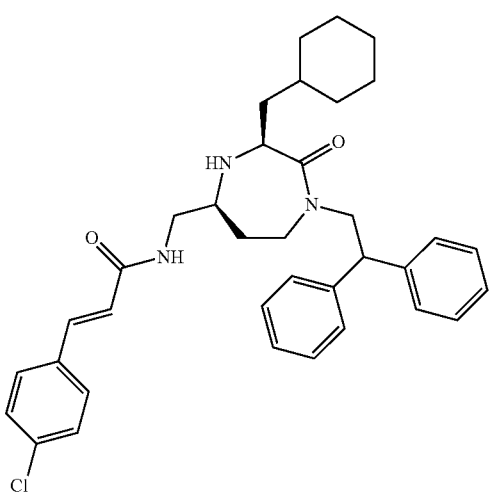
(317)
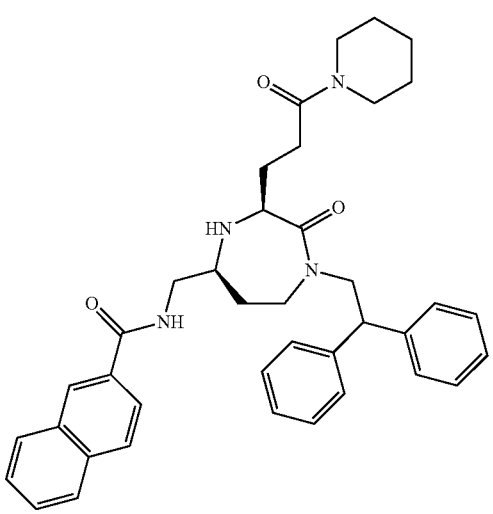

(318)

(319)

(320)

(321)

(322)

(323)

(324)
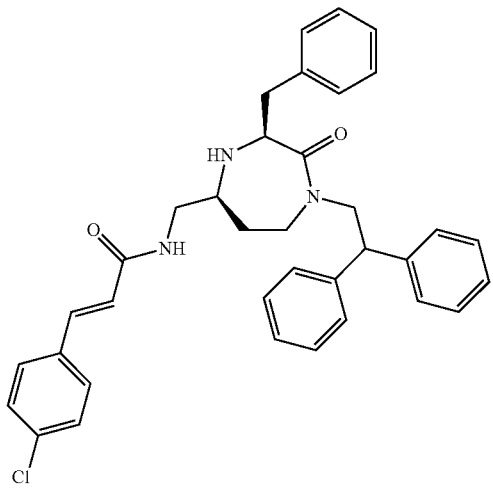
(325)
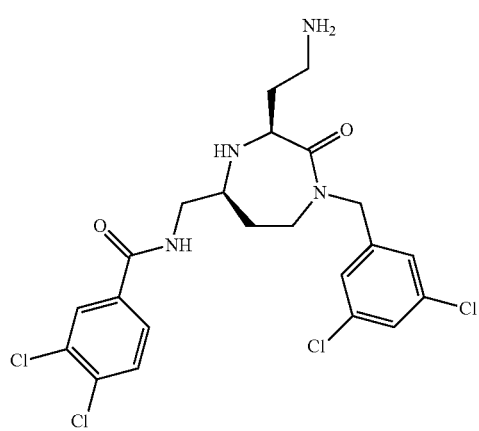
(326)
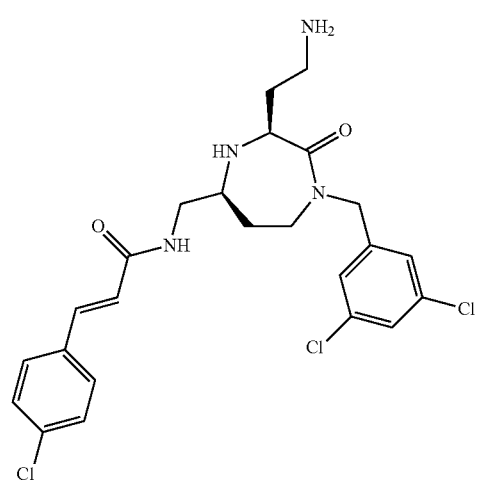
(327)
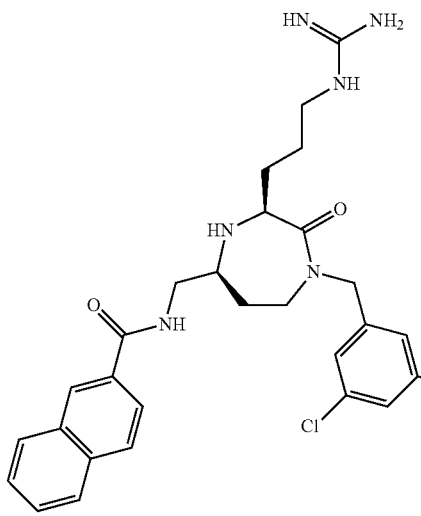
(328)
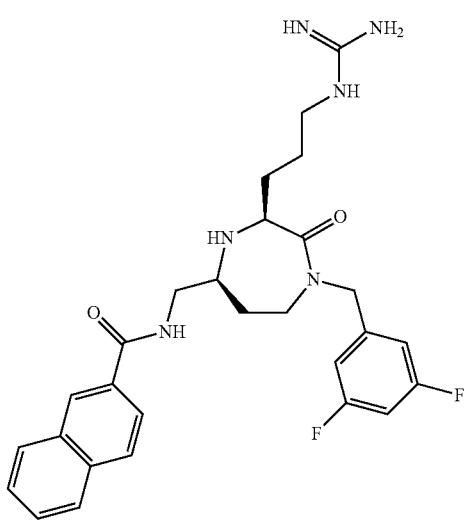
(329)
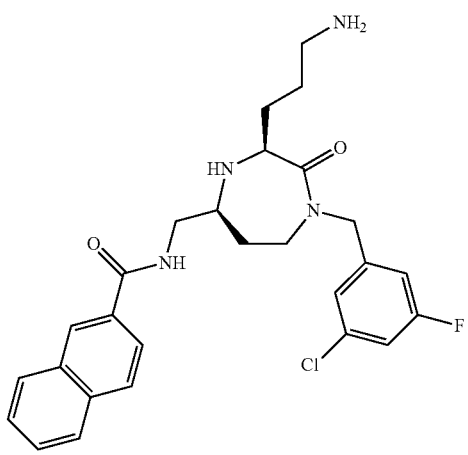

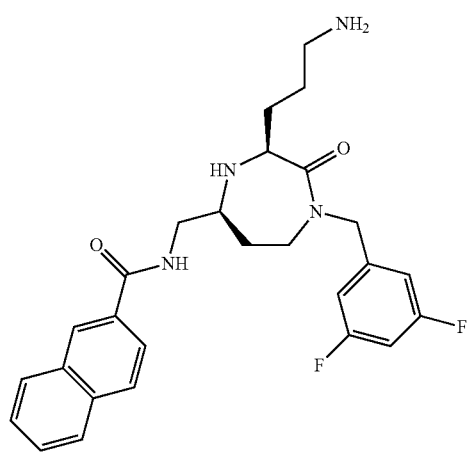
(330)
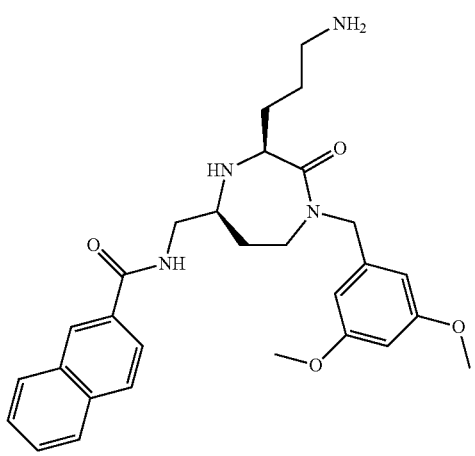
(333)
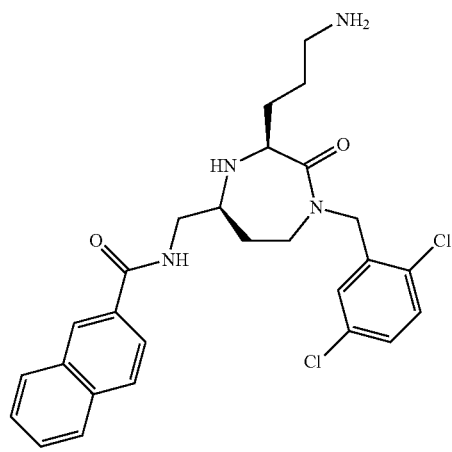
(331)
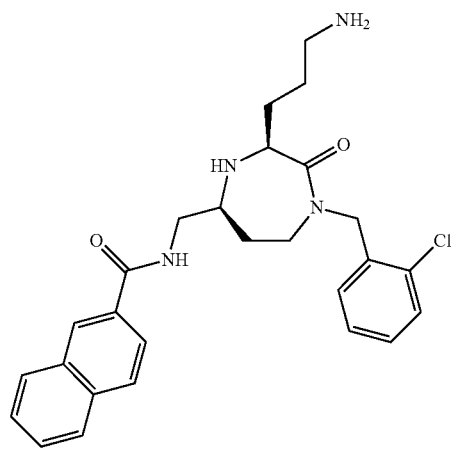
(334)
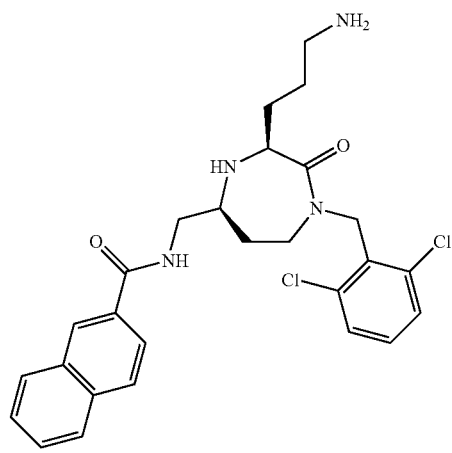
(332)
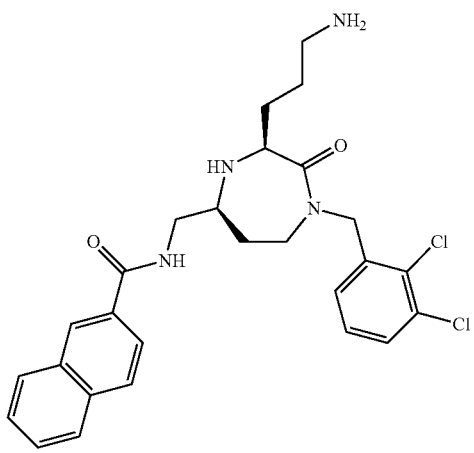
(335)

(336)
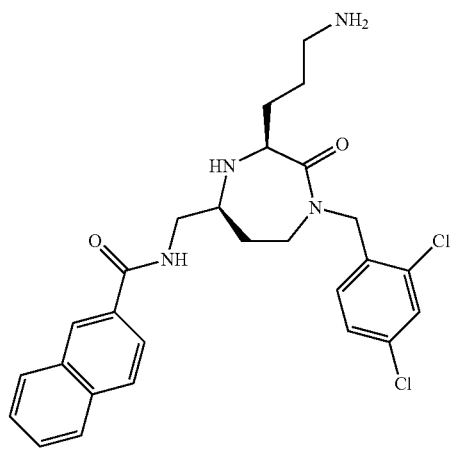
(337)
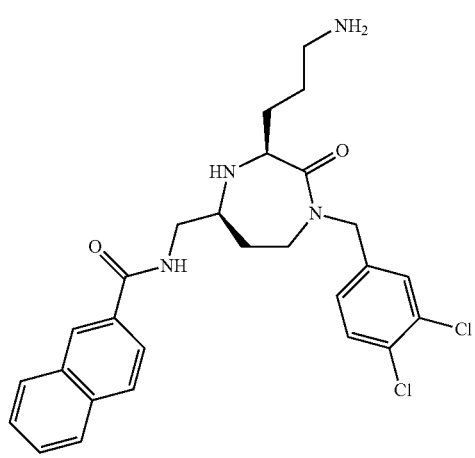
(338)
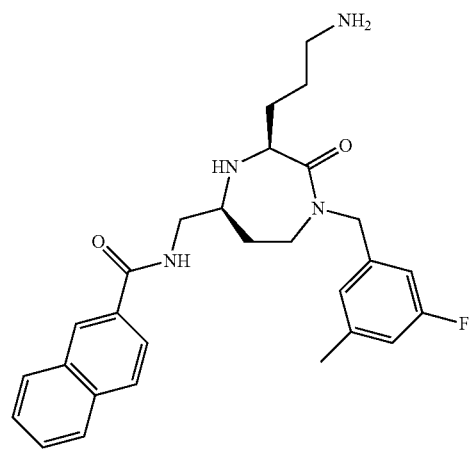
(339)
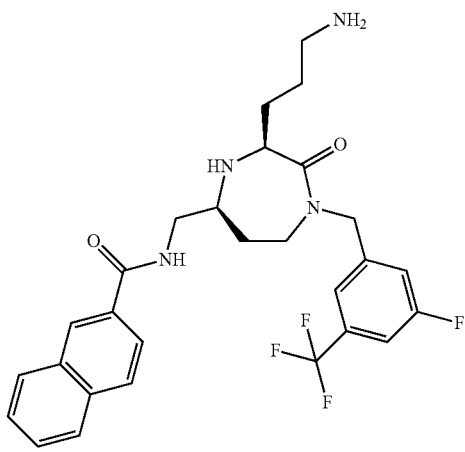
(340)
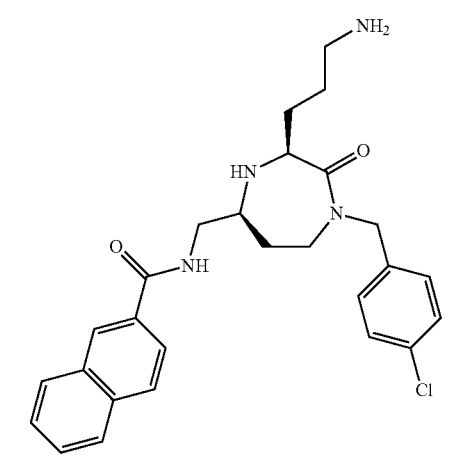
(341)
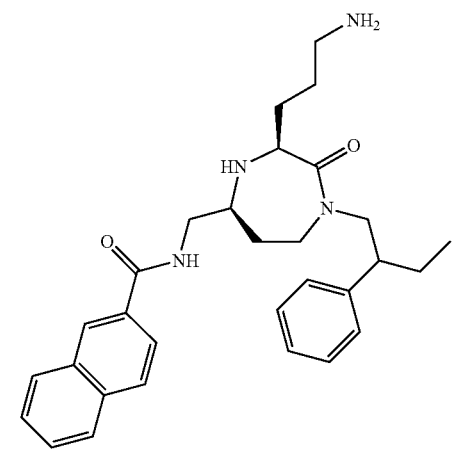

(342)
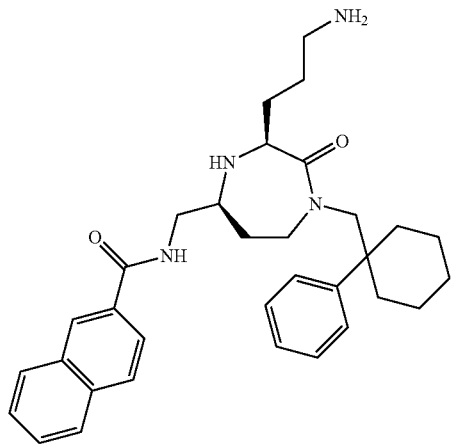
(343)
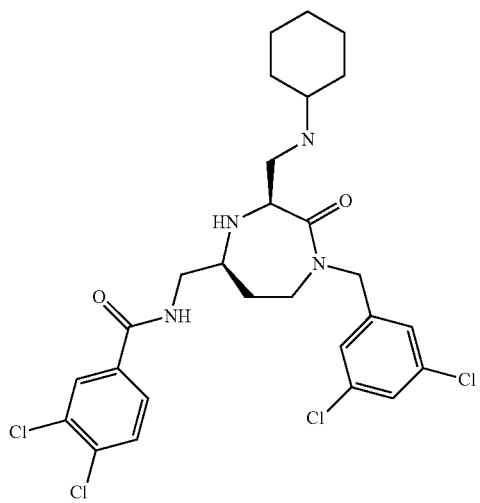
(344)
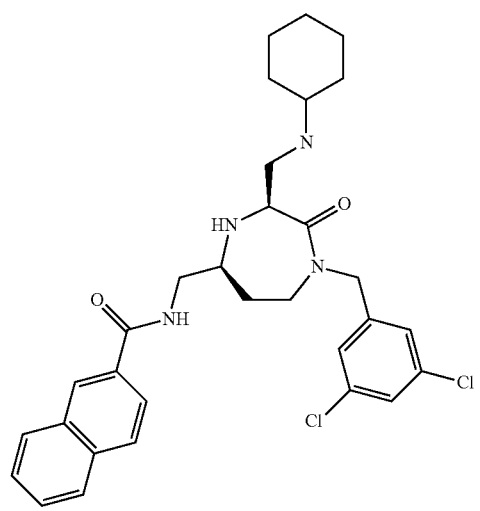
(345)
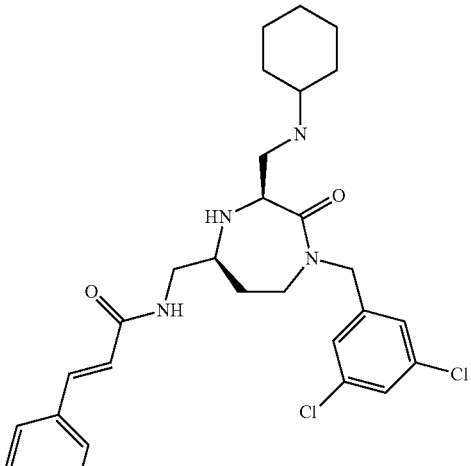
(346)
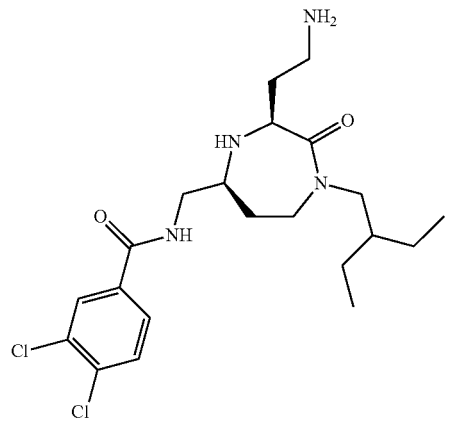
(347)
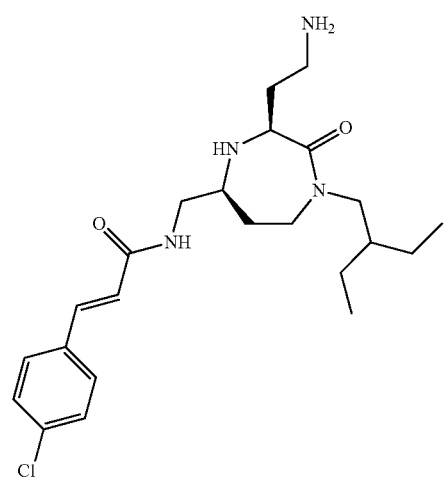

117
-continued
(348)
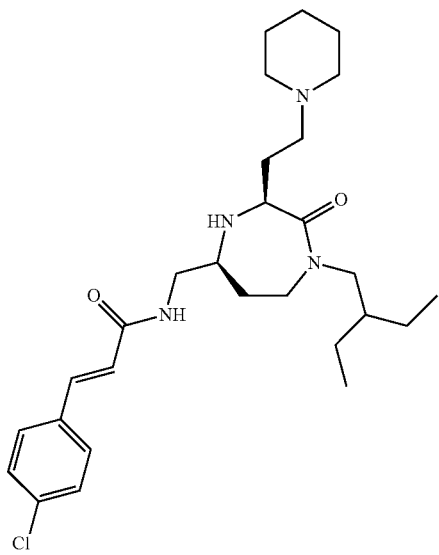
(349)
(350)
118
-continued
(351)
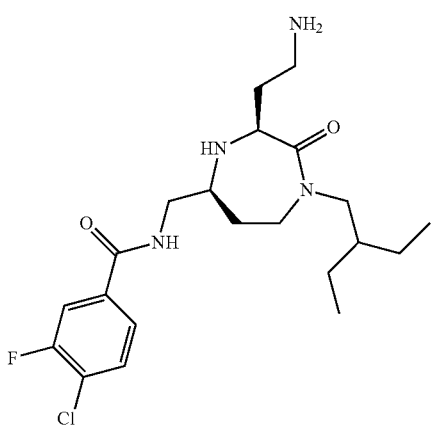
(352)
(353)
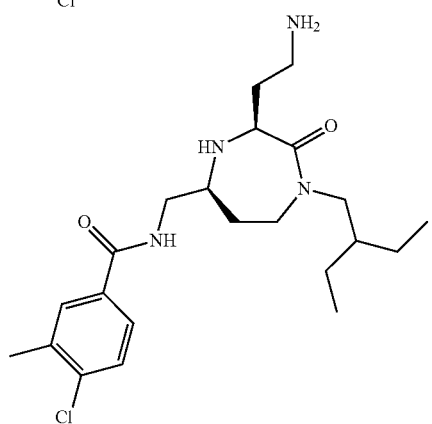
(354)
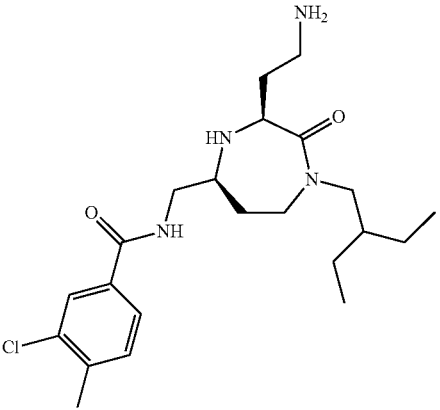

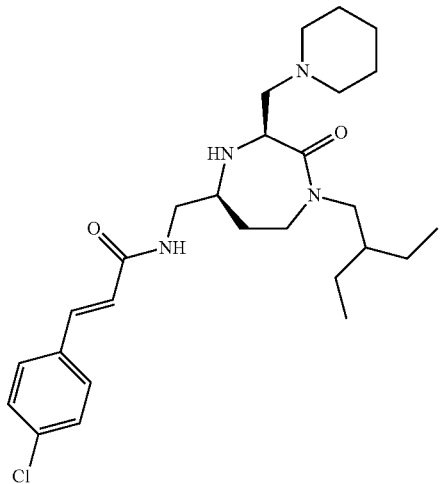
(355)
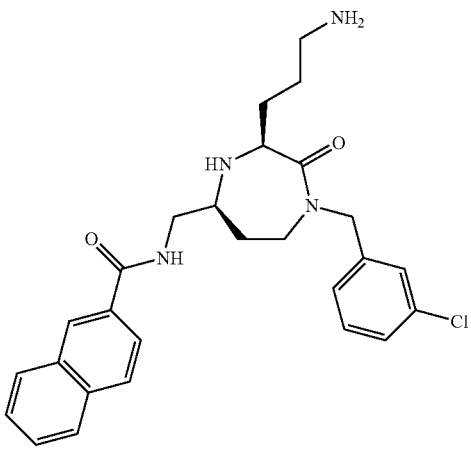
(358)
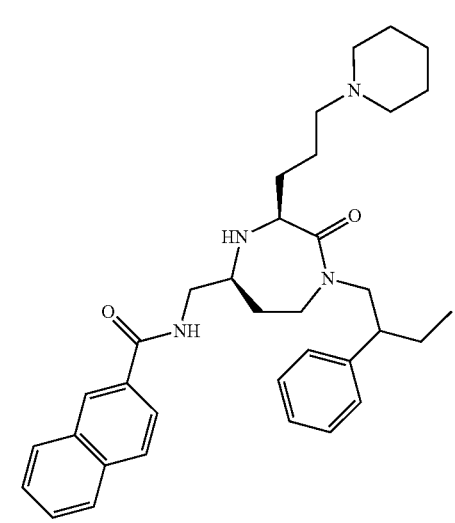
(356)
(359)
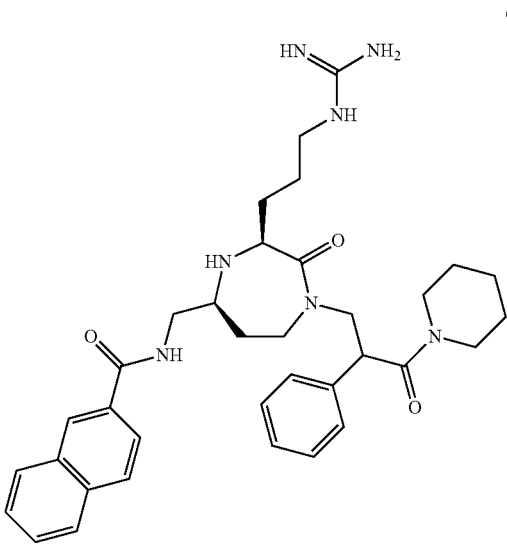
(357)
(360)

(361) 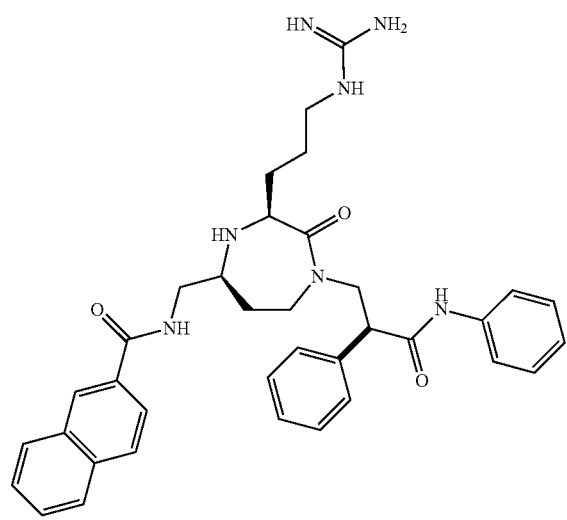
(362) 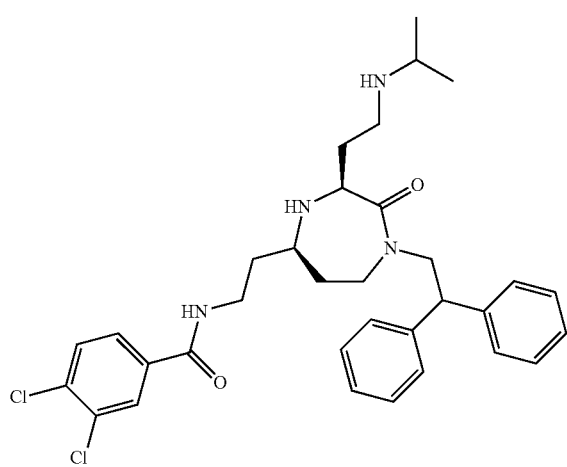
(363) 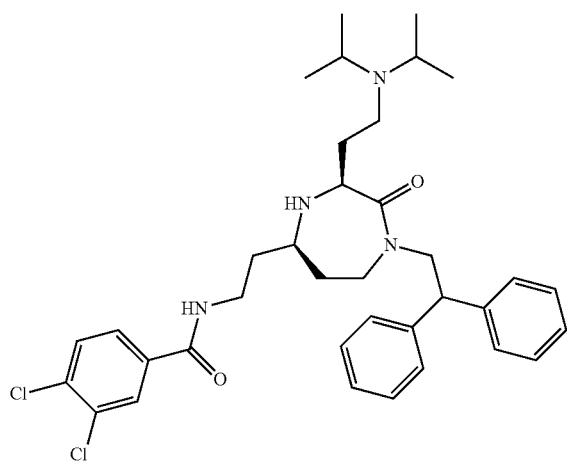
(364) 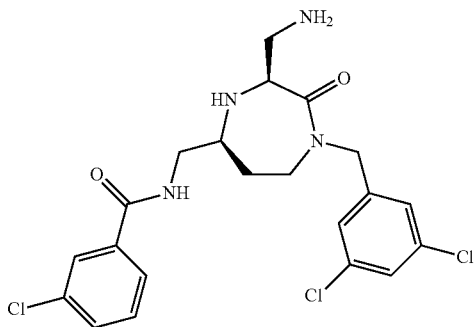
(365) 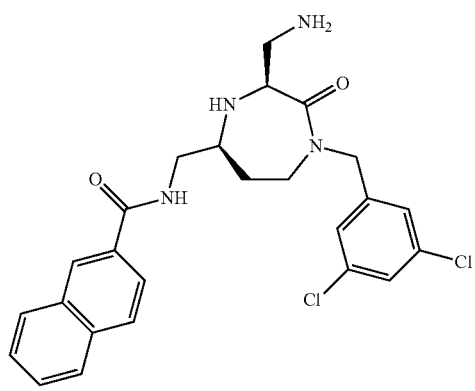
(366) 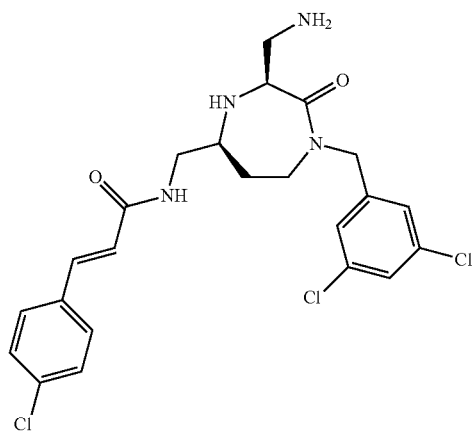
(367) 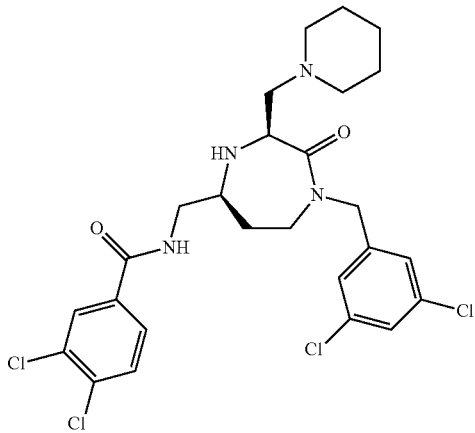

(368)
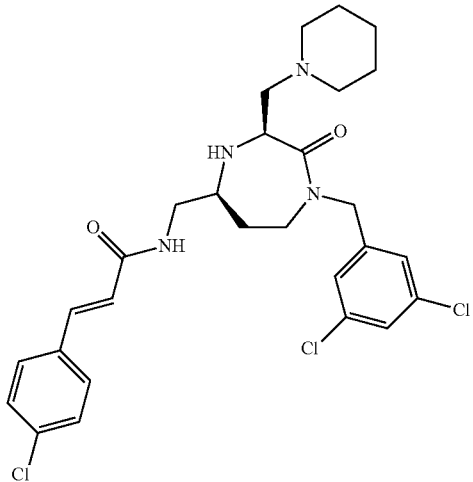
(369)
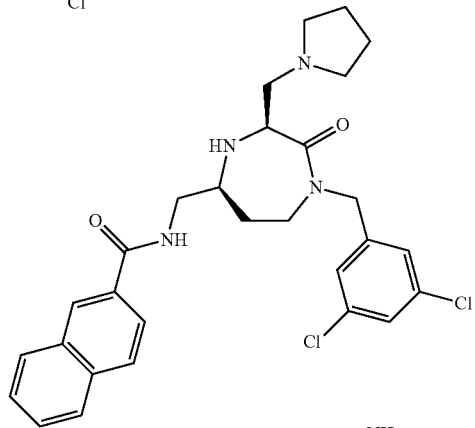
(370)
(371)
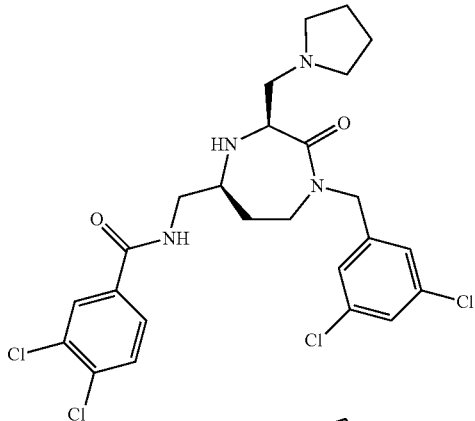
(372)
(373)
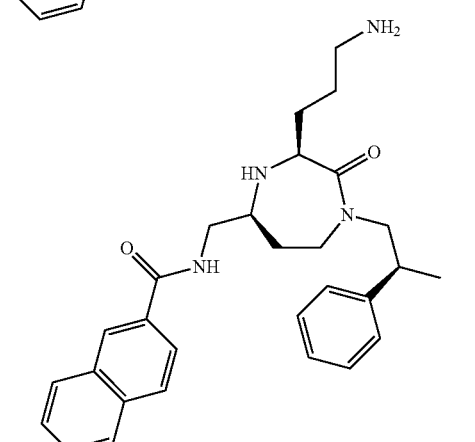
(374)
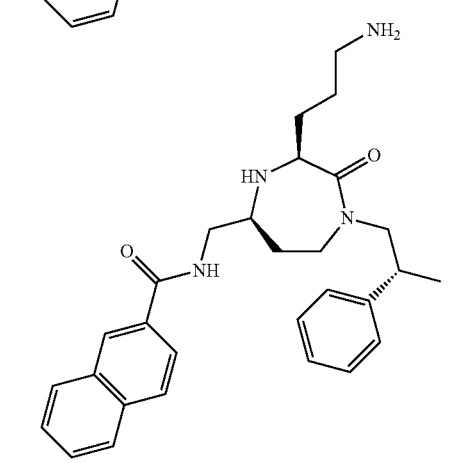

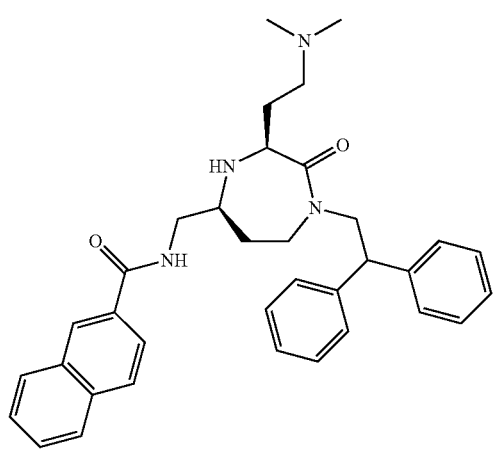
(375)
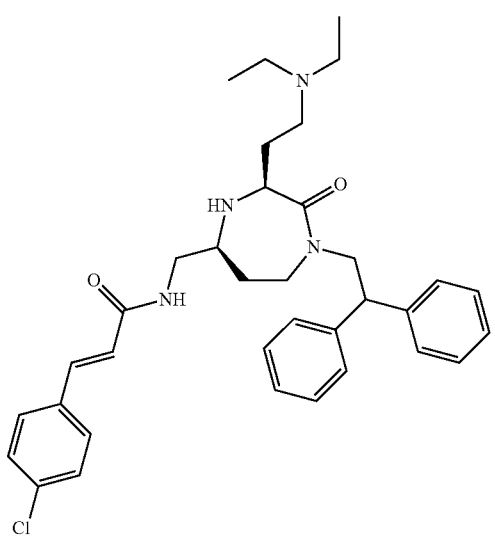
(378)
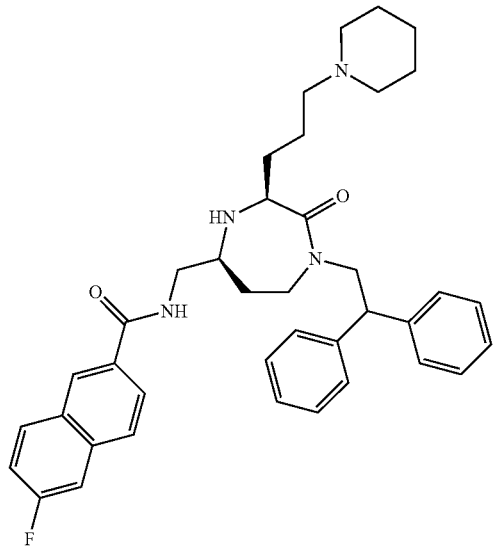
(376)
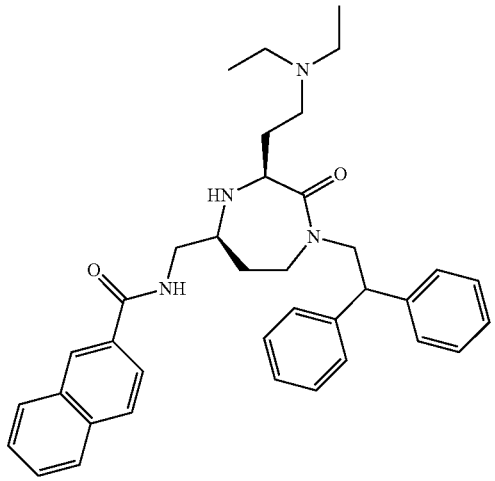
(379)
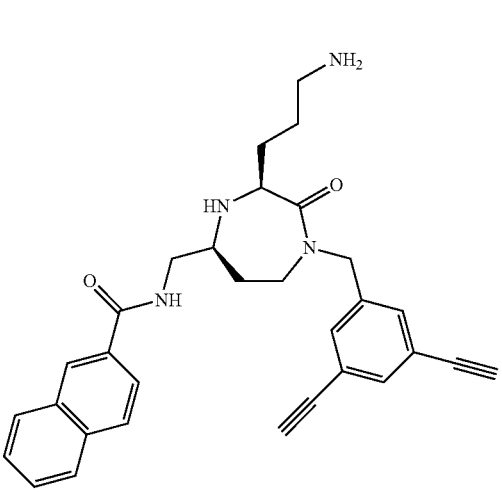
(377)
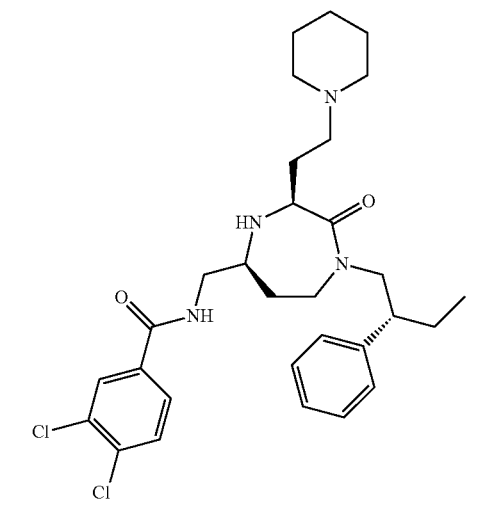
(380)

127
-continued
(381)
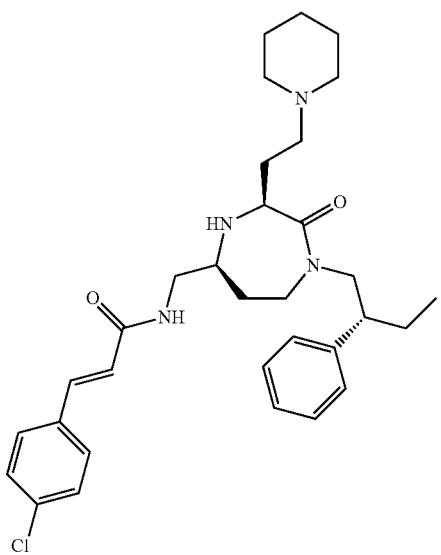
(382)
(383)
128
-continued
(384)
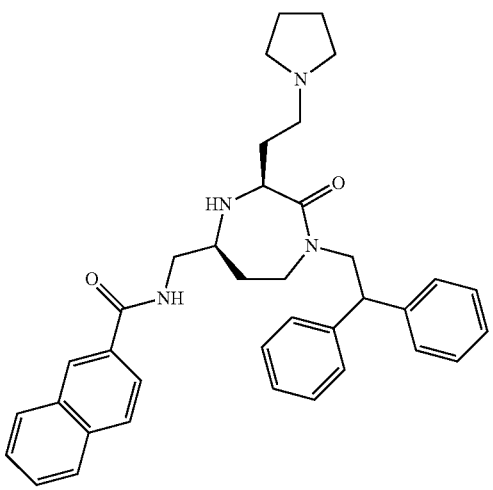
(385)
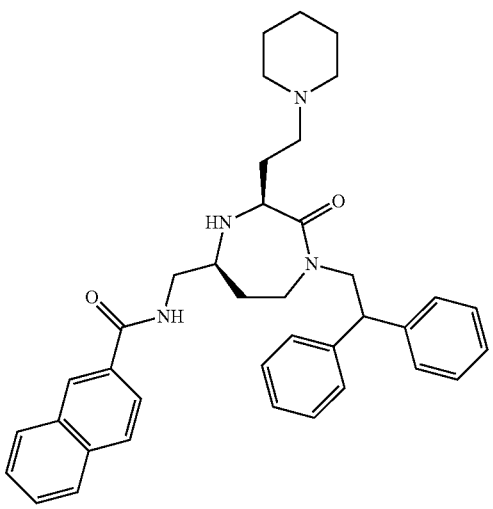
(386)
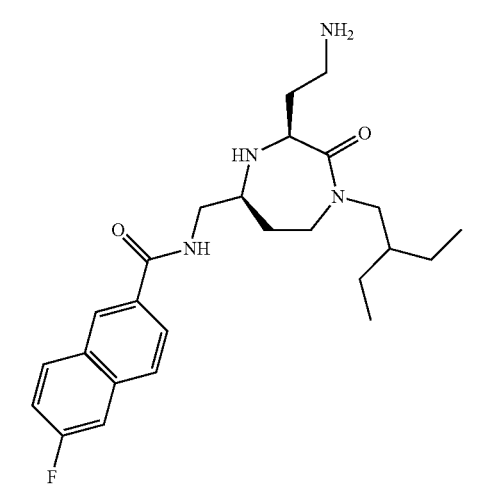

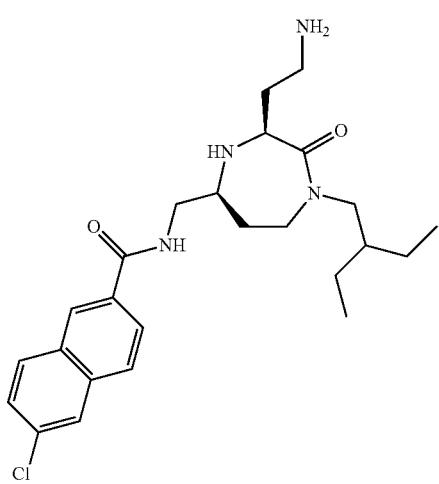
(387)
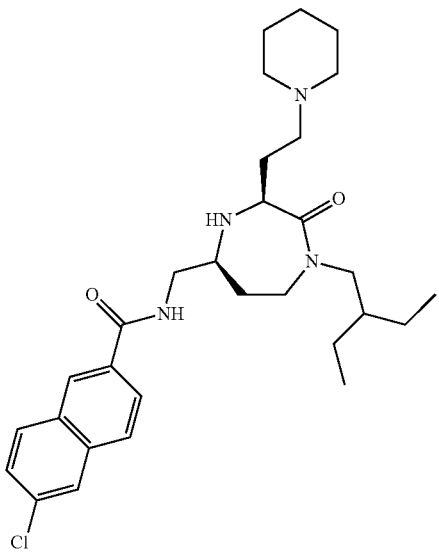
(390)
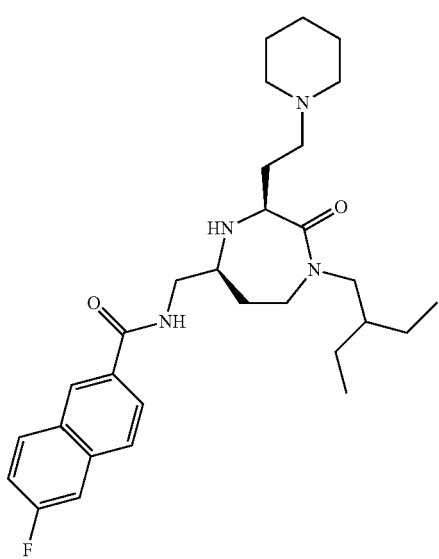
(388)
(389)
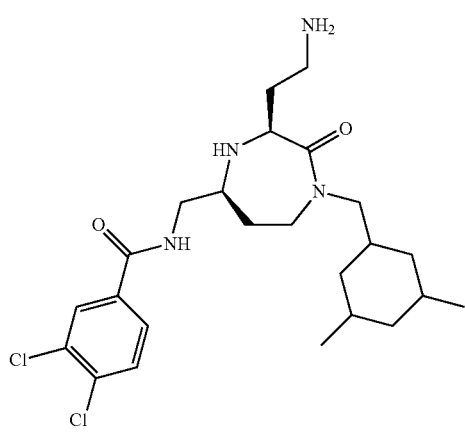
(391)
(392)

-continued
(393)
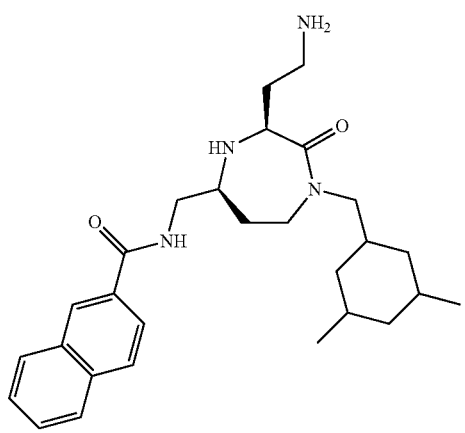
(394)
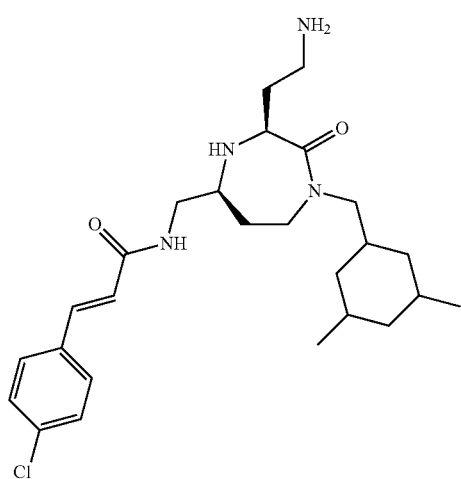
(395)
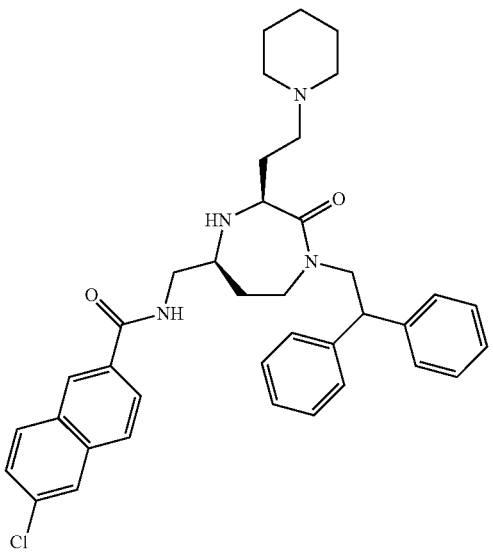
-continued
(396)
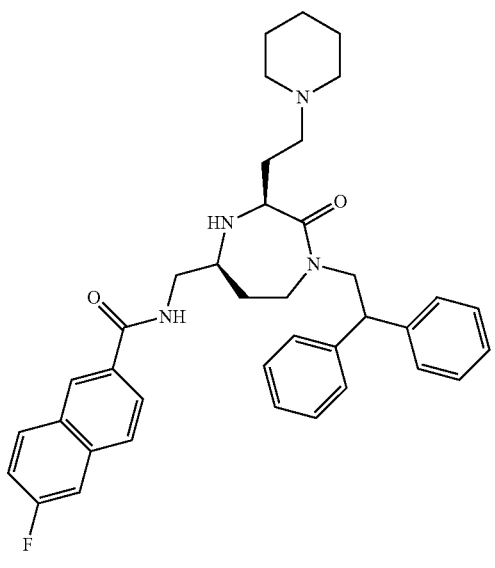
(397)
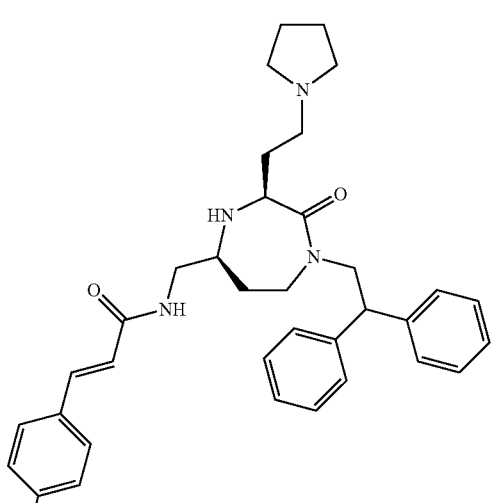
(398)
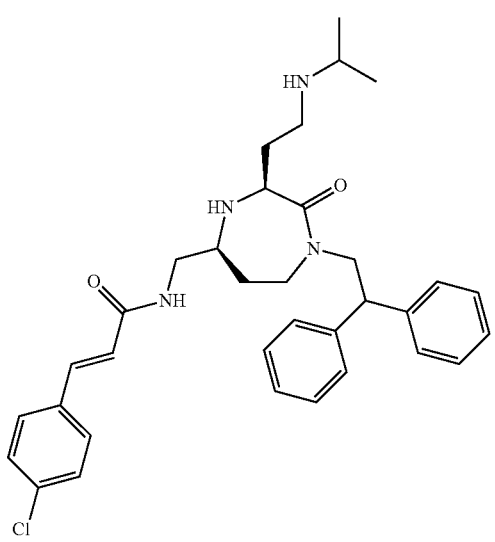

133
-continued
(399)
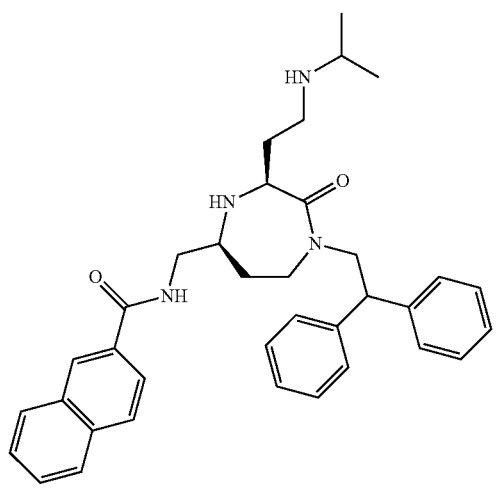
(400)
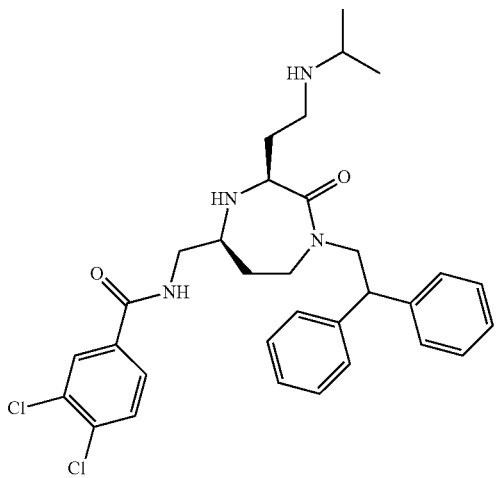
(401)
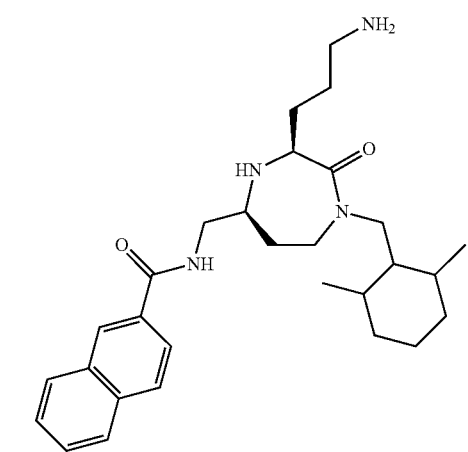
134
-continued
(402)
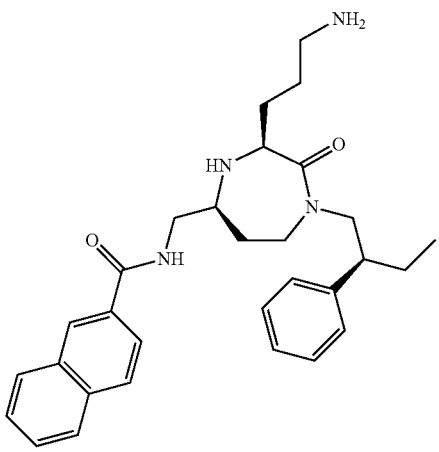
(403)
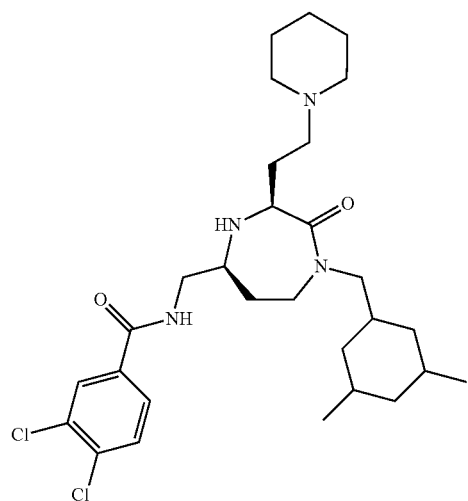
(404)
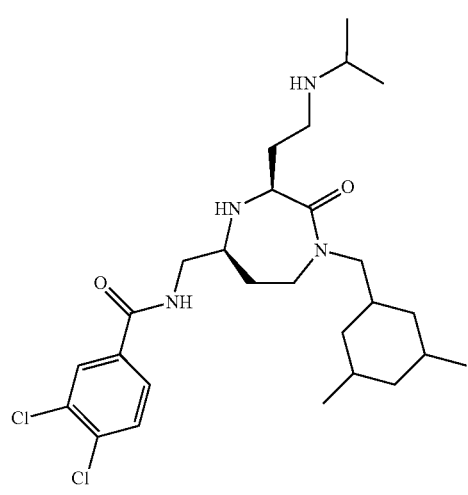

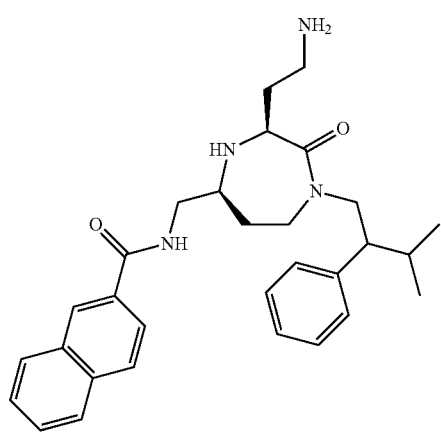
(405)
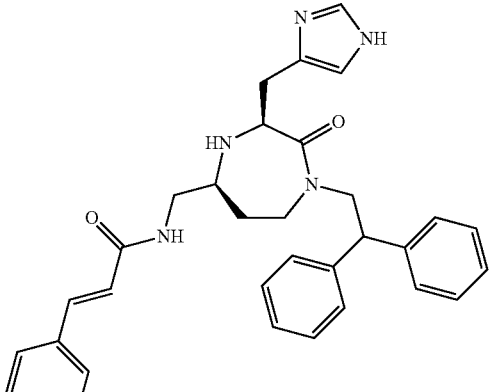
(408)
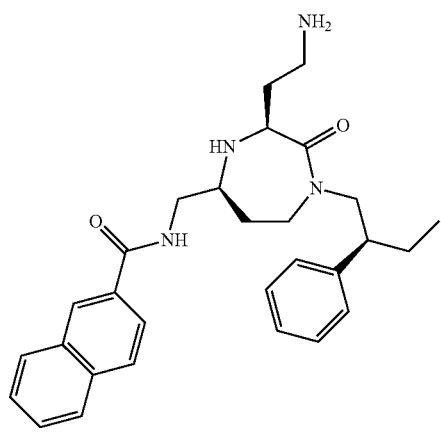
(406)
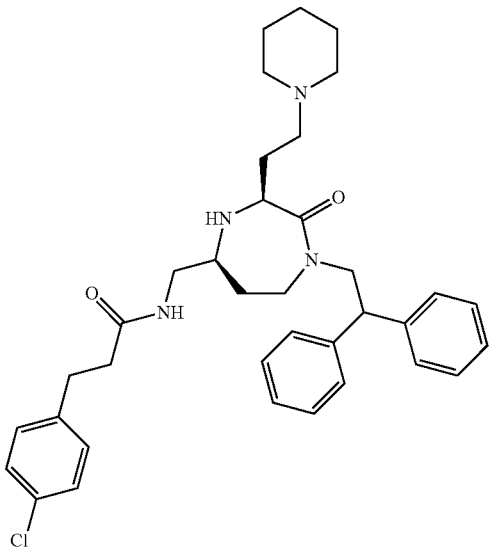
(409)
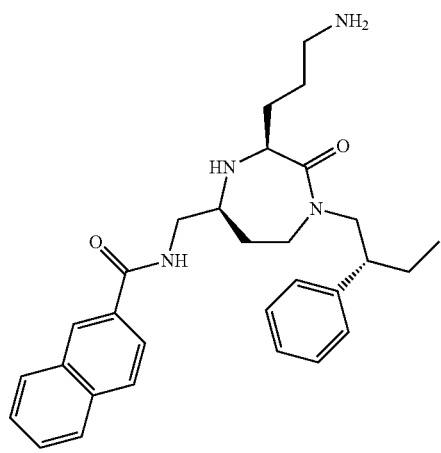
(407)
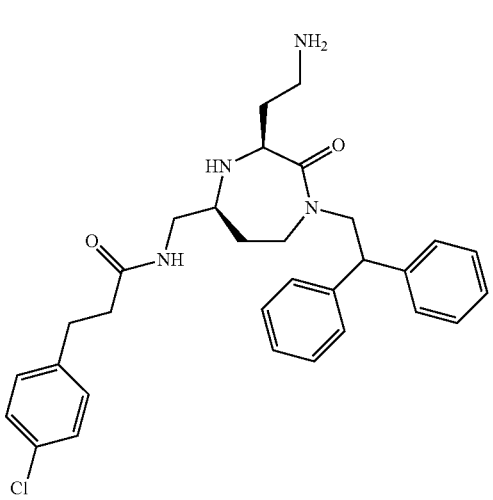
(410)

137
(411)
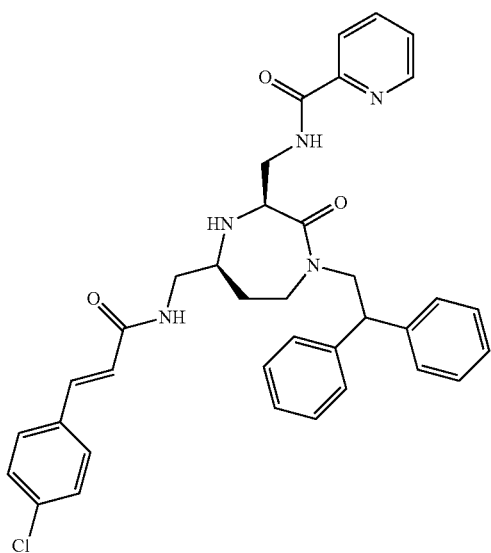
(412)
(413)
138
(414)
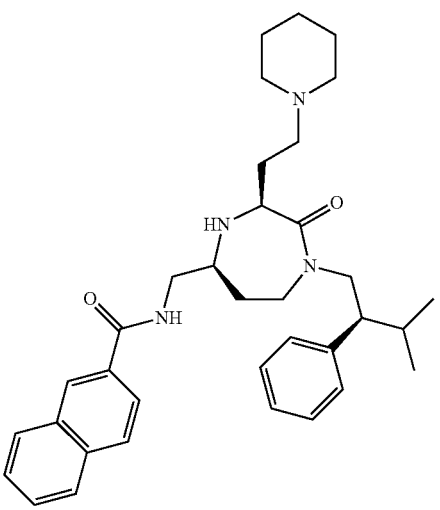
(415)
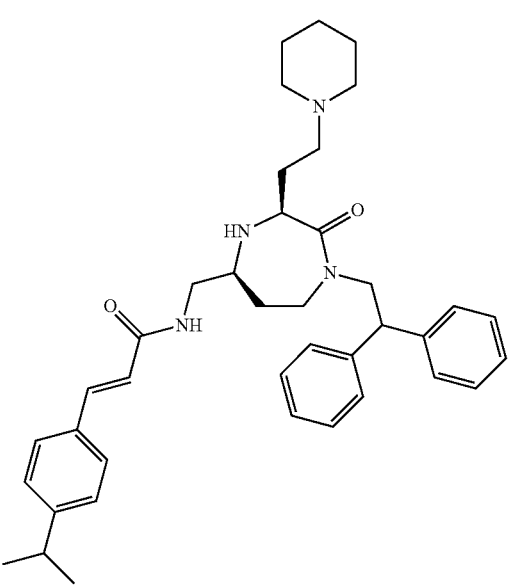
(416)
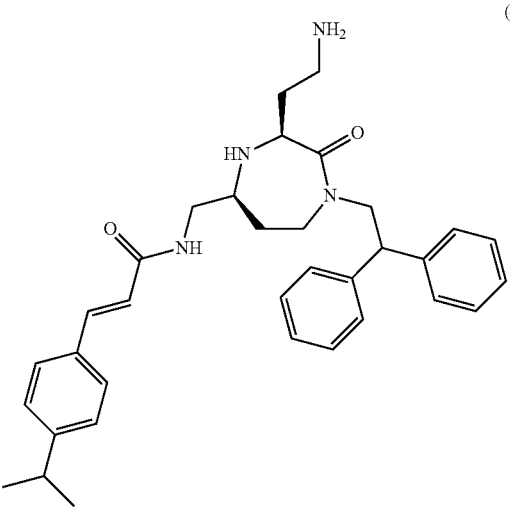

139 -continued (417)

140 -continued (420)

(418)

(421)

(419)

(422)

141
-continued
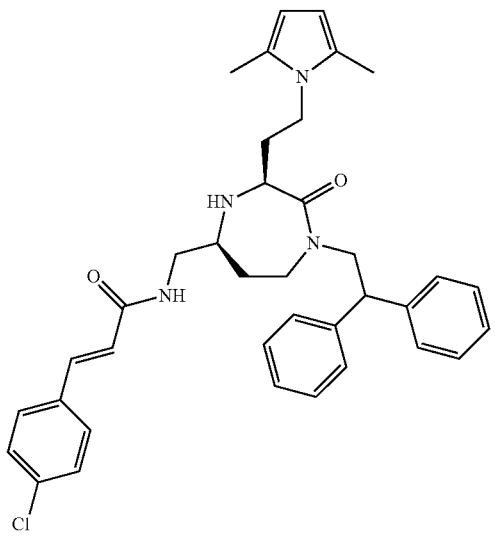
(423)
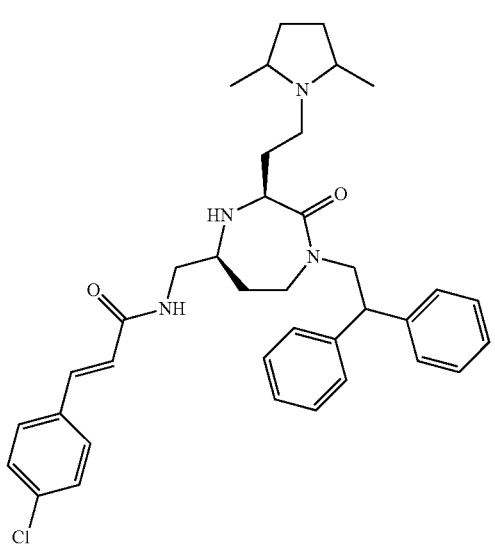
(424)
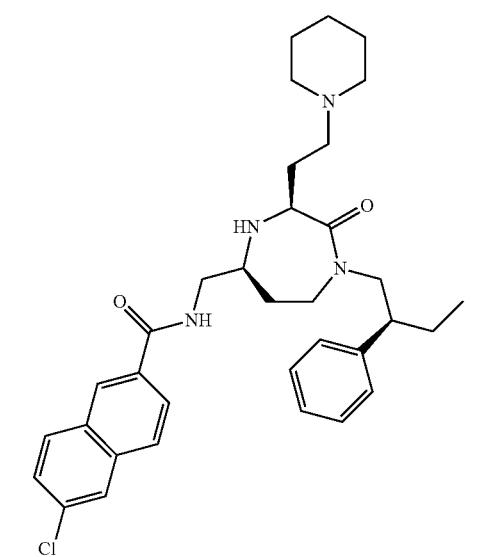
(425)
142
-continued
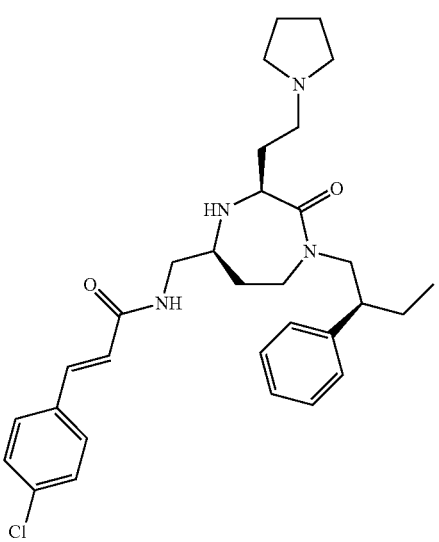
(426)
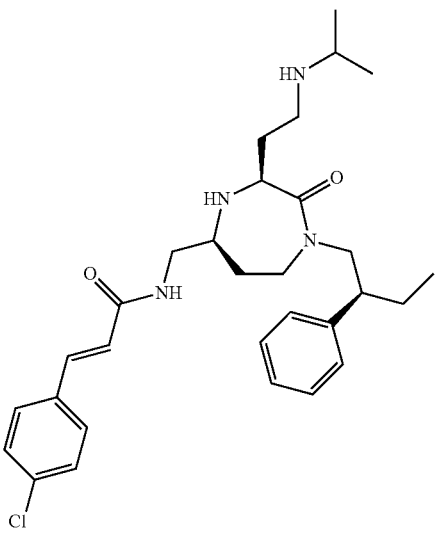
(427)
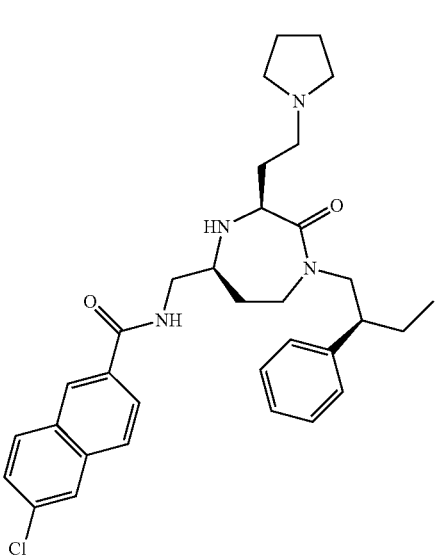
(428)

(429)
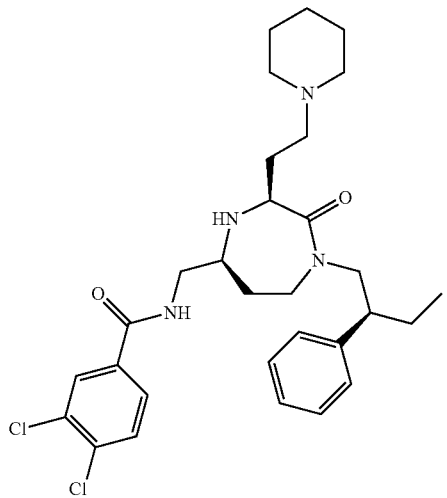
(430)
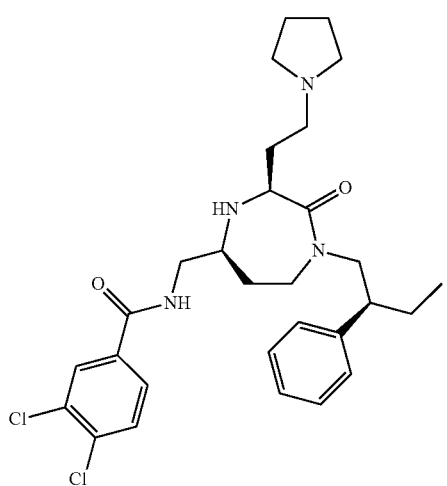
(431)
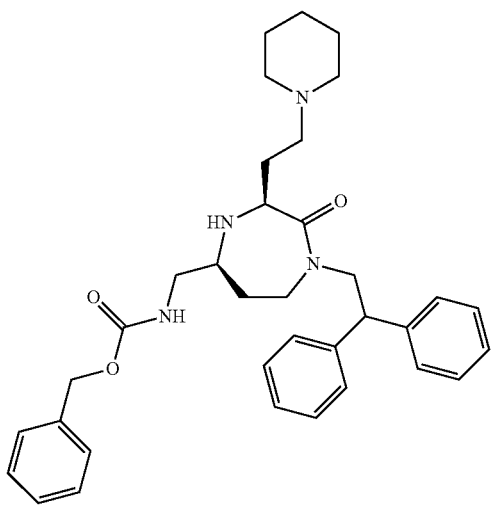
(432)
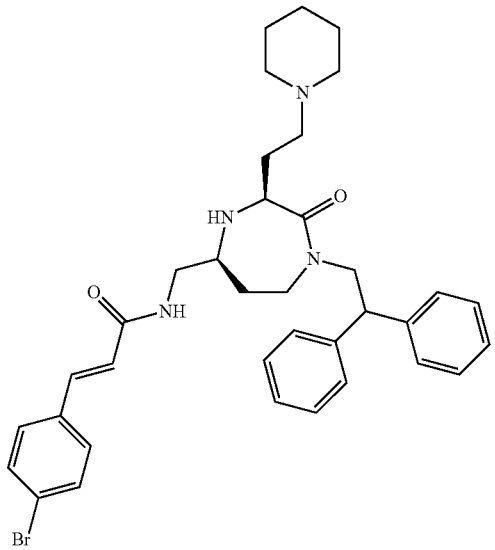
(433)
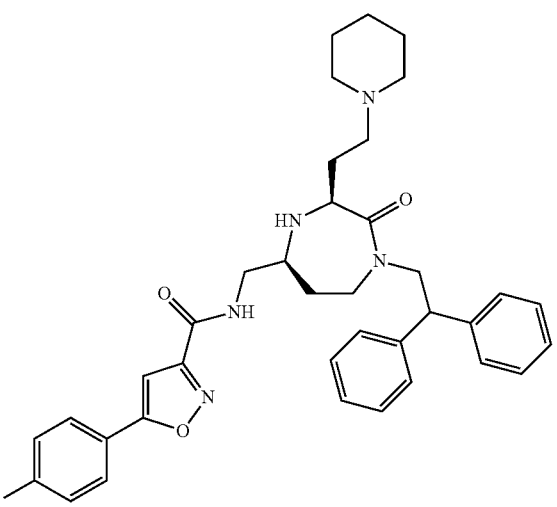
(434)
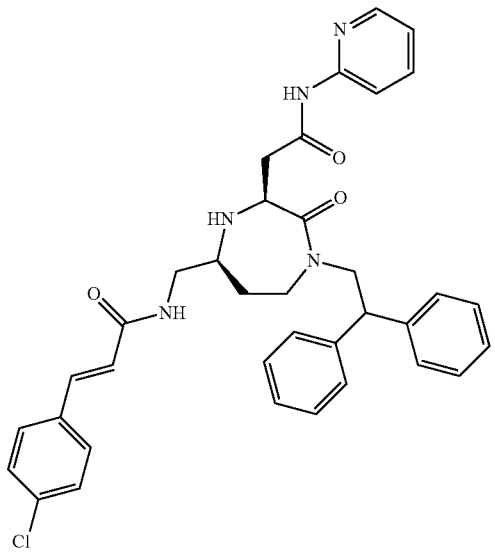

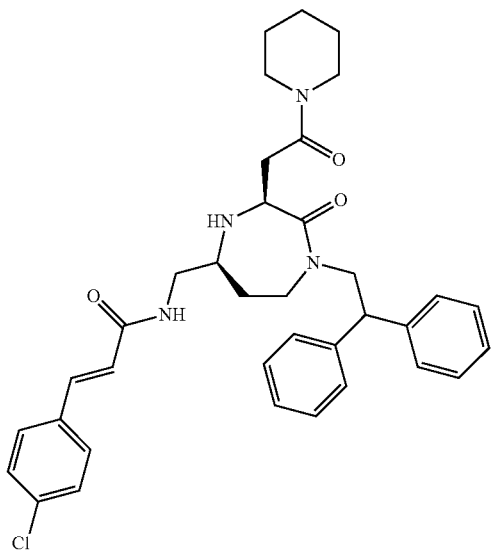
(435)
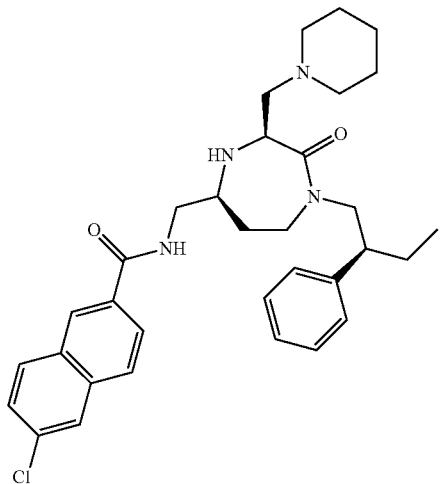
(438)
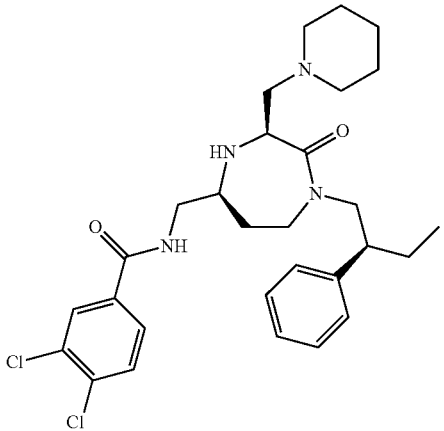
(436)
(439)
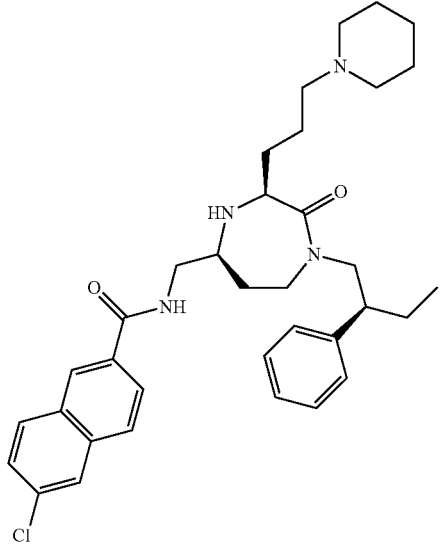
(437)
(440)

(441)
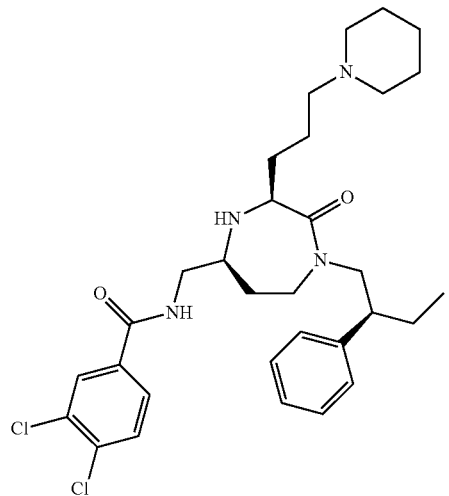
(442)
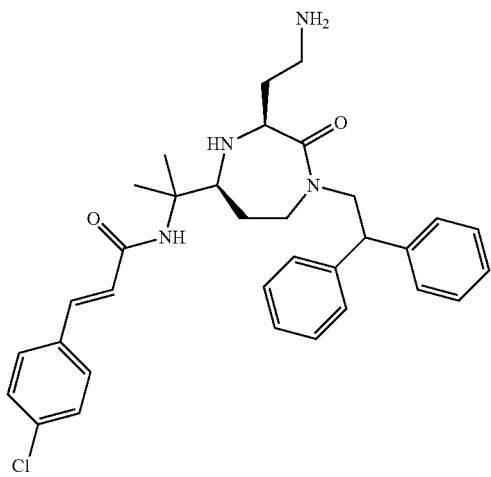
(443)
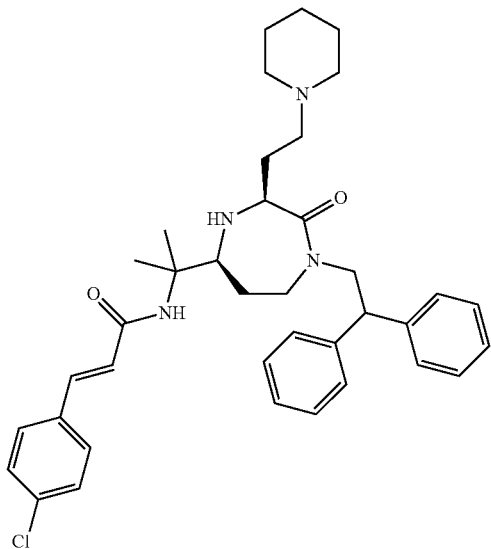
(444)
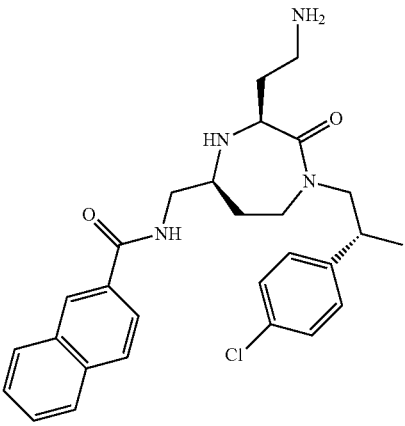
(445)
(446)
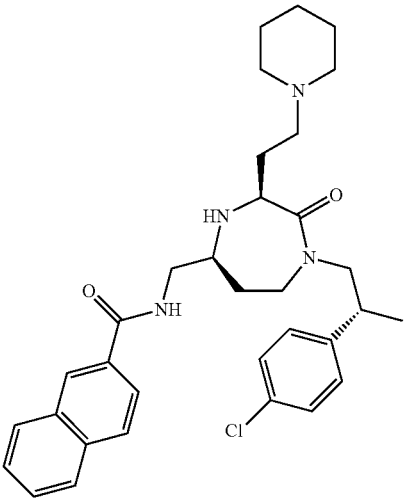

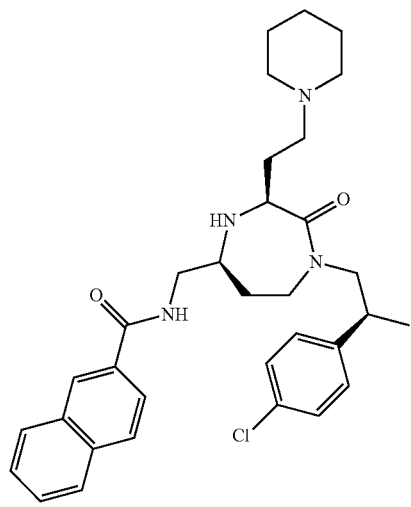
(447)
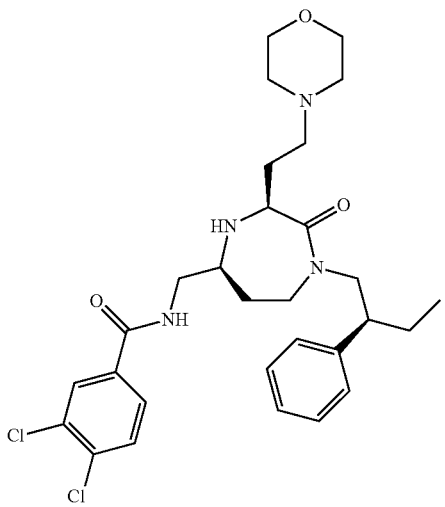
(450)
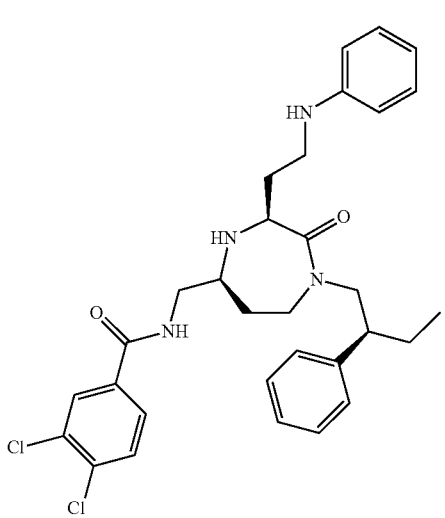
(448)
(451)
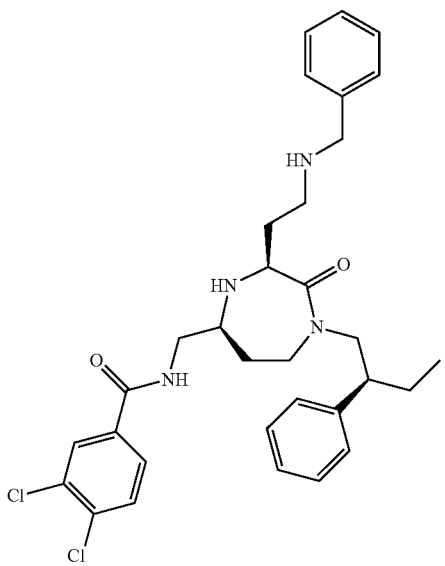
(449)
(452)

151
-continued
(453)
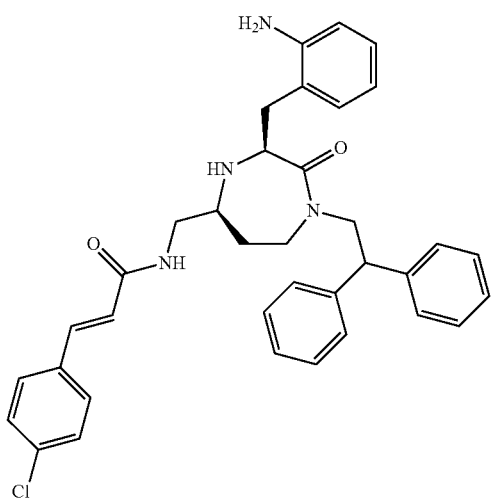
(454)
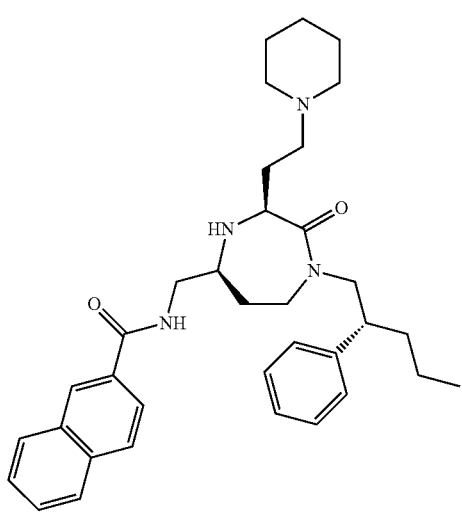
152
-continued
(456)
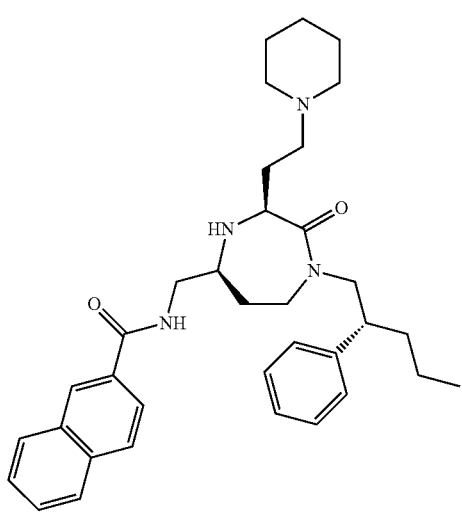
(457)
(455)
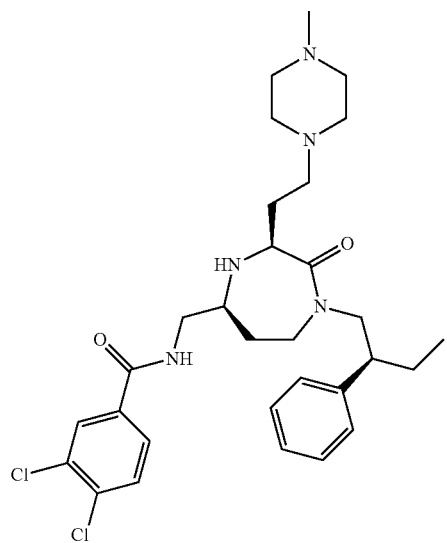
(458)
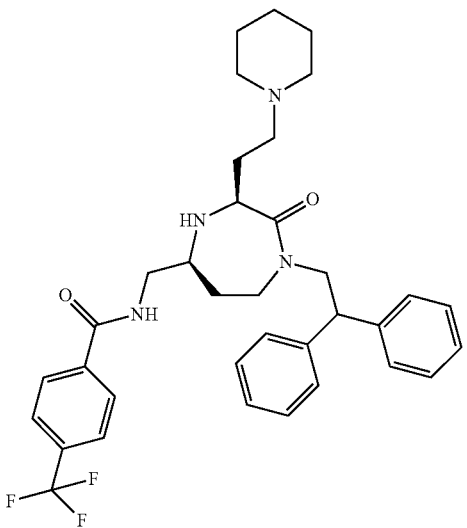

153
-continued
(459)
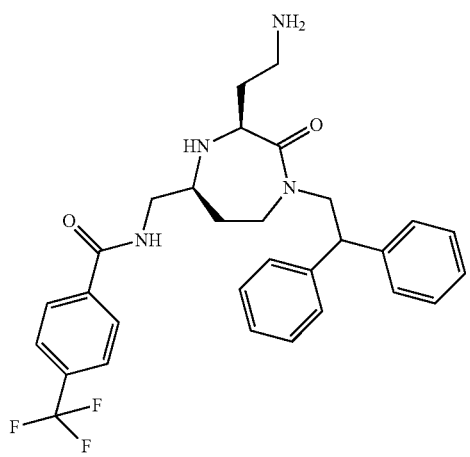
(460)
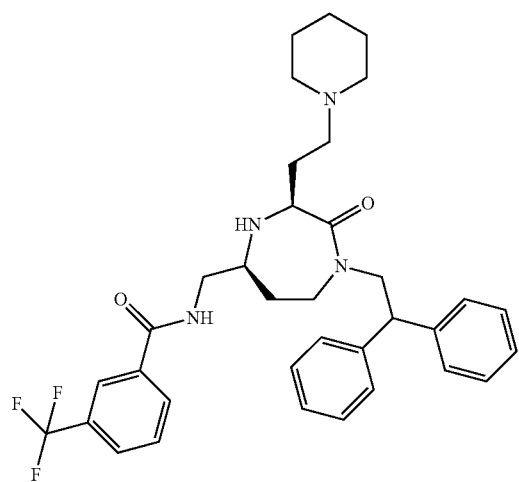
(461)
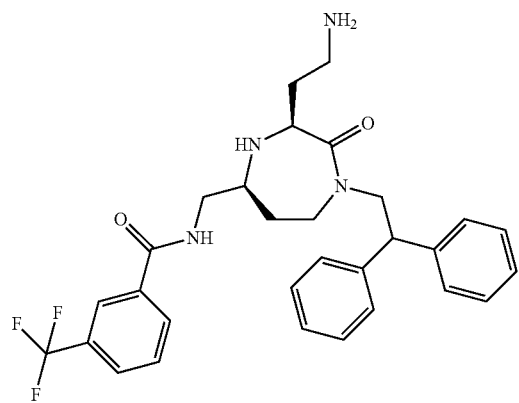
154
-continued
(462)
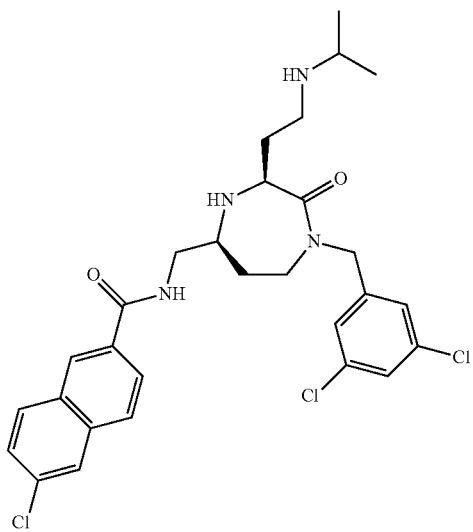
(463)
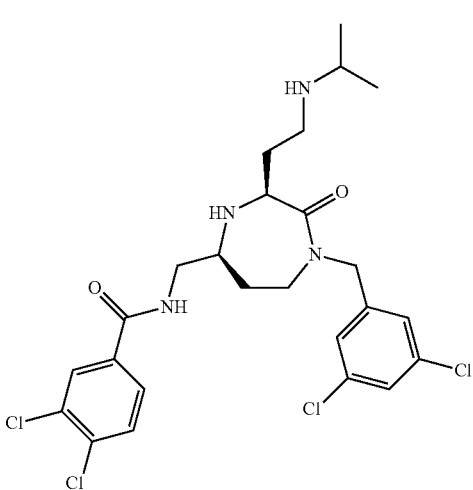
(464)
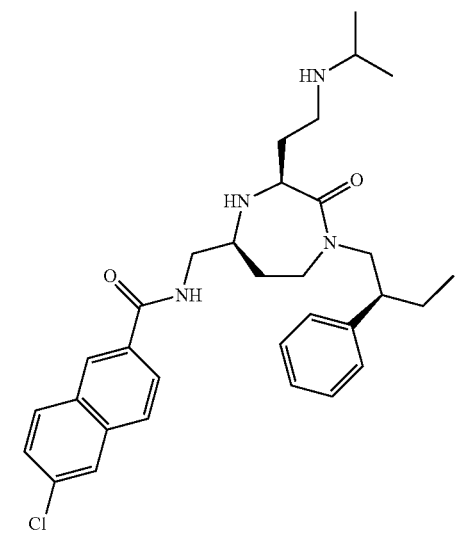

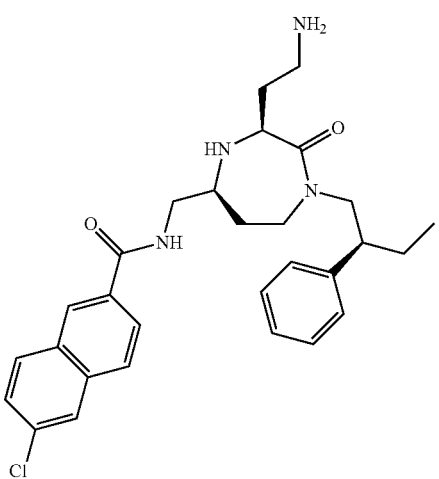
(465)
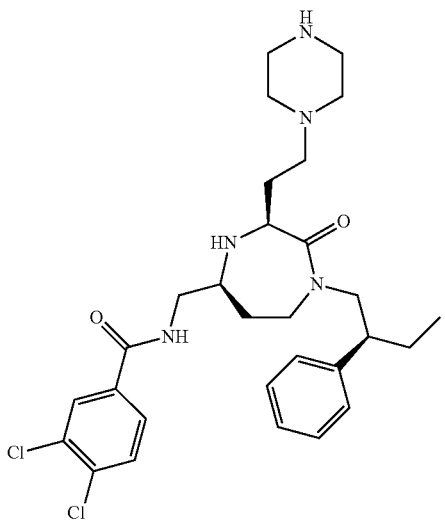
(468)
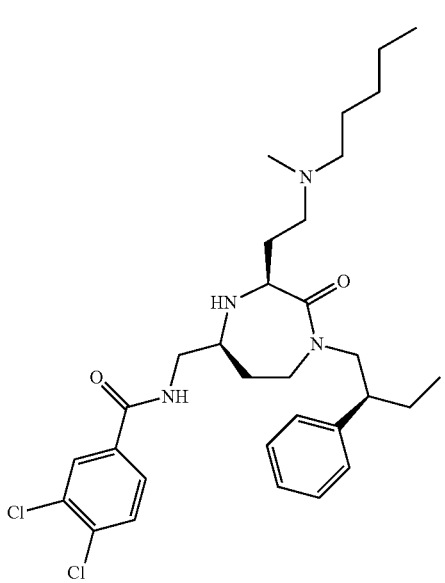
(466)
(469)
(467)
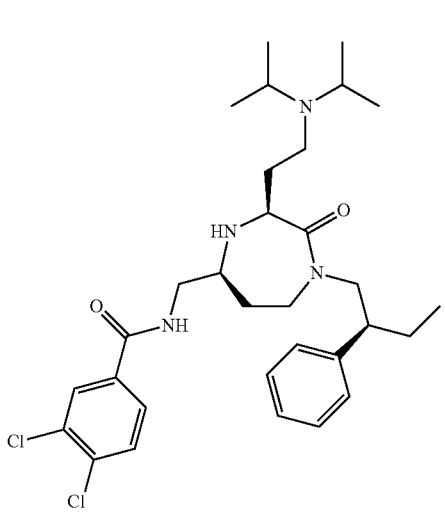
(470)

157
-continued
(471)
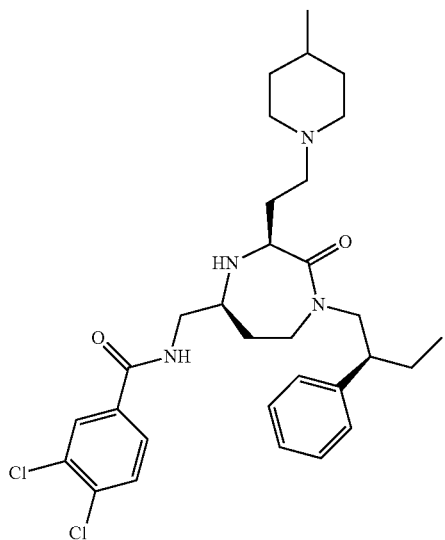
(472)
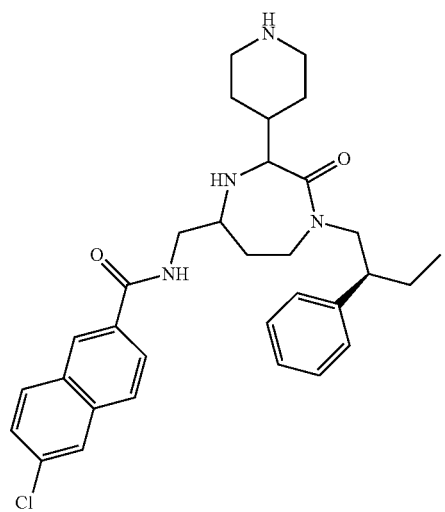
(473)
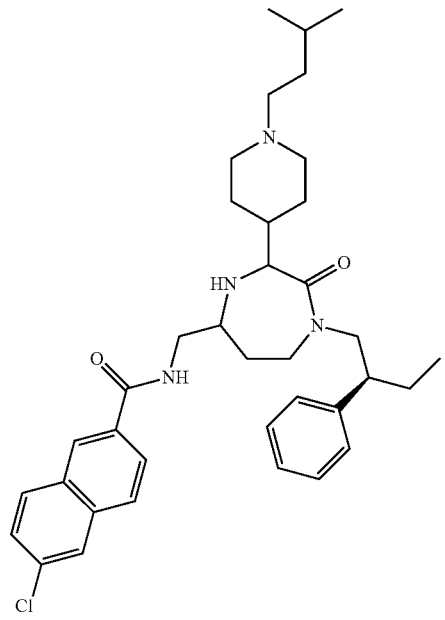
158
-continued
(474)
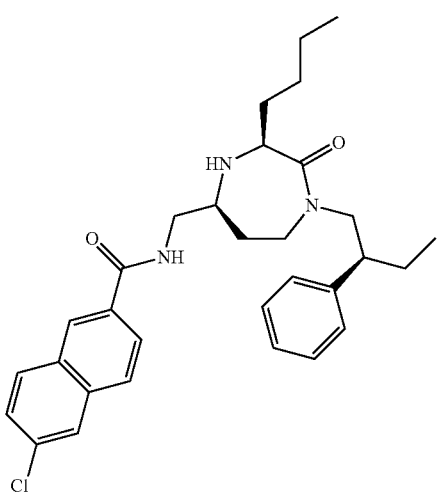
(475)
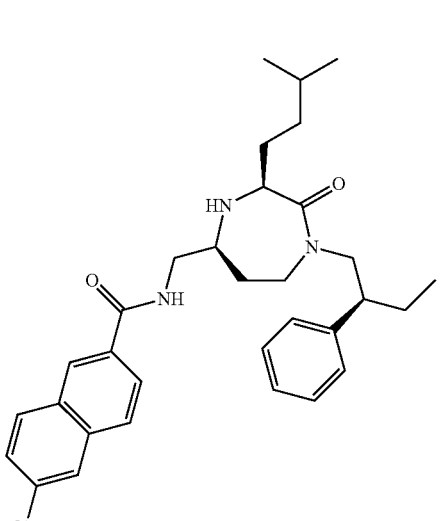
(476)
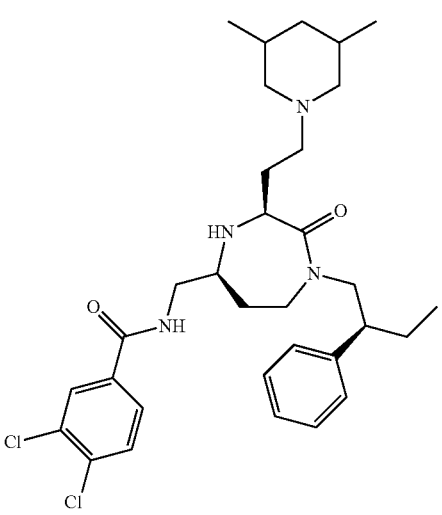

(477) 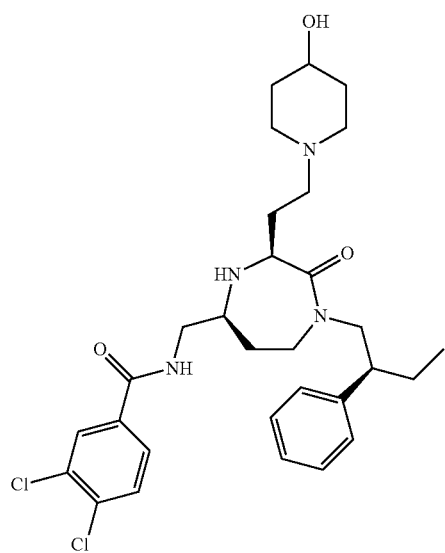
(480) 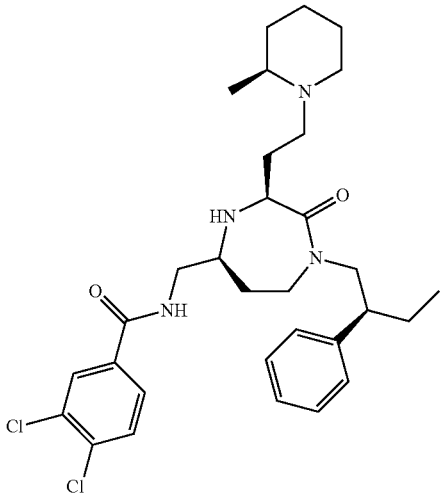
(478) 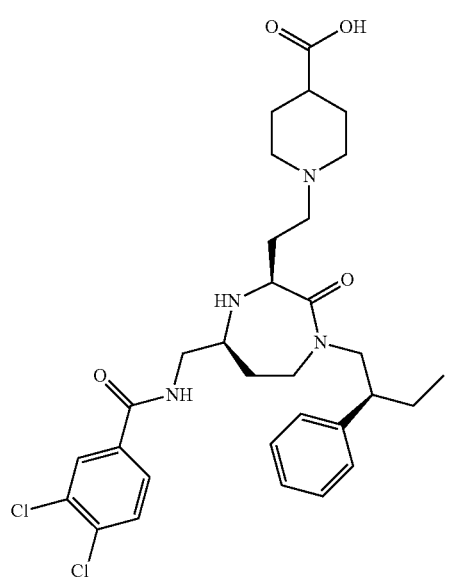
(481) 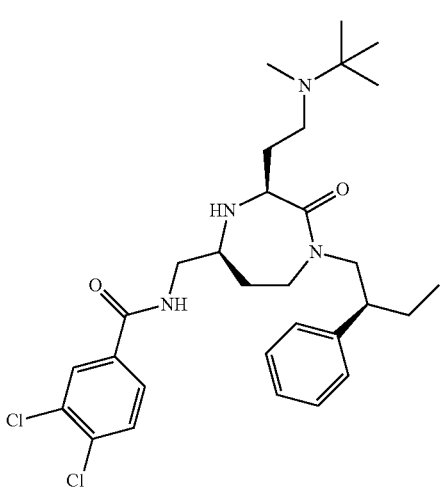
(479) 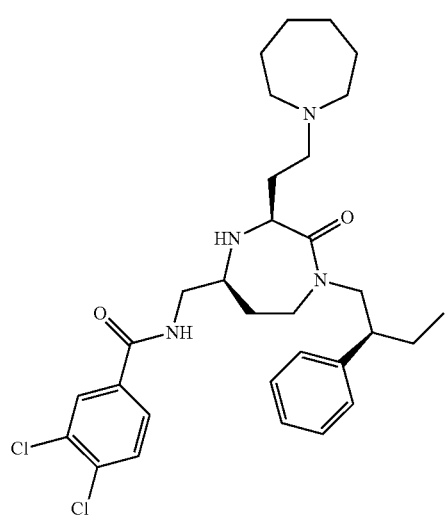
(482) 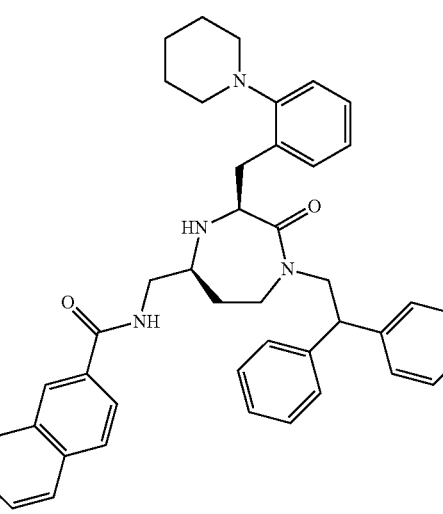

(483)
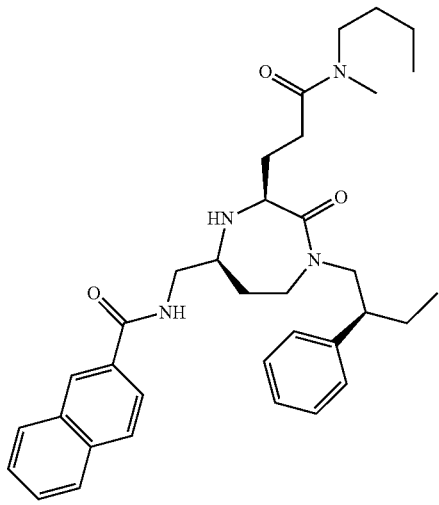
(484)
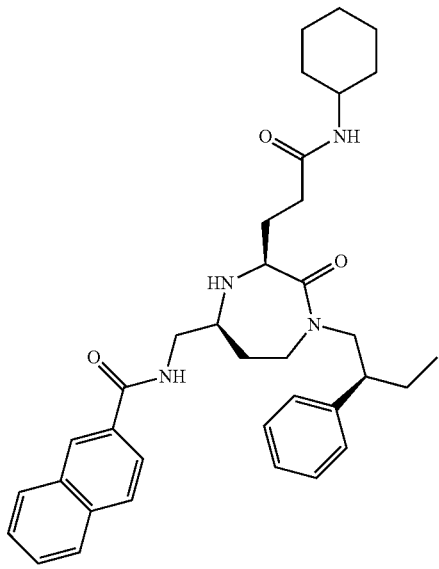
(485)
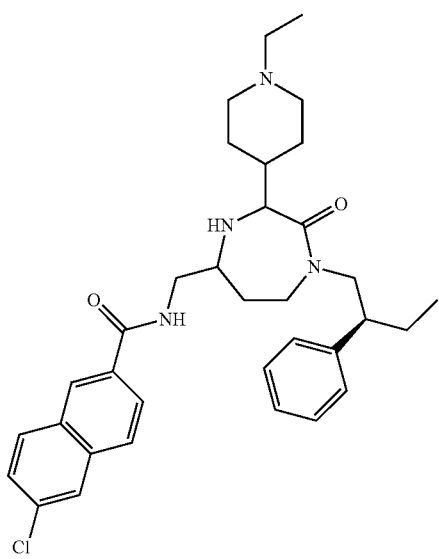
(486)
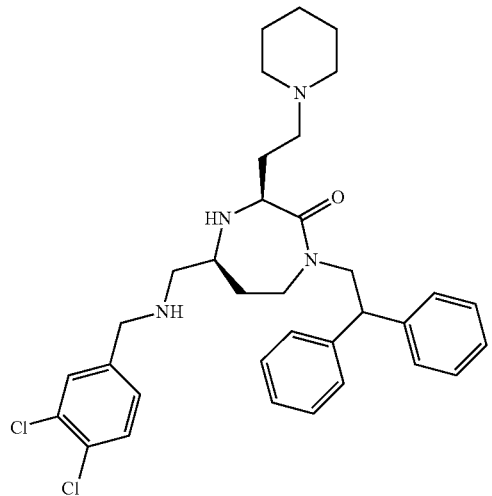
(487)
(488)
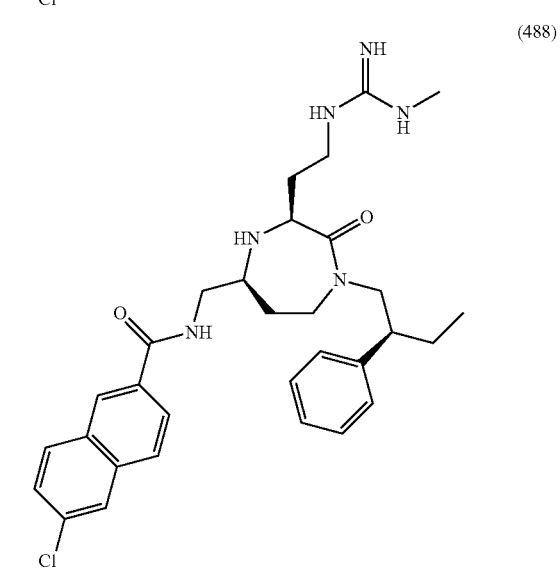

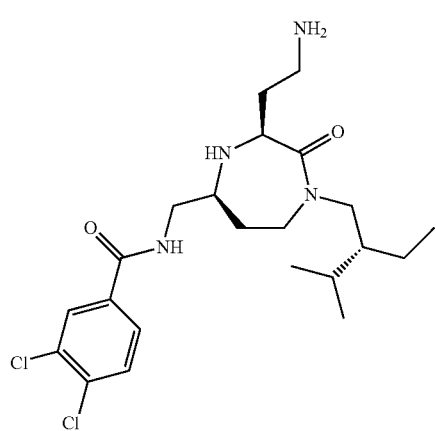
(489)
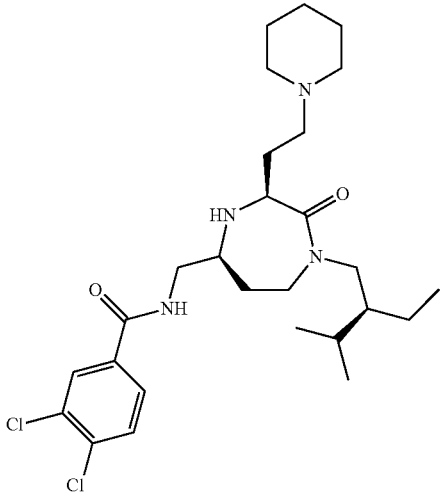
(492)
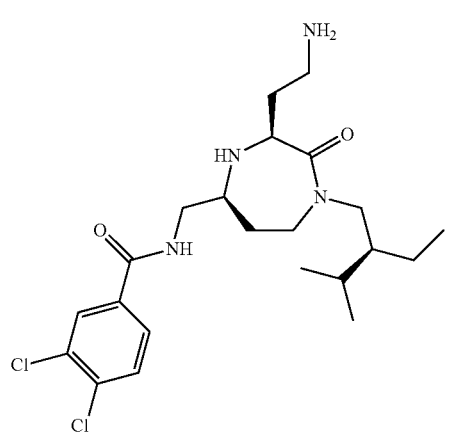
(490)
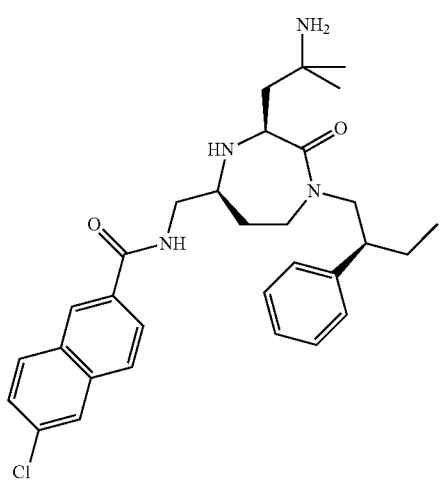
(493)
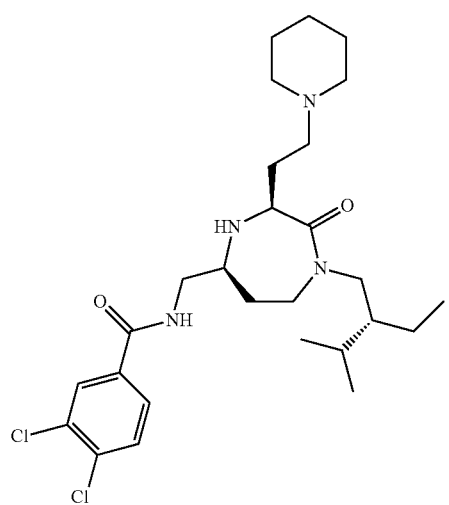
(491)
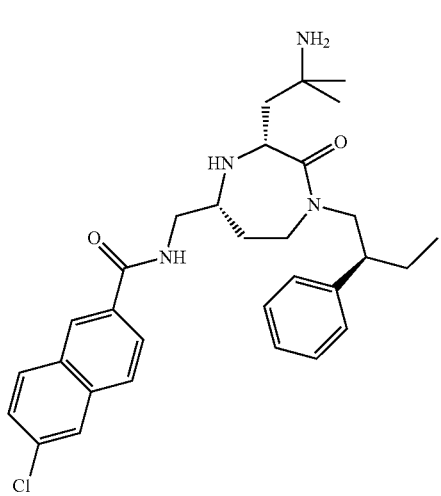
(494)

165
-continued
(495)
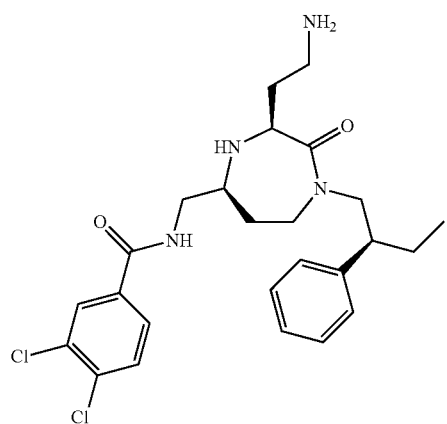
(496)
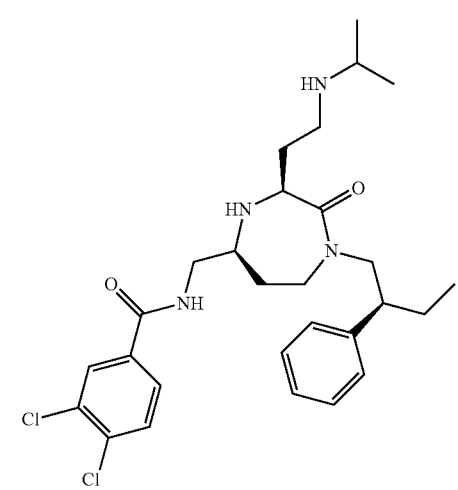
(497)
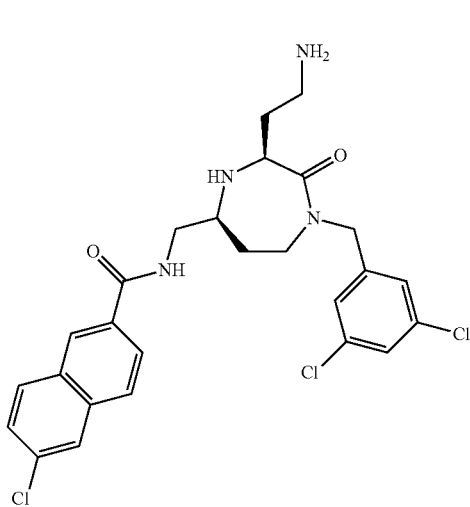
166
-continued
(498)
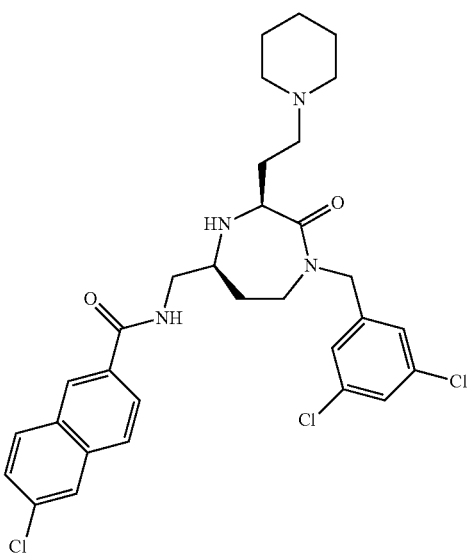
(499)
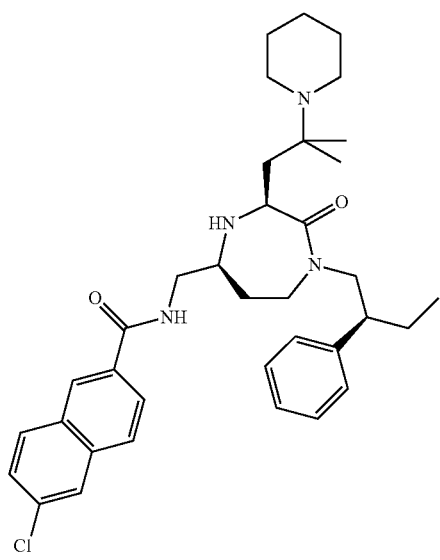
(500)
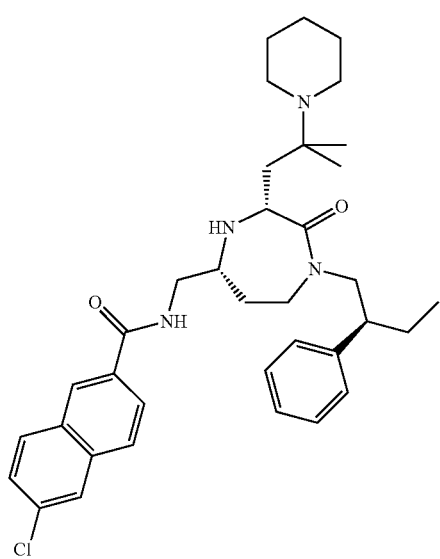

(501)
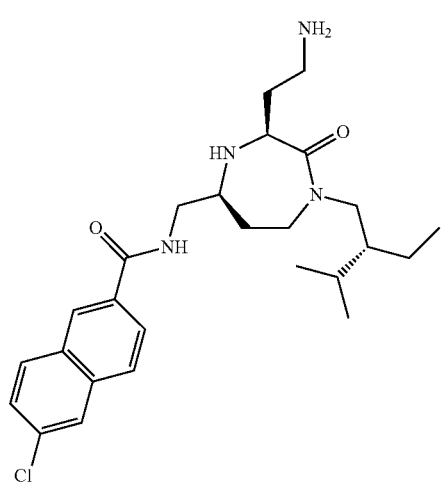
(502)
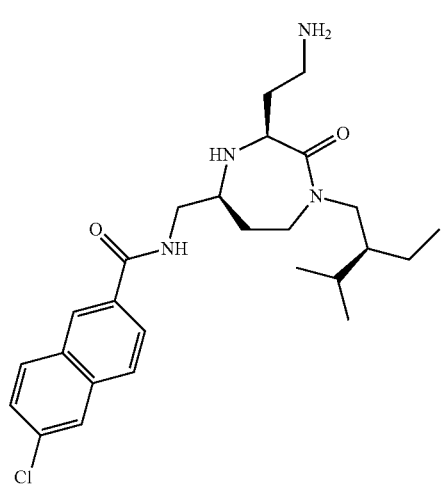
(503)
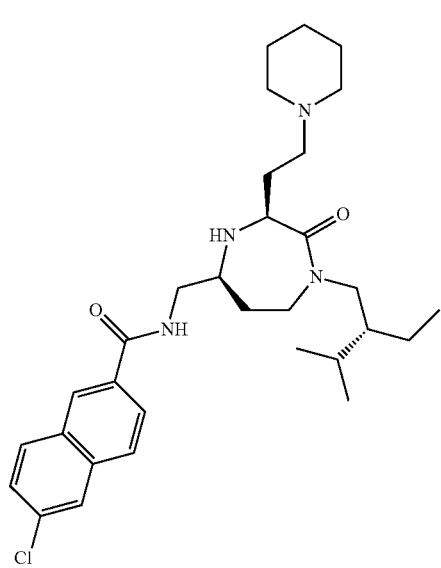
(504)
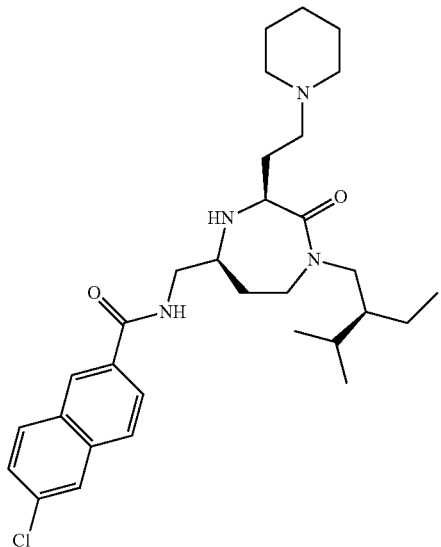
(505)
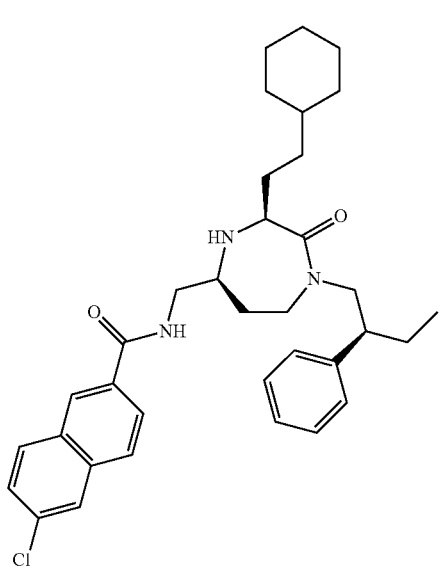
(506)
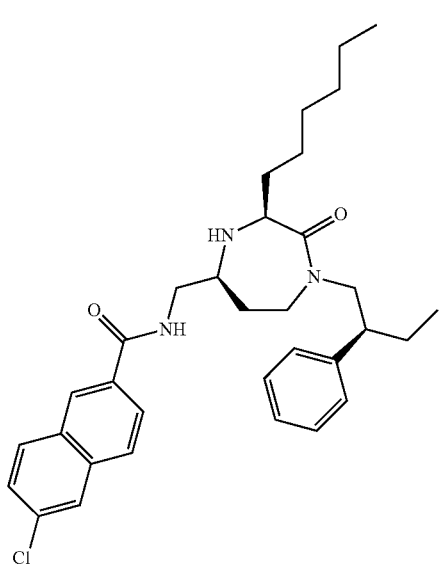

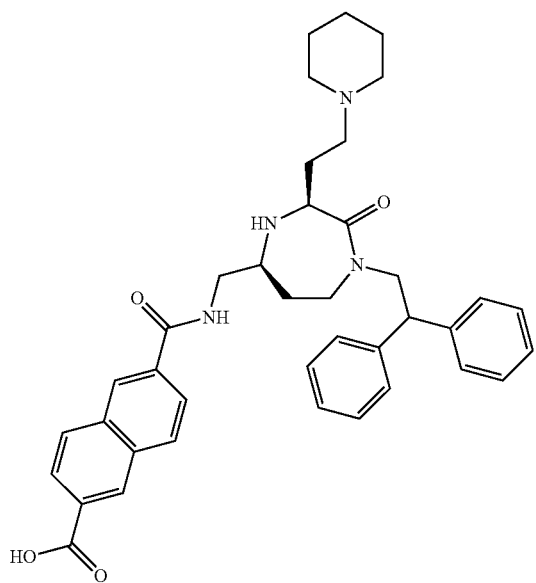
(507)
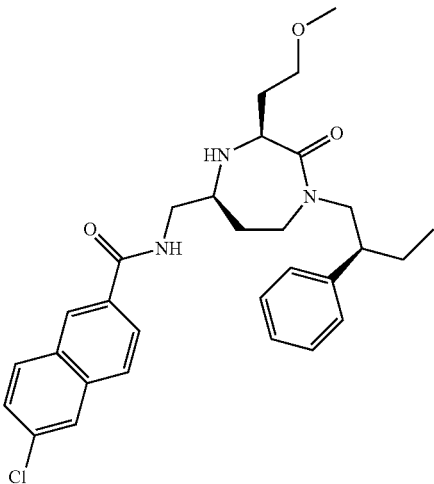
(510)
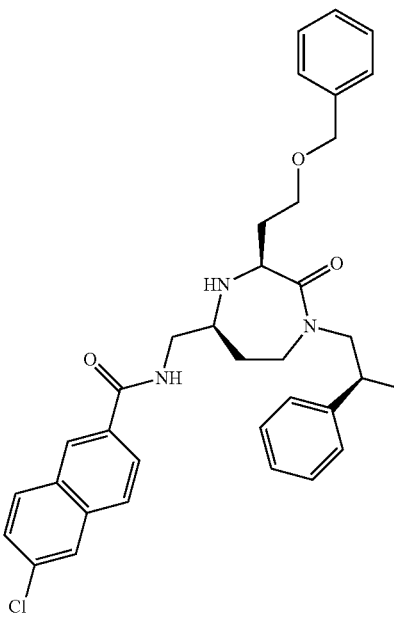
(508)
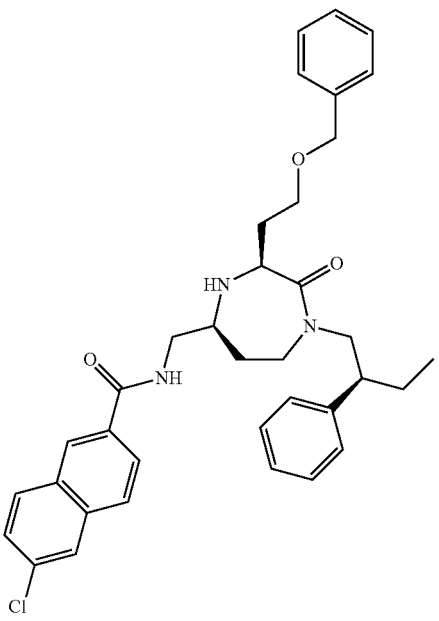
(511)
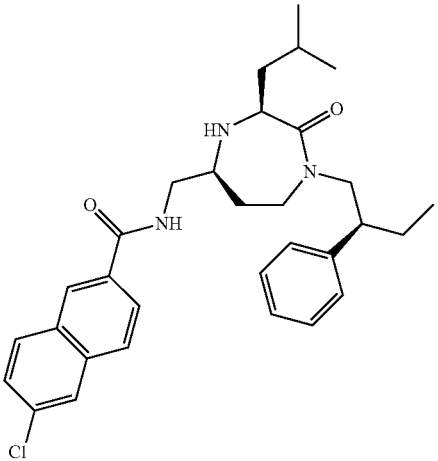
(509)
(512)

171
-continued
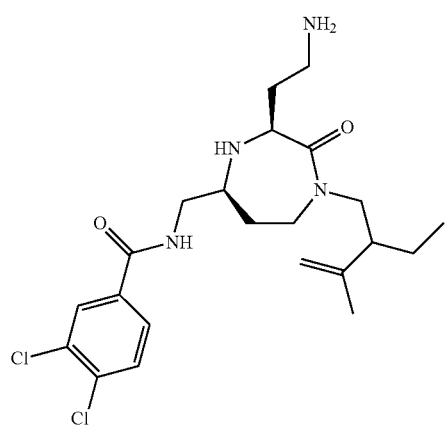
(513)
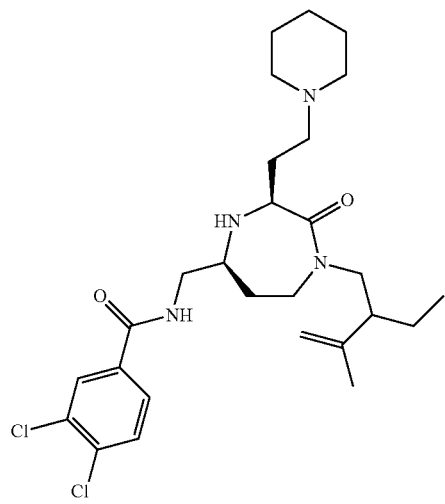
(514)
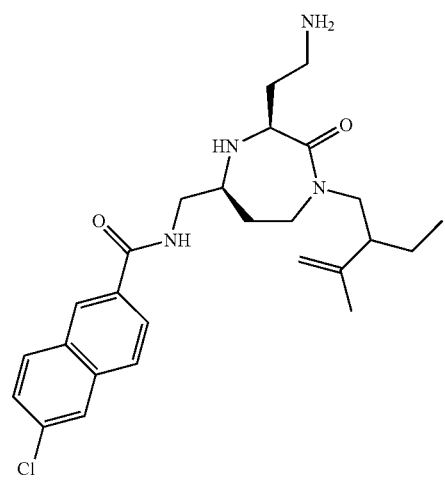
(515)
172
-continued
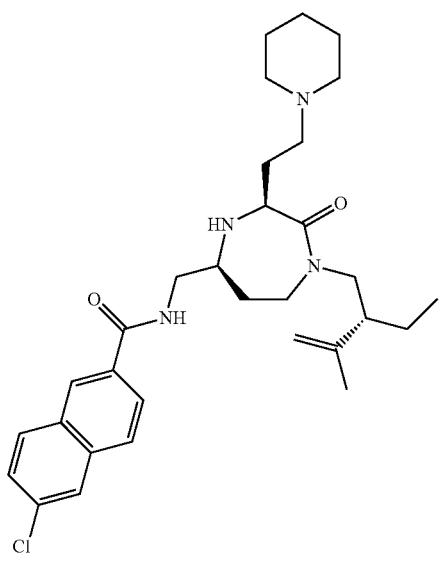
(516)
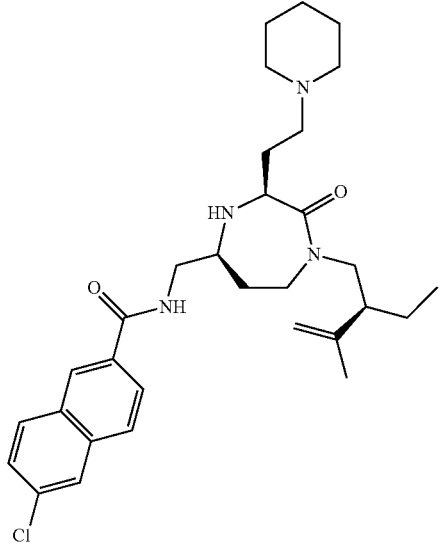
(517)
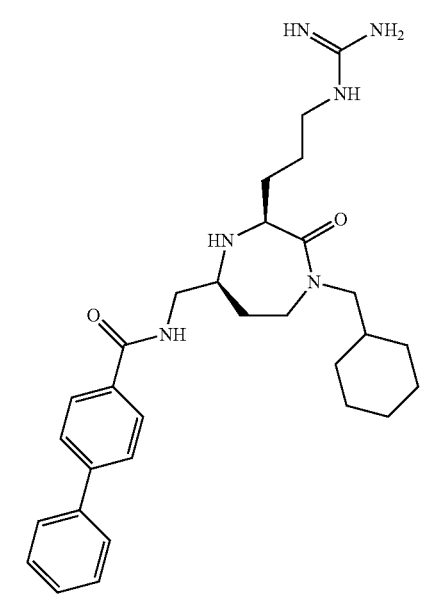
(518)

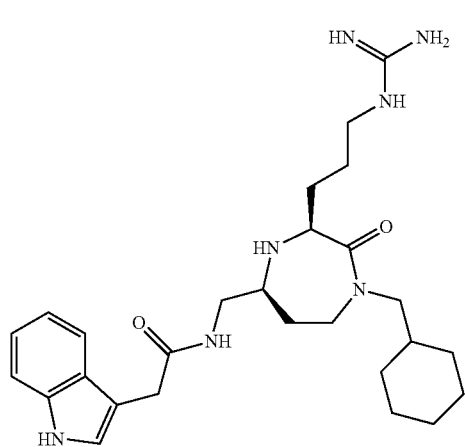
(519)
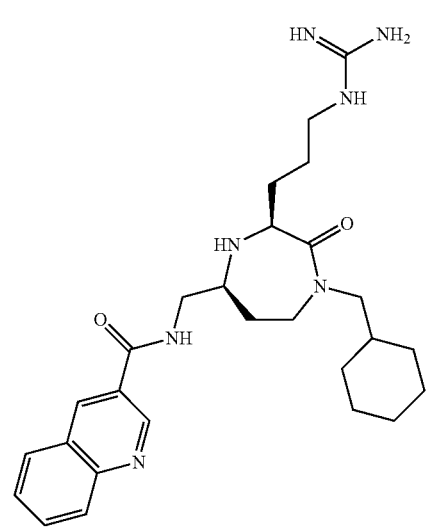
(520)
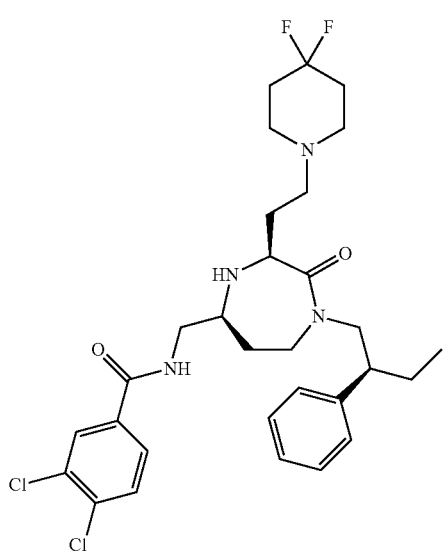
(521)
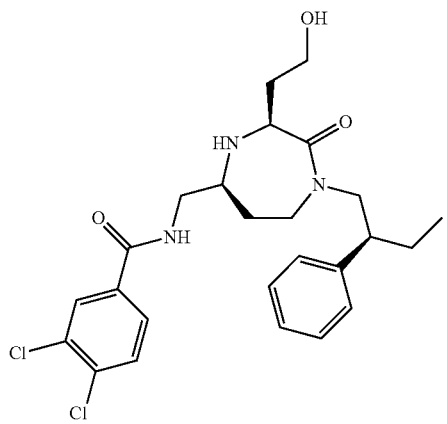
(522)
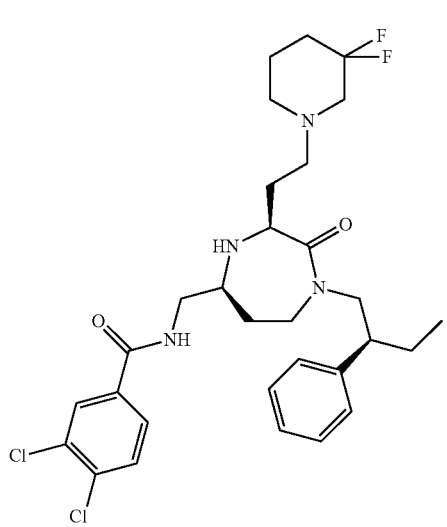
(523)
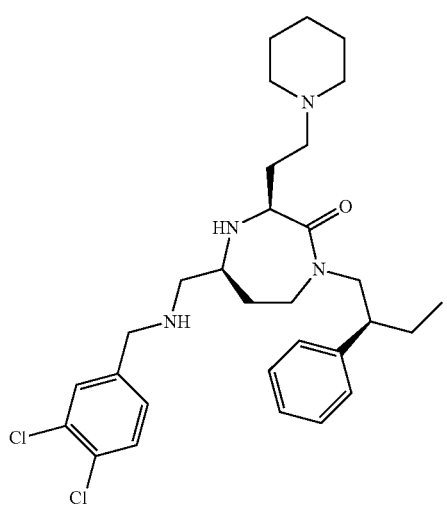
(524)

-continued
(525) 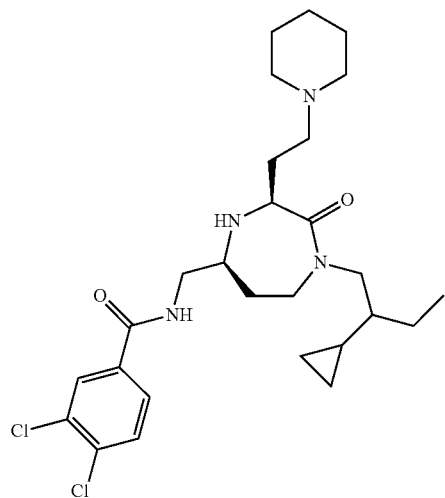
(526) 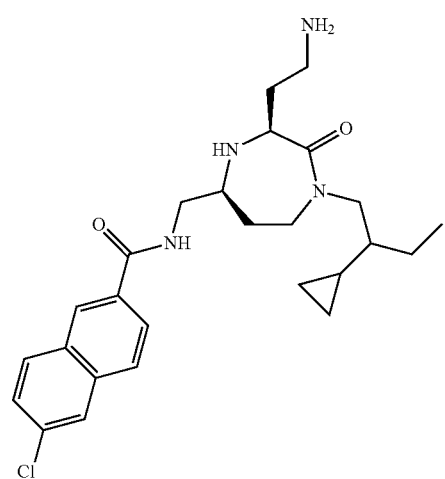
(527) 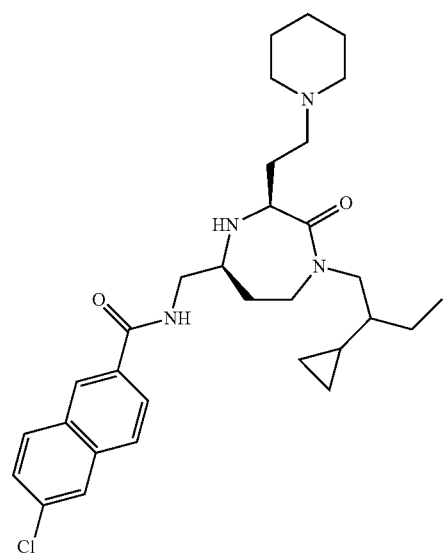
-continued
(528) 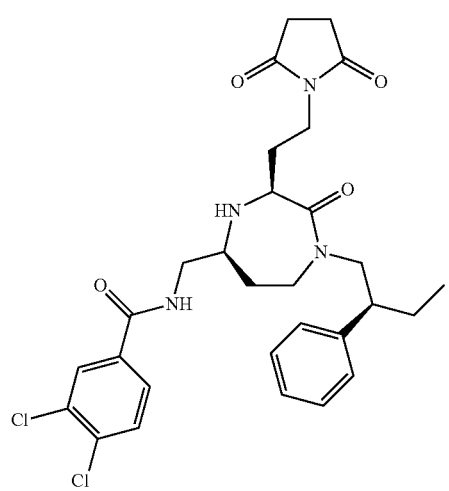
(529) 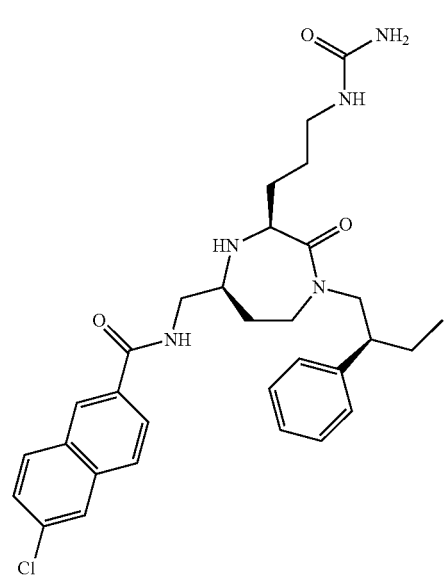
(530) 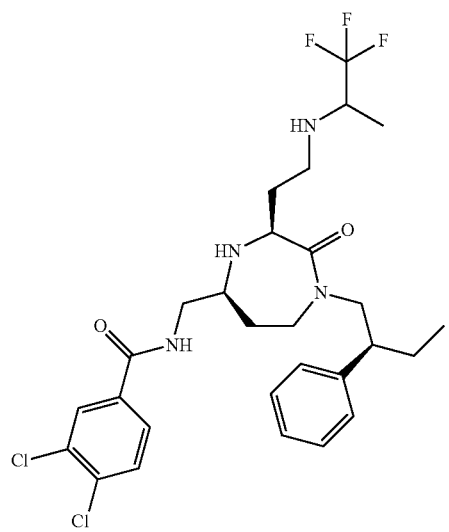

177
-continued
(531)
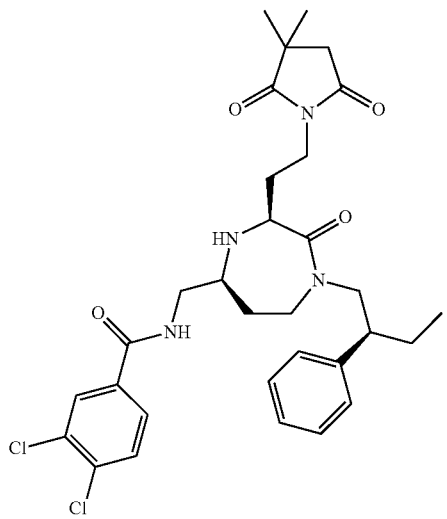
(532)
(533)
178
-continued
(534)
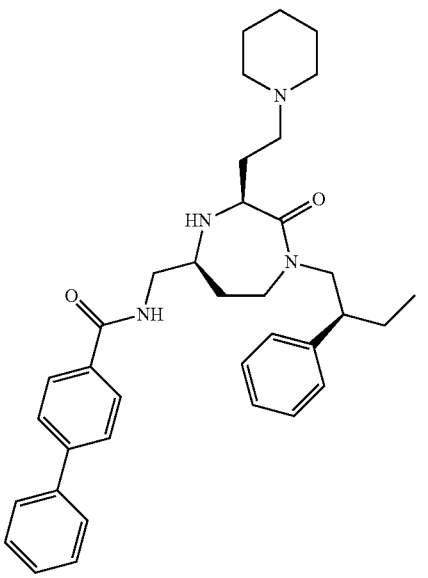
(535)
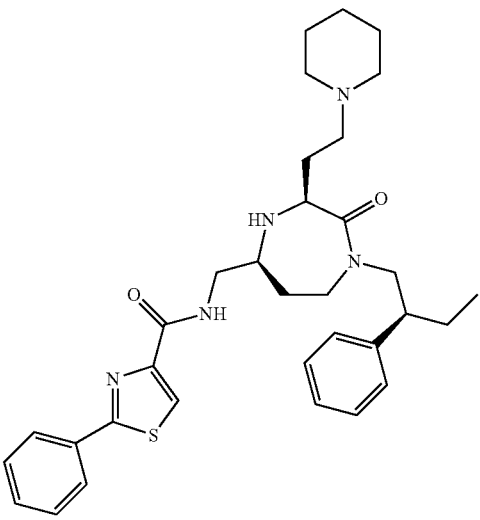
(536)
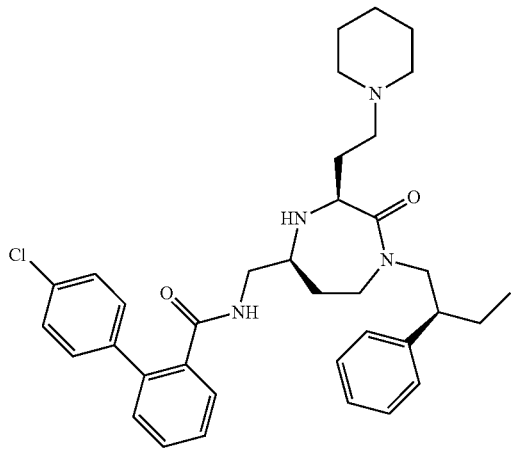

179 -continued
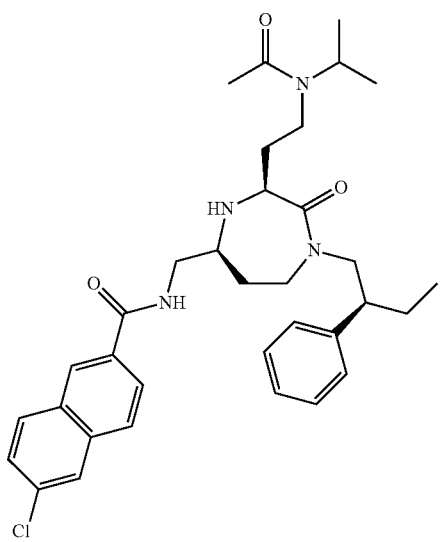
(537)
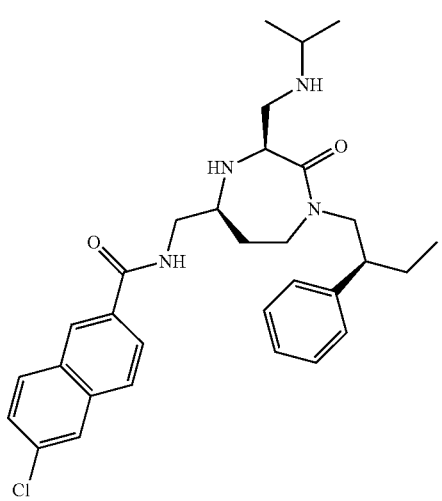
(538)
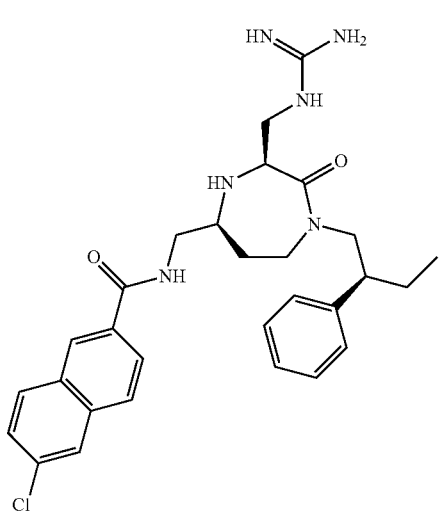
(539)
180 -continued
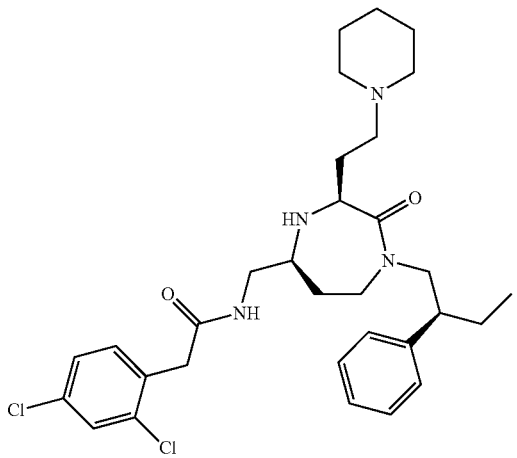
(540)
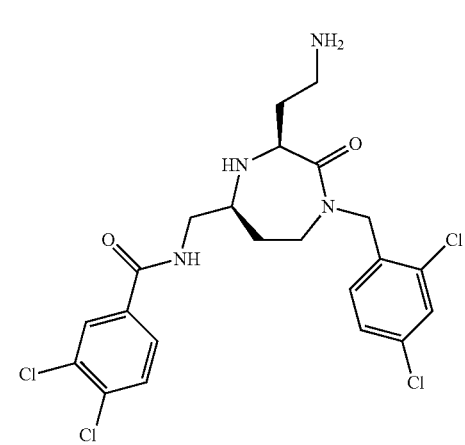
(541)
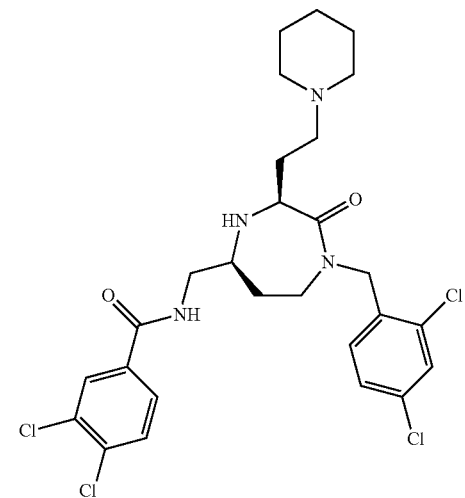
(542)

(543) 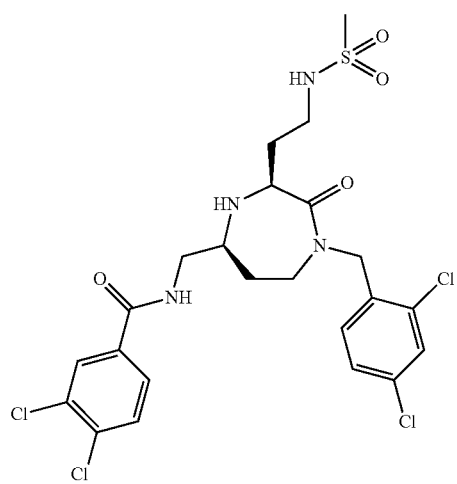
(544) 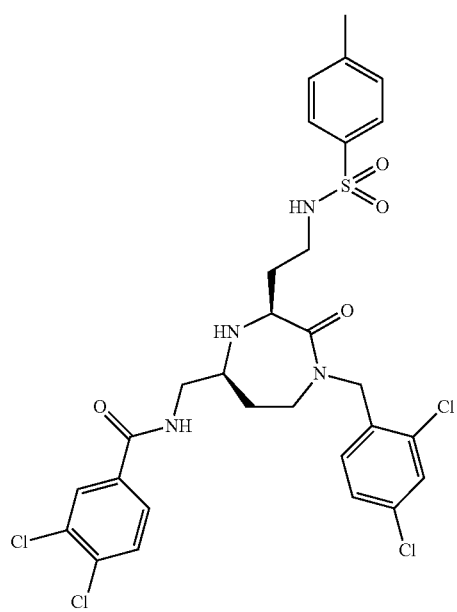
(545) 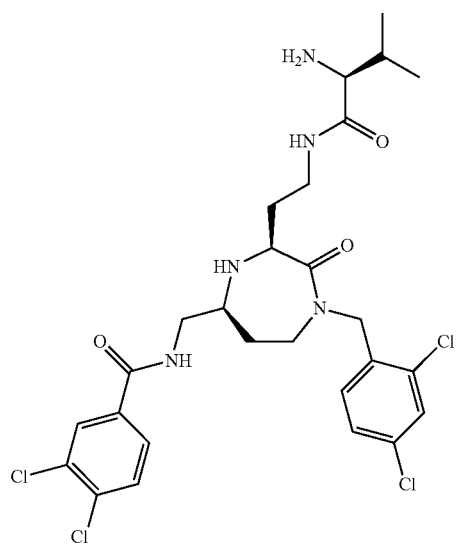
(546) 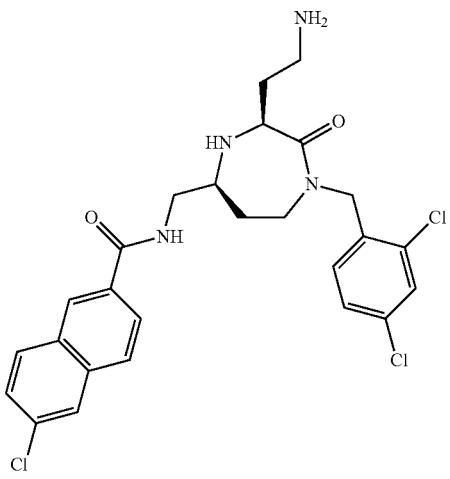
(547) 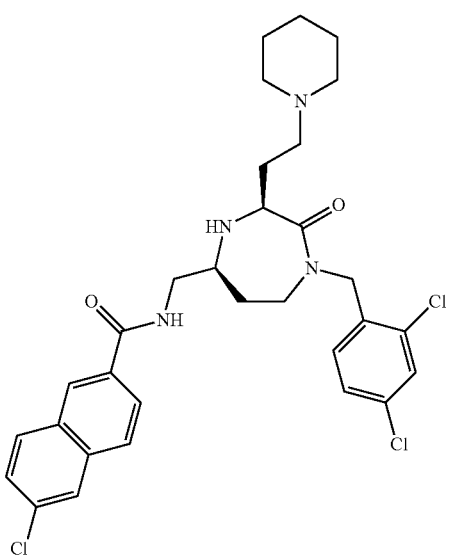
(548) 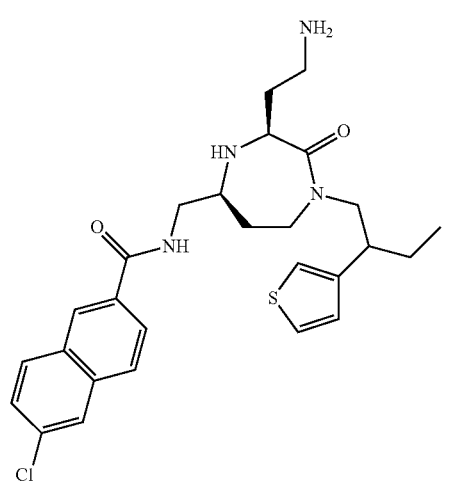

(549) 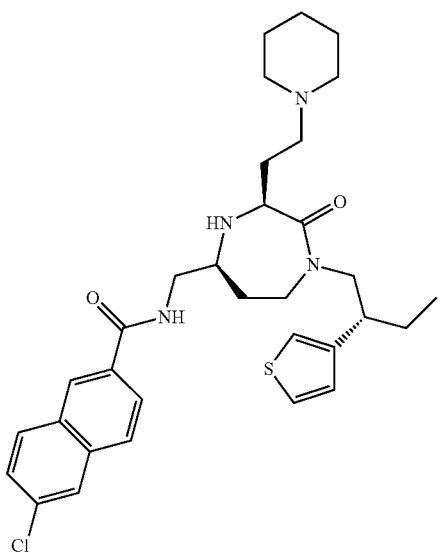
(550) 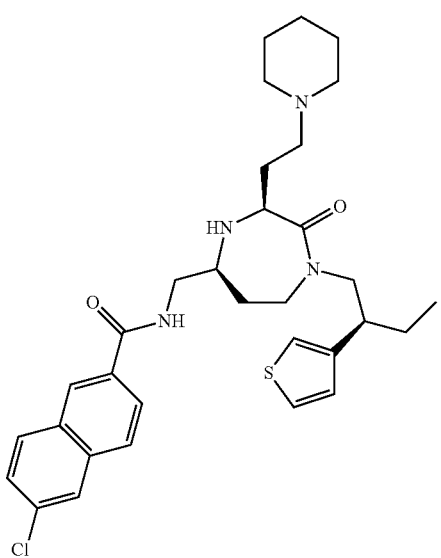
(551) 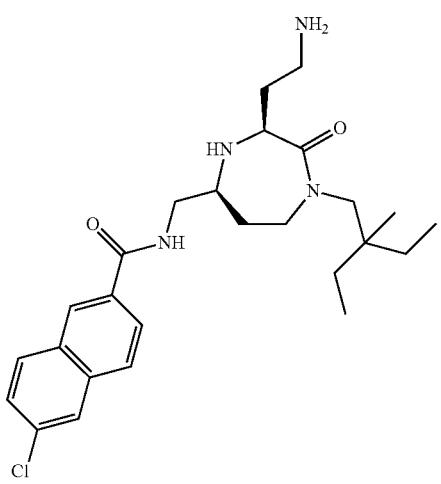
(552) 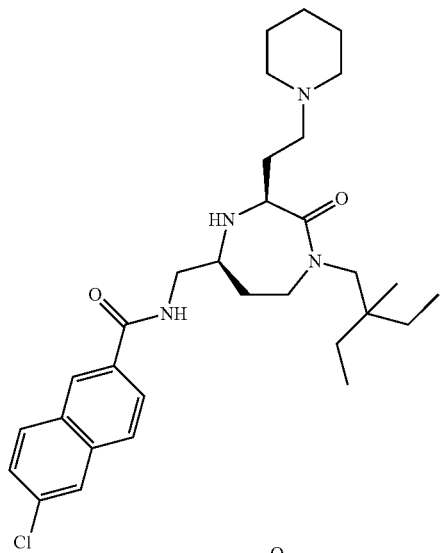
(553) 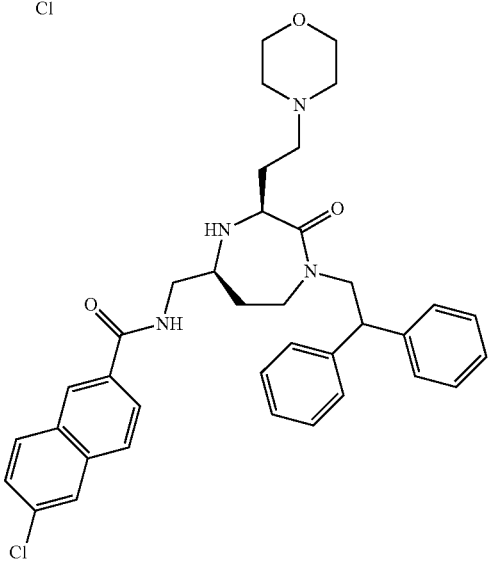
(554) 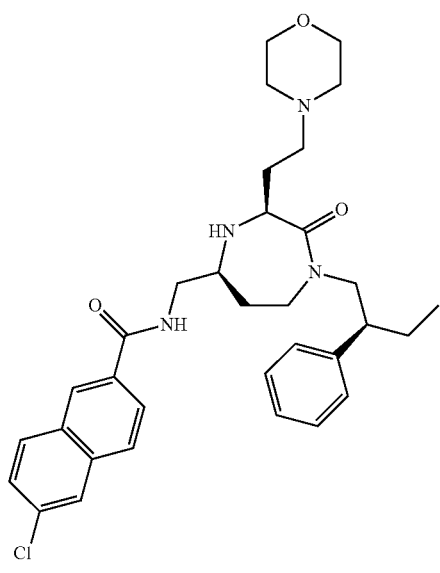

(555)
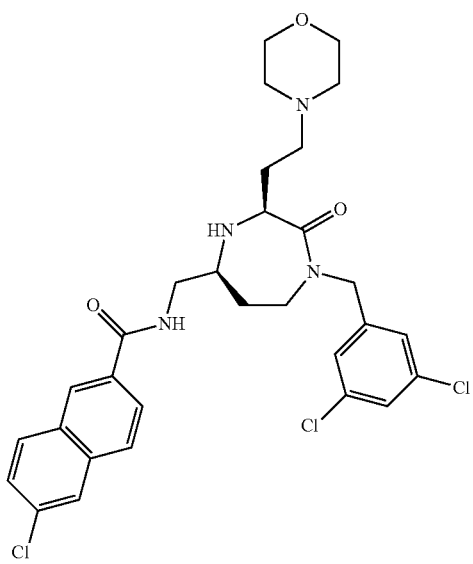
(556)
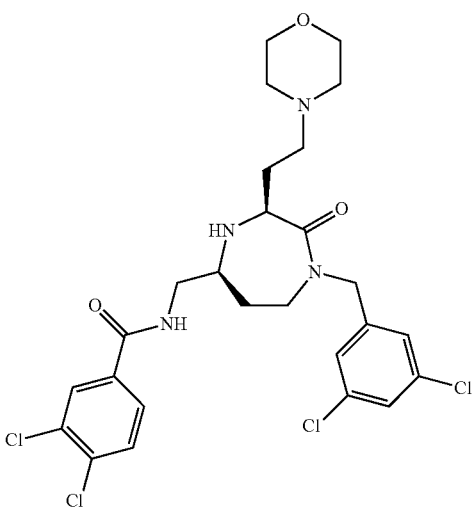
(557)
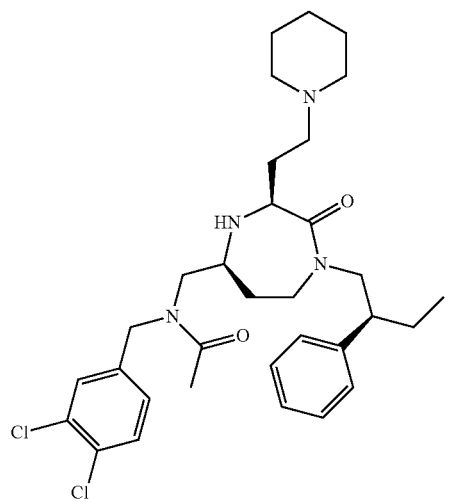
(558)
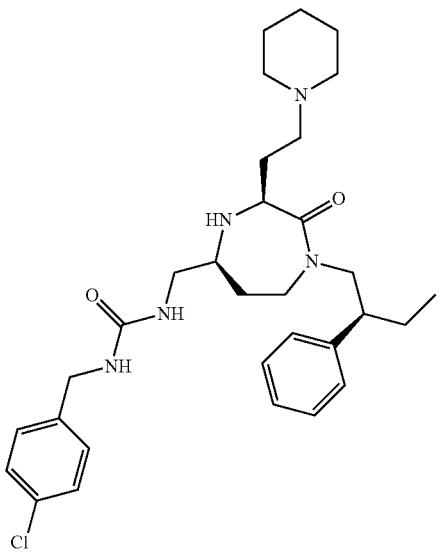
(559)
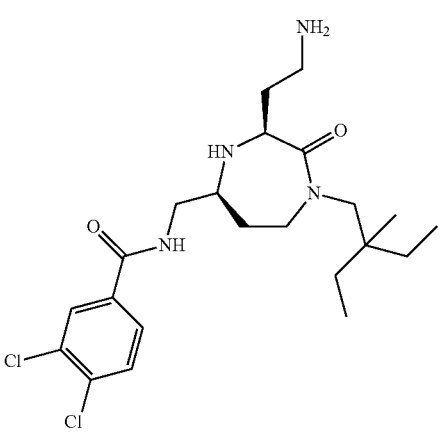
(560)
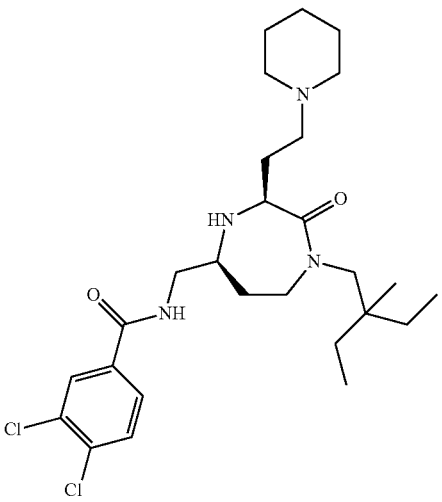

187
(561)
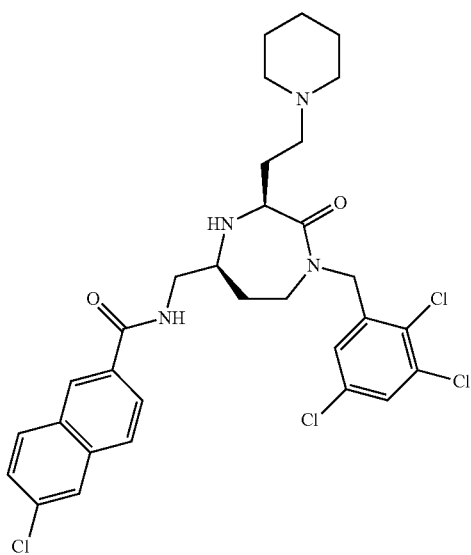
(562)
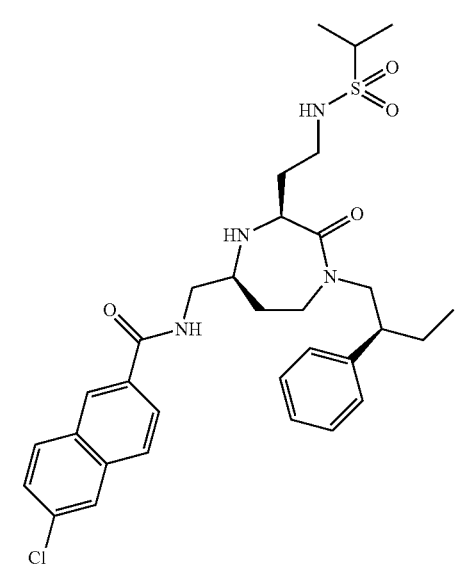
(563)
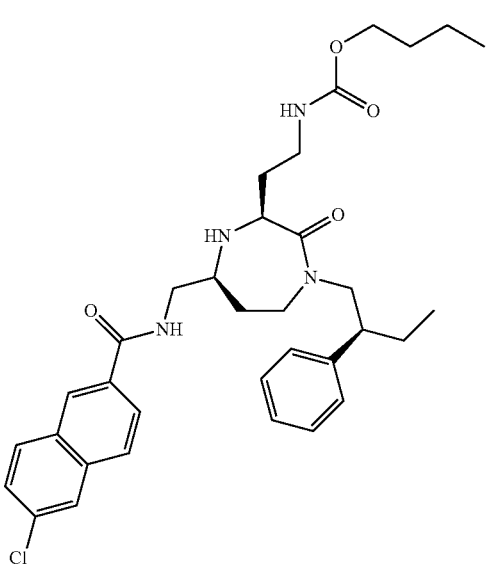
188
(564)
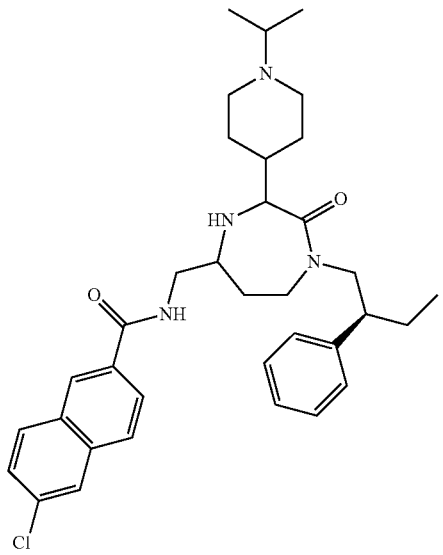
(565)
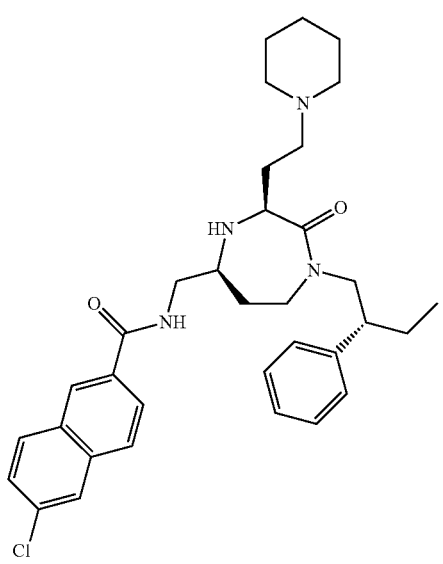
(566)
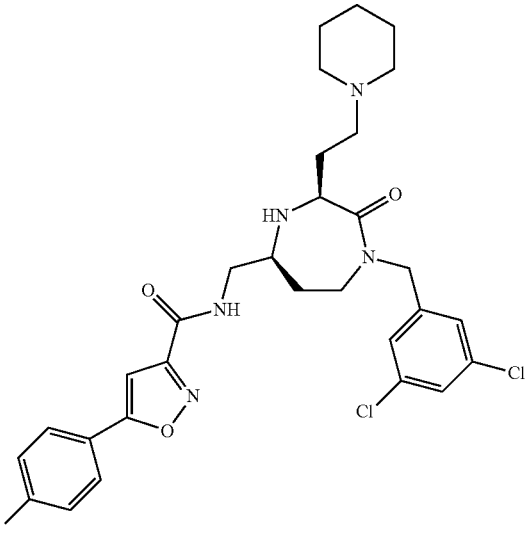

189
-continued
(567)
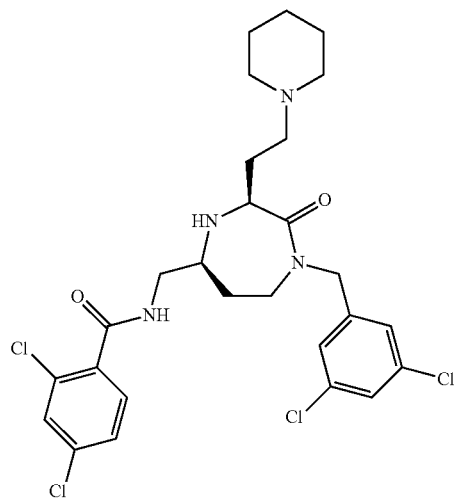
(568)
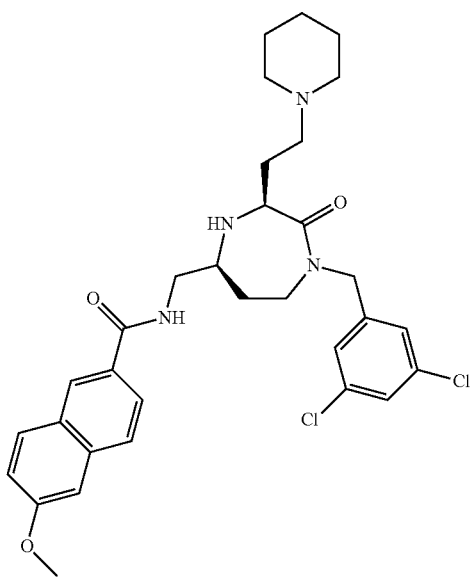
(569)
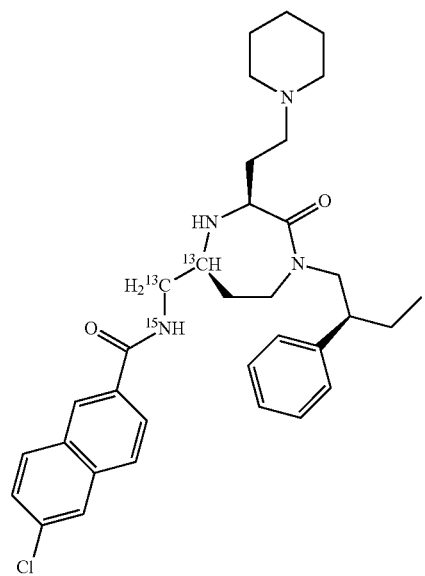
190
-continued
(570)
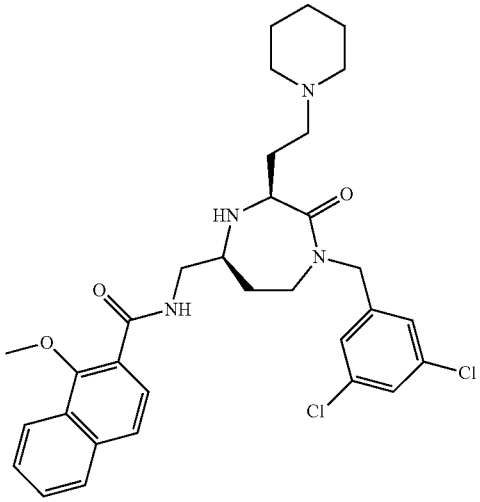
(571)
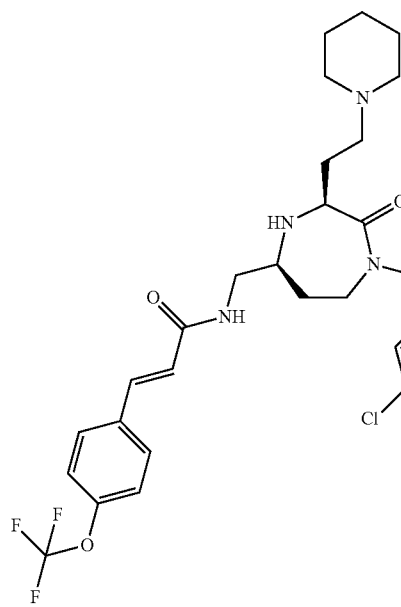
(572)
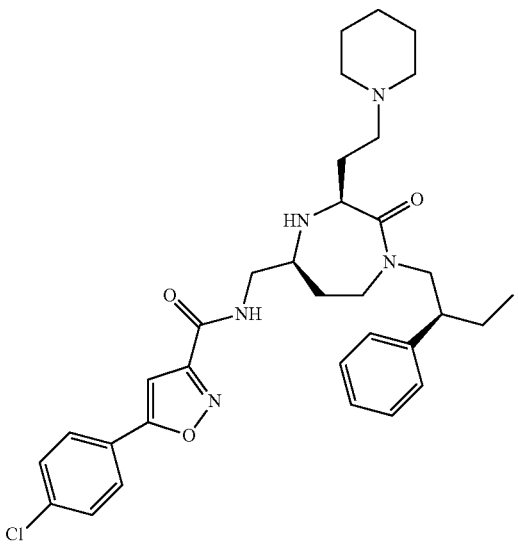

191
-continued
(573)
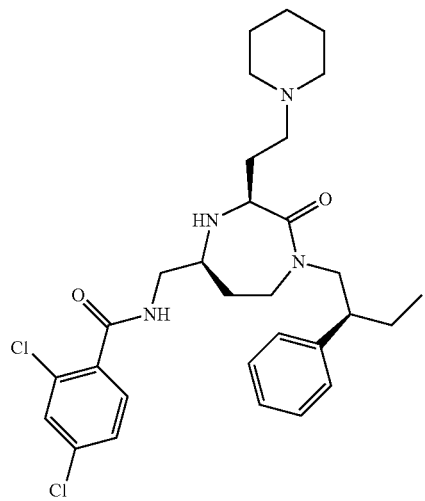
(574)
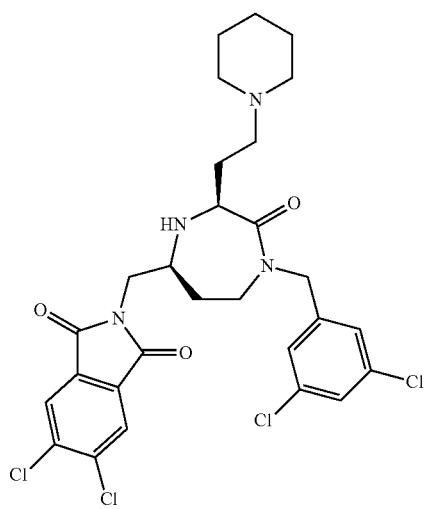
(575)
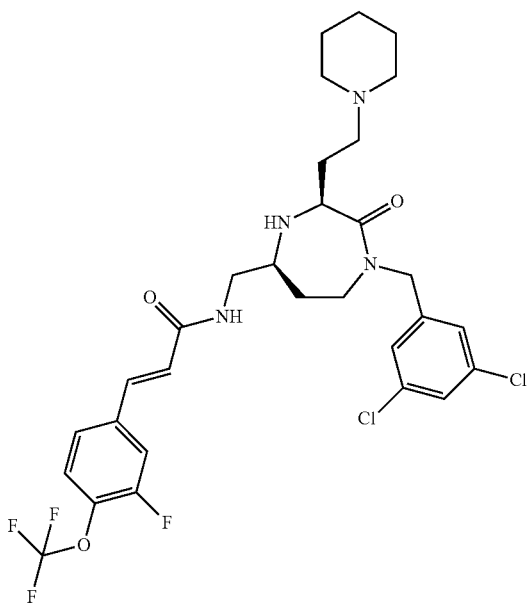
192
-continued
(576)
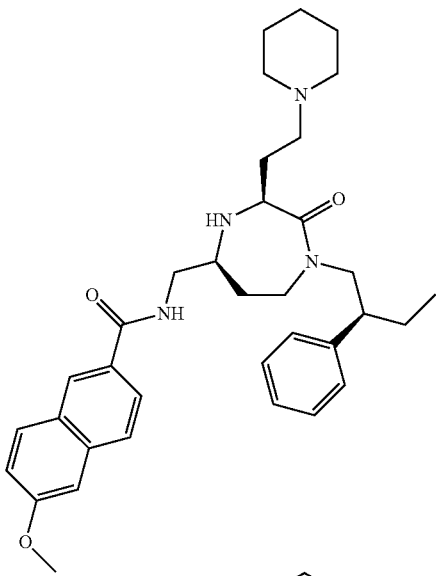
(577)
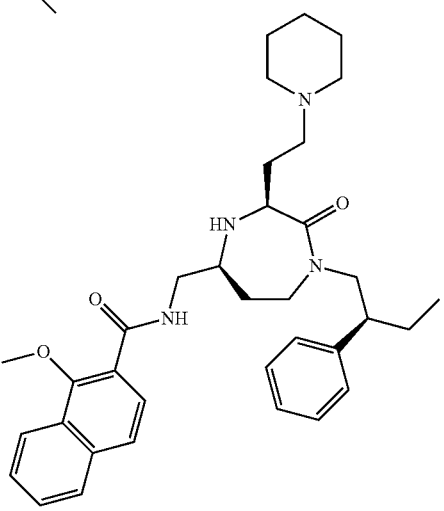
(578)
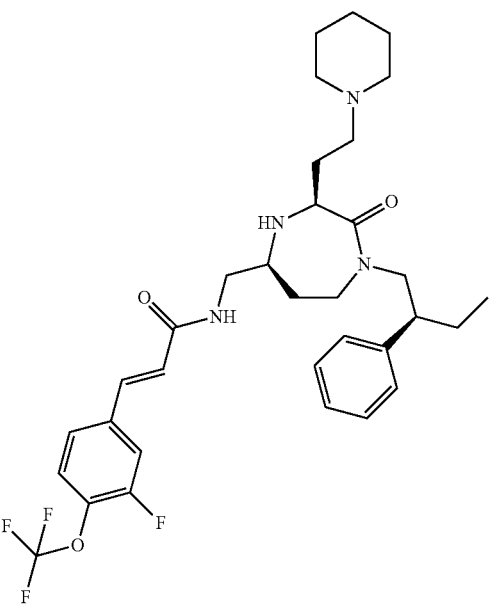

193
-continued
(579)
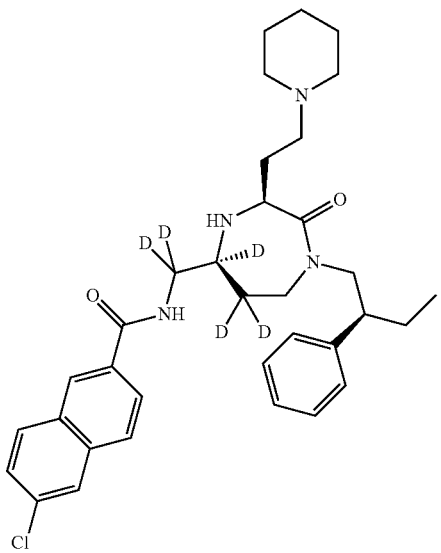
(580)
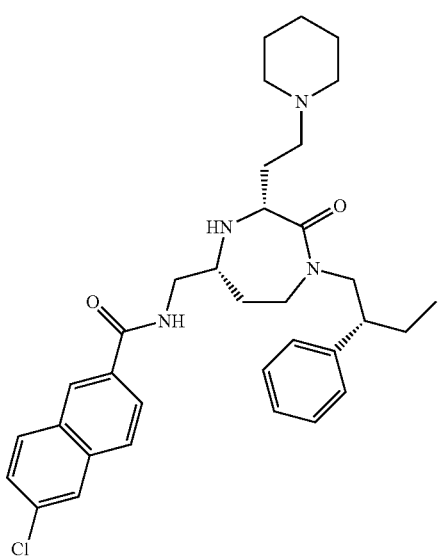
(581)
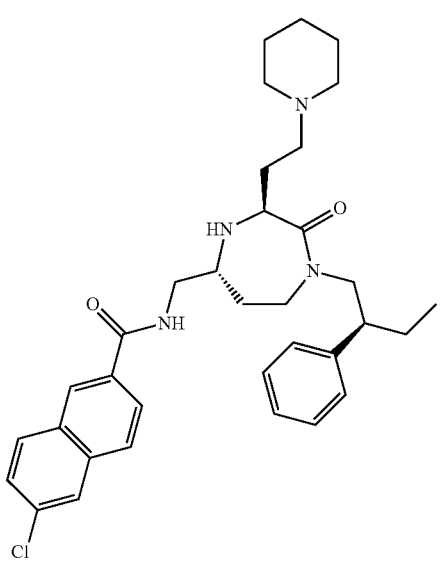
194
-continued
(582)
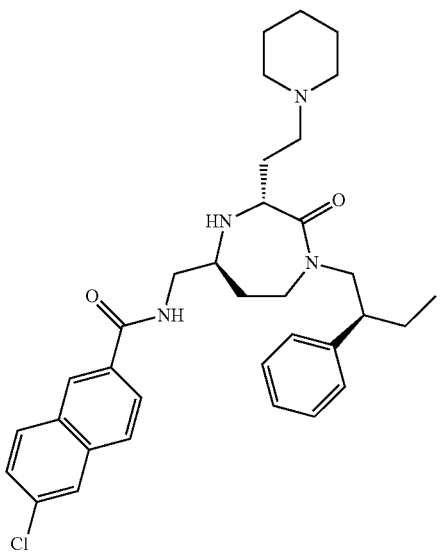
(583)
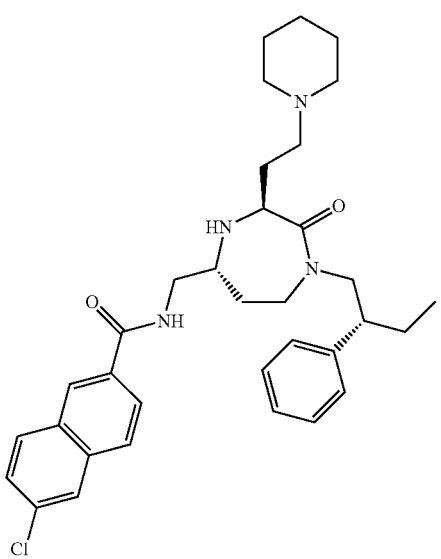
(584)
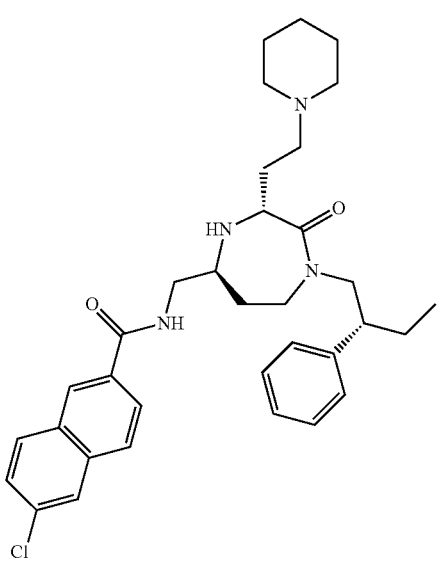

-continued (585)

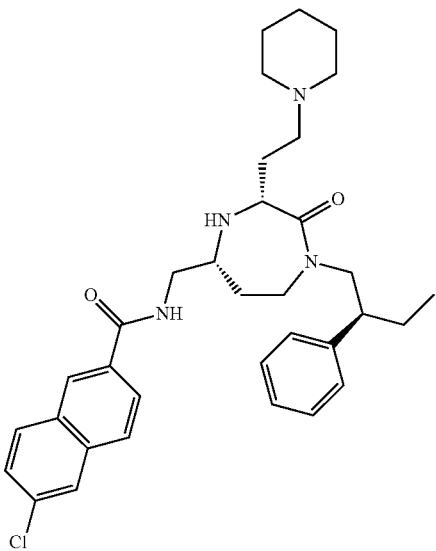

or a pharmaceutically acceptable salt or prodrug thereof.

In order to assist the reader the names of compounds suitable for use in the invention as discussed above are as follows:

(14) N-(((3S,5S)-1-((3,5-dichlorobenzyl)-3-(3-guanidinopropyl)-2-oxo-1,4-diazepan-5-yl)methyl)-2-naphthamide
(25) N-(((3S,5S)-3-(2-(diethylamino)ethyl)-1-(2,2-diphenylethyl)-2-oxo-1,4-diazepan-5-yl)methyl)-6-fluoro-2-naphthamide
(31) N-(((3S,5S)-3-(2-aminoethyl)-1-(2,2-diphenylethyl)-2-oxo-1,4-diazepan-5-yl)methyl)-6-fluoro-2-naphthamide
(33) (E)-3-(4-chlorophenyl)-N-(((3S,5S)-1-(2,2-diphenylethyl)-2-oxo-3-(2-(piperidin-1-yl)ethyl)-1,4-diazepan-5-yl)methyl)acrylamide
(37) N-(((3S,5S)-3-(2-aminoethyl)-2-oxo-1-(2-phenylbutyl)-1,4-diazepan-5-yl)methyl)-2-naphthamide
(38) N-(((3S,5S)-2-oxo-1-((S)-2-phenylbutyl)-3-(2-(piperidin-1-yl)ethyl)-1,4-diazepan-5-yl)methyl)-2-naphthamide
(39) N-(((3S,5S)-2-oxo-1-((R)-2-phenylbutyl)-3-(2-(piperidin-1-yl)ethyl)-1,4-diazepan-5-yl)methyl)-2-naphthamide
(49) N-(((3S,5S)-3-(2-aminoethyl)-1-(3,5-dichlorobenzyl)-2-oxo-1,4-diazepan-5-yl)methyl)-2-naphthamide
(50) N-(((3S,5S)-1-(2,2-diphenylethyl)-3-(3-guanidinopropyl)-2-oxo-1,4-diazepan-5-yl)methyl)naphthalene-2-sulfonamide
(54) N-(((3S,5S)-3-(2-aminoethyl)-1-(2-ethylbutyl)-2-oxo-1,4-diazepan-5-yl)methyl)-2-naphthamide
(60) N-(((3S,5S)-3-(3-aminopropyl)-1-(2,2-diphenylethyl)-2-oxo-1,4-diazepan-5-yl)methyl)-6-bromo-N-methyl-2-naphthamide
(62) N-(((3S,5S)-3-(3-aminopropyl)-1-(2,2-diphenylethyl)-4-methyl-2-oxo-1,4-diazepan-5-yl)methyl)-6-bromo-2-naphthamide
(63) N-(((3S,5S)-3-(3-aminopropyl)-1-(2,2-diphenylethyl)-2-oxo-1,4-diazepan-5-yl)methyl)-2-naphthamide
(64) N-(((3S,5S)-1-(2,2-diphenylethyl)-2-oxo-3-(3-(piperidin-1-yl)propyl)-1,4-diazepan-5-yl)methyl)-2-naphthamide
(65) N-(((3S,5S)-1-(2,2-diphenylethyl)-3-(3-(isopropylamino)propyl)-2-oxo-1,4-diazepan-5-yl)methyl)-2-naphthamide
(67) N-(((3S,5S)-1-(2,2-diphenylethyl)-3-(3-(3-methylguanidino)propyl)-2-oxo-1,4-diazepan-5-yl)methyl)-2-naphthamide
(71) (E)-N-(((3S,5S)-3-butyl-1-(2,2-diphenylethyl)-2-oxo-1,4-diazepan-5-yl)methyl)-3-(4-chlorophenyl)acrylamide
(79) N—((S)-1-((3S,5S)-1-(2,2-diphenylethyl)-3-(3-guanidinopropyl)-2-oxo-1,4-diazepan-5-yl)-2-(naphthalen-2-yl)ethyl)acetamide
(81) (S)-2-acetamido-N—((S)-1-((3S,5S)-1-(2,2-diphenylethyl)-3-(3-guanidinopropyl)-2-oxo-1,4-diazepan-5-yl)-2-(naphthalen-2-yl)ethyl)-3-(1H-imidazol-5-yl)propanamide
(83) propyl(S)-1-((3S,5S)-1-(2,2-diphenylethyl)-3-(3-guanidinopropyl)-2-oxo-1,4-diazepan-5-yl)-2-(naphthalen-2-yl)ethylcarbamate
(85) N—(R)-1-(3S,5S)-1-(2,2-diphenylethyl)-3-(3-guanidinopropyl)-2-oxo-1,4-diazepan-5-yl)-2-(naphthalen-2-yl)ethyl)acetamide
(86) (S)-2-acetamido-N—((R)-1-(3S,5S)-1-(2,2-diphenylethyl)-3-(3-guanidinopropyl)-2-oxo-1,4-diazepan-5-yl)-2-(naphthalen-2-yl)ethyl)-3-(1H-imidazol-4-yl)propanamide
(87) propyl(R)-1-(3S,5S)-1-(2,2-diphenylethyl)-3-(3-guanidinopropyl)-2-oxo-1,4-diazepan-5-yl)-2-(naphthalen-2-yl)ethylcarbamate
(102) N-(((3R,5S)-1-(2,2-diphenylethyl)-3-(3-guanidinopropyl)-2-oxo-1,4-diazepan-5-yl)methyl)-2-naphthamide
(103) N-(((3R,5R)-1-(2,2-diphenylethyl)-3-(3-guanidinopropyl)-2-oxo-1,4-diazepan-5-yl)methyl)-2-naphthamide
(104) N-(((3S,5R)-1-(2,2-diphenylethyl)-3-(3-guanidinopropyl)-2-oxo-1,4-diazepan-5-yl)methyl)-2-naphthamide
(105) N-(((3S,5S)-1-(2,2-diphenylethyl)-3-(3-guanidinopropyl)-2-oxo-1,4-diazepan-5-yl)methyl)-2-naphthamide
(106) N-(((3S,5S)-3-(3-aminopropyl)-1-(2,2-diphenylethyl)-2-oxo-1,4-diazepan-5-yl)methyl)biphenyl-4-carboxamide
(107) N-(((3S,5S)-3-(3-aminopropyl)-1-(2,2-diphenylethyl)-2-oxo-1,4-diazepan-5-yl)methyl)-1H-indole-2-carboxamide
(108) N-(((3S,5S)-1-(2,2-diphenylethyl)-3-(3-guanidinopropyl)-2-oxo-1,4-diazepan-5-yl)methyl)biphenyl-4-carboxamide
(109) N-(((3S,5S)-1-(2,2-diphenylethyl)-3-(3-guanidinopropyl)-2-oxo-1,4-diazepan-5-yl)methyl)-1H-indole-2-carboxamide
(110) N-(((3S,5S)-1-(2,2-diphenylethyl)-3-(3-guanidinopropyl)-2-oxo-1,4-diazepan-5-yl)methyl)-2-(naphthalen-2-yl)acetamide
(111) N-(((3S,5S)-1-(2,2-diphenylethyl)-3-(3-guanidinopropyl)-2-oxo-1,4-diazepan-5-yl)methyl)-1,2,3,4-tetrahydronaphthalene-2-carboxamide
(112) N-(((3S,5S)-1-(2,2-diphenylethyl)-3-(3-guanidinopropyl)-2-oxo-1,4-diazepan-5-yl)methyl)quinoline-3-carboxamide
(113) N-(((3S,5S)-1-(2,2-diphenylethyl)-3-(3-guanidinopropyl)-2-oxo-1,4-diazepan-5-yl)methyl)quinoxaline-2-carboxamide
(114) N-(((3S,5S)-1-(2,2-diphenylethyl)-3-(3-guanidinopropyl)-2-oxo-1,4-diazepan-5-yl)methyl)isoquinoline-3-carboxamide
(115) N-(((3S,5S)-1-(2,2-diphenylethyl)-3-(3-guanidinopropyl)-2-oxo-1,4-diazepan-5-yl)methyl)benzamide
(116) N-(((3S,5S)-1-(2,2-diphenylethyl)-3-(3-guanidinopropyl)-2-oxo-1,4-diazepan-5-yl)methyl)quinoline-2-carboxamide
(117) N-(((3S,5S)-3-(4-aminobutyl)-1-(naphthalen-1-ylmethyl)-2-oxo-1,4-diazepan-5-yl)methyl)-2-naphthamide (118) N-(((3S,5S)-3-(4-aminobutyl)-1-(naphthalen-1-ylmethyl)-2-oxo-1,4-diazepan-5-yl)methyl)-2-(naphthalen-2-yl)acetamide
(119) N-(((3S,5S)-3-(4-aminobutyl)-1-(naphthalen-1-ylmethyl)-2-oxo-1,4-diazepan-5-yl)methyl)-1-naphthamide
(120) N-(((3S,5S)-3-(4-aminobutyl)-1-(naphthalen-1-ylmethyl)-2-oxo-1,4-diazepan-5-yl)methyl)-2-(1H-indol-3-yl)acetamide
(121) N-(((3S,5S)-3-(4-aminobutyl)-1-(naphthalen-2-ylmethyl)-2-oxo-1,4-diazepan-5-yl)methyl)-2-(biphenyl-4-yl)acetamide
(122) N-(((3S,5S)-3-(4-aminobutyl)-1-(naphthalen-2-ylmethyl)-2-oxo-1,4-diazepan-5-yl)methyl)-2-naphthamide
(123) N-(((3S,5S)-3-(4-aminobutyl)-1-(naphthalen-2-ylmethyl)-2-oxo-1,4-diazepan-5-yl)methyl)-2-(naphthalen-2-yl)acetamide
(124) N-(((3S,5S)-3-(4-aminobutyl)-1-(naphthalen-2-ylmethyl)-2-oxo-1,4-diazepan-5-yl)methyl)-1-naphthamide
(125) N-(((3S,5S)-3-(4-aminobutyl)-1-(naphthalen-2-ylmethyl)-2-oxo-1,4-diazepan-5-yl)methyl)-2-(naphthalen-1-yl)acetamide
(126) N-(((3S,5S)-3-(4-aminobutyl)-1-(2,2-diphenylethyl)-2-oxo-1,4-diazepan-5-yl)methyl)-2-naphthamide
(127) (S)—N-(((3S,5S)-3-(4-aminobutyl)-1-(2,2-diphenylethyl)-2-oxo-1,4-diazepan-5-yl)methyl)-1,2,3,4-tetrahydroisoquinoline-3-carboxamide
(128) (R)—N-(((3S,5S)-3-(4-aminobutyl)-1-(2,2-diphenylethyl)-2-oxo-1,4-diazepan-5-yl)methyl)-1,2,3,4-tetrahydroisoquinoline-3-carboxamide
(129) N-(((3S,5S)-3-(4-aminobutyl)-1-(2,2-diphenylethyl)-2-oxo-1,4-diazepan-5-yl)methyl)benzofuran-2-carboxamide
(130) (R)—N-(((3S,5S)-1-(2,2-diphenylethyl)-3-(3-(3-methylguanidino)propyl)-2-oxo-1,4-diazepan-5-yl)methyl)-1,2,3,4-tetrahydroisoquinoline-3-carboxamide
(131) (S)—N-(((3S,5S)-1-(2,2-diphenylethyl)-3-(3-guanidinopropyl)-2-oxo-1,4-diazepan-5-yl)methyl)-1,2,3,4-tetrahydroisoquinoline-3-carboxamide
(132) N-(((3S,5S)-1-(2,2-diphenylethyl)-3-(3-guanidinopropyl)-2-oxo-1,4-diazepan-5-yl)methyl)benzofuran-2-carboxamide
(133) N-(((3S,5S)-1-(2,2-diphenylethyl)-3-(3-guanidinopropyl)-2-oxo-1,4-diazepan-5-yl)methyl)-2,3-dihydro-1H-indene-2-carboxamide
(134) (R)—N-(((3S,5S)-1-(2,2-diphenylethyl)-3-(3-guanidinopropyl)-2-oxo-1,4-diazepan-5-yl)methyl)-1,2,3,4-tetrahydroisoquinoline-3-carboxamide
(135) N-(((3S,5S)-1-(2,2-diphenylethyl)-3-(3-guanidinopropyl)-2-oxo-1,4-diazepan-5-yl)methyl)benzo[b]thiophene-2-carboxamide
(136) 2,4-dichloro-N-(((3S,5S)-1-(2,2-diphenylethyl)-3-(3-guanidinopropyl)-2-oxo-1,4-diazepan-5-yl)methyl)benzamide
(137) 2,5-dichloro-N-(((3S,5S)-1-(2,2-diphenylethyl)-3-(3-guanidinopropyl)-2-oxo-1,4-diazepan-5-yl)methyl)benzamide
(138) N-(((3S,5S)-1-(2,2-diphenylethyl)-3-(3-guanidinopropyl)-2-oxo-1,4-diazepan-5-yl)methyl)benzamide
(139) N-(((3S,5S)-1-(2,2-diphenylethyl)-3-(3-guanidinopropyl)-2-oxo-1,4-diazepan-5-yl)methyl)cyclohexanecarboxamide
(140) N-(((3S,5S)-1-(2,2-diphenylethyl)-3-(3-guanidinopropyl)-2-oxo-1,4-diazepan-5-yl)methyl)-3-phenoxybenzamide
(141) N-(((3S,5S)-1-(2,2-diphenylethyl)-3-(3-guanidinopropyl)-2-oxo-1,4-diazepan-5-yl)methyl)-4-phenoxybenzamide
(142) N-(((3S,5S)-1-(2,2-diphenylethyl)-3-(3-guanidinopropyl)-2-oxo-1,4-diazepan-5-yl)methyl)-1H-indole-2-carboxamide
(143) N-(((3S,5S)-1-(2,2-diphenylethyl)-3-(3-guanidinopropyl)-2-oxo-1,4-diazepan-5-yl)methyl)-3-phenylpropanamide
(144) N-(((3S,5S)-1-(2,2-diphenylethyl)-3-(3-guanidinopropyl)-2-oxo-1,4-diazepan-5-yl)methyl)-3,4-dimethylbenzamide
(145) 4-tert-butyl-N-(((3S,5S)-1-(2,2-diphenylethyl)-3-(3-guanidinopropyl)-2-oxo-1,4-diazepan-5-yl)methyl)benzamide
(146) N-(((3S,5S)-1-(2,2-diphenylethyl)-3-(3-guanidinopropyl)-2-oxo-1,4-diazepan-5-yl)methyl)-2,4-dimethoxybenzamide
(147) 2-cyclohexyl-N-(((3S,5S)-1-(2,2-diphenylethyl)-3-(3-guanidinopropyl)-2-oxo-1,4-diazepan-5-yl)methyl)acetamide
(148) N-(((3S,5S)-1-(2,2-diphenylethyl)-3-(3-guanidinopropyl)-2-oxo-1,4-diazepan-5-yl)methyl)benzo[d][1,3]dioxole-5-carboxamide
(149) N-(((3S,5S)-1-(2,2-diphenylethyl)-3-(3-guanidinopropyl)-2-oxo-1,4-diazepan-5-yl)methyl)-1H-benzo[d]imidazole-5-carboxamide
(150) N-(((3S,5S)-1-(2,2-diphenylethyl)-3-(3-guanidinopropyl)-2-oxo-1,4-diazepan-5-yl)methyl)-1H-benzo[d][1,2,3]triazole-5-carboxamide
(151) N-(((3S,5S)-1-(2,2-diphenylethyl)-3-(3-guanidinopropyl)-2-oxo-1,4-diazepan-5-yl)methyl)cyclopentanecarboxamide
(152) 3,4-dichloro-N-(((3S,5S)-1-(2,2-diphenylethyl)-3-(3-guanidinopropyl)-2-oxo-1,4-diazepan-5-yl)methyl)benzamide
(153) N-(((3S,5S)-1-(2,2-diphenylethyl)-3-(3-guanidinopropyl)-2-oxo-1,4-diazepan-5-yl)methyl)cinnamamide
(154) 3,5-dichloro-N-(((3S,5S)-1-(2,2-diphenylethyl)-3-(3-guanidinopropyl)-2-oxo-1,4-diazepan-5-yl)methyl)benzamide
(155) 2-(2,4-dichlorophenyl)-N-(((3S,5S)-1-(2,2-diphenylethyl)-3-(3-guanidinopropyl)-2-oxo-1,4-diazepan-5-yl)methyl)acetamide
(156) N-(((3S,5S)-1-(2,2-diphenylethyl)-3-(3-guanidinopropyl)-2-oxo-1,4-diazepan-5-yl)methyl)-1-methoxy-2-naphthamide
(157) 2-(3,4-dichlorophenyl)-N-(((3S,5S)-1-(2,2-diphenylethyl)-3-(3-guanidinopropyl)-2-oxo-1,4-diazepan-5-yl)methyl)acetamide
(158) N-(((3S,5S)-1-(2,2-diphenylethyl)-3-(3-guanidinopropyl)-2-oxo-1,4-diazepan-5-yl)methyl)-6-methoxy-2-naphthamide
(159) N-(((3S,5S)-1-(2,2-diphenylethyl)-3-(2-(guanidinooxy)ethyl)-2-oxo-1,4-diazepan-5-yl)methyl)-2-naphthamide
(160) (E)-3-(2,4-dichlorophenyl)-N-(((3S,5S)-1-(2,2-diphenylethyl)-3-(3-guanidino-propyl)-2-oxo-1,4-diazepan-5-yl)methyl)acrylamide
(161) N-(((3S,5S)-1-(2,2-diphenylethyl)-3-(3-guanidinopropyl)-2-oxo-1,4-diazepan-5-yl)methyl)-adamantane-1-carboxamide
(162) N-(((3S,5S)-1-(2,2-diphenylethyl)-3-(3-guanidinopropyl)-2-oxo-1,4-diazepan-5-yl)methyl)-2-phenoxyacetamide
(163) N-(((3S,5S)-1-(2,2-diphenylethyl)-3-(3-guanidinopropyl)-2-oxo-1,4-diazepan-5-yl)methyl)-3-methoxy-2-naphthamide (164) 4-bromo-N-(((3S,5S)-1-(2,2-diphenylethyl)-3-(3-guanidinopropyl)-2-oxo-1,4-diazepan-5-yl)methyl)benzamide
(165) (S)—N-(((3S,5S)-1-(2,2-diphenylethyl)-3-(3-guanidinopropyl)-2-oxo-1,4-diazepan-5-yl)methyl)-2,3-dihydrobenzo[b][1,4]dioxine-2-carboxamide
(166) (E)-3-(4-chlorophenyl)-N-(((3S,5S)-1-(2,2-diphenylethyl)-3-(3-guanidinopropyl)-2-oxo-1,4-diazepan-5-yl)methyl)acrylamide
(167) (E)-N-(((3S,5S)-1-(2,2-diphenylethyl)-3-(3-guanidinopropyl)-2-oxo-1,4-diazepan-5-yl)methyl)-3-(thiophen-2-yl)acrylamide
(168) (R)—N-(((3S,5S)-1-(2,2-diphenylethyl)-3-(3-guanidinopropyl)-2-oxo-1,4-diazepan-5-yl)methyl)-2,3-dihydrobenzo[b][1,4]dioxine-2-carboxamide
(169) (E)-N-(((3S,5S)-1-(2,2-diphenylethyl)-3-(3-guanidinopropyl)-2-oxo-1,4-diazepan-5-yl)methyl)-3-(4-hydroxyphenyl)acrylamide
(170) (E)-N-(((3S,5S)-1-(2,2-diphenylethyl)-3-(3-guanidinopropyl)-2-oxo-1,4-diazepan-5-yl)methyl)-3-(2-methoxyphenyl)acrylamide
(171) (E)-N-(((3S,5S)-1-(2,2-diphenylethyl)-3-(3-guanidinopropyl)-2-oxo-1,4-diazepan-5-yl)methyl)-3-p-tolylacrylamide
(172) (E)-N-(((3S,5S)-1-(2,2-diphenylethyl)-3-(3-guanidinopropyl)-2-oxo-1,4-diazepan-5-yl)methyl)-3-(2-(trifluoromethyl)phenyl)acrylamide
(173) (E)-N-(((3S,5S)-1-(2,2-diphenylethyl)-3-(3-guanidinopropyl)-2-oxo-1,4-diazepan-5-yl)methyl)-3-(3-fluorophenyl)acrylamide
(174) (E)-N-(((3S,5S)-1-(2,2-diphenylethyl)-3-(3-guanidinopropyl)-2-oxo-1,4-diazepan-5-yl)methyl)-2-methyl-3-phenylacrylamide
(175) N-(((3S,5S)-1-(2,2-diphenylethyl)-3-(3-guanidinopropyl)-2-oxo-1,4-diazepan-5-yl)methyl)-2-phenylcyclopropanecarboxamide
(176) 2-(2,4-dichlorophenoxy)-N-(((3S,5S)-1-(2,2-diphenylethyl)-3-(3-guanidinopropyl)-2-oxo-1,4-diazepan-5-yl)methyl)acetamide
(177) (E)-3-(3-chlorophenyl)-N-(((3S,5S)-1-(2,2-diphenylethyl)-3-(3-guanidinopropyl)-2-oxo-1,4-diazepan-5-yl)methyl)acrylamide
(178) N-(((3S,5S)-1-(2,2-diphenylethyl)-3-(3-guanidinopropyl)-2-oxo-1,4-diazepan-5-yl)methyl)benzo[d]thiazole-6-carboxamide
(179) N-(((3S,5S)-1-(2,2-diphenylethyl)-3-(3-guanidinopropyl)-2-oxo-1,4-diazepan-5-yl)methyl)-5-phenylfuran-2-carboxamide
(180) (E)-N-(((3S,5S)-1-(2,2-diphenylethyl)-3-(3-guanidinopropyl)-2-oxo-1,4-diazepan-5-yl)methyl)-3-(3-methoxyphenyl)acrylamide
(181) 6-bromo-N-(((3S,5S)-1-(2,2-diphenylethyl)-3-(3-guanidinopropyl)-2-oxo-1,4-diazepan-5-yl)methyl)-2-naphthamide
(182) N-(((3S,5S)-3-(3-guanidinopropyl)-2-oxo-1-phenethyl-1,4-diazepan-5-yl)methyl)-2-naphthamide
(183) N-(((3S,5S)-1-(3,4-dichlorophenethyl)-3-(3-guanidinopropyl)-2-oxo-1,4-diazepan-5-yl)methyl)-2-naphthamide
(184) N-(((3S,5S)-1-(2,4-dichlorophenethyl)-3-(3-guanidinopropyl)-2-oxo-1,4-diazepan-5-yl)methyl)-2-naphthamide
(185) N-(((3S,5S)-1-(2,2-diphenylethyl)-3-(3-guanidinopropyl)-2-oxo-1,4-diazepan-5-yl)methyl)benzo[b]thiophene-5-carboxamide
(186) N-(((3S,5S)-1-(2,2-diphenylethyl)-3-(3-guanidinopropyl)-2-oxo-1,4-diazepan-5-yl)methyl)-5-methyl-1-phenyl-1H-pyrazole-4-carboxamide
(187) (E)-N-(((3S,5S)-1-(2,2-diphenylethyl)-3-(3-guanidinopropyl)-2-oxo-1,4-diazepan-5-yl)methyl)-3-(4-methoxyphenyl)acrylamide
(188) N-(((3S,5S)-1-(2,2-diphenylethyl)-3-(3-guanidinopropyl)-2-oxo-1,4-diazepan-5-yl)methyl)-6-fluoro-2-naphthamide
(189) (E)-3-(2-chlorophenyl)-N-(((3S,5S)-1-(2,2-diphenylethyl)-3-(3-guanidinopropyl)-2-oxo-1,4-diazepan-5-yl)methyl)acrylamide
(190) (E)-N-(((3S,5S)-1-(2,2-diphenylethyl)-3-(3-guanidinopropyl)-2-oxo-1,4-diazepan-5-yl)methyl)-3-(2-hydroxyphenyl)acrylamide
(191) (E)-N-(((3S,5S)-1-(2,2-diphenylethyl)-3-(3-guanidinopropyl)-2-oxo-1,4-diazepan-5-yl)methyl)-3-m-tolylacrylamide
(192) (E)-N-(((3S,5S)-1-(2,2-diphenylethyl)-3-(3-guanidinopropyl)-2-oxo-1,4-diazepan-5-yl)methyl)-3-(3-(trifluoromethyl)phenyl)acrylamide
(193) (E)-N-(((3S,5S)-1-(2,2-diphenylethyl)-3-(3-guanidinopropyl)-2-oxo-1,4-diazepan-5-yl)methyl)-3-(3-hydroxyphenyl)acrylamide
(194) (E)-N-(((3S,5S)-1-(2,2-diphenylethyl)-3-(3-guanidinopropyl)-2-oxo-1,4-diazepan-5-yl)methyl)-3-(2-fluorophenyl)acrylamide
(195) (E)-N-(((3S,5S)-1-(2,2-diphenylethyl)-3-(3-guanidinopropyl)-2-oxo-1,4-diazepan-5-yl)methyl)-3-o-tolylacrylamide
(196) (Z)—N-(((3S,5S)-1-(2,2-diphenylethyl)-3-(3-guanidinopropyl)-2-oxo-1,4-diazepan-5-yl)methyl)-2-fluoro-3-phenylacrylamide
(197) N-((1-(2,2-diphenylethyl)-2-oxo-3-(piperidin-4-yl)-1,4-diazepan-5-yl)methyl)-2-naphthamide
(198) N-((1-(2,2-diphenylethyl)-2-oxo-3-(piperidin-4-ylmethyl)-1,4-diazepan-5-yl)methyl)-2-naphthamide
(199) (E)-N-(((3S,5S)-1-(2,2-diphenylethyl)-3-(3-guanidinopropyl)-2-oxo-1,4-diazepan-5-yl)methyl)-3-(4-fluorophenyl)acrylamide
(200) (E)-N-(((3S,5S)-1-(2,2-diphenylethyl)-3-(3-guanidinopropyl)-2-oxo-1,4-diazepan-5-yl)methyl)-3-(4-(trifluoromethyl)phenyl)acrylamide
(201) N-(((3S,5S)-1-(2,2-diphenylpropyl)-3-(3-guanidinopropyl)-2-oxo-1,4-diazepan-5-yl)methyl)-2-naphthamide
(202) N-(((3S,5S)-1-(cyclohexylmethyl)-3-(3-guanidinopropyl)-2-oxo-1,4-diazepan-5-yl)methyl)-2-naphthamide
(203) N-(((3S,5S)-1-(1-adamantylmethyl)-3-(3-guanidinopropyl)-2-oxo-1,4-diazepan-5-yl)methyl)-2-naphthamide
(204) N-(((3S,5S)-1-((S)-1,1-diphenylpropan-2-yl)-3-(3-guanidinopropyl)-2-oxo-1,4-diazepan-5-yl)methyl)-2-naphthamide
(205) N-(((3S,5S)-1-((R)-1,1-diphenylpropan-2-yl)-3-(3-guanidinopropyl)-2-oxo-1,4-diazepan-5-yl)methyl)-2-naphthamide
(206) N-(((3S,5S)-1-cyclohexyl-3-(3-guanidinopropyl)-2-oxo-1,4-diazepan-5-yl)methyl)-2-naphthamide
(207) N-(((3S,5S)-1-((R)-1-fluoro-1,1-diphenylpropan-2-yl)-3-(3-guanidinopropyl)-2-oxo-1,4-diazepan-5-yl)methyl)-2-naphthamide
(208) (E)-3-(2,6-difluorophenyl)-N-(((3S,5S)-1-(2,2-diphenylethyl)-3-(3-guanidinopropyl)-2-oxo-1,4-diazepan-5-yl)methyl)acrylamide
(209) (E)-3-(2-chloro-6-fluorophenyl)-N-(((3S,5S)-1-(2,2-diphenylethyl)-3-(3-guanidinopropyl)-2-oxo-1,4-diazepan-5-yl)methyl)acrylamide (210) (E)-3-(4-bromophenyl)-N-(((3S,5S)-1-(2,2-diphenylethyl)-3-(3-guanidinopropyl)-2-oxo-1,4-diazepan-5-yl)methyl)acrylamide
(211) (E)-N-(((3S,5S)-1-(2,2-diphenylethyl)-3-(3-guanidinopropyl)-2-oxo-1,4-diazepan-5-yl)methyl)-3-(4-ethoxyphenyl)acrylamide
(212) N-(((3S,5S)-3-(3-aminopropyl)-1-(2,2-diphenylethyl)-2-oxo-1,4-diazepan-5-yl)methyl)-6-bromo-2-naphthamide
(213) N-(((3S,5S)-3-(3-aminopropyl)-1-(2,2-diphenylethyl)-2-oxo-1,4-diazepan-5-yl)methyl)cinnamamide
(214) (E)-N-(((3S,5S)-3-(3-aminopropyl)-1-(2,2-diphenylethyl)-2-oxo-1,4-diazepan-5-yl)methyl)-3-(4-chlorophenyl)acrylamide
(215) N-(((3S,5S)-1-(2,2-diphenylethyl)-3-(3-guanidinopropyl)-2-oxo-1,4-diazepan-5-yl)methyl)-1,4-dimethoxy-2-naphthamide
(216) N-(((3S,5S)-3-(3-(3,3-dimethylguanidino)propyl)-1-(2,2-diphenylethyl)-2-oxo-1,4-diazepan-5-yl)methyl)-2-naphthamide
(217) N-(((3S,5S)-1-(2,2-diphenylethyl)-3-(3-guanidinopropyl)-2-oxo-1,4-diazepan-5-yl)methyl)-6-hydroxy-2-naphthamide
(218) 6-amino-N-(((3S,5S)-1-(2,2-diphenylethyl)-3-(3-guanidinopropyl)-2-oxo-1,4-diazepan-5-yl)methyl)-2-naphthamide
(219) (E)-N-(((3S,5S)-3-(3-aminopropyl)-1-(2,2-diphenylethyl)-2-oxo-1,4-diazepan-5-yl)methyl)-3-p-tolylacrylamide
(220) (E)-N-(((3S,5S)-3-(3-aminopropyl)-1-(2,2-diphenylethyl)-2-oxo-1,4-diazepan-5-yl)methyl)-3-(4-fluorophenyl)acrylamide
(221) N-(((3S,5S)-3-(3-aminopropyl)-1-(2,2-diphenylethyl)-2-oxo-1,4-diazepan-5-yl)methyl)-6-fluoro-2-naphthamide
(222) N-(((3S,5S)-3-(3-aminopropyl)-1-(2,2-diphenylethyl)-2-oxo-1,4-diazepan-5-yl)methyl)-2-ethylhexanamide
(223) N-(((3S,5S)-3-(3-aminopropyl)-1-(2,2-diphenylethyl)-2-oxo-1,4-diazepan-5-yl)methyl)-3,4-dimethylbenzamide
(224) N-(((3S,5S)-3-(3-aminopropyl)-1-(2,2-diphenylethyl)-2-oxo-1,4-diazepan-5-yl)methyl)-3,4-dichlorobenzamide
(225) N-(((3S,5S)-1-(2,2-diphenylethyl)-3-(3-guanidinopropyl)-2-oxo-1,4-diazepan-5-yl)methyl)-2-ethylhexanamide
(226) N-(((3S,5S)-3-(3-(cyclohexylamino)propyl)-1-(2,2-diphenylethyl)-2-oxo-1,4-diazepan-5-yl)methyl)-2-naphthamide
(227) N-(((3S,5S)-3-(3-guanidinopropyl)-1-(naphthalen-2-yl)-2-oxo-1,4-diazepan-5-yl)methyl)-2-naphthamide
(228) N-(((3S,5S)-1-(9H-fluoren-9-yl)methyl)-3-(3-guanidinopropyl)-2-oxo-1,4-diazepan-5-yl)methyl)-2-naphthamide
(229) N-(((3S,5S)-1-(2,2-diphenylethyl)-2-oxo-3-(pyridin-3-ylmethyl)-1,4-diazepan-5-yl)methyl)-2-naphthamide
(230) N-(((3S,5S)-1-(2,2-diphenylethyl)-2-oxo-3-(pyridin-4-ylmethyl)-1,4-diazepan-5-yl)methyl)-2-naphthamide
(231) (E)-N-(((3S,5S)-3-(3-(cyclohexylamino)propyl)-1-(2,2-diphenylethyl)-2-oxo-1,4-diazepan-5-yl)methyl)-3-(4-fluorophenyl)acrylamide
(232) N-(((3S,5S)-1-(2,2-diphenylethyl)-3-(4-(isopropylamino)butyl)-2-oxo-1,4-diazepan-5-yl)methyl)-2-naphthamide
(233) (E)-N-(((3S,5S)-3-(3-aminopropyl)-1-(2,2-diphenylethyl)-2-oxo-1,4-diazepan-5-yl)methyl)-3-(2,4-difluorophenyl)acrylamide
(234) (E)-N-(((3S,5S)-3-(3-aminopropyl)-1-(2,2-diphenylethyl)-2-oxo-1,4-diazepan-5-yl)methyl)-3-(4-cyanophenyl)acrylamide
(235) (E)-N-(((3S,5S)-3-(3-aminopropyl)-1-(2,2-diphenylethyl)-2-oxo-1,4-diazepan-5-yl)methyl)-3-(naphthalen-2-yl)acrylamide
(236) N-(((3S,5S)-3-(3-aminopropyl)-1-(2,2-diphenylethyl)-2-oxo-1,4-diazepan-5-yl)methyl)-2-(4-fluorophenoxy)acetamide
(237) N-(((3S,5S)-3-(3-aminopropyl)-1-(2,2-diphenylethyl)-2-oxo-1,4-diazepan-5-yl)methyl)-5-((4-chlorophenyl)furan-2-carboxamide
(238) N-(((3S,5S)-3-(3-aminopropyl)-1-(2,2-diphenylethyl)-2-oxo-1,4-diazepan-5-yl)methyl)-4-(1H-pyrrol-1-yl)benzamide
(239) N-(((3S,5S)-3-(3-aminopropyl)-1-(2,2-diphenylethyl)-2-oxo-1,4-diazepan-5-yl)methyl)-2-oxo-1-phenylpyrrolidine-3-carboxamide
(240) N-(((3S,5S)-3-(3-aminopropyl)-1-(2,2-diphenylethyl)-2-oxo-1,4-diazepan-5-yl)methyl)-5-((4-chlorophenyl)isoxazole-3-carboxamide
(241) N-(((3S,5S)-3-(3-aminopropyl)-1-(2,2-diphenylethyl)-2-oxo-1,4-diazepan-5-yl)methyl)-5-(furan-2-yl)isoxazole-3-carboxamide
(242) N-(((3S,5S)-3-(3-aminopropyl)-1-(2,2-diphenylethyl)-2-oxo-1,4-diazepan-5-yl)methyl)-2-phenylthiazole-4-carboxamide
(243) N-(((3S,5S)-3-(3-aminopropyl)-1-(2,2-diphenylethyl)-2-oxo-1,4-diazepan-5-yl)methyl)-4-(3,5-dimethyl-1H-pyrazol-1-yl)benzamide
(244) N-(((3S,5S)-3-(3-aminopropyl)-1-(2,2-diphenylethyl)-2-oxo-1,4-diazepan-5-yl)methyl)-5-methyl-1-phenyl-1H-pyrazole-4-carboxamide
(245) N-(((3S,5S)-1-(2-cyclohexylethyl)-3-(3-guanidinopropyl)-2-oxo-1,4-diazepan-5-yl)methyl)-2-naphthamide
(246) N-(((3S,5S)-1-(2-(bicyclo[2.2.1]heptan-2-yl)ethyl)-3-(3-guanidinopropyl)-2-oxo-1,4-diazepan-5-yl)methyl)-2-naphthamide
(247) N-(((3S,5S)-1-(2,2-bis(4-methoxyphenyl)ethyl)-3-(3-guanidinopropyl)-2-oxo-1,4-diazepan-5-yl)methyl)-2-naphthamide
(248) N-(((3S,5S)-3-(3-(benzylamino)propyl)-1-(2,2-diphenylethyl)-2-oxo-1,4-diazepan-5-yl)methyl)-2-naphthamide
(249) N-(((3S,5S)-3-(3-(cyclopentylamino)propyl)-1-(2,2-diphenylethyl)-2-oxo-1,4-diazepan-5-yl)methyl)-2-naphthamide
(250) N-(((3S,5S)-3-(3-(cyclobutylamino)propyl)-1-(2,2-diphenylethyl)-2-oxo-1,4-diazepan-5-yl)methyl)-2-naphthamide
(251) N-(((3S,5S)-3-(3-(dicyclobutylamino)propyl)-1-(2,2-diphenylethyl)-2-oxo-1,4-diazepan-5-yl)methyl)-2-naphthamide
(252) N-(((3S,5S)-1-benzyl-3-(3-guanidinopropyl)-2-oxo-1,4-diazepan-5-yl)methyl)-2-naphthamide
(253) N-(((3S,5S)-1-(2,2-bis(4-fluorophenyl)ethyl)-3-(3-guanidinopropyl)-2-oxo-1,4-diazepan-5-yl)methyl)-2-naphthamide
(254) N-(((3S,5S)-3-(3-guanidinopropyl)-1-(naphthalen-2-ylmethyl)-2-oxo-1,4-diazepan-5-yl)methyl)-2-naphthamide
(255) (E)-N-(((3S,5S)-3-(3-aminopropyl)-1-(2,2-diphenylethyl)-2-oxo-1,4-diazepan-5-yl)methyl)-3-(5-methylthiophen-2-yl)acrylamide (256) N-(((3S,5S)-3-(3-aminopropyl)-1-(2,2-diphenylethyl)-2-oxo-1,4-diazepan-5-yl)methyl)-3-phenyl-1H-pyrazole-5-carboxamide
(257) (E)-N-(((3S,5S)-3-(3-aminopropyl)-1-(2,2-diphenylethyl)-2-oxo-1,4-diazepan-5-yl)methyl)-3-(4-fluorophenyl)-N-methylacrylamide
(258) (E)-N-(((3S,5S)-3-(3-aminopropyl)-1-(2,2-diphenylethyl)-4-methyl-2-oxo-1,4-diazepan-5-yl)methyl)-3-(4-fluorophenyl)acrylamide
(259) N-(((3S,5S)-3-(3-aminopropyl)-1-(2,2-diphenylethyl)-2-oxo-1,4-diazepan-5-yl)methyl)-4-(3-methyl-5-oxo-4,5-dihydro-1H-pyrazol-1-yl)benzamide
(260) (E)-N-(((3S,5S)-3-(3-aminopropyl)-1-(2,2-diphenylethyl)-2-oxo-1,4-diazepan-5-yl)methyl)-3-(4-bromophenyl)acrylamide
(261) (E)-3-(4-chlorophenyl)-N-(((3S,5S)-1-(2,2-diphenylethyl)-2-oxo-3-(3-(pyrrolidin-1-yl)propyl)-1,4-diazepan-5-yl)methyl)acrylamide
(262) (E)-3-(4-chlorophenyl)-N-(((3S,5S)-1-(2,2-diphenylethyl)-2-oxo-3-(3-(piperidin-1-yl)propyl)-1,4-diazepan-5-yl)methyl)acrylamide
(263) N-(((3S,5S)-3-(2-aminoethyl)-1-(2,2-diphenylethyl)-2-oxo-1,4-diazepan-5-yl)methyl)-2-naphthamide
(264) N-(((3S,5S)-1-(2,2-diphenylethyl)-2-oxo-3-(3-(pyrrolidin-1-yl)propyl)-1,4-diazepan-5-yl)methyl)-2-naphthamide
(265) N-(((3S,5S)-3-(3-(azetidin-1-yl)propyl)-1-(2,2-diphenylethyl)-2-oxo-1,4-diazepan-5-yl)methyl)-2-naphthamide
(266) N-(((3S,5S)-3-(3-guanidinopropyl)-1-(naphthalen-1-ylmethyl)-2-oxo-1,4-diazepan-5-yl)methyl)-2-naphthamide
(267) N-(((3S,5S)-3-(3-guanidinopropyl)-1-(2-(naphthalen-2-yl)ethyl)-2-oxo-1,4-diazepan-5-yl)methyl)-2-naphthamide
(268) N-(((3S,5S)-1-((S)-2-acetamido-2-phenylethyl)-3-(3-guanidinopropyl)-2-oxo-1,4-diazepan-5-yl)methyl)-2-naphthamide
(269) N-(((3S,5S)-1-(2,2-diphenylethyl)-2-oxo-3-(3-(piperidin-1-yl)propyl)-1,4-diazepan-5-yl)methyl)cinnamamide
(270) N-(((3S,5S)-1-(2,2-diphenylethyl)-2-oxo-3-(3-(piperidin-1-yl)propyl)-1,4-diazepan-5-yl)methyl)-3,4-dimethylbenzamide
(271) 3,4-dichloro-N-(((3S,5S)-1-(2,2-diphenylethyl)-2-oxo-3-(3-(piperidin-1-yl)propyl)-1,4-diazepan-5-yl)methyl)benzamide
(272) N-(((3S,5S)-1-((S)-2-(cyclobutanecarboxamido)-2-phenylethyl)-3-(3-guanidinopropyl)-2-oxo-1,4-diazepan-5-yl)methyl)-2-naphthamide
(273) N-(((3S,5S)-1-((S)-2-(cyclohexanecarboxamido)-2-phenylethyl)-3-(3-guanidinopropyl)-2-oxo-1,4-diazepan-5-yl)methyl)-2-naphthamide
(274) N-(((3S,5S)-3-(aminomethyl)-1-(2,2-diphenylethyl)-2-oxo-1,4-diazepan-5-yl)methyl)-2-naphthamide
(275) (E)-N-(((3S,5S)-3-(aminomethyl)-1-(2,2-diphenylethyl)-2-oxo-1,4-diazepan-5-yl)methyl)-3-(4-chlorophenyl)acrylamide
(276) (E)-N-(((3S,5S)-3-(2-aminoethyl)-1-(2,2-diphenylethyl)-2-oxo-1,4-diazepan-5-yl)methyl)-3-(4-fluorophenyl)acrylamide
(277) (E)-N-(((3S,5S)-3-(2-aminoethyl)-1-(2,2-diphenylethyl)-2-oxo-1,4-diazepan-5-yl)methyl)-3-p-tolylacrylamide
(278) N-(((3S,5S)-1-(2,2-diphenylethyl)-2-oxo-3-(piperidin-1-ylmethyl)-1,4-diazepan-5-yl)methyl)-2-naphthamide
(279) (E)-3-(4-chlorophenyl)-N-(((3S,5S)-1-(2,2-diphenylethyl)-2-oxo-3-(piperidin-1-ylmethyl)-1,4-diazepan-5-yl)methyl)acrylamide
(280) N-(((3S,5S)-3-(2-aminoethyl)-1-(2,2-diphenylethyl)-2-oxo-1,4-diazepan-5-yl)methyl)-3,4-dichlorobenzamide
(281) N-(((3S,5S)-3-(2-aminoethyl)-1-(2,2-diphenylethyl)-2-oxo-1,4-diazepan-5-yl)methyl)-3,4-dimethylbenzamide
(282) N-(((3S,5S)-3-(2-aminoethyl)-1-(2,2-diphenylethyl)-2-oxo-1,4-diazepan-5-yl)methyl)cinnamamide
(283) (E)-N-(((3S,5S)-3-(2-aminoethyl)-1-(2,2-diphenylethyl)-2-oxo-1,4-diazepan-5-yl)methyl)-3-(4-chlorophenyl)acrylamide
(284) 3,4-dichloro-N-(((3S,5S)-1-(2,2-diphenylethyl)-2-oxo-3-(2-(piperidin-1-yl)ethyl)-1,4-diazepan-5-yl)methyl)benzamide
(285) N-(((3S,5S)-1-(2,2-diphenylethyl)-2-oxo-3-(2-(piperidin-1-yl)ethyl)-1,4-diazepan-5-yl)methyl)-3,4-dimethylbenzamide
(286) N-(((3S,5S)-1-(2,2-diphenylethyl)-2-oxo-3-(2-(piperidin-1-yl)ethyl)-1,4-diazepan-5-yl)methyl)cinnamamide
(287) (E)-N-(((3S,5S)-1-(2,2-diphenylethyl)-2-oxo-3-(2-(piperidin-1-yl)ethyl)-1,4-diazepan-5-yl)methyl)-3-(4-fluorophenyl)acrylamide
(288) (E)-N-(((3S,5S)-1-(2,2-diphenylethyl)-2-oxo-3-(2-(piperidin-1-yl)ethyl)-1,4-diazepan-5-yl)methyl)-3-p-tolylacrylamide
(289) N-(((3S,5S)-1-((3,5-dimethylbenzyl)-3-(3-guanidinopropyl)-2-oxo-1,4-diazepan-5-yl)methyl)-2-naphthamide
(290) N-(((3S,5S)-1-((S)-2-benzamido-2-phenylethyl)-3-(3-guanidinopropyl)-2-oxo-1,4-diazepan-5-yl)methyl)-2-naphthamide
(291) N-(((3S,5S)-1-((R)-2-benzamido-2-phenylethyl)-3-(3-guanidinopropyl)-2-oxo-1,4-diazepan-5-yl)methyl)-2-naphthamide
(292) N-(((3S,5S)-3-(3-guanidinopropyl)-1-(2-methoxy-2-phenylethyl)-2-oxo-1,4-diazepan-5-yl)methyl)-2-naphthamide
(293) N-(((3S,5S)-3-(3-guanidinopropyl)-2-oxo-1-(2-phenyl-2-propoxyethyl)-1,4-diazepan-5-yl)methyl)-2-naphthamide
(294) N-(((3S,5S)-1-(2-(benzyloxy)-2-phenylethyl)-3-(3-guanidinopropyl)-2-oxo-1,4-diazepan-5-yl)methyl)-2-naphthamide
(295) N-(((3S,5S)-1-(2-(allyloxy)-2-phenylethyl)-3-(3-guanidinopropyl)-2-oxo-1,4-diazepan-5-yl)methyl)-2-naphthamide
(296) N-(((3S,5S)-3-butyl-1-(2,2-diphenylethyl)-2-oxo-1,4-diazepan-5-yl)methyl)-2-naphthamide
(297) (E)-N-(((3S,5S)-3-butyl-1-(2,2-diphenylethyl)-2-oxo-1,4-diazepan-5-yl)methyl)-3-(4-chlorophenyl)acrylamide
(298) (E)-N-(((3S,5S)-3-(3-amino-3-oxopropyl)-1-(2,2-diphenylethyl)-2-oxo-1,4-diazepan-5-yl)methyl)-3-(4-chlorophenyl)acrylamide
(299) N-(((3S,5S)-3-(3-amino-3-oxopropyl)-1-(2,2-diphenylethyl)-2-oxo-1,4-diazepan-5-yl)methyl)-2-naphthamide
(300) (E)-N-(((3S,5S)-3-(3-acetamidopropyl)-1-(2,2-diphenylethyl)-2-oxo-1,4-diazepan-5-yl)methyl)-3-p-tolylacrylamide
(301) N-(3-((2S,7S)-4-(2,2-diphenylethyl)-3-oxo-7-(((E)-3-p-tolylacrylamido)methyl)-1,4-diazepan-2-yl)propyl)cyclohexanecarboxamide
(302) N-(((3S,5S)-3-(3-guanidinopropyl)-2-oxo-1-(2-phenoxy-2-phenylethyl)-1,4-diazepan-5-yl)methyl)-2-naphthamide (303) ethyl 3-((3S,5S)-5-((2-naphthamido)methyl)-3-(3-guanidinopropyl)-2-oxo-1,4-diazepan-1-yl)-2-phenylpropanoate
(304) N-(((3S,5S)-1-(2-ethylbutyl)-3-(3-guanidinopropyl)-2-oxo-1,4-diazepan-5-yl)methyl)-2-naphthamide
(305) N-(((3S,5S)-1-((3,5-dimethylcyclohexyl)methyl)-3-(3-guanidinopropyl)-2-oxo-1,4-diazepan-5-yl)methyl)-2-naphthamide
(306) N-(2-((2S,7S)-7-(((E)-3-(4-chlorophenyl)acrylamido)methyl)-4-(2,2-diphenylethyl)-3-oxo-1,4-diazepan-2-yl)ethyl)cyclohexanecarboxamide
(307) (E)-3-(4-chlorophenyl)-N-(((3S,5S)-3-(2-(2-cyclohexylacetamido)ethyl)-1-(2,2-diphenylethyl)-2-oxo-1,4-diazepan-5-yl)methyl)acrylamide
(308) N-(2-((3S,5R)-1-(2,2-diphenylethyl)-2-oxo-3-(2-aminoethyl)-1,4-diazepan-5-yl)ethyl)benzamide
(309) 3,4-dichloro-N-(2-((3S,5R)-1-(2,2-diphenylethyl)-2-oxo-3-(2-aminoethyl)-1,4-diazepan-5-yl)ethyl)benzamide
(310) N-(2-((3S,5R)-1-(2,2-diphenylethyl)-2-oxo-3-(2-aminoethyl)-1,4-diazepan-5-yl)ethyl)-2-naphthamide
(311) N-(2-((3S,5R)-1-(2,2-diphenylethyl)-2-oxo-3-(2-(piperidin-1-yl)ethyl)-1,4-diazepan-5-yl)ethyl)benzamide
(312) 3,4-dichloro-N-(2-((3S,5R)-1-(2,2-diphenylethyl)-2-oxo-3-(2-(piperidin-1-yl)ethyl)-1,4-diazepan-5-yl)ethyl)benzamide
(313) N-(2-((3S,5R)-1-(2,2-diphenylethyl)-2-oxo-3-(2-(piperidin-1-yl)ethyl)-1,4-diazepan-5-yl)ethyl)-2-naphthamide
(314) N-(((3S,5S)-1-(3-(dimethylamino)-3-oxo-2-phenylpropyl)-3-(3-guanidinopropyl)-2-oxo-1,4-diazepan-5-yl)methyl)-2-naphthamide
(315) N-(((3S,5S)-3-(cyclohexylmethyl)-1-(2,2-diphenylethyl)-2-oxo-1,4-diazepan-5-yl)methyl)-2-naphthamide
(316) N-(((3S,5S)-3-(2-aminoethyl)-1-(3,5-dichlorobenzyl)-2-oxo-1,4-diazepan-5-yl)methyl)-2-naphthamide
(317) N-(((3S,5S)-1-(2,2-diphenylethyl)-2-oxo-3-(3-oxo-3-(piperidin-1-yl)propyl)-1,4-diazepan-5-yl)methyl)-2-naphthamide
(318) (E)-3-(4-chlorophenyl)-N-(((3S,5S)-1-(2,2-diphenylethyl)-2-oxo-3-(3-oxo-3-(piperidin-1-yl)propyl)-1,4-diazepan-5-yl)methyl)acrylamide
(319) N-(((3S,5S)-1-(2,2-diphenylethyl)-2-oxo-3-phenethyl-1,4-diazepan-5-yl)methyl)-2-naphthamide
(320) (E)-3-(4-chlorophenyl)-N-(((3S,5S)-1-(2,2-diphenylethyl)-2-oxo-3-phenethyl-1,4-diazepan-5-yl)methyl)acrylamide
(321) N-(((3S,5S)-3-(2-cyclohexylethyl)-1-(2,2-diphenylethyl)-2-oxo-1,4-diazepan-5-yl)methyl)-2-naphthamide
(322) (E)-3-(4-chlorophenyl)-N-(((3S,5S)-3-(2-cyclohexylethyl)-1-(2,2-diphenylethyl)-2-oxo-1,4-diazepan-5-yl)methyl)acrylamide
(323) N-(((3S,5S)-3-benzyl-1-(2,2-diphenylethyl)-2-oxo-1,4-diazepan-5-yl)methyl)-2-naphthamide
(324) (E)-N-(((3S,5S)-3-benzyl-1-(2,2-diphenylethyl)-2-oxo-1,4-diazepan-5-yl)methyl)-3-(4-chlorophenyl)acrylamide
(325) N-(((3S,5S)-3-(2-aminoethyl)-1-(3,5-dichlorobenzyl)-2-oxo-1,4-diazepan-5-yl)methyl)-3,4-dichlorobenzamide
(326) (E)-N-(((3S,5S)-3-(2-aminoethyl)-1-(3,5-dichlorobenzyl)-2-oxo-1,4-diazepan-5-yl)methyl)-3-(4-chlorophenyl)acrylamide
(327) N-(((3S,5S)-1-(3-chloro-5-fluorobenzyl)-3-(3-guanidinopropyl)-2-oxo-1,4-diazepan-5-yl)methyl)-2-naphthamide
(328) N-(((3S,5S)-1-((3,5-difluorobenzyl)-3-(3-guanidinopropyl)-2-oxo-1,4-diazepan-5-yl)methyl)-2-naphthamide
(329) N-(((3S,5S)-3-(3-aminopropyl)-1-(3-chloro-5-fluorobenzyl)-2-oxo-1,4-diazepan-5-yl)methyl)-2-naphthamide
(330) N-(((3S,5S)-3-(3-aminopropyl)-1-(3,5-difluorobenzyl)-2-oxo-1,4-diazepan-5-yl)methyl)-2-naphthamide
(331) N-(((3S,5S)-3-(3-aminopropyl)-1-(2,5-dichlorobenzyl)-2-oxo-1,4-diazepan-5-yl)methyl)-2-naphthamide
(332) N-(((3S,5S)-3-(3-aminopropyl)-1-(2,6-dichlorobenzyl)-2-oxo-1,4-diazepan-5-yl)methyl)-2-naphthamide
(333) N-(((3S,5S)-3-(3-aminopropyl)-1-(3,5-dimethoxybenzyl)-2-oxo-1,4-diazepan-5-yl)methyl)-2-naphthamide
(334) N-(((3S,5S)-3-(3-aminopropyl)-1-(2-chlorobenzyl)-2-oxo-1,4-diazepan-5-yl)methyl)-2-naphthamide
(335) N-(((3S,5S)-3-(3-aminopropyl)-1-(2,3-dichlorobenzyl)-2-oxo-1,4-diazepan-5-yl)methyl)-2-naphthamide
(336) N-(((3S,5S)-3-(3-aminopropyl)-1-(2,4-dichlorobenzyl)-2-oxo-1,4-diazepan-5-yl)methyl)-2-naphthamide
(337) N-(((3S,5S)-3-(3-aminopropyl)-1-(3,4-dichlorobenzyl)-2-oxo-1,4-diazepan-5-yl)methyl)-2-naphthamide
(338) N-(((3S,5S)-3-(3-aminopropyl)-1-(3-fluoro-5-methylbenzyl)-2-oxo-1,4-diazepan-5-yl)methyl)-2-naphthamide
(339) N-(((3S,5S)-3-(3-aminopropyl)-1-(3-fluoro-5-(trifluoromethyl)benzyl)-2-oxo-1,4-diazepan-5-yl)methyl)-2-naphthamide
(340) N-(((3S,5S)-3-(3-aminopropyl)-1-(4-chlorobenzyl)-2-oxo-1,4-diazepan-5-yl)methyl)-2-naphthamide
(341) N-(((3S,5S)-3-(3-aminopropyl)-2-oxo-1-(2-phenylbutyl)-1,4-diazepan-5-yl)methyl)-2-naphthamide
(342) N-(((3S,5S)-3-(3-aminopropyl)-2-oxo-1-((1-phenylcyclohexyl)methyl)-1,4-diazepan-5-yl)methyl)-2-naphthamide
(343) 3,4-dichloro-N-(((3S,5S)-1-((3,5-dichlorobenzyl)-2-oxo-3-(2-(piperidin-1-yl)ethyl)-1,4-diazepan-5-yl)methyl)benzamide
(344) N-(((3S,5S)-1-((3,5-dichlorobenzyl)-2-oxo-3-(2-(piperidin-1-yl)ethyl)-1,4-diazepan-5-yl)methyl)-2-naphthamide
(345) (E)-3-(4-chlorophenyl)-N-(((3S,5S)-1-((3,5-dichlorobenzyl)-2-oxo-3-(2-(piperidin-1-yl)ethyl)-1,4-diazepan-5-yl)methyl)acrylamide
(346) N-(((3S,5S)-3-(2-aminoethyl)-1-(2-ethylbutyl)-2-oxo-1,4-diazepan-5-yl)methyl)-3,4-dichlorobenzamide
(347) (E)-N-(((3S,5S)-3-(2-aminoethyl)-1-(2-ethylbutyl)-2-oxo-1,4-diazepan-5-yl)methyl)-3-(4-chlorophenyl)acrylamide
(348) (E)-3-(4-chlorophenyl)-N-(((3S,5S)-1-(2-ethylbutyl)-2-oxo-3-(2-(piperidin-1-yl)ethyl)-1,4-diazepan-5-yl)methyl)acrylamide
(349) 3,4-dichloro-N-(((3S,5S)-1-(2-ethylbutyl)-2-oxo-3-(2-(piperidin-1-yl)ethyl)-1,4-diazepan-5-yl)methyl)benzamide
(350) N-(((3S,5S)-1-(2-ethylbutyl)-2-oxo-3-(2-(piperidin-1-yl)ethyl)-1,4-diazepan-5-yl)methyl)-2-naphthamide
(351) N-(((3S,5S)-3-(2-aminoethyl)-1-(2-ethylbutyl)-2-oxo-1,4-diazepan-5-yl)methyl)-4-chloro-3-fluorobenzamide
(352) N-(((3S,5S)-3-(2-aminoethyl)-1-(2-ethylbutyl)-2-oxo-1,4-diazepan-5-yl)methyl)-4-chloro-3-methylbenzamide
(353) N-(((3S,5S)-3-(2-aminoethyl)-1-(2-ethylbutyl)-2-oxo-1,4-diazepan-5-yl)methyl)-3-chloro-4-fluorobenzamide
(354) N-(((3S,5S)-3-(2-aminoethyl)-1-(2-ethylbutyl)-2-oxo-1,4-diazepan-5-yl)methyl)-3-chloro-4-methylbenzamide
(355) (E)-3-(4-chlorophenyl)-N-(((3S,5S)-1-(2-ethylbutyl)-2-oxo-3-(piperidin-1-ylmethyl)-1,4-diazepan-5-yl)methyl)acrylamide
(356) N-(2-((3S,5R)-1-(2,2-diphenylethyl)-2-oxo-3-(2-(pyrrolidin-1-yl)ethyl)-1,4-diazepan-5-yl)ethyl)-2-naphthamide (357) N-(((3S,5S)-3-(3-aminopropyl)-1-(3,5-bis(trifluoromethyl)benzyl)-2-oxo-1,4-diazepan-5-yl)methyl)-2-naphthamide
(358) N-(((3S,5S)-3-(3-aminopropyl)-1-(3-chlorobenzyl)-2-oxo-1,4-diazepan-5-yl)methyl)-2-naphthamide
(359) N-(((3S,5S)-2-oxo-1-(2-phenylbutyl)-3-(3-(piperidin-1-yl)propyl)-1,4-diazepan-5-yl)methyl)-2-naphthamide
(360) N-(((3S,5S)-3-(3-guanidinopropyl)-2-oxo-1-(3-oxo-2-phenyl-3-(piperidin-1-yl)propyl)-1,4-diazepan-5-yl)methyl)-2-naphthamide
(361) N-(((3S,5S)-3-(3-guanidinopropyl)-2-oxo-1-(3-oxo-2-phenyl-3-(phenylamino)propyl)-1,4-diazepan-5-yl)methyl)-2-naphthamide
(362) 3,4-dichloro-N-(2-((3S,5R)-1-(2,2-diphenylethyl)-3-(2-(isopropylamino)ethyl)-2-oxo-1,4-diazepan-5-yl)ethyl)benzamide
(363) 3,4-dichloro-N-(2-((3S,5R)-3-(2-(diisopropylamino)ethyl)-1-(2,2-diphenylethyl)-2-oxo-1,4-diazepan-5-yl)ethyl)benzamide
(364) N-(((3S,5S)-3-(aminomethyl)-1-(3,5-dichlorobenzyl)-2-oxo-1,4-diazepan-5-yl)methyl)-3,4-dichlorobenzamide
(365) N-(((3S,5S)-3-(aminomethyl)-1-(3,5-dichlorobenzyl)-2-oxo-1,4-diazepan-5-yl)methyl)-2-naphthamide
(366) (E)-N-(((3S,5S)-3-(aminomethyl)-1-(3,5-dichlorobenzyl)-2-oxo-1,4-diazepan-5-yl)methyl)-3-(4-chlorophenyl)acrylamide
(367) 3,4-dichloro-N-(((3S,5S)-1-((3,5-dichlorobenzyl)-2-oxo-3-(piperidin-1-ylmethyl)-1,4-diazepan-5-yl)methyl)benzamide
(368) (E)-3-(4-chlorophenyl)-N-(((3S,5S)-1-((3,5-dichlorobenzyl)-2-oxo-3-(piperidin-1-ylmethyl)-1,4-diazepan-5-yl)methyl)acrylamide
(369) N-(((3S,5S)-3-(2-aminoethyl)-2-oxo-1-(2-phenylbutyl)-1,4-diazepan-5-yl)methyl)-3,4-dichlorobenzamide
(370) (E)-N-(((3S,5S)-3-(2-aminoethyl)-2-oxo-1-(2-phenylbutyl)-1,4-diazepan-5-yl)methyl)-3-(4-chlorophenyl)acrylamide
(371) 3,4-dichloro-N-(((3S,5S)-1-((3,5-dichlorobenzyl)-2-oxo-3-(pyrrolidin-1-ylmethyl)-1,4-diazepan-5-yl)methyl)benzamide
(372) N-(((3S,5S)-1-((3,5-dichlorobenzyl)-2-oxo-3-(pyrrolidin-1-ylmethyl)-1,4-diazepan-5-yl)methyl)-2-naphthamide
(373) N-(((3S,5S)-3-(3-aminopropyl)-2-oxo-1-((S)-2-phenylpropyl)-1,4-diazepan-5-yl)methyl)-2-naphthamide
(374) N-(((3S,5S)-3-(3-aminopropyl)-2-oxo-1-((R)-2-phenylpropyl)-1,4-diazepan-5-yl)methyl)-2-naphthamide
(375) N-(((3S,5S)-3-(2-(dimethylamino)ethyl)-1-(2,2-diphenylethyl)-2-oxo-1,4-diazepan-5-yl)methyl)-2-naphthamide
(376) N-(((3S,5S)-1-(2,2-diphenylethyl)-2-oxo-3-(3-(piperidin-1-yl)propyl)-1,4-diazepan-5-yl)methyl)-6-fluoro-2-naphthamide
(377) N-(((3S,5S)-3-(3-aminopropyl)-1-(3,5-diethynylbenzyl)-2-oxo-1,4-diazepan-5-yl)methyl)-2-naphthamide
(378) (E)-3-(4-chlorophenyl)-N-(((3S,5S)-3-(2-(diethylamino)ethyl)-1-(2,2-diphenylethyl)-2-oxo-1,4-diazepan-5-yl)methyl)acrylamide
(379) N-(((3S,5S)-3-(2-(diethylamino)ethyl)-1-(2,2-diphenylethyl)-2-oxo-1,4-diazepan-5-yl)methyl)-2-naphthamide
(380) 3,4-dichloro-N-(((3S,5S)-2-oxo-1-((R)-2-phenylbutyl)-3-(2-(piperidin-1-yl)ethyl)-1,4-diazepan-5-yl)methyl)benzamide
(381) (E)-3-(4-chlorophenyl)-N-(((3S,5S)-2-oxo-1-((R)-2-phenylbutyl)-3-(2-(piperidin-1-yl)ethyl)-1,4-diazepan-5-yl)methyl)acrylamide
(382) (E)-3-(4-chlorophenyl)-N-(((3S,5S)-2-oxo-1-((S)-2-phenylbutyl)-3-(2-(piperidin-1-yl)ethyl)-1,4-diazepan-5-yl)methyl)acrylamide
(383) N-(((3S,5S)-3-(2-aminoethyl)-1-(2,2-diphenylethyl)-2-oxo-1,4-diazepan-5-yl)methyl)-6-chloro-2-naphthamide
(384) N-(((3S,5S)-1-(2,2-diphenylethyl)-2-oxo-3-(2-(pyrrolidin-1-yl)ethyl)-1,4-diazepan-5-yl)methyl)-2-naphthamide
(385) N-(((3S,5S)-1-(2,2-diphenylethyl)-2-oxo-3-(2-(piperidin-1-yl)ethyl)-1,4-diazepan-5-yl)methyl)-2-naphthamide
(386) N-(((3S,5S)-3-(2-aminoethyl)-1-(2-ethylbutyl)-2-oxo-1,4-diazepan-5-yl)methyl)-6-fluoro-2-naphthamide
(387) N-(((3S,5S)-3-(2-aminoethyl)-1-(2-ethylbutyl)-2-oxo-1,4-diazepan-5-yl)methyl)-6-chloro-2-naphthamide
(388) N-(((3S,5S)-3-(2-aminoethyl)-1-(2-ethylbutyl)-2-oxo-1,4-diazepan-5-yl)methyl)-6-bromo-2-naphthamide
(389) N-(((3S,5S)-1-(2-ethylbutyl)-2-oxo-3-(2-(piperidin-1-yl)ethyl)-1,4-diazepan-5-yl)methyl)-6-fluoro-2-naphthamide
(390) 6-chloro-N-(((3S,5S)-1-(2-ethylbutyl)-2-oxo-3-(2-(piperidin-1-yl)ethyl)-1,4-diazepan-5-yl)methyl)-2-naphthamide
(391) 6-bromo-N-(((3S,5S)-1-(2-ethylbutyl)-2-oxo-3-(2-(piperidin-1-yl)ethyl)-1,4-diazepan-5-yl)methyl)-2-naphthamide
(392) N-(((3S,5S)-3-(2-aminoethyl)-1-((3,5-dimethylcyclohexyl)methyl)-2-oxo-1,4-diazepan-5-yl)methyl)-3,4-dichlorobenzamide
(393) N-(((3S,5S)-3-(2-aminoethyl)-1-((3,5-dimethylcyclohexyl)methyl)-2-oxo-1,4-diazepan-5-yl)methyl)-2-naphthamide
(394) (E)-N-(((3S,5S)-3-(2-aminoethyl)-1-((3,5-dimethylcyclohexyl)methyl)-2-oxo-1,4-diazepan-5-yl)methyl)-3-(4-chlorophenyl)acrylamide
(395) 6-chloro-N-(((3S,5S)-1-(2,2-diphenylethyl)-2-oxo-3-(2-(piperidin-1-yl)ethyl)-1,4-diazepan-5-yl)methyl)-2-naphthamide
(396) N-(((3S,5S)-1-(2,2-diphenylethyl)-2-oxo-3-(2-(piperidin-1-yl)ethyl)-1,4-diazepan-5-yl)methyl)-6-fluoro-2-naphthamide
(397) (E)-3-(4-chlorophenyl)-N-(((3S,5S)-1-(2,2-diphenylethyl)-2-oxo-3-(2-(pyrrolidin-1-yl)ethyl)-1,4-diazepan-5-yl)methyl)acrylamide
(398) (E)-3-(4-chlorophenyl)-N-(((3S,5S)-1-(2,2-diphenylethyl)-3-(2-(isopropylamino)ethyl)-2-oxo-1,4-diazepan-5-yl)methyl)acrylamide
(399) N-(((3S,5S)-1-(2,2-diphenylethyl)-3-(2-(isopropylamino)ethyl)-2-oxo-1,4-diazepan-5-yl)methyl)-2-naphthamide
(400) 3,4-dichloro-N-(((3S,5S)-1-(2,2-diphenylethyl)-3-(2-(isopropylamino)ethyl)-2-oxo-1,4-diazepan-5-yl)methyl)benzamide
(401) N-(((3S,5S)-3-(3-aminopropyl)-1-((2,6-dimethylcyclohexyl)methyl)-2-oxo-1,4-diazepan-5-yl)methyl)-2-naphthamide
(402) N-(((3S,5S)-3-(3-aminopropyl)-2-oxo-1-((S)-2-phenylbutyl)-1,4-diazepan-5-yl)methyl)-2-naphthamide
(403) 3,4-dichloro-N-(((3S,5S)-1-((3,5-dimethylcyclohexyl)methyl)-2-oxo-3-(2-(piperidin-1-yl)ethyl)-1,4-diazepan-5-yl)methyl)benzamide
(404) 3,4-dichloro-N-(((3S,5S)-1-((3,5-dimethylcyclohexyl)methyl)-3-(2-(isopropylamino)ethyl)-2-oxo-1,4-diazepan-5-yl)methyl)benzamide
(405) N-(((3S,5S)-3-(2-aminoethyl)-1-(3-methyl-2-phenylbutyl)-2-oxo-1,4-diazepan-5-yl)methyl)-2-naphthamide (406) N-(((3S,5S)-3-(2-aminoethyl)-2-oxo-1-((S)-2-phenylbutyl)-1,4-diazepan-5-yl)methyl)-2-naphthamide
(407) N-(((3S,5S)-3-(3-aminopropyl)-2-oxo-1-((R)-2-phenylbutyl)-1,4-diazepan-5-yl)methyl)-2-naphthamide
(408) (E)-N-(((3S,5S)-3-((1H-imidazol-4-yl)methyl)-1-(2,2-diphenylethyl)-2-oxo-1,4-diazepan-5-yl)methyl)-3-(4-chlorophenyl)acrylamide
(409) 3-(4-chlorophenyl)-N-(((3S,5S)-1-(2,2-diphenylethyl)-2-oxo-3-(2-(piperidin-1-yl)ethyl)-1,4-diazepan-5-yl)methyl)propanamide
(410) N-(((3S,5S)-3-(2-aminoethyl)-1-(2,2-diphenylethyl)-2-oxo-1,4-diazepan-5-yl)methyl)-3-(4-chlorophenyl)propanamide
(411) N-(((2S,7S)-7-(((E)-3-(4-chlorophenyl)acrylamido)methyl)-4-(2,2-diphenylethyl)-3-oxo-1,4-diazepan-2-yl)methyl)picolinamide
(412) (E)-3-(4-chlorophenyl)-N-(((3S,5S)-1-(2,2-diphenylethyl)-2-oxo-3-(pyridin-2-ylmethyl)-1,4-diazepan-5-yl)methyl)acrylamide
(413) N-(((3S,5S)-1-((R)-3-methyl-2-phenylbutyl)-2-oxo-3-(2-(piperidin-1-yl)ethyl)-1,4-diazepan-5-yl)methyl)-2-naphthamide
(414) N-(((3S,5S)-1-((S)-3-methyl-2-phenylbutyl)-2-oxo-3-(2-(piperidin-1-yl)ethyl)-1,4-diazepan-5-yl)methyl)-2-naphthamide
(415) (E)-N-(((3S,5S)-1-(2,2-diphenylethyl)-2-oxo-3-(2-(piperidin-1-yl)ethyl)-1,4-diazepan-5-yl)methyl)-3-(4-isopropylphenyl)acrylamide
(416) (E)-N-(((3S,5S)-3-(2-aminoethyl)-1-(2,2-diphenylethyl)-2-oxo-1,4-diazepan-5-yl)methyl)-3-(4-isopropylphenyl)acrylamide
(417) (E)-3-(2,4-dimethylphenyl)-N-(((3S,5S)-1-(2,2-diphenylethyl)-2-oxo-3-(2-(piperidin-1-yl)ethyl)-1,4-diazepan-5-yl)methyl)acrylamide
(418) (E)-N-(((3S,5S)-3-(2-aminoethyl)-1-(2,2-diphenylethyl)-2-oxo-1,4-diazepan-5-yl)methyl)-3-(2,4-dimethylphenyl)acrylamide
(419) (E)-3-(2,4-difluorophenyl)-N-(((3S,5S)-1-(2,2-diphenylethyl)-2-oxo-3-(2-(piperidin-1-yl)ethyl)-1,4-diazepan-5-yl)methyl)acrylamide
(420) (E)-N-(((3S,5S)-3-(2-aminoethyl)-1-(2,2-diphenylethyl)-2-oxo-1,4-diazepan-5-yl)methyl)-3-(2,4-difluorophenyl)acrylamide
(421) N-(((2S,7S)-7-(((E)-3-(4-chlorophenyl)acrylamido)methyl)-4-(2,2-diphenylethyl)-3-oxo-1,4-diazepan-2-yl)methyl)cyclohexanecarboxamide
(422) (E)-3-(4-chlorophenyl)-N-(((3S,5S)-1-(2,2-diphenylethyl)-3-(2-morpholinoethyl)-2-oxo-1,4-diazepan-5-yl)methyl)acrylamide
(423) (E)-3-(4-chlorophenyl)-N-(((3S,5S)-3-(2-(2,5-dimethyl-1H-pyrrol-1-yl)ethyl)-1-(2,2-diphenylethyl)-2-oxo-1,4-diazepan-5-yl)methyl)acrylamide
(424) (E)-3-(4-chlorophenyl)-N-(((3S,5S)-3-(2-(2,5-dimethylpyrrolidin-1-yl)ethyl)-1-(2,2-diphenylethyl)-2-oxo-1,4-diazepan-5-yl)methyl)acrylamide
(425) 6-chloro-N-(((3S,5S)-2-oxo-1-((S)-2-phenylbutyl)-3-(2-(piperidin-1-yl)ethyl)-1,4-diazepan-5-yl)methyl)-2-naphthamide
(426) (E)-3-(4-chlorophenyl)-N-(((3S,5S)-2-oxo-1-((S)-2-phenylbutyl)-3-(2-(pyrrolidin-1-yl)ethyl)-1,4-diazepan-5-yl)methyl)acrylamide
(427) (E)-3-(4-chlorophenyl)-N-(((3S,5S)-3-(2-(isopropylamino)ethyl)-2-oxo-1-((S)-2-phenylbutyl)-1,4-diazepan-5-yl)methyl)acrylamide
(428) 6-chloro-N-(((3S,5S)-2-oxo-1-((S)-2-phenylbutyl)-3-(2-(pyrrolidin-1-yl)ethyl)-1,4-diazepan-5-yl)methyl)-2-naphthamide
(429) 3,4-dichloro-N-(((3S,5S)-2-oxo-1-((S)-2-phenylbutyl)-3-(2-(piperidin-1-yl)ethyl)-1,4-diazepan-5-yl)methyl)benzamide
(430) 3,4-dichloro-N-(((3S,5S)-2-oxo-1-((S)-2-phenylbutyl)-3-(2-(pyrrolidin-1-yl)ethyl)-1,4-diazepan-5-yl)methyl)benzamide
(431) benzyl((3S,5S)-1-(2,2-diphenylethyl)-2-oxo-3-(2-(piperidin-1-yl)ethyl)-1,4-diazepan-5-yl)methylcarbamate
(432) (E)-3-(4-bromophenyl)-N-(((3S,5S)-1-(2,2-diphenylethyl)-2-oxo-3-(2-(piperidin-1-yl)ethyl)-1,4-diazepan-5-yl)methyl)acrylamide
(433) 5-(4-chlorophenyl)-N-(((3S,5S)-1-(2,2-diphenylethyl)-2-oxo-3-(2-(piperidin-1-yl)ethyl)-1,4-diazepan-5-yl)methyl)isoxazole-3-carboxamide
(434) (E)-3-(4-chlorophenyl)-N-(((3S,5S)-1-(2,2-diphenylethyl)-2-oxo-3-(2-oxo-2-(pyridin-2-ylamino)ethyl)-1,4-diazepan-5-yl)methyl)acrylamide
(435) (E)-3-(4-chlorophenyl)-N-(((3S,5S)-1-(2,2-diphenylethyl)-2-oxo-3-(2-oxo-2-(piperidin-1-yl)ethyl)-1,4-diazepan-5-yl)methyl)acrylamide
(436) 6-chloro-N-(((3S,5S)-2-oxo-3-(3-oxo-3-(piperidin-1-yl)propyl)-1-((S)-2-phenylbutyl)-1,4-diazepan-5-yl)methyl)-2-naphthamide
(437) 3,4-dichloro-N-(((3S,5S)-2-oxo-3-(3-oxo-3-(piperidin-1-yl)propyl)-1-((S)-2-phenylbutyl)-1,4-diazepan-5-yl)methyl)benzamide
(438) 6-chloro-N-(((3S,5S)-2-oxo-1-((S)-2-phenylbutyl)-3-(piperidin-1-ylmethyl)-1,4-diazepan-5-yl)methyl)-2-naphthamide
(439) 3,4-dichloro-N-(((3S,5S)-2-oxo-1-((S)-2-phenylbutyl)-3-(piperidin-1-ylmethyl)-1,4-diazepan-5-yl)methyl)benzamide
(440) 6-chloro-N-(((3S,5S)-2-oxo-1-((S)-2-phenylbutyl)-3-(3-(piperidin-1-yl)propyl)-1,4-diazepan-5-yl)methyl)-2-naphthamide
(441) 3,4-dichloro-N-(((3S,5S)-2-oxo-1-((S)-2-phenylbutyl)-3-(3-(piperidin-1-yl)propyl)-1,4-diazepan-5-yl)methyl)benzamide
(442) (E)-N-(2-((3S,5S)-3-(2-aminoethyl)-1-(2,2-diphenylethyl)-2-oxo-1,4-diazepan-5-yl)propan-2-yl)-3-(4-chlorophenyl)acrylamide
(443) (E)-3-(4-chlorophenyl)-N-(2-((3S,5S)-1-(2,2-diphenylethyl)-2-oxo-3-(2-(piperidin-1-yl)ethyl)-1,4-diazepan-5-yl)propan-2-yl)acrylamide
(444) N-(((3S,5S)-3-(2-aminoethyl)-1-((R)-2-(4-chlorophenyl)propyl)-2-oxo-1,4-diazepan-5-yl)methyl)-2-naphthamide
(445) N-(((3S,5S)-3-(2-aminoethyl)-1-(2-(4-chlorophenyl)propyl)-2-oxo-1,4-diazepan-5-yl)methyl)-2-naphthamide
(446) N-(((3S,5S)-1-((R)-2-(4-chlorophenyl)propyl)-2-oxo-3-(2-(piperidin-1-yl)ethyl)-1,4-diazepan-5-yl)methyl)-2-naphthamide
(447) N-(((3S,5S)-1-((S)-2-(4-chlorophenyl)propyl)-2-oxo-3-(2-(piperidin-1-yl)ethyl)-1,4-diazepan-5-yl)methyl)-2-naphthamide
(448) 3,4-dichloro-N-(((3S,5S)-3-(2-(methyl(phenyl)amino)ethyl)-2-oxo-1-((S)-2-phenylbutyl)-1,4-diazepan-5-yl)methyl)benzamide
(449) 3,4-dichloro-N-(((3S,5S)-3-(2-(diethylamino)ethyl)-2-oxo-1-((S)-2-phenylbutyl)-1,4-diazepan-5-yl)methyl)benzamide
(450) 3,4-dichloro-N-(((3S,5S)-3-(2-morpholinoethyl)-2-oxo-1-((S)-2-phenylbutyl)-1,4-diazepan-5-yl)methyl)benzamide
(451) 3,4-dichloro-N-(((3S,5S)-2-oxo-3-(2-(phenylamino)ethyl)-1-((S)-2-phenylbutyl)-1,4-diazepan-5-yl)methyl)benzamide (452) N-(((3S,5S)-3-(2-(benzylamino)ethyl)-2-oxo-1-((S)-2-phenylbutyl)-1,4-diazepan-5-yl)methyl)-3,4-dichlorobenzamide
(453) (5S,9aS)-5-((2-aminobenzyl)-2-(E)-3-(4-chlorophenyl)acryloyl)-7-(2,2-diphenylethyl)hexahydro-1H-imidazo[1,5-d][1,4]diazepin-6(5H)-one
(454) N-(((3S,5S)-3-(2-(tert-butylamino)ethyl)-2-oxo-1-((S)-2-phenylbutyl)-1,4-diazepan-5-yl)methyl)-3,4-dichlorobenzamide
(455) 3,4-dichloro-N-(((3S,5S)-3-(2-(4-methylpiperazin-1-yl)ethyl)-2-oxo-1-((S)-2-phenylbutyl)-1,4-diazepan-5-yl)methyl)benzamide
(456) N-(((3S,5S)-2-oxo-1-((R)-2-phenylpentyl)-3-(2-(piperidin-1-yl)ethyl)-1,4-diazepan-5-yl)methyl)-2-naphthamide
(457) N-(((3S,5S)-2-oxo-1-((S)-2-phenylpentyl)-3-(2-(piperidin-1-yl)ethyl)-1,4-diazepan-5-yl)methyl)-2-naphthamide
(458) N-(((3S,5S)-1-(2,2-diphenylethyl)-2-oxo-3-(2-(piperidin-1-yl)ethyl)-1,4-diazepan-5-yl)methyl)-4-(trifluoromethyl)benzamide
(459) N-(((3S,5S)-3-(2-aminoethyl)-1-(2,2-diphenylethyl)-2-oxo-1,4-diazepan-5-yl)methyl)-4-(trifluoromethyl)benzamide
(460) N-(((3S,5S)-1-(2,2-diphenylethyl)-2-oxo-3-(2-(piperidin-1-yl)ethyl)-1,4-diazepan-5-yl)methyl)-3-(trifluoromethyl)benzamide
(461) N-(((3S,5S)-3-(2-aminoethyl)-1-(2,2-diphenylethyl)-2-oxo-1,4-diazepan-5-yl)methyl)-3-(trifluoromethyl)benzamide
(462) 6-chloro-N-(((3S,5S)-1-((3,5-dichlorobenzyl)-3-(2-(isopropylamino)ethyl)-2-oxo-1,4-diazepan-5-yl)methyl)-2-naphthamide
(463) 3,4-dichloro-N-(((3S,5S)-1-((3,5-dichlorobenzyl)-3-(2-(isopropylamino)ethyl)-2-oxo-1,4-diazepan-5-yl)methyl)benzamide
(464) 6-chloro-N-(((3S,5S)-3-(2-(isopropylamino)ethyl)-2-oxo-1-((S)-2-phenylbutyl)-1,4-diazepan-5-yl)methyl)-2-naphthamide
(465) N-(((3S,5S)-3-(2-aminoethyl)-2-oxo-1-((S)-2-phenylbutyl)-1,4-diazepan-5-yl)methyl)-6-chloro-2-naphthamide
(466) N-(((3S,5S)-3-(2-aminobenzyl)-1-(2,2-diphenylethyl)-2-oxo-1,4-diazepan-5-yl)methyl)-2-naphthamide
(467) N-(((3S,5S)-3-(2-(benzyl(methyl)amino)ethyl)-2-oxo-1-((S)-2-phenylbutyl)-1,4-diazepan-5-yl)methyl)-3,4-dichlorobenzamide
(468) 3,4-dichloro-N-(((3S,5S)-2-oxo-1-((S)-2-phenylbutyl)-3-(2-(piperazin-1-yl)ethyl)-1,4-diazepan-5-yl)methyl)benzamide
(469) 3,4-dichloro-N-(((3S,5S)-3-(2-(methyl(pentyl)amino)ethyl)-2-oxo-1-((S)-2-phenylbutyl)-1,4-diazepan-5-yl)methyl)benzamide
(470) 3,4-dichloro-N-(((3S,5S)-3-(2-(diisopropylamino)ethyl)-2-oxo-1-((S)-2-phenylbutyl)-1,4-diazepan-5-yl)methyl)benzamide
(471) 3,4-dichloro-N-(((3S,5S)-3-(2-(4-methylpiperidin-1-yl)ethyl)-2-oxo-1-((S)-2-phenylbutyl)-1,4-diazepan-5-yl)methyl)benzamide
(472) (S)-6-chloro-N-((2-oxo-1-(2-phenylbutyl)-3-(piperidin-4-yl)-1,4-diazepan-5-yl)methyl)-2-naphthamide
(473) (S)-6-chloro-N-(3-(1-isopentylpiperidin-4-yl)-2-oxo-1-(2-phenylbutyl)-1,4-diazepan-5-yl)methyl)-2-naphthamide
(474) N-(((3S,5S)-3-butyl-2-oxo-1-((S)-2-phenylbutyl)-1,4-diazepan-5-yl)methyl)-6-chloro-2-naphthamide
(475) 6-chloro-N-(((3S,5S)-3-isopentyl-2-oxo-1-((S)-2-phenylbutyl)-1,4-diazepan-5-yl)methyl)-2-naphthamide
(476) 3,4-dichloro-N-(((3S,5S)-3-(2-(3,5-dimethylpiperidin-1-yl)ethyl)-2-oxo-1-((S)-2-phenylbutyl)-1,4-diazepan-5-yl)methyl)benzamide
(477) 3,4-dichloro-N-(((3S,5S)-3-(2-(4-hydroxypiperidin-1-yl)ethyl)-2-oxo-1-((S)-2-phenylbutyl)-1,4-diazepan-5-yl)methyl)benzamide
(478) 1-(2-((2S,7S)-7-((3,4-dichlorobenzamido)methyl)-3-oxo-4-((S)-2-phenylbutyl)-1,4-diazepan-2-yl)ethyl)piperidine-4-carboxylic acid
(479) N-(((3S,5S)-3-(2-(azepan-1-yl)ethyl)-2-oxo-1-((S)-2-phenylbutyl)-1,4-diazepan-5-yl)methyl)-3,4-dichlorobenzamide
(480) 3,4-dichloro-N-(((3S,5S)-3-(2-((S)-2-methylpiperidin-1-yl)ethyl)-2-oxo-1-((S)-2-phenylbutyl)-1,4-diazepan-5-yl)methyl)benzamide
(481) N-(((3S,5S)-3-(2-(tert-butyl(methyl)amino)ethyl)-2-oxo-1-((S)-2-phenylbutyl)-1,4-diazepan-5-yl)methyl)-3,4-dichlorobenzamide
(482) N-(((3S,5S)-1-(2,2-diphenylethyl)-2-oxo-3-(2-(piperidin-1-yl)benzyl)-1,4-diazepan-5-yl)methyl)-2-naphthamide
(483) N-(((3S,5S)-3-(3-(butyl(methyl)amino)-3-oxopropyl)-2-oxo-1-((S)-2-phenylbutyl)-1,4-diazepan-5-yl)methyl)-2-naphthamide
(484) N-(((3S,5S)-3-(3-(cyclohexylamino)-3-oxopropyl)-2-oxo-1-((S)-2-phenylbutyl)-1,4-diazepan-5-yl)methyl)-2-naphthamide
(485) 6-chloro-N-((3-(1-ethylpiperidin-4-yl)-2-oxo-1-((S)-2-phenylbutyl)-1,4-diazepan-5-yl)methyl)-2-naphthamide
(486) (3S,5S)-5-((3,4-dichlorobenzylamino)methyl)-1-(2,2-diphenylethyl)-3-(2-(piperidin-1-yl)ethyl)-1,4-diazepan-2-one
(487) 6-chloro-N-(((3S,5S)-3-(2-guanidinoethyl)-2-oxo-1-((S)-2-phenylbutyl)-1,4-diazepan-5-yl)methyl)-2-naphthamide
(488) 6-chloro-N-(((3S,5S)-3-(2-(3-methylguanidino)ethyl)-2-oxo-1-((S)-2-phenylbutyl)-1,4-diazepan-5-yl)methyl)-2-naphthamide
(489) N-(((3S,5S)-3-(2-aminoethyl)-1-((R)-2-ethyl-3-methylbutyl)-2-oxo-1,4-diazepan-5-yl)methyl)-3,4-dichlorobenzamide
(490) N-(((3S,5S)-3-(2-aminoethyl)-1-((S)-2-ethyl-3-methylbutyl)-2-oxo-1,4-diazepan-5-yl)methyl)-3,4-dichlorobenzamide
(491) 3,4-dichloro-N-(((3S,5S)-1-((R)-2-ethyl-3-methylbutyl)-2-oxo-3-(2-(piperidin-1-yl)ethyl)-1,4-diazepan-5-yl)methyl)benzamide
(492) 3,4-dichloro-N-(((3S,5S)-1-((S)-2-ethyl-3-methylbutyl)-2-oxo-3-(2-(piperidin-1-yl)ethyl)-1,4-diazepan-5-yl)methyl)benzamide
(493) N-(((3S,5S)-3-(2-amino-2-methylpropyl)-2-oxo-1-((S)-2-phenylbutyl)-1,4-diazepan-5-yl)methyl)-6-chloro-2-naphthamide
(494) N-(((3R,5R)-3-(2-amino-2-methylpropyl)-2-oxo-1-((S)-2-phenylbutyl)-1,4-diazepan-5-yl)methyl)-6-chloro-2-naphthamide
(495) N-(((3S,5S)-3-(2-aminoethyl)-2-oxo-1-((S)-2-phenylbutyl)-1,4-diazepan-5-yl)methyl)-3,4-dichlorobenzamide
(496) 3,4-dichloro-N-(((3S,5S)-3-(2-(isopropylamino)ethyl)-2-oxo-1-((S)-2-phenylbutyl)-1,4-diazepan-5-yl)methyl)benzamide
(497) N-(((3S,5S)-3-(2-aminoethyl)-1-(3,5-dichlorobenzyl)-2-oxo-1,4-diazepan-5-yl)methyl)-6-chloro-2-naphthamide (498) 6-chloro-N-(((3S,5S)-1-((3,5-dichlorobenzyl)-2-oxo-3-(2-(piperidin-1-yl)ethyl)-1,4-diazepan-5-yl)methyl)-2-naphthamide
(499) 6-chloro-N-(((3S,5S)-3-(2-methyl-2-(piperidin-1-yl)propyl)-2-oxo-1-((S)-2-phenylbutyl)-1,4-diazepan-5-yl)methyl)-2-naphthamide
(500) 6-chloro-N-(((3R,5R)-3-(2-methyl-2-(piperidin-1-yl)propyl)-2-oxo-1-((S)-2-phenylbutyl)-1,4-diazepan-5-yl)methyl)-2-naphthamide
(501) N-(((3S,5S)-3-(2-aminoethyl)-1-((R)-2-ethyl-3-methylbutyl)-2-oxo-1,4-diazepan-5-yl)methyl)-6-chloro-2-naphthamide
(502) N-(((3S,5S)-3-(2-aminoethyl)-1-((S)-2-ethyl-3-methylbutyl)-2-oxo-1,4-diazepan-5-yl)methyl)-6-chloro-2-naphthamide
(503) 6-chloro-N-(((3S,5S)-1-((R)-2-ethyl-3-methylbutyl)-2-oxo-3-(2-(piperidin-1-yl)ethyl)-1,4-diazepan-5-yl)methyl)-2-naphthamide
(504) 6-chloro-N-(((3S,5S)-1-((S)-2-ethyl-3-methylbutyl)-2-oxo-3-(2-(piperidin-1-yl)ethyl)-1,4-diazepan-5-yl)methyl)-2-naphthamide
(505) 6-chloro-N-(((3S,5S)-3-(2-cyclohexylethyl)-2-oxo-1-((S)-2-phenylbutyl)-1,4-diazepan-5-yl)methyl)-2-naphthamide
(506) 6-chloro-N-(((3S,5S)-3-hexyl-2-oxo-1-((S)-2-phenylbutyl)-1,4-diazepan-5-yl)methyl)-2-naphthamide
(507) 6-(((3S,5S)-1-(2,2-diphenylethyl)-2-oxo-3-(2-(piperidin-1-yl)ethyl)-1,4-diazepan-5-yl)methylcarbamoyl)-2-naphthoic acid
(508) 6-chloro-N-(((3S,5S)-3-(2-(3-isopropylguanidino)ethyl)-2-oxo-1-((S)-2-phenylbutyl)-1,4-diazepan-5-yl)methyl)-2-naphthamide
(509) 6-chloro-N-(((3S,5S)-3-(4-hydroxybutyl)-2-oxo-1-((S)-2-phenylbutyl)-1,4-diazepan-5-yl)methyl)-2-naphthamide
(510) 6-chloro-N-(((3S,5S)-3-(2-methoxyethyl)-2-oxo-1-((S)-2-phenylbutyl)-1,4-diazepan-5-yl)methyl)-2-naphthamide
(511) N-(((3S,5S)-3-(2-(benzyloxy)ethyl)-2-oxo-1-((S)-2-phenylbutyl)-1,4-diazepan-5-yl)methyl)-6-chloro-2-naphthamide
(512) 6-chloro-N-(((3S,5S)-3-isobutyl-2-oxo-1-((S)-2-phenylbutyl)-1,4-diazepan-5-yl)methyl)-2-naphthamide
(513) N-(((3S,5S)-3-(2-aminoethyl)-1-(2-ethyl-3-methylbut-3-enyl)-2-oxo-1,4-diazepan-5-yl)methyl)-3,4-dichlorobenzamide
(514) 3,4-dichloro-N-(((3S,5S)-1-(2-ethyl-3-methylbut-3-enyl)-2-oxo-3-(2-(piperidin-1-yl)ethyl)-1,4-diazepan-5-yl)methyl)benzamide
(515) N-(((3S,5S)-3-(2-aminoethyl)-1-(2-ethyl-3-methylbut-3-enyl)-2-oxo-1,4-diazepan-5-yl)methyl)-6-chloro-2-naphthamide
(516) 6-chloro-N-(((3S,5S)-1-((R)-2-ethyl-3-methylbut-3-enyl)-2-oxo-3-(2-(piperidin-1-yl)ethyl)-1,4-diazepan-5-yl)methyl)-2-naphthamide
(517) 6-chloro-N-(((3S,5S)-1-((S)-2-ethyl-3-methylbut-3-enyl)-2-oxo-3-(2-(piperidin-1-yl)ethyl)-1,4-diazepan-5-yl)methyl)-2-naphthamide
(518) N-(((3S,5S)-1-(cyclohexylmethyl)-3-(3-guanidinopropyl)-2-oxo-1,4-diazepan-5-yl)methyl)biphenyl-4-carboxamide
(519) N-(((3S,5S)-1-(cyclohexylmethyl)-3-(3-guanidinopropyl)-2-oxo-1,4-diazepan-5-yl)methyl)-2-(1H-indol-3-yl)acetamide
(520) N-(((3S,5S)-1-(cyclohexylmethyl)-3-(3-guanidinopropyl)-2-oxo-1,4-diazepan-5-yl)methyl)quinoline-3-carboxamide
(521) 3,4-dichloro-N-(((3S,5S)-3-(2-(4,4-difluoropiperidin-1-yl)ethyl)-2-oxo-1-((S)-2-phenylbutyl)-1,4-diazepan-5-yl)methyl)benzamide
(522) 3,4-dichloro-N-(((3S,5S)-3-(2-hydroxyethyl)-2-oxo-1-((S)-2-phenylbutyl)-1,4-diazepan-5-yl)methyl)benzamide
(523) 3,4-dichloro-N-(((3S,5S)-3-(2-(3,3-difluoropiperidin-1-yl)ethyl)-2-oxo-1-((S)-2-phenylbutyl)-1,4-diazepan-5-yl)methyl)benzamide
(524) (3S,5S)-5-((3,4-dichlorobenzylamino)methyl)-1-((S)-2-phenylbutyl)-3-(2-(piperidin-1-yl)ethyl)-1,4-diazepan-2-one
(525) 3,4-dichloro-N-(((3S,5S)-1-(2-cyclopropylbutyl)-2-oxo-3-(2-(piperidin-1-yl)ethyl)-1,4-diazepan-5-yl)methyl)benzamide
(526) N-(((3S,5S)-3-(2-aminoethyl)-1-(2-cyclopropylbutyl)-2-oxo-1,4-diazepan-5-yl)methyl)-6-chloro-2-naphthamide
(527) 6-chloro-N-(((3S,5S)-1-(2-cyclopropylbutyl)-2-oxo-3-(2-(piperidin-1-yl)ethyl)-1,4-diazepan-5-yl)methyl)-2-naphthamide
(528) 3,4-dichloro-N-(((3S,5S)-3-(2-(2,5-dioxopyrrolidin-1-yl)ethyl)-2-oxo-1-((S)-2-phenylbutyl)-1,4-diazepan-5-yl)methyl)benzamide
(529) 6-chloro-N-(((3S,5S)-2-oxo-1-((S)-2-phenylbutyl)-3-(3-ureidopropyl)-1,4-diazepan-5-yl)methyl)-2-naphthamide
(530) 3,4-dichloro-N-(((3S,5S)-2-oxo-1-((S)-2-phenylbutyl)-3-(2-(1,1,1-trifluoropropan-2-ylamino)ethyl)-1,4-diazepan-5-yl)methyl)benzamide
(531) 3,4-dichloro-N-(((3S,5S)-3-(2-(3,3-dimethyl-2,5-dioxopyrrolidin-1-yl)ethyl)-2-oxo-1-((S)-2-phenylbutyl)-1,4-diazepan-5-yl)methyl)benzamide
(532) N-(((3S,5S)-3-(2-(azepan-1-yl)ethyl)-2-oxo-1-((S)-2-phenylbutyl)-1,4-diazepan-5-yl)methyl)-6-chloro-2-naphthamide
(533) 6-chloro-N-(((3S,5S)-3-(2-(3-isopropylureido)ethyl)-2-oxo-1-((S)-2-phenylbutyl)-1,4-diazepan-5-yl)methyl)-2-naphthamide
(534) N-(((3S,5S)-2-oxo-1-((S)-2-phenylbutyl)-3-(2-(piperidin-1-yl)ethyl)-1,4-diazepan-5-yl)methyl)biphenyl-4-carboxamide
(535) N-(((3S,5S)-2-oxo-1-((S)-2-phenylbutyl)-3-(2-(piperidin-1-yl)ethyl)-1,4-diazepan-5-yl)methyl)-2-phenylthiazole-4-carboxamide
(536) 4'-chloro-N-(((3S,5S)-2-oxo-1-((S)-2-phenylbutyl)-3-(2-(piperidin-1-yl)ethyl)-1,4-diazepan-5-yl)methyl)biphenyl-2-carboxamide
(537) 6-chloro-N-(((3S,5S)-3-(2-(N-isopropylacetamido)ethyl)-2-oxo-1-((S)-2-phenylbutyl)-1,4-diazepan-5-yl)methyl)-2-naphthamide
(538) 6-chloro-N-(((3S,5S)-3-((isopropylamino)methyl)-2-oxo-1-((S)-2-phenylbutyl)-1,4-diazepan-5-yl)methyl)-2-naphthamide
(539) 6-chloro-N-(((3S,5S)-3-(guanidinomethyl)-2-oxo-1-((S)-2-phenylbutyl)-1,4-diazepan-5-yl)methyl)-2-naphthamide
(540) 2-(2,4-dichlorophenyl)-N-(((3S,5S)-2-oxo-1-((S)-2-phenylbutyl)-3-(2-(piperidin-1-yl)ethyl)-1,4-diazepan-5-yl)methyl)acetamide
(541) N-(((3S,5S)-3-(2-aminoethyl)-1-(2,4-dichlorobenzyl)-2-oxo-1,4-diazepan-5-yl)methyl)-3,4-dichlorobenzamide
(542) 3,4-dichloro-N-(((3S,5S)-1-(2,4-dichlorobenzyl)-2-oxo-3-(2-(piperidin-1-yl)ethyl)-1,4-diazepan-5-yl)methyl)benzamide (543) 3,4-dichloro-N-(((3S,5S)-1-(2,4-dichlorobenzyl)-3-(2-(methylsulfonamido)ethyl)-2-oxo-1,4-diazepan-5-yl)methyl)benzamide (544) 3,4-dichloro-N-(((3S,5S)-1-(2,4-dichlorobenzyl)-3-(2-(4-methylphenylsulfonamido)ethyl)-2-oxo-1,4-diazepan-5-yl)methyl)benzamide (545) N-(((3S,5S)-3-(2-((S)-2-amino-3-methylbutanamido)ethyl)-1-(2,4-dichlorobenzyl)-2-oxo-1,4-diazepan-5-yl)methyl)-3,4-dichlorobenzamide (546) N-(((3S,5S)-3-(2-aminoethyl)-1-(2,4-dichlorobenzyl)-2-oxo-1,4-diazepan-5-yl)methyl)-6-chloro-2-naphthamide (547) 6-chloro-N-(((3S,5S)-1-(2,4-dichlorobenzyl)-2-oxo-3-(2-(piperidin-1-yl)ethyl)-1,4-diazepan-5-yl)methyl)-2-naphthamide (548) N-(((3S,5S)-3-(2-aminoethyl)-2-oxo-1-(2-(thiophen-3-yl)butyl)-1,4-diazepan-5-yl)methyl)-6-chloro-2-naphthamide (549) 6-chloro-N-(((3S,5S)-2-oxo-3-(2-(piperidin-1-yl)ethyl)-1-((R)-2-(thiophen-3-yl)butyl)-1,4-diazepan-5-yl)methyl)-2-naphthamide (550) 6-chloro-N-(((3S,5S)-2-oxo-3-(2-(piperidin-1-yl)ethyl)-1-((S)-2-(thiophen-3-yl)butyl)-1,4-diazepan-5-yl)methyl)-2-naphthamide (551) N-(((3S,5S)-3-(2-aminoethyl)-1-(2-ethyl-2-methylbutyl)-2-oxo-1,4-diazepan-5-yl)methyl)-6-chloro-2-naphthamide (552) 6-chloro-N-(((3S,5S)-1-(2-ethyl-2-methylbutyl)-2-oxo-3-(2-(piperidin-1-yl)ethyl)-1,4-diazepan-5-yl)methyl)-2-naphthamide (553) 6-chloro-N-(((3S,5S)-1-(2,2-diphenylethyl)-3-(2-morpholinoethyl)-2-oxo-1,4-diazepan-5-yl)methyl)-2-naphthamide (554) 6-chloro-N-(((3S,5S)-3-(2-morpholinoethyl)-2-oxo-1-((S)-2-phenylbutyl)-1,4-diazepan-5-yl)methyl)-2-naphthamide (555) 6-chloro-N-(((3S,5S)-1-((3,5-dichlorobenzyl)-3-(2-morpholinoethyl)-2-oxo-1,4-diazepan-5-yl)methyl)-2-naphthamide (556) 3,4-dichloro-N-(((3S,5S)-1-((3,5-dichlorobenzyl)-3-(2-morpholinoethyl)-2-oxo-1,4-diazepan-5-yl)methyl)benzamide (557) N-(3,4-dichlorobenzyl)-N-(((3S,5S)-2-oxo-1-((S)-2-phenylbutyl)-3-(2-(piperidin-1-yl)ethyl)-1,4-diazepan-5-yl)methyl)acetamide (558) 1-(4-chlorobenzyl)-3-(((3S,5S)-2-oxo-1-((S)-2-phenylbutyl)-3-(2-(piperidin-1-yl)ethyl)-1,4-diazepan-5-yl)methyl)urea (559) N-(((3S,5S)-3-(2-aminoethyl)-1-(2-ethyl-2-methylbutyl)-2-oxo-1,4-diazepan-5-yl)methyl)-3,4-dichlorobenzamide (560) 3,4-dichloro-N-(((3S,5S)-1-(2-ethyl-2-methylbutyl)-2-oxo-3-(2-(piperidin-1-yl)ethyl)-1,4-diazepan-5-yl)methyl)benzamide (561) 6-chloro-N-(((3S,5S)-2-oxo-3-(2-(piperidin-1-yl)ethyl)-1-(2,3,5-trichlorobenzyl)-1,4-diazepan-5-yl)methyl)-2-naphthamide (562) 6-chloro-N-(((3S,5S)-3-(2-(1-methylethylsulfonamido)ethyl)-2-oxo-1-((S)-2-phenylbutyl)-1,4-diazepan-5-yl)methyl)-2-naphthamide (563) butyl 2-((2S,7S)-7-((6-chloro-2-naphthamido)methyl)-3-oxo-4-((S)-2-phenylbutyl)-1,4-diazepan-2-yl)ethylcarbamate (564) (S)-6-chloro-N-((3-(1-isopropylpiperidin-4-yl)-2-oxo-1-(2-phenylbutyl)-1,4-diazepan-5-yl)methyl)-2-naphthamide (565) 6-chloro-N-(((3S,5S)-2-oxo-1-((R)-2-phenylbutyl)-3-(2-(piperidin-1-yl)ethyl)-1,4-diazepan-5-yl)methyl)-2-naphthamide (566) 5-(4-chlorophenyl)-N-(((3S,5S)-1-((3,5-dichlorobenzyl)-2-oxo-3-(2-(piperidin-1-yl)ethyl)-1,4-diazepan-5-yl)methyl)isoxazole-3-carboxamide (567) 2,4-dichloro-N-(((3S,5S)-1-((3,5-dichlorobenzyl)-2-oxo-3-(2-(piperidin-1-yl)ethyl)-1,4-diazepan-5-yl)methyl)benzamide (568) N-(((3S,5S)-1-((3,5-dichlorobenzyl)-2-oxo-3-(2-(piperidin-1-yl)ethyl)-1,4-diazepan-5-yl)methyl)-6-methoxy-2-naphthamide (569) 6-chloro-N-(([5-$^{13}$C,4-$^{15}$N](3S,5S)-2-oxo-1-((S)-2-phenylbutyl)-3-(2-(piperidin-1-yl)ethyl)-1,4-diazepan-5-yl)[$^{13}$C]methyl)-2-naphthamide (570) N-(((3S,5S)-1-((3,5-dichlorobenzyl)-2-oxo-3-(2-(piperidin-1-yl)ethyl)-1,4-diazepan-5-yl)methyl)-1-methoxy-2-naphthamide (571) (E)-N-(((3S,5S)-1-((3,5-dichlorobenzyl)-2-oxo-3-(2-(piperidin-1-yl)ethyl)-1,4-diazepan-5-yl)methyl)-3-(4-(trifluoromethoxy)phenyl)acrylamide (572) 5-(4-chlorophenyl)-N-(((3S,5S)-2-oxo-1-((S)-2-phenylbutyl)-3-(2-(piperidin-1-yl)ethyl)-1,4-diazepan-5-yl)methyl)isoxazole-3-carboxamide (573) 2,4-dichloro-N-(((3S,5S)-2-oxo-1-((S)-2-phenylbutyl)-3-(2-(piperidin-1-yl)ethyl)-1,4-diazepan-5-yl)methyl)benzamide (574) 5,6-dichloro-2-(((3S,5S)-1-((3,5-dichlorobenzyl)-2-oxo-3-(2-(piperidin-1-yl)ethyl)-1,4-diazepan-5-yl)methyl)isoindoline-1,3-dione (575) (E)-N-(((3S,5S)-1-((3,5-dichlorobenzyl)-2-oxo-3-(2-(piperidin-1-yl)ethyl)-1,4-diazepan-5-yl)methyl)-3-(3-fluoro-4-(trifluoromethoxy)phenyl)acrylamide (576) 6-methoxy-N-(((3S,5S)-2-oxo-1-((S)-2-phenylbutyl)-3-(2-(piperidin-1-yl)ethyl)-1,4-diazepan-5-yl)methyl)-2-naphthamide (577) 1-methoxy-N-(((3S,5S)-2-oxo-1-((S)-2-phenylbutyl)-3-(2-(piperidin-1-yl)ethyl)-1,4-diazepan-5-yl)methyl)-2-naphthamide (578) (E)-3-(3-fluoro-4-(trifluoromethoxy)phenyl)-N-(((3S,5S)-2-oxo-1-((S)-2-phenylbutyl)-3-(2-(piperidin-1-yl)ethyl)-1,4-diazepan-5-yl)methyl)acrylamide (579) 6-chloro-N-(([5,6,6-$^2$H$_3$](3S,5S)-2-oxo-1-((S)-2-phenylbutyl)-3-(2-(piperidin-1-yl)ethyl)-1,4-diazepan-5-yl)[$^2$H$_2$]methyl)-2-naphthamide (580) 6-chloro-N-(((3R,5R)-2-oxo-1-((R)-2-phenylbutyl)-3-(2-(piperidin-1-yl)ethyl)-1,4-diazepan-5-yl)methyl)-2-naphthamide (581) 6-chloro-N-(((3S,5R)-2-oxo-1-((S)-2-phenylbutyl)-3-(2-(piperidin-1-yl)ethyl)-1,4-diazepan-5-yl)methyl)-2-naphthamide (582) 6-chloro-N-(((3R,5S)-2-oxo-1-((S)-2-phenylbutyl)-3-(2-(piperidin-1-yl)ethyl)-1,4-diazepan-5-yl)methyl)-2-naphthamide (583) 6-chloro-N-(((3S,5R)-2-oxo-1-((R)-2-phenylbutyl)-3-(2-(piperidin-1-yl)ethyl)-1,4-diazepan-5-yl)methyl)-2-naphthamide (584) 6-chloro-N-(((3R,5R)-2-oxo-1-((R)-2-phenylbutyl)-3-(2-(piperidin-1-yl)ethyl)-1,4-diazepan-5-yl)methyl)-2-naphthamide (585) 6-chloro-N-(((3R,5R)-2-oxo-1-((S)-2-phenylbutyl)-3-(2-(piperidin-1-yl)ethyl)-1,4-diazepan-5-yl)methyl)-2-naphthamide As stated previously the compounds of formula (I) are antagonists of the MC5R and therefore may be used to modulate the activity of MC5R or a fragment or analogue or functional equivalent thereof by exposing MC5R or a fragment or analogue or functional equivalent thereof to a compound of the invention. This can occur in vitro in assays where the downregulation of MC5R activity is desirable, however it is typically more beneficial when utilised in downregulation of MC5R activity in a patient. The amount of downregulation provided by the compounds of the invention will vary from compound to compound and will also be affected by the amount of compound administered. In one embodiment the amount of downregulation is at least 10%. In another embodiment the amount of downregulation is at least 20%. In an even further embodiment the amount of downregulation is at least 50%.

Accordingly the methods of the present invention may be used in the treatment of any condition in which modulation of the activity of MC5R or a fragment or analogue or functional equivalent thereof would lead to a beneficial effect on that condition. As such the compounds suitable for use in the present invention may be used in methods of treating, preventing, or controlling a condition associated either directly or indirectly with the activity of MC5R or a fragment or analogue or functional equivalent thereof in a mammal wherein an MC5R modulating amount of the compound of the invention is administered to the mammal. One condition associated with MC5R activity is excess sebum secretion and conditions related thereto. In one embodiment of the method the condition is selected from the group consisting of acne, seborrhoea, and seborrheic dermatitis. In one embodiment the acne is selected from the group consisting of acne vulgaris, acne, acne conglobata and acne fulminans. In one specific embodiment the condition is acne vulgaris.

For example, downregulation of MC5R leads to a reduction of sebum secretion and can thus be used in the treatment or prophylaxis of a number of conditions in which excess sebum secretion is observed such as acne, seborrhoea and seborrheic dermatitis.

The methods of the invention may also be useful in the treatment, prevention or control of a number of conditions that relate to biological processes controlled by MC5R, such as diseases related to inflammation. The compounds of formula (I) may also be useful for the treatment or prevention of cancers, such as Muir-Torre syndrome or other cancers of the sebaceous gland.

Due to their impact on sebum secretion the compounds of formula (I) may also find application in treatments where reduced sebum secretion is desirable such as in cosmetic treatments. The compounds may thus be used in methods of reducing sebum secretion by a mammal, the method comprising administering an effective amount of a compound of formula (I).

The compounds of formula (I) may be used in the treatment of conditions in any species in which MC5R is present, most typically mammals. Examples of species in which MC5R is found and hence species in which the compounds may be used include humans, rats, mice, dogs, rhesus monkey, sheep, zebrafish, goldfish, spiny dogfish, rainbow trout and chickens. In a specific embodiment the mammal is a human.

Administration of compounds within Formula (I) to a patient such as humans can be by topical administration, by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose.

In using the compounds of formula (I) they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, $19^{th}$ edition, Mack Publishing Co. (1995) for further information.

The compounds of formula (I) can be administered alone or in the form of a pharmaceutical composition in combination with a pharmaceutically acceptable carrier, diluent or excipient. The compounds of formula (I), while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. The compositions are prepared in manners well known in the art.

A compound of formula (I) is typically combined with the carrier to produce a dosage form suitable for the particular patient being treated and the particular mode of administration. For example, a formulation intended for the oral administration to humans may contain from about 0.5 mg to about 5 g of the compound of the invention, compounded with an appropriate and convenient amount of carrier material which may vary from about 5 to about 99.95 percent of the total composition. Representative dosage forms will generally contain between from about 1 mg to about 500 mg of a compound of the invention, typically 25 mg, 50 mg, 100 mg, 200 mg, 300 mg, 400 mg, 500 mg, 600 mg, 800 mg, or 1000 mg. Compounds of the present invention may also be formulated for topical delivery in formulations such as solutions, ointments, lotions, gels, creams, microemulsions or transdermal patches. For example, these topical formulations may contain from 0.005 to 5% (wt/wt or wt/vol) of a compound of the invention.

The compounds of formula (I) may be used or administered in combination with one or more additional drug(s). The compounds of the present invention may be used in combination with one or more other pharmaceutically-active compounds, such as other anti-acne treatments. In one embodiment the other pharmaceutically active agent is selected from the group consisting of antibiotics, retinoids, anti-androgens, and steroids. Examples of other pharmaceutically active compounds that may be combined with a compound of formula (I) and administered in concurrent or sequential combination therewith may include, by way of non-limiting example, other anti-acne agents such as oral retinoids (e.g. isotretinoin), topical retinoids (e.g. isotretinoin, adapalene, tazarotene), oral or topical antibiotics (e.g. clindamycin, erythromycin, minocycline, tetracycline, benzoyl peroxide), or hormonal therapies (e.g. drospirenone, norgestimate—ethinyl estradiol, cyproterone acetate). As stated these components can be administered in the same formulation or in separate formulations. If administered in separate formulations the compounds of the invention may be administered sequentially or simultaneously with the other drug(s).

Pharmaceutical compositions suitable for use in the invention for parenteral injection comprise pharmaceutically acceptable sterile aqueous or non aqueous solutions, dispersions, suspensions or emulsions as well as sterile powders for reconstitution into sterile injectable solutions or dispersions just prior to use. Examples of suitable aqueous and non aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

For topical administration, the active agent may be in the form of an ointment, cream, suspension, lotion, powder, solution, paste, gel, spray, aerosol or oil. Alternatively, the composition may be delivered via a liposome, nanosome, rivosome, or nutri-diffuser vehicle. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen. Methods for producing formulations for topical administration are known in the art.

The compositions used for topical administration typically contain a pharmaceutically acceptable carrier which may be any vehicle that is toxicologically and pharmaceutically acceptable. Typical pharmaceutically acceptable carriers that can be used in compositions of the present invention include water, ethanol, acetone, isopropyl alcohol, stearyl alcohol, freons, polyvinyl pyrrolidone, propylene glycol, polyethlyene glycol, fragrances, gel-producing materials, mineral oil, stearic acid, spermaceti, sorbitan, monoleate, polysorbates, "Tweens," sorbitol, methyl cellulose, petrolatum, a mineral oil (vaseline oil), which may be any petroleum based product; modified or unmodified vegetable oils such as peanut oil, wheatgerm oil, linseed oil, jojoba oil, apricot kernel oil, walnut oil, palm oil, pistachio oil, sesame oil, colza oil, cade oil, corn germ oil, peach kernel oil, poppyseed oil, pine oil, castor oil, soya oil, safflower oil, coconut oil, hazelnut oil, grapeseed oil, avocado oil, soy oil, sweet almond oil, calophyllum oil, castor oil, olive oil, sunflower oil, or animal oils such as whale oil, seal oil, menhaden oil, halibut liver oil, cod liver oil, cod, tuna, turtle tallow, horse's hoof, sheep's foot, mink, otter, marmot oil and the like; synthetic oils such as silicon oil such as dimethylpolysiloxane; alkyl and alkenyl esters of fatty acids, such as isopropyl esters of myristic, palmitic and stearic acids and fatty esters which are solid at room temperature; waxes such as lanolin wax, candelilla wax, spermaceti, cocoa butter, karite butter, silicon waxes, hydrogenated oils which are solid at room temperature, sucro-glycerides, oleates, myristates, linoleates, stearates, paraffin, beeswax, carnauba wax, ozokerite, candelilla wax, microcrystalline wax; fatty alcohols such as lauryl, cetyl, myristyl, stearyl, palmityl and oleyl alcohols; polyoxyethylated fatty alcohols; and wax esters, lanolin and its derivatives, perhydrosqualene and saturated esters, ethyl palmitate, isopropyl palmitate, alkyl myristates such as isopropyl myristate, butyl myristate and decyl myristate, hexyl stearate, triglyceride esters, triglycerides of octanoic and decanoic acid, cetyl ricinoleate, stearyl octanoate (Purcellin oil), fatty acids, polyhydric alcohols, polyether derivatives, fatty acid monoglycerides, polyethylene glycol, propylene glycol, alkyl ethoxy ether sulfonates, ammonium alkyl sulfates, fatty acid soaps, and hydrogenated polyisobutene, and mixtures of waxes and oils.

The compositions for topical administration may be formulated in numerous forms. However, the composition may often take the form of an aqueous or oily solution or dispersion or emulsion or a gel or a cream. An emulsion may be an oil-in-water emulsion or a water-in-oil emulsion.

The oil phase of water-in-oil or oil-in-water emulsions may comprise for example: a) hydrocarbon oils such as paraffin or mineral oils; b) waxes such as beeswax or paraffin wax; c) natural oils such as sunflower oil, apricot kernel oil, shea butter or jojoba oil; d) silicone oils such as dimethicone, cyclomethicone or cetyldimethicone; e) fatty acid esters such as isopropyl palmitate, isopropyl myristate, dioctylmaleate, glyceryl oleate and cetostearyl isononanoate; f) fatty alcohols such as cetyl alcohol or stearyl alcohol and mixtures thereof (eg cetearyl alcohol); g) polypropylene glycol or polyethylene glycol ethers, eg PPG-14 butyl ether; or h) mixtures thereof.

Emulsifiers used may be any emulsifiers known in the art for use in water-in-oil or oil-in-water emulsions. Known cosmetically acceptable emulsifiers include: a) sesquioleates such as sorbitan sesquioleate, available commercially for example under the trade name Arlacel 83 (ICI), or polyglyceryl-2-sesquioleate; b) ethoxylated esters of derivatives of natural oils such as the polyethoxylated ester of hydrogenated castor oil available commercially for example under the trade name Arlacel 989 (ICI); c) silicone emulsifiers such as silicone polyols available commercially for example under the trade name ABIL WS08 (Th. Goldschmidt AG); d) anionic emulsifiers such as fatty acid soaps e.g. potassium stearate and fatty acid sulphates e.g. sodium cetostearyl sulphate available commercially under the trade name Dehydag (Henkel); e) ethoxylated fatty alcohols, for example the emulsifiers available commercially under the trade name Brij (ICI); f) sorbitan esters, for example the emulsifiers available commercially under the trade name Span (ICI); g) ethoxylated sorbitan esters, for example the emulsifiers available commercially under the trade name Tween (ICI); h) ethoxylated fatty acid esters such as ethoxylated stearates, for example the emulsifiers available commercially under the trade name Myrj (ICI); i) ethoxylated mono-, di-, and tri-glycerides, for example the emulsifiers available commercially under the trade name Labrafil (Alfa Chem.); j) non-ionic self-emulsifying waxes, for example the wax available commercially under the trade name Polawax (Croda); k) ethoxylated fatty acids, for example, the emulsifiers available commercially under the trade name Tefose (Alfa Chem.); l) methylglucose esters such as polyglycerol-3 methyl glucose distearate available commercially under the name Tegocare 450 (Degussa Goldschmidt); or m) mixtures thereof.

Gels for topical administration may be aqueous or non-aqueous. Aqueous gels are preferred. The gel will contain a thickening agent or gelling agent in order to give sufficient viscosity to the gel. A variety of thickening agents may be used according to the nature of the liquid carrier and the viscosity required and these are recited hereinafter. A particularly suitable thickener is a copolymer of acryloyl dimethyl tauric acid (or a salt thereof), preferably a copolymer of that monomer with another vinylic monomer. For example, the thickening agent is a copolymer of a salt of acryloyl dimethyl tauric acid with another vinylic monomer. The salt may be a salt of a Group I alkali metal, but is more preferably an ammonium salt. Examples of suitable copolymer thickening agents are: i) Ammonium acryloyl dimethyl taurate I vinyl pyrrolidone copolymer, ie a copolymer of ammonium acryloyl dimethyl taurate and vinyl pyrrolidone (1-vinyl-2-pyrrolidone).

The composition may additionally comprise other skincare active agents which are well known in the art which may be effective to aid the normal functioning of the skin. One group of preferred compositions comprise hydrolysed milk protein to regulate sebum production.

The composition may additionally comprise other components which will be well known to those skilled in the art such as emollients, humectants, emulsion stabilising salts, preservatives, chelating agents or sequestering agents (sequestrants), abrasives, anti-oxidants, stabilisers, pH adjusters, surfactants, thickeners, diluents, perfumes and colourings.

The topical formulations may desirably include a compound that enhances absorption or penetration of the active ingredient through the skin or other affected areas. Examples of such dermal penetration enhancers include dimethylsulfoxide and related analogues.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, sex, diet, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

Synthesis of Compounds for Use in the Invention

The general synthetic route to the compounds for use in the invention proceeds through the key intermediate A, produced as outlined in Schemes 1 or 2.

In Scheme 1, an amino acid derivative V—N($R^2$)—Y—$CO_2H$ (V=$R^1$X or an amine protecting group $P^1$) is converted to a Weinreb amide via activation of the carboxyl group and amidation with N-methyl methoxyamine. Addition of a vinyl Grignard reagent produces the aminoalkyl vinyl ketone, which undergoes conjugate addition by the $R^6R^7R^8C$—($CR^{5a}R^{5b}$)$_r$$NH_2$ amine component (shown as $WNH_2$ for simplicity). The resulting secondary amine is acylated under standard peptide coupling conditions with the protected amino acid, $P^2$—NHCH(U)—$CO_2H$, where U represents either the final R side chain, a protected final side chain R—$P^3$, or a precursor that requires chemical modification to form the final R side chain. Deprotection of the $P^2$ protecting group is followed by intramolecular reductive amination of the ketone using standard reduction conditions, such as $H_2$/Pd catalyst, $NaBH_4$, $NaBH_3CN$, or $NaBH(OAc)_3$, forming key intermediate A. If Y=$CH_2$ or $CH_2CH_2$, A is formed as the predominant diastereomer. If V=$R^1$X and U=R, A is the final product.

Scheme 1: Synthesis of Intermediate A via Intramolecular Reductive Amination

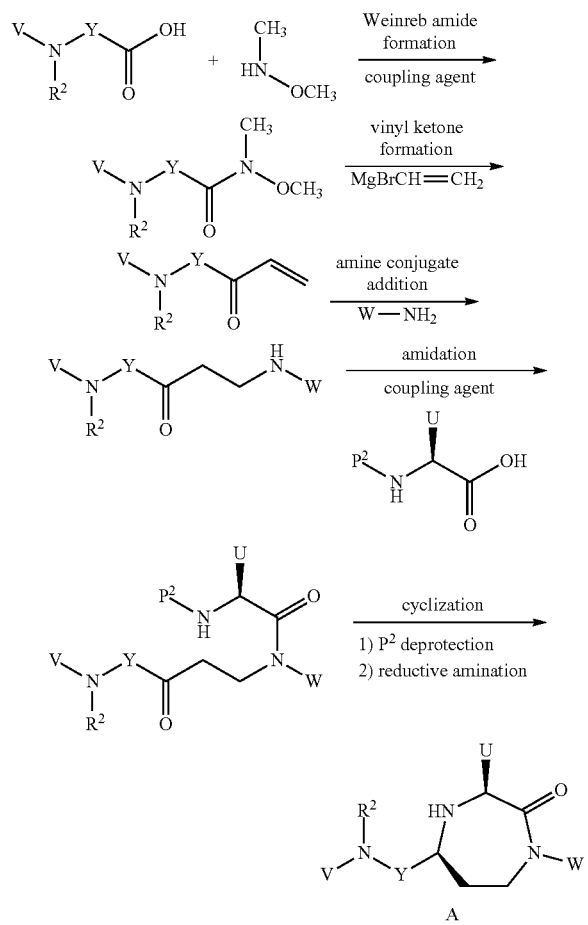

where U = R, a protected form thereof or a precursor thereof, V = $P^1$ or $R^1$X, and W = $R^6R^7R^8C(CR^{5a}R^{5b})_r$- Final product if V = $R^1$X, U = R In Scheme 2, an alternate route to the desired intermediate A begins with the same Weinreb amide formation, vinyl Grignard addition, and amine conjugate addition. At this point, the secondary amine is protected with an amine protecting group $P^4$. The ketone is then reductively aminated with a protected amino ester, $H_2NCH(U)$—$CO_2P^5$, producing a mixture of diastereomers that are carried through the next reaction steps. The ring system is generated by deprotection of the $P^4$ and $P^5$ protecting groups, followed by amide bond formation using standard peptide coupling reagents. Alternatively, the $P^4$ protecting group is removed and cyclization achieved by thermal or base-induced cyclization with the $P^5$-protected ester. The cyclization produces a mixture of two diastereomers, A and B, from which the preferred diastereomers A can be separated by chromatography.

Scheme 2: Synthesis of Intermediate A via Intramolecular Reductive Amination

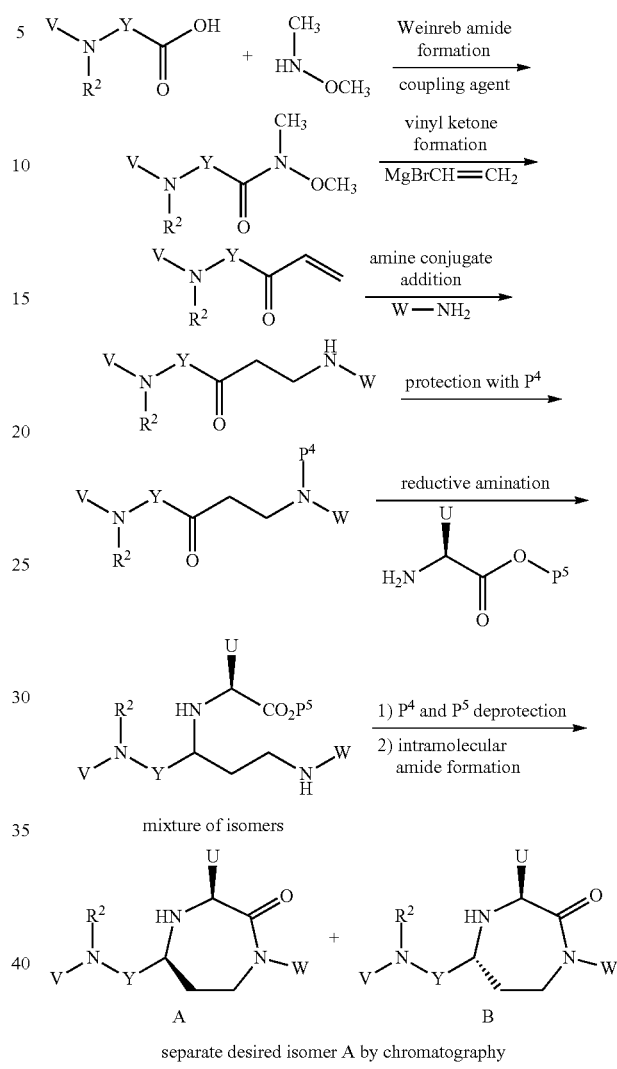

separate desired isomer A by chromatography where U = R, a protected form thereof or a precursor thereof, V = $P^1$ or $R^1$X, and W = $R^6R^7R^8C(CR^{5a}R^{5b})_r$- final product if V = $R^1$X, U = R The key intermediate A may be the final product if U=R and V=$R^1$X, but otherwise is converted into the final product as illustrated in Schemes 3, 4 and 5.

In Scheme 3, where V=$R^1$X, the final product is obtained by modification of the U side chain, such as removal of a $P^3$ protecting group, or removal of a $P^3$ protecting group followed by further chemical modification.

Scheme 3: V = $R^1$X

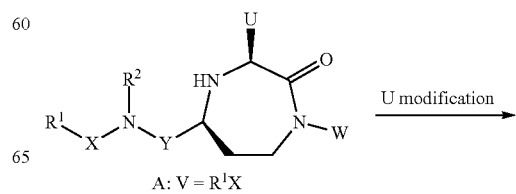

A: V = $R^1$X

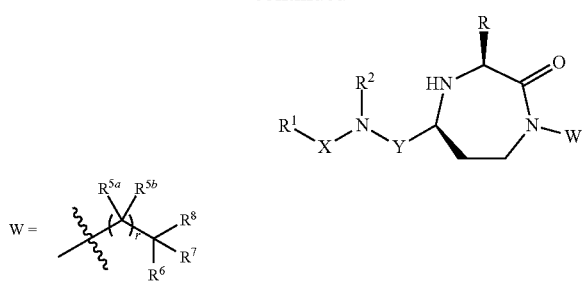

In Scheme 4, where V=P$^1$, the final product is obtained by removal of the P1 protecting group followed by introduction of the R$^1$X substituent. If U=R, this produces the final product. Alternatively, the U side chain is then modified to produce the final R group as in Scheme 3.

Scheme 4: V = P$^1$

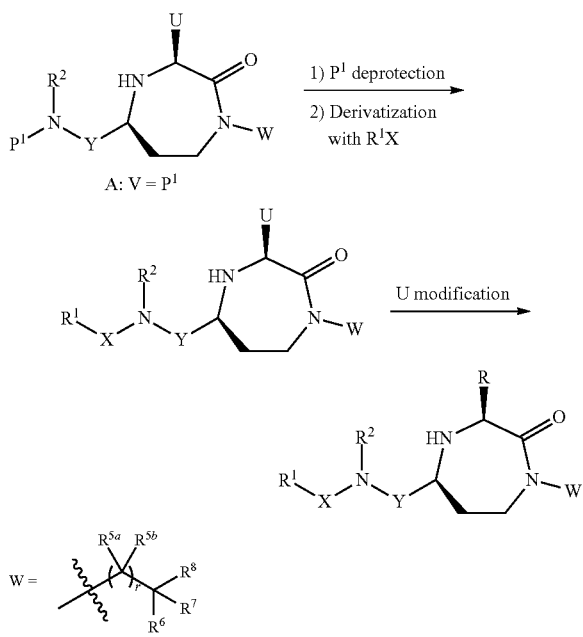

In Scheme 5, where V=P$^1$, the final product is obtained by first modifying the U side chain to produce the final R group as in Scheme 3. This is followed by removal of the P1 protecting group followed by introduction of the R$^1$X substituent.

Scheme 5: V = P$^1$

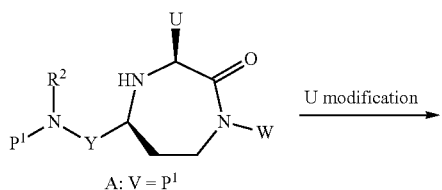

It is also possible to modify the W substituent, if desired, during these reaction sequences.

EXAMPLES

The following examples are intended to illustrate the embodiments disclosed and are not to be construed as being limitations thereto. Additional compounds, other than those described below, may be prepared using the following described reaction schemes as discussed above or appropriate variations or modifications thereof. All starting materials described in the Examples below are commercially available or readily synthesized by those skilled in the art.

Instrumentation

HPLC analyses were carried out on an Agilent 1100 Series Purification System with a Phenomenex Synergi 4μ Max-RP 80A, 50×2.00 mm analytical HPLC column, with peak detection by UV. The standard analysis employed a 1 mL/min flow rate of 0.05% trifluoroacetic acid (TFA) in water (Solvent A) and 0.05% TFA in 90:10 acetonitrile:water (Solvent B), using a gradient of 5% B (initial) to 95% B over 9 min. Mass spectra were run on an Applied Biosystems MDS Sciex API 2000 LC/MS/MS triple quadrupole mass spectrometer and analyzed by ion spray mass spectrometry (ISMS). Preparative scale HPLC was carried out on a Waters Delta Prep 3000 HPLC system with peak detection by UV (Waters model 486 tunable absorbance detector), using Phenomenex Luna 10μ C5 100A, 250×21.20 mm (20 mg scale), Phenomenex Luna 15μ C8(2) 100A, 250×30.00 mm (50 mg scale), or Phenomenex Luna 15μ C8(2) 100A, 250×50.00 mm (100 mg scale) HPLC columns. The solvent system employed various gradients of 0.05% TFA in water (Solvent A) and 0.05% TFA in 90:10 acetonitrile:water (Solvent B).

The following examples 1 to 7 provide general synthetic procedures that may be followed in order to carry out the transformations described in schemes 1 to 5. In order to make different end products using these procedures it is necessary to either vary a variable group on the starting material or to vary a variable group on one of the reagents depending upon the nature of the reaction. It will be apparent to a skilled addressee from a reading of the general procedures how to vary either the starting material or the reagents used in the procedure to produce differing end products. In addition depending upon the starting materials and the reagents it may be necessary and/or desirable to make slight modifications to the described general procedures in order to provide the most facile synthesis of the desired end product.

Example 1

General Procedure—Weinreb Amide Formation

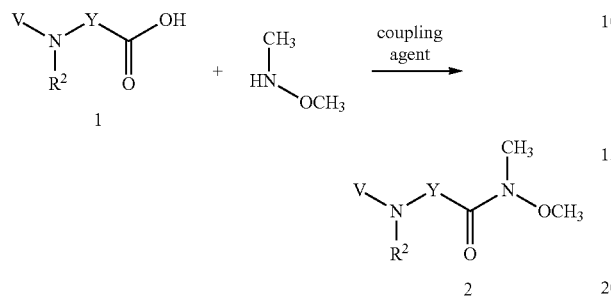

BOP reagent (100 mmol) and diisopropylethylamine (DIPEA) (100 mmol) is added to a stirred solution of the amino acid (1) (100 mmol) in dichloromethane (DCM) (100 mL). The solution is then stirred at room temperature for 10 mins, before addition of a premixed solution of N,O-dimethylhydroxylamine hydrochloride (100 mmol) and DIPEA (100 mmol) followed by stirring at room temperature overnight. The DCM is then removed by rotary evaporation and the residue taken up in ethyl acetate (EtOAc) (200 mL). The organic phase is then washed with 1N HCl (3×100 mL), $H_2O$ (3×100 mL), saturated $NaHCO_3$ aqueous solution (3×100 mL) and brine (1×10 mL). The organic phase is then dried ($MgSO_4$) and the EtOAc removed to give the Weinreb amide (2) as a white solid or an oil.

Example 2

General Procedure—Vinyl Grignard Addition to Weinreb Amide to Form α,β-Unsaturated Ketones of Formula (3)

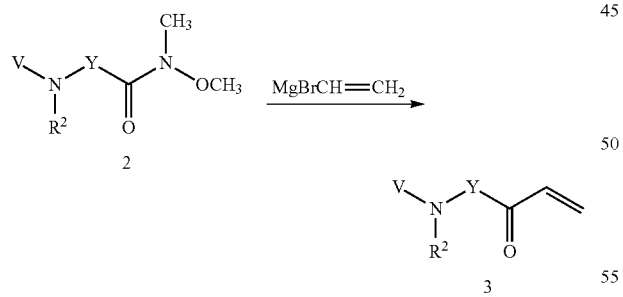

To the Weinreb amide (2) (15 mmol) in DCM (10 mL) at 0° C. is added vinyl magnesium bromide (45 mmol) in THF (45 mL). The reaction is stirred for 2 hrs and monitored by HPLC. The reaction is then quenched by adding it to a mixture of ice and 1M HCl (200 mL). The aqueous mixture is extracted with DCM (3×100 mL) and the organic layers combined and washed with 1M HCl (2×200 mL) and $H_2O$ (3×100 mL). The organic phase is dried ($MgSO_4$) to provide a solution of the α,β-unsaturated ketone (3). The α,β-unsaturated ketone (3) may be isolated by rotary evaporation or it may be used in solution without further purification. If the intention is to use the α,β-unsaturated ketone (3) in solution the volume is reduced to 100 mL by rotary evaporation and stored for later use.

Example 3

General Procedure—Conjugate Addition of Amine to α,β-Unsaturated Ketones of Formula (3) to Produce Compounds of Formula (4)

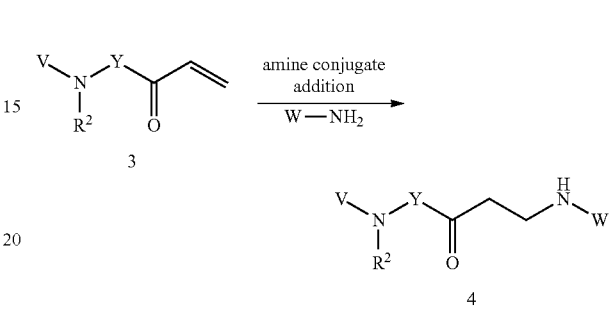

To the amine $W-NH_2$ (7.4 mmol) in DCM (10 mL) is added a solution of the α,β-unsaturated ketone (3) (5.7 mmol) in DCM (50 mL). The solution is stirred at room temperature for 15 mins, or until analysis indicates that all of (3) has been consumed. The solution of compound (4) is immediately used without purification for the subsequent reaction.

Example 4

General Procedure—Acylation of Aminoketone (4)

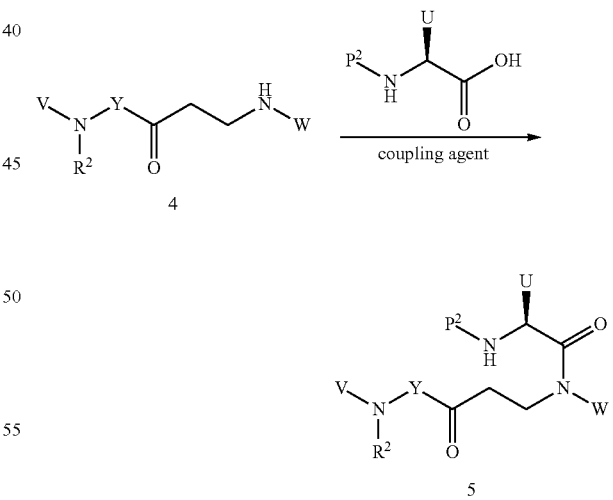

The amine acid $P^2-NHCH(U)-CO_2H$ (15 mmol) and DIC (15 mmol) is added to a solution of DCM containing 10 mmol of the conjugate addition adduct 4. The reaction is stirred at room temperature overnight. The DCM is removed by rotary evaporation and the residue is then subjected to column chromatography on silica gel using petroleum spirit: EtOAc to give 5.

As an alternative, the DIC may be replaced with HATU (15 mmol) and DIPEA (15 mmol). The reaction is stirred at room temperature overnight. The DCM is removed by rotary evaporation and the residue is taken up in EtOAc (100 mL). The organic layer is washed with saturated sodium bicarbonate solution (2×100 mL), saturated ammonium chloride solution (2×100 mL) and brine (2×100 mL). The organic phase is dried and the solvent removed under reduced pressure. The residue is subjected to column chromatography on silica gel using petroleum ether:EtOAc to give 5.

Example 5

General Procedure—$P^2$ Deprotection and Cyclization

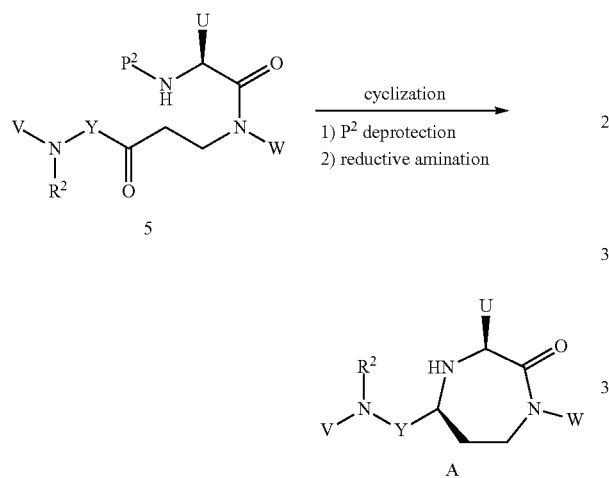

The procedure adopted for the removal of the P2 protecting group will vary depending upon the exact nature of the protecting group. As will be appreciated by a skilled addressee a large number of possible protecting groups may be used and a skilled worker in the art will readily be able to determine an appropriate procedure for the removal of any particular protecting group from procedures known in the art. Nevertheless in order to assist the reader general procedures for the removal of the more common protecting groups are provided.

$P^2$=Fmoc: To compound 5 (2 mmol) in DCM (3 mL) is added diethylamine (20 mmol). The reaction is stirred at room temperature for 1 hr. The DCM and diethylamine is then removed by rotary evaporation. DCM (5 mL) and sodium triacetoxyborohydride (3 mmol) are then added, and the reaction stirred overnight at room temperature. The organic phase is washed with saturated sodium bicarbonate solution (25 mL), dried (MgSO$_4$) and the DCM removed to give the cyclised product A. This may be purified by flash chromatography on silica gel or used without purification.

$P^2$=Boc: To compound 5 (2 mmol) in DCM (3 mL) is added TFA (3 mL) and the reaction stirred at room temperature for 2 hrs. The DCM and TFA are then removed by rotary evaporation. DCM (5 mL) and sodium triacetoxyborohydride (3 mmol) is then added, and the reaction stirred overnight at room temperature. The organic phase is washed with saturated sodium bicarbonate solution (25 mL), dried (MgSO$_4$) and the DCM removed to give the cyclised product A. This may be purified by flash chromatography on silica gel or used without purification.

$P^2$=Cbz: A mixture of crude 5 (1 mmol) and 5% Pd/C (200 mg) in 2-propanol (15 mL) is shaken at room temperature under hydrogen (30 psi) for 24 hrs. The mixture is then filtered through a pad of Celite and the filtrate concentrated under reduced pressure to give a crude product. Purification by flash chromatography on silica gel (100% EtOAc) may be used to give A.

Example 6

General Procedure—Deprotection and Derivatization with $R^1X$

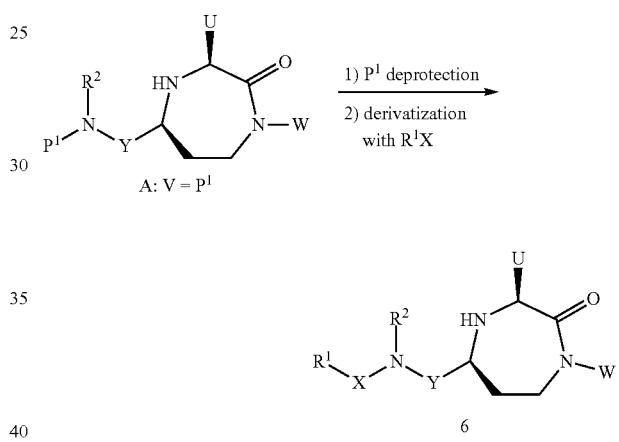

The procedure adopted for the removal of the P1 protecting group will vary depending upon the exact nature of the protecting group. As will be appreciated by a skilled addressee a large number of possible protecting groups may be used and a skilled worker in the art will readily be able to determine an appropriate procedure for the removal of any particular protecting group from procedures known in the art. Nevertheless in order to assist the reader general procedures for the removal of the more common protecting groups are provided.

Deprotection, $P^1$=Cbz:

To the cyclised product A (1 mmol) in methanol (5 mL) is added catalytic Pd/C. The reaction is stirred under a hydrogen atmosphere overnight. The reaction mixture is filtered through Celite and the methanol removed by rotary evaporation to give the free amine. The amine may be used in the next reaction without purification.

Deprotection, $P^1$=Boc:

To the cyclised product A (1 mmol) in DCM (1 mL) is added TFA (1 mL) and the reaction stirred at room temperature for 2 hrs. The solvent is removed by rotary evaporation to give the amine TFA salt, which may be used in the next reaction without purification.

Deprotection, P¹=Alloc:

To the cyclised product A (1 mmol) in DCM (6 mL) is added 1,3-dimethylbarbituric acid (0.2 mmol) and palladium tetrakis triphenylphosphine (10 mg). The reaction is evacuated and stirred at room temperature for 1 hr. The DCM is removed under reduced pressure to give the crude free amine, which may be used in the next reaction without purification.

Derivatisation with R¹X when X=C(=O):

To the free amine (1 mmol) in DCM (5 mL) is added DIPEA (1 mmol.), BOP reagent (1.5 mmol) and acid component $R^1CO_2H$ (1.5 mmol). The reaction is stirred at room temperature for 2 hrs. Rotary evaporation and preparative HPLC gives the purified adduct.

Example 7

General Procedure—U Modification Via P³ Deprotection and Dialkylation with Dibromide

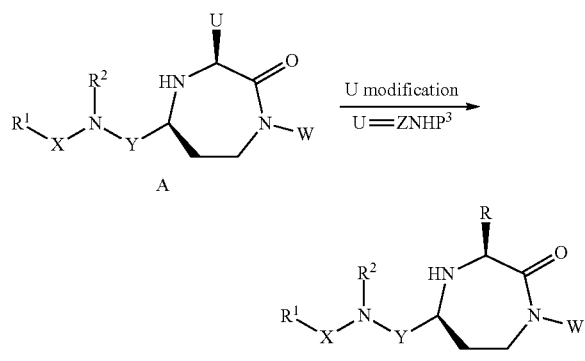

The procedure adopted for modification of U via deprotection and derivatization will vary depending on the exact nature of the U group. As will be appreciated by a skilled addressee a large number of modifications are possible, and a skilled worker in the art will readily be able to determine an appropriate procedure for the conversion into a desired R group. Nevertheless in order to assist the reader, one general modification procedure commonly employed for a number of the following examples is provided.

P³=Boc:

To the protected amine (1 mmol) in DCM (5 mL) is added TFA (5 mL) and the reaction stirred at room temperature for 2 hrs. DCM (20 mL) is added and the solution is washed with saturated sodium bicarbonate solution (20 mL), dried ($MgSO_4$) and evaporated to give the crude amine. To the crude amine is added DMF (0.5 mL), potassium carbonate (50 mg) and 1,5-dibromopentane (5 mmol). The reaction mixture is stirred at room temperature for 1.5 hrs, after which DCM (20 mL) is added, the organic layer washed with saturated sodium bicarbonate solution (20 mL) and $H_2O$ (20 mL), dried ($MgSO_4$) and evaporated. The residue may be purified by preparative HPLC to give the piperidinyl product. The purified product is isolated as the TFA salt, but is readily converted into the free base via neutralisation with aqueous $NaHCO_3$ and extraction into an organic solvent, or further converted into the HCl salt by acidification with 1N HCl.

Example 8

Synthesis of Compound 8 N-(2-(methoxy(methyl)amino)-2-oxoethyl)-2-naphthamide

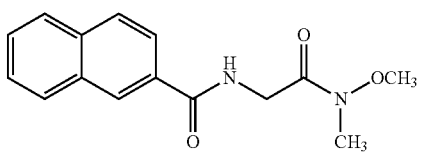

N-(2-(methoxy(methyl)amino)-2-oxoethyl)-2-naphthamide

To a mixture of 2-naphthoic acid (5.8 g, 33.7 mmol), 2-amino-N-methoxy-N-methylacetamide (Gly Weinreb amide; prepared from Boc-Gly Weinreb amide 15 as in Example 43) (3.8 g, 32.1 mmol) and DIPEA (12.0 mL, 68.9 mmol) in DCM (70 mL) was added BOP (14.9 g, 33.7 mmol) in one portion at room temperature. The resulting mixture was stirred for 1 hr then saturated $NaHCO_3$ aqueous solution was added. The organic layer was washed with brine (5×60 mL) and 1 N HCl (2×30 mL), dried over $MgSO_4$, filtered and concentrated under reduced pressure to give the crude product, which was used in the next reaction without further purification.

Example 9

Synthesis of Compound 9 N-(2-(methoxy(methyl)amino)-2-oxoethyl)-2-naphthamide

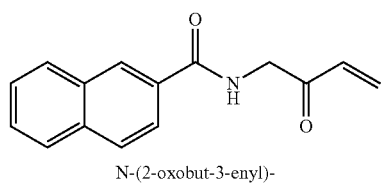

N-(2-oxobut-3-enyl)-2-naphthamide

To a solution of 8 (3.5 g, 12.85 mmol) in dry THF (10 mL) was added a solution of vinylmagnesium bromide in THF (1 M, 31 mL) slowly at 0° C. After addition, the resulting mixture was stirred at room temperature for 1 hr then was poured into an icy 1 N HCl solution (50 mL). The aqueous layer was extracted with DCM (3×80 mL) and the combined organic layers were dried over $MgSO_4$, filtered and concentrated under reduced pressure to give the crude product. MS (ESI) 240 (M+1); HPLC $t_R$ 5.46 min.

Example 10

Synthesis of Compound 10 N-(4-(3,5-dichlorobenzylamino)-2-oxobutyl)-2-naphthamide

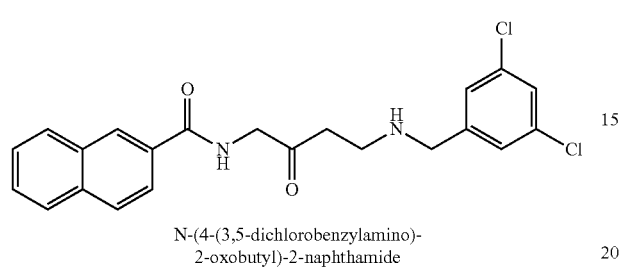

N-(4-(3,5-dichlorobenzylamino)-
2-oxobutyl)-2-naphthamide

To a solution of 3,5-dichlorobenzylamine (12 mg, 0.068 mmol) in DCM (0.2 mL) was added a solution of 9 (13 mg, 0.054 mmol) in DCM (0.5 mL) at room temperature. The resulting mixture was stirred until all of the 9 had been consumed (within one hr) and then was used straight in the next reaction. MS (ESI) 415 (M+1); HPLC $t_R$ 6.00 min.

Example 11

Synthesis of Compound 11 (S)—N-(4-(5-(3-Pbf-guanidino)-2-(Fmoc-amino)-N-(3,5-dichlorobenzyl)pentanamido)-2-oxobutyl)-2-naphthamide

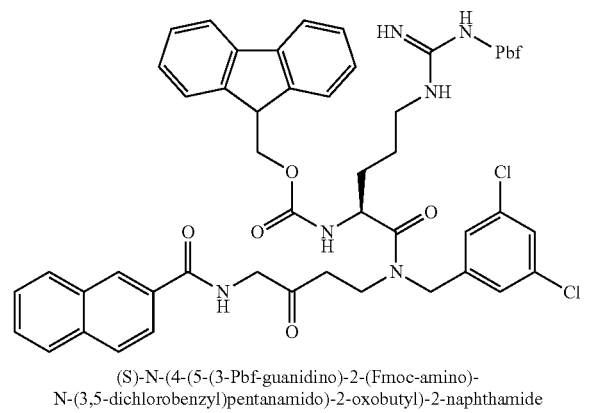

(S)-N-(4-(5-(3-Pbf-guanidino)-2-(Fmoc-amino)-
N-(3,5-dichlorobenzyl)pentanamido)-2-oxobutyl)-2-naphthamide To a solution of freshly prepared aminoketone 10 in DCM (2 mL) was added Fmoc-L-Arg(Pbf)-OH (53 mg, 0.082 mmol) followed by DIC (12.5 µl, 0.082 mmol) at room temperature. The resulting mixture was stirred for 2 hrs then the solvent was removed under reduced pressure. The residue was filtered through a short plug of silica gel eluting with DCM followed by EtOAc to give the desired product 11 as a white solid. It was used in the next step without further purification. MS (ESI) 1045 (M+1); HPLC $t_R$ 9.99 min.

Example 12

Synthesis of Compound 12 (S)—N-(4-(5-(3-Pbf-guanidino)-2-amino-N-(3,5-dichlorobenzyl)pentanamido)-2-oxobutyl)-2-naphthamide

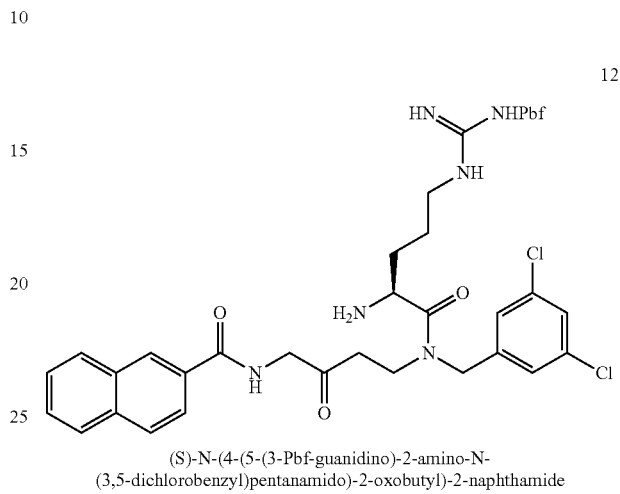

(S)-N-(4-(5-(3-Pbf-guanidino)-2-amino-N-
(3,5-dichlorobenzyl)pentanamido)-2-oxobutyl)-2-naphthamide Diethylamine (0.5 mL) was added to Fmoc-protected 11 (56 mg, 0.054 mmol) at room temperature and the resulting mixture was stirred for 30 min. The excess amount of the diethylamine was removed under reduced pressure to give the desired free amine 12. It was used in the next step without further purification. MS (ESI) 823 (M+1); HPLC $t_R$ 7.49 min.

Example 13

Synthesis of Compound 13 N-(((3S,5S)-3-(3-(3-Pbf-guanidino)propyl)-1-(3,5-dichlorobenzyl)-2-oxo-1,4-diazepan-5-yl)methyl)-2-naphthamide

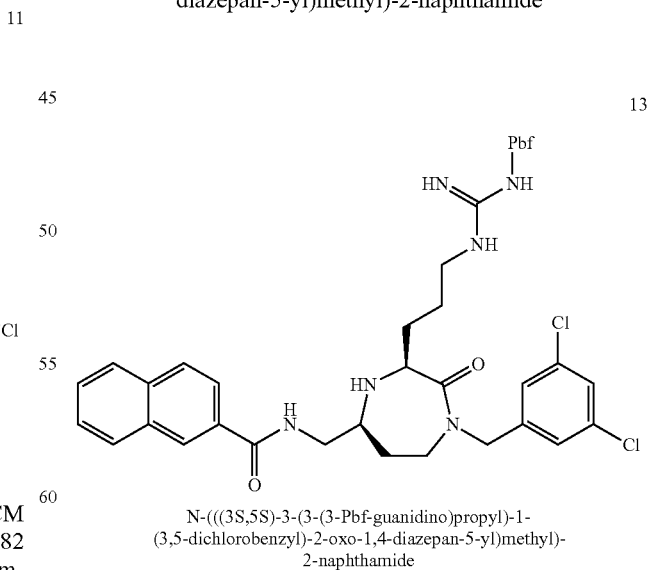

N-(((3S,5S)-3-(3-(3-Pbf-guanidino)propyl)-1-
(3,5-dichlorobenzyl)-2-oxo-1,4-diazepan-5-yl)methyl)-
2-naphthamide The amino ketone 12 (44 mg, 0.053 mmol) in DCM (2 mL) was cyclized by addition of NaBH(OAc)$_3$ (40 mg, 0.18 mmol) in one portion at room temperature. The resulting mixture was stirred for 3 hrs, followed by addition of saturated NaHCO₃ aqueous solution (3 mL). The aqueous layer was extracted with DCM (3×3 mL) and the combined organic layers were dried over MgSO₄, filtered and concentrated under reduced pressure. The residue was filtered through a short plug of silica gel eluting with DCM followed by EtOAc then EtOAc/IPA (9:1) to give the desired product 13 as a white solid. It was used in the next step without further purification. MS (ESI) 807 (M+1); HPLC $t_R$ 7.75 min.

Example 14

Synthesis of Compound 14 N-(((3S,5S)-1-((3,5-dichlorobenzyl)-3-(3-guanidinopropyl)-2-oxo-1,4-diazepan-5-yl)methyl)-2-naphthamide

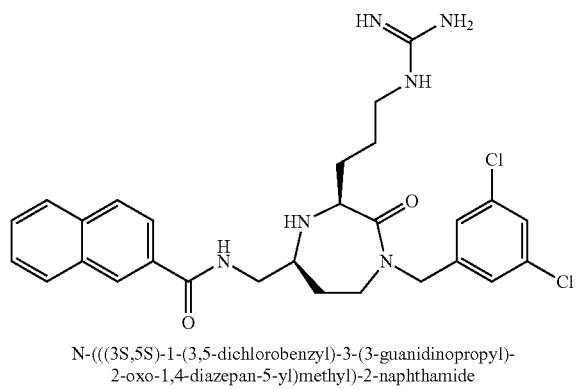

N-(((3S,5S)-1-(3,5-dichlorobenzyl)-3-(3-guanidinopropyl)-
2-oxo-1,4-diazepan-5-yl)methyl)-2-naphthamide A solution of TFA/DCM (2:1) (1 mL) with 5% H₂O was added to 13 at room temperature and the resulting mixture was stirred for 4 hrs. The solvents were removed under reduced pressure and the residue was purified by prep HPLC (100% H₂O to MeCN/H₂O 9:1, gradient) to give 14 (7.6 mg) as a white solid (TFA salt). The overall yield (from 9) was ca. 18%. MS (ESI) 556.2 (M+1); HPLC $t_R$ 5.74 min.

Example 15

Synthesis of Compound 15 tert-butyl 2-(methoxy(methyl)amino)-2-oxoethylcarbamate (Boc-Gly Weinreb amide)

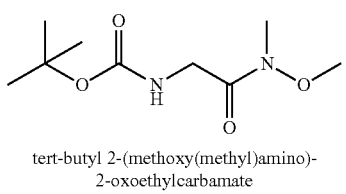

tert-butyl 2-(methoxy(methyl)amino)-
2-oxoethylcarbamate

To a stirred mixture of Boc-Gly-OH (20 g, 114.1 mmol), DIPEA (19.8 mL, 114.1 mmol) and BOP (50.5 g, 114.1 mmol) in DCM (20 mL) was added a pre-mixed solution of N,O-dimethylhydroxylamine hydrochloride (11.2 g, 114.1 mmol) and DIPEA (19.8 mL, 114.1 mmol) in DCM (20 mL) at room temperature. The resulting mixture was stirred for 16 h then washed with 1N HCl (3×120 mL), H₂O (3×120 mL), saturated NaHCO₃ aqueous solution (3×120 mL) and brine (40 mL), dried over MgSO₄, filtered and concentrated under reduced pressure to give 15 as a white solid (20 g, 80%), which was used in the next step without further purification. MS (ESI) 219 (M+1); HPLC $t_R$ 4.12 min.

Example 16

Synthesis of Compound 16 tert-butyl 2-oxobut-3-enylcarbamate

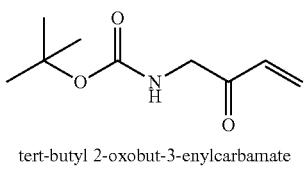

tert-butyl 2-oxobut-3-enylcarbamate

At 0° C. a solution of vinylmagnesium bromide in THF (184 mL, 1 M) was added in one portion to Weinreb amide 15 (20 g, 91.6 mmol) under nitrogen with stirring. The resulting mixture was allowed to stir for 2 h, and poured into a 1N HCl/ice mixture (400 mL). The aqueous mixture was extracted with DCM (5×100 mL), the combined DCM extract was washed with 1N HCl (2×100 mL), saturated NaHCO₃ aqueous solution (100 mL) and brine (100 mL), then dried over MgSO₄. Solvent was removed under reduced pressure gave the ketone 16 (12.9 g, 76%) as a pale yellow oil, which was used in the next step without further purification. MS (ESI) 186 (M+1); HPLC $t_R$ 4.19 min.

Example 17

Synthesis of Compound 17 tert-butyl 4-(2,2-diphenylethylamino)-2-oxobutylcarbamate

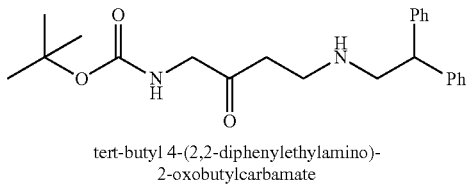

tert-butyl 4-(2,2-diphenylethylamino)-
2-oxobutylcarbamate

To a stirred solution of 2,2-diphenylethylamine (0.33 g, 1.66 mmol) in DCM (10 mL) was added α,β-unsaturated ketone 16 (0.31 g, 1.66 mmol) at room temperature. Stirring continued for 2 h; the crude reaction mixture of 17 was used in the next step without purification. MS (ESI) 383 (M+1); HPLC $t_R$ 5.98 min

Example 18

Synthesis of Compound 18 (S)-tert-butyl 3-methyl-4,8-dioxo-10-phenyl-2,9-dioxa-3,7-diazadecane-6-carboxylate

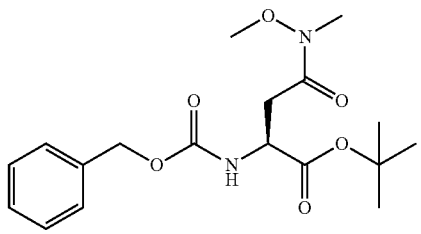

(S)-tert-butyl 3-methyl-4,8-dioxo-10-phenyl-2,9-dioxa-3,7-diazadecane-6-carboxylate To a suspension of Cbz-L-Asp-OtBu-DCHA salt (10.1 g, 20.0 mmol), N,O-dimethylhydroxylamine-HCl (5.9 g, 60.5 mmol) and DIPEA (12.0 mL, 68.9 mmol) in DCM (150 mL) was added BOP (10.6 g, 24.0 mmol) in one portion at room temperature. The resulting suspension was stirred for 3 hrs then H$_2$O (100 mL) was added. The organic layer was washed with 1 N HCl (2×100 mL), saturated NaHCO$_3$ aqueous solution (2×100 mL) and brine (3×100 mL) and then dried over MgSO$_4$, filtered and concentrated under reduced pressure to give the crude product. Purification by flash chromatography on silica gel (PET ether/EtOAc 1:2) gave 18 (6.4 g, 87%) as a colorless oil. MS (ESI) 367 (M+1); HPLC $t_R$ 6.87 min.

Example 19

Synthesis of Compound 19 (S)-3-methyl-4,8-dioxo-10-phenyl-2,9-dioxa-3,7-diazadecane-6-carboxylic acid

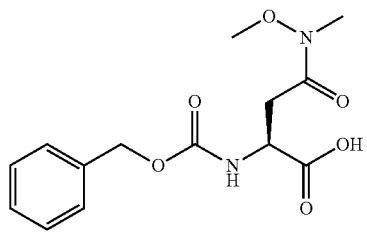

(S)-3-methyl-4,8-dioxo-10-phenyl-2,9-dioxa-3,7-diazadecane-6-carboxylic acid

Compound 18 (300 mg, 0.82 mmol) was dissolved in a TFA/DCM (1:1) solution (2 mL) and the resulting mixture was stirred at room temperature for 2 hrs. The solvents were removed under reduced pressure and the residue was re-dissolved in DCM (10 mL). This solution was washed with 1 N HCl (1×10 mL) and the organic layer was dried over MgSO$_4$, filtered and concentrated under reduced pressure to give the crude product 19 (235 mg, 92%), which was used in the next reaction without further purification. MS (ESI) 311 (M+1); HPLC $t_R$ 4.96 min.

Example 20

Synthesis of Compound 20 (S)-benzyl 8-(2,2-diphenylethyl)-3,16,16-trimethyl-4,7,11,14-tetraoxo-2,15-dioxa-3,8,13-triazaheptadecan-6-ylcarbamate

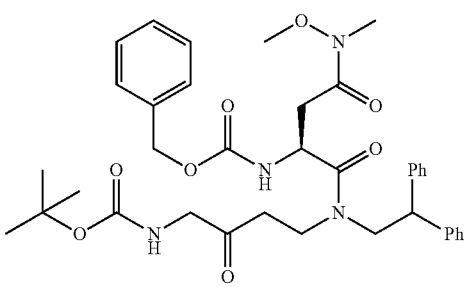

(S)-benzyl 8-(2,2-diphenylethyl)-3,16,16-trimethyl-4,7,11,14-tetraoxo-2,15-dioxa-3,8,13-triazaheptadecan-6-ylcarbamate Compound 20 was prepared from Compound 17 and 19 following the procedure of Example 5. MS (ESI) 675 (M+1); HPLC $t_R$ 8.31 min.

Example 21

Synthesis of Compound 21 tert-butyl((3S,5S)-1-(2,2-diphenylethyl)-3-(2-(methoxy(methyl)amino)-2-oxoethyl)-2-oxo-1,4-diazepan-5-yl) methylcarbamate

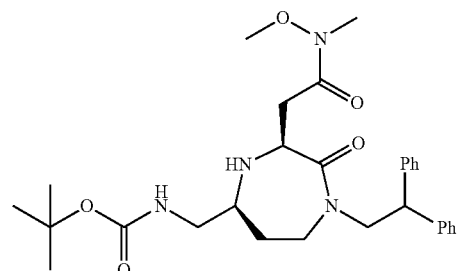

tert-butyl ((3S,5S)-1-(2,2-diphenylethyl)-3-(2-(methoxy(methyl)amino)-2-oxoethyl)-2-oxo-1,4-diazepan-5-yl)methylcarbamate A mixture of crude 20 (350 mg) and 5% Pd/C (200 mg) in 2-propanol (15 mL) was shaken at room temperature under hydrogen (30 psi) for 24 hrs. The mixture was then filtered through a pad of Celite and the filtrate was concentrated under reduced pressure to give the crude product. Purification by flash chromatography on silica gel (100% of EtOAc) gave 21 (175 mg, 65% over 3 steps) as a white solid. MS (ESI) 525 (M+1); HPLC $t_R$ 6.24 min.

Example 22

Synthesis of Compound 22 2-((2S,7S)-7-(aminomethyl)-4-(2,2-diphenylethyl)-3-oxo-1,4-diazepan-2-yl)-N-methoxy-N-methylacetamide

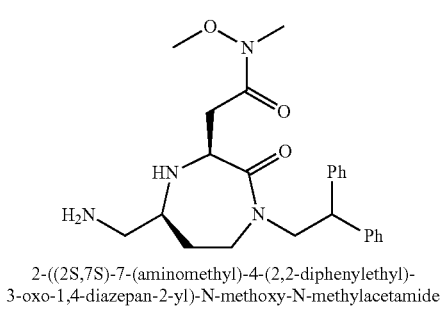

2-((2S,7S)-7-(aminomethyl)-4-(2,2-diphenylethyl)-3-oxo-1,4-diazepan-2-yl)-N-methoxy-N-methylacetamide Compound 21 (175 mg, 0.333 mmol) was dissolved in a TFA/DCM (1:1) solution (1 mL) and the resulting mixture was stirred at room temperature for 2 hrs. The solvents were removed under reduced pressure and the residue was re-dissolved in EtOAc (20 mL). Saturated NaHCO$_3$ aqueous solution (10 mL) and brine (10 mL) were added to the above solution and the aqueous layer was extracted with EtOAc (9×20 mL). The combined organic layers were dried over MgSO$_4$, filtered and concentrated under reduced pressure to give the crude product 22 (120 mg, 85%) as a yellow solid, which was used in the next reaction without further purification. MS (ESI) 425 (M+1); HPLC $t_R$ 5.20 min.

Example 23

Synthesis of Compound 23 N-(((3S,5S)-1-(2,2-diphenylethyl)-3-(2-(methoxy(methyl)amino)-2-oxoethyl)-2-oxo-1,4-diazepan-5-yl)methyl)-6-fluoro-2-naphthamide

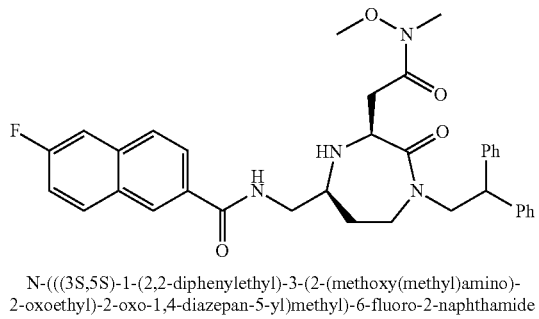

N-(((3S,5S)-1-(2,2-diphenylethyl)-3-(2-(methoxy(methyl)amino)-2-oxoethyl)-2-oxo-1,4-diazepan-5-yl)methyl)-6-fluoro-2-naphthamide To a solution of 22 (50 mg, 0.118 mmol) and 6-fluoro-2-naphthoic acid (27 mg, 0.142 mmol) in DCM (4 mL) was added DIC (22 μl, 0.142 mmol) at room temperature. The resulting mixture was stirred for 2 hrs then the solvent was removed under reduced pressure to give the crude product. Purification by flash chromatography on silica gel (eluting with Petroleum ether:EtOAc (1:1) then EtOAc) gave 23 (29 mg, 41%) as a white solid. MS (ESI) 597 (M+1); HPLC $t_R$ 6.75 min.

Example 24

Synthesis of Compound 24 N-(((3S,5S)-1-(2,2-diphenylethyl)-2-oxo-3-(2-oxoethyl)-1,4-diazepan-5-yl)methyl)-6-fluoro-2-naphthamide

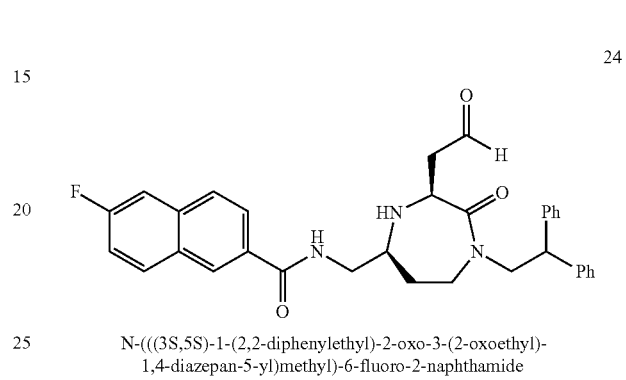

N-(((3S,5S)-1-(2,2-diphenylethyl)-2-oxo-3-(2-oxoethyl)-1,4-diazepan-5-yl)methyl)-6-fluoro-2-naphthamide To a solution of 23 (29 mg, 0.049 mmol) in dry THF (1 mL) was added LiAlH(OtBu)$_3$ (38 mg, 0.145 mmol) in one portion at room temperature and the resulting suspension was stirred overnight. This suspension was then slowly poured into a cold (0° C.) 0.4 M KHSO$_4$ aqueous solution (2 mL, 0.8 mmol) and the resulting mixture was diluted with EtOAc (3 mL). The aqueous layer was extracted with EtOAc (3×3 mL) and the combined organic layers were washed with 1 N HCl (3×6 mL), saturated NaHCO$_3$ aqueous solution (1×6 mL), and brine (1×6 mL). The organic solution was then dried over MgSO$_4$, filtered and concentrated under reduced pressure to give the crude product 24 (24 mg, 91%), which was used in the next reaction without further purification. MS (ESI) 538 (M+1); HPLC $t_R$ 6.41 min.

Example 25

Synthesis of Compound 25 N-(((3S,5S)-3-(2-(diethylamino)ethyl)-1-(2,2-diphenylethyl)-2-oxo-1,4-diazepan-5-yl)methyl)-6-fluoro-2-naphthamide

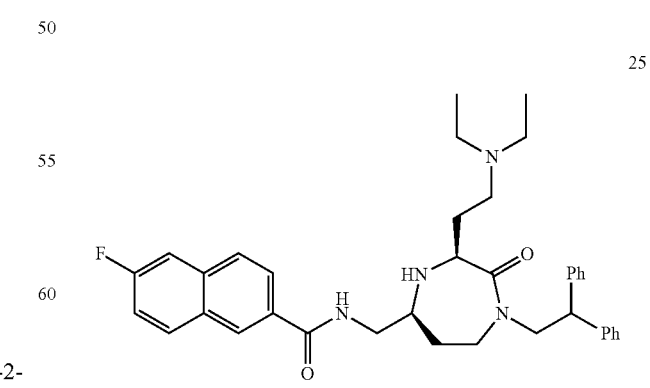

N-(((3S,5S)-3-(2-(diethylamino)ethyl)-1-(2,2-diphenylethyl)-2-oxo-1,4-diazepan-5-yl)methyl)-6-fluoro-2-naphthamide To a solution of 24 (24 mg, 0.044 mmol) in DCM (2 mL) was added diethylamine (55 μl, 0.532 mmol) at room temperature. After stirring for 5 mins, NaBH(OAc)₃ (20 mg, 0.090 mmol) was added to the above solution in one portion and the resulting suspension was stirred for another 10 mins. Saturated NaHCO₃ aqueous solution (4 mL) was added to the suspension and the aqueous layer was extracted with DCM (3×4 mL). The combined organic layers were washed with brine (10 mL), dried over MgSO₄, filtered and concentrated under reduced pressure to give the crude product. This crude product was purified by prep HPLC (100% H₂O to MeCN/H₂O 9:1, gradient) to give the 25 as a white solid (TFA salt). MS (ESI) 595.3 (M+1); HPLC $t_R$ 6.22 min.

Example 26

Synthesis of Compound 26 benzyl 2-(methoxy(methyl)amino)-2-oxoethylcarbamate

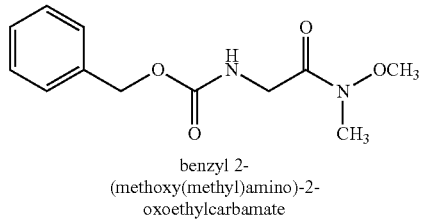

benzyl 2-(methoxy(methyl)amino)-2-oxoethylcarbamate

To Cbz-glycine (10 g, 47.8 mmol, Aldrich) in DCM (100 mL) was added BOP reagent (21.5 g, 48.6 mmol) and DIPEA (6.5 mL, 46.0 mmol). After stirring at room temperature for 10 mins, N,O-dimethylhydroxylamine hydrochloride (4.9 g, 50.2 mmol) and DIPEA (6.5 mL, 46.0 mmol) were added. The reaction was stirred at room temperature overnight. The DCM was removed by rotary evaporation and the residue taken up in EtOAc (100 mL). The organic phase was washed with H₂O (3×100 mL), saturated sodium bicarbonate solution (3×100 mL), H₂O (3×100 mL), 1M HCl (3×100 mL), brine (3×100 mL). The organic phase was dried (MgSO₄) and the EtOAc removed to give the Weinreb amide 26 as a white solid (7.78 g, 64%).

Example 27

Synthesis of Compound 27 benzyl 2-oxobut-3-enylcarbamate

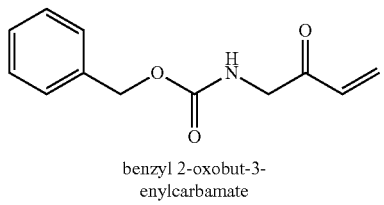

benzyl 2-oxobut-3-enylcarbamate

To the Weinreb amide 26 (3.89 g, 15.42 mmol) in DCM (10 mL) at 0° C. was added vinyl magnesium bromide (45 mmol) in THF (45 mL). The reaction was stirred for 2 hrs and monitored by HPLC. The reaction was added to a mixture of ice and 1M HCl (200 mL). The aqueous mixture was extracted with DCM (3×100 mL) and washed with 1M HCl (2×200 mL) and H₂O (3×100 mL). The organic phase was dried (MgSO₄) and the volume reduced to 100 mL by rotary evaporation. The α,β-unsaturated ketone 27 was stored and used in solution without purification Example 28

Synthesis of Compound 28 (S)-9-fluorenylmethyl 10-(2,2-diphenylethyl)-2,2-dimethyl-18-phenyl-4,9,13,16-tetraoxo-3,17-dioxa-5,10,15-triazaoctadecan-8-ylcarbamate

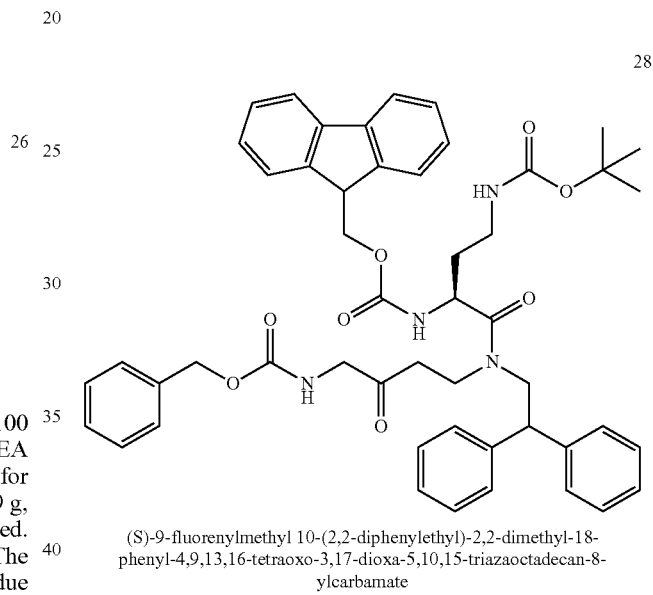

(S)-9-fluorenylmethyl 10-(2,2-diphenylethyl)-2,2-dimethyl-18-phenyl-4,9,13,16-tetraoxo-3,17-dioxa-5,10,15-triazaoctadecan-8-ylcarbamate To 2,2-diphenylethylamine (0.95 g, 7.4 mmol) in DCM (10 mL) was added the αβ-unsaturated ketone 27 (5.7 mmol) in DCM (75 mL). After stirring at room temperature for 15 mins, Fmoc-L-2,4-diaminobutyric acid(Boc)-OH (2.4 g, 8.55 mmol) and DIC (0.87 mL, 5.6 mmol) were added. The reaction was stirred at room temperature overnight. The DCM was removed by rotary evaporation and the residue was subjected to column chromatography on silica gel using petroleum spirit:EtOAc (1:1 to 0:1) to give 28 (1.5 g, 31%)

Alternatively, to 2,2-diphenylethylamine (0.97 g, 7.4 mmol) in DCM (20 mL) was added the α,β-unsaturated ketone 27 (5.95 mmol) in DCM (40 mL). After stirring at room temperature for 15 mins, Fmoc-L-2,4-diaminobutyric acid(Boc)-OH (2.4 g, 8.55 mmol), DIPEA (2.5 mL) and HATU (2.3 g, 6.0 mmol) were added. The reaction was stirred at room temperature overnight. The DCM was removed by rotary evaporation and the residue was taken up in EtOAc (100 mL). The organic layer was washed with saturated sodium bicarbonate solution (2×100 mL), saturated ammonium chloride solution (2×100 mL) and brine (2×100 mL). The organic phase was dried and the solvent removed under reduced pressure. The residue was subjected to column chromatography on silica gel using petroleum spirit:EtOAc (3:1 to 1:1 to 0:1) to give 28 (0.86 g, 17%).

Example 29

Synthesis of Compound 29 (3S,5S)-3-(2-tert-butoxycarbonylaminoethyl)-5-(benzyloxycarbonylaminomethyl)-1-(2,2-diphenylethyl)-1,4-diazepan-2-one

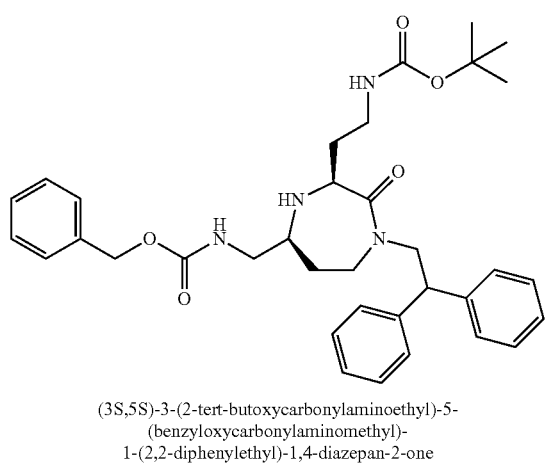

(3S,5S)-3-(2-tert-butoxycarbonylaminoethyl)-5-(benzyloxycarbonylaminomethyl)-1-(2,2-diphenylethyl)-1,4-diazepan-2-one To Compound 28 (1.5 g, 1.8 mmol) in DCM (3 mL) was added diethylamine (1.5 mL, 14.5 mmol). The reaction was stirred at room temperature for 1 hr. The DCM and diethylamine was removed by rotary evaporation. DCM (5 mL), sodium triacetoxyborohydride (0.4 g, 1.9 mmol) was added, and the reaction was stirred overnight at room temperature. The organic phase was washed with saturated sodium bicarbonate solution (25 mL), dried (MgSO$_4$) and the DCM removed to give the cyclised product 29, which was used in the next step without purification.

Example 30

Synthesis of Compound 30 (3S,5S)-3-(2-tert-butoxycarbonylaminoethyl)-5-aminomethyl-1-(2,2-diphenylethyl)-1,4-diazepan-2-one

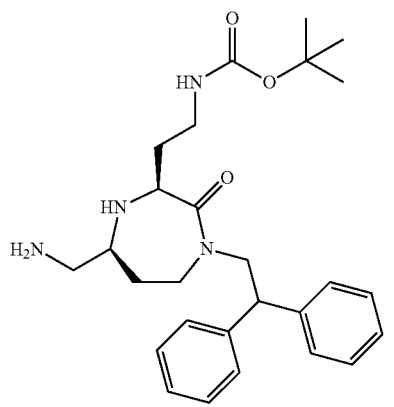

(3S,5S)-3-(2-tert-butoxycarbonylaminoethyl)-5-aminomethyl-1-(2,2-diphenylethyl)-1,4-diazepan-2-one To the cyclised product 29 in methanol (5 mL) was added catalytic Pd/C. The reaction was stirred under a hydrogen atmosphere overnight. The reaction mixture was filtered through Celite and the methanol removed by rotary evaporation to give the amine 30 (0.7 g, 83% from 28).

Example 31

Synthesis of Compound 31 N-(((3S,5S)-3-(2-aminoethyl)-1-(2,2-diphenylethyl)-2-oxo-1,4-diazepan-5-yl)methyl)-6-fluoro-2-naphthamide

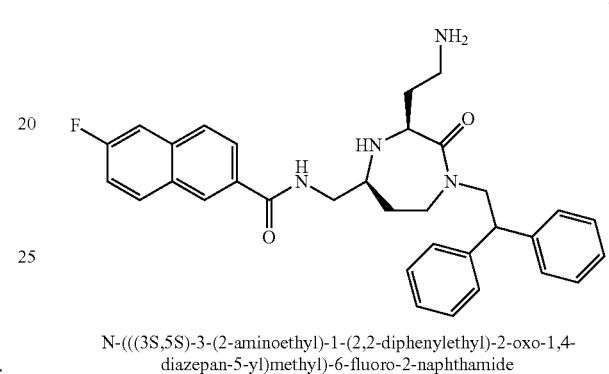

N-(((3S,5S)-3-(2-aminoethyl)-1-(2,2-diphenylethyl)-2-oxo-1,4-diazepan-5-yl)methyl)-6-fluoro-2-naphthamide To the amine 30 (0.08 g, 0.17 mmol) in DCM (1 mL) was added DIPEA (0.25 mL), BOP reagent (0.08 g, 0.18 mmol) and 6-fluoro-2-naphthoic acid (0.06 g, 0.32 mmol). The reaction was stirred at room temperature for 2 hrs. TFA (1 mL) was added and the reaction stirred at room temperature for 2 hrs. Rotary evaporation and preparative HPLC gave 31 (0.05 g, 54%). MS (ESI) 539.3 (M+1); HPLC $t_R$ min 5.92

Example 32

Synthesis of Compound 32 6-chloro-2-naphthoic acid

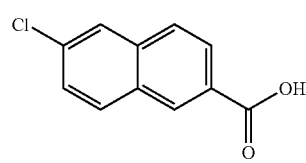

6-chloro-2-naphthpoic acid

A suspension of 6-bromo-2-naphthoic acid (3.0 g, 11.47 mmol), CuCl (11.7 g, 114.64 mmol) and CuI (2.19 g, 11.50 mmol) in degassed DMF (45 mL) was heated to reflux under argon in dark for 4 hrs. After cooling to room temperature, the solution was decanted into H$_2$O (200 mL) and the resulting mixture was extracted with EtOAc (2×500 mL). The combined organic layers were then washed with H$_2$O (4×500 mL) followed by brine (1×500 mL), dried over MgSO$_4$, filtered and concentrated under reduced pressure to dryness. The residue was triturated with CH$_3$CN and the solid obtained was then re-crystallized from EtOAc to give the pure product 32 (2.2 g, 93%) as a off-white solid. HPLC $t_R$ 6.47 min.

Example 33

Synthesis of Compound 33 (E)-3-(4-chlorophenyl)-N-(((3S,5S)-1-(2,2-diphenylethyl)-2-oxo-3-(2-(piperidin-1-yl)ethyl)-1,4-diazepan-5-yl)methyl)acrylamide

33

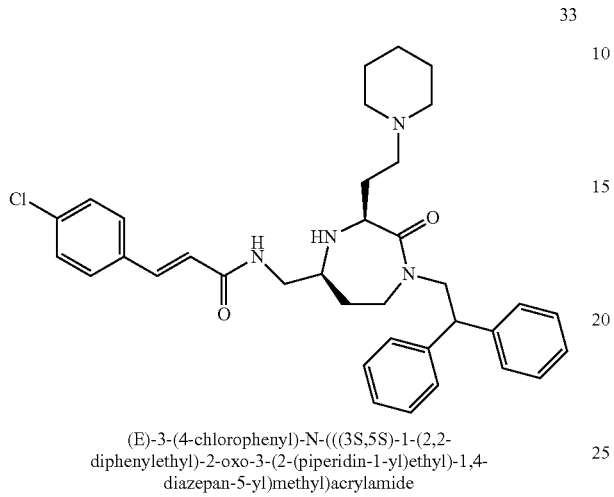

(E)-3-(4-chlorophenyl)-N-(((3S,5S)-1-(2,2-diphenylethyl)-2-oxo-3-(2-(piperidin-1-yl)ethyl)-1,4-diazepan-5-yl)methyl)acrylamide To the amine (E)-3-(4-chlorophenyl)-N-(((3S,5S)-1-(2,2-diphenylethyl)-2-oxo-3-(2-aminoethyl)-1,4-diazepan-5-yl)methyl)acrylamide (21 mg, 0.05 mmol) in DMF (0.25 mL) was added $K_2CO_3$ (5 mg) and 1,5-dibromopropane (0.066 mL, 0.5 mmol). The reaction mixture was left at room temperature for 4 hrs. The solvent was removed under high vacuum, and the residue purified by preparative HPLC to give 8 mg (~30%) of 33 as the TFA salt. MS (ESI) 599.4 (M+1); HPLC $t_R$ min 6.31

Example 34

Synthesis of Compound 34 (S)-9-fluorenylmethyl 10-(2-phenylbutyl)-2,2-dimethyl-18-phenyl-4,9,13,16-tetraoxo-3,17-dioxa-5,10,15-triazaoctadecan-8ylcarbamate

34

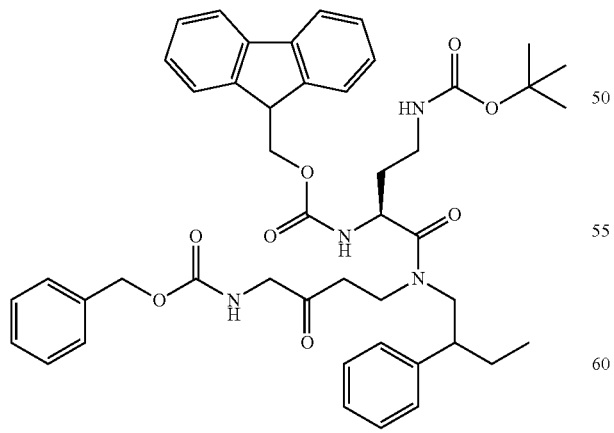

(S)-9-fluorenylmethyl 10-(2-phenylbutyl)-2,2-dimethyl-18-phenyl-4,9,13,16-tetraoxo-3,17-dioxa-5,10,15-triazaoctadecan-8-ylcarbamate To 2-phenylbutylamine hydrochloride (0.26 g, 1.4 mmol) in DCM (10 mL) and DIPEA (0.25 mL, 1.8 mmol) was added the α,β-unsaturated ketone 27 (1.06 mmol) in DCM (20 mL). After stirring at room temperature for 15 mins, Fmoc-diaminobutyric acid(Boc)-OH (0.7 g, 1.56 mmol) and DIC (0.25 mL, 1.61 mmol) were added. The reaction was stirred at room temperature overnight. The DCM was removed by rotary evaporation and the residue was subjected to column chromatography on silica gel using petroleum spirit:EtOAc (1:1 to 0:1), providing Compound 34 as a mixture of diastereomers (0.17 g, 21%).

Example 35

Synthesis of Compound 35 (3S,5S)-3-(2-tert-butoxycarbonylaminoethyl)-5-(benzyloxycarbonylaminomethyl)-1-(2-phenylbutyl)-1,4-diazepan-2-one

35

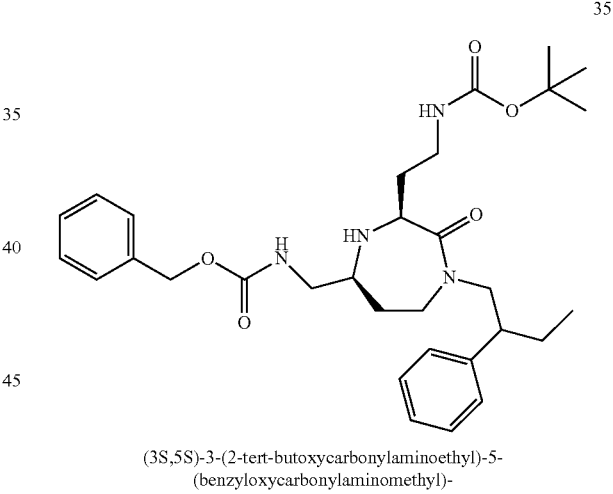

(3S,5S)-3-(2-tert-butoxycarbonylaminoethyl)-5-(benzyloxycarbonylaminomethyl)-1-(2-phenylbutyl)-1,4-diazepan-2-one To Compound 34 (0.17 g, 0.2 mmol) in DCM (3 mL) was added diethylamine (1.5 mL). The reaction was stirred at room temperature for 1 hr. The DCM and diethylamine was removed by rotary evaporation. DCM (5 mL) and sodium triacetoxyborohydride (0.1 g, 0.47 mmol) were added and the reaction was stirred overnight at room temperature. The organic phase was washed with saturated sodium bicarbonate solution (25 mL), dried ($MgSO_4$) and the DCM removed to give the cyclised product 35 as a mixture of diastereomers (0.11 g, 100%).

Example 36

Synthesis of Compound 36 (3S,5S)-3-(2-tert-butoxycarbonylaminoethyl)-5-(aminomethyl)-1-(2-phenylbutyl)-1,4-diazepan-2-one

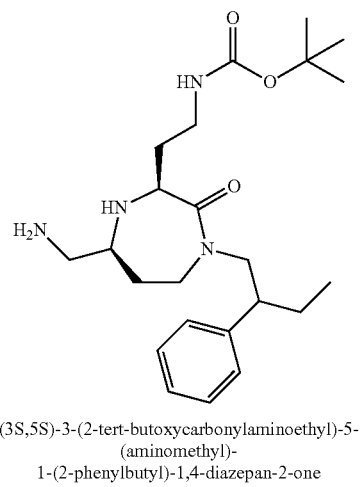

36

(3S,5S)-3-(2-tert-butoxycarbonylaminoethyl)-5-(aminomethyl)-1-(2-phenylbutyl)-1,4-diazepan-2-one To the cyclised product 35 (0.11 g) in methanol (5 mL) was added catalytic Pd/C. The reaction was stirred under a hydrogen atmosphere overnight. The reaction mixture was filtered through Celite and the methanol removed by rotary evaporation to give the amine 36 as a mixture of diastereomers (0.11 g, 100%).

Example 37

Synthesis of Compound 37 (3S,5S)-3-(2-aminoethyl)-5-(N-2-naphthamidomethyl)-1-(2-phenylbutyl)-1,4-diazepan-2-one

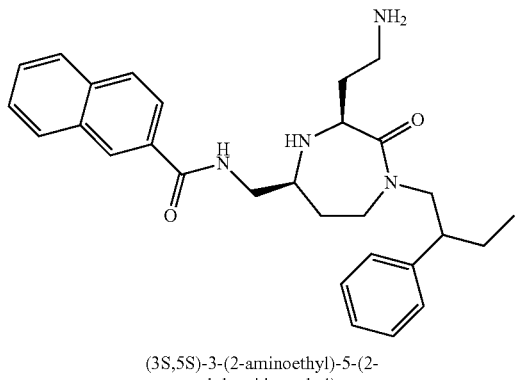

37

(3S,5S)-3-(2-aminoethyl)-5-(2-naphthamidomethyl)-1-(2-phenylbutyl)-1,4-diazepan-2-one To the amine 36 (0.02 mg, 0.05 mmol) in DCM (1 mL) was added DIPEA (0.1 mL, 0.7 mmol), BOP reagent (0.02 mg, 0.045 mmol) and 2-naphthoic acid (0.015 mg, 0.09 mmol). The reaction was stirred at room temperature for 2 hrs. TFA (1 mL) was added and the reaction stirred at room temperature for 2 hrs. Rotary evaporation and preparative HPLC gave 37 as a mixture of diastereomers (13.4 mg, 57%). MS (ESI) 473.4 (M+1); HPLC $t_R$ 5.59 min

Example 38

Synthesis of Compounds 38-39 N-(((3S,5S)-2-oxo-1-((S)-2-phenylbutyl)-3-(2-(piperidin-1-yl)ethyl)-1,4-diazepan-5-yl)methyl)-2-naphthamide and N-(((3S,5S)-2-oxo-1-((R)-2-phenylbutyl)-3-(2-(piperidin-1-yl)ethyl)-1,4-diazepan-5-yl)methyl)-2-naphthamide

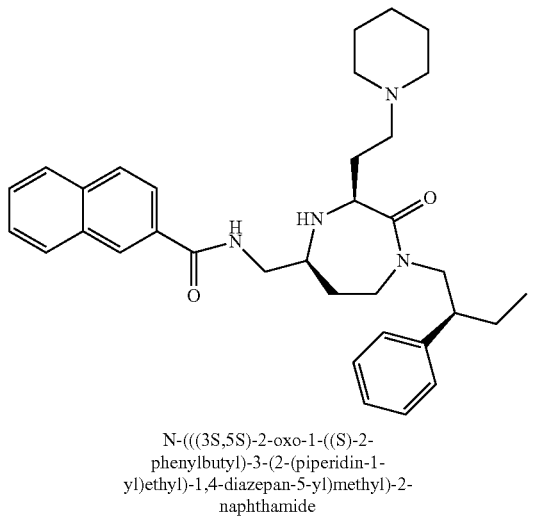

38

N-(((3S,5S)-2-oxo-1-((S)-2-phenylbutyl)-3-(2-(piperidin-1-yl)ethyl)-1,4-diazepan-5-yl)methyl)-2-naphthamide

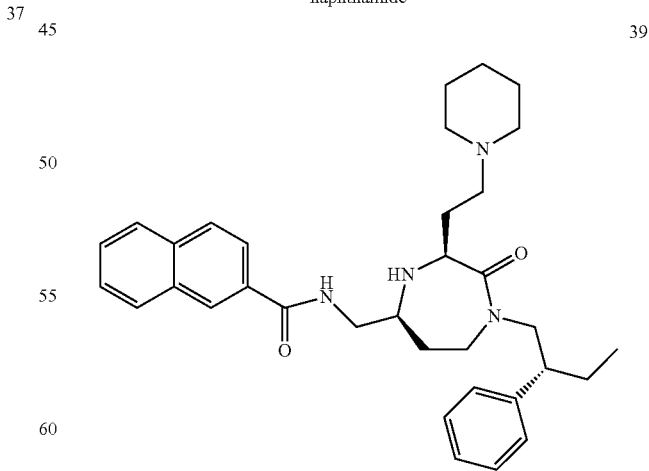

39

N-(((3S,5S)-2-oxo-1-((R)-2-phenylbutyl)-3-(2-(piperidin-1-yl)ethyl)-1,4-diazepan-5-yl)methyl)-2-naphthamide Prepared from Compound 37 by alkylation as in Example 33. Preparative HPLC purification separated the two diastereomers. The correct configuration was assigned by resynthesis of the compounds using (S)-2-phenylbutylamine 43 or (R)-2-phenylbutylamine. 38: MS (ESI) 541.3 (M+1); HPLC $t_R$ 5.78 min; 39: MS (ESI) 541.3 (M+1); HPLC $t_R$ 5.67 min Example 39

Synthesis of Compound 40 (S)-2-phenylbutanol

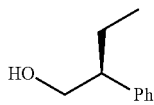

40

To a suspension of sodium borohydride (2.36 g, 62.4 mmol) in THF (50 mL) was added a solution of (S)-2-phenylbutyric acid (4.27 g, 26.0 mmol) in THF (40 mL) slowly at 0° C. The mixture was stirred until the evolution of gas ceased. A solution of iodine (6.60 g, 26.0 mmol) in THF (40 mL) was then added slowly at 0° C. After addition, the resulting mixture was allowed to warm to room temperature and stirred for 1 hr. The reaction solution was then slowly poured into a 1 N HCl solution (280 mL) and the resulting mixture was diluted with EtOAc (250 mL). The aqueous layer was extracted with EtOAc (150 mL×3) and the combined organic layers were then washed with saturated NaHCO$_3$ (aq), 0.5 M Na$_2$S$_2$O$_3$ (aq) and brine. This organic solution was dried over MgSO$_4$, filtered and concentrated under reduced pressure to give the crude product. Purification by flash chromatography on silica gel (Petroleum ether:EtOAc 4:1) gave the desired product 40 as a colorless oil in quantitative yield. HPLC $t_R$ 5.24 min.

Example 40

Synthesis of Compound 41 (S)-1-mesyloxy-2-phenylbutane

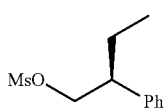

41

To a mixture of 40 (3.9 g, 26.0 mmol) and triethylamine (5.5 mL, 39.5 mmol) in DCM (90 mL) was added a solution of methanesulfonyl chloride (4.47 g, 39.0 mmol) in DCM (30 mL) slowly at 0° C. After addition, the resulting mixture was allowed to warm to room temperature and stirred for 2 hrs. 1 N HCl (70 mL) was then added to the above mixture and the aqueous layer was extracted with DCM (1×70 mL). The combined organic layers were washed with brine (150 mL), dried over MgSO$_4$, filtered and concentrated under reduced pressure to give the crude product 41 as a colorless oil. This crude product was used in the next step without further purification. HPLC $t_R$ 6.48 min.

Example 41

Synthesis of Compound 42 (S)-1-azido-2-phenylbutane

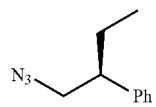

42

A suspension of 41 (5.93 g, 26.0 mmol) and sodium azide (5.7 g, 78.0 mmol) in DMF (60 mL) was heated at 85° C. for 3 hrs. After cooling to room temperature, the mixture was diluted with H$_2$O (200 mL) and extracted with EtOAc (250 mL). The organic layer was then washed with H$_2$O (4×150 mL) followed by brine (150 mL), dried over MgSO$_4$, filtered and concentrated under reduced pressure to give the crude product. Purification by flash chromatography on silica gel (100% petroleum ether as the eluent) gave the pure product 42 (4.03 g, 88%) as a colorless oil. HPLC $t_R$ 7.67 min.

Example 42

Synthesis of Compound 43 (S)-2-phenylbutylamine

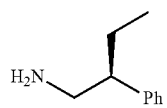

43

A mixture of 42 (4.0 g, 22.8 mmol) and Lindlar's catalyst (1.5 g) in EtOAc (50 mL) was shaken at room temperature under H$_2$ (40 psi) over-night. The mixture was then filtered through a pad of Celite and the filtrate was concentrated under reduced pressure to give the crude product 43 (3.4 g, 100%) as a light yellowish oil. This crude product was used for the conjugate addition reactions without further purification. MS (ESI) 150 (M+1); HPLC $t_R$ 1.84 min.

Example 43

Synthesis of Compound 44 allyl 2-(methoxy(methyl)amino)-2-oxoethylcarbamate

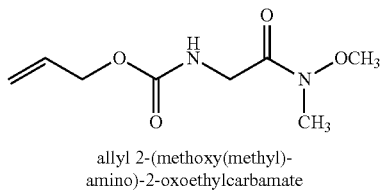

allyl 2-(methoxy(methyl)-amino)-2-oxoethylcarbamate

To Alloc-glycine (1.45 g, 9.1 mmol) in DCM (20 mL) was added BOP reagent (3.3 g, 7.46 mmol) and DIPEA (1.5 mL, 10.7 mmol). After stirring at room temperature for 10 mins, N,O-dimethylhydroxylamine hydrochloride (0.8 g, 8.2 mmol) and DIPEA (1.5 mL, 10.7 mmol) were added. The reaction was stirred at room temperature overnight. The DCM was removed by rotary evaporation and the residue taken up in EtOAc (100 mL). The organic phase was washed with $H_2O$ (3×100 mL), saturated sodium bicarbonate solution (3×50 mL), $H_2O$ (3×50 mL), 1M HCl (3×50 mL), brine (3×50 mL). The organic phase was dried ($MgSO_4$) and the EtOAc removed to give the Weinreb amide 44 as a white solid (0.43 g, 23%).

Alternatively, tert-butyl 2-(methoxy(methyl)amino)-2-oxoethylcarbamate 16 (Boc-Gly Weinreb amide, 1.4 g, 6.4 mmol) in DCM (5 mL) and TFA (3 mL) were stirred at room temperature 1 hr. The solvent was removed under reduced pressure, followed by addition of DCM (20 mL) and then DIPEA until basic. The solution was cooled to 0° C. and allyl chloroformate added (1.4 mL, 13.2 mmol). The reaction was stirred at room temperature overnight. The reaction mixture was neutralised with 1M HCl and extracted with EtOAc. The EtOAc was removed by rotary evaporation and the residue was subjected to column chromatography on silica gel using petroleum spirit:EtOAc (1:1 to 0:1), providing 44 (0.86 g, 66%).

Example 44

Synthesis of Compound 45 allyl 2-oxobut-3-enylcarbamate

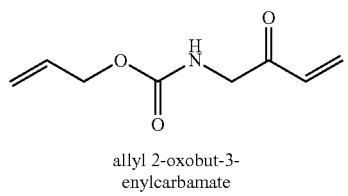

allyl 2-oxobut-3-enylcarbamate

To the Weinreb amide 44 (0.43 g, 2.1 mmol) in DCM (5 mL) at 0° C. was added vinyl magnesium bromide (10 mmol) in THF (10 mL). The reaction was stirred for 2 hrs and monitored by HPLC. The reaction was added to a mixture of ice and 1M HCl (100 mL). The aqueous mixture was extracted with DCM (3×50 mL) and washed with 1M HCl (2×100 mL) and $H_2O$ (3×50 mL). The organic phase was dried ($MgSO_4$) and the volume reduced to 50 mL by rotary evaporation. The α,β-unsaturated ketone 45 was stored and used in solution without further purification.

Example 45

Synthesis of Compound 46 (S)-9-fluorenylmethyl 10-(3,5-dichlorobenzyl)-2,2-dimethyl-4,9,13,16-tetraoxo-3,17-dioxa-5,10,15-triazaiscos-19-en-8-ylcarbamate

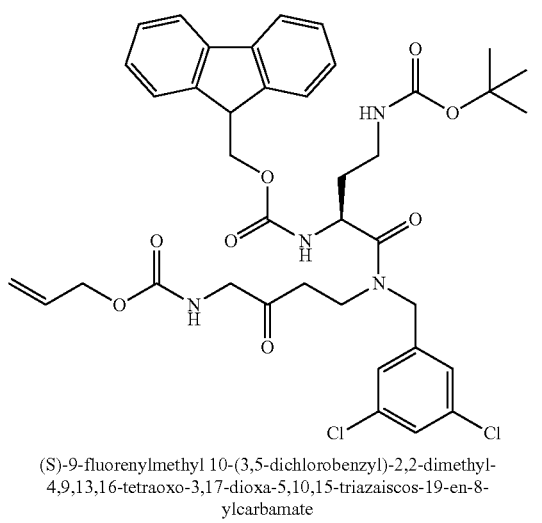

(S)-9-fluorenylmethyl 10-(3,5-dichlorobenzyl)-2,2-dimethyl-4,9,13,16-tetraoxo-3,17-dioxa-5,10,15-triazaiscos-19-en-8-ylcarbamate To 3,5-dichlorobenzylamine (0.49 g, 2.8 mmol) in DCM (5 mL) was added the α,β-unsaturated ketone 45 (2.12 mmol) in DCM (10 mL). After stirring at room temperature for 15 mins, Fmoc-diaminobutyric acid(Boc)-OH (1.35 g, 3.1 mmol) and DIC (0.5 mL, 3.2 mmol) was added. The reaction was stirred at room temperature overnight. The DCM was removed by rotary evaporation and the residue was subjected to column chromatography on silica gel using petroleum spirit:EtOAc (1:1 to 0:1), providing compound 46 (0.48 g, 22%).

Example 46

Synthesis of Compound 47 (3S,5S)-3-(2-tert-butoxycarbonylaminoethyl)-5-(allyloxycarbonylaminomethyl)-1-(3,5-dichlorobenzyll)-1,4-diazepan-2-one

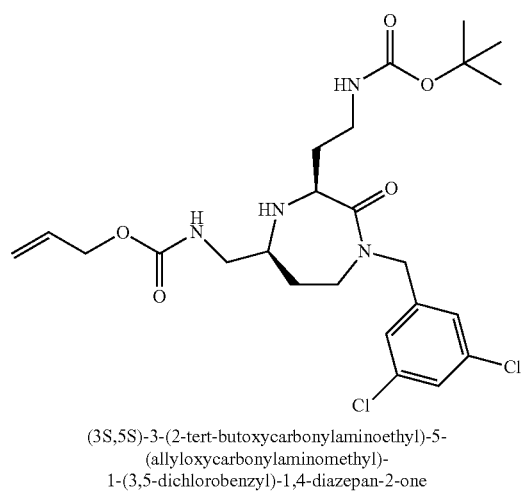

(3S,5S)-3-(2-tert-butoxycarbonylaminoethyl)-5-
(allyloxycarbonylaminomethyl)-
1-(3,5-dichlorobenzyl)-1,4-diazepan-2-one To Compound 46 (0.48 g, 0.63 mmol) in DCM (3 mL) was added diethylamine (1.5 mL). The reaction was stirred at room temperature for 1 hr. The DCM and diethylamine was removed by rotary evaporation. DCM (5 mL), sodium triacetoxyborohydride (0.2 g, 0.94 mmol) was added, and the reaction was stirred overnight at room temperature. The organic phase was washed with saturated sodium bicarbonate solution (25 mL), dried (MgSO$_4$) and the DCM removed to give the cyclised product 47 (0.24 g, 72%).

Example 47

Synthesis of Compound 48 (3S,5S)-3-(2-tert-butoxycarbonylaminoethyl)-5-aminomethyl-1-(3,5-dichlorobenzyl)-1,4-diazepan-2-one

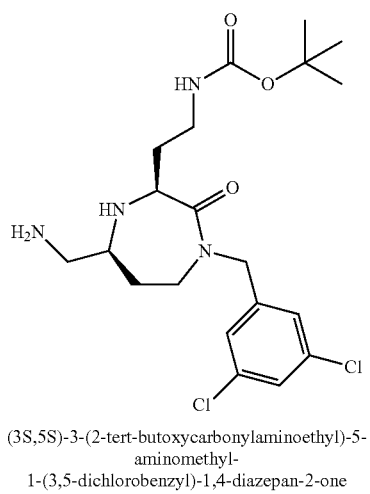

(3S,5S)-3-(2-tert-butoxycarbonylaminoethyl)-5-
aminomethyl-
1-(3,5-dichlorobenzyl)-1,4-diazepan-2-one To the cyclised product 47 (0.24 g, 0.45 mmol) in DCM (3 mL) was added 1,3-dimethylbarbituric acid (13 mg, 0.08 mmol) and palladium tetrakis triphenylphosphine (5 mg). The reaction was evacuated and stirred and room temperature for 1 hr. The DCM was removed under reduced pressure to give the crude product 48 (0.15 g. 75%) which was used in the next reaction without purification.

Example 48

Synthesis of Compound 49 (3S,5S)-3-(2-aminoethyl)-5-((2-naphthoylaminomethyl)-1-(3,5-dichlorobenzyl)-1,4-diazepan-2-one

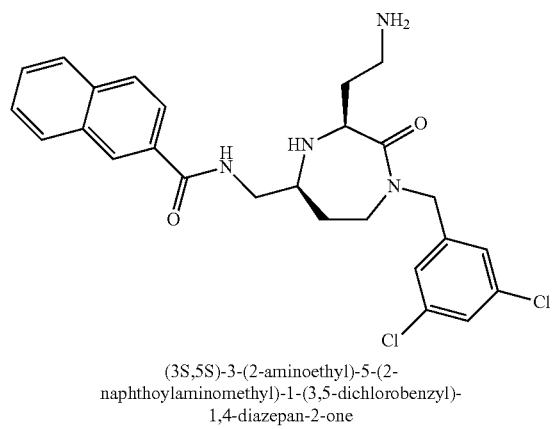

(3S,5S)-3-(2-aminoethyl)-5-(2-
naphthoylaminomethyl)-1-(3,5-dichlorobenzyl)-
1,4-diazepan-2-one To the amine 48 (0.05 mg, 0.11 mmol) in DCM (1 mL) was added DIPEA (0.1 mL, 0.7 mmol), BOP reagent (0.05 mg, 0.11 mmol) and 2-naphthoic acid (0.04 mg, 0.23 mmol). The reaction was stirred at room temperature for 2 hrs. TFA (1 mL) was added and the reaction stirred at room temperature for 2 hrs. Rotary evaporation and preparative HPLC gave 49 (48 mg, 90%). MS (ESI) 499.3 (M+1); HPLC t$_R$ 5.77 min

Example 49

Synthesis of Compound 50 N-(((3S,5S)-1-(2,2-diphenylethyl)-3-(3-guanidinopropyl)-2-oxo-1,4-diazepan-5-yl)methyl)-2-naphthalene-2-sulfonamide

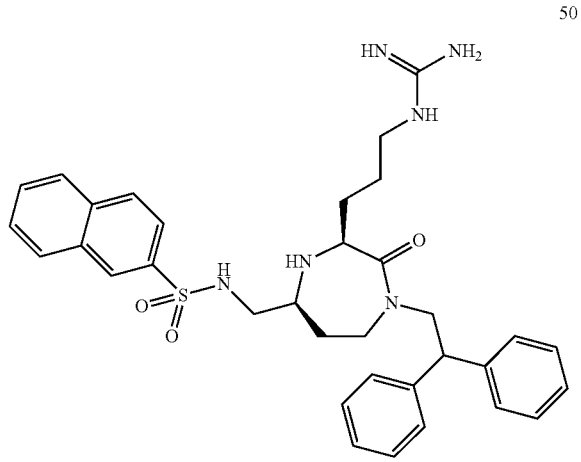

N-(((3S,5S)-1-(2,2-diphenylethyl)-3-(3-
guanidinopropyl)-2-oxo-1,4-diazepan-5-
yl)methyl)naphthalene-2-sulfonamide Prepared from allyl 2-oxobut-3-enylcarbamate 45, Boc-L-Arg(Fmoc)₂-OH and 2,2-diphenylethylamine according the procedures of Examples 46-48, with the following modification: the Boc group was removed with TFA during the deprotection/cyclization procedure of Example 47, rather thane using diethylamine for Fmoc removal. Following Alloc deprotection by the procedure of Example 48, the free amine was dissolved in DCM to which was added naphthalene-2-sulfonyl chloride (10 mg) and DIPEA (20 μL) and the reaction stirred for 2 h at room temperature. Diethylamine (1 mL) was added and stirred overnight to remove the Fmoc protection, and the reaction evaporated to dryness. Preparative HPLC gave title compound 50 (13 mg). MS (ESI) 613.5 (M+1); HPLC $t_R$ 5.89 min.

Example 50

Synthesis of Compound 51 (S)-9-fluorenylmethyl 10-(2-ethylbutyl)-2,2-dimethyl-18-phenyl-4,9,13,16-tetraoxo-3,17-dioxa-5,10,15-triazaoctadecan-8-ylcarbamate

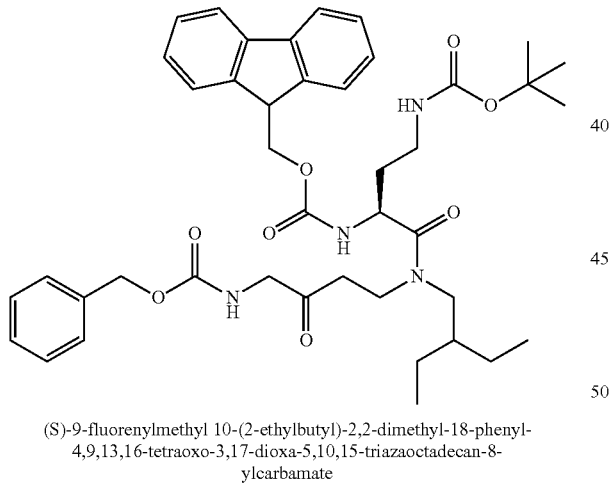

(S)-9-fluorenylmethyl 10-(2-ethylbutyl)-2,2-dimethyl-18-phenyl-4,9,13,16-tetraoxo-3,17-dioxa-5,10,15-triazaoctadecan-8-ylcarbamate To 2-ethylbutylamine (0.15 g, 1.48 mmol) in DCM (10 mL) was added the α,β-unsaturated ketone 27 (1.47 mmol) in DCM (30 mL). After stirring at room temperature for 15 mins, Fmoc-diaminobutyric acid(Boc)-OH (0.95 g, 2.16 mmol) and DIC (0.34 mL, 2.19 mmol) were added. The reaction was stirred at room temperature overnight. The DCM was removed by rotary evaporation and the residue was subjected to column chromatography on silica gel using petroleum spirit:EtOAc (1:1 to 0:1), providing Compound 51 (0.5 g, 46%).

Example 51

Synthesis of Compound 52 (3S,5S)-3-(2-tert-butoxycarbonylaminoethyl)-5-(benzyloxycarbonylaminomethyl)-1-(2-ethylbutyl)-1,4-diazepan-2-one

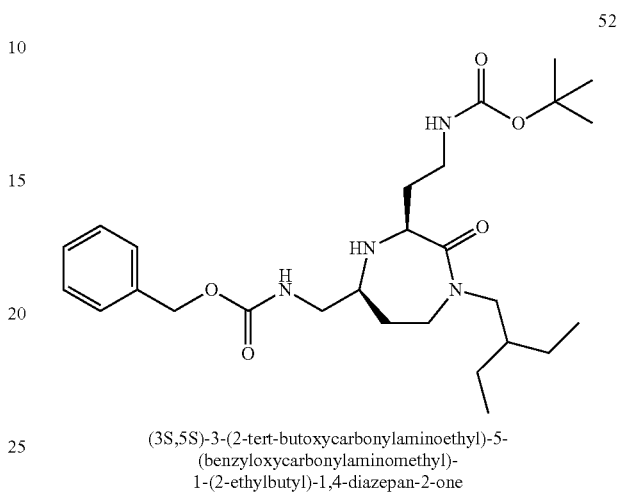

(3S,5S)-3-(2-tert-butoxycarbonylaminoethyl)-5-(benzyloxycarbonylaminomethyl)-1-(2-ethylbutyl)-1,4-diazepan-2-one To Compound 51 (0.5 g, 0.67 mmol) in DCM (3 mL) was added diethylamine (1.5 mL). The reaction was stirred at room temperature for 1 hr. The DCM and diethylamine were removed by rotary evaporation. DCM (5 mL) and sodium triacetoxyborohydride (0.2 g, 0.94 mmol) were added and the reaction was stirred overnight at room temperature. The organic phase was washed with saturated sodium bicarbonate solution (25 mL), dried (MgSO₄) and the DCM removed to give the crude cyclised product 52 (0.4 g).

Example 52

Synthesis of Compound 53 (3S,5S)-3-(2-tert-butoxycarbonylaminoethyl)-5-(aminomethyl)-1-(2-ethylbutyl)-1,4-diazepan-2-one

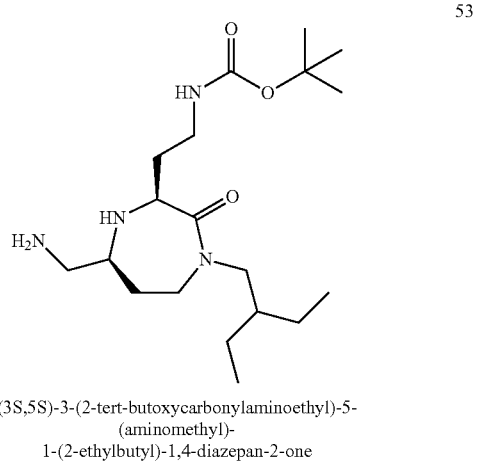 [SMILES: CCC(CC)CN1CC[C@@H](CN)N[C@@H](CCNC(=O)OC(C)(C)C)C1=O]

(3S,5S)-3-(2-tert-butoxycarbonylaminoethyl)-5-(aminomethyl)-1-(2-ethylbutyl)-1,4-diazepan-2-one To the cyclised product 52 (0.4 g) in methanol (5 mL) was added catalytic Pd/C. The reaction was stirred under a hydrogen atmosphere overnight. The reaction mixture was filtered through Celite and the methanol removed by rotary evaporation to give the amine 53 (0.17 g, 68% from 51).

Example 53

Synthesis of Compound 54 N-(((3S,5S)-3-(2-aminoethyl)-1-(2-ethylbutyl)-2-oxo-1,4-diazepan-5-yl)methyl)-2-naphthamide

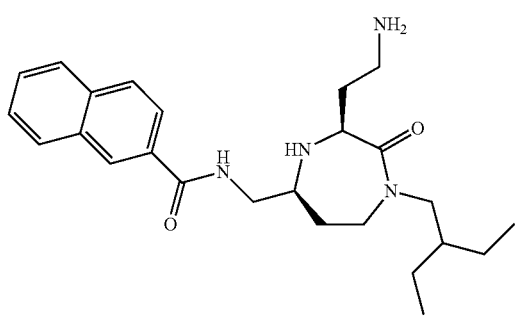

N-(((3S,5S)-3-(2-aminoethyl)-1-(2-ethylbutyl)-2-oxo-1,4-diazepan-5-yl)methyl)-2-naphthamide To the amine 53 (0.030 g, 0.08 mmol) in DCM (1 mL) was added DIPEA (0.1 mL, 0.7 mmol), BOP reagent (0.03 g, 0.07 mmol) and 2-naphthoic acid (0.025 g, 0.14 mmol). The reaction was stirred at room temperature for 2 hrs. TFA (1 mL) was added and the reaction stirred at room temperature for 2 hrs. Rotary evaporation and preparative HPLC gave Compound 54 (23 mg, 68%). MS (ESI) 425.7 (M+1); HPLC $t_R$ 5.27

Example 54

Synthesis of Compound 55 (3S,5S)-3-[2-(piperidin-1-yl)ethyl]-5-(benzyloxycarbonylaminomethyl)-1-(2-ethylbutyl)-1,4-diazepan-2-one

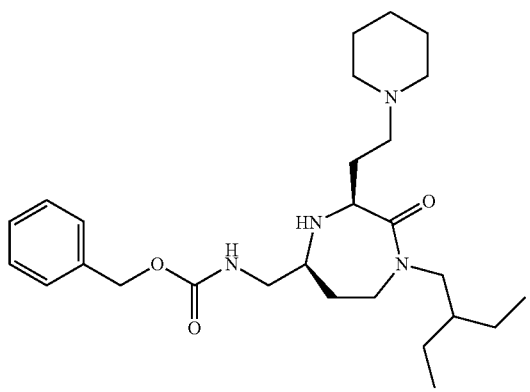

(3S,5S)-3-[2-(piperdin-1-yl)ethyl]-5-(benzyloxycarbonylaminomethyl)-1-(2-ethylbutyl)-1,4-diazepan-2-one To Compound 54 (0.25 g, 0.5 mmol) in DCM (3 mL) was added TFA (1.5 mL), with the solution stirred at room temperature for 1 hr. DCM (20 mL) was added and the solution was washed with saturated sodium bicarbonate solution (20 mL), dried over MgSO$_4$ and evaporated to give the crude amine (0.16 g). To this was added DMF (0.25 mL), potassium carbonate (10 mg) and 1,5-dibromopentane (0.35 mL, 2.5 mmol). The reaction mixture was stirred at room temperature for 1.5 hrs, after which DCM (20 mL) was added, the organic layer washed with saturated sodium bicarbonate solution (20 mL) and H$_2$O (20 mL), dried (MgSO$_4$) and evaporated to give crude 55, which was used in the next reaction without purification.

Example 55

Synthesis of Compound 56 (3S,5S)-3-[2-(piperidin-1-yl)ethyl]-5-aminomethyl-1-(2-ethylbutyl)-1,4-diazepan-2-one

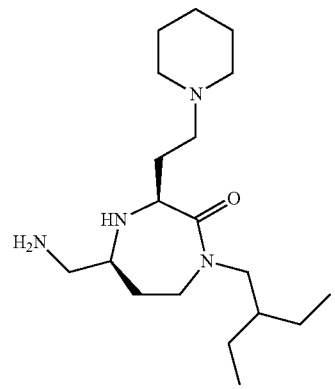

(3S,5S)-3-[2-(piperdin-1-yl)ethyl]-5-aminomethyl-1-(2-ethylbutyl)-1,4-diazepan-2-one To the cyclised product 55 (0.4 g) in methanol (5 mL) was added catalytic Pd/C. The reaction was stirred under a hydrogen atmosphere overnight. The reaction mixture was filtered through Celite and the methanol removed by rotary evaporation to give the amine 56 (0.12 g).

Example 56

Synthesis of Boc-L-Glu(piperidine)-OH 57 (S)-2-(tert-butoxycarbonylamino)-5-oxo-5-(piperidin-1-yl)pentanoic acid

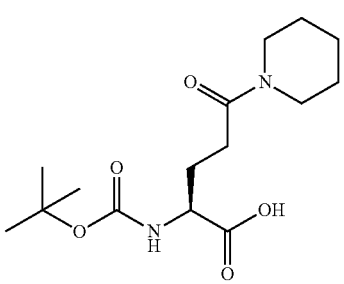

(S)-2-(tert-butyoxycarbonylamino)-5-oxo-5-(piperidin-1-yl)pentanoic acid

HATU (2.5 g) and DIPEA (1.5 mL) was added to Boc-L-Glu(OH)—OBn (2.0 g) in DCM (50 mL), stirred for 10 min, then piperidine (0.7 mL) was added and the reaction stirred overnight at room temperature. The reaction was washed with sodium bibicarbonate solution (2×), saturated NH₄Cl (2×), brine (2×), dried over MgSO₄, filtered, and evaporated to give 2.9 g of Boc-L-Glu(piperidine)-OBn. The benzyl ester (0.6 g) was dissolved in EtOH (15 mL) with catalytic Pd/C and hydrogenated for 1 h, filtered over Celite, and the EtOH evaporated by rotary evaporation to give 0.51 g of 57.

Example 57

Synthesis of Compound 58 (3S,5S)-3-(2-tert-butoxycarbonylaminopropyl)-5-[benzyloxycarbonyl(methylamino)methyl]-1-(2,2 diphenylethyl)-1,4-diazepan-2-one

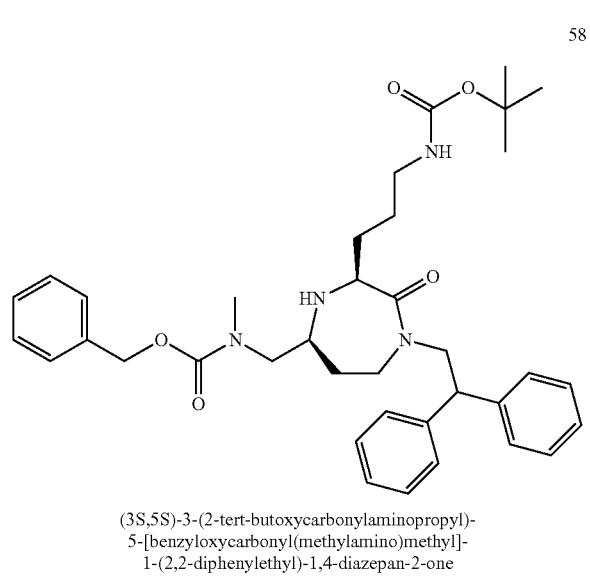 [SMILES: CN(C[C@@H]1CCN(CC(c2ccccc2)c2ccccc2)C(=O)[C@H](CCCNC(=O)OC(C)(C)C)N1)C(=O)OCc1ccccc1]

(3S,5S)-3-(2-tert-butoxycarbonylaminopropyl)-5-[benzyloxycarbonyl(methylamino)methyl]-1-(2,2-diphenylethyl)-1,4-diazepan-2-one Prepared from Cbz-Sar, 2,2-diphenylethylamine and Fmoc-L-Orn(Boc) according to the procedures of Examples 27-30.

Example 58

Synthesis of Compound 59 (3S,5S)-3-(2-tert-butoxycarbonylaminopropyl)-5-(methylamino)methyl-1-(2,2-diphenylethyl)-1,4 diazepan-2-one

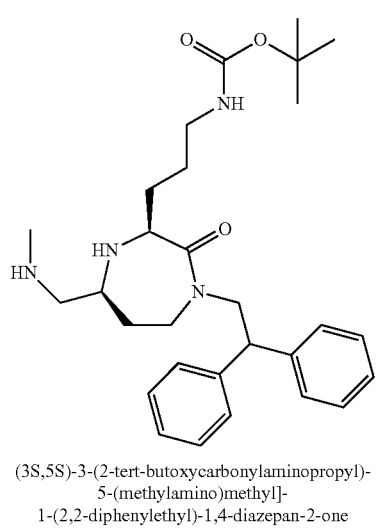

(3S,5S)-3-(2-tert-butoxycarbonylaminopropyl)-5-(methylamino)methyl]-1-(2,2-diphenylethyl)-1,4-diazepan-2-one The cyclised product 58 (1.9 g) was dissolved in methanol (10 mL) with catalytic Pd/C and hydrogenated under a hydrogen atmosphere (40 psi) overnight. The reaction mixture was filtered through Celite and the methanol removed by rotary evaporation to give the amine 59 (1.86 g, 97%).

Example 59

Synthesis of Compound 60 N-(((3S,5S)-3-(3-aminopropyl)-1-(2,2-diphenylethyl)-2-oxo-1,4-diazepan-5-yl)methyl)-6-bromo-N-methyl-2-naphthamide

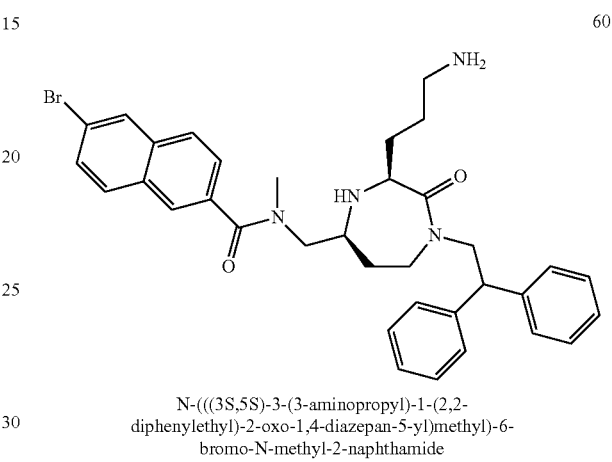

N-(((3S,5S)-3-(3-aminopropyl)-1-(2,2-diphenylethyl)-2-oxo-1,4-diazepan-5-yl)methyl)-6-bromo-N-methyl-2-naphthamide The amine 59 was coupled with 6-bromo-2-naphthoic acid then deprotected with TFA according to Example 31. Rotary evaporation and preparative HPLC gave 60 (7.8 mg). MS (ESI) 629.4 (M+1); HPLC $t_R$ 6.27 min.

Example 60

Synthesis of Compound 61 (3S,5S)-3-(tert-butoxycarbonylaminopropyl)-5-(6-bromo-2-naphthamidomethyl)-1-(2,2-diphenylethyl)-1,4-diazepan-2-one

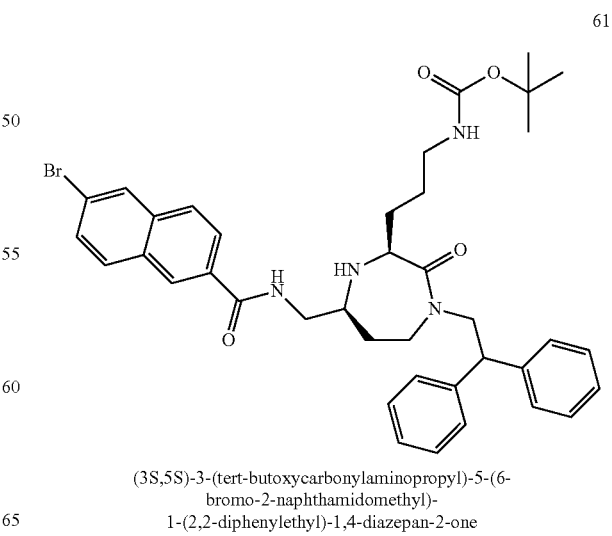

(3S,5S)-3-(tert-butoxycarbonylaminopropyl)-5-(6-bromo-2-naphthamidomethyl)-1-(2,2-diphenylethyl)-1,4-diazepan-2-one Prepared from 2,2-diphenylethylamine, Fmoc-L-Orn(Boc) and 6-bromo-2-naphthoic acid according to the procedures of Examples 28-31, without the TFA deprotection step of Example 31.

Example 61

Synthesis of Compound 62 N-(((3S,5S)-3-(3-aminopropyl)-1-(2,2-diphenylethyl)-4-methyl-2-oxo-1,4-diazepan-5-yl)methyl)-6-bromo-2-naphthamide

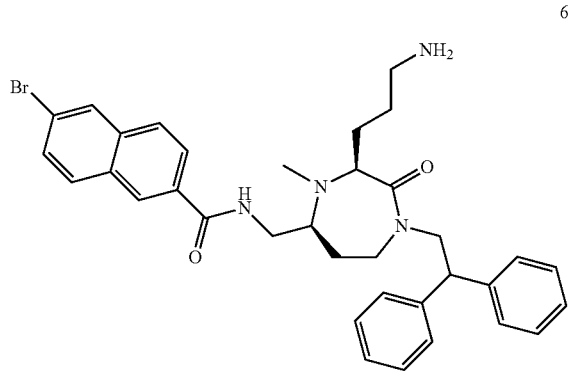

N-(((3S,5S)-3-(3-aminopropyl)-1-(2,2-diphenylethyl)-4-methyl-2-oxo-1,4-diazepan-5-yl)methyl)-6-bromo-2-naphthamide Compound 61 (20.8 mg) was dissolved in DMF (1 mL) and treated with methyl iodide (6 μL) at room temperature for 1 week. Additional methyl iodide (0.5 mL) and K$_2$CO$_3$ were added and the reaction left at room temperature for an additional 2 days. TFA (2 mL) was added and the reaction stirred at room temperature for 2 h. Rotary evaporation followed by evaporation under high vacuum then preparative HPLC gave 62 (8.5 mg). MS (ESI) 629.3 (M+1); HPLC t$_R$ 6.22 min.

Example 62

Synthesis of Compound 63 N-(((3S,5S)-3-(3-aminopropyl)-1-(2,2-diphenylethyl)-2-oxo-1,4-diazepan-5-yl)methyl)-2-naphthamide

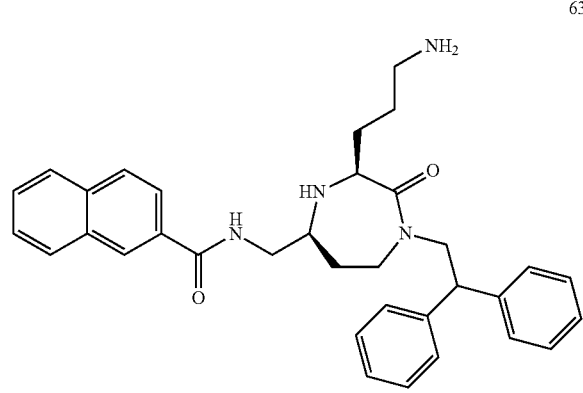

N-(((3S,5S)-3-(3-aminopropyl)-1-(2,2-diphenylethyl)-2-oxo-1,4-diazepan-5-yl)methyl)-2-naphthamide Obtained from 9,2,2-diphenylethylamine and Fmoc-L-Orn(Boc) according to Examples 10-12. The Boc group was removed under standard conditions to give the free amine. MS (ESI) 535 (M+1); HPLC t$_R$ 5.78 min

Example 63

Synthesis of Compound 64 N-(((3S,5S)-1-(2,2-diphenylethyl)-2-oxo-3-(3-(piperidin-1-yl)propyl)-1,4-diazepan-5-yl)methyl)-2-naphthamide

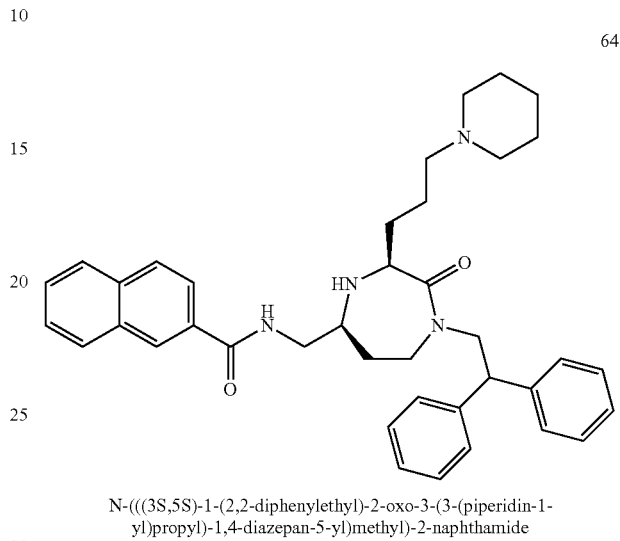

N-(((3S,5S)-1-(2,2-diphenylethyl)-2-oxo-3-(3-(piperidin-1-yl)propyl)-1,4-diazepan-5-yl)methyl)-2-naphthamide The amine 63 (0.79 g, 1.48 mmol), 1,5-dibromopentane (0.2 mL, 1.48 mmol) and K$_2$CO$_3$ (0.79 g) in DMF (11 mL) was stirred at room temperature for 4 h. The resulting mixture was diluted with ethylacetate (30 mL), washed with H$_2$O (5×30 mL), brine (10 mL) and dried over MgSO$_4$. Purification by preparative HPLC yielded 64 (0.23 g, 25%) MS (ESI) 603.3 (M+1); HPLC t$_R$ 6.04 min

Example 64

Synthesis of Compound 65 N-(((3S,5S)-1-(2,2-diphenylethyl)-3-(3-(isopropylamino)propyl)-2-oxo-1,4-diazepan-5-yl)methyl)-2-naphthamide

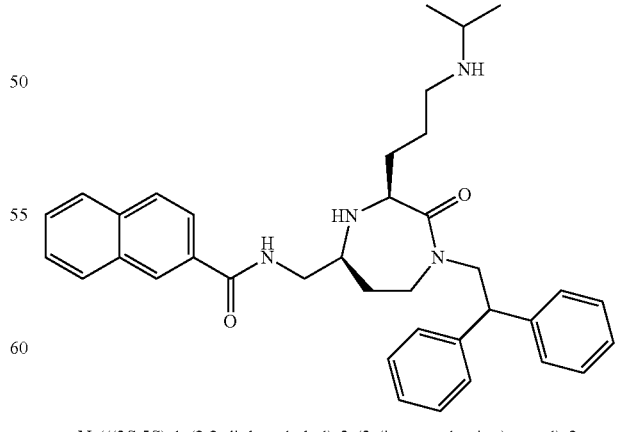

N-(((3S,5S)-1-(2,2-diphenylethyl)-3-(3-(isopropylamino)propyl)-2-oxo-1,4-diazepan-5-yl)methyl)-2-naphthamide To a stirred mixture of the amine 63 (11 mg, 0.02 mmol), acetone (2 mL) and MgSO$_4$ (50 mg) in DCM (5 mL) was added sodium triacetoxyborohydride (8.5 mg, 0.04 mmol) at room temperature. Stirring continued for 2 h, the mixture was concentrated, re-dissolved in EtOAc (5 mL), washed with saturated aqueous NaHCO$_3$ solution (10 mL) and brine (10 mL), dried over MgSO$_4$ and concentrated under reduced pressure. Purification by preparative HPLC yielded 65 (9.5 mg, 80%). MS (ESI) 577.2 (M+1); HPLC $t_R$ 5.97 min.

Example 65

Synthesis of Compound 66 tert-butyl(methylamino) (methylthio)methylenecarbamate

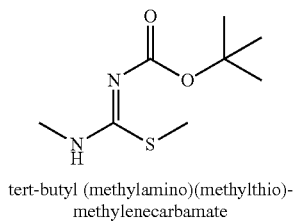

tert-butyl (methylamino)(methylthio)- methylenecarbamate

DIAD (2.7 mL, 13.8 mmol) was added to a stirred mixture of thiopseudourea (2.0 g, 6.9 mmol), PPh$_3$ (3.6 g, 13.8 mmol), and MeOH (0.55 mL, 13.8 mmol) in dry THF (5 mL) at 0° C. under nitrogen. Stirring continued at 0° C. for 3 h then at room temperature for 16 h. The solvent was removed under reduced pressure and the resulting residue was re-dissolved in EtOAc, washed with saturated aqueous NaHCO$_3$ solution (20 mL) and brine (20 mL), and dried over MgSO$_4$. Purification by silica gel chromatography using 20% EtOAc in petroleum ether as eluent gave 66 (1.63 g, 78%) as a colourless oil. MS (ESI) 305 (M+1); HPLC $t_R$ 7.97 min.

Example 66

Synthesis of Compound 67 N-(((3S,5S)-1-(2,2-diphenylethyl)-3-(3-(3-methylguanidino)propyl)-2-oxo-1,4-diazepan-5-yl)methyl)-2-naphthamide

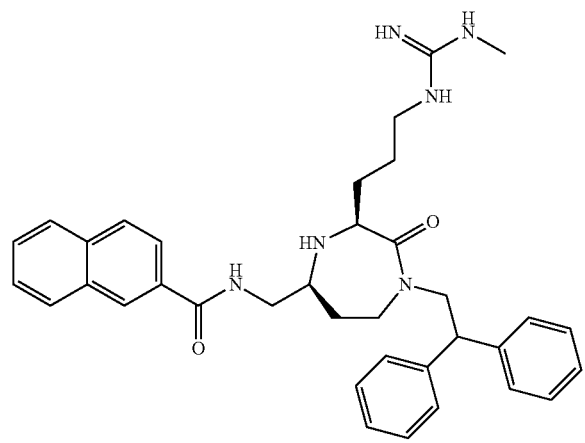

N-(((3S,5S)-1-(2,2-diphenylethyl)-3-(3-(3-methylguanidino)propyl)-2-oxo-1,4-diazepan-5-yl)methyl)-2-naphthamide A mixture of Compound 63 (10 mg, 0.019 mmol), guanylating agent 66 (56.9 mg, 0.19 mmol) and DIPEA (6.6 µL, 0.038 mmol) in DCM (5 mL) was stirred at room temperature for 16 h. TFA (5 mL) was added, and the resulting mixture was stirred at room temperature for 30 min. Solvent was removed under reduced pressure, and the crude product was purified by preparative HPLC to give 67 (0.53 mg, 4.7%) as a white solid. MS (ESI) 591.3 (M+1); HPLC $t_R$ 5.94 min Example 67

Synthesis of Compound 68 (S)-9-fluorenylmethyl 1-phenyl-10-(2,2-diphenylethyl)-18,18-dimethyl-4,9,13,16-tetraoxo-2,17-dioxa-4,10,15-triazanonadecan-8-ylcarbamate

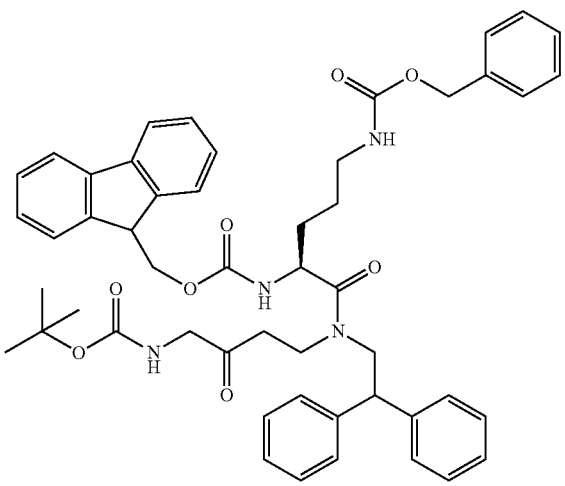

(S)-9-fluorenylmethyl 1-phenyl-10-(2,2-diphenylethyl)-18,18-dimethyl-4,9,13,16-tetraoxo-2,17-dioxa-4,10,15-triazanonadecan-8-ylcarbamate To a stirred mixture of Fmoc-L-Orn(Cbz)-OH (1.78 g, 3.65 mmol), DIPEA (0.64 mL, 3.65 mmol) and HATU (1.39 g, 3.65 mmol) in DCM (10 mL) was added a solution of amine 17 at room temperature. Stirring continued for 3 h, the reaction mixture was washed with saturated NaHCO$_3$ aqueous solution (20 mL) and brine (20 mL), and dried over MgSO$_4$. The solvent was removed under reduced pressure, with the crude 68 used in the next step without further purification. MS (ESI) 853 (M+1); HPLC $t_R$ 9.90 min.

Example 68

Synthesis of Compound 69 (S)-(9H-fluoren-9-yl)methyl 7-((4-(tert-butoxycarbonylamino)-3-oxobutyl)(2,2-diphenylethyl)carbamoyl)-3-methyl-1,3-diazepane-1-carboxylate

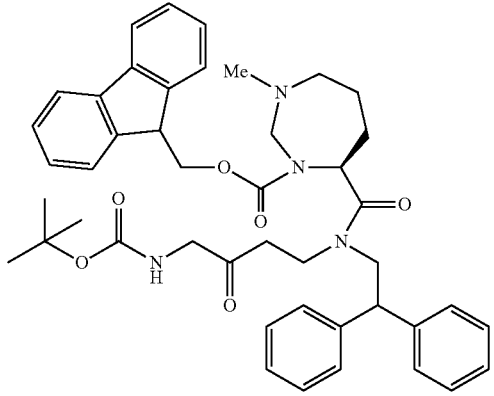

(S)-(9H-fluoren-9-yl)methyl 7-((4-(tert-butoxycarbonylamino)-3-oxobutyl)(2,2-diphenylethyl)carbamoyl)-3-methyl-1,3-dizaepane-1-carboxylate A mixture of 68 (136 mg, 0.159 mmol) and Pd/C (20 mg) in ethanol (5 mL) was shaken under $H_2$ at 30 psi for 16 h, then filtered, concentrated under reduced pressure to give the crude amine (90 mg, 78%). The amine (90 mg, 0.125 mmol) was treated with excess formaldehyde solution in $H_2O$ (37 mmol) in MeOH (5 mL) followed by sodium triacetoxyborohydride (23.5 mg, 0.375 mmol). After 1 h, the reaction mixture was washed with saturated $NaHCO_3$ aqueous solution (10 mL) and brine (10 mL), dried over $MgSO_4$, filtered and concentrated. The crude material was used in the next step without further purification. MS (ESI) 745 (M+1); HPLC; HPLC $t_R$ 7.83 min.

Example 69

Synthesis of Compound 70 (S)-(9H-fluoren-9-yl)methyl 7-((4-(2-naphthamido)-3-oxobutyl)(2,2-diphenylethyl)-carbamoyl)-3-methyl-1,3-diazepane-1-carboxylate

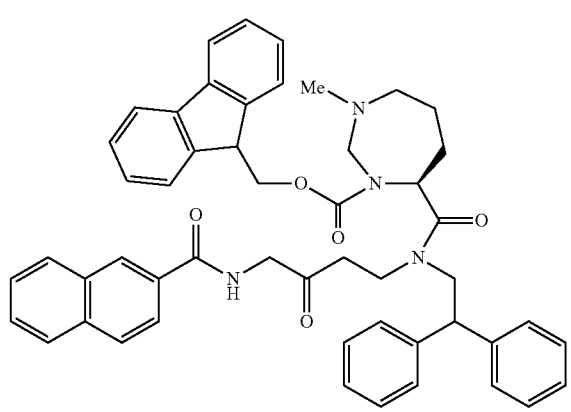

(S)-(9H-fluoren-9-yl)methyl 7-((4-(2-naphthamido)-3-oxobutyl)(2,2-diphenylethyl)carbamoyl)-3-methyl-1,3-diazepane-1-carboxylate Compound 69 (8 mg, 0.011 mmol) was treated with 1:1 v/v trifluoacetic acid/DCM mixture (2 mL) for 30 min at room temperature. The mixture was concentrated under reduced pressure, re-dissolved in DCM (5 mL), washed with saturated $NaHCO_3$ aqueous solution (5 mL) and brine (5 mL), dried over $MgSO_4$ and filtered. The filtrate was then treated with a mixture of 2-naphthoic acid (1.8 mg, 0.011 mmol), DIPEA (5.7 µL, 0.033 mmol) and BOP (4.8 mg, 0.011 mmol) in DCM (1 mL) with stirring at room temperature. After 3 h, the reaction mixture was washed with saturated $NaHCO_3$ aqueous solution (10 mL) and brine (10 mL), dried over $MgSO_4$, filtered and concentrated. The crude material was used in the next step without further purification. MS (ESI) 799 (M+1); HPLC $t_R$ 7.90 min.

Example 70

Synthesis of Compound 71 N-(((3S,5S)-1-(2,2-diphenylethyl)-3-(3-(methylamino)propyl)-2-oxo-1,4-diazepan-5-yl)methyl)-2-naphthamide

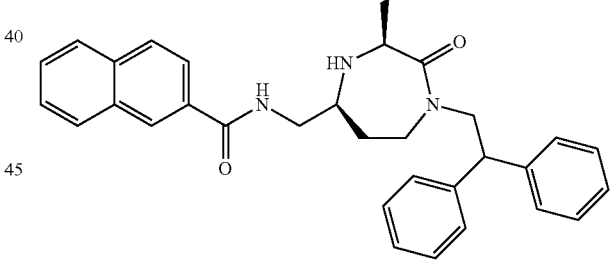

N-(((3S,5S)-1-(2,2-diphenylethyl)-3-(3-(methylamino)propyl)-2-oxo-1,4-diazepan-5-yl)methyl)-2-naphthamide To a stirred solution of 70 (0.011 mmol) in DCM (5 mL) was added diethylamine (5 mL) at room temperature. The reaction was stirred for 1 h, then concentrated under reduced pressure. The residue was re-dissolved in DCM (5 mL) followed by addition sodium triacetoxyborohydride (5 mg, 0.08 mmol) at room temperature. Stirring continued for 1 h, with the resulting mixture washed with saturated $NaHCO_3$ aqueous solution (10 mL) and brine (10 mL), dried over $MgSO_4$, filtered and concentrated. Purification by preparative HPLC yielded 71 (0.21 mg) as a white solid. MS (ESI) 549.3 (M+1); HPLC $t_R$ 5.93 min

Example 71

Synthesis of Compound 72 (S)-2-(allyloxycarbonylamino)-3-(naphthalen-2-yl)propanoic acid

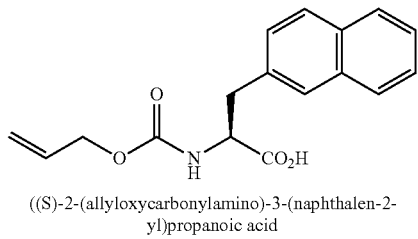

((S)-2-(allyloxycarbonylamino)-3-(naphthalen-2-yl)propanoic acid

To a stirred mixture of L-3-(2-naphthyl)alanine hydrochloride (5.0 g, 19.8 mmol), $Na_2CO_3$ (7.3 g, 69.3 mmol) and 1,4-dioxane (30 mL) in $H_2O$ (50 mL) was added allylchloroformate (2.1 mL, 19.8 mmol) at 0° C. The resulting mixture was stirred for 16 h then concentrated under reduced pressure. The residue was diluted with ethylacetate (50 mL), and at 0° C. acidified to pH 2. The aqueous phase was extracted with ethylacetate (3×20 mL), the combined organic phase was washed with $H_2O$ (50 mL) and brine (20 mL), dried over $MgSO_4$, filtered and concentrated under reduced pressure to give 72 as a colourless oil (5.8 g, 97%), which was used in the next step without further purification. HPLC $t_R$ 6.60 min.

Example 72

Synthesis of Compound 73 (S)-allyl 1-(methoxy(methyl)amino)-3-(naphthalen-2-yl)-1-oxopropan-2-ylcarbamate

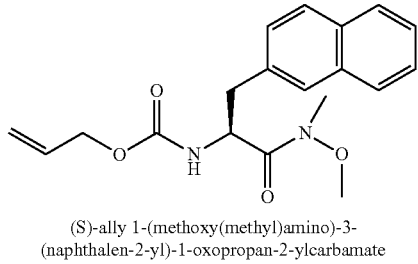

(S)-ally 1-(methoxy(methyl)amino)-3-(naphthalen-2-yl)-1-oxopropan-2-ylcarbamate

To a stirred mixture of the acid 72 (5.84 g, 19.5 mmol), DIPEA (3.7 mL, 2.09 mmol) and BOP (8.63 g, 19.5 mmol) in DCM (10 mL) was added a pre-mixed solution of N,O-dimethylhydroxylamine hydrochloride (1.9 g, 19.5 mmol) and DIPEA (7.3 mL, 41.6 mmol) in DCM (10 mL) at room temperature. Stirring continued for 16 h the reaction mixture was washed with 1N HCl (3×60 mL), $H_2O$ (3×60 mL), saturated $NaHCO_3$ aqueous solution (3×60 mL) and brine (60 mL), dried over $MgSO_4$. Purification by silica gel chromatography using 20% ethylacetate in petroleum ether as eluent gave 73 (4.83 g, 71%) as a colourless oil. MS (ESI) 343 (M+1); HPLC $t_R$ 7.07 min.

Example 73

Synthesis of Compound 74 (S)-allyl 1-(naphthalen-2-yl)-3-oxopent-4-en-2-ylcarbamate

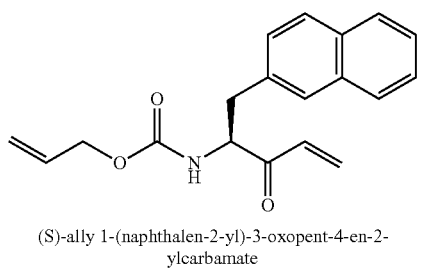

(S)-ally 1-(naphthalen-2-yl)-3-oxopent-4-en-2-ylcarbamate

At 0° C. a solution of vinylmagnesium bromide in THF (11.5 mL, 1 M) was added in one portion to Weinreb amide 73 (1.58 g, 4.62 mmol) under nitrogen with stirring. The resulting mixture was allowed to stir for 2 h, and poured into a 1N HCl/ice mixture (50 mL). The aqueous mixture was extracted with DCM (3×20 mL), the combined DCM extract was washed with 1N HCl (50 mL), saturated $NaHCO_3$ aqueous solution (50 mL) and brine (20 mL), dried over $MgSO_4$. Solvent was removed under reduced pressure producing the product 74 (1.14 g, 80%), which was used in the next step without further purification. MS (ESI) 310 (M+1); HPLC $t_R$ 7.51 min.

Example 74

Synthesis of Compound 75 (S)-allyl 5-(2,2-diphenylethylamino)-1-(naphthalen-2-yl)-3-oxopentan-2-ylcarbamate

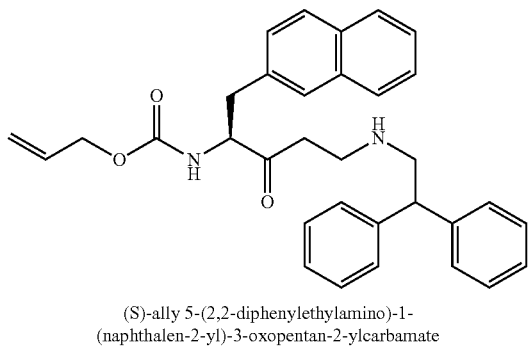

(S)-ally 5-(2,2-diphenylethylamino)-1-(naphthalen-2-yl)-3-oxopentan-2-ylcarbamate To a stirred solution of 2,2-diphenylethylamine (0.45 g, 2.3 mmol) in DCM (55 mL) was added the vinyl ketone 74 (0.71 g, 2.3 mmol) in one portion. Stirring continued for 2 h, with the reaction mixture used in the next step without purification. MS (ESI) 507 (M+1); HPLC $t_R$ 7.22 min.

Example 75

Synthesis of Compound 76 (S)-allyl 5-(N-(Boc-L-Arg(Cbz)₂)2,2-diphenylethylamino)-1-(naphthalen-2-yl)-3-oxopentan-2-ylcarbamate

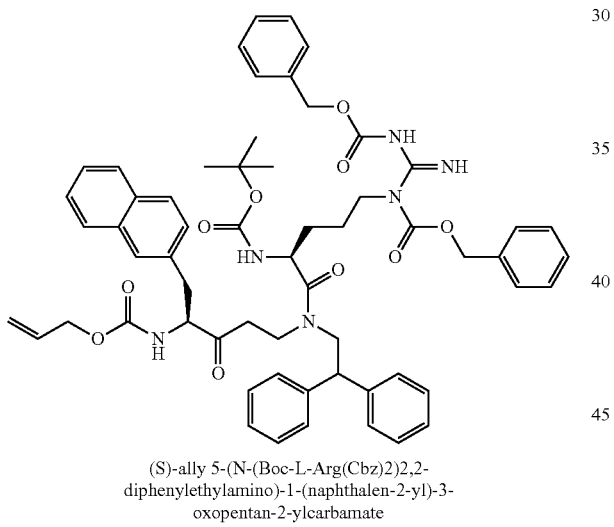

(S)-ally 5-(N-(Boc-L-Arg(Cbz)2)2,2-diphenylethylamino)-1-(naphthalen-2-yl)-3-oxopentan-2-ylcarbamate To a stirred solution of the amine adduct 75 (2.3 mmol) was added a mixture of Boc-Arg(Cbz)₂-OH (1.25 g, 2.3 mmol), DIPEA (0.8 mL, 4.6 mmol) and HATU (0.87 g, 2.3 mmol) in DCM (15 mL) at room temperature. Stirring continued for 16 h, after which the reaction mixture was washed with saturated NaHCO₃ aqueous solution (3×20 mL) and brine (10 mL) then dried over MgSO₄. Purification by silica gel chromatography using 20% ethylacetate in petroleum ether as eluent gave 76 as a colourless oil (708 mg, 30% over 3 steps). MS (ESI) 1031 (M+1); HPLC $t_R$ 10.80 min.

Example 76

Synthesis of Compound 77 allyl(S)-1-((3S,5RS)-1-(2,2-diphenylethyl)-3-(bis Cbz 3-guanidinopropyl)-2-oxo-1,4-diazepan-5-yl)-2-(naphthalen-2-yl)ethyl-carbamate

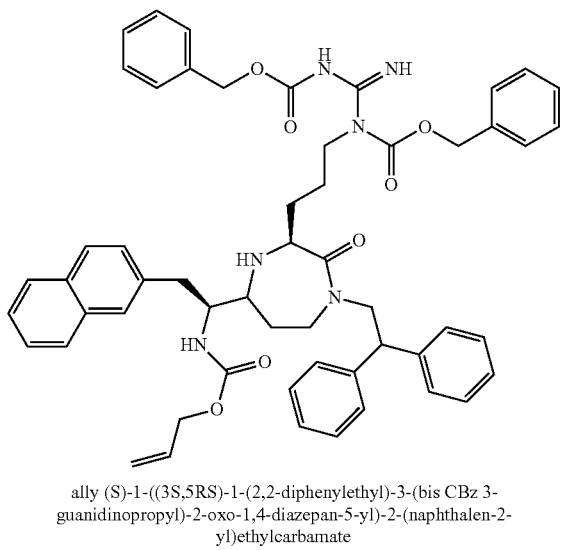

ally (S)-1-((3S,5RS)-1-(2,2-diphenylethyl)-3-(bis CBz 3-guanidinopropyl)-2-oxo-1,4-diazepan-5-yl)-2-(naphthalen-2-yl)ethylcarbamate To a stirred solution of acyclic intermediate 76 (0.48 g, 0.47 mmol) in DCM (5 mL) was added TFA (5 mL) at room temperature. Stirring continued for 30 min, after which the mixture was diluted with DCM (20 mL) then washed with saturated NaHCO₃ aqueous solution (3×20 mL) and brine (10 mL), and dried over MgSO₄. To the resulting solution was added sodium triacetoxyborohydride (0.2 g, 0.94 mmol) with stirring at room temperature, after 30 min the mixture was washed with saturated NaHCO₃ aqueous solution (3×20 mL) and brine (10 mL), then dried over MgSO₄. The crude 77, a mixture of diastereomers at the diazepan-2-one C5, was used in the next step without further purification. MS (ESI) 915 (M+1)

Example 77

Synthesis of Compound 78 bis(Cbz) 1-(3-((2S,7RS)-7-((S)-1-amino-2-(naphthalen-2-yl)ethyl)-4-(2,2-diphenylethyl)-3-oxo-1,4-diazepan-2-yl)propyl)guanidine

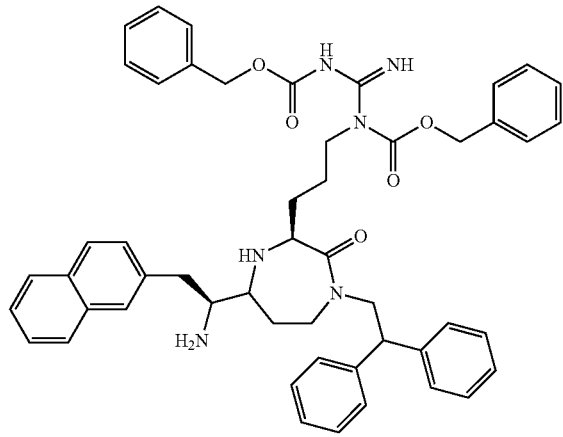

bis (Cbz) 1-(3-((2S,7RS)-7-((S)-1-amino-2-(naphthalen-2-yl)ethyl)-4-(2,2-diphenylethyl)-3-oxo-1,4-diazepan-2-yl)propyl)guanidine A mixture of compound 77 (36 mg, 0.039 mmol), 1,3-dimethylbarbituric acid (7.4 mg, 0.047 mmol) and Pd(PPh$_3$)$_4$ in DCM (5 mL) was stirred at room temperature under vacuum for 4 h. The resulting mixture was used in the next step without further purification. MS (ESI) 832 (M+1)

Example 78

Synthesis of Compounds 79 and 80 N—((S)-1-((3S,5S)-1-(2,2-diphenylethyl)-3-(3-guanidinopropyl)-2-oxo-1,4-diazepan-5-yl)-2-(naphthalen-2-yl)ethyl)acetamide and N—((S)-1-((3S,5R)-1-(2,2-diphenylethyl)-3-(3-guanidinopropyl)-2-oxo-1,4-diazepan-5-yl)-2-(naphthalen-2-yl)ethyl)acetamide

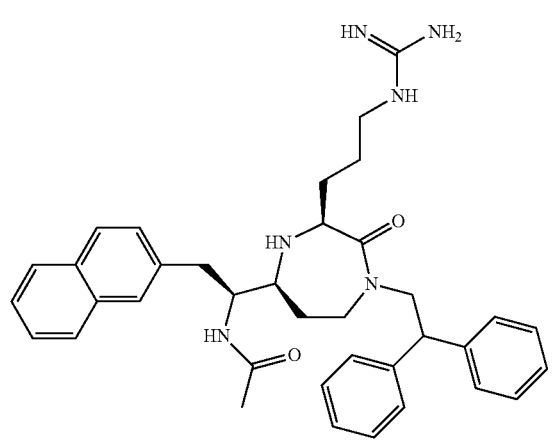

N-((S)-1(3S,5S)-1-(2,2-diphenylethyl)-3-(3-guanidinopropyl)-2-oxo-1,4-diazepan-5-yl)-2-(naphthalen-2-yl)ethyl)acetamide

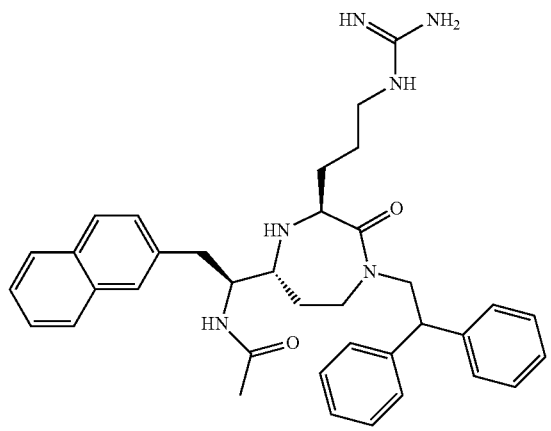

N-((S)-1-(3S,5R)-1-(2,2-diphenylethyl)-3-(3-guanidinopropyl)-2-oxo-1,4-diazepan-5-yl)-2-(naphthalen-2-yl)ethyl)acetamide A solution of the amine 78 (0.09 mmol) in DCM (5 mL) was treated with acetic anhydride (8.6 µL, 0.09 mmol) with stirring at room temperature. After 3 h the mixture was concentrated, re-dissolved in EtOAc, washed with saturated NaHCO$_3$ aqueous solution (10 mL) and brine (10 mL), dried over MgSO$_4$, then concentrated under reduced pressure. The residue was dissolved in MeOH (10 mL), Pd/C (5 mg) was added, and the solution shaken under H$_2$ at 20 psi for 16 h. The reaction was filtered, concentrated and purified by preparative HPLC to give the preferred diastereomer 79 (3 mg) and the less preferred diastereomer 80 (6 mg) as white solids.

79: MS (ESI) 606.4 (M+1); HPLC $t_R$ 6.033 min
80: MS (ESI) 606.3 (M+1); HPLC $t_R$ 6.046 min

Example 79

Synthesis of Compounds 81 and 82 (S)-2-acetamido-N—((S)-1-((3S,5S)-1-(2,2-diphenylethyl)-3-(3-guanidinopropyl)-2-oxo-1,4-diazepan-5-yl)-2-(naphthalen-2-yl)ethyl)-3-(1H-imidazol-5-yl)propanamide and (S)-2-acetamido-N—((S)-1-((3S,5R)-1-(2,2-diphenylethyl)-3-(3-guanidinopropyl)-2-oxo-1,4-diazepan-5-yl)-2-(naphthalen-2-yl)ethyl)-3-(1H-imidazol-5-yl)propanamide

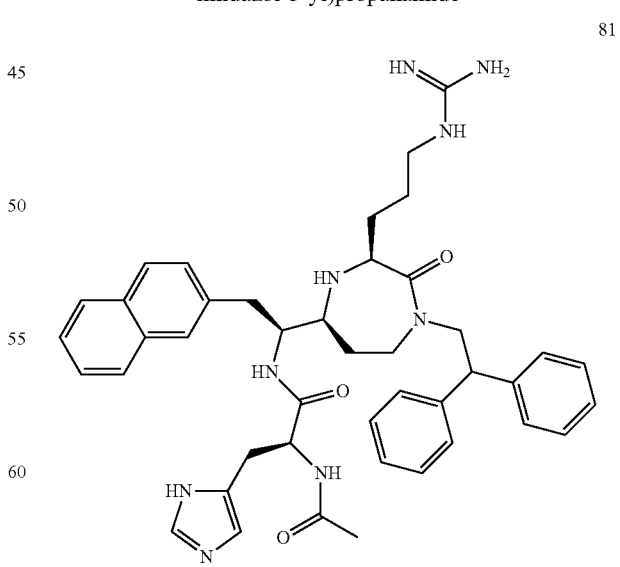

(S)-2-acetamido-N-((S)-1-((3S,5S)-1-(2,2-diphenylethyl)-3-(3-guanidinopropyl)-2-oxo-1,4-diazepan-5-yl)-2-(naphthalen-2-yl)ethyl)-3-(1H-imidazol-5-yl)propanamide

Example 80

Synthesis of Compounds 83 and 84 propyl(S)-1-((3S,5S)-1-(2,2-diphenylethyl)-3-(3-guanidinopropyl)-2-oxo-1,4-diazepan-5-yl)-2-(naphthalen-2-yl)ethylcarbamate and propyl(S)-1-((3S,5R)-1-(2,2-diphenylethyl)-3-(3-guanidinopropyl)-2-oxo-1,4-diazepan-5-yl)-2-(naphthalen-2-yl)ethylcarbamate

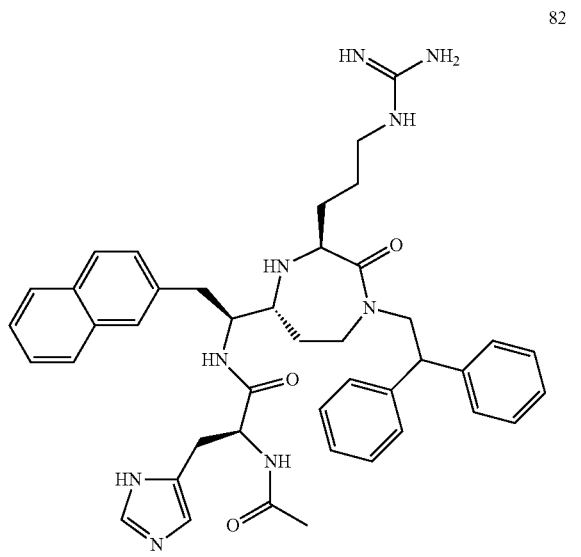

(S)-2-acetamido-N-((S)-1-((3S,5R)-1-(2,2-diphenylethyl)-3-(3-guanidinopropyl)-2-oxo-1,4-diazepan-5-yl)-2-(naphthalen-2-yl)ethyl)-3-(1H-imidazol-5-yl)propanamide To a stirred mixture of Ac-L-His-OH (33.6 mg, 0.156 mmol), DIPEA (112.5 µL, 0.312 mmol) and BOP (68.8 mg, 0.156 mmol) in DMF (1 mL) was added the amine 78 (0.039 mmol) at room temperature. Stirring continued for 16 h, then the reaction mixture was diluted with DCM/H$_2$O mixture (10 mL, 1:1 v/v), and the aqueous phase was extracted with DCM (3×5 mL). The combined DCM extracts were washed with saturated NaHCO$_3$ aqueous solution (3×20 mL) and brine (10 mL), dried over MgSO$_4$, and concentrated under reduced pressure. The residue was re-dissolved in MeOH (5 mL), and Pd/C (20 mg) was added. The resulting mixture was shaken under H$_2$ at 30 psi for 16 h, then was filtered, concentrated and purified by preparative HPLC to give the preferred diastereomer 81 (1.9 mg) and the less preferred diastereomer 82 (0.9 mg) as white solids.

81: MS (ESI) 743.4 (M+1); HPLC t$_R$ 5.489 min

82: MS (ESI) 743.4 (M+1); HPLC t$_R$ 5.555 min

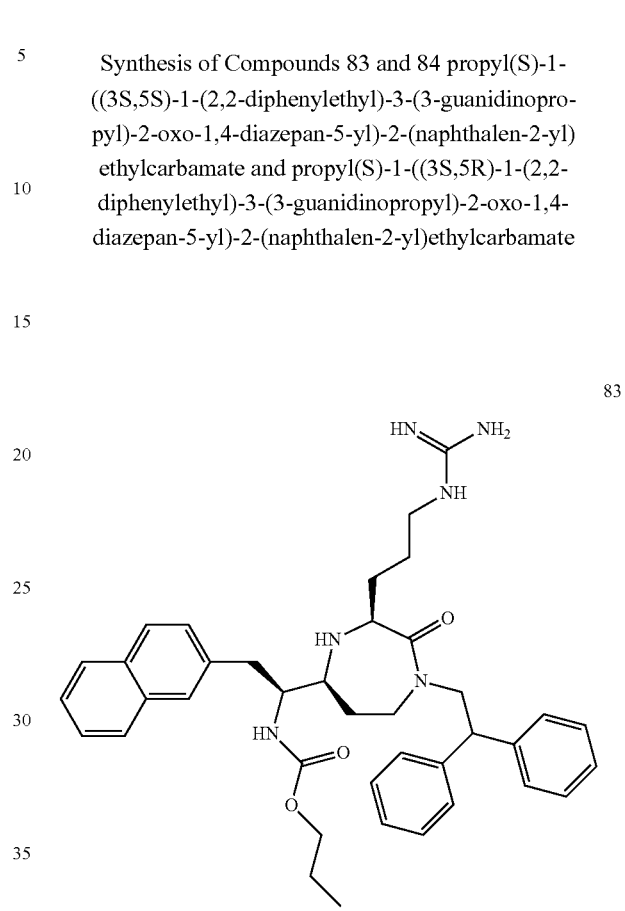

propyl (S)-1-((3S,5S)-1-(2,2-diphenylethyl)-3-(3-guanidinopropyl)-2-oxo-1,4-diazepan-5-yl)-2-(naphthalen-2-yl)ethylcarbamate

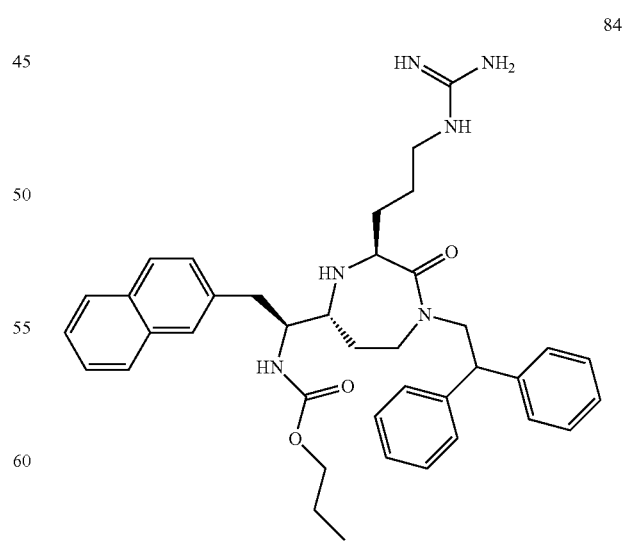

propyl (S)-1-((3S,5R)-1-(2,2-diphenylethyl)-3-(3-guanidinopropyl)-2-oxo-1,4-diazepan-5-yl)-2-(naphthalen-2-yl)ethylcarbamate A mixture of 77 (36 mg, 0.039 mmol) and Pd/C (5 mg) in MeOH (5 mL) was shaken under $H_2$ at 20 psi for 16 h, then was filtered, concentrated and purified by preparative HPLC to give the preferred diastereomer 83 (0.07 mg) and the less preferred diastereomer 84 (2.7 mg) as white solids.

83: MS (ESI) 650.3 (M+1); HPLC $t_R$ 6.52 min
84: MS (ESI) 650.2 (M+1); HPLC $t_R$ 6.64 min Example 81

Synthesis of Compounds 85-87 1-(3-((2S,7S)-7-(N—R1(R)-1-amino-2-(naphthalen-2-yl)ethyl)-4-(2,2-diphenylethyl)-3-oxo-1,4-diazepan-2-yl)propyl)guanidine

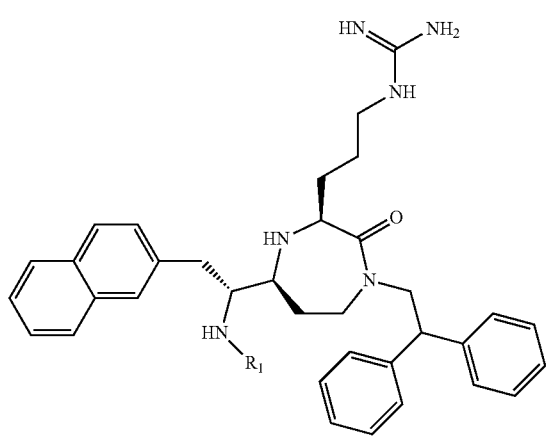

1-(3-((2S,7S)-7-(N-R1(R)-1-amino-2-(naphthalen-2-yl)ethyl)-4-(2,2-diphenylethyl)-3-oxo-1,4-diazepan-2-yl)propyl)guanidine Compounds 85-87 were prepared in the same fashion as the preferred diastereomers Compounds 79, 81 and 83 using the procedures described in Examples 72-81 with D-(2-naphthyl)alanine hydrochloride as the starting material.

| Compound | $R_1$ group | MS (M + 1) | $t_R$ (min) |
|---|---|---|---|
| 85 | Ac | 606.2 | 6.01 |
| 86 | Ac-His | 743.5 | 5.41 |
| 87 | Propyloxycarbonyl | 650.4 | 6.42 |

Examples 82-90

Synthesis via Scheme 2: Preparation of all Four Diastereomers of N-((1-(2,2-diphenylethyl)-3-(3-guanidinopropyl)-2-oxo-1,4-diazepan-5-yl)methyl)-2-naphthamide 88

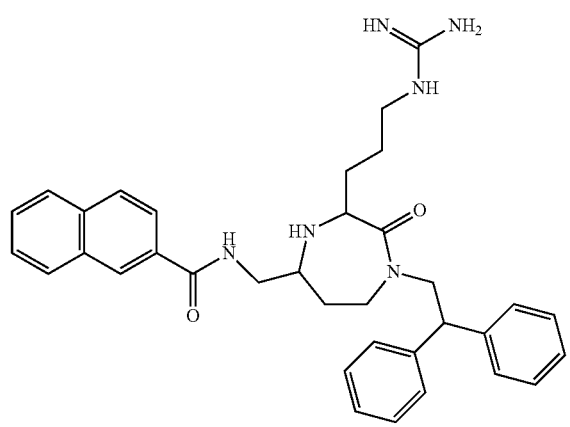

N-((1-(2,2-diphenylethyl)-3-(3-guanidinopropyl)-2-oxo-1,4-diazepan-5-yl)methyl)-2-naphthamide Example 82

Synthesis of Compound 89 2,2-dimethyl-10-(2,2-diphenylethyl)-4,7,11-trioxo-3,12-dioxa-5,10-diazapentadec-14-ene

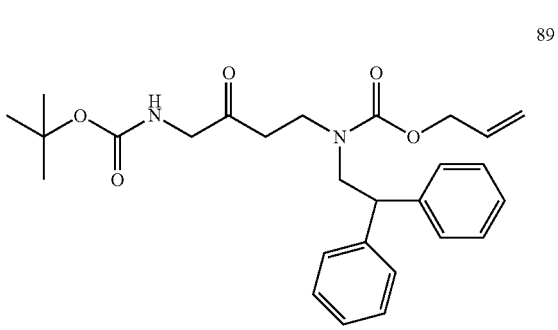

2,2-dimethyl-10-(2,2-diphenylethyl)-4,7,11-trioxo-3,12-dioxa-5,10-diazapentadec-14-ene 2,2-diphenylethylamine (3 g) was added to Boc-vinylketone 16 (2.8 g) as in Example 17. To the crude adduct 17 was added Alloc-Cl (1.6 mL) and the reaction stirred until TLC indicated consumption of the secondary amine. THE solvent was evaporated and the residue purified by column chromatography (SiO2 gel, pet. ether/EtOAc) to give 3.2 g (57%) of 89.

Example 83

Synthesis of Compound 90 (S)-allyl 2-amino-5-(benzyloxycarbonylamino)pentanoate L-H-Orn(Cbz)-Oallyl

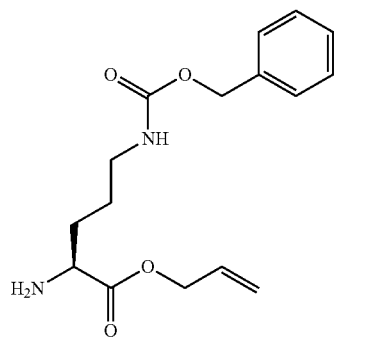

(S)-allyl 2-amino-5-(benzyloxycarbonylamino)pentanoate

H-L-Orn(Cbz)-OH (6.66 g, 25 mmol), allyl alcohol (17.56 mL, 25 mmol) and p-TsOH (5.7 g, 30 mmol) were dissolved in benzene (200 mL) and refluxed under Dean-Stark conditions for 5 h. The majority of the solvent was then distilled off, with the remainder removed under vacuum. The resulting solid was recrystallized from DCM, filtered and dried to give 11.19 g (94%) of the tosylate salt. To obtain the free amine the solid was dissolved in DCM, washed with sat. NaHCO$_3$, the aqueous layer washed with DCM (3×), and the organic layers dried over MgSO$_4$ and evaporated to dryness.

Example 84

Synthesis of Compound 91 (R)-allyl 2-amino-5-(benzyloxycarbonylamino)pentanoate D-H-Orn(Cbz)-Oallyl

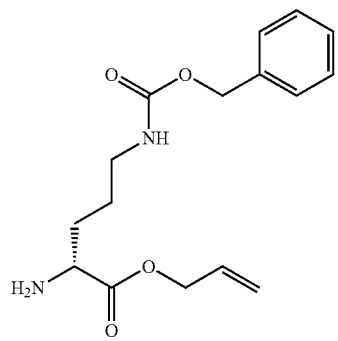

(R)-allyl 2-amino-5-(benzyloxycarbonylamino)pentanoate

H-D-Orn(Cbz)-OH (6.66 g, 25 mmol) was converted into 10.93 g (91%) of the tosylate salt of 91 as in Example 83, then converted into the free amine.

Example 85

Synthesis of Compound 92 (2R)-allyl 5-(benzyloxycarbonylamino)-2-(10-(2,2-diphenylethyl)-2,2-dimethyl-4,11-dioxo-3,12-dioxa-5,10-diazapentadec-14-en-7-ylamino)pentanoate

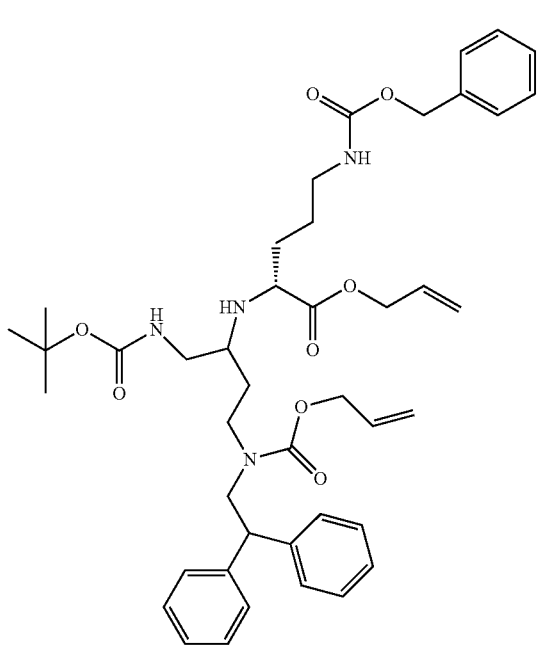

(2R)-allyl 5-(benzyloxycarbonylamino)-2-(10-(2,2-diphenylethyl)-2,2-dimethyl-4,11-dioxo-3,12-dioxa-5,10-diazapentadec-14-en-7-ylamino)pentanoate The protected aminoketone 89 (746 mg, 1.6 mmol), D-Orn(Cbz)-Oallyl 91 (538 mg, 1.76 mmol) and NaBH(OAc)$_3$ (678 mg, 3.2 mmol) in a minimum volume of DCM were stirred for 24 h. A drop of AcOH was added just before workup, at which point saturated NaHCO$_3$ was added, extracted with DCM (3×), and the organic extracts combined and washed with saturated NaHCO$_3$ and H$_2$O, dried over MgSO$_4$, and evaporated to dryness. The product was purified by column chromatography (SiO$_2$ gel, pet. ether/EtOAc) to give 890 mg (74%) of 92 as a mixture of diastereoisomers.

Example 86

Synthesis of Compound 93 (2S)-allyl 5-(benzyloxycarbonylamino)-2-(10-(2,2-diphenylethyl)-2,2-dimethyl-4,11-dioxo-3,12-dioxa-5,10-diazapentadec-14-en-7-ylamino)pentanoate

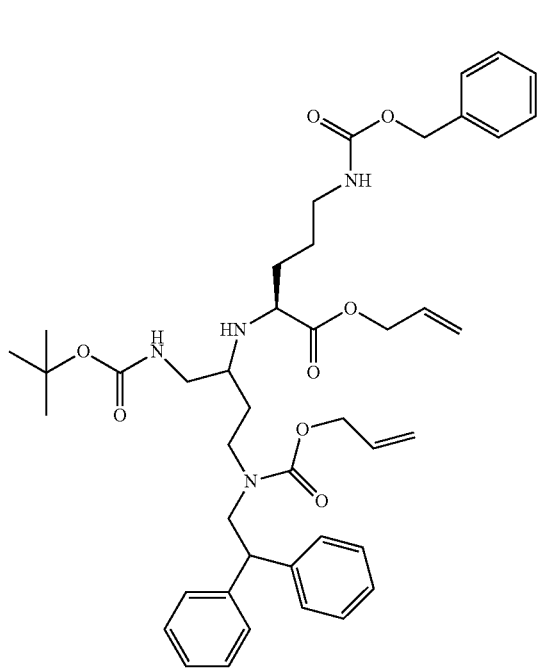

(2S)-allyl 5-(benzyloxycarbonylamino)-2-(10-(2,2-diphenylethyl)-2,2-dimethyl-4,11-dioxo-3,12-dioxa-5,10-diazapentadec-14-en-7-ylamino)pentanoate L-Orn(Cbz)-Oallyl 90 (592 mg, 1.93 mmol) was converted into a mixture of the set of diastereomers 93 (925 mg, 76%) following the procedures of Example 86.

Example 87

Synthesis of Compounds 94 and 95 (3R,5S)-5-(N-Boc aminomethyl)-3-(N-Cbz 3-aminopropyl)-1-(2,2-diphenylethyl)-1,4-diazepan-2-one and (3R,5R)-5-(N-Boc aminomethyl)-3-(N-Cbz 3-aminopropyl)-1-(2,2-diphenylethyl)-1,4-diazepan-2-one

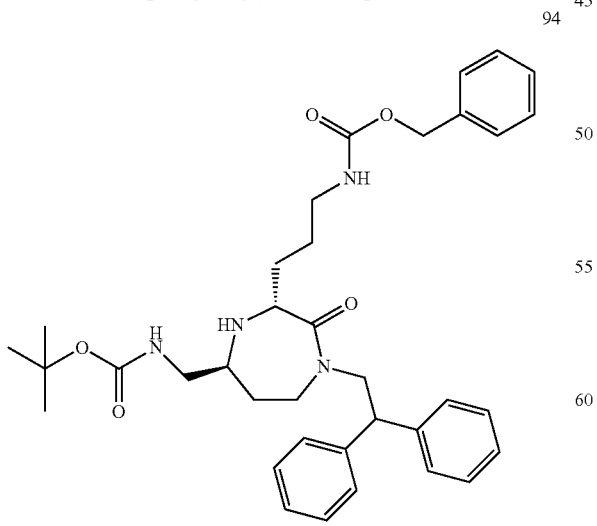

(3R,5S)-5-(N-Boc aminomethyl)-3-(N-Cbz 3-aminopropyl)-1-(2,2-diphenylethyl)-1,4-diazepan-2-one

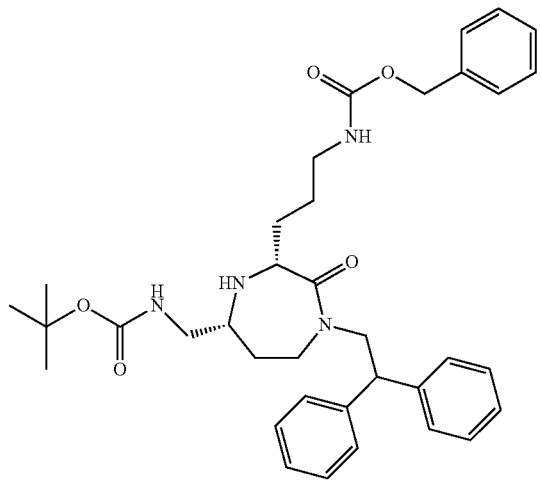

(3R,5R)-5-(N-Boc aminomethyl)-3-(N-Cbz 3-aminopropyl)-1-(2,2-diphenylethyl)-1,4-diazepan-2-one The Alloc/allyl protected derivative 92 (840 mg, 1.11 mmol) was dissolved in a minimum of DCM. 1,3-Dimethylbarbituric acid (346 mg, 2.22 mmol) and catalytic Pd(PPh$_3$)$_4$ were added, and the reaction degassed under vacuum, sealed and stirred overnight. The reaction was diluted to 50 mL with DCM, DIPEA (430 mg, 3.33 mmol) and BOP (540 mg, 1.22 mmol) were added, and the reaction stirred for 30 min. The DCM was removed under vacuum and the residue taken up in EtOAc, washed (saturated NaHCO$_3$, H$_2$O, saturated NaCl), dried (MgSO$_4$) and evaporated to dryness (TLC: EtOAc, 2 spots, R$_f$ 0.33 and 0.57). The two diastereomeric products were separated by column chromatography (SiO$_2$ gel, pet. ether/EtOAc) to give 362 mg of the earlier eluting (3R,5S) isomer 94, and 342 mg of the later eluting (3R,5R) isomer 95.

Example 88

Synthesis of Compounds 96 and 97 (3S,5R)-5-(N-Boc aminomethyl)-3-(N-Cbz 3-aminopropyl)-1-(2,2-diphenylethyl)-1,4-diazepan-2-one and (3S,5S)-5-(N-Boc aminomethyl)-3-(N-Cbz 3-aminopropyl)-1-(2,2-diphenylethyl)-1,4-diazepan-2-one

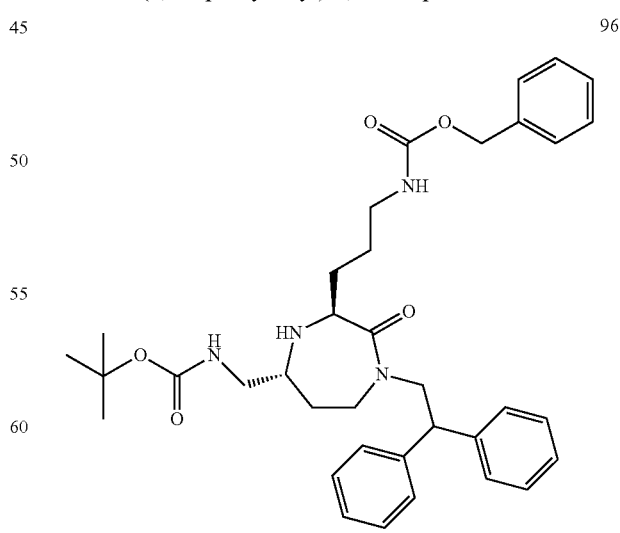

(3R,5S)-5-(N-Boc aminomethyl)-3-(N-Cbz 3-aminopropyl)-1-(2,2-diphenylethyl)-1,4-diazepan-2-one

281

-continued

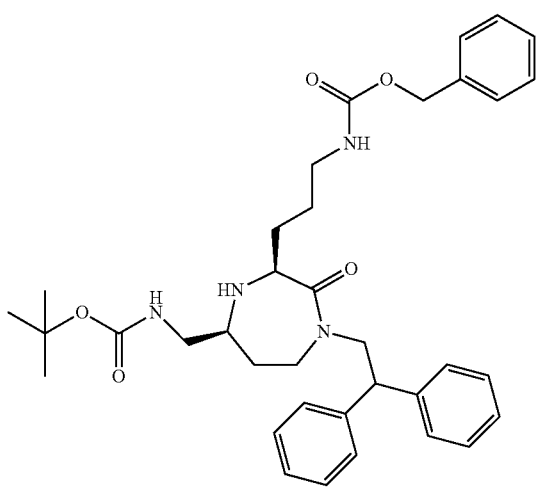

(3R,5R)-5-(N-Boc aminomethyl)-3-(N-Cbz 3-aminopropyl)-1-
(2,2-diphenylethyl)-1,4-diazepan-2-one The (3S,5R) (312 mg) and (3S,5S) (331 mg) isomers were obtained from the L-Orn-derived acyclic material 93 (870 mg) following the procedure of Example 87.

Example 89

Synthesis of Compounds 98-101 5-(N-Boc aminomethyl)-3-(N,N'-Cbz$_2$ 3-guanidinopropyl)-1-(2,2-diphenylethyl)-1,4-diazepan-2-one 98-101

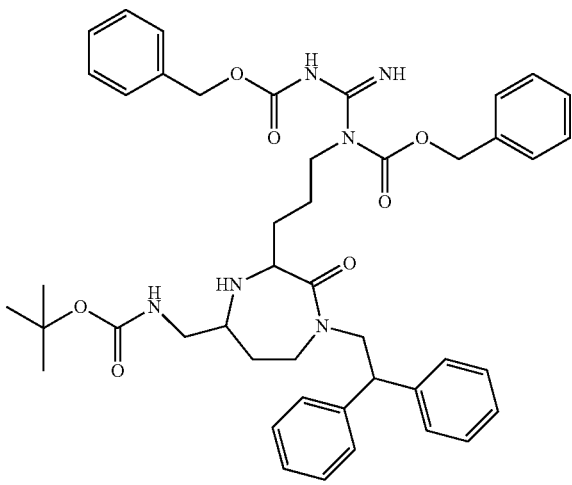

The Orn Cbz group of 94 was removed by hydrogenation (H$_2$, 30 psi) over catalytic Pd/C in methanol overnight. The solution was filtered through Celite and evaporated to give a solid. A solution of the resulting amine (187 mg, 0.39 mmol) in DCM was mixed with a solution of the guanylating reagent CbzNHC(=NCbz)NHTf (196 mg, 0.43 mmol) in DCM. TEA (43 mg, 0.43 mmol) was added, and the reaction stirred overnight. The solution was diluted with DCM, washed (KHSO$_4$, sat. NaHCO$_3$, brine), dried (MgSO$_4$) and evapo-

282 rated to dryness, then purified by flash chromatography over SiO$_2$ using hexanes/EtOAc as eluent, to give (3R,5S) 98 (182 mg, 59%). The other isomers 95-97 were converted in a similar manner to give:

99 (3R,5R): 171 mg (68%) from 148 mg of amine 100 (3S,5S): 80 mg (65%) from 72 mg of amine 101 (3S,5R):142 mg (58%) from 144 mg of amine

Example 90

Synthesis of Compounds 102-105

102   N-(((3R,5S)-1-(2,2-diphenylethyl)-3-(3-guanidinopropyl)-2-oxo-1,4-diazepan-5-yl)methyl)-2-naphthamide 103   N-(((3R,5R)-1-(2,2-diphenylethyl)-3-(3-guanidinopropyl)-2-oxo-1,4-diazepan-5-yl)methyl)-2-naphthamide 104   N-(((3S,5R)-1-(2,2-diphenylethyl)-3-(3-guanidinopropyl)-2-oxo-1,4-diazepan-5-yl)methyl)-2-naphthamide 105   N-(((3S,5S)-1-(2,2-diphenylethyl)-3-(3-guanidinopropyl)-2-oxo-1,4-diazepan-5-yl)methyl)-2-naphthamide

102

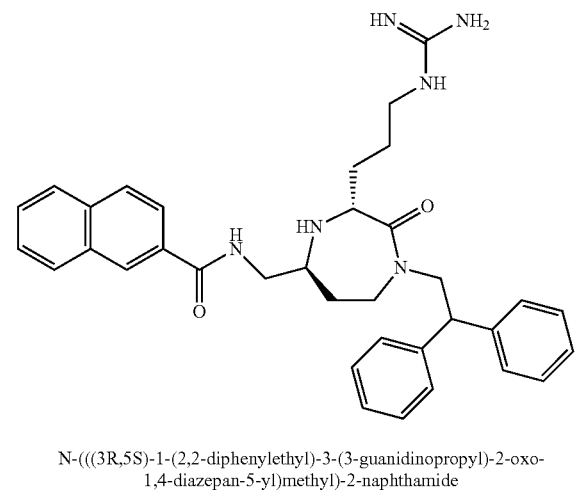

N-(((3R,5S)-1-(2,2-diphenylethyl)-3-(3-guanidinopropyl)-2-oxo-
1,4-diazepan-5-yl)methyl)-2-naphthamide

103

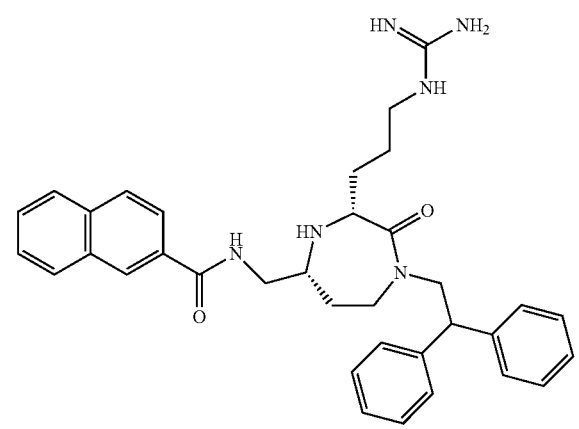

N-(((3R,5R)-1-(2,2-diphenylethyl)-3-(3-guanidinopropyl)-2-oxo-
1,4-diazepan-5-yl)methyl)-2-naphthamide

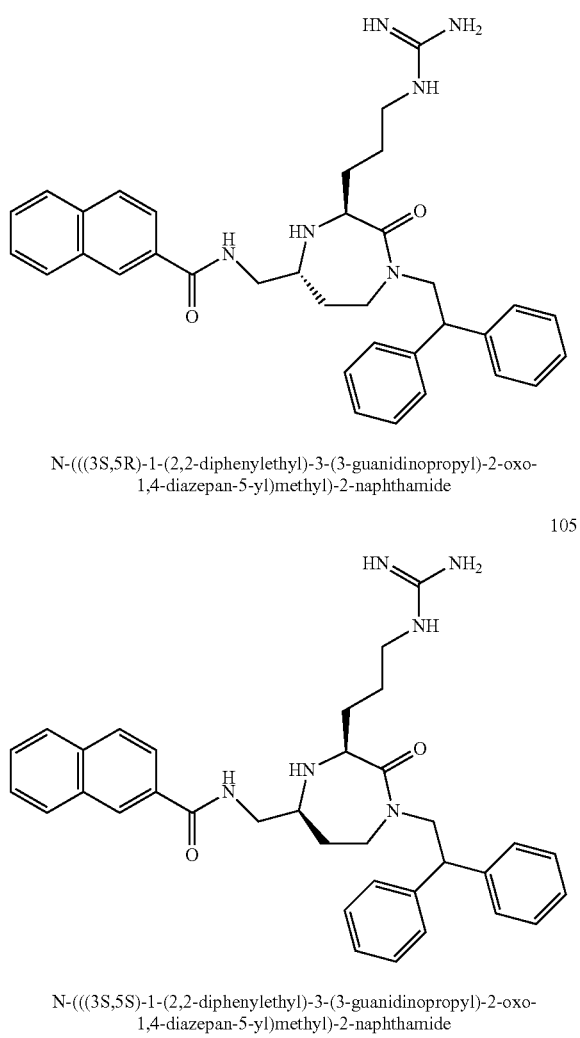

104
N-(((3S,5R)-1-(2,2-diphenylethyl)-3-(3-guanidinopropyl)-2-oxo-1,4-diazepan-5-yl)methyl)-2-naphthamide 105
N-(((3S,5S)-1-(2,2-diphenylethyl)-3-(3-guanidinopropyl)-2-oxo-1,4-diazepan-5-yl)methyl)-2-naphthamide The Boc derivative 99 (180 mg) in DCM (1 mL) was treated with TFA (1 mL) for 20 mL. The solvent was removed by evaporation, a solution of NaHCO$_3$ was added, and extracted 3× with DCM. The dichoromethane solution was dried over MgSO$_4$, filtered and evaporated to dryness. A portion (56 mg, 0.086 mmol) of the crude deprotected amine in DCM was stirred with 2-naphthoic acid (16 mg), DIPEA (60 uL) and BOP (42 mg) for 30 min. MeOH was added and the reaction stirred overnight. The reaction was filtered, then purified by flash chromatography over SiO$_2$ using petroleum ether/EtOAc as eluent, to give the (3R,5R) isomer (43 mg, 94%). The other isomers were converted in a similar manner to give: (3R,5S): 41 mg (85%) from 60 mg 98, (3S,5R): 27 mg (70%) from 40 mg 101, and (3S,5S): 13 mg (74%) from 20 mg 100 Each compound was dissolved in dioxane:MeOH and hydrogenated over catalytic Pd/C under 30 psi H$_2$ overnight. The solution was filtered through Celite and evaporated to give a solid. 102 (3R,5S): 27 mg (96%) from 41 mg, 103 (3R,5R): 25 mg (85%) from 43 mg, 104 (3S,5R): 11 mg (quantitative) from 13 mg, and 105 (3S,5S): 3 mg (73%) from 6 mg.

| Compound | stereochemistry | MS (M + 1) | $t_R$ (min) |
|---|---|---|---|
| 102 | (3R,5S) | 577.4 | 5.775 |
| 103 | (3R,5R) | 577.5 | 5.750 |
| 104 | (3S,5R) | 577.5 | 5.783 |
| 105 | (3S,5S) | 577.3 | 5.787 |

Example 91

Synthesis of Compounds 425, 565, 580-585

425  6-chloro-N-(((3S,5S)-2-oxo-1-((S)-2-phenylbutyl)-3-(2-(piperidin-1-yl)ethyl)-1,4-diazepan-5-yl)methyl)-2-naphthamide 565  6-chloro-N-(((3S,5S)-2-oxo-1-((R)-2-phenylbutyl)-3-(2-(piperidin-1-yl)ethyl)-1,4-diazepan-5-yl)methyl)-2-naphthamide 580  6-chloro-N-(((3R,5R)-2-oxo-1-((R)-2-phenylbutyl)-3-(2-(piperidin-1-yl)ethyl)-1,4-diazepan-5-yl)methyl)-2-naphthamide 581  6-chloro-N-(((3S,5R)-2-oxo-1-((S)-2-phenylbutyl)-3-(2-(piperidin-1-yl)ethyl)-1,4-diazepan-5-yl)methyl)-2-naphthamide 582  6-chloro-N-(((3R,5S)-2-oxo-1-((S)-2-phenylbutyl)-3-(2-(piperidin-1-yl)ethyl)-1,4-diazepan-5-yl)methyl)-2-naphthamide 583  6-chloro-N-(((3S,5R)-2-oxo-1-((R)-2-phenylbutyl)-3-(2-(piperidin-1-yl)ethyl)-1,4-diazepan-5-yl)methyl)-2-naphthamide 584  6-chloro-N-(((3R,5S)-2-oxo-1-((R)-2-phenylbutyl)-3-(2-(piperidin-1-yl)ethyl)-1,4-diazepan-5-yl)methyl)-2-naphthamide 585  6-chloro-N-(((3R,5R)-2-oxo-1-((S)-2-phenylbutyl)-3-(2-(piperidin-1-yl)ethyl)-1,4-diazepan-5-yl)methyl)-2-naphthamide

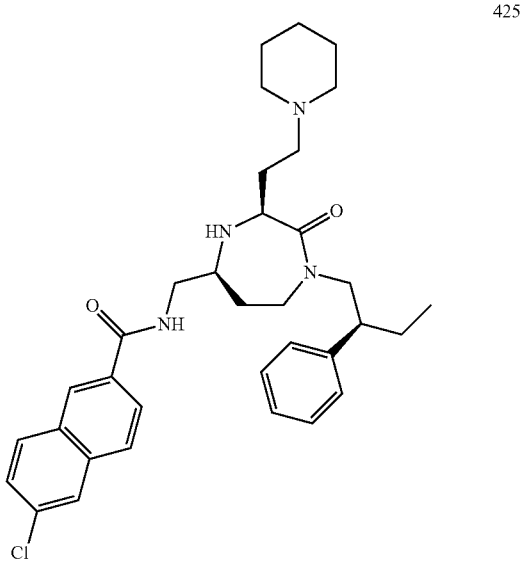

425

285
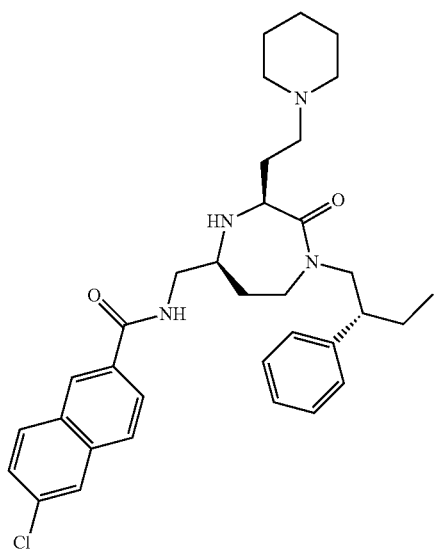
565
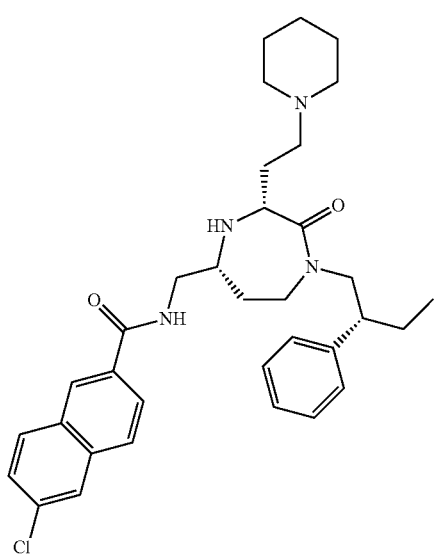
580
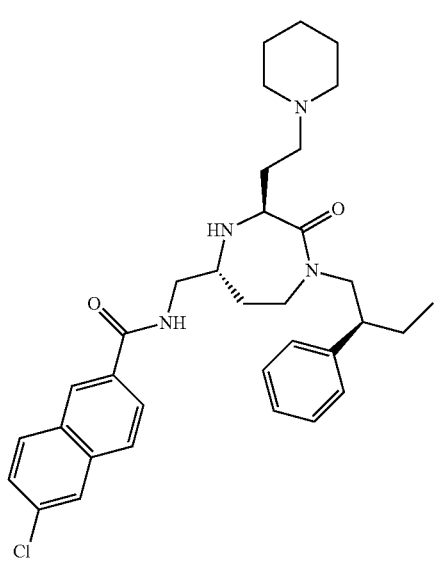
581
286
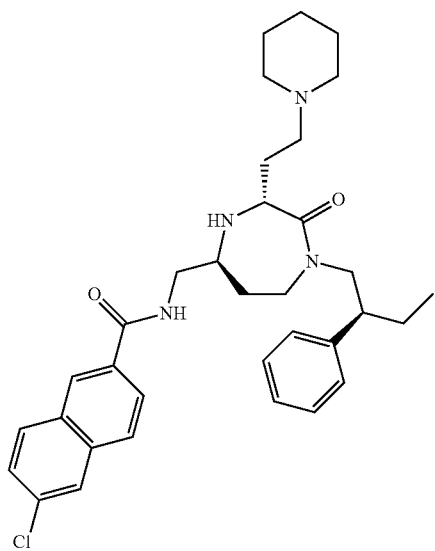
582
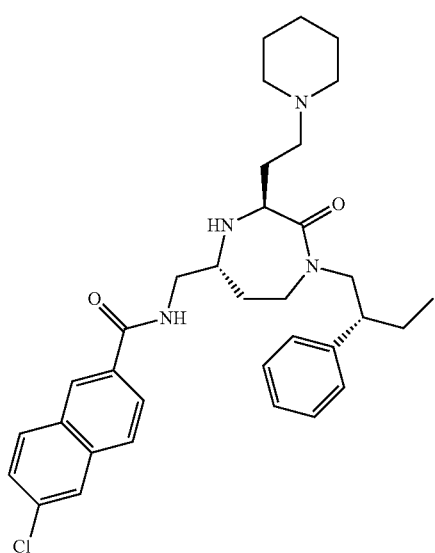
583
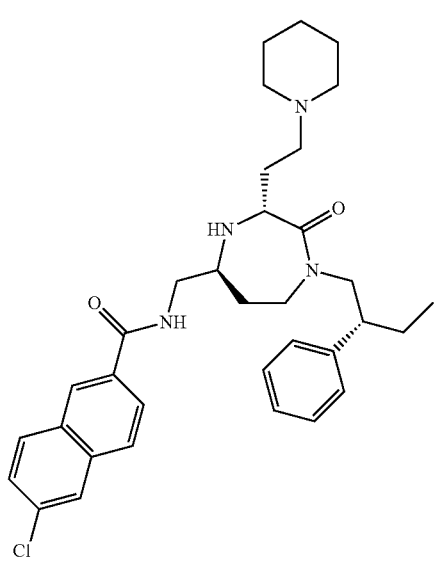
584

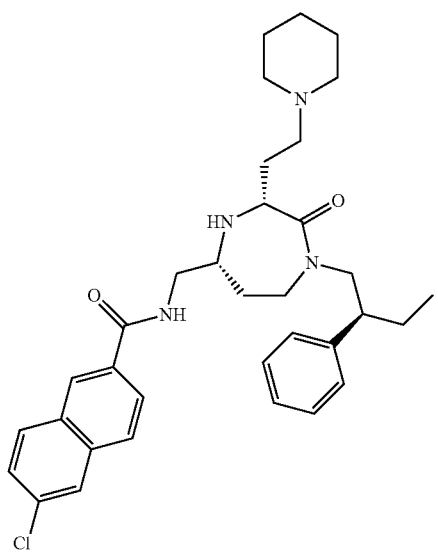

Compounds 425, 565, and 580-585 were prepared following similar procedures as used to prepare Compounds 102-104 (Scheme 2 route). In addition, compounds 425, 565, 580 and 585 were prepared according to the Scheme 1 route; a detailed procedure for the preparation of Compound 425 is contained in Examples 92-99.

| Compound | stereochemistry | MS (M + 1) | $t_R$ (min) |
|---|---|---|---|
| 425 | (3S,5S,2'S) | 575.3 | 6.269 |
| 565 | (3S,5S,2'R) | 574.8 | 6.265 |
| 580 | (3R,5R,2'R) | 575.4 | 6.404 |
| 581 | (3S,5R,2'S) | 575.2 | 6.262 |
| 582 | (3R,5S,2'S) | 575.2 | 6.110 |
| 583 | (3S,5R,2'R) | 575.1 | 6.211 |
| 584 | (3R,5S,2'R) | 575.2 | 6.253 |
| 585 | (3R,5R,2'S) | 575.4 | 6.274 |

Example 92

Synthesis of Compound 586 (S)—N-(2-oxo-4-(2-phenylbutylamino)butyl)-3-phenylpropanamide

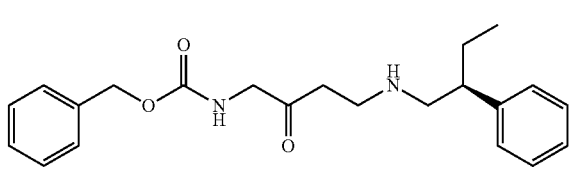

To a solution of (S)-phenylbutylamine (8.5 g, 57.07 mmol) in DCM (100 ml) was added a solution of α,β-unsaturated ketone 27 (12.5 g, 57.1 mmol) in DCM (100 ml) at room temperature in one portion. The resulting mixture was stirred until all of the α,β-unsaturated ketone had been consumed (within one hour), then the conjugate addition adduct 586 was used straight in the next reaction.

HPLC $t_R$ 5.71 min

MS (ESI) 369.3 (M+1)

Example 93

Synthesis of Compound 587 (S)-9-fluorenylmethyl 10-[(S)-2-phenylbutyl]-2,2-dimethyl-18-phenyl-4,9,13,16-tetraoxo-3,17-dioxa-5,10,15-triazaoctadecan-8-ylcarbamate

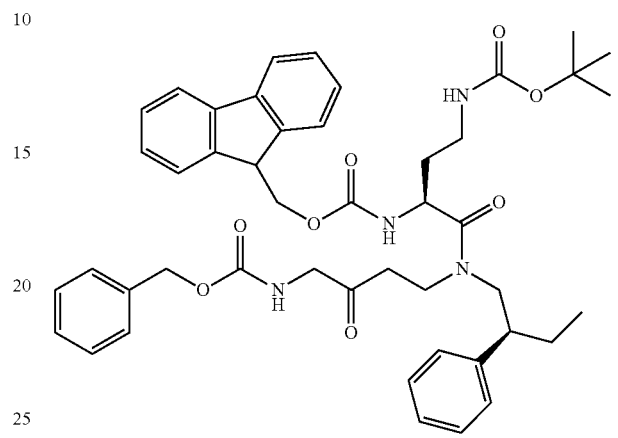

To the freshly prepared amine 586 in DCM (200 mL) was added Fmoc-L-Dab(Boc)OH (32.7 g, 74.2 mmol) followed by DIPC (11.5 g, 74.2 mmol) at room temperature. The resulting mixture was stirred for 2 hours, the by-product diisopropylurea was removed by filtration through a pad of Celite®, and the filtrate was concentrated under reduced pressure to give the crude product, which was purified by silica gel column chromatography using 30-70% EtOAc/Pet. Spirit as eluent to give 587 (19.9 g, 44% yield over two steps).

TLC if 0.23 (50% EtOAc/Pet. Spirit)

HPLC $t_R$ 10.03 min

MS (ESI) 791.2 (M+1)

Example 94

Synthesis of Compound 588 (S)-10-[(S)-2-phenylbutyl]-2,2-dimethyl-8-amino-18-phenyl-4,9,13,16-tetraoxo-3,17-dioxa-5,10,15-triazaoctadecane

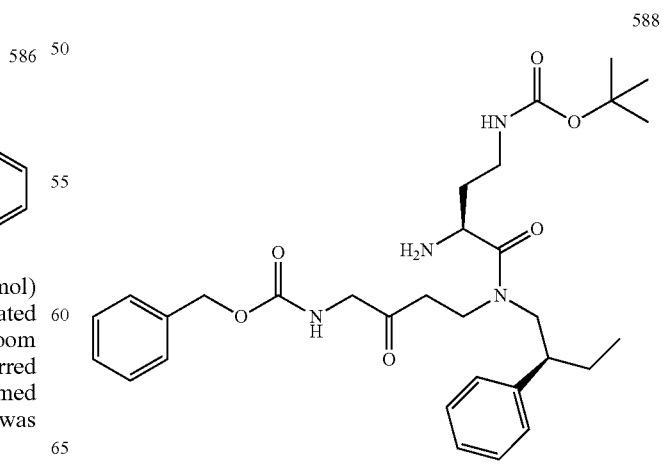

Diethylamine (30 mL) was added to a solution of the acylated amine 587 (19.9 g, 25.19 mmol) in DCM (30 mL) at room temperature and the resulting mixture was stirred for 30 min. The solvent and diethylamine were removed under reduced pressure to give the desired product 588. It was used in the next step without further purification.

HPLC $t_R$ 6.85 min
MS (ESI) 569.3 (M+1)

Example 95

Synthesis of Compound 589 (3S,5S)-3-(2-tert-butoxycarbonylaminoethyl)-5-(benzyloxycarbonylaminomethyl)-1-[(S)-2-phenylbutyl]-1,4-diazepan-2-one

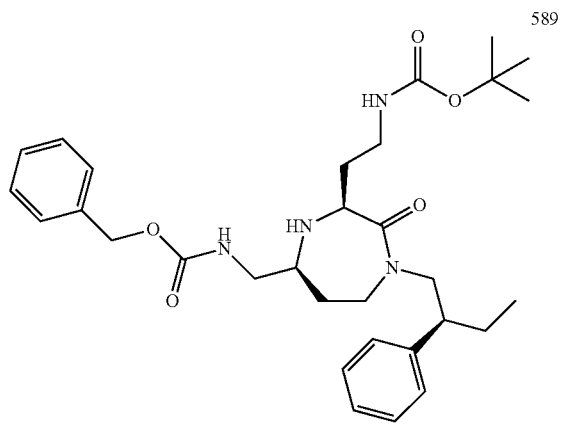 [SMILES: CC[C@H](CN1CC[C@@H](CNC(=O)OCc2ccccc2)N[C@@H](CCNC(=O)OC(C)(C)C)C1=O)c1ccccc1]

To a solution of crude Fmoc deprotected material 588 in DCM (50 ml) was added AcOH (15 mL) followed by NaBH(OAc)$_3$ (5.34 g, 25.2 mmol) in one portion at room temperature. The resulting mixture was stirred for 30 min, then washed with saturated NaHCO$_3$(aq) solution (80 mL×3), brine (80 mL) and dried over MgSO$_4$. Filtration and concentration of the organic phase under reduced pressure gave the crude product, which was purified by silica gel column chromatography using 50-100% EtOAc/Pet. Spirit followed by 20% MeCN/EtOAc to give the product 589 (12.3 g, 88% over two steps).

TLC rf 0.19 (70% EtOAc/Pet. Spirit)
HPLC $t_R$ 7.06 min
MS (ESI) 553.3 (M+1)

Example 96

Synthesis of Compound 590 tert-butyl 2-{(2S,7S)-7-aminomethyl-3-oxo-4-[(S)-2-phenylbutyl]-1,4-diazepan-2-yl}ethylcarbamate

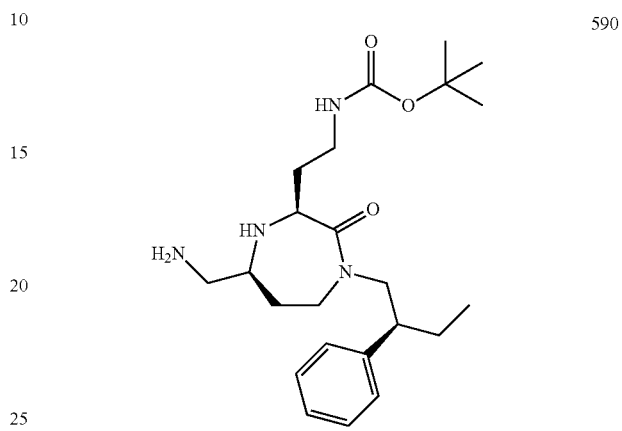

A mixture of Cbz-protected product 589 (12.3 g, 22.3 mmol) and 5% Pd/C (2 g) in MeOH (100 mL) was shaken at room temperature under hydrogen at atmospheric pressure for one hour. The mixture was then filtered through a pad of Celite®, and the filtrate was concentrated under reduced pressure to give the crude amine 590. The crude material was used in the next step without further purification.

HPLC $t_R$ 5.77 min
MS (ESI) 419.3 (M+1)

Example 97

Synthesis of Compound 591 tert-butyl 2-((2S,7S)-7-((6-chloro-2-naphthamido)methyl)-3-oxo-4-((S)-2-phenylbutyl)-1,4-diazepan-2-yl)ethylcarbamate

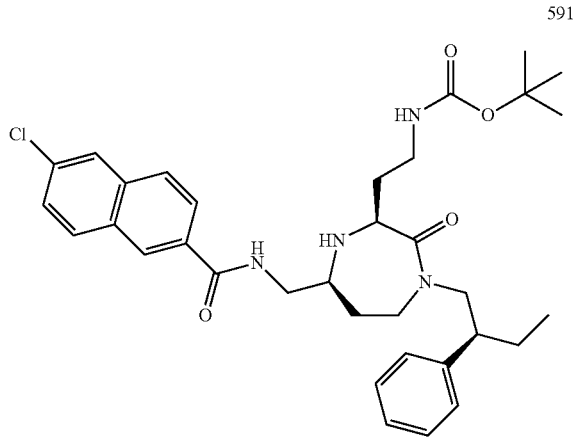 [SMILES: CC[C@H](CN1CC[C@@H](CNC(=O)c2ccc3cc(Cl)ccc3c2)N[C@@H](CCNC(=O)OC(C)(C)C)C1=O)c1ccccc1]

To a solution of the free amine 590 and 6-chloro-2-naphthoic acid (4.58 g, 22.3 mmol) in DCM (125 ml) was added diisopropylethylamine (7.74 mL, 44.5 mmol) and BOP (9.84 g, 22.3 mmol) at room temperature. The resulting mixture was stirred for 16 hours then DCM was removed under reduced pressure. The residue was taken up in EtOAc (80 mL), then washed with saturated NaHCO$_3$(aq) (100 mL×5), brine (100 mL) and dried over MgSO$_4$. Filtration and concentration of the organic phase gave the crude material, which was purified by silica gel column chromatography using 80-100% EtOAc/Pet. Spirit as eluent to give the product 591 (10.7 g, 79%).

TLC if 0.31 (80% EtOAc/Pet. Spirit)

HPLC t$_R$ 7.66 min

MS (ESI) 607.2 (M+1)

Example 98

Synthesis of Compound 465 N-(((3S,5S)-3-(2-aminoethyl)-2-oxo-1-((S)-2-phenylbutyl)-1,4-diazepan-5-yl)methyl)-6-chloro-2-naphthamide

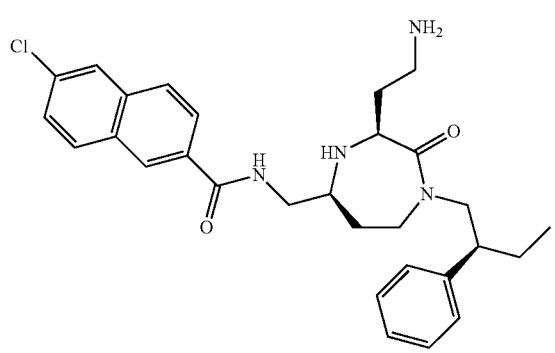

465

To the Boc protected material 591 (10.7 g, 17.6 mmol) in DCM (26 mL) was added TFA (26 ml) in one portion, the resulting mixture was stirred at room temperature for one hour. DCM was removed under reduced pressure and the residue was taken up in EtOAc (30 mL), washed with saturated NaHCO$_3$(aq) (30 mL×3), brine (30 mL) and dried over MgSO$_4$. Filtration and concentration of the organic phase under reduced pressure gave the crude amine 465, which was used in the next step without further purification.

HPLC t$_R$ 5.98 min

MS (ESI) 507.0 (M+1)

Example 99

Synthesis of Compound 425 6-chloro-N-(((3S,5S)-2-oxo-1-((S)-2-phenylbutyl)-3-(2-(piperidin-1-yl)ethyl)-1,4-diazepan-5-yl)methyl)-2-naphthamide

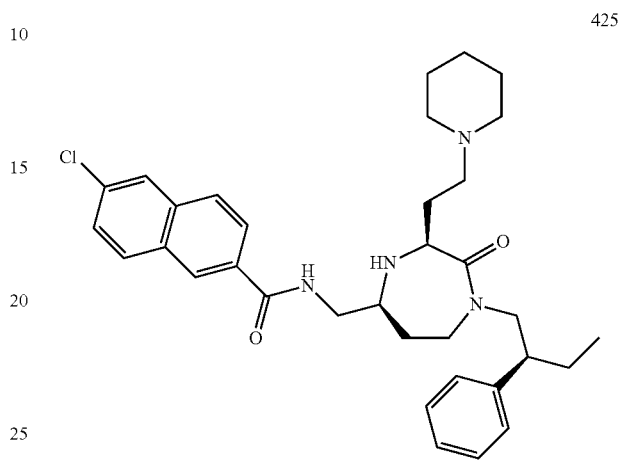

425

To a mixture of crude amine 465 in CH$_3$CN (800 mL) was added 1,5-dibromopentane (23.9 mL, 175.7 mmol) followed by K$_2$CO$_3$ (48.6 g, 351.4 mmol). The resulting mixture was stirred at room temperature for 44 hours, monitored by HPLC for conversion of sm (6.0 min) to product (6.4 min), avoiding extended reaction times leading to overalkylation to generate a bromopentyl-alkylated byproduct (7.1 min). During isolation, excessive heating/concentration of the crude solution must be avoided before removal of excess dibromopropane, to avoid overalkylation of the piperidine ring. The K$_2$CO$_3$ was removed by filtration through a pad of Celite®, and the filtrate was washed with Pet. Spirit (800 mL×2). The MeCN phase was concentrated under reduced pressure to 400 mL, and was washed with Pet. Spirit (400 mL×2). The MeCN was further concentrated under reduced pressure to 200 mL, and was washed with Pet. Spirit (200 mL×2). Evaporation of the final Pet. Spirit washing showed no more 1,5-dibromopentane was extracted, so the MeCN phase was concentrated under reduced pressure.

Aminopropyl-functionalized TLC rf 0.05-0.47 (80% EtOAc/Pet. Spirit)

Analytical HPLC t$_R$ 6.41 min

MS (ESI) 575.2 (M+1).

The crude product was purified by a combination of flash column chromatography over aminopropyl-functionalized silica gel, and/or by recrystallization from acetonitrile.

Flash column: To a column packed with amino propyl-functionalized silica gel (154 g) in 20% ethyl acetate/petroleum spirit was loaded the crude free base oil (7.2 g). The column was eluted with 20% ethyl acetate/petroleum spirit (150 mL), followed by 50% ethyl acetate/petroleum spirit (150 mL), 80% ethyl acetate/petroleum spirit (150 mL×2), 100% ethyl acetate (150 mL) and finally 100% acetonitrile (150 mL). Fractions containing 425 were combined and evaporated to dryness to yield a white crystalline solid.

Crystallization: The white crystalline solid (2.87 g) obtained by column purification was dissolved in boiling acetonitrile (50 mL) 85° C. Activated carbon (Darco® G-60, −100 mesh, Sigma-Aldrich) (200 mg) was added to remove colour impurity. A further portion of acetonitrile (50 mL) was added, and the resulting mixture was heated to boiling for 5 min. The charcoal was filtered off while the solution was hot, with the filter paper and the charcoal rinsed with hot acetonitrile (25 mL). The clear acetonitrile solution was reduced down to 50 mL and left to stand to cool to room temperature for 16 h. The white crystals were filtered off and dried by suction to give 2.22 g (99.0% pure by HPLC analysis). An additional 117.2 mg (93.3% purity) was recovered by additional crystallization from the filtrate.

Conversion to bisHCl Salt: The free base (2.4229 g, 42.1 mmol) was suspended in a 1:1 mixture of acetonitrile and milliQ $H_2O$ (10 mL). A solution of 1 M HCl (aq.) was added until all the solids dissolved (approximately 5 mL). An additional quantity of milliQ $H_2O$ was then added (20 mL) and the resulting solution frozen and lypholised overnight, resulting in a white powder (2.61 g, 95.6% yield).

HPLC $t_R$ 6.27 min

MS (ESI) 575.1 (M+1).

$^1$H NMR (600 MHz, CDCl$_3$): δ 0.75 (t, 3H, J=7.2 Hz), 1.40 (m, 1H), 1.56 (m, 1H), 1.65 (m, 1H), 1.76-1.90 (m, 4H), 1.90-2.06 (m, 2H), 2.13 (m, 1H), 2.30 (br, 1H), 2.57 (m, 1H), 2.64-2.86 (m, 4H), 2.90-3.10 (m, 2H), 3.25 (dd, 1H, J=15.2, 10.4 Hz), 3.53 (m, 2H), 3.70-3.85 (m, 3H), 4.00 (m, 2H), 4.10 (dd, 1H, J=13.6, 5.6 Hz), 4.45 (m, 1H), 7.10 (d, 2H, J=7.2 Hz), 7.18 (t, 1H, J=7.2 Hz), 7.26 (t, 1H, J=7.2 Hz), 7.37 (dd, 1H, J=9.0, 1.8 Hz), 7.71 (d, 1H, J=8.4 Hz), 7.75 (s, 1H), 7.86 (d, 1H, J=9.0 Hz), 8.09 (d, 1H, J=9.0 Hz), 8.64 (s, 1H), 8.68 (m, 1H), 9.85 (br, 1H).

$^{13}$C NMR (100 MHz, CDCl$_3$): δ 11.78, 21.86, 23.08 (2), 24.59, 26.14, 28.09, 42.01, 46.24, 47.22, 53.14, 53.53, 54.03, 56.74, 57.79, 61.96, 125.35, 126.24, 126.89, 127.20, 127.33, 127.85, 128.51, 128.72, 130.69, 130.76, 130.91, 133.48, 135.28, 142.29, 167.18, 167.74

Example 100

Synthesis of Compound 579 6-chloro-N-(([5,6,6-$^2$H$_3$](3S,5S)-2-oxo-1-((S)-2-phenylbutyl)-3-(2-(piperidin-1-yl)ethyl)-1,4-diazepan-5-yl)[$^2$H$_2$]methyl)-2-naphthamide

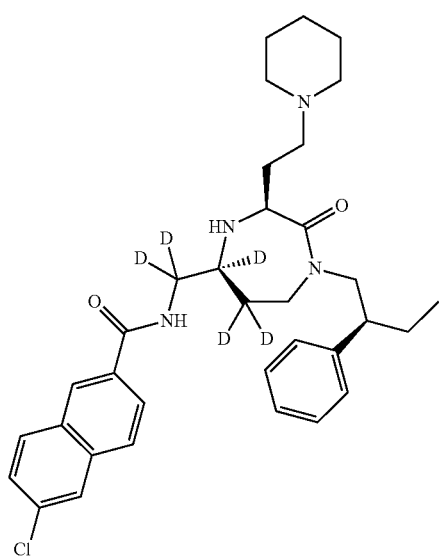

579

Compound 579 was synthesized according to the procedures in Examples 92-99, except that the Fmoc deprotection/reductive amination steps of Examples 94 and 95 were replaced by the following procedures in order to introduce the deuterium atoms.

To a solution of (S)-9-fluorenylmethyl 10-[(S)-2-phenylbutyl]-2,2-dimethyl-18-phenyl-4,9,13,16-tetraoxo-3,17-dioxa-5,10,15-triazaoctadecan-8-ylcarbamate 587 (370.5 mg, 0.47 mmol) in dry THF (7.5 ml) was added dry triethylamine (7.5 mL, 54 mmol) in one portion at room temperature followed by D$_2$O (99.96 atom % deuterium, 3.0 ml, 168 mmol). This mixture was stirred under nitrogen at room temperature for 16 h, with the reaction mixture used in the next step without isolation.

MS (ESI) 573.0 (M+1).

$t_R$ 6.95 min.

To the crude deuterium exchange reaction mixture was added NaBD$_3$CN (152 mg, 2.31 mmol) in one portion, with the reaction stirred at room temperature for 24 h. A further portion of NaBD$_3$CN (182.4 mg, 3.28 mmol) was added and stirring continued at room temperature for 24 h. The reaction was quenched by the addition of saturated NaHCO$_3$(aq) and the aqueous mixture extracted with EtOAc (3×10 mL×3). The combined organic extracts were washed with brine (15 mL), dried over MgSO$_4$ and concentrated in vacuo. Flash chromatography (60% EtOAc/Pet. Spirit) yielded the product (175.8 mg, 67%).

TLC R$_f$ 0.32 (70% EtOAc/Pet. Spirit)

Analytical HPLC $t_R$ 7.06 min; MS (ESI) m/z 558.0 (M+1), 559.0, 557.0, 560.0.

Example 101

Syntheses of Compounds 106-520

Compounds 106-520, with substituents as identified in Table 1, were prepared as in the previous examples according to the routes identified in Schemes 1-5, as summarized in Table 2, with experimental properties summarized in Table 4.

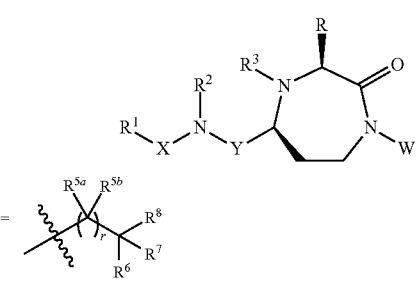

TABLE 1

Identity of Compounds

| Cpd. | R¹X | R² | R³ | Y | R | W |
|---|---|---|---|---|---|---|
| 14 | 2-naphthoyl | H | H | CH$_2$ | (CH$_2$)$_3$NHC(=NH)NH$_2$ | 3,5-dichlorobenzyl |
| 25 | 6-fluoro-2-naphthoyl | H | H | CH$_2$ | (CH$_2$)$_2$N(CH$_2$CH$_3$)$_2$ | 2,2-diphenylethyl |
| 31 | 6-fluoro-2-naphthoyl | H | H | CH$_2$ | (CH$_2$)$_2$NH$_2$ | 2,2-diphenylethyl |
| 33 | 4-chlorocinnamoyl | H | H | CH$_2$ | (CH$_2$)$_2$(1-piperidinyl) | 2,2-diphenylethyl |
| 37 | 2-naphthoyl | H | H | CH$_2$ | (CH$_2$)$_2$NH$_2$ | 2-phenylbutyl |
| 38 | 2-naphthoyl | H | H | CH$_2$ | (CH$_2$)$_2$(1-piperidinyl) | (S)-2-phenylbutyl |
| 39 | 2-naphthoyl | H | H | CH$_2$ | (CH$_2$)$_2$(1-piperidinyl) | (R)-2-phenylbutyl |
| 49 | 2-naphthoyl | H | H | CH$_2$ | (CH$_2$)$_2$NH$_2$ | 3,5-dichlorobenzyl |
| 50 | 2-naphthylsulfonyl | H | H | CH$_2$ | (CH$_2$)$_3$NHC(=NH)NH$_2$ | 2,2-diphenylethyl |
| 54 | 2-naphthoyl | H | H | CH$_2$ | (CH$_2$)$_2$NH$_2$ | 2-ethylbutyl |
| 60 | 6-bromo-2-naphthoyl | Me | H | CH$_2$ | (CH$_2$)$_3$NH$_2$ | 2,2-diphenylethyl |
| 62 | 6-bromo-2-naphthoyl | H | Me | CH$_2$ | (CH$_2$)$_3$NH$_2$ | 2,2-diphenylethyl |
| 63 | 2-naphthoyl | H | H | CH$_2$ | (CH$_2$)$_3$NH$_2$ | 2,2-diphenylethyl |
| 64 | 2-naphthoyl | H | H | CH$_2$ | (CH$_2$)$_3$(1-piperidinyl) | 2,2-diphenylethyl |
| 65 | 2-naphthoyl | H | H | CH$_2$ | (CH$_2$)$_3$NHCH(CH$_3$)$_2$ | 2,2-diphenylethyl |
| 67 | 2-naphthoyl | H | H | CH$_2$ | (CH$_2$)$_3$NHC(=NH)NHMe | 2,2-diphenylethyl |
| 71 | 2-naphthoyl | H | H | CH$_2$ | (CH$_2$)$_2$CH$_2$NHMe | 2,2-diphenylethyl |
| 79 | acetyl | H | H | (S)-CHCH$_2$-(2-naphthyl) | (CH$_2$)$_3$NHC(=NH)NH$_2$ | 2,2-diphenylethyl |
| 81 | Ac-L-His | H | H | (S)-CHCH$_2$-(2-naphthyl) | (CH$_2$)$_3$NHC(=NH)NH$_2$ | 2,2-diphenylethyl |
| 83 | propyloxycarbonyl | H | H | (S)-CHCH$_2$-(2-naphthyl) | (CH$_2$)$_3$NHC(=NH)NH$_2$ | 2,2-diphenylethyl |
| 85 | acetyl | H | H | (R)-CHCH$_2$-(2-naphthyl) | (CH$_2$)$_3$NHC(=NH)NH$_2$ | 2,2-diphenylethyl |
| 86 | Ac-L-His | H | H | (R)-CHCH$_2$-(2-naphthyl) | (CH$_2$)$_3$NHC(=NH)NH$_2$ | 2,2-diphenylethyl |
| 87 | propyloxycarbonyl | H | H | (R)-CHCH$_2$-(2-naphthyl) | (CH$_2$)$_3$NHC(=NH)NH$_2$ | 2,2-diphenylethyl |
| 105 | 2-naphthoyl | H | H | CH$_2$ | (CH$_2$)$_3$NHC(=NH)NH$_2$ | 2,2-diphenylethyl |
| 106 | 4-biphenylcarbonyl | H | H | CH$_2$ | (CH$_2$)$_3$NH$_2$ | 2,2-diphenylethyl |
| 107 | indole-2-carbonyl | H | H | CH$_2$ | (CH$_2$)$_3$NH$_2$ | 2,2-diphenylethyl |
| 108 | 4-biphenylcarbonyl | H | H | CH$_2$ | (CH$_2$)$_3$NHC(=NH)NH$_2$ | 2,2-diphenylethyl |
| 109 | indole-2-carbonyl | H | H | CH$_2$ | (CH$_2$)$_3$NHC(=NH)NH$_2$ | 2,2-diphenylethyl |
| 110 | 2-naphthylacetyl | H | H | CH$_2$ | (CH$_2$)$_3$NHC(=NH)NH$_2$ | 2,2-diphenylethyl |
| 111 | 1,2,3,4-tetrahydro-2-naphthoyl | H | H | CH$_2$ | (CH$_2$)$_3$NHC(=NH)NH$_2$ | 2,2-diphenylethyl |
| 112 | quinolin-3-carbonyl | H | H | CH$_2$ | (CH$_2$)$_3$NHC(=NH)NH$_2$ | 2,2-diphenylethyl |
| 113 | quinoxaline-2-carbonyl | H | H | CH$_2$ | (CH$_2$)$_3$NHC(=NH)NH$_2$ | 2,2-diphenylethyl |
| 114 | isoquinoline-3-carbonyl | H | H | CH$_2$ | (CH$_2$)$_3$NHC(=NH)NH$_2$ | 2,2-diphenylethyl |
| 115 | benzoyl | H | H | CH$_2$ | (CH$_2$)$_3$NHC(=NH)NH$_2$ | 2,2-diphenylethyl |
| 116 | quinaldoyl | H | H | CH$_2$ | (CH$_2$)$_3$NHC(=NH)NH$_2$ | 2,2-diphenylethyl |
| 117 | 2-naphthoyl | H | H | CH$_2$ | (CH$_2$)$_4$NH$_2$ | 1-naphthylmethyl |
| 118 | 2-naphthylacetyl | H | H | CH$_2$ | (CH$_2$)$_4$NH$_2$ | 1-naphthylmethyl |
| 119 | 1-naphthoyl | H | H | CH$_2$ | (CH$_2$)$_4$NH$_2$ | 1-naphthylmethyl |
| 120 | indole-3-acetyl | H | H | CH$_2$ | (CH$_2$)$_4$NH$_2$ | 1-naphthylmethyl |
| 121 | 4-biphenylacetyl | H | H | CH$_2$ | (CH$_2$)$_4$NH$_2$ | 2-naphthylmethyl |
| 122 | 2-naphthoyl | H | H | CH$_2$ | (CH$_2$)$_4$NH$_2$ | 2-naphthylmethyl |
| 123 | 2-naphthylacetyl | H | H | CH$_2$ | (CH$_2$)$_4$NH$_2$ | 2-naphthylmethyl |
| 124 | 1-naphthoyl | H | H | CH$_2$ | (CH$_2$)$_4$NH$_2$ | 2-naphthylmethyl |
| 125 | 1-naphthylacetyl | H | H | CH$_2$ | (CH$_2$)$_4$NH$_2$ | 2-naphthylmethyl |
| 126 | 2-naphthoyl | H | H | CH$_2$ | (CH$_2$)$_4$NH$_2$ | 2,2-diphenylethyl |
| 127 | S-Tic | H | H | CH$_2$ | (CH$_2$)$_4$NH$_2$ | 2,2-diphenylethyl |
| 128 | R-Tic | H | H | CH$_2$ | (CH$_2$)$_4$NH$_2$ | 2,2-diphenylethyl |
| 129 | 2-benzofurananoyl | H | H | CH$_2$ | (CH$_2$)$_4$NH$_2$ | 2,2-diphenylethyl |
| 130 | R-Tic | H | H | CH$_2$ | (CH$_2$)$_3$NHC(=NH)NHMe | 2,2-diphenylethyl |
| 131 | S-Tic | H | H | CH$_2$ | (CH$_2$)$_3$NHC(=NH)NH$_2$ | 2,2-diphenylethyl |
| 132 | 2-benzofuranoyl | H | H | CH$_2$ | (CH$_2$)$_3$NHC(=NH)NH$_2$ | 2,2-diphenylethyl |
| 133 | indane-2-carbonyl | H | H | CH$_2$ | (CH$_2$)$_3$NHC(=NH)NH$_2$ | 2,2-diphenylethyl |
| 134 | R-Tic | H | H | CH$_2$ | (CH$_2$)$_3$NHC(=NH)NH$_2$ | 2,2-diphenylethyl |
| 135 | benzothiophene-2-carbonyl | H | H | CH$_2$ | (CH$_2$)$_3$NHC(=NH)NH$_2$ | 2,2-diphenylethyl |
| 136 | 2,4-dichlorobenzoyl | H | H | CH$_2$ | (CH$_2$)$_3$NHC(=NH)NH$_2$ | 2,2-diphenylethyl |
| 137 | 2,5-dichlorobenzoyl | H | H | CH$_2$ | (CH$_2$)$_3$NHC(=NH)NH$_2$ | 2,2-diphenylethyl |
| 138 | benzoyl | H | H | CH$_2$ | (CH$_2$)$_3$NHC(=NH)NH$_2$ | 2,2-diphenylethyl |
| 139 | cyclohexanoyl | H | H | CH$_2$ | (CH$_2$)$_3$NHC(=NH)NH$_2$ | 2,2-diphenylethyl |
| 140 | 3-phenoxybenzoyl | H | H | CH$_2$ | (CH$_2$)$_3$NHC(=NH)NH$_2$ | 2,2-diphenylethyl |
| 141 | 4-phenoxybenzoyl | H | H | CH$_2$ | (CH$_2$)$_3$NHC(=NH)NH$_2$ | 2,2-diphenylethyl |
| 142 | indole-2-carbonyl | H | H | CH$_2$ | (CH$_2$)$_3$NHC(=NH)NH$_2$ | 2,2-diphenylethyl |
| 143 | 3-phenyl-propanoyl | H | H | CH$_2$ | (CH$_2$)$_3$NHC(=NH)NH$_2$ | 2,2-diphenylethyl |
| 144 | 3,4-dimethylbenzoyl | H | H | CH$_2$ | (CH$_2$)$_3$NHC(=NH)NH$_2$ | 2,2-diphenylethyl |
| 145 | 4-tert-butylbenzoyl | H | H | CH$_2$ | (CH$_2$)$_3$NHC(=NH)NH$_2$ | 2,2-diphenylethyl |
| 146 | 2,4-dimethoxybenzoyl | H | H | CH$_2$ | (CH$_2$)$_3$NHC(=NH)NH$_2$ | 2,2-diphenylethyl |

TABLE 1-continued

Identity of Compounds

| Cpd. | R¹X | R² | R³ | Y | R | W |
|---|---|---|---|---|---|---|
| 147 | cyclohexylacetyl | H | H | CH₂ | (CH₂)₃NHC(=NH)NH₂ | 2,2-diphenylethyl |
| 148 | piperonyloyl | H | H | CH₂ | (CH₂)₃NHC(=NH)NH₂ | 2,2-diphenylethyl |
| 149 | benzimidazole-5-carbonyl | H | H | CH₂ | (CH₂)₃NHC(=NH)NH₂ | 2,2-diphenylethyl |
| 150 | benzotriazole-5-carbonyl | H | H | CH₂ | (CH₂)₃NHC(=NH)NH₂ | 2,2-diphenylethyl |
| 151 | cyclopentanoyl | H | H | CH₂ | (CH₂)₃NHC(=NH)NH₂ | 2,2-diphenylethyl |
| 152 | 3,4-dichlorobenzoyl | H | H | CH₂ | (CH₂)₃NHC(=NH)NH₂ | 2,2-diphenylethyl |
| 153 | trans-cinnamoyl | H | H | CH₂ | (CH₂)₃NHC(=NH)NH₂ | 2,2-diphenylethyl |
| 154 | 3,5-dichlorobenzoyl | H | H | CH₂ | (CH₂)₃NHC(=NH)NH₂ | 2,2-diphenylethyl |
| 155 | 2,4-dichloro-phenylacetyl | H | H | CH₂ | (CH₂)₃NHC(=NH)NH₂ | 2,2-diphenylethyl |
| 156 | 1-methoxy-2-naphthoyl | H | H | CH₂ | (CH₂)₃NHC(=NH)NH₂ | 2,2-diphenylethyl |
| 157 | 3,4-dichloro-phenylacetyl | H | H | CH₂ | (CH₂)₃NHC(=NH)NH₂ | 2,2-diphenylethyl |
| 158 | 6-methoxy-2-naphthoyl | H | H | CH₂ | (CH₂)₃NHC(=NH)NH₂ | 2,2-diphenylethyl |
| 159 | 2-naphthoyl | H | H | CH₂ | (CH₂)₃NHC(=NH)NH₂ | 2,2-diphenylethyl |
| 160 | 2,4-dichloro-cinnamoyl | H | H | CH₂ | (CH₂)₃NHC(=NH)NH₂ | 2,2-diphenylethyl |
| 161 | adamantane-1-carbonyl | H | H | CH₂ | (CH₂)₃NHC(=NH)NH₂ | 2,2-diphenylethyl |
| 162 | phenoxyacetyl | H | H | CH₂ | (CH₂)₃NHC(=NH)NH₂ | 2,2-diphenylethyl |
| 163 | 3-methoxy-2-napthoyl | H | H | CH₂ | (CH₂)₃NHC(=NH)NH₂ | 2,2-diphenylethyl |
| 164 | 4-bromobenzoyl | H | H | CH₂ | (CH₂)₃NHC(=NH)NH₂ | 2,2-diphenylethyl |
| 165 | S-benzodioxan-2-carbonyl | H | H | CH₂ | (CH₂)₃NHC(=NH)NH₂ | 2,2-diphenylethyl |
| 166 | 4-chlorocinnamoyl | H | H | CH₂ | (CH₂)₃NHC(=NH)NH₂ | 2,2-diphenylethyl |
| 167 | 3-(2-thienyl)acryloyl | H | H | CH₂ | (CH₂)₃NHC(=NH)NH₂ | 2,2-diphenylethyl |
| 168 | R-benzodioxan-2-carbonyl | H | H | CH₂ | (CH₂)₃NHC(=NH)NH₂ | 2,2-diphenylethyl |
| 169 | 4-hydroxycinnamoyl | H | H | CH₂ | (CH₂)₃NHC(=NH)NH₂ | 2,2-diphenylethyl |
| 170 | 2-methoxycinnamoyl | H | H | CH₂ | (CH₂)₃NHC(=NH)NH₂ | 2,2-diphenylethyl |
| 171 | 4-methylcinnamoyl | H | H | CH₂ | (CH₂)₃NHC(=NH)NH₂ | 2,2-diphenylethyl |
| 172 | 2-trifluoromethyl-cinnamoyl | H | H | CH₂ | (CH₂)₂NHC(=NH)NH₂ | 2,2-diphenylethyl |
| 173 | 3-fluorocinnamoyl | H | H | CH₂ | (CH₂)₃NHC(=NH)NH₂ | 2,2-diphenylethyl |
| 174 | alpha-methyl cinnamoyl | H | H | CH₂ | (CH₂)₃NHC(=NH)NH₂ | 2,2-diphenylethyl |
| 175 | trans-2-phenylcyclopropane-1-carbonyl | H | H | CH₂ | (CH₂)₃NHC(=NH)NH₂ | 2,2-diphenylethyl |
| 176 | 2,4-dichloro-phenoxyacetyl | H | H | CH₂ | (CH₂)₃NHC(=NH)NH₂ | 2,2-diphenylethyl |
| 177 | 3-chlorocinnamoyl | H | H | CH₂ | (CH₂)₃NHC(=NH)NH₂ | 2,2-diphenylethyl |
| 178 | 1,3-benzothiazole-6-carbonyl | H | H | CH₂ | (CH₂)₃NHC(=NH)NH₂ | 2,2-diphenylethyl |
| 179 | 5-phenyl-2-furoyl | H | H | CH₂ | (CH₂)₃NHC(=NH)NH₂ | 2,2-diphenylethyl |
| 180 | 3-methoxycinnamoyl | H | H | CH₂ | (CH₂)₃NHC(=NH)NH₂ | 2,2-diphenylethyl |
| 181 | 6-bromo-2-naphthoyl | H | H | CH₂ | (CH₂)₃NHC(=NH)NH₂ | 2,2-diphenylethyl |
| 182 | 2-naphthoyl | H | H | CH₂ | (CH₂)₃NHC(=NH)NH₂ | phenethyl |
| 183 | 2-naphthoyl | H | H | CH₂ | (CH₂)₃NHC(=NH)NH₂ | 3,4-dichlorophenethyl |
| 184 | 2-naphthoyl | H | H | CH₂ | (CH₂)₃NHC(=NH)NH₂ | 2,4-dichlorophenethyl |
| 185 | benzothiophene-5-carbonyl | H | H | CH₂ | (CH₂)₃NHC(=NH)NH₂ | 2,2-diphenylethyl |
| 186 | 3-methyl-2-phenyl-pyrazole-4-carbonyl | H | H | CH₂ | (CH₂)₃NHC(=NH)NH₂ | 2,2-diphenylethyl |
| 187 | 4-methoxycinnamoyl | H | H | CH₂ | (CH₂)₃NHC(=NH)NH₂ | 2,2-diphenylethyl |
| 188 | 6-fluoro-2-naphthoyl | H | H | CH₂ | (CH₂)₃NHC(=NH)NH₂ | 2,2-diphenylethyl |
| 189 | 2-chlorocinnamoyl | H | H | CH₂ | (CH₂)₃NHC(=NH)NH₂ | 2,2-diphenylethyl |
| 190 | 2-hydroxycinnamoyl | H | H | CH₂ | (CH₂)₃NHC(=NH)NH₂ | 2,2-diphenylethyl |
| 191 | 3-methylcinnamoyl | H | H | CH₂ | (CH₂)₃NHC(=NH)NH₂ | 2,2-diphenylethyl |
| 192 | 3-trifluoromethyl-cinnamoyl | H | H | CH₂ | (CH₂)₃NHC(=NH)NH₂ | 2,2-diphenylethyl |
| 193 | 3-hydroxycinnamoyl | H | H | CH₂ | (CH₂)₃NHC(=NH)NH₂ | 2,2-diphenylethyl |
| 194 | 2-fluorocinnamoyl | H | H | CH₂ | (CH₂)₃NHC(=NH)NH₂ | 2,2-diphenylethyl |
| 195 | 2-methylcinnamoyl | H | H | CH₂ | (CH₂)₃NHC(=NH)NH₂ | 2,2-diphenylethyl |
| 196 | alpha-fluorocinnamoyl | H | H | CH₂ | (CH₂)₃NHC(=NH)NH₂ | 2,2-diphenylethyl |
| 197 | 2-naphthoyl | H | H | CH₂ | 4-piperidinyl | 2,2-diphenylethyl |
| 198 | 2-naphthoyl | H | H | CH₂ | CH₂(4-piperidinyl) | 2,2-diphenylethyl |
| 199 | 4-fluorocinnamoyl | H | H | CH₂ | (CH₂)₃NHC(=NH)NH₂ | 2,2-diphenylethyl |
| 200 | 4-trifluoromethyl-cinnamoyl | H | H | CH₂ | (CH₂)₃NHC(=NH)NH₂ | 2,2-diphenylethyl |
| 201 | 2-naphthoyl | H | H | CH₂ | (CH₂)₃NHC(=NH)NH₂ | 2,2-diphenylpropyl |
| 202 | 2-naphthoyl | H | H | CH₂ | (CH₂)₃NHC(=NH)NH₂ | cyclohexanemethyl |

TABLE 1-continued

Identity of Compounds

| Cpd. | R¹X | R² | R³ | Y | R | W |
|------|-----|----|----|---|---|---|
| 203 | 2-naphthoyl | H | H | $CH_2$ | $(CH_2)_3NHC(=NH)NH_2$ | 1-adamantane-methyl |
| 204 | 2-naphthoyl | H | H | $CH_2$ | $(CH_2)_3NHC(=NH)NH_2$ | (S)-1,1-diphenyl-2-propyl |
| 205 | 2-naphthoyl | H | H | $CH_2$ | $(CH_2)_3NHC(=NH)NH_2$ | (R)-1,1-diphenyl-2-propyl |
| 206 | 2-naphthoyl | H | H | $CH_2$ | $(CH_2)_3NHC(=NH)NH_2$ | cyclohexyl |
| 207 | 2-naphthoyl | H | H | $CH_2$ | $(CH_2)_3NHC(=NH)NH_2$ | (R)-1,1-diphenyl-1-fluoro-2-propyl |
| 208 | 2,6-difluorocinnamoyl | H | H | $CH_2$ | $(CH_2)_3NHC(=NH)NH_2$ | 2,2-diphenylethyl |
| 209 | 2-chloro-6-fluorocinnamoyl | H | H | $CH_2$ | $(CH_2)_3NHC(=NH)NH_2$ | 2,2-diphenylethyl |
| 210 | 4-bromocinnamoyl | H | H | $CH_2$ | $(CH_2)_3NHC(=NH)NH_2$ | 2,2-diphenylethyl |
| 211 | 4-ethoxycinnamoyl | H | H | $CH_2$ | $(CH_2)_3NHC(=NH)NH_2$ | 2,2-diphenylethyl |
| 212 | 6-bromonaphthoyl | H | H | $CH_2$ | $(CH_2)_3NH_2$ | 2,2-diphenylethyl |
| 213 | trans-cinnamoyl | H | H | $CH_2$ | $(CH_2)_3NH_2$ | 2,2-diphenylethyl |
| 214 | 4-chlorocinnamoyl | H | H | $CH_2$ | $(CH_2)_3NH_2$ | 2,2-diphenylethyl |
| 215 | 1,4-dimethoxy-2-naphthoyl | H | H | $CH_2$ | $(CH_2)_3NHC(=NH)NH_2$ | 2,2-diphenylethyl |
| 216 | 2-naphthoyl | H | H | $CH_2$ | $(CH_2)_3NHC(=NH)N(Me)_2$ | 2,2-diphenylethyl |
| 217 | 6-hydroxy-2-naphthoyl | H | H | $CH_2$ | $(CH_2)_3NHC(=NH)NH_2$ | 2,2-diphenylethyl |
| 218 | 6-amino-2-naphthoyl | H | H | $CH_2$ | $(CH_2)_3NHC(=NH)NH_2$ | 2,2-diphenylethyl |
| 219 | 4-Me cinnamoyl | H | H | $CH_2$ | $(CH_2)_3NH_2$ | 2,2-diphenylethyl |
| 220 | 4-fluoro cinnamoyl | H | H | $CH_2$ | $(CH_2)_3NH_2$ | 2,2-diphenylethyl |
| 221 | 6-fluoro-2-napthoyl | H | H | $CH_2$ | $(CH_2)_3NH_2$ | 2,2-diphenylethyl |
| 222 | 2-ethylhexanoyl | H | H | $CH_2$ | $(CH_2)_3NH_2$ | 2,2-diphenylethyl |
| 223 | 3,4-dimethylbenzoyl | H | H | $CH_2$ | $(CH_2)_3NH_2$ | 2,2-diphenylethyl |
| 224 | 3,4-dichlorobenzoyl | H | H | $CH_2$ | $(CH_2)_3NH_2$ | 2,2-diphenylethyl |
| 225 | 2-ethylhexanoyl | H | H | $CH_2$ | $(CH_2)_3NHC(=NH)NH_2$ | 2,2-diphenylethyl |
| 226 | 2-naphthoyl | H | H | $CH_2$ | $(CH_2)_3NH(cyclohexyl)$ | 2,2-diphenylethyl |
| 227 | 2-naphthoyl | H | H | $CH_2$ | $(CH_2)_3NHC(=NH)NH_2$ | 2-naphthyl |
| 228 | 2-naphthoyl | H | H | $CH_2$ | $(CH_2)_3NHC(=NH)NH_2$ | (9-fluorenyl)methyl |
| 229 | 2-naphthoyl | H | H | $CH_2$ | $CH_2(3\text{-pyridinyl})$ | 2,2-diphenylethyl |
| 230 | 2-naphthoyl | H | H | $CH_2$ | $CH_2(4\text{-pyridinyl})$ | 2,2-diphenylethyl |
| 231 | 4-fluorocinnamoyl | H | H | $CH_2$ | $(CH_2)_3NH(cyclohexyl)$ | 2,2-diphenylethyl |
| 232 | 2-naphthoyl | H | H | $CH_2$ | $(CH_2)_4NHCH(CH_3)_2$ | 2,2-diphenylethyl |
| 233 | 2,4-difluorocinnamoyl | H | H | $CH_2$ | $(CH_2)_3NH_2$ | 2,2-diphenylethyl |
| 234 | 4-cyanocinnamoyl | H | H | $CH_2$ | $(CH_2)_3NH_2$ | 2,2-diphenylethyl |
| 235 | 3-(2-naphthyl)acryloyl | H | H | $CH_2$ | $(CH_2)_3NH_{22}$ | 2,2-diphenylethyl |
| 236 | 4-fluoro-phenoxyacetyl | H | H | $CH_2$ | $(CH_2)_3NH_2$ | 2,2-diphenylethyl |
| 237 | 5-(4-chlorophenyl)-2-furoyl | H | H | $CH_2$ | $(CH_2)_3NH_2$ | 2,2-diphenylethyl |
| 238 | 4-(pyrrol-1-yl)-benzoyl | H | H | $CH_2$ | $(CH_2)_3NH_2$ | 2,2-diphenylethyl |
| 239 | 2-oxo-1-phenyl-pyrrolidine-3-carbonyl | H | H | $CH_2$ | $(CH_2)_3NH_2$ | 2,2-diphenylethyl |
| 240 | 5-(4-chlorophenyl)-isoxazole-3-carbonyl | H | H | $CH_2$ | $(CH_2)_3NH_2$ | 2,2-diphenylethyl |
| 241 | 5-(2-furyl)-isoxazole-3-carbonyl | H | H | $CH_2$ | $(CH_2)_3NH_2$ | 2,2-diphenylethyl |
| 242 | 2-phenyl-4-thiazole carbonyl | H | H | $CH_2$ | $(CH_2)_3NH_2$ | 2,2-diphenylethyl |
| 243 | 4-(3,5-dimethyl1H-pyrazol-1-yl) benzoyl | H | H | $CH_2$ | $(CH_2)_3NH_2$ | 2,2-diphenylethyl |
| 244 | 3-methyl-2-phenyl pyrazole-4-carbonyl | H | H | $CH_2$ | $(CH_2)_3NH_2$ | 2,2-diphenylethyl |
| 245 | 2-naphthoyl | H | H | $CH_2$ | $(CH_2)_3NHC(=NH)NH_2$ | cyclohexaneethyl |
| 246 | 2-naphthoyl | H | H | $CH_2$ | $(CH_2)_3NHC(=NH)NH_2$ | 2-norbornaneethyl |
| 247 | 2-naphthoyl | H | H | $CH_2$ | $(CH_2)_3NHC(=NH)NH_2$ | 2,2-bis(4-methoxyphenyl)ethyl |
| 248 | 2-naphthoyl | H | H | $CH_2$ | $(CH_2)_4NHCH_2Ph$ | 2,2-diphenylethyl |
| 249 | 2-naphthoyl | H | H | $CH_2$ | $(CH_2)_4NH(cyclopentyl)$ | 2,2-diphenylethyl |
| 250 | 2-naphthoyl | H | H | $CH_2$ | $(CH_2)_4NH(cyclobutyl)$ | 2,2-diphenylethyl |
| 251 | 2-naphthoyl | H | H | $CH_2$ | $CH_2)_4NH(cyclobutyl)_2$ | 2,2-diphenylethyl |
| 252 | 2-naphthoyl | H | H | $CH_2$ | $(CH_2)_3NHC(=NH)NH_2$ | benzyl |
| 253 | 2-naphthoyl | H | H | $CH_2$ | $(CH_2)_3NHC(=NH)NH_2$ | 2,2-bis(4-fluorophenyl)ethyl |
| 254 | 2-naphthoyl | H | H | $CH_2$ | $(CH_2)_3NHC(=NH)NH_2$ | 2-naphthalenemethyl |
| 255 | 3-(5-methyl-2-thienyl)-acryloyl | H | H | $CH_2$ | $(CH_2)_3NH_2$ | 2,2-diphenylethyl |
| 256 | 5-phenyl-pyrazole-3-carbonyl | H | H | $CH_2$ | $(CH_2)_3NH_2$ | 2,2-diphenylethyl |
| 257 | 4-fluorocinnamoyl | Me | H | $CH_2$ | $(CH_2)_3NH_2$ | 2,2-diphenylethyl |
| 258 | 4-fluorocinnamoyl | H | Me | $CH_2$ | $(CH_2)_3NH_2$ | 2,2-diphenylethyl |
| 259 | 4-(3-methyl-5-oxo-2-pyrazolin-1yl)benzoyl | H | H | $CH_2$ | $(CH_2)_3NH_2$ | 2,2-diphenylethyl |

TABLE 1-continued

Identity of Compounds

| Cpd. | R¹X | R² | R³ | Y | R | W |
|---|---|---|---|---|---|---|
| 260 | 4-bromocinnamoyl | H | H | $CH_2$ | $(CH_2)_3NH_2$ | 2,2-diphenylethyl |
| 261 | 4-chlorocinnamoyl | H | H | $CH_2$ | $(CH_2)_3$(1-pyrrolidinyl) | 2,2-diphenylethyl |
| 262 | 4-chlorocinnamoyl | H | H | $CH_2$ | $(CH_2)_3$(1-piperidinyl) | 2,2-diphenylethyl |
| 263 | 2-naphthoyl | H | H | $CH_2$ | $(CH_2)_2NH_2$ | 2,2-diphenylethyl |
| 264 | 2-naphthoyl | H | H | $CH_2$ | $(CH_2)_3$(1-pyrrolidinyl) | 2,2-diphenylethyl |
| 265 | 2-naphthoyl | H | H | $CH_2$ | $(CH_2)_3$(1-azetidinyl) | 2,2-diphenylethyl |
| 266 | 2-naphthoyl | H | H | $CH_2$ | $(CH_2)_3NHC(=NH)NH_2$ | 1-naphthalenemethyl |
| 267 | 2-naphthoyl | H | H | $CH_2$ | $(CH_2)_3NHC(=NH)NH_2$ | 2-(2-naphthyl)ethyl |
| 268 | 2-naphthoyl | H | H | $CH_2$ | $(CH_2)_3NHC(=NH)NH_2$ | (S)-$CH_2CH(Ph)NHCOMe$ |
| 269 | trans-cinnamoyl | H | H | $CH_2$ | $(CH_2)3$(1-piperidinyl) | 2,2-diphenylethyl |
| 270 | 3,4-dimethylbenzoyl | H | H | $CH_2$ | $(CH_2)_3$(1-piperidinyl) | 2,2-diphenylethyl |
| 271 | 3,4-dichlorobenzoyl | H | H | $CH_2$ | $(CH_2)_3$(1-piperidinyl) | 2,2-diphenylethyl |
| 272 | 2-naphthoyl | H | H | $CH_2$ | $(CH_2)_3NHC(=NH)NH_2$ | (S)-$CH_2CH(Ph)$-NHCOcBu |
| 273 | 2-naphthoyl | H | H | $CH_2$ | $(CH_2)_3NHC(=NH)NH_2$ | (S)-$CH_2CH(Ph)$-NHCOcHex |
| 274 | 2-naphthoyl | H | H | $CH_2$ | $CH_2NH_2$ | 2,2-diphenylethyl |
| 275 | 4-chlorocinnamoyl | H | H | $CH_2$ | $CH_2NH_2$ | 2,2-diphenylethyl |
| 276 | 4-fluorocinnamoyl | H | H | $CH_2$ | $(CH_2)_2NH_2$ | 2,2-diphenylethyl |
| 277 | 4-methylcinnamoyl | H | H | $CH_2$ | $(CH_2)_2NH_2$ | 2,2-diphenylethyl |
| 278 | 2-naphthoyl | H | H | $CH_2$ | $CH_2$(1-piperidinyl) | 2,2-diphenylethyl |
| 279 | 4-chlorocinnamoyl | H | H | $CH_2$ | $CH_2$(1-piperidinyl) | 2,2-diphenylethyl |
| 280 | 3,4-dichlorobenzoyl | H | H | $CH_2$ | $(CH_2)_2NH_2$ | 2,2-diphenylethyl |
| 281 | 3,4-dimethylbenzoyl | H | H | $CH_2$ | $(CH_2)_2NH_2$ | 2,2-diphenylethyl |
| 282 | trans-cinnamoyl | H | H | $CH_2$ | $(CH_2)_2NH_2$ | 2,2-diphenylethyl |
| 283 | 4-chlorocinnamoyl | H | H | $CH_2$ | $(CH_2)_2NH_2$ | 2,2-diphenylethyl |
| 284 | 3,4-dichlorobenzoyl | H | H | $CH_2$ | $(CH_2)_2$(1-piperidinyl) | 2,2-diphenylethyl |
| 285 | 3,4-dimethylbenzoyl | H | H | $CH_2$ | $(CH_2)_2$(1-piperidinyl) | 2,2-diphenylethyl |
| 286 | trans-cinnamoyl | H | H | $CH_2$ | $(CH_2)_2$(1-piperidinyl) | 2,2-diphenylethyl |
| 287 | 4-fluorocinnamoyl | H | H | $CH_2$ | $(CH_2)_2$(1-piperidinyl) | 2,2-diphenylethyl |
| 288 | 4-methylcinnamoyl | H | H | $CH_2$ | $(CH_2)_2$(1-piperidinyl) | 2,2-diphenylethyl |
| 289 | 2-naphthoyl | H | H | $CH_2$ | $(CH_2)_3NHC(=NH)NH_2$ | 3,5-dimethylbenzyl |
| 290 | 2-naphthoyl | H | H | $CH_2$ | $(CH_2)_3NHC(=NH)NH_2$ | (S)-$CH_2CH(Ph)NHCOPh$ |
| 291 | 2-naphthoyl | H | H | $CH_2$ | $(CH_2)_3NHC(=NH)NH_2$ | (R)-$CH_2CH(Ph)NHCOPh$ |
| 292 | 2-naphthoyl | H | H | $CH_2$ | $(CH_2)_3NHC(=NH)NH_2$ | $CH_2CH(Ph)OMe$ |
| 293 | 2-naphthoyl | H | H | $CH_2$ | $(CH_2)_3NHC(=NH)NH_2$ | $CH_2CH(Ph)OnPr$ |
| 294 | 2-naphthoyl | H | H | $CH_2$ | $(CH_2)_3NHC(=NH)NH_2$ | $CH_2CH(Ph)OBn$ |
| 295 | 2-naphthoyl | H | H | $CH_2$ | $(CH_2)_3NHC(=NH)NH_2$ | $CH_2CH(Ph)Oallyl$ |
| 296 | 2-naphthoyl | H | H | $CH_2$ | $(CH_2)_3CH_3$ | 2,2-diphenylethyl |
| 297 | 4-chlorocinnamoyl | H | H | $CH_2$ | $(CH_2)_3CH_3$ | 2,2-diphenylethyl |
| 298 | 4-chlorocinnamoyl | H | H | $CH_2$ | $(CH_2)_2CONH_2$ | 2,2-diphenylethyl |
| 299 | 2-naphthoyl | H | H | $CH_2$ | $(CH_2)_2CONH_2$ | 2,2-diphenylethyl |
| 300 | 4-methylcinnamoyl | H | H | $CH_2$ | $(CH_2)_3NHCOCH_3$ | 2,2-diphenylethyl |
| 301 | 4-methylcinnamoyl | H | H | $CH_2$ | $(CH_2)_3$NHCO(cyclohexyl) | 2,2-diphenylethyl |
| 302 | 2-naphthoyl | H | H | $CH_2$ | $(CH_2)_3NHC(=NH)NH_2$ | $CH_2CH(Ph)OPh$ |
| 303 | 2-naphthoyl | H | H | $CH_2$ | $(CH_2)_3NHC(=NH)NH_2$ | $CH_2CH(Ph)CO_2Et$ |
| 304 | 2-naphthoyl | H | H | $CH_2$ | $(CH_2)_3NHC(=NH)NH_2$ | 2-ethylbutyl |
| 305 | 2-naphthoyl | H | H | $CH_2$ | $(CH_2)_3NHC(=NH)NH_2$ | 3,5-dimethyl-cyclohexylmethyl |
| 306 | 4-chlorocinnamoyl | H | H | $CH_2$ | $(CH_2)_2$NHCO(cyclohexyl) | 2,2-diphenylethyl |
| 307 | 4-chlorocinnamoyl | H | H | $CH_2$ | $(CH_2)_2NHCOCH_2$(cyclohexyl) | 2,2-diphenylethyl |
| 308 | benzoyl | H | H | $(CH_2)_2$ | $(CH_2)_2NH_2$ | 2,2-diphenylethyl |
| 309 | 3,4-dichlorobenzoyl | H | H | $(CH_2)_2$ | $(CH_2)_2NH_2$ | 2,2-diphenylethyl |
| 310 | 2-naphthoyl | H | H | $(CH_2)_2$ | $(CH_2)_2NH_2$ | 2,2-diphenylethyl |
| 311 | benzoyl | H | H | $(CH_2)_2$ | $(CH_2)_2$(1-piperidinyl) | 2,2-diphenylethyl |
| 312 | 3,4-dichlorobenzoyl | H | H | $(CH_2)_2$ | $(CH_2)_2$(1-piperidinyl) | 2,2-diphenylethyl |
| 313 | 2-naphthoyl | H | H | $(CH_2)_2$ | $(CH_2)_2$(1-piperidinyl) | 2,2-diphenylethyl |
| 314 | 2-naphthoyl | H | H | $CH_2$ | $(CH_2)_3NHC(=NH)NH_2$ | $CH_2CH(Ph)CONMe_2$ |
| 315 | 2-naphthoyl | H | H | $CH_2$ | $CH_2$cyclohexyl | 2,2-diphenylethyl |
| 316 | 4-chlorocinnamoyl | H | H | $CH_2$ | $CH_2$cyclohexyl | 2,2-diphenylethyl |
| 317 | 2-naphthoyl | H | H | $CH_2$ | $(CH_2)_2CO$(1-piperidinyl) | 2,2-diphenylethyl |
| 318 | 4-chlorocinnamoyl | H | H | $CH_2$ | $(CH_2)_2CO$(1-piperidinyl) | 2,2-diphenylethyl |
| 319 | 2-naphthoyl | H | H | $CH_2$ | $CH_2CH_2Ph$ | 2,2-diphenylethyl |
| 320 | 4-chlorocinnamoyl | H | H | $CH_2$ | $CH_2CH_2Ph$ | 2,2-diphenylethyl |
| 321 | 2-naphthoyl | H | H | $CH_2$ | $(CH_2)_2$cyclohexyl | 2,2-diphenylethyl |
| 322 | 4-chlorocinnamoyl | H | H | $CH_2$ | $(CH_2)_2$cyclohexyl | 2,2-diphenylethyl |
| 323 | 2-naphthoyl | H | H | $CH_2$ | $CH_2Ph$ | 2,2-diphenylethyl |
| 324 | 4-chlorocinnamoyl | H | H | $CH_2$ | $CH_2Ph$ | 2,2-diphenylethyl |
| 325 | 3,4-dichlorobenzoyl | H | H | $CH_2$ | $(CH_2)_2NH_2$ | 3,5-dichlorobenzyl |
| 326 | 4-chlorocinnamoyl | H | H | $CH_2$ | $(CH_2)_2NH_2$ | 3,5-dichlorobenzyl |
| 327 | 2-naphthoyl | H | H | $CH_2$ | $(CH_2)_3NHC(=NH)NH_2$ | 3-chloro-5-fluorobenzyl |

TABLE 1-continued

Identity of Compounds

| Cpd. | R¹X | R² | R³ | Y | R | W |
|---|---|---|---|---|---|---|
| 328 | 2-naphthoyl | H | H | $CH_2$ | $(CH_2)_3NHC(=NH)NH_2$ | 3,5-difluorobenzyl |
| 329 | 2-naphthoyl | H | H | $CH_2$ | $(CH_2)_3NH_2$ | 3-chloro-5-fluorobenzyl |
| 330 | 2-naphthoyl | H | H | $CH_2$ | $(CH_2)_3NH_2$ | 3,5-difluorobenzyl |
| 331 | 2-naphthoyl | H | H | $CH_2$ | $(CH_2)_3NH_2$ | 2,5-dichlorobenzyl |
| 332 | 2-naphthoyl | H | H | $CH_2$ | $(CH_2)_3NH_2$ | 2,6-dichlorobenzyl |
| 333 | 2-naphthoyl | H | H | $CH_2$ | $(CH_2)_3NH_2$ | 3,5-dimethoxybenzyl |
| 334 | 2-naphthoyl | H | H | $CH_2$ | $(CH_2)_3NH_2$ | 2-chlorobenzyl |
| 335 | 2-naphthoyl | H | H | $CH_2$ | $(CH_2)_3NH_2$ | 2,3-dichlorobenzyl |
| 336 | 2-naphthoyl | H | H | $CH_2$ | $(CH_2)_3NH_2$ | 2,4-dichlorobenzyl |
| 337 | 2-naphthoyl | H | H | $CH_2$ | $(CH_2)_3NH_2$ | 3,4-dichlorobenzyl |
| 338 | 2-naphthoyl | H | H | $CH_2$ | $(CH_2)_3NH_2$ | 3-fluoro-5-methylbenzyl |
| 339 | 2-naphthoyl | H | H | $CH_2$ | $(CH_2)_3NH_2$ | 3-fluoro-5-(trifluoromethyl)-benzyl |
| 340 | 2-naphthoyl | H | H | $CH_2$ | $(CH_2)_3NH_2$ | 4-chlorobenzyl |
| 341 | 2-naphthoyl | H | H | $CH_2$ | $(CH_2)_3NH_2$ | 2-phenylbutyl |
| 342 | 2-naphthoyl | H | H | $CH_2$ | $(CH_2)_3NH_2$ | 1-(1-phenyl-cyclohexyl)-methyl |
| 343 | 3,4-dichlorobenzoyl | H | H | $CH_2$ | $(CH_2)_2(1\text{-piperidinyl})$ | 3,5-dichlorobenzyl |
| 344 | 2-naphthoyl | H | H | $CH_2$ | $(CH_2)_2(1\text{-piperidinyl})$ | 3,5-dichlorobenzyl |
| 345 | 4-chlorocinnamoyl | H | H | $CH_2$ | $(CH_2)_2(1\text{-piperidinyl})$ | 3,5-dichlorobenzyl |
| 346 | 3,4-dichlorobenzoyl | H | H | $CH_2$ | $(CH_2)_2NH_2$ | 2-ethylbutyl |
| 347 | 4-chlorocinnamoyl | H | H | $CH_2$ | $(CH_2)_2NH_2$ | 2-ethylbutyl |
| 348 | 4-chlorocinnamoyl | H | H | $CH_2$ | $(CH_2)_2(1\text{-piperidinyl})$ | 2-ethylbutyl |
| 349 | 3,4-dichlorobenzoyl | H | H | $CH_2$ | $(CH_2)_2(1\text{-piperidinyl})$ | 2-ethylbutyl |
| 350 | 2-naphthoyl | H | H | $CH_2$ | $(CH_2)_2(1\text{-piperidinyl})$ | 2-ethylbutyl |
| 351 | 4-chloro-3-fluoro-benzoyl | H | H | $CH_2$ | $(CH_2)_2NH_2$ | 2-ethylbutyl |
| 352 | 4-chloro-3-methyl-benzoyl | H | H | $CH_2$ | $(CH_2)_2NH_2$ | 2-ethylbutyl |
| 353 | 3-chloro-4-fluoro-benzoyl | H | H | $CH_2$ | $(CH_2)_2NH_2$ | 2-ethylbutyl |
| 354 | 3-chloro-4-methyl-benzoyl | H | H | $CH_2$ | $(CH_2)_2NH_2$ | 2-ethylbutyl |
| 355 | 4-chlorocinnamoyl | H | H | $CH_2$ | $CH_2(1\text{-piperidinyl})$ | 2-ethylbutyl |
| 356 | 2-naphthoyl | H | H | $(CH_2)_2$ | $CH_2CH_2(1\text{-pyrrolidinyl})$ | 2,2-diphenylethyl |
| 357 | 2-naphthoyl | H | H | $CH_2$ | $(CH_2)_3NH_2$ | 3,5-bis(trifluoromethyl)-benzyl |
| 358 | 2-naphthoyl | H | H | $CH_2$ | $(CH_2)_3NH_2$ | 3-chlorobenzyl |
| 359 | 2-naphthoyl | H | H | $CH_2$ | $(CH_2)_3(1\text{-piperidinyl})$ | 2-phenylbutyl |
| 360 | 2-naphthoyl | H | H | $CH_2$ | $(CH_2)_3NHC(=NH)NH_2$ | $CH_2CH(Ph)CON[-(CH_2)_5-]$ |
| 361 | 2-naphthoyl | H | H | $CH_2$ | $(CH_2)_3NHC(=NH)NH_2$ | $CH_2CH(Ph)CONHPh$ |
| 362 | 3,4-dichlorobenzoyl | H | H | $(CH_2)_2$ | $(CH_2)_2NHCH(CH_3)_2$ | 2,2-diphenylethyl |
| 363 | 3,4-dichlorobenzoyl | H | H | $(CH_2)_2$ | $(CH_2)_2N(CH(CH_3)_2)_2$ | 2,2-diphenylethyl |
| 364 | 3,4-dichlorobenzoyl | H | H | $CH_2$ | $CH_2NH_2$ | 3,5-dichlorobenzyl |
| 365 | 2-naphthoyl | H | H | $CH_2$ | $CH_2NH_2$ | 3,5-dichlorobenzyl |
| 366 | 4-chlorocinnamoyl | H | H | $CH_2$ | $CH_2NH_2$ | 3,5-dichlorobenzyl |
| 367 | 3,4-dichlorobenzoyl | H | H | $CH_2$ | $CH_2(1\text{-piperidinyl})$ | 3,5-dichlorobenzyl |
| 368 | 4-chlorocinnamoyl | H | H | $CH_2$ | $CH_2(1\text{-piperidinyl})$ | 3,5-dichlorobenzyl |
| 369 | 3,4-dichlorobenzoyl | H | H | $CH_2$ | $(CH_2)_2NH_2$ | 2-phenylbutyl |
| 370 | 4-chlorocinnamoyl | H | H | $CH_2$ | $(CH_2)_2NH_2$ | 2-phenylbutyl ( |
| 371 | 3,4-dichlorobenzoyl | H | H | $CH_2$ | $CH_2(1\text{-pyrrolidinyl})$ | 3,5-dichlorobenzyl |
| 372 | 2-naphthoyl | H | H | $CH_2$ | $CH_2(1\text{-pyrrolidinyl})$ | 3,5-dichlorobenzyl |
| 373 | 2-naphthoyl | H | H | $CH_2$ | $(CH_2)_3NH_2$ | (S)-β-methylphenethyl |
| 374 | 2-naphthoyl | H | H | $CH_2$ | $(CH_2)_2CH_2NH_2$ | (R)-β-methylphenethyl |
| 375 | 2-naphthoyl | H | H | $CH_2$ | $(CH_2)_2N(CH_3)_2$ | 2,2-diphenylethyl |
| 376 | 6-fluoro-2-napthoyl | H | H | $CH_2$ | $(CH_2)_3(1\text{-piperidinyl})$ | 2,2-diphenylethyl |
| 377 | 2-naphthoyl | H | H | $CH_2$ | $(CH_2)_3NH_2$ | 3,5-diethynylbenzyl |
| 378 | 4-chlorocinnamoyl | H | H | $CH_2$ | $(CH_2)_2N(CH_2CH_2)_2$ | 2,2-diphenylethyl |
| 379 | 2-naphthoyl | H | H | $CH_2$ | $(CH_2)_2N(CH_2CH_2)_2$ | 2,2-diphenylethyl |
| 380 | 3,4-dichlorobenzoyl | H | H | $CH_2$ | $(CH_2)_2(1\text{-piperidinyl})$ | (R)-2-phenylbutyl |
| 381 | 4-chlorocinnamoyl | H | H | $CH_2$ | $(CH_2)_2(1\text{-piperidinyl})$ | (R)-2-phenylbutyl |
| 382 | 4-chlorocinnamoyl | H | H | $CH_2$ | $(CH_2)_2(1\text{-piperidinyl})$ | (S)-2-phenylbutyl |
| 383 | 6-chloro-2-naphthoyl | H | H | $CH_2$ | $(CH_2)_2NH_2$ | 2,2-diphenylethyl |
| 384 | 2-naphthoyl | H | H | $CH_2$ | $(CH_2)_2(1\text{-pyrrolidinyl})$ | 2,2-diphenylethyl |
| 385 | 2-naphthoyl | H | H | $CH_2$ | $(CH_2)_2(1\text{-pyrrolidinyl})$ | 2,2-diphenylethyl |
| 386 | 6-fluoro-2-naphthoyl | H | H | $CH_2$ | $(CH_2)_2NH_2$ | 2-ethylbutyl |
| 387 | 6-chloro-2-naphthoyl | H | H | $CH_2$ | $(CH_2)_2NH_2$ | 2-ethylbutyl |
| 388 | 6-bromo-2-naphthoyl | H | H | $CH_2$ | $(CH_2)_2NH_2$ | 2-ethylbutyl |
| 389 | 6-fluoro-2-naphthoyl | H | H | $CH_2$ | $(CH_2)_2(1\text{-piperidinyl})$ | 2-ethylbutyl |
| 390 | 6-chloro-2-naphthoyl | H | H | $CH_2$ | $(CH_2)_2(1\text{-piperidinyl})$ | 2-ethylbutyl |
| 391 | 6-bromo-2-naphthoyl | H | H | $CH_2$ | $(CH_2)_2(1\text{-piperidinyl})$ | 2-ethylbutyl |

TABLE 1-continued

Identity of Compounds

| Cpd. | R¹X | R² | R³ | Y | R | W |
|---|---|---|---|---|---|---|
| 392 | 3,4-dichlorobenzoyl | H | H | $CH_2$ | $(CH_2)_2NH_2$ | 3,5-dimethyl-cyclohexyl |
| 393 | 2-naphthoyl | H | H | $CH_2$ | $(CH_2)_2NH_2$ | 3,5-dimethyl-cyclohexyl |
| 394 | 4-chlorocinnamoyl | H | H | $CH_2$ | $(CH_2)_2NH_2$ | 3,5-dimethyl-cyclohexyl |
| 395 | 6-chloro-2-naphthoyl | H | H | $CH_2$ | $(CH_2)_2$(1-piperidinyl) | 2,2-diphenylethyl |
| 396 | 6-fluoro-2-naphthoyl | H | H | $CH_2$ | $(CH_2)_2$(1-piperidinyl) | 2,2-diphenylethyl |
| 397 | 4-chlorocinnamoyl | H | H | $CH_2$ | $(CH_2)_2$(1-pyrrolidinyl) | 2,2-diphenylethyl |
| 398 | 4-chlorocinnamoyl | H | H | $CH_2$ | $(CH_2)_2NHCH(CH_3)_2$ | 2,2-diphenylethyl |
| 399 | 2-naphthoyl | H | H | $CH_2$ | $(CH_2)_2NHCH(CH_3)_2$r | 2,2-diphenylethyl |
| 400 | 3,4-dichlorobenzoyl | H | H | $CH_2$ | $(CH_2)_2NHCH(CH_3)_2$ | 2,2-diphenylethyl |
| 401 | 2-naphthoyl | H | H | $CH_2$ | $(CH_2)_3NH_2$ | 2,6-dimethyl-cyclohexylmethyl |
| 402 | 2-naphthoyl | H | H | $CH_2$ | $(CH_2)_3NH_2$ | (S)-2-phenylbutyl |
| 403 | 3,4-dichlorobenzoyl | H | H | $CH_2$ | $(CH_2)_2$(1-piperidinyl) | 3,5-dimethyl-cyclohexylmethyl |
| 404 | 3,4-dichlorobenzoyl | H | H | $CH_2$ | $CH_2CH_2NHCH(CH_3)_2$ | 3,5-dimethyl-cyclohexylmethyl |
| 405 | 2-naphthoyl | H | H | $CH_2$ | $(CH_2)_2NH_2$ | 3-methyl-2-phenylbutyl |
| 406 | 2-naphthoyl | H | H | $CH_2$ | $(CH_2)_2NH_2$ | (S)-2-phenylbutyl |
| 407 | 2-naphthoyl | H | H | $CH_2$ | $(CH_2)_3NH_2$ | (R)-2-phenylbutyl |
| 408 | 4-chlorocinnamoyl | H | H | $CH_2$ | $CH_2$(imidazol-3-yl) | 2,2-diphenylethyl |
| 409 | 3-(4-chlorophenyl)-propanoyl | H | H | $CH_2$ | $(CH_2)_2$(1-piperidinyl) | 2,2-diphenylethyl |
| 410 | 3-(4-chlorophenyl)-propanoyl | H | H | $CH_2$ | $(CH_2)_2NH_2$ | 2,2-diphenylethyl |
| 411 | 4-chlorocinnamoyl | H | H | $CH_2$ | $CH_2NHCO$(2-pyridyl) | 2,2-diphenylethyl |
| 412 | 4-chlorocinnamoyl | H | H | $CH_2$ | $CH_2$(2-pyridinyl) | 2,2-diphenylethyl |
| 413 | 2-naphthoyl | H | H | $CH_2$ | $(CH_2)_2$(1-piperidinyl) | (R)-3-methyl-2-phenylbutyl |
| 414 | 2-naphthoyl | H | H | $CH_2$ | $(CH_2)_2$(1-piperidinyl) | (S)-3-methyl-2-phenylbutyl |
| 415 | 4-isopropylcinnamoyl | H | H | $CH_2$ | $(CH_2)_2$(1-piperidinyl) | 2,2-diphenylethyl |
| 416 | 4-isopropylcinnamoyl | H | H | $CH_2$ | $(CH_2)_2NH_2$ | 2,2-diphenylethyl |
| 417 | 2,4-dimethylcinnamoyl | H | H | $CH_2$ | $(CH_2)_2$(1-piperidinyl) | 2,2-diphenylethyl |
| 418 | 2,4-dimethylcinnamoyl | H | H | $CH_2$ | $(CH_2)_2NH_2$ | 2,2-diphenylethyl |
| 419 | 2,4-difluorocinnamoyl | H | H | $CH_2$ | $(CH_2)_2$1-piperidinyl) | 2,2-diphenylethyl |
| 420 | 2,4-difluorocinnamoyl | H | H | $CH_2$ | $(CH_2)_2NH_2$ | 2,2-diphenylethyl |
| 421 | 4-chlorocinnamoyl | H | H | $CH_2$ | $CH_2NHCO$(cyclohexyl) | 2,2-diphenylethyl |
| 422 | 4-chlorocinnamoyl | H | H | $CH_2$ | $(CH_2)_2$(4-morpholinyl) | 2,2-diphenylethyl |
| 423 | 4-chlorocinnamoyl | H | H | $CH_2$ | $CH_2CH_2N$[—C(Me)=CHCH=C(Me)—] | 2,2-diphenylethyl |
| 424 | 4-chlorocinnamoyl | H | H | $CH_2$ | $CH_2CH_2$(2,5-dimethyl-2-pyrrolidin-1-yl) | 2,2-diphenylethyl |
| 425 | 6-chloro-2-naphthoyl | H | H | $CH_2$ | $(CH_2)_2$(1-piperidinyl) | (S)-2-phenylbutyl |
| 426 | 4-chlorocinnamoyl | H | H | $CH_2$ | $(CH_2)_2$(1-pyrrolidinyl) | (S)-2-phenylbutyl |
| 427 | 4-chlorocinnamoyl | H | H | $CH_2$ | $(CH_2)_2NHCH(CH_3)_2$ | (S)-2-phenylbutyl |
| 428 | 6-chloro-2-naphthoyl | H | H | $CH_2$ | $CH_2CH_2$(1-pyrrolidinyl) | (S)-2-phenylbutyl |
| 429 | 3,4-dichlorobenzoyl | H | H | $CH_2$ | $(CH_2)_2$(1-piperidinyl) | (S)-2-phenylbutyl |
| 430 | 3,4-dichlorobenzoyl | H | H | $CH_2$ | $(CH_2)_2$1-pyrrolidinyl) | (S)-2-phenylbutyl |
| 431 | Cbz | H | H | $CH_2$ | $(CH_2)_2$(1-piperidinyl) | 2,2-diphenylethyl |
| 432 | 4-bromocinnamoyl | H | H | $CH_2$ | $(CH_2)_2$(1-piperidinyl) | 2,2-diphenylethyl |
| 433 | 5-(4-chlorophenyl)-isoxazole-3-carbonyl | H | H | $CH_2$ | $(CH_2)_2$(1-piperidinyl) | 2,2-diphenylethyl |
| 434 | 4-chlorocinnamoyl | H | H | $CH_2$ | $CH_2CONH$(2-pyridyl) | 2,2-diphenylethyl |
| 435 | 4-chlorocinnamoyl | H | H | $CH_2$ | $CH_2CO$(1-piperidinyl) | 2,2-diphenylethyl |
| 436 | 6-chloro-2-naphthoyl | H | H | $CH_2$ | $(CH_2)_2CO$(1-piperidinyl) | (S)-2-phenylbutyl |
| 437 | 3,4-dichlorobenzoyl | H | H | $CH_2$ | $(CH_2)CO$(1-piperidinyl) | (S)-2-phenylbutyl |
| 438 | 6-chloro-2-naphthoyl | H | H | $CH_2$ | $CH_2$(1-piperidinyl) | (S)-2-phenylbutyl |
| 439 | 3,4-dichlorobenzoyl | H | H | $CH_2$ | $CH_2$(1-piperidinyl) | (S)-2-phenylbutyl |
| 440 | 6-chloro-2-naphthoyl | H | H | $CH_2$ | $(CH_2)_3$(1-piperidinyl) | (S)-2-phenylbutyl |
| 441 | 3,4-dichlorobenzoyl | H | H | $CH_2$ | $(CH_2)_3$(1-piperidinyl) | (S)-2-phenylbutyl |
| 442 | 4-chlorocinnamoyl | H | H | $C(Me)_2$ | $CH_2CH_2NH_2$ | 2,2-diphenylethyl |
| 443 | 4-chlorocinnamoyl | H | H | $C(Me)$ v | $(CH_2)_2$(1-piperidinyl) | 2,2-diphenylethyl |
| 444 | 2-naphthoyl | H | H | $CH_2$ | $(CH_2)_2NH_2$ | (R)-2-(4-chloro-phenyl)propyl |
| 445 | 2-naphthoyl | H | H | $CH_2$ | $(CH_2)_2NH_2$ | 2-(4-chloro-phenyl)propyl |
| 446 | 2-naphthoyl | H | H | $CH_2$ | $(CH_2)_2$(1-piperidinyl) | (R)-2-(4-chloro-phenyl)propyl |
| 447 | 2-naphthoyl | H | H | $CH_2$ | $(CH_2)_2$(1-piperidinyl) | (S)-2-(4-chloro-phenyl)propyl |

TABLE 1-continued

Identity of Compounds

| Cpd. | R¹X | R² | R³ | Y | R | W |
|---|---|---|---|---|---|---|
| 448 | 3,4-dichlorobenzoyl | H | H | CH$_2$ | (CH$_2$)$_2$N(phenyl)CH$_2$ | (S)-2-phenylbutyl |
| 449 | 3,4-dichlorobenzoyl | H | H | CH$_2$ | (CH$_2$)$_2$N(CH$_2$CH$_3$)$_2$ | (S)-2-phenylbutyl |
| 450 | 3,4-dichlorobenzoyl | H | H | CH$_2$ | (CH$_2$)$_2$(4-morpholinyl) | (S)-2-phenylbutyl |
| 451 | 3,4-dichlorobenzoyl | H | H | CH$_2$ | (CH$_2$)$_2$NH(phenyl) | (S)-2-phenylbutyl |
| 452 | 3,4-dichlorobenzoyl | H | H | CH$_2$ | (CH$_2$)$_2$NH(benzyl) | (S)-2-phenylbutyl |
| 453 | 4-chlorocinnamoyl | H | H | CH$_2$ | CH$_2$(2-NH$_2$—Ph) | 2,2-diphenylethyl |
| 454 | 3,4-dichlorobenzoyl | H | H | CH$_2$ | (CH$_2$)$_2$NHC(CH$_3$)$_3$ | (S)-2-phenylbutyl |
| 455 | 3,4-dichlorobenzoyl | H | H | CH$_2$ | (CH$_2$)$_2$(4-CH$_3$-piperazin-1-yl) | (S)-2-phenylbutyl |
| 456 | 2-naphthoyl | H | H | CH$_2$ | (CH$_2$)$_2$(1-piperidinyl) | (R)-2-phenylpentyl |
| 457 | 2-naphthoyl | H | H | CH$_2$ | (CH$_2$)$_2$(1-piperidinyl) | (S)-2-phenylpentyl |
| 458 | p-trifluoromethyl-benzoyl | H | H | CH$_2$ | (CH$_2$)$_2$(1-piperidinyl) | 2,2-diphenylethyl |
| 459 | p-trifluoromethyl-benzoyl | H | H | CH$_2$ | (CH$_2$)$_2$NH$_2$ | 2,2-diphenylethyl |
| 460 | m-trifluoromethyl-benzoyl | H | H | CH2$_2$ | (CH$_2$)$_2$(1-piperidinyl) | 2,2-diphenylethyl |
| 461 | m-trifluoromethyl-benzoyl | H | H | CH$_2$ | (CH$_2$)$_2$NH$_2$ | 2,2-diphenylethyl |
| 462 | 6-chloro-2-naphthoyl | H | H | CH$_2$ | (CH$_2$)$_2$NHCH(CH$_3$)$_2$ | 3,5-dichlorobenzyl |
| 463 | 3,4-dichlorobenzoyl | H | H | CH$_2$ | (CH$_2$)$_2$NHCH(CH$_3$)$_2$ | 3,5-dichlorobenzyl |
| 464 | 6-chloro-2-naphthoyl | H | H | CH$_2$ | (CH$_2$)$_2$NHCH(CH$_3$)$_2$ | (S)-2-phenylbutyl |
| 465 | 6-chloro-2-naphthoyl | H | H | CH$_2$ | (CH$_2$)$_2$NH$_2$ | (S)-2-phenylbutyl |
| 466 | 2-naphthoyl | H | H | CH$_2$ | CH$_2$(2-NH$_2$—Ph) | 2,2-diphenylethyl |
| 467 | 3,4-dichlorobenzoyl | H | H | CH$_2$ | (CH$_2$)$_2$N(benzyl)CH$_3$ | (S)-2-phenylbutyl |
| 468 | 3,4-dichlorobenzoyl | H | H | CH$_2$ | (CH$_2$)$_2$(piperazin-1-yl) | (S)-2-phenylbutyl |
| 469 | 3,4-dichlorobenzoyl | H | H | CH$_2$ | (CH$_2$)$_2$N(n-pentyl)CH$_3$ | (S)-2-phenylbutyl |
| 470 | 3,4-dichlorobenzoyl | H | H | CH$_2$ | (CH$_2$)$_2$N[(CH(CH$_3$)$_2$]$_2$ | (S)-2-phenylbutyl |
| 471 | 3,4-dichlorobenzoyl | H | H | CH$_2$ | (CH$_2$)$_2$(4-CH$_3$-piperidin-1-yl) | (S)-2-phenylbutyl |
| 472 | 6-chloro-2-naphthoyl | H | H | CH$_2$ | 4-piperidinyl | (S)-2-phenylbutyl |
| 473 | 6-chloro-2-naphthoyl | H | H | CH$_2$ | 1-isopentyl-4-piperidinyl | (S)-2-phenylbutyl |
| 474 | 6-chloro-2-naphthoyl | H | H | CH$_2$ | (CH$_2$)$_3$CH$_3$ | (S)-2-phenylbutyl |
| 475 | 6-chloro-2-naphthoyl | H | H | CH$_2$ | CH$_2$CH$_2$iPr | (S)-2-phenylbutyl |
| 476 | 3,4-dichlorobenzoyl | H | H | CH$_2$ | (CH$_2$)$_2$(3,5-Me$_2$-piperidin-1-yl) | (S)-2-phenylbutyl |
| 477 | 3,4-dichlorobenzoyl | H | H | CH$_2$ | (CH$_2$)$_2$(4-OH-piperidin-1-yl) | (S)-2-phenylbutyl |
| 478 | 3,4-dichlorobenzoyl | H | H | CH$_2$ | (CH$_2$)$_2$(4-CO$_2$H-piperidin-1-yl) | (S)-2-phenylbutyl |
| 479 | 3,4-dichlorobenzoyl | H | H | CH$_2$ | (CH$_2$)$_2$NH[—(CH$_2$)$_6$—] | (S)-2-phenylbutyl |
| 480 | 3,4-dichlorobenzoyl | H | H | CH$_2$ | (CH$_2$)$_2$[(S)-2-Me-piperidin-1-yl] | (S)-2-phenylbutyl |
| 481 | 3,4-dichlorobenzoyl | H | H | CH$_2$ | (CH$_2$)$_2$N(tBu)CH$_3$ | (S)-2-phenylbutyl |
| 482 | 2-naphthoyl | H | H | CH$_2$ | CH$_2$(2-(piperidin-1-yl)phenyl)- | 2,2-diphenylethyl |
| 483 | 2-naphthoyl | H | H | CH$_2$ | (CH$_2$)$_2$CON(Me)nBu | (S)-2-phenylbutyl |
| 484 | 2-naphthoyl | H | H | CH$_2$ | (CH$_2$)$_2$CONHcHex | (S)-2-phenylbutyl |
| 485 | 6-chloro-2-naphthoyl | H | H | CH$_2$ | 1-ethyl-piperidin-4-yl | (S)-2-phenylbutyl |
| 486 | 3,4-dichlorobenzyl | H | H | CH$_2$ | (CH$_2$)$_2$(1-piperidinyl) | 2,2-diphenylethyl |
| 487 | 6-chloro-2-naphthoyl | H | H | CH$_2$ | (CH$_2$)$_2$NHC(=NH)NH$_2$ | (S)-2-phenylbutyl |
| 488 | 6-chloro-2-naphthoyl | H | H | CH$_2$ | (CH$_2$)$_2$NHC(=NH)NHMe | (S)-2-phenylbutyl |
| 489 | 3,4-dichlorobenzoyl | H | H | CH$_2$ | (CH$_2$)$_2$NH$_2$ | (R)-2-isopropylbutyl |
| 490 | 3,4-dichlorobenzoyl | H | H | CH$_2$ | (CH$_2$)$_2$NH$_2$ | (S)-2-isopropylbutyl |
| 491 | 3,4-dichlorobenzoyl | H | H | CH$_2$ | (CH$_2$)$_2$(1-piperidinyl) | (R)-2-isopropylbutyl |
| 492 | 3,4-dichlorobenzoyl | H | H | CH$_2$ | (CH$_2$)$_2$(1-piperidinyl) | (S)-2-isopropylbutyl |
| 493 | 6-chloro-2-naphthoyl | H | H | CH$_2$ | S-CH$_2$C(Me$_2$)NH$_2$ | (S)-2-phenylbutyl |
| 494 | 6-chloro-2-naphthoyl | H | H | CH$_2$ | R-CH$_2$C(Me$_2$)NH$_2$ | (S)-2-phenylbutyl |
| 495 | 3,4-dichlorobenzoyl | H | H | CH$_2$ | (CH$_2$)$_2$NH$_2$ | (S)-2-phenylbutyl |
| 496 | 3,4-dichlorobenzoyl | H | H | CH$_2$ | (CH$_2$)$_2$NHCH(CH$_2$)$_2$ | (S)-2-phenylbutyl |
| 497 | 6-chloro-2-naphthoyl | H | H | CH$_2$ | (CH$_2$)$_2$NH$_2$ | 3,5-dichlorobenzyl |
| 498 | 6-chloro-2-naphthoyl | H | H | CH$_2$ | (CH$_2$)$_2$(1-piperidinyl) | 3,5-dichlorobenzyl |
| 499 | 6-chloro-2-naphthoyl | H | H | CH$_2$ | S-CH$_2$C(Me$_2$)(1-piperidinyl) | (S)-2-phenylbutyl |
| 500 | 6-chloro-2-naphthoyl | H | H | CH$_2$ | R-CH$_2$C(Me$_2$)(1-piperidinyl) | (S)-2-phenylbutyl |
| 501 | 6-chloro-2-naphthoyl | H | H | CH$_2$ | (CH$_2$)$_2$NH$_2$ | (R)-2-isopropylbutyl |
| 502 | 6-chloro-2-naphthoyl | H | H | CH$_2$ | (CH$_2$)$_2$NH$_2$ | (S)-2-isopropylbutyl |
| 503 | 6-chloro-2-naphthoyl | H | H | CH$_2$ | (CH$_2$)$_2$(1-piperidinyl) | (R)-2-isopropylbutyl |
| 504 | 6-chloro-2-naphthoyl | H | H | CH$_2$ | (CH$_2$)$_2$(1-piperidinyl) | (S)-2-isopropylbutyl |
| 505 | 6-chloro-2-naphthoyl | H | H | CH$_2$ | (CH$_2$)$_2$cHex | (S)-2-phenylbutyl |
| 506 | 6-chloro-2-naphthoyl | H | H | CH$_2$ | nHex | (S)-2-phenylbutyl |
| 507 | 6-carboxy-2-naphthoyl | H | H | CH$_2$ | CH$_2$)$_2$(1-piperidinyl) | 2,2-diphenylethyl |
| 508 | 6-chloro-2-naphthoyl | H | H | CH$_2$ | (CH$_2$)$_2$NHC(=NH)NH—CH(CH$_3$)$_2$ | (S)-2-phenylbutyl |
| 509 | 6-chloro-2-naphthoyl | H | H | CH$_2$ | (CH$_2$)$_4$OH | (S)-2-phenylbutyl |
| 510 | 6-chloro-2-naphthoyl | H | H | CH$_2$ | (CH$_2$)$_2$OMe | (S)-2-phenylbutyl |
| 511 | 6-chloro-2-naphthoyl | H | H | CH$_2$ | (CH$_2$)$_2$OBn | (S)-2-phenylbutyl |
| 512 | 6-chloro-2-naphthoyl | H | H | CH$_2$ | iBu | (S)-2-phenylbutyl |
| 513 | 3,4-dichlorobenzoyl | H | H | CH$_2$ | (CH$_2$)$_2$NH$_2$ | 2-ethyl-3-methyl-but-3-enyl |
| 514 | 3,4-dichlorobenzoyl | H | H | CH$_2$ | (CH$_2$)$_2$(1-piperidinyl) | 2-ethyl-3-methyl-but-3-enyl |
| 515 | 6-chloro-2-naphthoyl | H | H | CH$_2$ | (CH$_2$)$_2$NH$_2$ | 2-ethyl-3-methyl-but-3-enyl |

TABLE 1-continued

Identity of Compounds

| Cpd. | R¹X | R² | R³ | Y | R | W |
|---|---|---|---|---|---|---|
| 516 | 6-chloro-2-naphthoyl | H | H | CH$_2$ | (CH$_2$)$_2$(1-piperidinyl) | (R)-2-ethyl-3-methyl-but-3-enyl |
| 517 | 6-chloro-2-naphthoyl | H | H | CH$_2$ | (CH$_2$)$_2$(1-piperidinyl) | (S)-2-ethyl-3-methyl-but-3-enyl |
| 518 | 4-biphenylcarboxylyl | H | H | CH$_2$ | (CH$_2$)$_3$NHC(=NH)NH$_2$ | cyclohexanemethyl |
| 519 | indole-3-acetyl | H | H | CH$_2$ | (CH$_2$)$_3$NHC(=NH)NH$_2$ | cyclohexanemethyl |
| 520 | 3-quinolinecarboxylyl | H | H | CH$_2$ | (CH$_2$)$_3$NHC(=NH)NH$_2$ | cyclohexanemethyl |
| 521 | 3,4-dichlorobenzoyl | H | H | CH$_2$ | (CH$_2$)$_2$(4,4-difluoro-1-piperidinyl) | (S)-2-phenylbutyl |
| 522 | 3,4-dichlorobenzoyl | H | H | CH$_2$ | (CH$_2$)$_2$OH) | (S)-2-phenylbutyl |
| 523 | 3,4-dichlorobenzoyl | H | H | CH$_2$ | (CH$_2$)$_2$(3,3-difluoro-1-piperidinyl) | (S)-2-phenylbutyl |
| 524 | 3,4-dichlorobenzyl | H | H | CH$_2$ | (CH$_2$)$_2$(1-piperidinyl) | (S)-2-phenylbutyl |
| 525 | 3,4-dichlorobenzoyl | H | H | CH$_2$ | (CH$_2$)$_2$(1-piperidinyl) | 2-cyclopropylbutyl |
| 526 | 6-chloro-2-naphthoyl | H | H | CH$_2$ | (CH$_2$)$_2$NH$_2$ | 2-cyclopropylbutyl |
| 527 | 6-chloro-2-naphthoyl | H | H | CH$_2$ | (CH$_2$)$_2$(1-piperidinyl) | 2-cyclopropylbutyl |
| 528 | 3,4-dichlorobenzoyl | H | H | CH$_2$ | (CH$_2$)$_2$N[—CO(CH$_2$)$_2$CO—] | (S)-2-phenylbutyl |
| 529 | 6-chloro-2-naphthoyl | H | H | CH$_2$ | (CH$_2$)$_2$NHCONH$_2$ | (S)-2-phenylbutyl |
| 530 | 3,4-dichlorobenzoyl | H | H | CH$_2$ | (CH$_2$)$_2$NHCH(Me)CF$_3$ | (S)-2-phenylbutyl |
| 531 | 3,4-dichlorobenzoyl | H | H | CH$_2$ | CH$_2$CH$_2$N[—COC(Me)$_2$CH$_2$CO—] | (S)-2-phenylbutyl |
| 532 | 6-chloro-2-naphthoyl | H | H | CH$_2$ | (CH$_2$)$_2$N[—(CH$_2$)$_6$—] | (S)-2-phenylbutyl |
| 533 | 6-chloro-2-naphthoyl | H | H | CH$_2$ | (CH$_2$)$_2$NHCONHiPr | (S)-2-phenylbutyl |
| 534 | 4-biphenyl carboxylic | H | H | CH$_2$ | (CH$_2$)$_2$(1-piperidinyl) | (S)-2-phenylbutyl |
| 535 | 2-phenylthiazole-4-carbonyl | H | H | CH$_2$ | (CH$_2$)$_2$(1-piperidinyl) | (S)-2-phenylbutyl |
| 536 | 4-chloro-biphenyl-2-carbonyl | H | H | CH$_2$ | (CH$_2$)$_2$(1-piperidinyl) | (S)-2-phenylbutyl |
| 537 | 6-chloro-2-naphthoyl | H | H | CH$_2$ | (CH$_2$)$_2$N(Ac)iPr | (S)-2-phenylbutyl |
| 538 | 6-chloro-2-naphthoyl | H | H | CH$_2$ | CH$_2$NHiPr | (S)-2-phenylbutyl |
| 539 | 6-chloro-2-naphthoyl | H | H | CH$_2$ | CH$_2$NC(=NH)NH$_2$ | (S)-2-phenylbutyl |
| 540 | 2,4-dichlorophenylacetyl | H | H | CH$_2$ | (CH$_2$)$_2$(1-piperidinyl) | (S)-2-phenylbutyl |
| 541 | 3,4-dichlorobenzoyl | H | H | CH$_2$ | (CH$_2$)$_2$NH$_2$ | 2,4-dichlorobenzyl |
| 542 | 3,4-dichlorobenzoyl | H | H | CH$_2$ | (CH$_2$)$_2$(1-piperidinyl) | 2,4-dichlorobenzyl |
| 543 | 3,4-dichlorobenzoyl | H | H | CH$_2$ | (CH$_2$)$_2$NHSO$_2$Me | 2,4-dichlorobenzyl |
| 544 | 3,4-dichlorobenzoyl | H | H | CH$_2$ | (CH$_2$)$_2$NHSO$_2$(4-Me—Ph) | 2,4-dichlorobenzyl |
| 545 | 3,4-dichlorobenzoyl | H | H | CH$_2$ | (S)-(CH$_2$)$_2$NHCO—CH(iPr)NH$_2$ | 2,4-dichlorobenzyl |
| 546 | 6-chloro-2-naphthoyl | H | H | CH$_2$ | (CH$_2$)$_2$NH$_2$ | 2,4-dichlorobenzyl |
| 547 | 6-chloro-2-naphthoyl | H | H | CH$_2$ | (CH$_2$)$_2$(1-piperidinyl) | 2,4-dichlorobenzyl |
| 548 | 6-chloro-2-naphthoyl | H | H | CH$_2$ | (CH$_2$)$_2$NH$_2$ | 2-(3-thienyl)butyl |
| 549 | 6-chloro-2-naphthoyl | H | H | CH$_2$ | (CH$_2$)$_2$(1-piperidinyl) | (R)-2-(3-thienyl)butyl |
| 550 | 6-chloro-2-naphthoyl | H | H | CH$_2$ | (CH$_2$)$_2$(1-piperidinyl) | (S)-2-(3-thienyl)butyl |
| 551 | 6-chloro-2-naphthoyl | H | H | CH$_2$ | (CH$_2$)$_2$NH$_2$ | 2-ethyl-2-methylbutyl |
| 552 | 6-chloro-2-naphthoyl | H | H | CH$_2$ | (CH$_2$)$_2$(1-piperidinyl) | 2-ethyl-2-methylbutyl |
| 553 | 6-chloro-2-naphthoyl | H | H | CH$_2$ | (CH$_2$)$_2$(4-morpholinyl) | 2,2-diphenylethyl |
| 554 | 6-chloro-2-naphthoyl | H | H | CH$_2$ | (CH$_2$)$_2$(4-morpholinyl) | (S)-2-phenylbutyl |
| 555 | 6-chloro-2-naphthoyl | H | H | CH$_2$ | (CH$_2$)$_2$(4-morpholinyl) | 3,5-dichlorobenzyl |
| 556 | 3,4-dichlorobenzoyl | H | H | CH$_2$ | (CH$_2$)$_2$(4-morpholinyl) | 3,5-dichlorobenzyl |
| 557 | (4-chloro-benzyl)NHCO | H | H | CH$_2$ | (CH$_2$)$_2$(1-piperidinyl) | (S)-2-phenylbutyl |
| 558 | 3,4-dichlorobenzyl + MeCO | Ac | H | CH$_2$ | (CH$_2$)$_2$(1-piperidinyl) | (S)-2-phenylbutyl |
| 560 | 3,4-dichlorobenzoyl | H | H | CH$_2$ | (CH$_2$)$_2$(1-piperidinyl) | 2-ethyl-2-methylbutyl |
| 561 | 6-chloro-2-naphthoyl | H | H | CH$_2$ | (CH$_2$)$_2$(1-piperidinyl) | 2,3,5-trichlorobenzyl |
| 562 | 6-chloro-2-naphthoyl | H | H | CH$_2$ | (CH$_2$)$_2$NHSO$_2$iPr | (S)-2-phenylbutyl |
| 563 | 6-chloro-2-naphthoyl | H | H | CH$_2$ | (CH$_2$)$_2$NHCO$_2$nBu | (S)-2-phenylbutyl |
| 564 | 6-chloro-2-naphthoyl | H | H | CH$_2$ | 1-iPr-4-piperidinyl | (S)-2-phenylbutyl |
| 565 | 6-chloro-2-naphthoyl | H | H | CH$_2$ | (CH$_2$)$_2$(1-piperidinyl) | (R)-2-phenylbutyl |
| 566 | 5-(4-chlorophenyl)-isoxazole-3-carbonyl | H | H | CH$_2$ | (CH$_2$)$_2$(1-piperidinyl) | 3,5-dichlorobenzyl |
| 567 | 2,4-dichlorobenzoyl | H | H | CH$_2$ | (CH$_2$)$_2$(1-piperidinyl) | 3,5-dichlorobenzyl |
| 568 | 6-methoxy-2-naphthoyl | H | H | CH$_2$ | (CH$_2$)$_2$(1-piperidinyl) | 3,5-dichlorobenzyl |
| 569 | 6-chloro-2-naphthoyl | H | H | $^{13}$CH$_2$ | (CH$_2$)$_2$(1-piperidinyl) | (S)-2-phenylbutyl |
| 570 | 1-methoxy-2-napthoyl | H | H | CH$_2$ | (CH$_2$)$_2$(1-piperidinyl) | 3,5-dichlorobenzyl |
| 571 | 4-(trifluoro-methoxy)cinnamoyl | H | H | CH$_2$ | (CH$_2$)$_2$(1-piperidinyl) | 3,5-dichlorobenzyl |
| 572 | 5-(4-chlorophenyl)-isoxazole-3-carbonyl | H | H | CH$_2$ | (CH$_2$)$_2$(1-piperidinyl) | (S)-2-phenylbutyl |
| 573 | 2,4-dichlorobenzoyl | H | H | CH$_2$ | (CH$_2$)$_2$(1-piperidinyl) | (S)-2-phenylbutyl |
| 574 | 4,5-dichlorophthaloyl | R1 | H | CH$_2$ | (CH$_2$)$_2$(1-piperidinyl) | 3,5-dichlorobenzyl |
| 575 | 3-fluoro-4-(trifluoro-methoxy)cinnamoyl | H | H | CH$_2$ | (CH$_2$)$_2$(1-piperidinyl) | 3,5-dichlorobenzyl |
| 576 | 6-methoxy-2-naphthoyl | H | H | CH$_2$ | (CH$_2$)$_2$(1-piperidinyl) | (S)-2-phenylbutyl |
| 577 | 1-methoxy-2-napthoyl | H | H | CH$_2$ | (CH$_2$)$_2$(1-piperidinyl) | (S)-2-phenylbutyl |

TABLE 1-continued

Identity of Compounds

| Cpd. | R$^1$X | R$^2$ | R$^3$ | Y | R | W |
|---|---|---|---|---|---|---|
| 578 | 3-fluoro-4-(trifluoro-methoxy)cinnamoyl | H | H | CH$_2$ | (CH$_2$)$_2$(1-piperidinyl) | (S)-2-phenylbutyl |
| 579 | 6-chloro-2-naphthoyl | H | H | CD$_2$ | (CH$_2$)$_2$(1-piperidinyl) | (S)-2-phenylbutyl |

TABLE 2

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 14 | Scheme 1 | 2-naphthoic-Gly-OH | Fmoc-L-Arg(Pbf)-OH | Scheme 3 | P3 deprotection |
| 25 | Scheme 1 | Boc-Gly-OH | Cbz-L-Asp[(NMe)OMe-OH | Scheme 4 | reduction to aldehyde then reductive amination |
| 31 | Scheme 1 | Cbz-Gly-OH | Fmoc-L-Dab(Boc)-OH | Scheme 4 | P3 deprotection |
| 33 | Scheme 1 | Cbz-Gly-OH | Fmoc-L-Dab(Boc)-OH | Scheme 4 | P3 deprotection then dialkylation with alkyl dibromide |
| 37 | Scheme 1 | Cbz-Gly-OH | Fmoc-L-Dab(Boc)-OH | Scheme 4 | P3 deprotection |
| 38 | Scheme 1 | Cbz-Gly-OH | Fmoc-L-Dab(Boc)-OH | Scheme 4 | P3 deprotection then dialkylation with alkyl dibromide |
| 38 | Scheme 1 | 2-naphthoic-Gly-OH | Fmoc-L-Dab(Boc)-OH | Scheme 3 | P3 deprotection then dialkylation with alkyl dibromide |
| 39 | Scheme 1 | Cbz-Gly-OH | Fmoc-L-Dab(Boc)-OH | Scheme 4 | P3 deprotection then dialkylation with alkyl dibromide |
| 49 | Scheme 1 | Alloc-Gly-OH | Fmoc-L-Dab(Boc)-OH | Scheme 4 | P3 deprotection |
| 50 | Scheme 1 | Alloc-Gly-OH | Boc-L-Arg(Fmoc)$_2$-OH | Scheme 4 | P3 deprotection |
| 54 | Scheme 1 | Cbz-Gly-OH | Fmoc-L-Dab(Boc)-OH | Scheme 4 | P3 deprotection |
| 60 | Scheme 1 | Cbz-Sar | Fmoc-L-Orn(Boc)-OH | Scheme 4 | P3 deprotection |
| 62 | Scheme 1 | Cbz-Gly-OH | Fmoc-L-Orn(Boc)-OH | Scheme 3 | P1 deprotect, R1 acylate, ring methylate, P3 deprotect |
| 63 | Scheme 2 | Boc-Gly-OH | H-L-Orn(Cbz)-Oallyl | Scheme 4 | P3 deprotection |
| 63 | Scheme 1 | 2-naphthoic-Gly-OH | Fmoc-L-Orn(Boc)-OH | Scheme 3 | P3 deprotection |
| 64 | Scheme 1 | 2-naphthoic-Gly-OH | Fmoc-L-Orn(Boc)-OH | Scheme 3 | P3 deprotection then dialkylation with alkyl dibromide |
| 65 | Scheme 1 | 2-naphthoic-Gly-OH | Fmoc-L-Orn(Boc)-OH | Scheme 3 | P3 deprotection, reductive alkylation |
| 67 | Scheme 1 | 2-naphthoic-Gly-OH | Fmoc-L-Orn(Boc)-OH | Scheme 3 | P3 deprotection, guanylation |
| 79 | Scheme 1 | Alloc-β-(2-naphthyl)-L-Ala | Boc-L-Arg-(Cbz)$_2$-OH | Scheme 4 | P3 deprotection |
| 81 | Scheme 1 | Alloc-β-(2-naphthyl)-L-Ala | Boc-L-Arg-(Cbz)$_2$-OH | Scheme 4 | P3 deprotection |
| 83 | Scheme 1 | Alloc-β-(2-naphthyl)-L-Ala | Boc-L-Arg-(Cbz)$_2$-OH | Scheme 4 | P3 deprotection |
| 85 | Scheme 1 | Alloc-β-(2-naphthyl)-L-Ala | Boc-L-Arg-(Cbz)$_2$-OH | Scheme 4 | P3 deprotection |
| 86 | Scheme 1 | Alloc-β-(2-naphthyl)-L-Ala | Boc-L-Arg-(Cbz)$_2$-OH | Scheme 4 | P3 deprotection |
| 87 | Scheme 1 | Alloc-β-(2-naphthyl)-L-Ala | Boc-L-Arg-(Cbz)$_2$-OH | Scheme 4 | P3 deprotection |
| 105 | Scheme 2 | Boc-Gly-OH | H-L-Orn(Cbz)-Oallyl | Scheme 5 | P3 deprotection, guanidinylation, deprotection |
| 105 | Scheme 2 | Boc-Gly-OH | H-L-Arg(Cbz)$_2$-Oallyl | Scheme 4 | P3 deprotection |
| 105 | Scheme 1 | Alloc-Gly-OH | Boc-L-Arg(Fmoc)$_2$-OH | Scheme 4 | P3 deprotection |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 105 | Scheme 1 | 2-naphthoic-Gly-OH | Fmoc-L-Arg(Pbf)-OH | Scheme 3 | P3 deprotection |
| 106 | Scheme 2 | Boc-Gly-OH | H-L-Orn(Cbz)-Oallyl | Scheme 4 | P3 deprotection |
| 106 | Scheme 2 | Boc-Gly-OH | H-L-Orn(Cbz)-Oallyl | Scheme 4 | P3 deprotection |
| 107 | Scheme 2 | Boc-Gly-OH | H-L-Orn(Cbz)-Oallyl | Scheme 4 | P3 deprotection |
| 108 | Scheme 2 | Boc-Gly-OH | H-L-Orn(Cbz)-Oallyl | Scheme 5 | P3 deprotection, guanidinylation, deprotection |
| 109 | Scheme 2 | Boc-Gly-OH | H-L-Orn(Cbz)-Oallyl | Scheme 5 | P3 deprotection, guanidinylation, deprotection |
| 110 | Scheme 2 | Boc-Gly-OH | H-L-Orn(Cbz)-Oallyl | Scheme 5 | P3 deprotection, guanidinylation, deprotection |
| 111 | Scheme 2 | Boc-Gly-OH | H-L-Arg(Cbz)$_2$-Oallyl | Scheme 4 | P3 deprotection |
| 112 | Scheme 2 | Boc-Gly-OH | H-L-Arg(Cbz)$_2$-Oallyl | Scheme 4 | P3 deprotection |
| 113 | Scheme 2 | Boc-Gly-OH | H-L-Arg(Cbz)$_2$-Oallyl | Scheme 4 | P3 deprotection |
| 114 | Scheme 2 | Boc-Gly-OH | H-L-Arg(Cbz)$_2$-Oallyl | Scheme 4 | P3 deprotection |
| 115 | Scheme 2 | Boc-Gly-OH | H-L-Arg(Cbz)$_2$-Oallyl | Scheme 4 | P3 deprotection |
| 116 | Scheme 2 | Boc-Gly-OH | H-L-Arg(Cbz)$_2$-Oallyl | Scheme 4 | P3 deprotection |
| 117 | Scheme 2 | Boc-Gly-OH | Boc-L-Lys(Cbz)-OH | Scheme 4 | P3 deprotection |
| 118 | Scheme 2 | Boc-Gly-OH | Boc-L-Lys(Cbz)-OH | Scheme 4 | P3 deprotection |
| 119 | Scheme 2 | Boc-Gly-OH | Boc-L-Lys(Cbz)-OH | Scheme 4 | P3 deprotection |
| 120 | Scheme 2 | Boc-Gly-OH | Boc-L-Lys(Cbz)-OH | Scheme 4 | P3 deprotection |
| 121 | Scheme 2 | Boc-Gly-OH | Boc-L-Lys(Cbz)-OH | Scheme 4 | P3 deprotection |
| 122 | Scheme 2 | Boc-Gly-OH | Boc-L-Lys(Cbz)-OH | Scheme 4 | P3 deprotection |
| 123 | Scheme 2 | Boc-Gly-OH | Boc-L-Lys(Cbz)-OH | Scheme 4 | P3 deprotection |
| 124 | Scheme 2 | Boc-Gly-OH | Boc-L-Lys(Cbz)-OH | Scheme 4 | P3 deprotection |
| 125 | Scheme 2 | Boc-Gly-OH | Boc-L-Lys(Cbz)-OH | Scheme 4 | P3 deprotection |
| 126 | Scheme 2 | Boc-Gly-OH | Boc-L-Lys(Cbz)-OH | Scheme 4 | P3 deprotection |
| 127 | Scheme 2 | Boc-Gly-OH | Boc-L-Lys(Cbz)-OH | Scheme 4 | P3 deprotection |
| 128 | Scheme 2 | Boc-Gly-OH | Boc-L-Lys(Cbz)-OH | Scheme 4 | P3 deprotection |
| 129 | Scheme 2 | Boc-Gly-OH | Boc-L-Lys(Cbz)-OH | Scheme 4 | P3 deprotection |
| 130 | Scheme 2 | Boc-Gly-OH | H-L-Arg(Cbz)$_2$-Oallyl | Scheme 4 | P3 deprotection |
| 131 | Scheme 2 | Boc-Gly-OH | H-L-Arg(Cbz)$_2$-Oallyl | Scheme 4 | P3 deprotection |
| 132 | Scheme 2 | Boc-Gly-OH | H-L-Arg(Cbz)$_2$-Oallyl | Scheme 4 | P3 deprotection |
| 133 | Scheme 2 | Boc-Gly-OH | H-L-Arg(Cbz)$_2$-Oallyl | Scheme 4 | P3 deprotection |
| 134 | Scheme 2 | Boc-Gly-OH | H-L-Arg(Cbz)$_2$-Oallyl | Scheme 4 | P3 deprotection |
| 135 | Scheme 2 | Boc-Gly-OH | H-L-Arg(Cbz)$_2$-Oallyl | Scheme 4 | P3 deprotection |
| 136 | Scheme 2 | Boc-Gly-OH | H-L-Arg(Cbz)$_2$-Oallyl | Scheme 4 | P3 deprotection |
| 137 | Scheme 2 | Boc-Gly-OH | H-L-Arg(Cbz)$_2$-Oallyl | Scheme 4 | P3 deprotection |
| 138 | Scheme 2 | Boc-Gly-OH | H-L-Arg(Cbz)$_2$-Oallyl | Scheme 4 | P3 deprotection |
| 139 | Scheme 2 | Boc-Gly-OH | H-L-Arg(Cbz)$_2$-Oallyl | Scheme 4 | P3 deprotection |
| 140 | Scheme 2 | Boc-Gly-OH | H-L-Arg(Cbz)$_2$-Oallyl | Scheme 4 | P3 deprotection |
| 141 | Scheme 2 | Boc-Gly-OH | H-L-Arg(Cbz)$_2$-Oallyl | Scheme 4 | P3 deprotection |
| 142 | Scheme 2 | Boc-Gly-OH | H-L-Arg(Cbz)$_2$-Oallyl | Scheme 4 | P3 deprotection |
| 143 | Scheme 2 | Boc-Gly-OH | H-L-Arg(Cbz)$_2$-Oallyl | Scheme 4 | P3 deprotection |
| 144 | Scheme 2 | Boc-Gly-OH | H-L-Arg(Cbz)$_2$-Oallyl | Scheme 4 | P3 deprotection |
| 145 | Scheme 2 | Boc-Gly-OH | H-L-Arg(Cbz)$_2$-Oallyl | Scheme 4 | P3 deprotection |
| 146 | Scheme 2 | Boc-Gly-OH | H-L-Arg(Cbz)$_2$-Oallyl | Scheme 4 | P3 deprotection |
| 147 | Scheme 2 | Boc-Gly-OH | H-L-Arg(Cbz)$_2$-Oallyl | Scheme 4 | P3 deprotection |
| 148 | Scheme 2 | Boc-Gly-OH | H-L-Arg(Cbz)$_2$-Oallyl | Scheme 4 | P3 deprotection |
| 149 | Scheme 2 | Boc-Gly-OH | H-L-Arg(Cbz)$_2$-Oallyl | Scheme 4 | P3 deprotection |
| 150 | Scheme 2 | Boc-Gly-OH | H-L-Arg(Cbz)$_2$-Oallyl | Scheme 4 | P3 deprotection |
| 151 | Scheme 1 | Alloc-Gly-OH | Boc-L-Arg(Fmoc)$_2$-OH | Scheme 4 | P3 deprotection |
| 152 | Scheme 1 | Alloc-Gly-OH | Boc-L-Arg(Fmoc)$_2$-OH | Scheme 4 | P3 deprotection |
| 153 | Scheme 1 | Alloc-Gly-OH | Boc-L-Arg(Fmoc)$_2$-OH | Scheme 4 | P3 deprotection |
| 154 | Scheme 1 | Alloc-Gly-OH | Boc-L-Arg(Fmoc)$_2$-OH | Scheme 4 | P3 deprotection |
| 155 | Scheme 1 | Alloc-Gly-OH | Boc-L-Arg(Fmoc)$_2$-OH | Scheme 4 | P3 deprotection |
| 156 | Scheme 1 | Alloc-Gly-OH | Boc-L-Arg(Fmoc)$_2$-OH | Scheme 4 | P3 deprotection |
| 157 | Scheme 1 | Alloc-Gly-OH | Boc-L-Arg(Fmoc)$_2$-OH | Scheme 4 | P3 deprotection |
| 158 | Scheme 1 | Alloc-Gly-OH | Boc-L-Arg(Fmoc)$_2$-OH | Scheme 4 | P3 deprotection |
| 159 | Scheme 1 | Alloc-Gly-OH | Boc-L-Canavanine (Fmoc)-OH | Scheme 4 | P3 deprotection |
| 160 | Scheme 1 | Alloc-Gly-OH | Boc-L-Arg(Fmoc)$_2$-OH | Scheme 4 | P3 deprotection |
| 161 | Scheme 1 | Alloc-Gly-OH | Boc-L-Arg(Fmoc)$_2$-OH | Scheme 4 | P3 deprotection |
| 162 | Scheme 1 | Alloc-Gly-OH | Boc-L-Arg(Fmoc)$_2$-OH | Scheme 4 | P3 deprotection |
| 163 | Scheme 1 | Alloc-Gly-OH | Boc-L-Arg(Fmoc)$_2$-OH | Scheme 4 | P3 deprotection |
| 164 | Scheme 1 | Alloc-Gly-OH | Boc-L-Arg(Fmoc)$_2$-OH | Scheme 4 | P3 deprotection |
| 165 | Scheme 1 | Alloc-Gly-OH | Boc-L-Arg(Fmoc)$_2$-OH | Scheme 4 | P3 deprotection |
| 166 | Scheme 1 | Alloc-Gly-OH | Boc-L-Arg(Fmoc)$_2$-OH | Scheme 4 | P3 deprotection |
| 167 | Scheme 1 | Alloc-Gly-OH | Boc-L-Arg(Fmoc)$_2$-OH | Scheme 4 | P3 deprotection |
| 168 | Scheme 1 | Alloc-Gly-OH | Boc-L-Arg(Fmoc)$_2$-OH | Scheme 4 | P3 deprotection |
| 169 | Scheme 1 | Alloc-Gly-OH | Boc-L-Arg(Fmoc)$_2$-OH | Scheme 4 | P3 deprotection |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 170 | Scheme 1 | Alloc-Gly-OH | Boc-L-Arg(Fmoc)$_2$-OH | Scheme 4 | P3 deprotection |
| 171 | Scheme 1 | Alloc-Gly-OH | Boc-L-Arg(Fmoc)$_2$-OH | Scheme 4 | P3 deprotection |
| 172 | Scheme 1 | Alloc-Gly-OH | Boc-L-Arg(Fmoc)$_2$-OH | Scheme 4 | P3 deprotection |
| 173 | Scheme 1 | Alloc-Gly-OH | Boc-L-Arg(Fmoc)$_2$-OH | Scheme 4 | P3 deprotection |
| 174 | Scheme 1 | Alloc-Gly-OH | Boc-L-Arg(Fmoc)$_2$-OH | Scheme 4 | P3 deprotection |
| 175 | Scheme 1 | Alloc-Gly-OH | Boc-L-Arg(Fmoc)$_2$-OH | Scheme 4 | P3 deprotection |
| 176 | Scheme 1 | Alloc-Gly-OH | Boc-L-Arg(Fmoc)$_2$-OH | Scheme 4 | P3 deprotection |
| 177 | Scheme 1 | Alloc-Gly-OH | Boc-L-Arg(Fmoc)$_2$-OH | Scheme 4 | P3 deprotection |
| 178 | Scheme 1 | Alloc-Gly-OH | Boc-L-Arg(Fmoc)$_2$-OH | Scheme 4 | P3 deprotection |
| 179 | Scheme 1 | Alloc-Gly-OH | Boc-L-Arg(Fmoc)$_2$-OH | Scheme 4 | P3 deprotection |
| 180 | Scheme 1 | Alloc-Gly-OH | Boc-L-Arg(Fmoc)$_2$-OH | Scheme 4 | P3 deprotection |
| 181 | Scheme 1 | Alloc-Gly-OH | Boc-L-Arg(Fmoc)$_2$-OH | Scheme 4 | P3 deprotection |
| 182 | Scheme 1 | 2-naphthoic-Gly-OH | Fmoc-L-Arg(Pbf)-OH | Scheme 3 | P3 deprotection |
| 183 | Scheme 1 | 2-naphthoic-Gly-OH | Fmoc-L-Arg(Pbf)-OH | Scheme 3 | P3 deprotection |
| 184 | Scheme 1 | 2-naphthoic-Gly-OH | Fmoc-L-Arg(Pbf)-OH | Scheme 3 | P3 deprotection |
| 185 | Scheme 1 | Alloc-Gly-OH | Boc-L-Arg(Fmoc)$_2$-OH | Scheme 4 | P3 deprotection |
| 186 | Scheme 1 | Alloc-Gly-OH | Boc-L-Arg(Fmoc)$_2$-OH | Scheme 4 | P3 deprotection |
| 187 | Scheme 1 | Alloc-Gly-OH | Boc-L-Arg(Fmoc)$_2$-OH | Scheme 4 | P3 deprotection |
| 188 | Scheme 1 | Alloc-Gly-OH | Boc-L-Arg(Fmoc)$_2$-OH | Scheme 4 | P3 deprotection |
| 189 | Scheme 1 | Alloc-Gly-OH | Boc-L-Arg(Fmoc)$_2$-OH | Scheme 4 | P3 deprotection |
| 190 | Scheme 1 | Alloc-Gly-OH | Boc-L-Arg(Fmoc)$_2$-OH | Scheme 4 | P3 deprotection |
| 191 | Scheme 1 | Alloc-Gly-OH | Boc-L-Arg(Fmoc)$_2$-OH | Scheme 4 | P3 deprotection |
| 192 | Scheme 1 | Alloc-Gly-OH | Boc-L-Arg(Fmoc)$_2$-OH | Scheme 4 | P3 deprotection |
| 193 | Scheme 1 | Alloc-Gly-OH | Boc-L-Arg(Fmoc)$_2$-OH | Scheme 4 | P3 deprotection |
| 194 | Scheme 1 | Alloc-Gly-OH | Boc-L-Arg(Fmoc)$_2$-OH | Scheme 4 | P3 deprotection |
| 195 | Scheme 1 | Alloc-Gly-OH | Boc-L-Arg(Fmoc)$_2$-OH | Scheme 4 | P3 deprotection |
| 196 | Scheme 1 | Alloc-Gly-OH | Boc-L-Arg(Fmoc)$_2$-OH | Scheme 4 | P3 deprotection |
| 197 | Scheme 1 | 2-naphthoic-Gly-OH | Fmoc-β-(1-Boc-4-piperidinyl)-DL-Gly-OH | Scheme 3 | P3 deprotection |
| 198 | Scheme 1 | 2-naphthoic-Gly-OH | Fmoc-β-(1-Boc-4-piperidinyl)-DL-Ala-OH | Scheme 3 | P3 deprotection |
| 199 | Scheme 1 | Alloc-Gly-OH | Boc-L-Arg(Fmoc)$_2$-OH | Scheme 4 | P3 deprotection |
| 200 | Scheme 1 | Alloc-Gly-OH | Boc-L-Arg(Fmoc)$_2$-OH | Scheme 4 | P3 deprotection |
| 201 | Scheme 1 | 2-naphthoic-Gly-OH | Fmoc-L-Arg(Pbf)-OH | Scheme 3 | P3 deprotection |
| 202 | Scheme 1 | 2-naphthoic-Gly-OH | Fmoc-L-Arg(Pbf)-OH | Scheme 3 | P3 deprotection |
| 203 | Scheme 1 | 2-naphthoic-Gly-OH | Fmoc-L-Arg(Pbf)-OH | Scheme 3 | P3 deprotection |
| 204 | Scheme 1 | 2-naphthoic-Gly-OH | Fmoc-L-Arg(Pbf)-OH | Scheme 3 | P3 deprotection |
| 205 | Scheme 1 | 2-naphthoic-Gly-OH | Fmoc-L-Arg(Pbf)-OH | Scheme 3 | P3 deprotection |
| 206 | Scheme 1 | 2-naphthoic-Gly-OH | Fmoc-L-Arg(Pbf)-OH | Scheme 3 | P3 deprotection |
| 207 | Scheme 1 | 2-naphthoic-Gly-OH | Fmoc-L-Arg(Pbf)-OH | Scheme 3 | P3 deprotection |
| 208 | Scheme 1 | Alloc-Gly-OH | Boc-L-Arg(Fmoc)$_2$-OH | Scheme 4 | P3 deprotection |
| 209 | Scheme 1 | Alloc-Gly-OH | Boc-L-Arg(Fmoc)$_2$-OH | Scheme 4 | P3 deprotection |
| 210 | Scheme 1 | Alloc-Gly-OH | Boc-L-Arg(Fmoc)$_2$-OH | Scheme 4 | P3 deprotection |
| 211 | Scheme 1 | Alloc-Gly-OH | Boc-L-Arg(Fmoc)$_2$-OH | Scheme 4 | P3 deprotection |
| 212 | Scheme 1 | Cbz-Gly-OH | Fmoc-L-Orn(Boc)-OH | Scheme 4 | P3 deprotection |
| 213 | Scheme 1 | Cbz-Gly-OH | Fmoc-L-Orn(Boc)-OH | Scheme 4 | P3 deprotection |
| 214 | Scheme 1 | Cbz-Gly-OH | Fmoc-L-Orn(Boc)-OH | Scheme 4 | P3 deprotection |
| 215 | Scheme 1 | Alloc-Gly-OH | Boc-L-Arg(Fmoc)$_2$-OH | Scheme 4 | P3 deprotection |
| 216 | Scheme 1 | 2-naphthoic-Gly-OH | Fmoc-L-Arg(NMe)$_2$Pbf-OH | Scheme 3 | P3 deprotection |
| 217 | Scheme 1 | Alloc-Gly-OH | Boc-L-Arg(Fmoc)$_2$-OH | Scheme 4 | P3 deprotection |
| 218 | Scheme 1 | Alloc-Gly-OH | Boc-L-Arg(Fmoc)$_2$-OH | Scheme 4 | P3 deprotection |
| 219 | Scheme 1 | Cbz-Gly-OH | Fmoc-L-Orn(Boc)-OH | Scheme 4 | P3 deprotection |
| 220 | Scheme 1 | Cbz-Gly-OH | Fmoc-L-Orn(Boc)-OH | Scheme 4 | P3 deprotection |
| 221 | Scheme 1 | Cbz-Gly-OH | Fmoc-L-Orn(Boc)-OH | Scheme 4 | P3 deprotection |
| 222 | Scheme 1 | Cbz-Gly-OH | Fmoc-L-Orn(Boc)-OH | Scheme 4 | P3 deprotection |
| 223 | Scheme 1 | Cbz-Gly-OH | Fmoc-L-Orn (Boc)-OH | Scheme 4 | P3 deprotection |
| 224 | Scheme 1 | Cbz-Gly-OH | Fmoc-L-Orn(Boc)-OH | Scheme 4 | P3 deprotection |
| 225 | Scheme 1 | Cbz-Gly-OH | Fmoc-L-Orn(Boc)-OH | Scheme 4 | P3 deprotection, guanidinylation |
| 226 | Scheme 1 | 2-naphthoic-Gly-OH | Fmoc-L-Orn(Boc)-OH | Scheme 3 | P3 deprotection, reductive alkylation |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 227 | Scheme 1 | 2-naphthoic-Gly-OH | Fmoc-L-Arg(Pbf)-OH | Scheme 3 | P3 deprotection |
| 228 | Scheme 1 | 2-naphthoic-Gly-OH | Fmoc-L-Arg(Pbf)-OH | Scheme 3 | P3 deprotection |
| 229 | Scheme 1 | 2-naphthoic-Gly-OH | Fmoc-L-3-PyridylAla-OH | Scheme 3 | none |
| 230 | Scheme 1 | 2-naphthoic-Gly-OH | Fmoc-L-4-PyridylAla-OH | Scheme 3 | none |
| 231 | Scheme 1 | Cbz-Gly-OH | Fmoc-L-Orn(Boc)-OH | Scheme 4 | P3 deprotection, reductive alkylation |
| 232 | Scheme 1 | 2-naphthoic-Gly-OH | Fmoc-L-Lys(i-Pr)Fmoc-OH | Scheme 3 | P3 deprotection |
| 233 | Scheme 1 | Cbz-Gly-OH | Fmoc-L-Orn(Boc)-OH | Scheme 4 | P3 deprotection |
| 234 | Scheme 1 | Cbz-Gly-OH | Fmoc-L-Orn(Boc)-OH | Scheme 4 | P3 deprotection |
| 235 | Scheme 1 | Cbz-Gly-OH | Fmoc-L-Orn(Boc)-OH | Scheme 4 | P3 deprotection |
| 236 | Scheme 1 | Cbz-Gly-OH | Fmoc-L-Orn(Boc)-OH | Scheme 4 | P3 deprotection |
| 237 | Scheme 1 | Cbz-Gly-OH | Fmoc-L-Orn(Boc)-OH | Scheme 4 | P3 deprotection |
| 238 | Scheme 1 | Cbz-Gly-OH | Fmoc-L-Orn(Boc)-OH | Scheme 4 | P3 deprotection |
| 239 | Scheme 1 | Cbz-Gly-OH | Fmoc-L-Orn(Boc)-OH | Scheme 4 | P3 deprotection |
| 240 | Scheme 1 | Cbz-Gly-OH | Fmoc-L-Orn(Boc)-OH | Scheme 4 | P3 deprotection |
| 241 | Scheme 1 | Cbz-Gly-OH | Fmoc-L-Orn(Boc)-OH | Scheme 4 | P3 deprotection |
| 242 | Scheme 1 | Cbz-Gly-OH | Fmoc-L-Orn(Boc)-OH | Scheme 4 | P3 deprotection |
| 243 | Scheme 1 | Cbz-Gly-OH | Fmoc-L-Orn(Boc)-OH | Scheme 4 | P3 deprotection |
| 244 | Scheme 1 | Cbz-Gly-OH | Fmoc-L-Orn(Boc)-OH | Scheme 4 | P3 deprotection |
| 245 | Scheme 1 | 2-naphthoic-Gly-OH | Fmoc-L-Arg(Pbf)-OH | Scheme 3 | P3 deprotection |
| 246 | Scheme 1 | 2-naphthoic-Gly-OH | Fmoc-L-Arg(Pbf)-OH | Scheme 3 | P3 deprotection |
| 247 | Scheme 1 | 2-naphthoic-Gly-OH | Fmoc-L-Arg(Pbf)-OH | Scheme 3 | P3 deprotection |
| 248 | Scheme 1 | 2-naphthoic-Gly-OH | Fmoc-L-Orn(Boc)-OH | Scheme 3 | P3 deprotection, reductive alkylation |
| 249 | Scheme 1 | 2-naphthoic-Gly-OH | Fmoc-L-Orn(Boc)-OH | Scheme 3 | P3 deprotection, reductive alkylation |
| 250 | Scheme 1 | 2-naphthoic-Gly-OH | Fmoc-L-Orn(Boc)-OH | Scheme 3 | P3 deprotection, reductive alkylation |
| 251 | Scheme 1 | 2-naphthoic-Gly-OH | Fmoc-L-Orn(Boc)-OH | Scheme 3 | P3 deprotection, reductive alkylation |
| 252 | Scheme 1 | 2-naphthoic-Gly-OH | Fmoc-L-Arg(Pbf)-OH | Scheme 3 | P3 deprotection |
| 253 | Scheme 1 | 2-naphthoic-Gly-OH | Fmoc-L-Arg(Pbf)-OH | Scheme 3 | P3 deprotection |
| 254 | Scheme 1 | 2-naphthoic-Gly-OH | Fmoc-L-Arg(Pbf)-OH | Scheme 3 | P3 deprotection |
| 255 | Scheme 1 | Cbz-Gly-OH | Fmoc-L-Orn(Boc)-OH | Scheme 4 | P3 deprotection |
| 256 | Scheme 1 | Cbz-Gly-OH | Fmoc-L-Orn(Boc)-OH | Scheme 4 | P3 deprotection |
| 257 | Scheme 1 | Cbz-Gly-OH | Fmoc-L-Orn(Boc)-OH | Scheme 4 | P3 deprotection |
| 258 | Scheme 1 | Cbz-Gly-OH | Fmoc-L-Orn(Boc)-OH | Scheme 4 | P1 deprotect, R1 acylate, ring methylate, P3 deprotect |
| 259 | Scheme 1 | Cbz-Gly-OH | Fmoc-L-Orn(Boc)-OH | Scheme 4 | P3 deprotection |
| 260 | Scheme 1 | Cbz-Gly-OH | Fmoc-L-Orn(Boc)-OH | Scheme 4 | P3 deprotection |
| 261 | Scheme 1 | Cbz-Gly-OH | Fmoc-L-Orn(Boc)-OH | Scheme 4 | P3 deprotection then dialkylation with alkyl dibromide |
| 262 | Scheme 1 | Cbz-Gly-OH | Fmoc-L-Orn(Boc)-OH | Scheme 4 | P3 deprotection then dialkylation with alkyl dibromide |
| 262 | Scheme 1 | Boc-Gly-OH | Fmoc-L-Orn(Cbz)-OH | Scheme 5 | P3 deprotection, dialkylation |
| 263 | Scheme 1 | 2-naphthoic-Gly-OH | Fmoc-L-Dab(Boc)-OH | Scheme 3 | P3 deprotection |
| 263 | Scheme 1 | Cbz-Gly-OH | Fmoc-L-Dab(Boc)-OH | Scheme 4 | P3 deprotection |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 264 | Scheme 1 | 2-naphthoic-Gly-OH | Fmoc-L-Orn(Boc)-OH | Scheme 3 | P3 deprotection then dialkylation with alkyl dibromide |
| 265 | Scheme 1 | 2-naphthoic-Gly-OH | Fmoc-L-Orn(Boc)-OH | Scheme 3 | P3 deprotection then dialkylation with alkyl dibromide |
| 266 | Scheme 1 | 2-naphthoic-Gly-OH | Fmoc-L-Arg(Pbf)-OH | Scheme 3 | P3 deprotection |
| 267 | Scheme 1 | 2-naphthoic-Gly-OH | Fmoc-L-Arg(Pbf)-OH | Scheme 3 | P3 deprotection |
| 268 | Scheme 1 | 2-naphthoic-Gly-OH | Fmoc-L-Arg(Pbf)-OH | Scheme 3 | P3 deprotection |
| 269 | Scheme 1 | Cbz-Gly-OH | Fmoc-L-Orn(Boc)-OH | Scheme 4 | P3 deprotection then dialkylation with alkyl dibromide |
| 270 | Scheme 1 | Cbz-Gly-OH | Fmoc-L-Orn (Boc)-OH | Scheme 4 | P3 deprotection then dialkylation with alkyl dibromide |
| 271 | Scheme 1 | Cbz-Gly-OH | Fmoc-L-Orn(Boc)-OH | Scheme 4 | P3 deprotection then dialkylation with alkyl dibromide |
| 272 | Scheme 1 | 2-naphthoic-Gly-OH | Fmoc-L-Arg(Pbf)-OH | Scheme 3 | P3 deprotection |
| 273 | Scheme 1 | 2-naphthoic-Gly-OH | Fmoc-L-Arg(Pbf)-OH | Scheme 3 | P3 deprotection |
| 274 | Scheme 1 | Cbz-Gly-OH | Fmoc-L-Dap(Boc)-OH | Scheme 4 | P3 deprotection |
| 275 | Scheme 1 | Cbz-Gly-OH | Fmoc-L-Dap(Boc)-OH | Scheme 4 | P3 deprotection |
| 276 | Scheme 1 | Cbz-Gly-OH | Boc-L-Dab(Fmoc)-OH | Scheme 4 | P3 deprotection |
| 276 | Scheme 1 | Cbz-Gly-OH | Fmoc-L-Dab(Boc)-OH | Scheme 4 | P3 deprotection |
| 277 | Scheme 1 | Cbz-Gly-OH | Boc-L-Dab(Fmoc)-OH | Scheme 4 | P3 deprotection |
| 277 | Scheme 1 | Cbz-Gly-OH | Fmoc-L-Dab(Boc)-OH | Scheme 4 | P3 deprotection |
| 278 | Scheme 1 | Cbz-Gly-OH | Fmoc-L-Dap(Boc)-OH | Scheme 4 | P3 deprotection then dialkylation with alkyl dibromide |
| 279 | Scheme 1 | Cbz-Gly-OH | Fmoc-L-Dap(Boc)-OH | Scheme 4 | P3 deprotection then dialkylation with alkyl dibromide |
| 279 | Scheme 1 | Cbz-Gly-OH | Fmoc-L-Dap(Boc)-OH | Scheme 5 | P3 deprotection then dialkylation with alkyl dibromide |
| 280 | Scheme 1 | Cbz-Gly-OH | Fmoc-L-Dab(Boc)-OH | Scheme 4 | P3 deprotection |
| 281 | Scheme 1 | Cbz-Gly-OH | Fmoc-L-Dab(Boc)-OH | Scheme 4 | P3 deprotection |
| 282 | Scheme 1 | Cbz-Gly-OH | Fmoc-L-Dab(Boc)-OH | Scheme 4 | P3 deprotection |
| 283 | Scheme 1 | Cbz-Gly-OH | Fmoc-L-Dab(Boc)-OH | Scheme 4 | P3 deprotection |
| 284 | Scheme 1 | Cbz-Gly-OH | Fmoc-L-Dab(Boc)-OH | Scheme 4 | P3 deprotection then dialkylation with alkyl dibromide |
| 285 | Scheme 1 | Cbz-Gly-OH | Fmoc-L-Dab(Boc)-OH | Scheme 4 | P3 deprotection then dialkylation with alkyl dibromide |
| 286 | Scheme 1 | Cbz-Gly-OH | Fmoc-L-Dab(Boc)-OH | Scheme 4 | P3 deprotection then dialkylation with alkyl dibromide |
| 287 | Scheme 1 | Cbz-Gly-OH | Fmoc-L-Dab(Boc)-OH | Scheme 4 | P3 deprotection then dialkylation with alkyl dibromide |
| 288 | Scheme 1 | Cbz-Gly-OH | Fmoc-L-Dab(Boc)-OH | Scheme 4 | P3 deprotection then dialkylation with alkyl dibromide |
| 289 | Scheme 1 | 2-naphthoic-Gly-OH | Fmoc-L-Arg(Pbf)-OH | Scheme 3 | P3 deprotection |

TABLE 2-continued

Synthesis of Compounds

| Cpd. | Route to A | Scheme 1: VN(R²)—Y—CO₂H | P²NH—CH(U)—CO₂H | Conversion of A to Product | U modification |
|---|---|---|---|---|---|
| 290 | Scheme 1 | 2-naphthoic-Gly-OH | Fmoc-L-Arg(Pbf)-OH | Scheme 3 | P3 deprotection |
| 291 | Scheme 1 | 2-naphthoic-Gly-OH | Fmoc-L-Arg(Pbf)-OH | Scheme 3 | P3 deprotection |
| 292 | Scheme 1 | 2-naphthoic-Gly-OH | Fmoc-L-Arg(Pbf)-OH | Scheme 3 | P3 deprotection |
| 293 | Scheme 1 | 2-naphthoic-Gly-OH | Fmoc-L-Arg(Pbf)-OH | Scheme 3 | P3 deprotection |
| 294 | Scheme 1 | 2-naphthoic-Gly-OH | Fmoc-L-Arg(Pbf)-OH | Scheme 3 | P3 deprotection |
| 295 | Scheme 1 | 2-naphthoic-Gly-OH | Fmoc-L-Arg(Pbf)-OH | Scheme 3 | P3 deprotection |
| 296 | Scheme 1 | Cbz-Gly-OH | Boc-L-Nle-OH | Scheme 4 | none |
| 297 | Scheme 1 | Cbz-Gly-OH | Boc-L-Nle-OH | Scheme 4 | none |
| 298 | Scheme 1 | Cbz-Gly-OH | Boc-L-Gln-OH | Scheme 4 | none |
| 299 | Scheme 1 | Cbz-Gly-OH | Boc-L-Gln-OH | Scheme 4 | none |
| 300 | Scheme 1 | Cbz-Gly-OH | Fmoc-L-Orn(Boc)-OH | Scheme 4 | P3 deprotection then acylation |
| 301 | Scheme 1 | Cbz-Gly-OH | Fmoc-L-Orn(Boc)-OH | Scheme 4 | P3 deprotection then acylation |
| 302 | Scheme 1 | 2-naphthoic-Gly-OH | Fmoc-L-Arg(Pbf)-OH | Scheme 3 | P3 deprotection |
| 303 | Scheme 1 | 2-naphthoic-Gly-OH | Fmoc-L-Arg(Pbf)-OH | Scheme 3 | P3 deprotection |
| 304 | Scheme 1 | 2-naphthoic-Gly-OH | Fmoc-L-Arg(Pbf)-OH | Scheme 3 | P3 deprotection |
| 305 | Scheme 1 | 2-naphthoic-Gly-OH | Fmoc-L-Arg(Pbf)-OH | Scheme 3 | P3 deprotection |
| 306 | Scheme 1 | Cbz-Gly-OH | Fmoc-L-Dab(Boc)-OH | Scheme 4 | P3 deprotection then acylation |
| 307 | Scheme 1 | Cbz-Gly-OH | Fmoc-L-Dab(Boc)-OH | Scheme 4 | P3 deprotection then acylation |
| 308 | Scheme 1 | Cbz-β-Ala | Fmoc-L-Dab(Boc)-OH | Scheme 4 | P3 deprotection |
| 309 | Scheme 1 | Cbz-β-Ala | Fmoc-L-Dab(Boc)-OH | Scheme 4 | P3 deprotection |
| 310 | Scheme 1 | Cbz-β-Ala | Fmoc-L-Dab(Boc)-OH | Scheme 4 | P3 deprotection |
| 311 | Scheme 1 | Cbz-β-Ala | Fmoc-L-Dab(Boc)-OH | Scheme 4 | P3 deprotection then dialkylation with alkyl dibromide |
| 312 | Scheme 1 | Cbz-β-Ala | Fmoc-L-Dab(Boc)-OH | Scheme 4 | P3 deprotection then dialkylation with alkyl dibromide |
| 313 | Scheme 1 | Cbz-β-Ala | Fmoc-L-Dab(Boc)-OH | Scheme 4 | P3 deprotection then dialkylation with alkyl dibromide |
| 314 | Scheme 1 | 2-naphthoic-Gly-OH | Fmoc-L-Arg(Pbf)-OH | Scheme 3 | R5 deprotection and amidation then P3 deprotection |
| 315 | Scheme 1 | Cbz-Gly-OH | Boc-L-Cha-OH | Scheme 4 | none |
| 316 | Scheme 1 | Cbz-Gly-OH | Boc-L-Cha-OH | Scheme 4 | none |
| 317 | Scheme 1 | Cbz-Gly-OH | Boc-L-Glu(1-piperidinyl)-OH | Scheme 4 | none |
| 318 | Scheme 1 | Cbz-Gly-OH | Boc-L-Glu(1-piperidinyl)-OH | Scheme 4 | none |
| 319 | Scheme 1 | Cbz-Gly-OH | Boc-L-Hfe-OH | Scheme 4 | none |
| 320 | Scheme 1 | Cbz-Gly-OH | Boc-L-Hfe-OH | Scheme 4 | none |
| 321 | Scheme 1 | Cbz-Gly-OH | Boc-L-hCha-OH | Scheme 4 | none |
| 322 | Scheme 1 | Cbz-Gly-OH | Boc-L-hCha-OH | Scheme 4 | none |
| 323 | Scheme 1 | Cbz-Gly-OH | Boc-L-Phe-OH | Scheme 4 | none |
| 324 | Scheme 1 | Cbz-Gly-OH | Boc-L-Phe-OH | Scheme 4 | none |
| 325 | Scheme 1 | Alloc-Gly-OH | Fmoc-L-Dab(Boc)-OH | Scheme 4 | P3 deprotection |
| 326 | Scheme 1 | Alloc-Gly-OH | Fmoc-L-Dab(Boc)-OH | Scheme 4 | P3 deprotection |
| 327 | Scheme 1 | 2-naphthoic-Gly-OH | Fmoc-L-Arg(Pbf)-OH | Scheme 3 | P3 deprotection |
| 328 | Scheme 1 | 2-naphthoic-Gly-OH | Fmoc-L-Arg(Pbf)-OH | Scheme 3 | P3 deprotection |
| 329 | Scheme 1 | 2-naphthoic-Gly-OH | Fmoc-L-Orn(Boc)-OH | Scheme 3 | P3 deprotection |
| 330 | Scheme 1 | 2-naphthoic-Gly-OH | Fmoc-L-Orn(Boc)-OH | Scheme 3 | P3 deprotection |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 331 | Scheme 1 | 2-naphthoic-Gly-OH | Fmoc-L-Orn(Boc)-OH | Scheme 3 | P3 deprotection |
| 332 | Scheme 1 | 2-naphthoic-Gly-OH | Fmoc-L-Orn(Boc)-OH | Scheme 3 | P3 deprotection |
| 333 | Scheme 1 | 2-naphthoic-Gly-OH | Fmoc-L-Orn(Boc)-OH | Scheme 3 | P3 deprotection |
| 334 | Scheme 1 | 2-naphthoic-Gly-OH | Fmoc-L-Orn(Boc)-OH | Scheme 3 | P3 deprotection |
| 335 | Scheme 1 | 2-naphthoic-Gly-OH | Fmoc-L-Orn(Boc)-OH | Scheme 3 | P3 deprotection |
| 336 | Scheme 1 | 2-naphthoic-Gly-OH | Fmoc-L-Orn(Boc)-OH | Scheme 3 | P3 deprotection |
| 337 | Scheme 1 | 2-naphthoic-Gly-OH | Fmoc-L-Orn(Boc)-OH | Scheme 3 | P3 deprotection |
| 338 | Scheme 1 | 2-naphthoic-Gly-OH | Fmoc-L-Orn(Boc)-OH | Scheme 3 | P3 deprotection |
| 339 | Scheme 1 | 2-naphthoic-Gly-OH | Fmoc-L-Orn(Boc)-OH | Scheme 3 | P3 deprotection |
| 340 | Scheme 1 | 2-naphthoic-Gly-OH | Fmoc-L-Orn(Boc)-OH | Scheme 3 | P3 deprotection |
| 341 | Scheme 1 | 2-naphthoic-Gly-OH | Fmoc-L-Orn(Boc)-OH | Scheme 3 | P3 deprotection |
| 342 | Scheme 1 | 2-naphthoic-Gly-OH | Fmoc-L-Orn(Boc)-OH | Scheme 3 | P3 deprotection |
| 343 | Scheme 1 | Alloc-Gly-OH | Fmoc-L-Dab(Boc)-OH | Scheme 4 | P3 deprotection then dialkylation with alkyl dibromide |
| 344 | Scheme 1 | Alloc-Gly-OH | Fmoc-L-Dab(Boc)-OH | Scheme 4 | P3 deprotection then dialkylation with alkyl dibromide |
| 345 | Scheme 1 | Alloc-Gly-OH | Fmoc-L-Dab(Boc)-OH | Scheme 4 | P3 deprotection then dialkylation with alkyl dibromide |
| 346 | Scheme 1 | Cbz-Gly-OH | Fmoc-L-Dab(Boc)-OH | Scheme 4 | P3 deprotection |
| 347 | Scheme 1 | Cbz-Gly-OH | Fmoc-L-Dab(Boc)-OH | Scheme 4 | P3 deprotection |
| 348 | Scheme 1 | Cbz-Gly-OH | Fmoc-L-Dab(Boc)-OH | Scheme 5 | P3 deprotection then dialkylation with alkyl dibromide |
| 348 | Scheme 1 | Cbz-Gly-OH | Fmoc-L-Dab(Boc)-OH | Scheme 4 | P3 deprotection then dialkylation with alkyl dibromide |
| 349 | Scheme 1 | Cbz-Gly-OH | Fmoc-L-Dab(Boc)-OH | Scheme 5 | P3 deprotection then dialkylation with alkyl dibromide |
| 350 | Scheme 1 | Cbz-Gly-OH | Fmoc-L-Dab(Boc)-OH | Scheme 5 | P3 deprotection then dialkylation with alkyl dibromide |
| 351 | Scheme 1 | Cbz-Gly-OH | Fmoc-L-Dab(Boc)-OH | Scheme 4 | P3 deprotection |
| 352 | Scheme 1 | Cbz-Gly-OH | Fmoc-L-Dab(Boc)-OH | Scheme 4 | P3 deprotection |
| 353 | Scheme 1 | Cbz-Gly-OH | Fmoc-L-Dab(Boc)-OH | Scheme 4 | P3 deprotection |
| 354 | Scheme 1 | Cbz-Gly-OH | Fmoc-L-Dab(Boc)-OH | Scheme 4 | P3 deprotection |
| 355 | Scheme 1 | Cbz-Gly-OH | Fmoc-L-Dap(Boc)-OH | Scheme 5 | P3 deprotection then dialkylation with alkyl dibromide |
| 356 | Scheme 1 | Cbz-Gly-OH | Fmoc-L-Dap(Boc)-OH | Scheme 4 | P3 deprotection then dialkylation with alkyl dibromide |
| 357 | Scheme 1 | 2-naphthoic-Gly-OH | Fmoc-L-Orn(Boc)-OH | Scheme 3 | P3 deprotection |
| 358 | Scheme 1 | 2-naphthoic-Gly-OH | Fmoc-L-Orn(Boc)-OH | Scheme 3 | P3 deprotection |
| 359 | Scheme 1 | 2-naphthoic-Gly-OH | Fmoc-L-Orn(Boc)-OH | Scheme 3 | P3 deprotection then dialkylation with alkyl dibromide |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 360 | Scheme 1 | 2-naphthoic-Gly-OH | Fmoc-L-Arg(Pbf)-OH | Scheme 3 | R5 deprotection and amidation then P3 deprotection |
| 361 | Scheme 1 | 2-naphthoic-Gly-OH | Fmoc-L-Arg(Pbf)-OH | Scheme 3 | R5 deprotection and amidation then P3 deprotection |
| 362 | Scheme 1 | Cbz-Gly-OH | Fmoc-L-Dap(Boc)-OH | Scheme 4 | P3 deprotection, alkylation |
| 363 | Scheme 1 | Cbz-Gly-OH | Fmoc-L-Dap(Boc)-OH | Scheme 4 | P3 deprotection, dialkylation |
| 364 | Scheme 1 | Alloc-Gly-OH | Fmoc-L-Dap(Boc)-OH | Scheme 4 | P3 deprotection |
| 365 | Scheme 1 | Alloc-Gly-OH | Fmoc-L-Dap(Boc)-OH | Scheme 4 | P3 deprotection |
| 366 | Scheme 1 | Cbz-Gly-OH | Fmoc-L-Dab(Boc)-OH | Scheme 4 | P3 deprotection |
| 367 | Scheme 1 | Cbz-Gly-OH | Fmoc-L-Dap(Boc)-OH | Scheme 5 | P3 deprotection then dialkylation with alkyl dibromide |
| 367 | Scheme 1 | Cbz-Gly-OH | Fmoc-L-Dap(Boc)-OH | Scheme 4 | P3 deprotection then dialkylation with alkyl dibromide |
| 368 | Scheme 1 | Cbz-Gly-OH | Fmoc-L-Dap(Boc)-OH | Scheme 5 | P3 deprotection then dialkylation with alkyl dibromide |
| 369 | Scheme 1 | Cbz-Gly-OH | Fmoc-L-Dab(Boc)-OH | Scheme 4 | P3 deprotection |
| 370 | Scheme 1 | Cbz-Gly-OH | Fmoc-L-Dab(Boc)-OH | Scheme 4 | P3 deprotection |
| 371 | Scheme 1 | Alloc-Gly-OH | Fmoc-L-Dap(Boc)-OH | Scheme 5 | P3 deprotection then dialkylation with alkyl dibromide |
| 372 | Scheme 1 | Alloc-Gly-OH | Fmoc-L-Dap(Boc)-OH | Scheme 5 | P3 deprotection then dialkylation with alkyl dibromide |
| 373 | Scheme 1 | 2-naphthoic-Gly-OH | Fmoc-L-Orn(Boc)-OH | Scheme 3 | P3 deprotection |
| 374 | Scheme 1 | 2-naphthoic-Gly-OH | Fmoc-L-Orn(Boc)-OH | Scheme 3 | P3 deprotection |
| 375 | Scheme 1 | 2-naphthoic-Gly-OH | Cbz-L-Asp[N(Me)OMe]-OH | Scheme 3 | P3 conversion to aldehyde then reductive amination |
| 376 | Scheme 1 | Cbz-Gly-OH | Fmoc-L-Orn(Boc)-OH | Scheme 4 | P3 deprotection then dialkylation with alkyl dibromide |
| 377 | Scheme 1 | 2-naphthoic-Gly-OH | Fmoc-L-Orn(Boc)-OH | Scheme 3 | P3 deprotection |
| 378 | Scheme 1 | Boc-Gly-OH | Cbz-L-Asp[N(Me)OMe]-OH | Scheme 4 | P3 conversion to aldehyde then reductive amination |
| 379 | Scheme 1 | Boc-Gly-OH | Cbz-L-Asp[N(Me)OMe]-OH | Scheme 4 | P3 conversion to aldehyde then reductive amination |
| 380 | Scheme 1 | Cbz-Gly-OH | Fmoc-L-Dab(Boc)-OH | Scheme 4 | P3 deprotection then dialkylation with alkyl dibromide |
| 381 | Scheme 1 | Cbz-Gly-OH | Fmoc-L-Dab(Boc)-OH | Scheme 4 | P3 deprotection then dialkylation with alkyl dibromide |
| 382 | Scheme 1 | Cbz-Gly-OH | Fmoc-L-Dab(Boc)-OH | Scheme 4 | P3 deprotection then dialkylation with alkyl dibromide |
| 383 | Scheme 1 | Cbz-Gly-OH | Fmoc-L-Dab(Boc)-OH | Scheme 4 | P3 deprotection |

TABLE 2-continued

Synthesis of Compounds

| Cpd. | Route to A | Scheme 1: VN(R²)—Y—CO₂H | P²NH—CH(U)—CO₂H | Conversion of A to Product | U modification |
|---|---|---|---|---|---|
| 384 | Scheme 1 | Cbz-Gly-OH | Fmoc-L-Dab(Boc)-OH | Scheme 4 | P3 deprotection then dialkylation with alkyl dibromide |
| 385 | Scheme 1 | Cbz-Gly-OH | Fmoc-L-Dab(Boc)-OH | Scheme 4 | P3 deprotection then dialkylation with alkyl dibromide |
| 386 | Scheme 1 | Cbz-Gly-OH | Fmoc-L-Dab(Boc)-OH | Scheme 4 | P3 deprotection |
| 387 | Scheme 1 | Cbz-Gly-OH | Fmoc-L-Dab(Boc)-OH | Scheme 4 | P3 deprotection |
| 388 | Scheme 1 | Cbz-Gly-OH | Fmoc-L-Dab(Boc)-OH | Scheme 4 | P3 deprotection |
| 389 | Scheme 1 | Cbz-Gly-OH | Fmoc-L-Dab(Boc)-OH | Scheme 5 | P3 deprotection then dialkylation with alkyl dibromide |
| 390 | Scheme 1 | Cbz-Gly-OH | Fmoc-L-Dab(Boc)-OH | Scheme 5 | P3 deprotection then dialkylation with alkyl dibromide |
| 391 | Scheme 1 | Cbz-Gly-OH | Fmoc-L-Dab(Boc)-OH | Scheme 5 | P3 deprotection then dialkylation with alkyl dibromide |
| 392 | Scheme 1 | Cbz-Gly-OH | Fmoc-L-Dab(Boc)-OH | Scheme 4 | P3 deprotection |
| 393 | Scheme 1 | Cbz-Gly-OH | Fmoc-L-Dab(Boc)-OH | Scheme 4 | P3 deprotection |
| 394 | Scheme 1 | Cbz-Gly-OH | Fmoc-L-Dab(Boc)-OH | Scheme 4 | P3 deprotection |
| 395 | Scheme 1 | Cbz-Gly-OH | Fmoc-L-Dab(Boc)-OH | Scheme 4 | P3 deprotection then dialkylation with alkyl dibromide |
| 396 | Scheme 1 | Cbz-Gly-OH | Fmoc-L-Dab(Boc)-OH | Scheme 4 | P3 deprotection then dialkylation with alkyl dibromide |
| 397 | Scheme 1 | Cbz-Gly-OH | Fmoc-L-Dab(Boc)-OH | Scheme 4 | P3 deprotection then dialkylation with alkyl dibromide |
| 398 | Scheme 1 | Cbz-Gly-OH | Fmoc-L-Dab(Boc)-OH | Scheme 4 | P3 deprotection, alkylation |
| 399 | Scheme 1 | Cbz-Gly-OH | Fmoc-L-Dab(Boc)-OH | Scheme 4 | P3 deprotection, alkylation |
| 400 | Scheme 1 | Cbz-Gly-OH | Fmoc-L-Dab(Boc)-OH | Scheme 4 | P3 deprotection, alkylation |
| 401 | Scheme 1 | 2-naphthoic-Gly-OH | Fmoc-L-Orn(Boc)-OH | Scheme 3 | P3 deprotection |
| 402 | Scheme 1 | 2-naphthoic-Gly-OH | Fmoc-L-Orn(Boc)-OH | Scheme 3 | P3 deprotection |
| 403 | Scheme 1 | Cbz-Gly-OH | Fmoc-L-Dab(Boc)-OH | Scheme 4 | P3 deprotection then dialkylation with alkyl dibromide |
| 404 | Scheme 1 | Cbz-Gly-OH | Fmoc-L-Dab(Boc)-OH | Scheme 4 | P3 deprotection, alkylation |
| 405 | Scheme 1 | 2-naphthoic-Gly-OH | Fmoc-L-Dab(Boc)-OH | Scheme 3 | P3 deprotection |
| 406 | Scheme 1 | 2-naphthoic-Gly-OH | Fmoc-L-Dab(Boc)-OH | Scheme 3 | P3 deprotection |
| 407 | Scheme 1 | 2-naphthoic-Gly-OH | Fmoc-L-Orn(Boc)-OH | Scheme 3 | P3 deprotection |
| 408 | Scheme 1 | Cbz-Gly-OH | Fmoc-L-His(Boc)-OH | Scheme 4 | P3 deprotection |
| 409 | Scheme 1 | Cbz-Gly-OH | Fmoc-L-Dab(Boc)-OH | Scheme 4 | P3 deprotection then dialkylation with alkyl dibromide |
| 410 | Scheme 1 | Cbz-Gly-OH | Fmoc-L-Dab(Boc)-OH | Scheme 4 | P3 deprotection |
| 411 | Scheme 1 | Cbz-Gly-OH | Fmoc-L-Dap(Boc)-OH | Scheme 4 | P3 deprotection, acylation |
| 412 | Scheme 2 | Cbz-Gly-OH | H-β-(2-pyridyl)-L-Ala-Oallyl | Scheme 4 | none |
| 413 | Scheme 1 | 2-naphthoic-Gly-OH | Fmoc-L-Dab(Boc)-OH | Scheme 3 | P3 deprotection then dialkylation with alkyl dibromide |

TABLE 2-continued

Synthesis of Compounds

| Cpd. | Route to A | Scheme 1: VN(R²)—Y—CO₂H | P²NH—CH(U)—CO₂H | Conversion of A to Product | U modification |
|---|---|---|---|---|---|
| 414 | Scheme 1 | 2-naphthoic-Gly-OH | Fmoc-L-Dab(Boc)-OH | Scheme 3 | P3 deprotection then dialkylation with alkyl dibromide |
| 415 | Scheme 1 | Cbz-Gly-OH | Fmoc-L-Dab(Boc)-OH | Scheme 4 | P3 deprotection then dialkylation with alkyl dibromide |
| 416 | Scheme 1 | Cbz-Gly-OH | Fmoc-L-Dab(Boc)-OH | Scheme 4 | P3 deprotection |
| 417 | Scheme 1 | Cbz-Gly-OH | Fmoc-L-Dab(Boc)-OH | Scheme 4 | P3 deprotection then dialkylation with alkyl dibromide |
| 418 | Scheme 1 | Cbz-Gly-OH | Fmoc-L-Dab(Boc)-OH | Scheme 4 | P3 deprotection |
| 419 | Scheme 1 | Cbz-Gly-OH | Fmoc-L-Dab(Boc)-OH | Scheme 4 | P3 deprotection then dialkylation with alkyl dibromide |
| 420 | Scheme 1 | Cbz-Gly-OH | Fmoc-L-Dab(Boc)-OH | Scheme 4 | P3 deprotection |
| 421 | Scheme 1 | Cbz-Gly-OH | Fmoc-L-Dap(Boc)-OH | Scheme 4 | P3 deprotection, acylation |
| 422 | Scheme 1 | Cbz-Gly-OH | Fmoc-L-Dab(Boc)-OH | Scheme 4 | P3 deprotection then dialkylation with alkyl dibromide |
| 423 | Scheme 1 | Cbz-Gly-OH | Fmoc-L-Dab(Boc)-OH | Scheme 4 | P3 deprotection, condensation |
| 424 | Scheme 1 | Cbz-Gly-OH | Fmoc-L-Dab(Boc)-OH | Scheme 4 | P3 deprotection, condensation, reduction |
| 425 | Scheme 1 | Cbz-Gly-OH | Fmoc-L-Dab(Boc)-OH | Scheme 4 | P3 deprotection then dialkylation with alkyl dibromide |
| 426 | Scheme 1 | Cbz-Gly-OH | Fmoc-L-Dab(Boc)-OH | Scheme 4 | P3 deprotection then dialkylation with alkyl dibromide |
| 427 | Scheme 1 | Cbz-Gly-OH | Fmoc-L-Dab(Boc)-OH | Scheme 4 | P3 deprotection then dialkylation with alkyl dibromide |
| 428 | Scheme 1 | Cbz-Gly-OH | Fmoc-L-Dab(Boc)-OH | Scheme 4 | P3 deprotection then dialkylation with alkyl dibromide |
| 429 | Scheme 1 | Cbz-Gly-OH | Fmoc-L-Dab(Boc)-OH | Scheme 4 | P3 deprotection then dialkylation with alkyl dibromide |
| 430 | Scheme 1 | Cbz-Gly-OH | Fmoc-L-Dab(Boc)-OH | Scheme 4 | P3 deprotection then dialkylation with alkyl dibromide |
| 431 | Scheme 1 | Cbz-Gly-OH | Fmoc-L-Dab(Boc)-OH | Scheme 3 | P3 deprotection then dialkylation with alkyl dibromide |
| 432 | Scheme 1 | Cbz-Gly-OH | Fmoc-L-Dab(Boc)-OH | Scheme 5 | P3 deprotection then dialkylation with alkyl dibromide |
| 433 | Scheme 1 | Cbz-Gly-OH | Fmoc-L-Dab(Boc)-OH | Scheme 5 | P3 deprotection then dialkylation with alkyl dibromide |
| 434 | Scheme 1 | Cbz-Gly-OH | Fmoc-L-Asp(OtBu)-OH | Scheme 4 | P3 deprotection, amidation |
| 435 | Scheme 1 | Cbz-Gly-OH | Fmoc-L-Asp(OtBu)-OH | Scheme 4 | P3 deprotection, amidation |
| 436 | Scheme 1 | Cbz-Gly-OH | Boc-L-Gln(piperidyl)-OH | Scheme 4 | none |
| 437 | Scheme 1 | Cbz-Gly-OH | Boc-L-Gln(piperidyl)-OH | Scheme 4 | none |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 438 | Scheme 1 | Cbz-Gly-OH | Fmoc-L-Dap(Boc)-OH | Scheme 5 | P3 deprotection then dialkylation with alkyl dibromide |
| 439 | Scheme 1 | Cbz-Gly-OH | Fmoc-L-Dap(Boc)-OH | Scheme 5 | P3 deprotection then dialkylation with alkyl dibromide |
| 440 | Scheme 1 | Cbz-Gly-OH | Fmoc-L-Orn(Boc)-OH | Scheme 5 | P3 deprotection then dialkylation with alkyl dibromide |
| 441 | Scheme 1 | Cbz-Gly-OH | Fmoc-L-Orn(Boc)-OH | Scheme 5 | P3 deprotection then dialkylation with alkyl dibromide |
| 442 | Scheme 1 | Boc-Aib | Fmoc-L-Dab(Boc)-OH | Scheme 4 | P3 deprotection |
| 443 | Scheme 1 | Boc-Aib | Fmoc-L-Dab(Boc)-OH | Scheme 4 | P3 deprotection then dialkylation with alkyl dibromide |
| 444 | Scheme 1 | 2-naphthoic-Gly-OH | Fmoc-L-Dab(Boc)-OH | Scheme 3 | P3 deprotection |
| 445 | Scheme 1 | 2-naphthoic-Gly-OH | Fmoc-L-Dab(Boc)-OH | Scheme 3 | P3 deprotection |
| 446 | Scheme 1 | 2-naphthoic-Gly-OH | Fmoc-L-Dab(Boc)-OH | Scheme 3 | P3 deprotection then dialkylation with alkyl dibromide |
| 447 | Scheme 1 | 2-naphthoic-Gly-OH | Fmoc-L-Dab(Boc)-OH | Scheme 3 | P3 deprotection then dialkylation with alkyl dibromide |
| 448 | Scheme 1 | Cbz-Gly-OH | Fmoc-L-Asp[N(Me)OMe]-OH | Scheme 4 | P3 conversion to aldehyde then reductive amination |
| 449 | Scheme 1 | Cbz-Gly-OH | Fmoc-L-Asp[N(Me)OMe]-OH | Scheme 4 | P3 conversion to aldehyde then reductive amination |
| 450 | Scheme 1 | Cbz-Gly-OH | Fmoc-L-Asp[N(Me)OMe]-OH | Scheme 4 | P3 conversion to aldehyde then reductive amination |
| 451 | Scheme 1 | Cbz-Gly-OH | Fmoc-L-Dab(Boc)-OH | Scheme 4 | P3 conversion to aldehyde then reductive amination |
| 452 | Scheme 1 | Cbz-Gly-OH | Fmoc-L-Dab(Boc)-OH | Scheme 4 | P3 conversion to aldehyde then reductive amination |
| 453 | Scheme 1 | Fmoc-Gly-OH | Boc-L-(2-NO2)-Phe-OH | Scheme 5 | nitro hydrogenation |
| 454 | Scheme 1 | Cbz-Gly-OH | Fmoc-L-Dab(Boc)-OH | Scheme 4 | P3 conversion to aldehyde then reductive amination |
| 455 | Scheme 1 | Cbz-Gly-OH | Fmoc-L-Dab(Boc)-OH | Scheme 4 | P3 conversion to aldehyde then reductive amination |
| 456 | Scheme 1 | 2-naphthoic-Gly-OH | Fmoc-L-Dab(Boc)-OH | Scheme 3 | P3 deprotection then dialkylation with alkyl dibromide |
| 457 | Scheme 1 | 2-naphthoic-Gly-OH | Fmoc-L-Dab(Boc)-OH | Scheme 3 | P3 deprotection then dialkylation with alkyl dibromide |

TABLE 2-continued

Synthesis of Compounds

| Cpd. | Route to A | Scheme 1: VN($R^2$)—Y—$CO_2$H | $P^2$NH—CH(U)—$CO_2$H | Conversion of A to Product | U modification |
|---|---|---|---|---|---|
| 458 | Scheme 1 | Cbz-Gly-OH | Fmoc-L-Dab(Boc)-OH | Scheme 4 | P3 deprotection then dialkylation with alkyl dibromide |
| 459 | Scheme 1 | Cbz-Gly-OH | Fmoc-L-Dab(Boc)-OH | Scheme 4 | none |
| 460 | Scheme 1 | Cbz-Gly-OH | Fmoc-L-Dab(Boc)-OH | Scheme 4 | P3 deprotection then dialkylation with alkyl dibromide |
| 461 | Scheme 1 | Cbz-Gly-OH | Fmoc-L-Dab(Boc)-OH | Scheme 4 | none |
| 462 | Scheme 1 | Alloc-Gly-OH | Fmoc-L-Dab(Boc)-OH | Scheme 4 | P3 deprotection, reductive alkylation |
| 463 | Scheme 1 | Alloc-Gly-OH | Fmoc-L-Dab(Boc)-OH | Scheme 4 | P3 deprotection, reductive alkylation |
| 464 | Scheme 1 | Alloc-Gly-OH | Fmoc-L-Dab(Boc)-OH | Scheme 4 | P3 deprotection, reductive alkylation |
| 465 | Scheme 1 | Alloc-Gly-OH | Fmoc-L-Dab(Boc)-OH | Scheme 3 | P3 deprotection |
| 466 | Scheme 1 | Fmoc-Gly-OH | Boc-L-(2-NO2)-Phe-OH | Scheme 4 | nitro hydrogenation |
| 467 | Scheme 1 | Cbz-Gly-OH | Fmoc-L-Asp[N(Me)OMe]-OH | Scheme 4 | P3 conversion to aldehyde then reductive amination |
| 468 | Scheme 1 | Cbz-Gly-OH | Fmoc-L-Asp[N(Me)OMe]-OH | Scheme 4 | P3 conversion to aldehyde then reductive amination |
| 469 | Scheme 1 | Cbz-Gly-OH | Fmoc-L-Asp[N(Me)OMe]-OH | Scheme 4 | P3 conversion to aldehyde then reductive amination |
| 470 | Scheme 1 | Cbz-Gly-OH | Fmoc-L-Asp[N(Me)OMe]-OH | Scheme 4 | P3 conversion to aldehyde then reductive amination |
| 471 | Scheme 1 | Cbz-Gly-OH | Fmoc-L-Asp[N(Me)OMe]-OH | Scheme 4 | P3 conversion to aldehyde then reductive amination |
| 472 | Scheme1 | Cbz-Gly-OH | N-Fmoc-1(1-Boc-piperidin-4yl)-D,L-Gly-OH | Scheme 4 | P3 deprotection |
| 473 | Scheme1 | Cbz-Gly-OH | N-Fmoc-1(1-Boc-piperidin-4yl)-D,L-Gly-OH | Scheme 4 | P3 deprotection, reductive alkylation |
| 474 | Scheme 1 | Cbz-Gly-OH | Boc-L-Nle-OH | Scheme 4 | none |
| 475 | Scheme 1 | Cbz-Gly-OH | Fmoc-L-HoLeu-OH | Scheme 4 | none |
| 476 | Scheme 1 | Cbz-Gly-OH | Fmoc-L-Asp[N(Me)OMe]-OH | Scheme 4 | P3 conversion to aldehyde then reductive amination |
| 477 | Scheme 1 | Cbz-Gly-OH | Fmoc-L-Asp[N(Me)OMe]-OH | Scheme 4 | P3 conversion to aldehyde then reductive amination |
| 478 | Scheme 1 | Cbz-Gly-OH | Fmoc-L-Asp[N(Me)OMe]-OH | Scheme 4 | P3 conversion to aldehyde then reductive amination |
| 479 | Scheme 1 | Cbz-Gly-OH | Fmoc-L-Asp[N(Me)OMe]-OH | Scheme 4 | P3 conversion to aldehyde then reductive amination |
| 480 | Scheme 1 | Cbz-Gly-OH | Fmoc-L-Asp[N(Me)OMe]-OH | Scheme 4 | P3 conversion to aldehyde then reductive amination |
| 481 | Scheme 1 | Cbz-Gly-OH | Fmoc-L-Asp[N(Me)OMe]-OH | Scheme 4 | P3 conversion to aldehyde then reductive amination |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 482 | Scheme 1 | Fmoc-Gly-OH | Boc-L-(2-NO$_2$)-Phe-OH | Scheme 5 | nitro hydrogenation then dialkylation with alkyl dibromide |
| 483 | Scheme 1 | 2-naphthoic-Gly-OH | Boc-L-Gln(Me,nBu)-OH | Scheme 4 | none |
| 484 | Scheme 1 | 2-naphthoic-Gly-OH | Boc-L-Gln(chex)-OH | Scheme 4 | none |
| 485 | Scheme 1 | Cbz-Gly-OH | N-Fmoc-1-(1-Boc-piperidin-4-yl)-D,L-Gly-OH | Scheme 4 | P3 deprotection, reductive alkylation |
| 486 | Scheme 1 | Cbz-Gly-OH | Fmoc-L-Dab(Boc)-OH | Scheme 5 | P3 deprotection, alkylation |
| 487 | Scheme 1 | Cbz-Gly-OH | Fmoc-L-Dab(Boc)-OH | Scheme 5 | P3 deprotection, alkylation |
| 488 | Scheme 1 | Cbz-Gly-OH | Fmoc-L-Dab(Boc)-OH | Scheme 5 | P3 deprotection, alkylation |
| 489 | Scheme 1 | Boc-Gly-OH | Cbz-DL-γ-nitro-Leu-OH | Scheme 4 | P3 reduction to amine |
| 490 | Scheme 1 | Boc-Gly-OH | Cbz-DL-γ-nitro-Leu-OH | Scheme 4 | P3 reduction to amine |
| 491 | Scheme 1 | Cbz-Gly-OH | Fmoc-L-Dab(Boc)-OH | Scheme 4 | P3 deprotection |
| 492 | Scheme 1 | Cbz-Gly-OH | Fmoc-L-Dab(Boc)-OH | Scheme 4 | P3 deprotection |
| 493 | Scheme 1 | Cbz-Gly-OH | Fmoc-L-Dab(Boc)-OH | Scheme 4 | P3 deprotection, dialkylation with alkyl dibromide |
| 494 | Scheme 1 | Cbz-Gly-OH | Fmoc-L-Dab(Boc)-OH | Scheme 4 | P3 deprotection, dialkylation with alkyl dibromide |
| 495 | Scheme 1 | Cbz-Gly-OH | Fmoc-L-Dab(Boc)-OH | Scheme 4 | P3 deprotection |
| 496 | Scheme 1 | Cbz-Gly-OH | Fmoc-L-Dab(Boc)-OH | Scheme 4 | P3 deprotection then reductive alkylation |
| 497 | Scheme 1 | Cbz-Gly-OH | Fmoc-L-Dab(Boc)-OH | Scheme 4 | P3 deprotection |
| 498 | Scheme 1 | Cbz-Gly-OH | Fmoc-L-Dab(Boc)-OH | Scheme 4 | P3 deprotection then dialkylation |
| 499 | Scheme 1 | Boc-Gly-OH | Cbz-DL-γ-nitro-Leu-OH | Scheme 4 | P3 reduction to amine then dialkylation with alkyl dibromide |
| 500 | Scheme 1 | Boc-Gly-OH | Cbz-DL-γ-nitro-Leu-OH | Scheme 4 | P3 reduction to amine then dialkylation with alkyl dibromide |
| 501 | Scheme 1 | Cbz-Gly-OH | Fmoc-L-Dab(Boc)-OH | Scheme 4 | P3 deprotection |
| 502 | Scheme 1 | Cbz-Gly-OH | Fmoc-L-Dab(Boc)-OH | Scheme 4 | P3 deprotection |
| 503 | Scheme 1 | Cbz-Gly-OH | Fmoc-L-Dab(Boc)-OH | Scheme 4 | P3 deprotection, dialkylation with alkyl dibromide |
| 504 | Scheme 1 | Cbz-Gly-OH | Fmoc-L-Dab(Boc)-OH | Scheme 4 | P3 deprotection, dialkylation with alkyl dibromide |
| 505 | Scheme 1 | Cbz-Gly-OH | Fmoc-L-HoCha-OH | Scheme 4 | none |
| 506 | Scheme 1 | Cbz-Gly-OH | Fmoc-L-2-aminooctanoic acid | Scheme 4 | none |
| 507 | Scheme 1 | Cbz-Gly-OH | Fmoc-L-Dab(Boc)-OH | Scheme 5 | P3 deprotection, alkylation |
| 508 | Scheme 1 | Cbz-Gly-OH | Fmoc-L-Dab(Boc)-OH | Scheme 5 | P3 deprotection, alkylation |
| 509 | Scheme 1 | Cbz-Gly-OH | Boc-L-5-HO-Nle-OH | Scheme 4 | none |
| 510 | Scheme 1 | Cbz-Gly-OH | Fmoc-L-HoSer(Me)-OH | Scheme 4 | none |
| 511 | Scheme 1 | Alloc-Gly-OH | Boc-L-HoSer(Bzl)-OH | Scheme 4 | none |
| 512 | Scheme 1 | Cbz-Gly-OH | Boc-L-Leu-OH | Scheme 4 | none |
| 513 | Scheme 1 | Cbz-Gly-OH | Fmoc-L-Dab(Boc)-OH | Scheme 4 | P3 deprotection |
| 514 | Scheme 1 | Cbz-Gly-OH | Fmoc-L-Dab(Boc)-OH | Scheme 4 | P3 deprotection, dialkylation with alkyl dibromide |
| 515 | Scheme 1 | Cbz-Gly-OH | Fmoc-L-Dab(Boc)-OH | Scheme 4 | P3 deprotection |
| 516 | Scheme 1 | Cbz-Gly-OH | Fmoc-L-Dab(Boc)-OH | Scheme 4 | P3 deprotection, dialkylation with alkyl dibromide |

TABLE 2-continued

Synthesis of Compounds

| Cpd. | Route to A | Scheme 1: VN(R²)—Y—CO₂H | P²NH—CH(U)—CO₂H | Conversion of A to Product | U modification |
|---|---|---|---|---|---|
| 517 | Scheme 1 | Cbz-Gly-OH | Fmoc-L-Dab(Boc)-OH | Scheme 4 | P3 deprotection, dialkylation with alkyl dibromide |
| 518 | Scheme 2 | Boc-Gly-OH | Boc-L-Arg(Cbz)₂-OH | Scheme 4 | P3 deprotection |
| 519 | Scheme 2 | Boc-Gly-OH | Boc-L-Arg(Cbz)₂-OH | Scheme 4 | P3 deprotection |
| 520 | Scheme 2 | Boc-Gly-OH | Boc-L-Arg(Cbz)₂-OH | Scheme 4 | P3 deprotection |
| 521 | Scheme 1 | Boc-Gly-OH | Cbz-L-Asp[N(Me)OMe] | Scheme 4 | P3 conversion to aldehyde then reductive amination |
| 522 | Scheme 1 | Boc-Gly-OH | Cbz-L-Asp[N(Me)OMe] | Scheme 4 | P3 conversion to aldehyde then reduction |
| 523 | Scheme 1 | Boc-Gly-OH | Cbz-L-Asp[N(Me)OMe] | Scheme 4 | P3 conversion to aldehyde then reductive amination |
| 524 | Scheme 1 | Cbz-Gly-OH | Fmoc-L-Dab(Boc)-OH | Scheme 5; reductive alkylation for R1X | P3 deprotection then dialkylation with alkyl dibromide |
| 525 | Scheme 1 | Cbz-Gly-OH | Fmoc-L-Dab(Boc)-OH | Scheme 4 | P3 deprotection then dialkylation with alkyl dibromide |
| 526 | Scheme 1 | Cbz-Gly-OH | Fmoc-L-Dab(Boc)-OH | Scheme 4 | P3 deprotection |
| 527 | Scheme 1 | Cbz-Gly-OH | Fmoc-L-Dab(Boc)-OH | Scheme 4 | P3 deprotection then dialkylation with alkyl dibromide |
| 528 | Scheme 1 | Cbz-Gly-OH | Fmoc-L-Dab(Boc) | Scheme 4 | P3 deprotection, diacylation with anhydride |
| 529 | Scheme 1 | Cbz-Gly-OH | Boc-L-citrulline-OH | Scheme 4 | none |
| 530 | Scheme 1 | Cbz-Gly-OH | Fmoc-L-Dab(Boc) | Scheme 4 | P3 deprotection, reductive alkylation |
| 531 | Scheme 1 | Cbz-Gly-OH | Fmoc-L-Dab(Boc) | Scheme 4 | P3 deprotection, diacylation with anhydride |
| 532 | Scheme 1 | Cbz-Gly-OH | Fmoc-L-Dab(Boc) | Scheme 4 | P3 deprotection then dialkylation with alkyl dibromide |
| 533 | Scheme 1 | Cbz-Gly-OH | Fmoc-L-Dab(Boc) | Scheme 4 | P3 deprotection, then acylation with isocyanate |
| 534 | Scheme 1 | Cbz-Gly-OH | Fmoc-L-Dab(Boc)-OH | Scheme 5 | P3 deprotection then dialkylation with alkyl dibromide |
| 535 | Scheme 1 | Cbz-Gly-OH | Fmoc-L-Dab(Boc)-OH | Scheme 5 | P3 deprotection then dialkylation with alkyl dibromide |
| 536 | Scheme 1 | Cbz-Gly-OH | Fmoc-L-Dab(Boc)-OH | Scheme 5 | P3 deprotection then dialkylation with alkyl dibromide |
| 537 | Scheme 1 | Cbz-Gly-OH | Fmoc-L-Dab(Boc)-OH | Scheme 4 | P3 deprotection then reductive alkylation then acetylation |
| 538 | Scheme 1 | Cbz-Gly-OH | Fmoc-L-Dap(Boc)-OH | Scheme 4 | P3 deprotection then reductive alkylation |
| 539 | Scheme 1 | Cbz-Gly-OH | Fmoc-L-Dap(Boc)-OH | Scheme 4 | P3 deprotection then guanylation |
| 540 | Scheme 1 | Cbz-Gly-OH | Fmoc-L-Dab(Boc)-OH | Scheme 5 | P3 deprotection, guanidinylation, deprotection |
| 541 | Scheme 1 | Alloc-Gly-OH | Fmoc-L-Dab(Boc)-OH | Scheme 4 | P3 deprotection |

TABLE 2-continued

Synthesis of Compounds

| Cpd. | Route to A | Scheme 1: $VN(R^2)$—Y—$CO_2H$ | $P^2NH$—CH(U)—$CO_2H$ | Conversion of A to Product | U modification |
|---|---|---|---|---|---|
| 542 | Scheme 1 | Alloc-Gly-OH | Fmoc-L-Dab(Boc)-OH | Scheme 4 | P3 deprotection then dialkylation with alkyl dibromide |
| 543 | Scheme 1 | Alloc-Gly-OH | Fmoc-L-Dab(Boc)-OH | Scheme 4 | P3 deprotection then sulfonylation |
| 544 | Scheme 1 | Alloc-Gly-OH | Fmoc-L-Dab(Boc)-OH | Scheme 4 | P3 deprotection then sulfonylation |
| 545 | Scheme 1 | Alloc-Gly-OH | Fmoc-L-Dab(Boc)-OH | Scheme 4 | P3 deprotection, acylation, deprotection |
| 546 | Scheme 1 | Alloc-Gly-OH | Fmoc-L-Dab(Boc)-OH | Scheme 4 | P3 deprotection |
| 547 | Scheme 1 | Alloc-Gly-OH | Fmoc-L-Dab(Boc)-OH | Scheme 4 | P3 deprotection then dialkylation with alkyl dibromide |
| 548 | Scheme 1 | N-(6-Cl-2-napthoic)-Gly-OH | Fmoc-L-Dab(Boc)-OH | Scheme 3 | P3 deprotection |
| 549 | Scheme 1 | N-(6-Cl-2-napthoic)-Gly-OH | Fmoc-L-Dab(Boc)-OH | Scheme 3 | P3 deprotection then dialkylation with alkyl dibromide |
| 550 | Scheme 1 | N-(6-Cl-2-napthoic)-Gly-OH | Fmoc-L-Dab(Boc)-OH | Scheme 3 | P3 deprotection then dialkylation with alkyl dibromide |
| 551 | Scheme 1 | Cbz-Gly-OH | Fmoc-L-Dab(Boc)-OH | Scheme 4 | P3 deprotection |
| 552 | Scheme 1 | Cbz-Gly-OH | Fmoc-L-Dab(Boc)-OH | Scheme 4 | P3 deprotection then dialkylation with alkyl dibromide |
| 553 | Scheme 1 | Cbz-Gly-OH | Fmoc-L-Dab(Boc)-OH | Scheme 4 | P3 deprotection then dialkylation with alkyl dibromide |
| 554 | Scheme 1 | Cbz-Gly-OH | Fmoc-L-Dab(Boc)-OH | Scheme 4 | P3 deprotection then dialkylation with alkyl dibromide |
| 555 | Scheme 1 | Alloc-Gly-OH | Fmoc-L-Dab(Boc)-OH | Scheme 4 | P3 deprotection then dialkylation with alkyl dibromide |
| 556 | Scheme 1 | Alloc-Gly-OH | Fmoc-L-Dab(Boc)-OH | Scheme 4 | P3 deprotection then dialkylation with alkyl dibromide |
| 557 | Scheme 1 | Cbz-Gly-OH | Fmoc-L-Dab(Boc)-OH | Scheme 5, use isocyanate for R1X | P3 deprotection then dialkylation with alkyl dibromide |
| 558 | Scheme 1 | Cbz-Gly-OH | Fmoc-L-Dab(Boc)-OH | Scheme 5; reductive alkylation then acetylation for R1X and R2 | P3 deprotection then dialkylation with alkyl dibromide |
| 559 | Scheme 1 | Cbz-Gly-OH | Fmoc-L-Dab(Boc)-OH | Scheme 4 | P3 deprotection |
| 560 | Scheme 1 | Cbz-Gly-OH | Fmoc-L-Dab(Boc)-OH | Scheme 4 | P3 deprotection then dialkylation with alkyl dibromide |
| 561 | Scheme 1 | Cbz-Gly-OH | Fmoc-L-Dab(Boc)-OH | Scheme 4 | P3 deprotection then dialkylation with alkyl dibromide |
| 562 | Scheme 1 | Cbz-Gly-OH | Fmoc-L-Dab(Boc)-OH | Scheme 4 | P3 deprotection then sulfonylation |
| 563 | Scheme 1 | Cbz-Gly-OH | Fmoc-L-Dab(Boc)-OH | Scheme 4 | P3 deprotection then acylation with chloroformate |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 564 | Scheme 1 | Cbz-Gly-OH | Fmoc-DL-2-(1-Boc-4-piperidyl)-Gly-OH | Scheme 4 | P3 deprotection then reductive alkylation with ketone |
| 565 | Scheme 1 | Cbz-Gly-OH | Fmoc-L-Dab(Boc)-OH | Scheme 4 | P3 deprotection then dialkylation with alkyl dibromide |
| 566 | Scheme 1 | Alloc-Gly-OH | Fmoc-L-Dab(Boc)-OH | Scheme 5 | P3 deprotection then dialkylation with alkyl dibromide |
| 567 | Scheme 1 | Alloc-Gly-OH | Fmoc-L-Dab(Boc)-OH | Scheme 5 | P3 deprotection then dialkylation with alkyl dibromide |
| 568 | Scheme 1 | Alloc-Gly-OH | Fmoc-L-Dab(Boc)-OH | Scheme 5 | P3 deprotection then dialkylation with alkyl dibromide |
| 569 | Scheme 1 | Cbz-[$^{15}$N,1,2-$^{13}$C$_2$]Gly-OH | Fmoc-L-Dab(Boc)-OH | Scheme 4 | P3 deprotection then reductive alkylation then acetylation |
| 570 | Scheme 1 | Alloc-Gly-OH | Fmoc-L-Dab(Boc)-OH | Scheme 5 | P3 deprotection then dialkylation with alkyl dibromide |
| 571 | Scheme 1 | Alloc-Gly-OH | Fmoc-L-Dab(Boc)-OH | Scheme 5 | P3 deprotection then dialkylation with alkyl dibromide |
| 572 | Scheme 1 | Cbz-Gly-OH | Fmoc-L-Dab(Boc)-OH | Scheme 5 | P3 deprotection then dialkylation with alkyl dibromide |
| 573 | Scheme 1 | Cbz-Gly-OH | Fmoc-L-Dab(Boc)-OH | Scheme 5 | P3 deprotection then dialkylation with alkyl dibromide |
| 574 | Scheme 1 | Alloc-Gly-OH | Fmoc-L-Dab(Boc)-OH | Scheme 5 | P3 deprotection then dialkylation with alkyl dibromide |
| 575 | Scheme 1 | Alloc-Gly-OH | Fmoc-L-Dab(Boc)-OH | Scheme 5 | P3 deprotection then dialkylation with alkyl dibromide |
| 576 | Scheme 1 | Cbz-Gly-OH | Fmoc-L-Dab(Boc)-OH | Scheme 5 | P3 deprotection then dialkylation with alkyl dibromide |
| 577 | Scheme 1 | Cbz-Gly-OH | Fmoc-L-Dab(Boc)-OH | Scheme 5 | P3 deprotection then dialkylation with alkyl dibromide |
| 578 | Scheme 1 | Cbz-Gly-OH | Fmoc-L-Dab(Boc)-OH | Scheme 5 | P3 deprotection then dialkylation with alkyl dibromide |
| 579 | Scheme 1 with D$_2$O exchange during Fmoc deprotection and NaBD$_3$CN reduction | Cbz-Gly-OH | Fmoc-L-Dab(Boc)-OH | Scheme 4 | P3 deprotection then reductive alkylation then acetylation |
| 580 | Scheme 1 | Cbz-Gly-OH | Fmoc-D-Dab(Boc)-OH | Scheme 4 | P3 deprotection then dialkylation with alkyl dibromide |

TABLE 2-continued

Synthesis of Compounds

| Cpd. | Route to A | Scheme 1: VN(R$^2$)—Y—CO$_2$H | P$^2$NH—CH(U)—CO$_2$H | Conversion of A to Product | U modification |
|---|---|---|---|---|---|
| 581 | Scheme 2 | Cbz-Gly-OH | Fmoc-L-Dab(Boc)-OH | Scheme 4 | P3 deprotection then dialkylation with alkyl dibromide |
| 582 | Scheme 2 | Cbz-Gly-OH | Fmoc-D-Dab(Boc)-OH | Scheme 4 | P3 deprotection then dialkylation with alkyl dibromide |
| 583 | Scheme 2 | Cbz-Gly-OH | Fmoc-L-Dab(Boc)-OH | Scheme 4 | P3 deprotection then dialkylation with alkyl dibromide |
| 584 | Scheme 2 | Cbz-Gly-OH | Fmoc-D-Dab(Boc)-OH | Scheme 4 | P3 deprotection then dialkylation with alkyl dibromide |
| 585 | Scheme 1 | Cbz-Gly-OH | Fmoc-D-Dab(Boc)-OH | Scheme 4 | P3 deprotection then dialkylation with alkyl dibromide |

Example 102

Human MC5R Radioligand Binding Assay

Assessments of compound binding to human MC5R (hMC5R)) by displacement of an $^{125}$I-labeled NDP-MSH receptor ligand peptide were performed essentially as described in the data sheets produced by Perkin Elmer to accompany their frozen hMC5R membranes (Perkin Elmer catalog number RBXMC5M400UA).

[$^{125}$I] NDP-MSH: Radiolabeled in House and Purified by HPLC:

Na$^{125}$I (0.5 mCi, 17.4 Ci/mg) was added to 50 µL sodium phosphate (50 mM, pH 7.4) in an eppendorf tube precoated with IODOGEN. After incubation for 10 mins the phosphate buffer containing the iodine was added to NDP-MSH (10 ul at 1 mg/mL) in a separate eppendorf tube. This was incubated for a further 10 mins. The iodinated NDP-MSH was purified by HPLC on a Zorbax SB 300 column using solvent A: 0.05% TFA and solvent B: 90% acetonitrile 0.045% TFA with a linear gradient, 0-67% B over 60 mins. The $^{125}$I NDP-MSH eluted at 52 mins after the unlabeled starting material (48 min) and was counted and stored in the freezer. It was used within 48 hrs, as radioactive decay and ligand decomposition resulted in greatly reduced specific binding observed after 72 hrs.

Reagents:

Incubation buffer: 25 mM HEPES-KOH (pH 7.0), 1.5 mM CaCl$_2$, 1 mM MgSO$_4$, 0.1 M NaCl, 1 mM 1,10-phenanthroline, and 1 Complete™ protease inhibitor tablet/100 mL (Roche, catalog number 1873580)

Perkin Elmer frozen hMC5 membranes: catalog number RBXMC5M400UA, 0.4 mL/vial; 400 microassays/vial, 0.78 mg/mL protein concentration Vials of frozen membranes were thawed rapidly immediately before use, diluted with binding buffer and vortexed. Resuspended membranes were kept on ice until they were added to the wells of the plate.

Binding Protocol for 400 Microassays Per Vial:

Assays were performed in 96 well polypropylene plates. Membranes (0.78 µg 40 µL of a 1:40 dilution in incubation buffer) were added to [$^{125}$I] NDP-MSH (0.84 nM; 2200 Ci/mmol) and test compounds in a total volume of 140 µL. This was incubated for 1 hr at 37° C. Non-specific binding was determined with 3 mM NDP-MSH. Plates were filtered using a Tomtec cell harvester with GF/A filters (Wallac) (presoaked in 0.6% polyethylenimine) and washed three times with 1.0 mL ice-cold wash buffer (the above incubation buffer without 1,10-phenanthroline and Complete™ protease inhibitor tablet). The filters were dried in a 37° C. oven, placed in a sample bag and 5 mL Betaplatescint (Wallac) was added. Prepared filters were counted in cassettes in a Microbeta Trilux (Wallac) for 1 min. Non-specific binding just under 5%. Data analysis was performed using GraphPad Prism 4, employing competition binding with a single site model and a fixed Hill coefficient. The following equation was used: Y=Bottom+(Top-Bottom)/1/10^(X−logEC$_{50}$), where X=log(concentration) and Y=binding to fit the data.

Example 103

Identification of Preferred Diastereomer for Binding to MC5R

The four diastereomers of one set of substituents were tested for binding in the hMC5R assay as in Examples 102, as listed in Table 3.

TABLE 3

Activity of Four Diastereomers

| Cpd. | stereochemistry | human MC5R IC$_{50}$ (nM) |
|---|---|---|
| 102 | (3R,5S) | 3500 |
| 103 | (3R,5R) | 500 |
| 104 | (3S,5R) | 1500 |
| 105 | (3S,5S) | 56 |

As can be seen the 3S, 5S isomer is almost ten times more active than the next most active isomer and significantly more active than the other two possible isomers. This unexpectedly high level of differential activity and hence specificity of the (S,S) diastereoisomer was unexpected and is not predictable from a knowledge of the hMC5R or its previously known ligands.

Example 104

Activity of Selected Compounds: hMC5R Binding

Representative compounds of the present invention were tested for binding in the hMC5R assay as in Example 102, as listed in Table 4. The compounds were tested as their trifluoroacetate or hydrochloride salts, or as their free base.

TABLE 4

Properties of Compounds

| Cpd. | MS (M + 1) | $t_R$ (min) | MC5R radioligand IC$_{50}$ |
|---|---|---|---|
| 14 | 556.2 | 5.74 | xxx |
| 25 | 595.3 | 6.22 | xxx |
| 31 | 539.3 | 5.92 | xx |
| 33 | 599.4 | 6.31 | xxxx |
| 37 | 473.4 | 5.59 | xxx |
| 38 | 541.3 | 5.78 | xxx |
| 39 | 541.3 | 5.67 | xxx |
| 49 | 499.3 | 5.77 | xx |
| 50 | 613.5 | 5.89 | x |
| 54 | 425.7 | 5.27 | xx |
| 60 | 629.4 | 6.27 | x |
| 62 | 629.3 | 6.22 | xx |
| 63 | 535.3 | 5.76 | xx |
| 64 | 603.3 | 6.04 | xxx |
| 65 | 577.2 | 5.97 | xxx |
| 67 | 591.3 | 5.94 | xxxx |
| 71 | 549.3 | 5.93 | xx |
| 79 | 606.4 | 6.033 | x |
| 81 | 743.4 | 5.489 | xx |
| 83 | 650.3 | 6.524 | xx |
| 85 | 606.2 | 6.008 | x |
| 86 | 743.5 | 5.410 | xx |
| 87 | 650.4 | 6.424 | x |
| 102 | 577.4 | 5.775 | x |
| 103 | 577.5 | 5.750 | xx |
| 104 | 577.5 | 5.783 | x |
| 105 | 577.3 | 5.79 | xxx |
| 106 | 561.4 | 6.05 | xx |
| 107 | 524.3 | 5.63 | xx |
| 108 | 603.3 | 6.11 | xxx |
| 109 | 566.2 | 5.65 | xx |
| 110 | 591.2 | 5.82 | xx |
| 111 | 581.3 | 5.95 | xxx |
| 112 | 578.3 | 5.26 | xxx |
| 113 | 579.3 | 5.52 | xx |
| 114 | 578.3 | 5.72 | xx |
| 115 | 527.3 | 5.41 | xx |
| 116 | 578.3 | 5.78 | xx |
| 117 | 509.2 | 5.51 | xx |
| 118 | 523.3 | 5.56 | x |
| 119 | 523.2 | 5.51 | x |
| 120 | 512.3 | 5.10 | x |
| 121 | 549.4 | 5.96 | xx |
| 122 | 509.2 | 5.56 | xx |
| 123 | 523.4 | 5.63 | x |
| 124 | 509.2 | 5.41 | x |
| 125 | 523.3 | 5.68 | x |
| 126 | 549.3 | 5.79 | xx |
| 127 | 554.2 | 5.87 | x |
| 128 | 554.2 | 5.87 | xx |
| 129 | 539.1 | 5.58 | x |
| 130 | 596.5 | 5.87 | x |
| 131 | 582.4 | 5.88 | x |
| 132 | 567.4 | 5.62 | x |
| 133 | 567.4 | 5.62 | x |
| 134 | 582.4 | 5.88 | xx |
| 135 | 583.4 | 5.86 | xx |
| 136 | 595.4 | 5.31 | xxx |
| 137 | 595.4 | 5.87 | xx |

TABLE 4-continued

Properties of Compounds

| Cpd. | MS (M + 1) | $t_R$ (min) | MC5R radioligand IC$_{50}$ |
|---|---|---|---|
| 138 | 527.2 | 5.33 | xx |
| 139 | 533.3 | 5.54 | x |
| 140 | 620.2 | 6.16 | xxx |
| 141 | 620.2 | 6.21 | xx |
| 142 | 566.3 | 5.70 | xxx |
| 143 | 555.2 | 5.55 | xx |
| 144 | 555.2 | 5.74 | xxx |
| 145 | 583.4 | 6.21 | xx |
| 146 | 587.2 | 4.90 | x |
| 147 | 547.4 | 5.78 | xx |
| 148 | 571.2 | 5.34 | xx |
| 149 | 567.1 | 4.48 | x |
| 150 | 568.1 | 4.87 | x |
| 151 | 519.5 | 5.23 | x |
| 152 | 595.4 | 5.92 | xxx |
| 153 | 553.5 | 5.58 | xxx |
| 154 | 595.4 | 5.95 | xx |
| 155 | 609.4 | 5.88 | xx |
| 156 | 607.5 | 5.96 | xxx |
| 157 | 609.4 | — | x |
| 158 | 607.4 | 5.88 | xxx |
| 159 | 579.3 | 5.83 | xx |
| 160 | 621.3 | 6.22 | xxx |
| 161 | 585.6 | 6.00 | x |
| 162 | 557.4 | 5.50 | x |
| 163 | 607.5 | 5.94 | xx |
| 164 | 607.2 | 5.69 | xx |
| 165 | 585.4 | 5.64 | xx |
| 166 | 557.3 | 6.06 | xxx |
| 167 | 559.5 | 5.47 | xxx |
| 168 | 585.5 | 5.58 | xx |
| 169 | 569.5 | 5.17 | xx |
| 170 | 583.6 | 5.70 | xx |
| 171 | 567.6 | 5.79 | xxx |
| 172 | 621.4 | 6.01 | xx |
| 173 | 571.5 | 5.65 | xxx |
| 174 | 567.5 | 5.50 | xx |
| 175 | 567.5 | 5.37 | xx |
| 176 | 625.5 | 5.81 | xxx |
| 177 | 587.4 | 5.65 | xxx |
| 178 | 584.5 | 4.84 | xx |
| 179 | 593.4 | 5.60 | xx |
| 180 | 583.6 | 5.41 | xx |
| 181 | 655.2 | 5.97 | xxxx |
| 182 | 501.4 | 5.20 | xx |
| 183 | 570.2 | 5.64 | x |
| 184 | 570.2 | 5.66 | xx |
| 185 | 583.5 | 5.43 | xxx |
| 186 | 607.3 | 5.28 | xxx |
| 187 | 583.4 | 5.37 | xxx |
| 188 | 595.6 | 5.64 | xxx |
| 189 | 587.4 | 5.78 | xx |
| 190 | 569.5 | 5.23 | xx |
| 191 | 567.7 | 5.92 | xxx |
| 192 | 621.4 | 6.19 | xx |
| 193 | 569.6 | 5.23 | xx |
| 194 | 571.5 | 5.69 | xxx |
| 195 | 567.5 | 5.98 | xxx |
| 196 | 571.5 | 6.00 | xx |
| 197 | 561.3 | 5.84 | xx |
| 198 | 575.4 | 5.98 | xx |
| 199 | 571.1 | 5.69 | xxx |
| 200 | 621.3 | 6.19 | xxx |
| 201 | 591.2 | 6.02 | xx |
| 202 | 493.3 | 5.41 | xx |
| 203 | 545.2 | 5.91 | xx |
| 204 | 591.3 | 5.88 | xxx |
| 205 | 591.3 | 5.90 | xx |
| 206 | 479.4 | 5.09 | xx |
| 207 | 609.4 | 6.13 | xx |
| 208 | 589.3 | 5.69 | xxx |
| 209 | 605.3 | 5.85 | xxx |
| 210 | 631.4 | 6.09 | xxxx |
| 211 | 597.4 | 5.89 | xxx |
| 212 | 615.3 | 6.20 | xxx |

TABLE 4-continued

Properties of Compounds

| Cpd. | MS (M + 1) | $t_R$ (min) | MC5R radioligand $IC_{50}$ |
|---|---|---|---|
| 213 | 511.3 | 5.63 | xx |
| 214 | 545.4 | 5.92 | xxx |
| 215 | 637.6 | 6.15 | xx |
| 216 | 605.5 | 5.94 | xxx |
| 217 | 553.3 | 5.88 | xxx |
| 218 | 592.4 | 4.99 | x |
| 219 | 525.3 | 5.79 | xxx |
| 220 | 529.5 | 5.59 | xxx |
| 221 | 553.5 | 5.87 | xxx |
| 222 | 507.2 | 5.64 | x |
| 223 | 513.5 | 5.68 | xx |
| 224 | 553.3 | 5.89 | xxx |
| 225 | 549.7 | 5.87 | xx |
| 226 | 617.4 | 6.21 | xxx |
| 227 | 523.3 | 5.49 | x |
| 228 | 575.5 | 5.72 | x |
| 229 | 569.2 | 5.87 | xx |
| 230 | 569.2 | 5.83 | x |
| 231 | 611.2 | 6.20 | xxxx |
| 232 | 591.4 | 6.03 | xxx |
| 233 | 547.5 | 5.70 | xxx |
| 234 | 536.5 | 5.47 | xx |
| 235 | 561.7 | 6.11 | xx |
| 236 | 533.5 | 5.53 | xx |
| 237 | 585.5 | 6.23 | xxx |
| 238 | 550.5 | 5.81 | xxx |
| 239 | 568.5 | 5.45 | x |
| 240 | 586.5 | 6.18 | xxx |
| 241 | 542.5 | 5.57 | xx |
| 242 | 568.4 | 5.91 | xx |
| 243 | 579.7 | 5.60 | xx |
| 244 | 565.5 | 5.42 | x |
| 245 | 506.4 | 5.73 | xx |
| 246 | 519.3 | 5.78 | xx |
| 247 | 637.5 | 5.84 | x |
| 248 | 624.3 | 6.28 | xxx |
| 249 | 603.2 | 6.14 | xxx |
| 250 | 589.4 | 6.04 | xxx |
| 251 | 543.3 | 6.30 | xxx |
| 252 | 487.2 | 5.13 | x |
| 253 | 613.5 | 6.06 | xxx |
| 254 | 537.4 | 5.66 | x |
| 255 | 531.6 | 5.65 | xx |
| 256 | 551.5 | 5.47 | xx |
| 257 | 543.5 | 5.77 | x |
| 258 | 543.5 | 5.66 | xx |
| 259 | 581.5 | 5.10 | xx |
| 260 | 591.4 | 5.94 | xxx |
| 261 | 599.4 | 5.99 | xxx |
| 262 | 613.5 | 6.08 | xxx |
| 263 | 521.4 | 5.85 | xx |
| 264 | 589.3 | 5.81 | xxx |
| 265 | 575.5 | 5.79 | xxx |
| 266 | 537.2 | 5.61 | x |
| 267 | 551.4 | 5.70 | x |
| 268 | 558.4 | 4.86 | x |
| 269 | 579.6 | 5.73 | xxx |
| 270 | 581.4 | 5.84 | xxx |
| 271 | 621.2 | 6.07 | xxx |
| 272 | 598.6 | 5.27 | xx |
| 273 | 626.7 | 5.64 | x |
| 274 | 507.3 | 6.35 | xx |
| 275 | 517.4 | 6.51 | xxx |
| 276 | 515.3 | 5.18 | xxx |
| 277 | 511.4 | 5.81 | xxx |
| 278 | 575.3 | 6.71 | xxx |
| 279 | 585.4 | 6.83 | xxxx |
| 280 | 539.3 | 5.87 | xx |
| 281 | 499.5 | 5.62 | xx |
| 282 | 497.6 | 5.58 | xx |
| 283 | 531.4 | 5.89 | xxx |
| 284 | 607.3 | 6.29 | xxxx |
| 285 | 567.3 | 5.99 | xxx |
| 286 | 565.4 | 5.93 | xxx |
| 287 | 583.5 | 6.02 | xxxx |
| 288 | 579.6 | 6.18 | xxx |
| 289 | 515.3 | 5.58 | xx |
| 290 | 620.5 | 5.44 | xx |
| 291 | 620.5 | 5.38 | x |
| 292 | 531.5 | 5.22 | xx |
| 293 | 559.5 | 5.74 | xx |
| 294 | 607.4 | 6.06 | xx |
| 295 | 557.4 | 5.61 | xx |
| 296 | 534.4 | 7.27 | xx |
| 297 | 544.5 | 7.42 | xx |
| 298 | 559.4 | 6.59 | xx |
| 299 | 549.4 | 6.42 | xx |
| 300 | 567.3 | 6.52 | xx |
| 301 | 635.5 | 7.34 | xx |
| 302 | 593.5 | 6.02 | xxx |
| 303 | 573.4 | 5.47 | xx |
| 304 | 481.4 | 5.47 | xx |
| 305 | 521.5 | 6.10 | xxx |
| 306 | 641.4 | 7.38 | xx |
| 307 | 655.3 | 7.59 | xx |
| 308 | 485.3 | 5.17 | x |
| 309 | 553.3 | 5.82 | xx |
| 310 | 535.3 | 5.72 | xx |
| 311 | 553.5 | 5.39 | x |
| 312 | 621.2 | 6.06 | xx |
| 313 | 603.4 | 5.94 | xx |
| 314 | 572.3 | 4.91 | x |
| 315 | 574.5 | 7.69 | xx |
| 316 | 584.5 | 7.83 | xx |
| 317 | 617.7 | 7.04 | xx |
| 318 | 627.5 | 7.11 | xxx |
| 319 | 582.3 | 7.44 | xx |
| 320 | 592.4 | 7.55 | xx |
| 321 | 588.4 | 8.00 | xx |
| 322 | 598.4 | 8.15 | xx |
| 323 | 568.1 | 7.28 | xx |
| 324 | 578.3 | 7.45 | xx |
| 325 | 519.2 | 5.93 | xx |
| 326 | 511.2 | 5.94 | xxx |
| 327 | 540.3 | 5.61 | xx |
| 328 | 523.2 | 5.37 | xx |
| 329 | 498.4 | 5.49 | xx |
| 330 | 481.5 | 5.27 | x |
| 331 | 514.3 | 5.52 | x |
| 332 | 514.2 | 5.42 | x |
| 333 | 505.4 | 5.27 | x |
| 334 | 480.3 | 5.33 | x |
| 335 | 514.4 | 5.65 | x |
| 336 | 514.4 | 5.62 | xx |
| 337 | 514.3 | 5.63 | x |
| 338 | 477.3 | 5.35 | x |
| 339 | 531.5 | 5.65 | x |
| 340 | 480.4 | 5.38 | x |
| 341 | 487.2 | 5.55 | xx |
| 342 | 527.3 | 5.96 | xx |
| 343 | 587.2 | 6.33 | xxx |
| 344 | 567.3 | 6.12 | xxx |
| 345 | 577.2 | 6.31 | xxxx |
| 346 | 443.2 | 5.43 | xx |
| 347 | 435.3 | 5.46 | xx |
| 348 | 503.1 | 5.58 | xx |
| 349 | 511.4 | 5.73 | xxx |
| 350 | 493.7 | 5.71 | xxx |
| 351 | 427.3 | 5.04 | x |
| 352 | 423.4 | 5.28 | x |
| 353 | 427.3 | 5.13 | x |
| 354 | 423.3 | 5.32 | x |
| 355 | 489.4 | 6.42 | xx |
| 356 | 589.4 | 5.92 | xx |
| 357 | 581.3 | 6.03 | x |
| 358 | 480.4 | 5.33 | x |
| 359 | 555.4 | 5.81 | xxx |
| 360 | 612.6 | 5.49 | x |
| 361 | 620.5 | — | x |
| 362 | 595.4 | 6.12 | xx |

TABLE 4-continued

Properties of Compounds

| Cpd. | MS (M + 1) | $t_R$ (min) | MC5R radioligand $IC_{50}$ |
|---|---|---|---|
| 363 | 637.2 | 6.30 | x |
| 364 | 505.1 | 6.46 | xx |
| 365 | 485.2 | 6.26 | xx |
| 366 | 491.2 | 5.69 | xx |
| 367 | 573.1 | 6.07 | xx |
| 368 | 565.2 | 6.88 | xxx |
| 369 | 491.2 | 5.69 | xx |
| 370 | 483.4 | 5.77 | xxx |
| 371 | 559.1 | 6.12 | xx |
| 372 | 539.2 | 5.84 | xx |
| 373 | 473.3 | 5.29 | xx |
| 374 | 473.2 | 5.21 | x |
| 375 | 549.4 | 6.03 | xx |
| 376 | 621.4 | 6.13 | xxx |
| 377 | 493.3 | 5.32 | xx |
| 378 | 587.2 | 6.17 | xxx |
| 379 | 577.4 | 6.04 | xxx |
| 380 | 559.3 | 6.01 | xxx |
| 381 | 551.3 | 5.99 | xxx |
| 382 | 551.4 | 6.04 | xxxx |
| 383 | 555.3 | 6.19 | xxx |
| 384 | 575.4 | 6.11 | xxx |
| 385 | 589.3 | 6.06 | xxx |
| 386 | 443.6 | 5.36 | xx |
| 387 | 459.9 | 5.66 | xx |
| 388 | 503.2 | 5.74 | xx |
| 389 | 511.4 | 5.65 | xxx |
| 390 | 527.3 | 5.95 | xxx |
| 391 | 573.2 | 6.07 | xxx |
| 392 | 483.3 | 5.97 | xx |
| 393 | 465.4 | 5.81 | xx |
| 394 | 475.3 | 5.98 | xx |
| 395 | 623.2 | 6.41 | xxxx |
| 396 | 607.4 | 6.17 | xxxx |
| 397 | 585.4 | 6.12 | xxx |
| 398 | 573.2 | 6.12 | xxx |
| 399 | 563.4 | 5.95 | xx |
| 400 | 581.3 | 6.12 | xx |
| 401 | 479.1 | 5.68 | x |
| 402 | 487.4 | 5.45 | xx |
| 403 | 551.5 | 6.42 | xxx |
| 404 | 525.3 | 6.31 | xx |
| 405 | 487.3 | 5.69 | x |
| 406 | 473.4 | 5.51 | xx |
| 407 | 487.4 | 5.40 | x |
| 408 | 568.1 | 5.91 | x |
| 409 | 601.3 | 6.08 | xxx |
| 410 | 533.3 | 5.82 | x |
| 411 | 622.3 | 6.90 | x |
| 412 | 579.3 | 6.60 | x |
| 413 | 555.4 | 6.00 | xx |
| 414 | 555.4 | 6.10 | xxx |
| 415 | 607.5 | 6.60 | xxx |
| 416 | 539.4 | 6.32 | xx |
| 417 | 593.5 | 6.26 | xxx |
| 418 | 525.3 | 6.03 | xx |
| 419 | 601.3 | 6.09 | xxx |
| 420 | 533.2 | 5.81 | xx |
| 421 | 627.4 | 7.20 | x |
| 422 | 601.3 | 6.10 | xxx |
| 423 | 609.4 | 7.64 | xx |
| 424 | 613.4 | 6.31 | xxx |
| 425 | 575.3 | 6.26 | xxxx |
| 426 | 537.4 | 5.98 | xxx |
| 427 | 525.1 | 5.96 | xxx |
| 428 | 561.4 | 6.26 | xxxx |
| 429 | 559.1 | 6.11 | xxx |
| 430 | 545.1 | 6.01 | xxx |
| 431 | 569.3 | 5.92 | xx |
| 432 | 645.3 | 6.28 | xxxx |
| 433 | 640.2 | 6.70 | xxx |
| 434 | 622.3 | 6.49 | xx |
| 435 | 613.4 | 7.03 | xx |
| 436 | 603.2 | 7.23 | xxx |
| 437 | 587.2 | 7.01 | x |
| 438 | 561.4 | 6.88 | xxx |
| 439 | 545.1 | 6.68 | xx |
| 440 | 589.4 | 6.24 | xxx |
| 441 | 573.1 | 5.95 | xxx |
| 442 | 559.1 | 5.90 | xx |
| 443 | 627.4 | 6.56 | xx |
| 444 | 493.2 | 5.68 | x |
| 445 | 493.2 | 5.71 | x |
| 446 | 561.4 | 5.93 | x |
| 447 | 561.4 | 6.09 | xx |
| 448 | 581.3 | 6.93 | xx |
| 449 | 547.3 | 6.00 | xxx |
| 450 | 561.2 | 5.92 | xxx |
| 451 | 567.2 | 6.94 | xx |
| 452 | 581.2 | 6.45 | xxx |
| 453 | 593.3 | 6.56 | xx |
| 454 | 547.2 | 6.12 | xxx |
| 455 | 574.3 | 5.67 | xxx |
| 456 | 555.3 | 6.15 | xxx |
| 457 | 555.3 | 6.25 | xxx |
| 458 | 607.2 | 6.20 | xxx |
| 459 | 539.2 | 5.90 | x |
| 460 | 607.3 | 6.11 | xx |
| 461 | 539.1 | 5.94 | x |
| 462 | 577.1 | 6.37 | xxxx |
| 463 | 561.1 | 6.17 | xxx |
| 464 | 549.2 | 6.28 | xxxx |
| 465 | 507.2 | 6.00 | xxx |
| 466 | 583.3 | 6.38 | xx |
| 467 | 595.2 | 6.50 | xxxx |
| 468 | 560.3 | 5.64 | xxx |
| 469 | 575.2 | 6.62 | xxx |
| 470 | 575.2 | 6.27 | xxxx |
| 471 | 573.2 | 6.28 | xxxx |
| 472 | 547.2 | 5.96 | xxx |
| 473 | 617.2 | 6.52 | xxx |
| 474 | 520.2 | 7.40 | xx |
| 475 | 534.3 | 7.66 | xxx |
| 476 | 587.4 | 6.55 | xxx |
| 477 | 575.2 | 5.82 | xxx |
| 478 | 603.4 | 5.98 | xxx |
| 479 | 573.1 | 6.32 | xxx |
| 480 | 573.1 | 6.18 | xxxx |
| 481 | 561.2 | 6.21 | xxx |
| 482 | 651.3 | 6.85 | x |
| 483 | 571.1 | 7.11 | xx |
| 484 | 583.3 | 6.98 | xx |
| 485 | 575.2 | 6.06 | xxx |
| 486 | 593.4 | 6.01 | xxx |
| 487 | 549.2 | 5.87 | xxx |
| 488 | 563.3 | 6.05 | xxx |
| 489 | 457.2 | 5.64 | x |
| 490 | 457.2 | 5.78 | x |
| 491 | 525.2 | 6.05 | xxx |
| 492 | 525.3 | 6.13 | xxx |
| 493 | 535.2 | 6.33 | xx |
| 494 | 535.2 | 6.50 | x |
| 495 | 491.3 | 5.63 | xx |
| 496 | 533.2 | 5.94 | xxx |
| 497 | 533.1 | 6.44 | xxx |
| 498 | 603.3 | 6.44 | xxx |
| 499 | 603.2 | 7.15 | xxx |
| 500 | 603.2 | 6.96 | xxx |
| 501 | 473.1 | 5.99 | xx |
| 502 | 473.2 | 6.09 | xx |
| 503 | 541.2 | 6.34 | xxx |
| 504 | 541.1 | 6.43 | xxx |
| 505 | 574.2 | 8.16 | x |
| 506 | 548.3 | 7.86 | xxx |
| 507 | 633.4 | 5.66 | xx |
| 508 | 591.1 | 6.36 | xxxx |
| 509 | 536.2 | 6.57 | xxx |
| 510 | 522.4 | 6.72 | xxx |

TABLE 4-continued

Properties of Compounds

| Cpd. | MS (M + 1) | $t_R$ (min) | MC5R radioligand IC$_{50}$ |
|---|---|---|---|
| 511 | 598.2 | 7.49 | x |
| 512 | 520.1 | 7.36 | x |
| 513 | 455.2 | 5.16 | x |
| 514 | 523.3 | 6.09 | xx |
| 515 | 471.1 | 5.53 | xxxx |
| 516 | 539.3 | 6.11 | xxx |
| 517 | 539.2 | 6.19 | xxxx |
| 518 | 519.3 | 5.72 | xx |
| 519 | 496.3 | 4.91 | xxx |
| 520 | 494.4 | 4.65 | xx |
| 521 | 595.3 | 6.30 | xxx |
| 522 | 492.2 | 6.16 | x |
| 523 | 595.3 | 6.39 | xx |
| 524 | 545.2 | 5.91 | xxx |
| 525 | 523.0 | 5.88 | xx |
| 526 | 471.1 | 5.79 | xx |
| 527 | 539.3 | 6.14 | xxx |
| 528 | 573.1 | 6.50 | x |
| 529 | 564.5 | 6.60 | xx |
| 530 | 587.2 | 6.61 | xx |
| 531 | 601.3 | 7.03 | x |
| 532 | 589.3 | 6.59 | xxx |
| 533 | 592.3 | 7.08 | xx |
| 534 | 567.3 | 6.34 | xxx |
| 535 | 574.2 | 6.14 | xxx |
| 536 | 601.3 | 6.69 | xxx |
| 537 | 591.3 | 7.24 | xx |
| 538 | 535.3 | 6.94 | xxx |
| 539 | 535.3 | 6.37 | xxx |
| 540 | 573.1 | 6.13 | xx |
| 541 | 519.2 | 5.98 | xx |
| 542 | 587.1 | 6.34 | xx |
| 543 | 597.1 | 6.61 | x |
| 544 | 673.0 | 7.50 | x |
| 545 | 618.4 | — | x |
| 546 | 533.1 | 6.20 | xxx |
| 547 | 603.1 | 6.57 | xxx |
| 548 | 513.3 | 6.00 | xxx |
| 549 | 581.2 | 6.22 | xxx |
| 550 | 581.0 | 6.33 | xxxx |
| 551 | 473.3 | 6.03 | xx |
| 552 | 541.1 | 6.36 | xxx |
| 553 | 625.4 | 6.57 | xxx |
| 554 | 577.2 | 6.30 | xxx |
| 555 | 603.1 | 6.45 | xxx |
| 556 | 589.1 | 6.23 | xxx |
| 557 | 554.3 | 6.02 | xx |
| 558 | 587.1 | 6.50 | x |
| 559 | 457.0 | 5.73 | x |
| 560 | 525.2 | 6.20 | xxx |
| 561 | 637.0 | 6.75 | xxx |
| 562 | 613.3 | 7.03 | xxx |
| 563 | 607.2 | — | xx |
| 564 | 589.5 | 6.19 | xxx |
| 565 | 574.8 | 6.27 | xxxx |
| 566 | 618.9 | 6.74 | xxx |
| 567 | 587.7 | 6.19 | xxxx |
| 568 | 596.9 | 6.20 | xxx |
| 569 | 578.0 | 6.38 | xxxx |
| 570 | 597.0 | 6.42 | xxx |
| 571 | 626.9 | 6.70 | xxxx |
| 572 | 591.9 | 6.61 | xxxx |
| 573 | 559.0 | 6.03 | xxxx |
| 574 | 612.8 | 7.04 | xx |
| 575 | 644.9 | 6.79 | xxx |
| 576 | 570.9 | 6.04 | xxx |
| 577 | 570.8 | 6.21 | xxx |
| 578 | 618.8 | 6.61 | xxxx |
| 579 | 579.9 | 6.39 | xxxx |
| 580 | 575.4 | 6.40 | xx |
| 581 | 575.2 | 6.26 | xxx |
| 582 | 575.2 | 6.11 | xxx |
| 583 | 575.1 | 6.21 | xx |
| 584 | 575.2 | 6.25 | xx |
| 585 | 575.4 | 6.27 | x | x = <10 μM; xx = <1 μM, xxx = <100 nM, xxxx = <10 nM

Example 105

MC5R Radioligand Binding Assay Using MC5 Receptors from Other Species

Radioligand binding and cAMP assays were also conducted using membranes and cells expressing MC5R cloned from other species (mouse MC5R membranes were obtained from Euroscreen; canine, rhesus monkey, cyno monkey and guinea pig MC5 receptors were cloned and expressed from cDNA libraries and transiently transfected as described in Examples 107 and 109. Plasma membranes from the cells were tested in the radioligand assay as in Example 102.

Example 106

Activity of Selected Compounds: Other Species MC5R

Representative compounds of the present invention were tested for binding to MC5R from other species, as described in Example 105, the results are listed in Table 5.

TABLE 5

Binding of Selected Compounds to MC5R from Different Species

| Cpd. | human MC5R (membrane) IC$_{50}$ (nM) | human MC5R (whole cells) IC$_{50}$ (nM) | mouse MC5R (membrane) IC$_{50}$ (nM) | canine MC5R (whole cells) IC$_{50}$ (nM) | rhesus monkey MC5R (membranes) IC$_{50}$ (nM) | rhesus monkey MC5R (whole cells) IC$_{50}$ (nM) |
|---|---|---|---|---|---|---|
| 105 | 57 | 219 | 4000 | 6400 | 6027 | 3000 |
| 64 | 30 | 127 | — | 13000 | 7307 | >5000 |

These results show the selectivity of the compounds of the invention for human MC5R in comparison to MC5R in other species. Whilst there is activity in other species it is significantly reduced in comparison to human MC5R, which would not be expected given the high receptor homology between species.

Example 107

Human MC1R, MC3R and MC4R Radioligand Binding Assay

Radioligand binding assays were carried out using commercial or in-house prepared hMC1R, hMC3R and hMC4R membranes and [$^{125}$I] NDP-MSH, as per the hMC5R procedure in Example 102.

In-house plasma membranes were prepared from transfected mammalian cells (prepared as in Example 109, using plasmid DNA containing the human MC1R, MC3R or MC4R gene or other gene of interest in a plasmid vector with a mammalian origin of replication):

Adherent cells were washed with warm Hanks buffered saline solution (HBSS). 1 mL of cold HBSS was added to each flask and the cells were scraped off with a rubber policeman. The scraped cells were added to a 50 mL tube on ice. The plates were then rinsed twice with 5 mL cold HBSS and this was also added to the tube. The cells were centrifuged at 1000×g for 5 mins in a bench top centrifuge and the supernatant was decanted. The remaining cell pellet was resuspended in 0.25 M sucrose. The cell suspension was centrifuged again as previously and the pellet resuspended in 5 mL of 0.25 M sucrose containing protease inhibitors. The cells were homogenised by a 10 second pulse with an Ika disperser followed by 30 seconds on ice. The homogenisation and ice incubation was repeated three times. The mixture was then centrifuged at 1260×g for 5 mins. The supernatant was decanted into another centrifuge tube, to which a buffer containing 50 mM Tris, pH 7.4, 12.5 mM $MgCl_2$, 5 mM EGTA and protease inhibitors was added to make the volume up to 30 mL. This was centrifuged at 30,000×g for 90 mins at 4° C. The resulting pellet was resuspended in 1 mL of the buffer above also containing 10% glycerol. Membranes were aliquoted into cryovials which were snap-frozen in a dry-ice/ethanol bath before being stored at −80° C. until required for use.

Example 108

Selectivity of Selected Compounds: hMCR binding

Representative compounds of the present invention were tested for binding in the hMC1R, hMC3R, hMC4R and hMC5R assays, as in Examples 102 and 107, as listed in Table 6.

TABLE 6 hMCR Binding Selectivity of Selected Compounds

| Cpd. | human MC5R $IC_{50}$ (nM) | human MC1R $IC_{50}$ (nM) | human MC3R $IC_{50}$ (nM) | human MC4R $IC_{50}$ (nM) |
|---|---|---|---|---|
| 105 | 57 | 6660 | 1750 | 3280 |
| 64 | 31 | 9220 | 2240 | 3490 |
| 33 | 9 | 2850 | 1500 | 6060 |
| 348 | 150 | 20000 | 1830 | 20000 |

These results demonstrate the selectivity of the compounds of the invention for human MC5R in comparison to other receptor subtypes of the human melanocortin receptor family.

Example 109

Inhibition or Stimulation of cAMP Signal in Cells Expressing Human MC5R

Transient Transfection of Mammalian Cell Lines:

The mammalian cell line, human embryonic kidney cells (HEK 293), were maintained in Dulbeccos Modified Eagle's medium (DMEM) with 5% fetal bovine serum, L-glutamine, high glucose and antibiotics/antimycotics. On the day prior to transfection, cells were passaged using trypsin/EDTA and seeded into 75 $cm^2$ flasks so that they would be approximately 90% confluent the next day. The next day, the cell media was replaced with fresh antibiotic/antimycotic-containing DMEM. Approximately 100 µl of the transfection lipid Turbofectin 8.0 (Origene Technologies, MD, USA), was diluted in 1.0 mL of serum and antibiotic/antimycotic-free Opti-MEM in a sterile 15 mL tube and incubated for 5 mins at room temperature. Following incubation, approximately 10-20 µg of plasmid DNA expressing the gene of interest (for example: pCMV6-XL4:*Homo sapiens* melanocortin 5 receptor (Origene Technologies, MD, USA)) was diluted into the transfection mix and incubated for a further 30 mins at room temperature. The DNA/lipid solution was then added drop-wise to the media covering the cells while rocking the flask gently. 24 hrs post-transfection, the cells were passaged and seeded directly into two, 75 $cm^2$ flasks and left to recover. 48 hrs post transfection, cells were harvested for use in assays with cell dissociation solution.

Cyclic-Adenosine Monophosphate [cAMP] Stimulation Assay:

HEK 293 cells transiently expressing the melanocortin MC5 receptor were suspended in stimulation buffer (Hanks buffered saline solution (HBSS), 0.1% bovine serum albumin, protease inhibitors and 0.5 mM 3-Isobutyl-1-methylxanthine) at 4×10$^6$ cells/mL. 5 µl of cells, plus the compounds/peptides as described below, were added to wells of a 384-well plate as soon as possible after resuspension.

To detect antagonist activity, test compounds at varying concentrations were diluted in stimulation buffer at four times concentrate and 2.5 µl was added to wells containing cells. 2.5 µl of a four times required concentration of NDP-MSH or alpha-MSH was added to all wells containing compounds. Negative control wells contained two times concentrated NDP-MSH or alpha-MSH alone without compound.

To detect agonist activity, test compounds at varying concentrations were diluted in stimulation buffer at two times concentrate and 5 µl was added to wells containing cells. Positive control wells contained NDP-MSH or alpha-MSH alone (no compound) at two times concentrate Basal level (of cAMP) control wells contained stimulation buffer only (no agonist or compounds). Known concentrations of cAMP (standards) in stimulation buffer were included on the plate, but no cells were added to these wells. The plate was then incubated for 30 mins at 37° C. with gentle shaking. After incubation, 10 µl of lysis buffer (10% Tween 20, 1 M HEPES, 0.1% BSA, protease inhibitors, dd$H_2O$) was added to all wells to be measured. Detection of cAMP was then achieved using the Alphascreen cAMP kit (Perkin Elmer, USA), briefly described as follows. A dilution of 10 µl acceptor beads/mL of lysis buffer was prepared in low light conditions. 5 µl of diluted acceptor beads were added to each well to be measured, then the plate was incubated for 30 mins at room temperature, in the dark, with gentle shaking. In low light conditions, donor beads were diluted at 10 μl/mL of lysis buffer, to which 0.75 μl biotinylated cAMP/mL of lysis buffer was added. This mixture was allowed to incubate for 30 mins at room temperature (in the dark) before proceeding with the assay. Following incubation, 5 μl/mL of biotinylated cAMP/Donor bead mix were added per well in low light conditions and the plate was incubated in the dark, at room temperature, for a further hr. Plates were read on an Envision plate reader (Perkin Elmer) after 1 hr and ~16 hrs incubation. cAMP concentration in the cells was determined by the use of a 'standard curve' generated from the output of known cAMP concentrations as described below.

Each assay plate contained a "standard curve" of known concentrations of cAMP, in 10 fold dilutions. This is an essential part of the assay as there is high inter-plate variability. The plates were read on an Envision multilabel plate reader fitted with Alphascreen technology and the raw data was imported into GraphPad Prism 4 software (GraphPad, USA) for analysis. A curve was fitted to the known concentrations using non-linear regression, specifically using a sigmoidal dose-response equation (Y=Bottom+(Bottom+(Top-Bottom)/1+$10^{logEC50-X}$), where the equation shows the response as a function of the logarithm of concentration. X is the logarithm of peptide/compound concentration and Y is the response. Also considered in this equation are bottom plateau, top plateau of the curve and $EC_{50}$ (effective concentration, 50%)

Example 110

Activity of Selected Compounds: hMC5R

Representative compounds of the present invention were tested for agonism or antagonism of the hMC5R, as in Example 109, results are listed in Table 7.

TABLE 7

Agonism and Antagonism of hMC5 by Selected Compounds

| Cpd. | human MC5R $EC_{50}$ (cAMP, agonism) (nM) | human MC5R $IC_{50}$ (cAMP, antagonism of $10^{-6}$ M alpha-MSH) (nM) |
|---|---|---|
| 105 | >10000 | 400 |
| 64 | >10000 | 70 |
| 33 | >10000 | 190 |
| 348 | >10000 | 94 |

REFERENCES

Andersen, G. N.; Hägglund, M.; Nagaeva, O.; Frängsmyr, L.; Petrovska, R.; Mincheva-Nilsson, L.; Wikberg, J. E. S. *Scand. J. Immunol.* 2005, 61, 279-284 "Quantitative measurement of the levels of melanocortin receptor subtype 1, 2, 3 and 5 and pro-opio-melanocortin peptide gene expression in substes of human peripheral blood leukocytes"

Barrett, P.; MacDonald, A.; Helliwell, R.; Davidson, G.; Morgan, P. *J. Molec. Endocrin.* 1994, 12, 203-213 "Cloning and expression of a new member of the melanocyte-stimulating hormone receptor family"

Bataille, V.; Snieder, H.; MacGregor, A. J.; Sasieni, P.; Spector, T. D. *J. Invest. Dermatol.* 2002, 119, 1317-1322 "The Influence of Genetics and Environmental Factors in the Pathogenesis of Acne: A Twin Study of Acne in Women"

Bhardwaj, S. S.; Rohrer, T. E.; Arndt, K. A. *Semin. Cutan. Med. Surg.* 2005, 24, 107-112 "Lasers and light therapy for acne vulgaris"

Bohm, M.; Luger, T. A.; Tobin, D. J.; Garcia-Borron, J. C. *J. Invest. Dermatol.* 2006, 126, 1966-1975 "Melanocortin Receptor Ligands: New Horizons for Skin Biology and Clinical Dermatology"

Buggy, J. J. *Biochem J.* 1998, 331, 211-216 "Binding of a-melanocyte-stimulating hormone to its G-protein-coupled receptor on B-lymphocytes activates the Jak/STAT pathway"

Burke, B. M.; Cunliffe, W. J.; *Br. J. Dermatol.* 1984, 112 124-126 "Oral spironolactone therapy for female patients with acne, hirsutism or androgenic alopecia"

Caldwell, H. K.; Lepri, J. J. *Chem. Senses* 2002, 27, 91-94 "Disruption of the fifth melanocortin receptor alters the urinary excretion of aggression-modifying pheromones in male house mice"

Cerdá-Reverter, J. M.; Ling, M. K.; Schiöth, H. B.; Peter, R. E. *J. Neurochem.* 2003, 1354-1367 "Molecular cloning, characterization and brain mapping of the melanocortin 5 receptor in goldfish"

Chen, W.; Kelly, M. A.; Opitz-Araya, X.; Thomas, R. E.; Low, M. J.; Cone, R. D. *Cell,* 1997, 91, 789-798 "Exocrine gland dysfunction in MC5-R-deficient micee: evidence for coordinated regulation of exocrine gland function by melanocortin peptides"

Chhajlani, V.; Muceniece, R.; Wikberg, J. E. S. *BBRC* 1993, 195, 866-873 "Molecular Cloning of a Novel Human Melanocortin Receptor"

Clarke, S. B.; Nelson, A. M.; George, R. E.; Thiboutot, D. M. *Dermatol. Clin.* 2007, 25, 137-146 "Pharmacologic Modulation of Sebaceous Gland Activity: Mechanisms and Clinical Applications".

Cordain, L. *Sem. Cut. Med. Surg.* 2005, 24, 84-91 "Implications for the Role of Diet in Acne"

Cotterill, J. A.; Cunliffe, W. J.; Williamson, B. *Brit. J. Dermatol.* 1971, 85, 93-94 "Severity of Acne and Sebum Excretion Rate"

Danby, F. W. *J. Am. Acad. Dermatol.* 2005, 52, 1071-1072 "Why we have sebaceous glands"

Eisinger, M.; Fitzpatrick, L. J.; Lee, D. H.; Pan, K.; Plata-Salaman, C.; Reitz, A. B.; Smith-Swintosky, V. L.; Zhao, B. WO03/040117 15 May 2003a "Novel 1,2,4-thiadiazole derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. WO03040118A1 15 May 2003b "Novel 1,2,4-thiadiazolium derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2003/0162819A1 Aug. 28 2003c "Novel 1,2,4-thiadiazolium derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2003/0176425A1 Sep. 18 2003d "Novel 1,2,4-thiadiazole derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2006/0030604A1 Feb. 9 2006a "Novel 1,2,4-thiadiazolium derivatives as melanocortin receptor modulators"

Eisinger, M.; Fitzpatrick, L. J.; Lee, D. H.; Pan, K.; Plata-Salaman, C.; Reitz, A. B.; Smith-Swintosky, V. L.; Zhao, B. US2006/0128772A1 Jun. 15 2006b "Novel 1,2,4-thiadiazole derivatives as melanocortin receptor modulators"

Fathi, Z.; Iben, L. G.; Parker, E. M. Neurochemical Res. 1995, 20, 107-113 "Cloning, Expression, and Tissue Distribution of a Fifth Melanocortin Receptor Subtype"

Follador, I.; Campelo, L. *Expert Rev. Dermatol.* 2006, 1 181-184 "Impact of acne on quality of life"

Fong, T. M.; Van der Ploeg, L. H. T.; Huang, R.-R. C. US6645738B1 Nov. 11 2003 "DNA molecules encoding the melanocortin 5 receptor protein from rhesus monkey"

Gantz, I.; Shimoto, Y.; Konda, Y.; Miwa, H.; Dickinson, C. J.; Yamada, T. *BBRC* 1994, 200, 1214-1220 "Molecular cloning, expression and characterization of a fifth melanocortin receptor"

Goldstein, J. A.; Socha-Szott, A.; Thomsen, R. J.; Pochi, P. E.; Shalita, A. R.; Strauss, J. S. *Am. J. Dermatol.* 1982, 6, 760-765 "Comparative effect of isotretinoin and etretinate on acne and sebaceous gland secretion"

Goodfellow, A.; Alaghband-Zadeh, J.; Carter, G.; Cream, J. J.; Holland, S.; Scully, J.; Wise, P. *Brit. J. Dermatol.* 1984, 111, 209-214 "Oral spironolactone improves acne vulgaris and reduces sebum excretion"

Goulden, V.; Mcgeown, C. H.; Cunliffe, W. J. *Brit. J. Dermatol.* 1999, 141, 297-300 "Familial Risk of Adult Acne: A comparison between first-degree relatives of affected and unaffected individuals"

Graefe, T.; Wollina, U.; Schulz, H.-J.; Burgdorf, W. *Dermatology* 2000, 200, 331-333 "Muir-Torre Syndrome—Treatment with Isotretinoin and Interferon Alpha-2a Can Prevent Tumour Development"

Griffon, N.; Mignon, V.; Facchinetti, P.; Diaz, J.; Schwartz, J.-C.; Sokoloff, P. *BBRC* 1994, 200, 1007-1014 "Molecular cloning and characterization of the rat fifth melanocortin receptor"

Gupta, A. K.; Bluhm, R. *Journal of the European Academy of Dermatology and Venereology* 2004 18:1 13 "Seborrheic dermatitis"

Haitina, T.; Klovins, J.; Andersson, J.; Fredriksson, R.; Lagerström, M. C.; Larhammar, D.; Larson, E. T.; Schiöth, H. B. *Biochem. J.* 2004, 380, 475-486 "Cloning, tissue distribution, pharmacology and three-dimensional modelling of melanocortin receeotors 4 and 5 in rainbow trout suggest close evolutionary relationships of these subtypes"

Harper, J. C. *Semin. Cutan. Med. Surg.* 2005, 24, 103-106 "Hormonal Therapy for Acne using oral contraceptive pills"

Harris, H. H.; Downing, D. T.; Stewart, M. E.; Strauss, J. S. *J. Am. Acad. Dermatol.* 1983, 8, 200-203 "Sustainable rates of sebum secretion in acne patients and mayched normal controls"

Hatta, N.; Dixon, C.; Ray, A. J.; Phillips, S. R.; Cunliffe, W. J.; Dale, M.; Todd, C.; Meggit, S.; Birch-Machin, M. A.; Rees, J. L. *J. Invest. Dermatol.* 2001, 116, 564-570 "Expression, candidate gene, and population studies of the melanocortin 5 receptor"

Houseknecht, K. L.; Robertson, A. S.; Xiao, X. US2003/0110518A1 Jun. 12 2003 "Melanocortin-5 receptor sequences and uses thereof"

Huang, R.-R. C.; Singh, G.; Van der Ploeg, L. H. T.; Fong, T. M. *J. Receptor & Signal Transduction Res.* 2000, 20, 47-59 "Species-dependent pharmacological properties of the melanocortin-5 receptor"

Ide, F.; Shimoyama, T.; Horie, N.; Kaneko, T.; Matsumoto, M. *Oral Surg. Oral Med. Oral Pathol. Oral Radiol. Endod.* 1999, 87, 721-724 "Benign lymphoepithelial lesion of the parotid gland with sebaceous differentiation"

Jeong, S. K.; Hwang, S. W.; Choi, S. Y.; An, J. M.; Seo, J. T.; Zouboulis, C. C.; Lee, S. H. *J. Investigative Dermatol.* 2007, 127, pS72 "Intracellular calcium mobilization is mediated by the melanocortin receptors in SZ95 sebocytes" (Abstract 431, Society for Investigative Dermatology, May 2007, Los Angeles Calif.)

Jih, M. H.; Friedman, P. M.; Goldberg, L. H.; Robles, M.; Glaich, A. S.; Kimyai-Asadi, A. *J. Am. Acad. Dermatol.* 2006, 55, 80-87 "The 1450-nm diode laser for facial inflammatory acne vulgaris: Dose-response and 12-month follow-up study". Jones, D. H.; King, K.; Miller, A. J.; Cunliffe, W. J. *Brit. J. Dermatol.* 1983, 108, 333-343 "A dose-response study of 13-cis-retinoic acid in acne vulgaris"

Kim, K. S.; Marklund, S.; Rothschild, M. F. *Animal Genetics* 2000, 31, 230-231. "The porcine melanocortin-5-receptor (MC5R) gene: polymorphisms, linkage and physical mapping"

King, K.; Jones, D. H.; Daltrey, D. C.; Cunliffe, W. J. *Brit. J. Dermatol.* 1982, 107, 583-590 "A double-blind study of the effects of 13-cis-retinoic acid on acne, sebum excretion rate and microbial population"

Kligman, A. M. Brit. J. Dermatol. 1963, 75, 307-319 "The uses of sebum"

Klovins, J.; Haitina, T.; Ringholm, A.; Löwgren, M.; Fridmanis, D.; Slaidina, M.; Stier, S.; Schiöth, H. B. *Eur. J. Biochem.* 2004, 271, 4320-4331 "Cloning of two melanocortin (MC) receptors in spiny dogfish"

Kruse, R.; Rütten, A.; Schweiger, N.; Jakob, E.; Mathiak, M.; Propping, P.; Mangold, E.; Bisceglia, M; Ruzicka, T. *J. Invest. Dermatol.* 2003, 120, 858-864 "Frequency of Microsatellite Instability in Unselected Sebaceous Gland Neoplasias and Hyperplasias"

Labbé, O.; Desarnaud, F.; Eggerickx, D.; Vassart, G.; Parmentier, M. *Biochem.* 1994, 33, 4543-4549 "Molecular Cloning of a mouse melanocortin 5 receptor gene widely expressed in peripheral tisssues"

Ling, M. K.; Hotta, E.; Kilianova, Z.; Haitina, T.; Ringholm, A.; Johansson, L.; Gallo-Payet, N.; Takeuchi, S.; Schiöth, H. B. *Brit. J. Pharmacol.* 2004, 143, 626-637 "The melanocortin receptor subtypes in chicken have high preference to ACTH-derived peptides"

Makrantonaki, E.; Zouboulis, C. C. *Brit. J. Dermatol.* 2007, 156, 428-432 "Testosterone metabolism to 5a-dihydrotestosterone and synthesis of sebaceous lipids is regulated by the peroxisome proliferator-activated receptor ligand linoleic acid in human sebocytes"

Mariappan, M. R.; Fadare, O.; Jain, D. *Arch. Pathol. Lab. Med.* 2004, 128, 245-246 "Sebaceous Differentiation in Salivary Glands"

Mallon, E.; Newton, J. N.; Klassen, A.; Stewart-Brown, S. L.; Ryan, T. J.; Finlay, A. Y. *Brit. J. Dermatol.* 1999, 140, 672-676 "The quality of life in acne: a comparison with general medical conditions using generic questionanaires"

Marqueling A. L.; Zane, L. T. *Semin. Cutan. Med. Surg.* 2005, 24, 92-102 "Depression and Suicidal Behavior in Acne Patients Treated with Isotretinoin: A Systematic Review"

Morgan, C.; Thomas, R. E.; Ma, W.; Novotny, M. V.; Cone, R. D. *Chem. Senses* 2004a, 29, 111-115 "Melanocortin-5 receptor deficiency reduces a pheromonal signal for aggression in male mice"

Morgan, C.; Thomas, R. E.; Cone, R. D. *Horm. Behav.* 2004b, 45, 58-83 "Melanocortin-5 receptor deficiency promotes defensive behaviour in male mice"

Morgan, C.; Cone, R. D. *Behaviour Genetics* 2006, 36, 291-300 "Melanocortin-5 receptor deficiency in mice blocks a novel pathway influencing pheromone-induced aggression"

Mourelatos, K.; Eady, E. A.; Cunliffe, W. J.; Clark, S. M.; Cove, J. H. *Brit. J. Dermatol.* 2007, 156, 22-31 "Temporal changes in sebum excretion and propionibacterial colonization in preadolescent children with and without acne"

Nelson, A. M.; Gilliland, K. L.; Cong, Z.; Thiboutot, D. M. *J. Investigative Dermatol.* 2006, 126, 2178-2189 "13-cis-Retinoic Acid Induces Apoptosis and Cell Cycle Arrest in Human SEB-1 Sebocytes"

Phan, J.; Kanchanapoomi, M.; Liu, P.; Jalian, H.; Gilliland, K.; Nelson, A.; Thiboutot, D.; Kim, J. *J. Investigative Dermatol.* 2007, 127, pS126 "P. acnes induces inflammation via TLR2 and upregulates antimicrobial activity in sebocytes" (Abstract 754, Society for Investigative Dermatology, May 2007, Los Angeles Calif.)

Piérard, G. E.; Pierrard-Franchimont, T. L. *Dermatologica* 1987, 175, 5-9 "Seborrhoea in Acne-Prone and Acne-Free Patients"

Plewig G, Jansen T. Seborrheic dermatitis. In: Freedberg I M, EisenAZ, Wolff K, Austen K F, Goldsmith L A, Katz S I, Fitzpatrick T B, (Eds). Dermatology in General Medicine, 5th ed. New York: McGraw Hill, 1999: 1482-1489

Pochi, P. E.; Strauss, J. S. *J. Invest. Dematol.* 1964, 43, 383-388 "Sebum production, casual sebum levels, titratable acidity of sebum and urinary fractional 17-ketosteroid excretion in males with acne"

Porter, A. M. W. *J. Royal Soc. Med.* 2001, 94, 236-237 "Why do we have apocrine and sebaceous glands"

Ringholm, A.; Fredriksson, R.; Poliakova, N.; Yan, Y.-L.; Postlethwait, J. H.; Larhammar, D.; Schiöth, H. B. *J. Neurochem.* 2002, 82, 6-18 "One melanocortin 4 and two melanocortin 5 receptors from zebrafish show remarkable conservation in structure and pharmacology"

Shuster, S. *Lancet* 1976, 7973, 1328-1329 "Biological purpose of acne"

Simpson, N. B. and Cunliffe, W. J. in Rooks' Textbook of Dermatology, 7$^{th}$ Ed 2004 Blackwell Science, Malden Mass., p 43.1-43.75 "Chapter 43. Disorders of the Sebaceous Glands"

Smith, K. R.; Nelson, A.; Cong, Z.; Thiboutot, D. *J. Investigative Dermatol.* 2007a, 127, pS68 "Iron status affects human sebocyte survival" (Abstract 408, Society for Investigative Dermatology, May 2007, Los Angeles Calif.)

Smith, R. N.; Mann, N. J.; Braue, A.; Makelainen, H.; Varigos, G. A. *J. Am. Acad. Dermatol.* 2007b, 57, 247-256 "The effect of a high-protein, low glycemic-load diet versus a conventional, high glycemic-load diet on biochemical parameters associated with acne vulgaris: A randomized investigator-masked, controlled trial"

Taylor, A.; Namba, K. *Immunologyy Cell Biol.* 2001, 79, 358-367 "In vitro induction of CD25+CD4+ regulatory T cells by the neuropeptide alpha-melanocyte stimulating hormone (α-MSH)"

Thiboutot, D.; Sivarajah, A.; Gilliland, K.; Cong, Z.; Clawson, G. *J. Invest. Dermatol.* 2000, 115, 614-619 "The melanocortin 5 receptor is expressed in human sebaceous glands and rat preputial cells"

Thody, A. J.; Shuster, S, *Nature* 1973, 245, 207-209 "Possible role of MSH in the mammal"

Thody, A. J.; Cooper, M. F.; Bowden, P. E.; Shuster, S. *J. Endocrinol.* 1975a, 67, 18P-19P "The sebaceous gland response to α-melanocyte-stimulating hormone and testosterone"

Thody, A. J.; Shuster, S. *J. Endocrinol.* 1975b, 64, 503-510 "Control of sebaceous gland function in the rat by α-melanocyte-stimulating hormone"

Thody, A. J.; Goolamali, S. K.; Burton, J. L.; Plummer, N. A.; Shuster, S. *Brit. J. Dermatol.* 1975c, 92, 43-47 "Plasma β-MSH levels in acne vulgaris"

Wikberg, J. E. S. *Exp. Opin. Ther. Patents* 2001, 11, 61-76 "Melanocortin receptors: new opportunities in drug discovery";

Wikberg, J.; Chhajlani, V. U.S. Pat. No. 6,448,032B1 Sep. 10 2002 "Human melanocyte stimulating hormone receptor polypeptide and DNA"

Williams, C.; Layton, A. M. *Exp. Rev. Dermatol.* 2006, 1, 429-438 "Treatment of Acne: an update"

Yamada, T.; Gantz, I. U.S. Pat. No. 5,622,860, Apr. 22 1997, "Genes Encoding Melanocortin Receptors"

Yaswen, L.; Diehl, N.; Brennan, M. B.; Hochgeschwender, U. *Nature Med.* 1999, 5, 1066-1070 "Obesity on the mouse model of proo-opiomelanocortin deficiency responds to peripheral melanocortin"

Youn, S.-W.; Park, E.-S.; Lee, D.-H.; Huh, C.-H.; Park, K.-C. *Brit. J. Dermatol.* 2005, 153, 919-924 "Does facial sebum secretion really affect the development of acne?"

Zhang, L.; Anthonavage, M.; Huang, Q.; Li, W.-H.; Eisinger, M. *Ann. N.Y. Acad. Sci.* 2003, 994, 154-161 "Proopiomelanocortin peptides and sebogenesis"

Zhang, L.; Li, W.-H.; Anthonavage, M.; Eisinger, M. *Peptides* 2006, 27, 413-420 "Melanocortin-5 receptor: a marker of human sebocyte differentiation"

Zouboulis, C. C.; Böhm, M. Exp. Dermatol. 2004, 13, 31-35 "Neurocrine regulation of sebocytes—a pathogenetic link between stress and acne"

The details of specific embodiments described in this invention are not to be construed as limitations. Various equivalents and modifications may be made without departing from the essence and scope of this invention, and it is understood that such equivalent embodiments are part of this invention.

What is claimed is:

1. A method of treating or controlling a melanocortin 5 receptor (MC5R)-associated condition selected from one or more conditions of the group consisting of acne, seborrhea, and seborrheic dermatitis, comprising administering to a mammal in need thereof a therapeutically effective amount of a compound of formula (Ib):

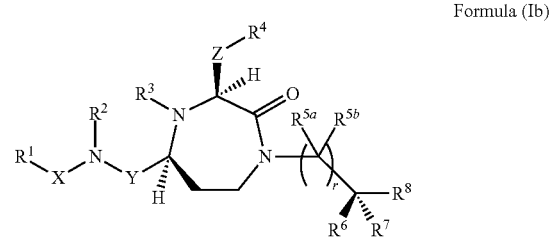

Formula (Ib)

wherein
Y is $CH_2$;
X is —C(=O)—;
Z is —$(CH_2)_q$—;
r is 0 or 1;
q is 1, 2, 3, or 4;
$R^1$ is selected from the group consisting of (a) optionally substituted $C_6$-$C_{18}$ aryl wherein the $C_6$-$C_{18}$ aryl is phenyl, biphenyl, or naphthyl; (b) optionally substituted $C_1$-$C_{18}$ heteroaryl wherein the $C_1$-$C_{18}$ heteroaryl is indol-2-yl, indol-3-yl, quinolin-2-yl, quinolin-3-yl, isoquinolin-3-yl, quinoxaline-2-yl, benzo[b]furan-2-yl, benzo[b]thiophen-2-yl, benzo[b]thiophen-5-yl, thiazole-4-yl, benzimidazole-5-yl, benzotriazol-5-yl, furan- 2-yl, benzo[d]thiazole-6-yl, pyrazole-1-yl, pyrazole-4-yl or thiophen-2-yl; and (c) optionally substituted alkenyl of the formula:

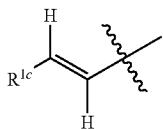

wherein $R^{1c}$ is optionally substituted $C_6$-$C_{18}$ aryl wherein the $C_6$-$C_{18}$ aryl is selected from phenyl and naphthyl;

$R^2$ is H or $C_1$-$C_6$ alkyl;

$R^3$ is H or $C_1$-$C_6$ alkyl;

$R^4$ is selected from the group consisting of H, $C_1$-$C_{12}$alkyl, optionally substituted $C_3$-$C_{12}$cycloalkyl, optionally substituted $C_6$ aryl, $OR^{20}$, and $OCR^{17}R^{18}R^{20}$;

$R^{5a}$ and $R^{5b}$ are each H;

$R^6$ and $R^8$ are each independently H, methyl, trifluoromethyl, ethyl, 2,2,2-trifluoroethyl, isopropyl, isopropenyl, propyl, 2-ethyl-propyl, 3,3-dimethylpropyl, butyl, 2-methylbutyl, isobutyl, 3,3-dimethyl-butyl, 2-ethylbutyl, pentyl, 2-methyl-pentyl, optionally substituted phenyl, optionally substituted $C_1$-$C_5$ heteroaryl, wherein the $C_1$-$C_5$ heteroaryl is thiophene, furan, pyrrole, imidazole, pyrazole, pyridine, pyrazine, or tetrazole;

$R^7$ is H;

each of $R^{17}$, $R^{18}$, and $R^{20}$ is selected from the group consisting of H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof; and wherein each optional substituent is independently selected from the group consisting of F, Cl, Br, I, $CH_3$, $CH_2CH_3$, OH, $OCH_3$, $CF_3$, $OCF_3$, $NO_2$, $NH_2$, and CN;

or a pharmaceutically acceptable salt thereof.

2. A method according to claim 1 wherein the condition is acne and wherein the mammal is a human.

3. The method according to claim 1 wherein $R^4$ is optionally substituted $C_3$-$C_{12}$cycloalkyl.

4. The method according to claim 1 wherein $R^4$ is $C_1$-$C_{12}$ alkyl.

5. The method according to claim 1 wherein the compound of formula (Ib) is selected from the group consisting of:

N-(((3S,5S)-3-butyl-1-(2,2-diphenyiethyl)-2-oxo-1,4-diazepan-5-yl)methyl)-2-naphthamide;

(E)-N-(((3S,5S)-3-butyl-1-(2,2-diphenyiethyl)-2-oxo-1,4-diazepan-5-yl)methyl)-3-(4-chlorophenyl)acrylamide;

N-(((3S,5S)-3-(cyclohexylmethyl)-1-(2,2-diphenylethyl)-2-oxo-1,4-diazepan-5-yl)methyl)-2-naphthamide;

N-(((3S,5S)-1-(2,2-diphenylethyl)-2-oxo-3-phenethyl-1,4-diazepan-5-yl)methyl)-2-naphthamide;

(E)-3-(4-chlorophenyl)-N-(((3S,5S)-1-(2,2-diphenylethyl)-2-oxo-3-phenethyl-1,4-diazepan-5-yl)methyl) acryiamide;

N-(((3S,5S)-3-(2-cyclohexylethyl)-1-(2,2-diphenylethyl)-2-oxo-1,4-diazepan-5-yl)methyl)-2-naphthamide;

(E)-3-(4-chlorophenyl)-N-(((3S,5S)-3-(2-cyclohexylethyl)-1-(2,2-diphenylethyl)-2-oxo-1,4-diazepan-5-yl)methyl)acrylamide;

N-(((3S,5S)-3-benzyl-1-(2,2-diphenylethyl)-2-oxo-1,4-diazepan-5-yl)methyl)-2-naphthamide;

(E)-N-(((3S,5S)-3-benzyl-1-(2,2-diphenylethyl)-2-oxo-1,4-diazepan-5-yl)methyl)-3-(4-chlorophenyl)acrylamide;

N-(((3S,5S)-3-butyl-2-oxo-1-((S)-2-phenylbutyl)-1,4-diazepan-5-yl)methyl)-6-chloro-2-naphthamide;

6-chloro-N-(((3S,5S)-3-isopentyl-2-oxo-1-((S)-2-phenylbutyl)-1,4-diazepan-5-yl)methyl)-2-naphthamide;

6-chloro-N-(((3S,5S)-3-(2-cyclohexylethyl)-2-oxo-1-((S)-2-phenylbutyl)-1,4-diazepan-5-yll)methyl)-2-haphthamide;

6-chloro-N-(((3S,5S)-3-hexyl-2-oxo-1-((S)-2-phenylbutyl)-1,4-diazepan-5-yl)methyl)-2-naphthamide;

6-chloro-N-(((3S,5S)-3-(4-hydroxybutyl)-2-oxo-1-((S)-2-phenylbutyl)-diazepan-5-yl)methyl)-2-naphthamide;

6-chloro-N-(((3S,5S)-3-(2-methoxyethyl)-2-oxo-1-((S)-2-phenylbutyl)-1,4-diazepan-5-yl)methyl)-2-naphthamide;

N-(((3S,5S)-3-(2-(benzyloxy)ethyl)-2-oxo-1-((S)-2-phenylbutyl)-1,4-diazepan-5-yl)methyl)-6-chloro-2-naphthamide;

6-chloro-N-(((3S,5S)-3-isobutyl-2-oxo-1-((S)-2-phenylbutyl)-1,4-diazepan-5-yl)methyl)-2-naphthamide; and 3,4-dichloro-N-(((3S,5S)-3-(2-hydroxyethyl)-2-oxo-1-((S)-2-phenylbutyl)-1,4-diazepan-5-yl)methyl)benzamide;

or a pharmaceutically acceptable salt thereof.

6. The method according to claim 1 wherein the compound of formula (Ib) is N-(((3S,5S)-3-butyl-1-(2,2-diphenylethyl)-2-oxo-1,4-diazepan-5-yl)methyl)-2-naphthamide, represented by the formula

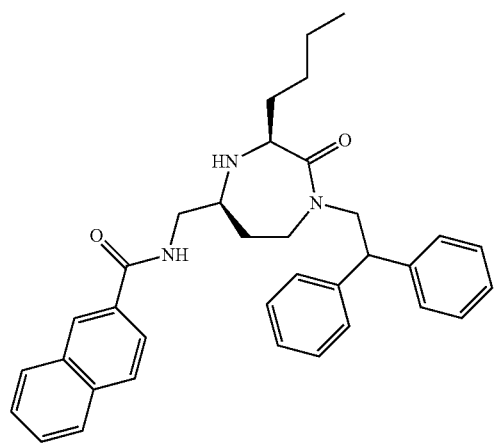 [SMILES: CCCC[C@@H]1N[C@H](CNC(=O)c2ccc3ccccc3c2)CCN(CC(c2ccccc2)c2ccccc2)C1=O]

or a pharmaceutically acceptable salt thereof.

7. The method according to claim 1 wherein the compound of formula (Ib) is (E)-N-(((3S,5S)-3-butyl-1-(2,2-diphenylethyl)-2-oxo-1,4-diazepan-5-yl)methyl)-3-(4-chlorophenyl)acrylamide, represented by the formula

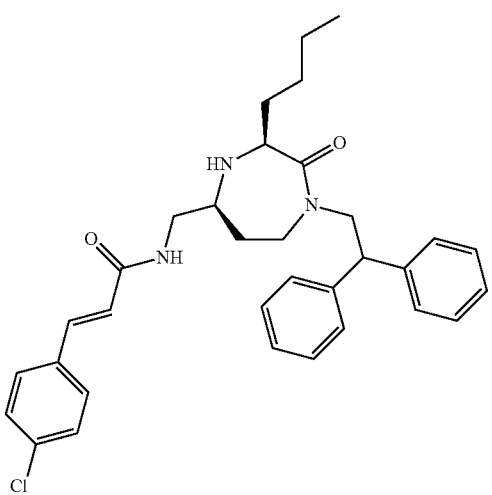 [SMILES: CCCC[C@@H]1N[C@H](CNC(=O)/C=C/c2ccc(Cl)cc2)CCN(CC(c2ccccc2)c2ccccc2)C1=O]

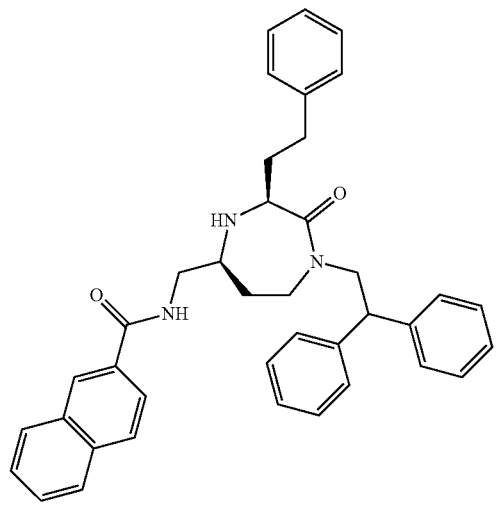

or a pharmaceutically acceptable salt thereof.

8. The method according to claim 1 wherein the compound of formula (Ib) is N-(((3S,5S)-3-(cyclohexylmethyl)-1-(2,2-diphenylethyl)-2-oxo-1,4-diazepan-5-yl)methyl)-2-naphthamide, represented by the formula or a pharmaceutically acceptable salt thereof.

10. The method according to claim 1 wherein the compound of formula (Ib) is (E)-3-(4-chlorophenyl)-N-(((3S,5S)-1-(2,2-diphenylethyl)-2-oxo-3-phenethyl-1,4-diazepan-5-yl)methyl)acrylamide, represented by the formula

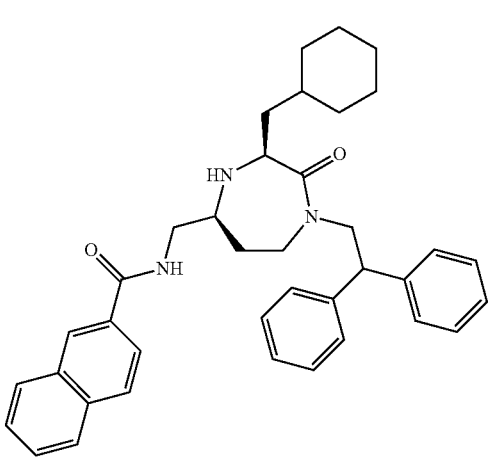 [SMILES: O=C(NC[C@@H]1CCN(CC(c2ccccc2)c2ccccc2)C(=O)[C@H](CC2CCCCC2)N1)c1ccc2ccccc2c1]

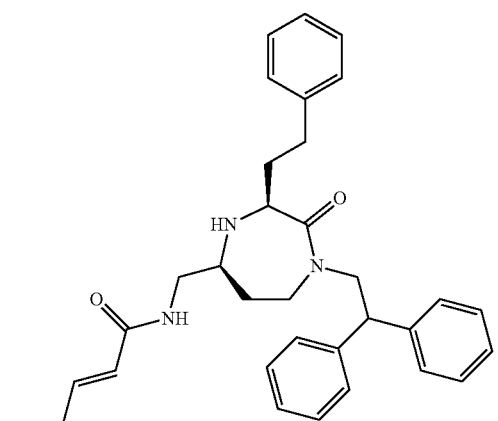

or a pharmaceutically acceptable salt thereof.

9. The method according to claim 1 wherein the compound of formula (Ib) is N-(((3S,5S)-1-(2,2-diphenylethyl)-2-oxo-3-phenethyl-1,4-diazepan-5-yl)methyl)-2-naphthamide, represented by the formula or a pharmaceutically acceptable salt thereof.

11. The method according to claim 1 wherein the compound of formula (Ib) is N-(((3S,5S)-3-(2-cyclohexylethyl)-1-(2,2-diphenylethyl)-2-oxo-1,4-diazepan-5-yl)methyl)-2-naphthamide, represented by the formula

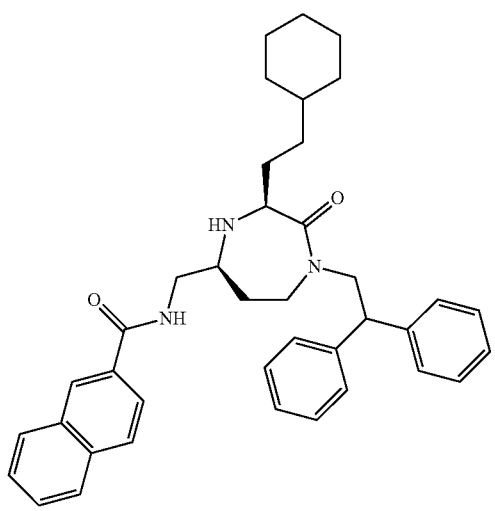 [SMILES: O=C(NC[C@@H]1CCN(CC(c2ccccc2)c2ccccc2)C(=O)[C@H](CCC2CCCCC2)N1)c1ccc2ccccc2c1]

or a pharmaceutically acceptable salt thereof.

12. The method according to claim 1 wherein the compound of formula (Ib) is (E)-3-(4-chlorophenyl)-N-(((3S,5S)-3-(2-cyclohexylethyl)-1-(2,2-diphenylethyl)-2-oxo-1,4-diazepan-5-yl)methyl)acrylamide, represented by the formula

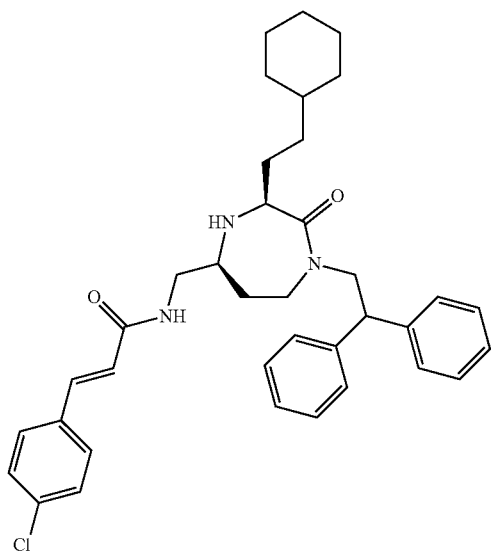 [SMILES: O=C(/C=C/c1ccc(Cl)cc1)NC[C@@H]1CCN(CC(c2ccccc2)c2ccccc2)C(=O)[C@H](CCC2CCCCC2)N1]

or a pharmaceutically acceptable salt thereof.

13. The method according to claim 1 wherein the compound of formula (Ib) is N-(((3S,5S)-3-benzyl-1-(2,2-diphenylethyl)-2-oxo-1,4-diazepan-5-yl)methyl)-2-naphthamide, represented by the formula

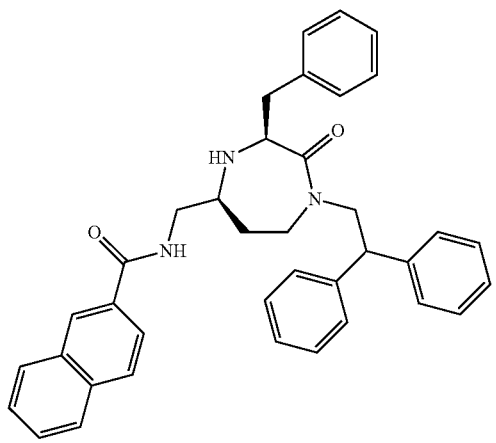 [SMILES: O=C(NC[C@@H]1CCN(CC(c2ccccc2)c2ccccc2)C(=O)[C@H](Cc2ccccc2)N1)c1ccc2ccccc2c1]

or a pharmaceutically acceptable salt thereof.

14. The method according to claim 1 wherein the compound of formula (Ib) is (E)-N-(((3S,5S)-3-benzyl-1-(2,2-diphenylethyl)-2-oxo-1,4-diazepan-5-Amethyl)-3-(4-chlorophenyl)acrylamide, represented by the formula

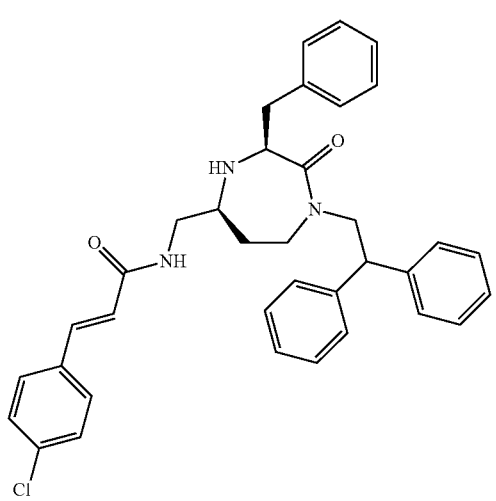 [SMILES: O=C(/C=C/c1ccc(Cl)cc1)NC[C@@H]1CCN(CC(c2ccccc2)c2ccccc2)C(=O)[C@H](Cc2ccccc2)N1]

or a pharmaceutically acceptable salt thereof.

15. The method according to claim 1 wherein the compound of formula (Ib) is N-(((3S,5S)-3-butyl-2-oxo-1-((S)-2-phenylbutyl)-1,4-diazepan-5-yl)methyl)-6-chloro-2-naphthamide, represented by the formula

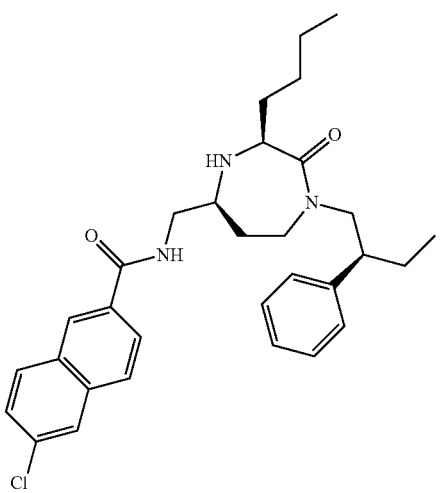 [SMILES: CCCC[C@@H]1N[C@H](CNC(=O)c2ccc3cc(Cl)ccc3c2)CCN(C[C@@H](CC)c2ccccc2)C1=O]

or a pharmaceutically acceptable salt thereof.

16. The method according to claim 1 wherein the compound of formula (Ib) is 6-chloro-N-(((3S,5S)-3-isopentyl-2-oxo-1-((S)-2-phenylbutyl)-1,4-diazepan-5-yl)methyl)-2-naphthamide, represented by the formula

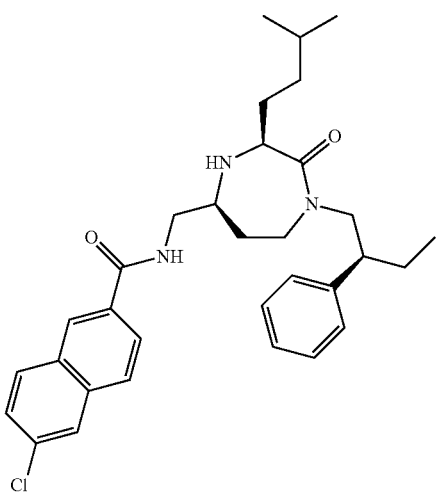 [SMILES: CC[C@H](CN1CC[C@@H](CNC(=O)c2ccc3cc(Cl)ccc3c2)N[C@@H](CCC(C)C)C1=O)c1ccccc1]

or a pharmaceutically acceptable salt thereof.

17. The method according to claim 1 wherein the compound of formula (Ib) is selected from the group consisting of:

6-chloro-N-(((3S,5S)-3-(2-cyclohexylethyl)-2-oxo-1-((S)-2-phenylbutyl)-1,4-diazepan-5-yl)methyl)-2-naphthamide, represented by the formula

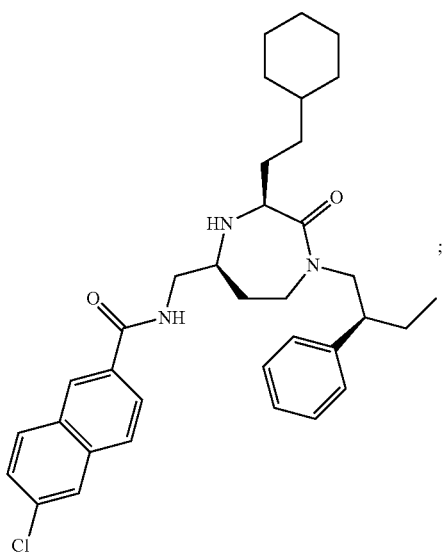 [SMILES: CC[C@H](CN1CC[C@@H](CNC(=O)c2ccc3cc(Cl)ccc3c2)N[C@@H](CCC2CCCCC2)C1=O)c1ccccc1]

6-chloro-N-(((3S,5S)-3-hexyl-2-oxo-1-((S)-2-phenylbutyl)-1,4-diazepan-5-yl)methyl)-2-naphthamide, represented by the formula 6-chloro-N-(((3S,5S)-3-(4-hydroxybutyl)-2-oxo-1-((S)-2-phenylbutyl)-1,4-diazepan-5-yl)methyl)-2-naphthamide, represented by the formula

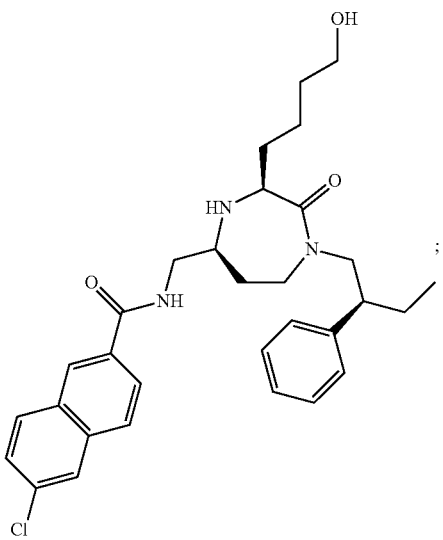 [SMILES: CC[C@H](CN1CC[C@@H](CNC(=O)c2ccc3cc(Cl)ccc3c2)N[C@@H](CCCCO)C1=O)c1ccccc1]

6-chloro-N-(((3S,5S)-3-(2-methoxyethyl)-2-oxo-1-((S)-2-phenylbutyl)-1,4-diazepan-5-yl)methyl)-2-naphthamide, represented by the formula

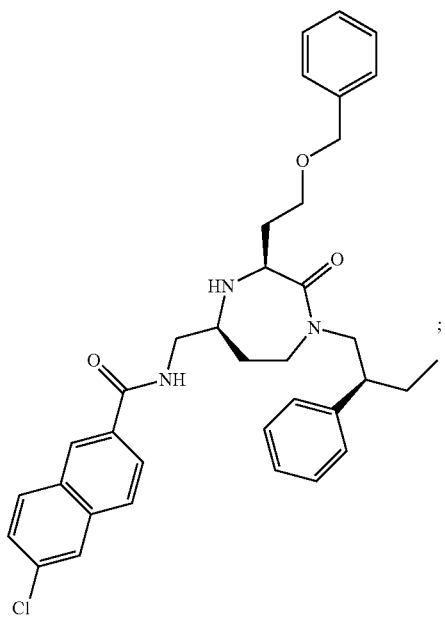

6-chloro-N-(((3S,5S)-3-isobutyl-2-oxo-1-((S)-2-phenylbutyl)-1,4-diazepan-5-yl)methyl)-2-naphthamide, represented by the formula

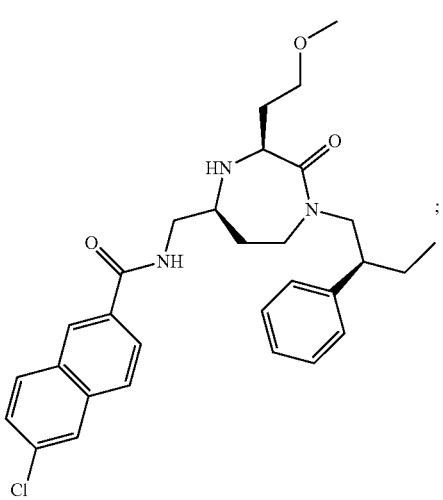 [SMILES: CC[C@H](CN1CC[C@@H](CNC(=O)c2ccc3cc(Cl)ccc3c2)N[C@@H](CCOC)C1=O)c1ccccc1]

N-(((3S,5S)-3-(2-(benzyloxy)ethyl)-2-oxo-1-((S)-2-phenylbutyl)-1,4-diazepan-5-yl)methyl)-6-chloro-2-naphthamide, represented by the formula 3,4-dichloro-N-(((3S,5S)-3-(2-hydroxyethyl)-2-oxo-1-((S)-2-phenylbutyl)-1,4-diazepan-5-yl)methyl)benzamide, represented by the formula

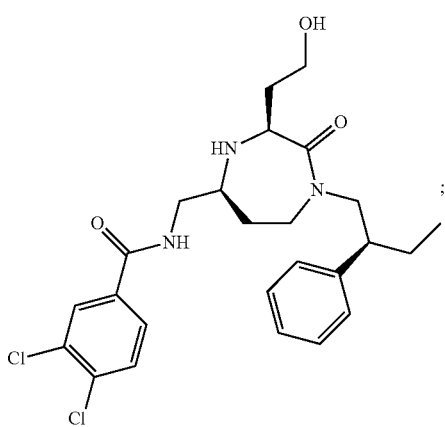 [SMILES: CC[C@H](CN1CC[C@@H](CNC(=O)c2ccc(Cl)c(Cl)c2)N[C@@H](CCO)C1=O)c1ccccc1]

or a pharmaceutically acceptable salt thereof.

18. A method of reducing sebum secretion comprising administering to a mammal in need thereof a therapeutically effective amount of a compound of formula (Ib):

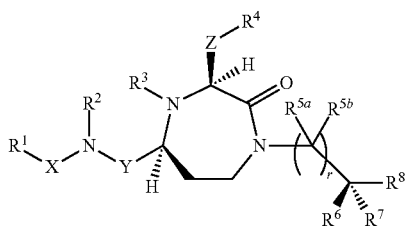

Formula (Ib)

wherein
Y is $CH_2$;
X is $-C(=O)-$;
Z is $-(CH_2)_q-$;
r is 0 or 1;
q is 1, 2, 3, or 4;
$R^1$ is selected from the group consisting of (a) optionally subsituted $C_6$-$C_{18}$ aryl wherein the $C_6$-$C_{18}$ aryl is phenyl, biphenyl, or naphthyl; (b) optionally substituted $C_1$-$C_{18}$ heteroaryl wherein the $C_1$-$C_{18}$ heteroaryl is indol-2-yl, indol-3-yl, quinolin-2-yl, quinolin-3-yl, isoquinolin-3-yl, quinoxaline-2-yl, benzo[b]furan-2-yl, benzo[b]thiophen-2-yl, benzo[b]thiophen-5-yl, thiazole-4-yl, benzimidazole-5-yl, benzotriazol-5-yl, furan-2-yl, benzo[d]thiazole-6-yl, pyrazole-1-yl, pyrazole-4-yl or thiophen-2-yl; and (c) optionally substituted alkenyl of the formula:

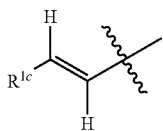

wherein $R^{1c}$ is optionally substituted $C_6$-$C_{18}$ aryl wherein the $C_6$-$C_{18}$ aryl is selected from phenyl and naphthyl;
$R^2$ is H or $C_1$-$C_6$ alkyl;
$R^3$ is H or $C_1$-$C_6$ alkyl;
$R^4$ is selected from the group consisting of H, $C_1$-$C_{12}$ alkyl, optionally substituted $C_3$-$C_{12}$ cycloalkyl, optionally substituted $C_6$ aryl, $OR^{20}$, and $OCR^{17}R^{18}R^{20}$;

$R^{5a}$ and $R^{5b}$ are each H;
$R^6$ and $R^8$ are each independently H, methyl, trifluoromethyl, ethyl, 2,2,2-trifluoroethyl, isopropyl, isopropenyl, propyl, 2-ethyl-propyl, 3,3-dimethylpropyl, butyl, 2-methylbutyl, isobutyl, 3,3-dimethyl-butyl, 2-ethylbutyl, pentyl, 2-methyl-pentyl, optionally substituted phenyl, or optionally substituted $C_1$-$C_5$ heteroaryl, wherein the $C_1$-$C_5$ heteroaryl is thiophene, furan, pyrrole, imidazole, pyrazole, pyridine, pyrazine, or tetrazole;
$R^7$ is H;
each of $R^{17}$, $R^{18}$, and $R^{20}$ is selected from the group consisting of H, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, cyclopropyl, cyclobutyl, cyclopentyl, cyclohexyl, benzyl, and phenyl, or a halogenated derivative thereof; and
wherein each optional substituent is independently selected from the group consisting of F, Cl, Br, I, $CH_3$, $CH_2CH_3$, OH, $OCH_3$, $CF_3$, $OCF_3$, $NO_2$, $NH_2$, and CN,
or a pharmaceutically acceptable salt thereof.

19. The method according to claim 18 wherein the compound of formula (Ib) is selected from the group consisting of:
N-(((3S,5S)-3-butyl-1-(2,2-diphenylethyl)-2-oxo-1,4-diazepan-5-yl)methy)-2-naphthamide;
(E)-N-(((3S,5S)-3-butyl-1-(2,2-diphenylethyl)-2-oxo-1,4-diazepan-5-yl)methyl)-3-(4-chlorophenyl)acrylamide;
N-(((3S,5S)-3-(cyclohexylmethyl)-1-(2,2-diphenylethyl)-2-oxo-diazepan-5-yl)methyl)-2-naphthamide;
N-(((3S,5S)-1-(2,2-diphenylethyl)-2-oxo-3-phenethyl-1,4-diazepan-5-yl)methyl)-2-naphthamide;
(E)-3-(4-chlorophenyl)-N-(((3S,5S)-1-(2,2-diphenylethyl)-2-oxo-3-phenethyl-1,4-diazepan-5-yl)methyl) acrylamide;
N-(((3S,5S)-3-(2-cyclohexylethyl)-1-(2,2-diphenylethyl)-2-oxo-1,4-diazepan-5-yl)methyl)-2-naphthamide;
(E)-3-(4-chlorophenyl)-N-(((3S,5S)-3-(2-cyclohexylethyl)-1-(2,2-diphenylethyl)-2-oxo-1,4-diazepan-5-yl) methyl)acrylamide;
N-(((3S,5S)-3-benzyl-1-(2,2-diphenylethyl)-2-oxo-1,4-diazepan-5-yl)methyl)-2-naphthamide;
(E)-N-(((3S,5S)-3-benzyl-1-(2,2-diphenylethyl)-2-oxo-1,4-diazepan-5-yl)methyl)-3-(4-chlorophenyl)acrylamide;
N-(((3S,5S)-3-butyl-2-oxo-1-((S)-2-phenylbutyl)-1,4-diazepan-5-yl)methyl)-6-chloro-2-naphthamide;
6-chloro-N-(((3S,5S)-3-isopentyl-2-oxo-1-((S)-2-phenylbutyl)-1,4-diazepan-5-yl)methyl)-2-naphthamide;
6-chloro-N-(((3S,5S)-3-(2-cyclohexylethyl)-2-oxo-1-((S)-2-phenylbuty)-diazepan-5-yl)methyl)-2-naphthamide;
6-chloro-N-(((3S,5S)-3-hexyl-2-oxo-1-((S)-2-phenylbutyl)-1,4-diazepan-5-yl)methyl)-2-naphthamide;
6-chloro-N-(((3S,5S)-3-(4-hydroxybutyl)-2-oxo-1-((S)-2-phenylbutyl)-1,4-diazepan-5-yl)methyl)-2-naphthamide;
6-chloro-N-(((3S,5S)-3-(2-methoxyethyl)-2-oxo-1-((S)-2-phenylbutyl)-1,4-diazepan-5-yl)methyl)-2-naphthamide;
N-(((3S,5S)-3-(2-(benzyloxy)ethyl)-2-oxo-1-((S)-2-phenylbutyl)-1,4-diazepan-5-yl)methyl)-6-chloro-2-naphthamide;
6-chloro-N-(((3S,5S)-3-isobutyl-2-oxo-1-((S)-2-phenylbutyl)-1,4-diazepan-5-yl)methyl)-2-naphthamide; and 3,4-dichloro-N-(((3S,5S)-3-(2-hydroxyethyl)-2-oxo-1-((S)-2-phenylbutyl)-1,4-diazepan-5-yl)methyl)benzamide;

or a pharmaceutically acceptable salt thereof.

* * * * *